United States Patent
Maiti et al.

(10) Patent No.: US 9,393,239 B2
(45) Date of Patent: *Jul. 19, 2016

(54) BICYCLIC COMPOUNDS AND THEIR USE AS ANTIBACTERIAL AGENTS AND BETALACTAMASE INHIBITORS

(71) Applicant: FEDORA PHARMACEUTICALS INC., Edmonton (CA)

(72) Inventors: Samarendra N. Maiti, Edmonton (CA); Dai Nguyen, Edmonton (CA); Jehangir Khan, Edmonton (CA); Rong Ling, Edmonton (CA)

(73) Assignee: FEDORA PHARMACEUTICALS INC., Edmonton (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/253,085

(22) Filed: Apr. 15, 2014

(65) Prior Publication Data

US 2014/0221341 A1 Aug. 7, 2014

Related U.S. Application Data

(63) Continuation of application No. 13/690,398, filed on Nov. 30, 2012, now Pat. No. 8,796,257.

(60) Provisional application No. 61/641,087, filed on May 1, 2012, provisional application No. 61/566,240, filed on Dec. 2, 2011.

(51) Int. Cl.
| | |
|---|---|
| *A61K 31/439* | (2006.01) |
| *A61K 31/5377* | (2006.01) |
| *A61K 31/4985* | (2006.01) |
| *A61K 45/06* | (2006.01) |
| *A61K 31/553* | (2006.01) |
| *A61K 31/55* | (2006.01) |
| *A61K 31/541* | (2006.01) |
| *A61K 31/496* | (2006.01) |
| *C07D 471/08* | (2006.01) |
| *A61K 31/46* | (2006.01) |
| *C07D 519/00* | (2006.01) |
| *C07D 451/06* | (2006.01) |

(52) U.S. Cl.
CPC .............. *A61K 31/46* (2013.01); *A61K 31/439* (2013.01); *A61K 31/496* (2013.01); *A61K 31/4985* (2013.01); *A61K 31/5377* (2013.01); *A61K 31/541* (2013.01); *A61K 31/55* (2013.01); *A61K 31/553* (2013.01); *A61K 45/06* (2013.01); *C07D 451/06* (2013.01); *C07D 471/08* (2013.01); *C07D 519/00* (2013.01)

(58) Field of Classification Search
USPC ............... 514/210.21, 211.15, 217.07, 228.2, 514/233.2, 249, 253.04, 278, 300; 540/544, 540/597; 544/58.6, 127, 349, 362; 564/15, 564/16, 121

See application file for complete search history.

(56) References Cited

U.S. PATENT DOCUMENTS

| | | |
|---|---|---|
| 7,112,592 B2 | 9/2006 | Lampilas et al. |
| 7,439,253 B2 | 10/2008 | Lampilas et al. |
| 9,181,250 B2 | 11/2015 | Abe et al. |
| 2003/0199541 A1 | 10/2003 | Lampilas et al. |
| 2004/0097490 A1 | 5/2004 | Musicki |
| 2004/0157826 A1 | 8/2004 | Lampilas et al. |
| 2005/0020572 A1 | 1/2005 | Aszodi et al. |
| 2005/0245505 A1 | 11/2005 | Aszodi |
| 2006/0046995 A1 | 3/2006 | Lampilas et al. |
| 2006/0189652 A1 | 8/2006 | Lampilas et al. |
| 2007/0191312 A1 | 8/2007 | Musicki |
| 2007/0299108 A1 | 12/2007 | Aszodi |
| 2009/0018329 A1 | 1/2009 | Lampilas et al. |
| 2009/0215747 A1 | 8/2009 | Aszodi et al. |
| 2010/0048528 A1 | 2/2010 | Aszodi et al. |
| 2010/0092443 A1 | 4/2010 | Levasseur et al. |

(Continued)

FOREIGN PATENT DOCUMENTS

| | | |
|---|---|---|
| CA | 2 780 403 | 12/2012 |
| EP | 1 307 457 B1 | 5/2003 |

(Continued)

OTHER PUBLICATIONS

U.S. Appl. No. 61/566,240, filed Dec. 2, 2011, Maiti et al.

(Continued)

*Primary Examiner* — Kathrien Cruz
(74) *Attorney, Agent, or Firm* — Wenderoth, Lind & Ponack, L.L.P.

(57) ABSTRACT

A compound of formula (I):

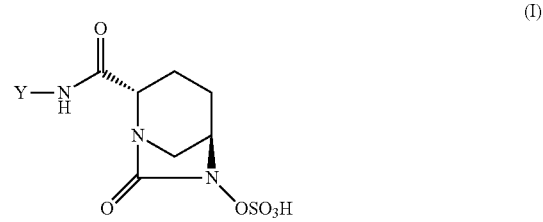

wherein:
M is hydrogen or a pharmaceutically acceptable salt-forming cation;
Y is $OR^1$ or $NR^2R^3$,
and $R^1$, $R^2$, $R^3$ and M are as defined herein. Also, methods of treating bacterial infection, pharmaceutical compositions, molecular complexes and processes for preparing compounds.

3 Claims, No Drawings

(56) References Cited

U.S. PATENT DOCUMENTS

| | | |
|---|---|---|
| 2010/0137355 A1 | 6/2010 | Lampilas et al. |
| 2010/0197928 A1 | 8/2010 | Priour et al. |
| 2011/0021772 A1 | 1/2011 | Lampilas et al. |
| 2011/0213147 A1 | 9/2011 | Lampilas et al. |
| 2011/0245254 A1 | 10/2011 | Aszodi et al. |
| 2011/0294777 A1 | 12/2011 | Blizzard et al. |
| 2012/0053350 A1 | 3/2012 | Mangion et al. |
| 2012/0165533 A1 | 6/2012 | Abe et al. |
| 2012/0323010 A1 | 12/2012 | Ronsheim et al. |
| 2013/0012712 A1 | 1/2013 | Priour et al. |
| 2013/0296555 A1 | 11/2013 | Gu et al. |

FOREIGN PATENT DOCUMENTS

| | | |
|---|---|---|
| EP | 1 537 117 BI | 6/2005 |
| WO | 02/10172 | 2/2002 |
| WO | 02/100860 | 12/2002 |
| WO | 03/063864 | 8/2003 |
| WO | 2004/022563 | 3/2004 |
| WO | 2004/052891 | 6/2004 |
| WO | 2008/142285 | 11/2008 |
| WO | 2009/090320 | 7/2009 |
| WO | 2009/091856 | 7/2009 |
| WO | 2010/126820 | 11/2010 |
| WO | 2012/172368 | 12/2012 |
| WO | 2013/030733 | 3/2013 |
| WO | 2013/030735 | 3/2013 |
| WO | 2013/149121 | 10/2013 |
| WO | 2013/180197 | 12/2013 |
| WO | 2014/033560 | 3/2014 |

OTHER PUBLICATIONS

U.S. Appl. No. 61/641,087, filed May 1, 2012, Maiti et al.
International Search Report and the Written Opinion of the International Searching Authority mailed Sep. 4, 2013, 12 pages, PCT/IB2012/002675.
Extended European Search Report issued May 3, 2016 in corresponding European Application No. 12889814.5.

BICYCLIC COMPOUNDS AND THEIR USE AS ANTIBACTERIAL AGENTS AND BETALACTAMASE INHIBITORS

CROSS-REFERENCE TO RELATED APPLICATIONS

This application is a continuation of U.S. application Ser. No. 13/690,398, filed Nov. 30, 2012, which claims the benefit of U.S. Provisional Patent Application No. 61/566,240, filed Dec. 2, 2011, and U.S. Provisional Patent Application No. 61/641,087, filed May 1, 2012, the entirety of each of which is incorporated herein by reference.

FIELD OF THE INVENTION

The present invention relates to new bicyclic compounds, their preparation and their use as antibacterial agents either alone or in combination with an antibiotic (or plural antibiotics) for the treatment of infections caused by β-lactamase-producing pathogenic bacteria. The compounds of the present invention are β-lactamase inhibiting or non-β-lactamase inhibiting (i.e., some of the compounds of the present invention by themselves would directly inhibit β-lactamase enzymatic function, and others of the compounds of the present invention by themselves would not inhibit some β-lactamase's enzymatic function though they provide synergy and increased potency of activity in combination with antibiotics, e.g., β-lactam antibiotics or non-β-lactam antibiotics). More particularly, the invention is concerned with methods for overcoming antibiotic resistance caused by β-lactamase producing bacteria, the method of preparation of the new compounds, pharmaceutical compositions containing the new compounds, methods of treatment, uses of the compounds, and other subject matter.

BACKGROUND OF THE INVENTION

Microbial drug resistance is an unavoidable consequence resulting from abuse and overuse of antimicrobial agents. The rate at which resistance arises among microbial population is often dictated by the extent of use of particular agents in a given environment. Given the degree of popularity of β-lactam (also known as β-lactam) antibiotics, it is not surprising that the prevalence of β-lactamase (also known as β-lactamase) producing strains is increasing worldwide. The most significant known mechanism related to the development of bacterial resistance to the β-lactam antibiotics is the production of class-A, class-B, class-C and class-D β-lactamases that are able to hydrolyze the β-lactam antibiotics resulting in the loss of antibacterial activity. Class-A enzymes preferentially hydrolyze penicillins, class-B enzymes hydrolyze all β-lactams including carbapenems, class-C β-lactamases have a substrate profile favoring cephalosporin hydrolysis, whereas substrate preference for class D β-lactamases include oxacillin and cloxacillin.

The possibility of rescuing individual β-lactam antibiotics by combination with a β-lactamase inhibitor that inactivates the β-lactamase before it can hydrolyze the β-lactam antibiotic has been demonstrated with clinically useful combination between penicillins such as amoxicillin, ampicillin, piperacillin and ticarcillin and β-lactamase inhibitors such as clavulanic acid, sulbactam and tazobactam. Further potential combinations have been described involving various β-lactam antibiotics and newly reported β-lactamase inhibitors including bicyclic monobactams, exomethylene penems and 7-oxo-6-diazabicyclo[3.2.1]octane-2-carboxamide derivatives.

As a result of point mutations and plasmid transfer, the diversity of β-lactamases is increasing constantly. The currently commercial β-lactamase inhibitors are insufficient to counter these new β-lactamases—particularly ineffective against class C producing organisms, newly emerged extended-spectrum β-lactamases (ESBLs) and carbapenemases like IMP, VIM, OXA, KPC, and NDM. Thus there is a need for broad-spectrum β-lactamase inhibitor to combat over 900 β-lactamases including the newly emerged β-lactamases.

Recently, certain diazabicyclic compounds have been disclosed in WO 2009/091856 which is hereby incorporated by reference in its entirety. In addition, a number of diazabicyclic heterocycles have been disclosed in the following patents as β-lactamase inhibitors: US 2003/0199541 A1, US 2004/0157826 A1, US 2004/0097490 A1, US 2005/0020572 A1, US 2006/7112592 B2, US 2006/0189652 A1, US 2008/7439253 B2, US 2009/0018329 A1, EP 1307457 B1, EP 1537117 B1, WO 2002/100860 A2, WO 2002/10172 A1, WO 2003/063864 A2, WO 2004/052891 A1, WO 2004/022563 A1, WO 2008/142285 A1, WO 2009/090320 A1, US 2010/0092443 A1, WO 2010/126820 A2, US 2012/0165533 A1.

The compounds of the present invention are new and the structural features are significantly distinct from the compounds described in the patent references cited above.

DETAILED DESCRIPTION OF THE INVENTION

In one aspect, the present invention relates to new, low molecular weight diazabicyclic compounds (some of which have potent broad-spectrum β-lactamase inhibitory activity and others do not have such activity) that when used in combination with a β-lactam antibiotic or with other non β-lactam antibiotics enhance the activity of the antibiotic against class A, Class B, class C, and class D enzyme producing organisms and thereby enhance the antibacterial properties. The compounds are therefore useful in the treatment of bacterial infections in humans or animals either alone or in combination with β-lactam antibiotics and/or with other non β-lactam antibiotics.

In accordance with the present invention, there are provided (A) new compounds of general formula (I), (B) pharmaceutically acceptable salts of the compounds of formula (I), (C) pharmaceutically acceptable solvates of the compounds of formula (I) and of their salts, and (D) deuterated compounds of compounds of (A), (B) and (C), (namely, (i) compounds of formula (I) modified in that they have been deuterated, (ii) pharmaceutically acceptable salts of compounds of formula (I) modified in that they have been deuterated, and (iii) pharmaceutically solvates of compounds of formula (I) and of their salts modified in that they have been deuterated):

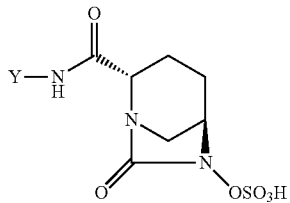
(I)

Wherein;

M is hydrogen or a pharmaceutically acceptable salt forming cation, a "pharmaceutically acceptable salt" refers to a salt of a compound, which salt possesses the desired pharmacological activity of the parent compound, reference to specified compounds "modified in that they have been deuterated" refers to compounds obtained by modifying the specified compounds so that one or more hydrogen atoms in the compound have been replaced with or converted to deuterium, $Y=OR^1$ or $NR^2R^3$, In the formula (I), when $Y=OR^1$, $R^1$ is a radical selected from any of the following groups:

(1) $C_{1-6}$ straight or branched chain alkyl which is optionally substituted. Non-limiting examples of such compounds are:

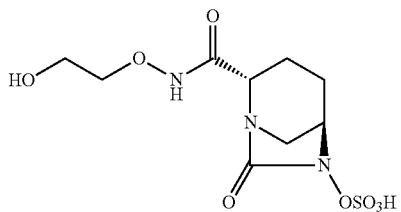

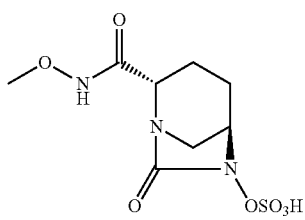

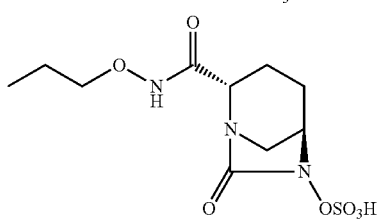

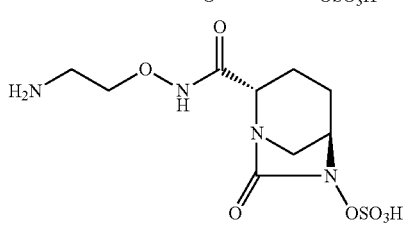

-continued

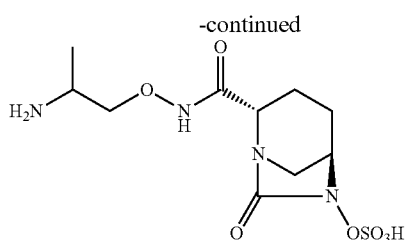

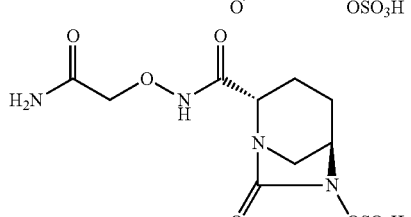

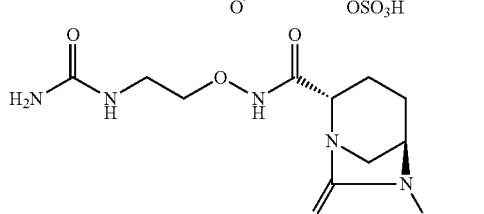

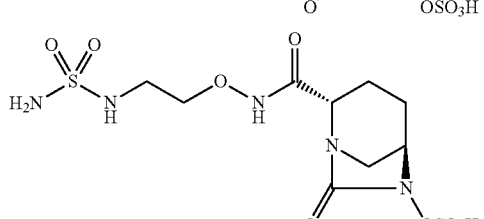

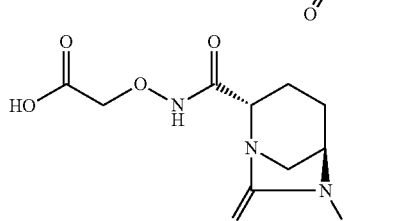

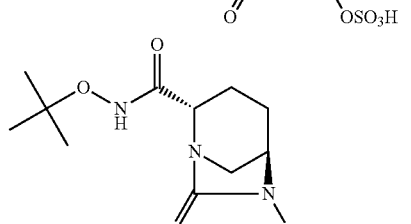

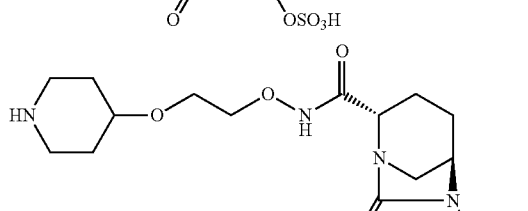

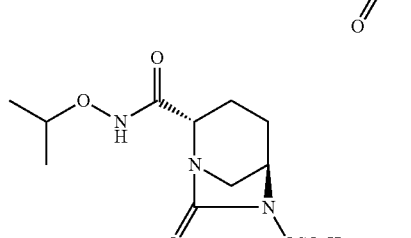

-continued
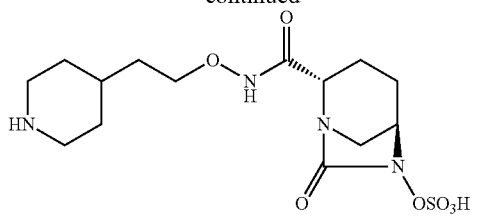
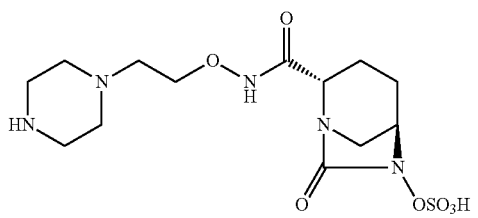
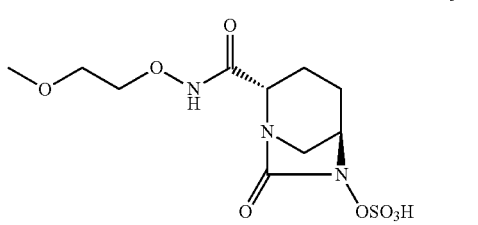
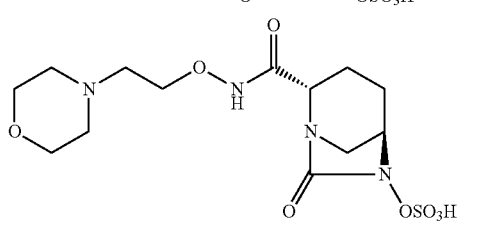
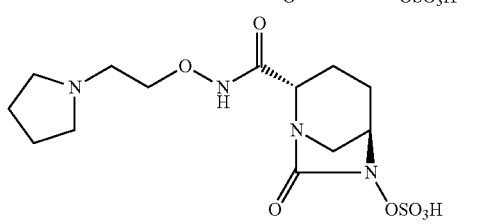
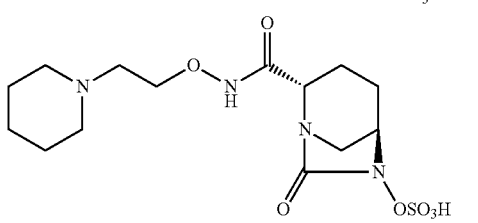
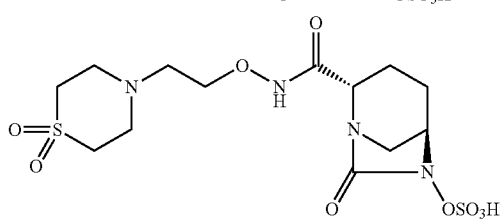
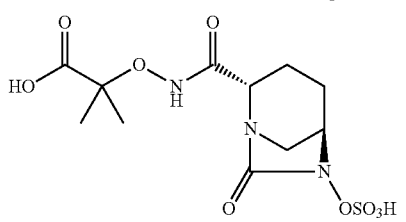
-continued
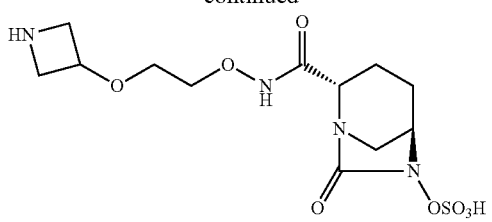
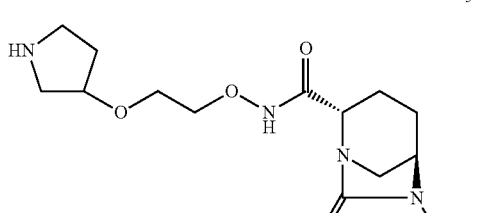
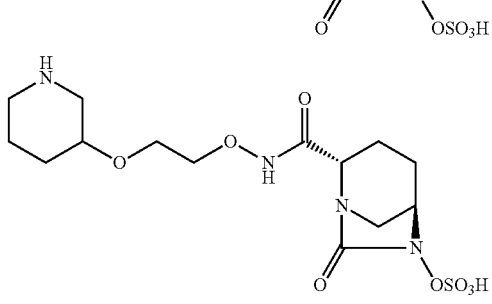
(2) $C_{3-7}$ cycloalkyl which is optionally substituted. Non-limiting examples of such compounds are:
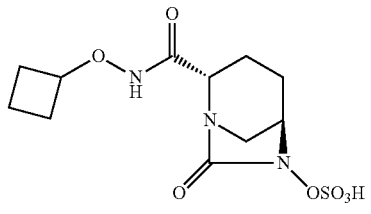
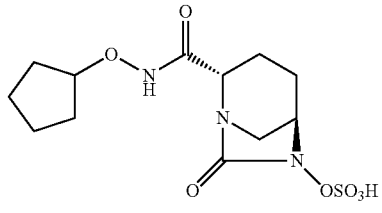
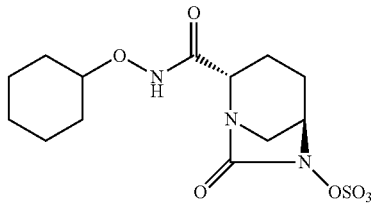
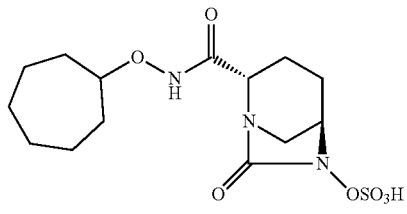

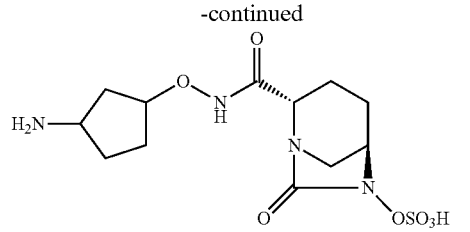
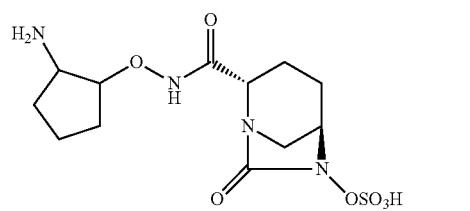
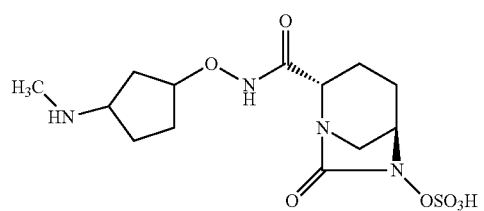
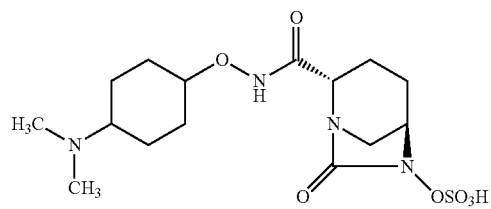
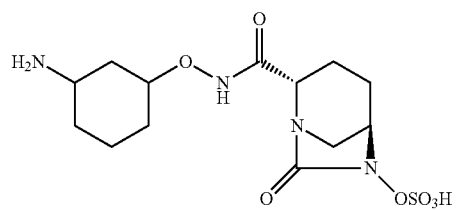
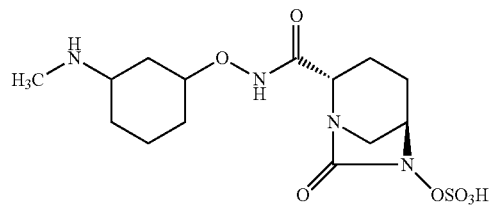
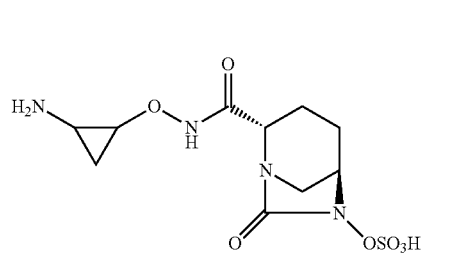
(3) C<sub>4-7</sub> saturated heterocycles containing at least one heteroatom selected from O, N and S wherein the said heterocycle is optionally substituted. Furthermore the ring S is optionally oxidized to S(O) or S(O)$_2$ and the free ring N atom may optionally take a substituent. Non-limiting examples of such compounds are:
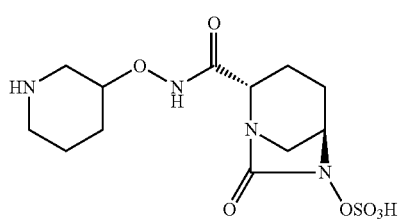
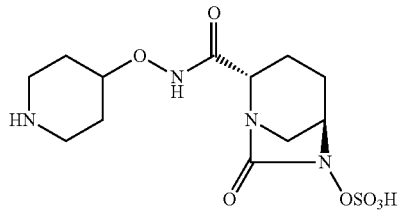
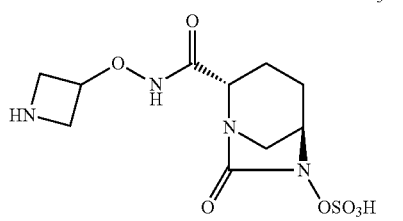
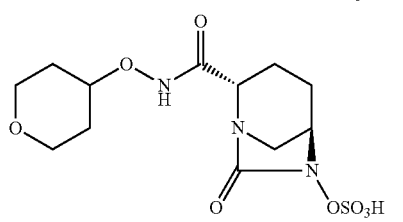
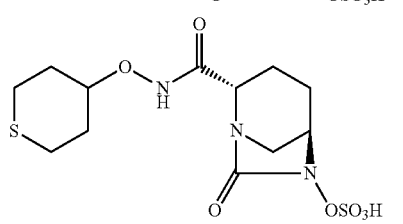
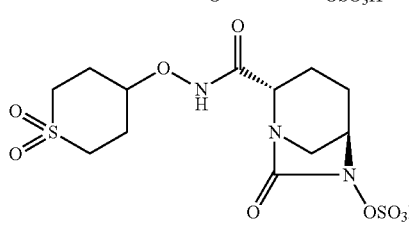
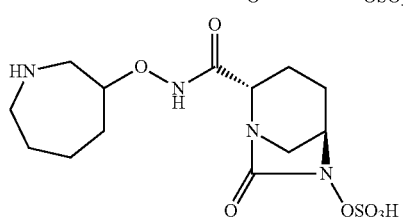
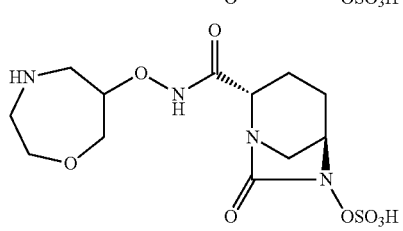

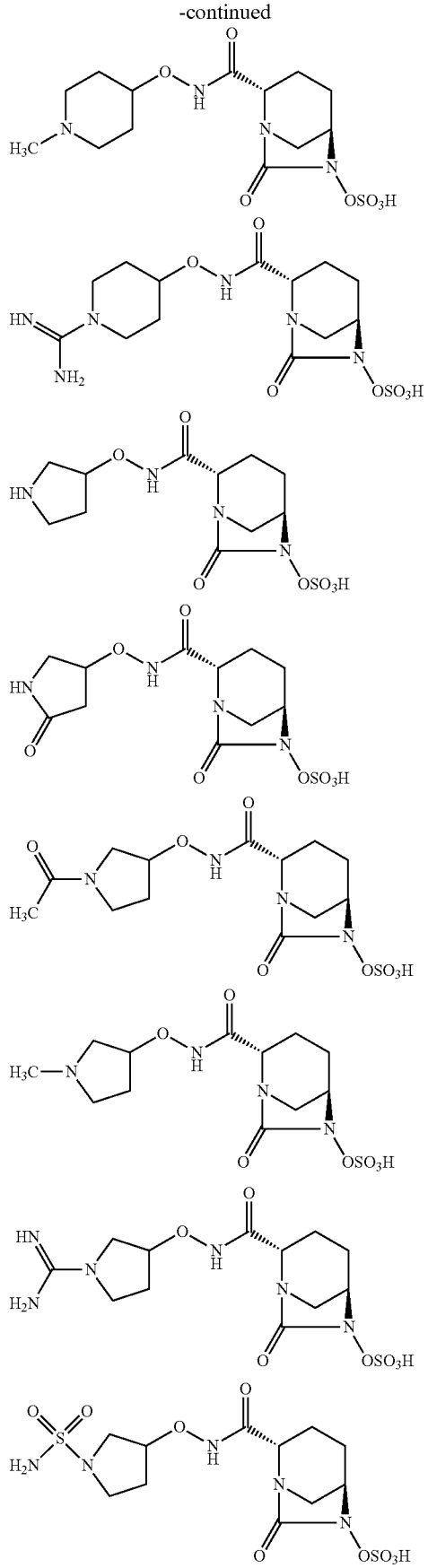
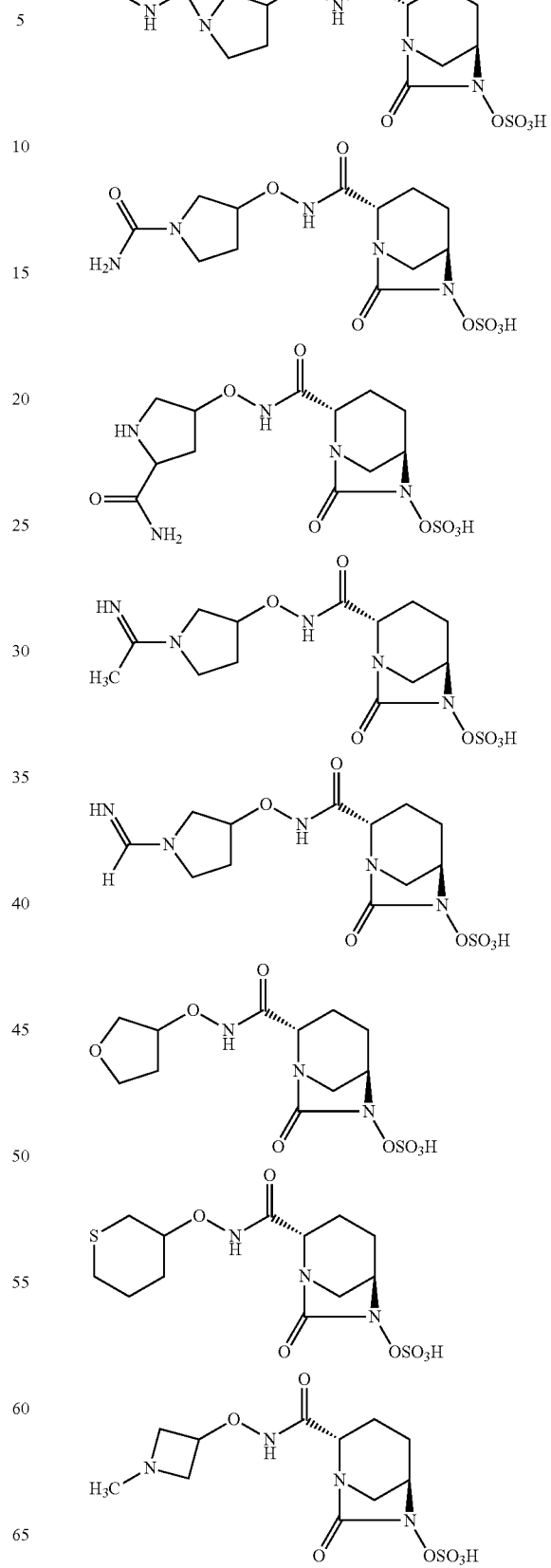

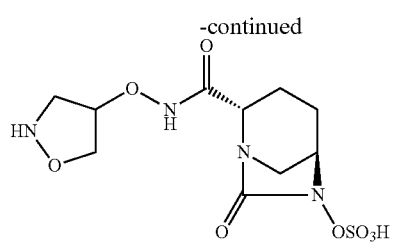
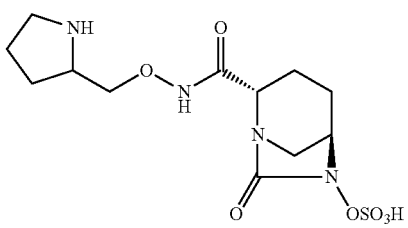
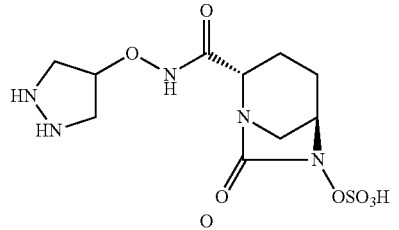
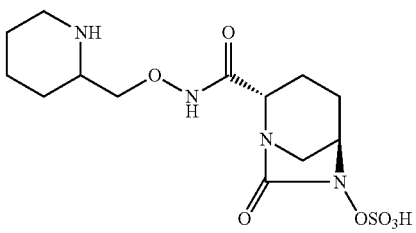
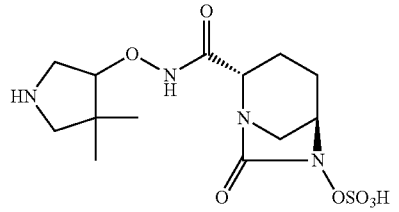
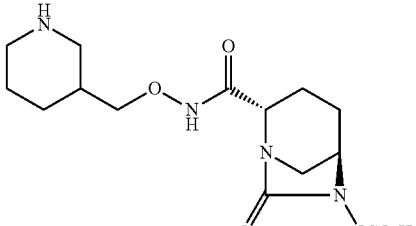
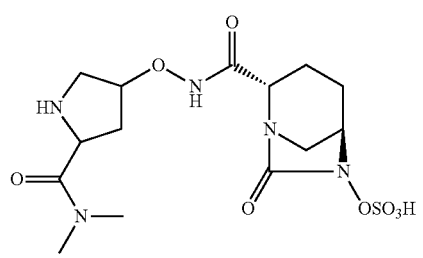
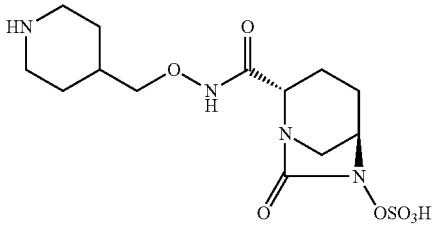
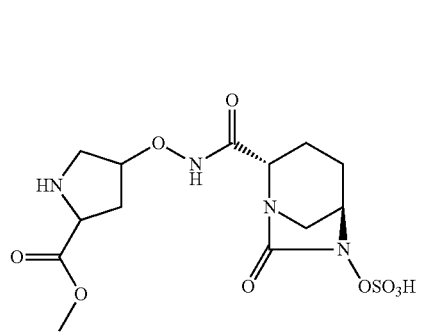
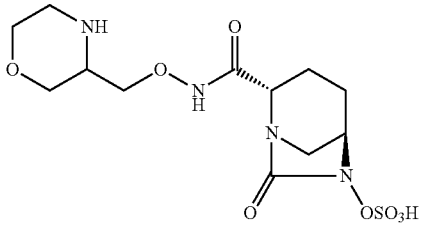
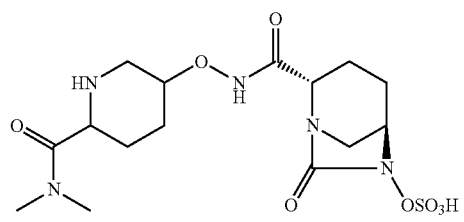
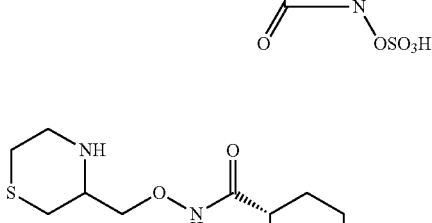
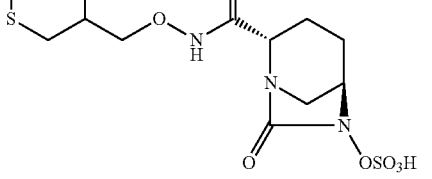
(4) Heterocyclyl ($C_{1-6}$) alkyl wherein the said heterocycle has the same definition as defined in (3). Furthermore, the said heterocycle is optionally substituted. Non-limiting examples of such compounds are:

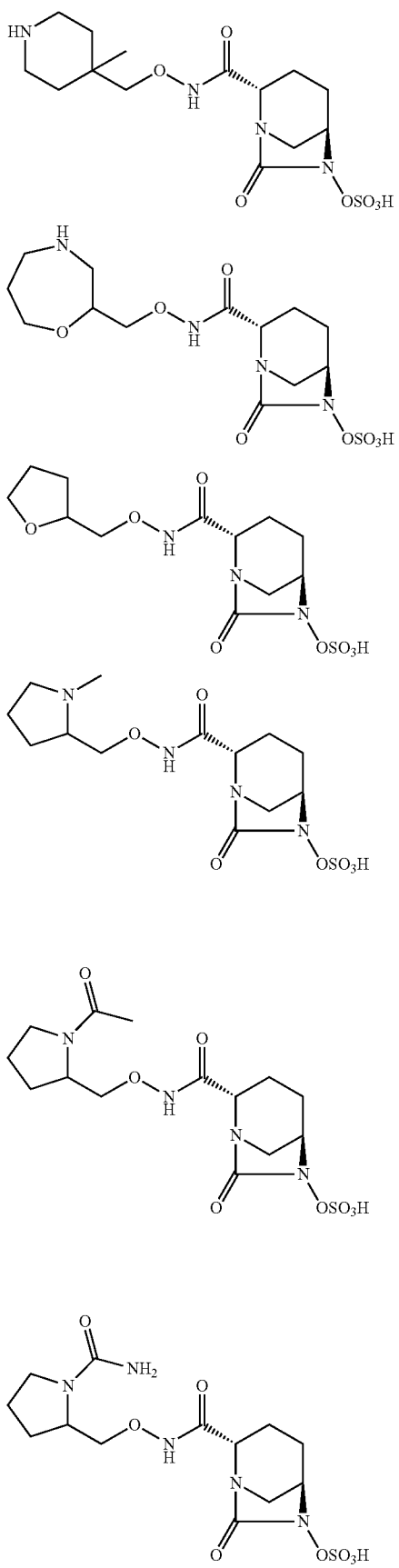
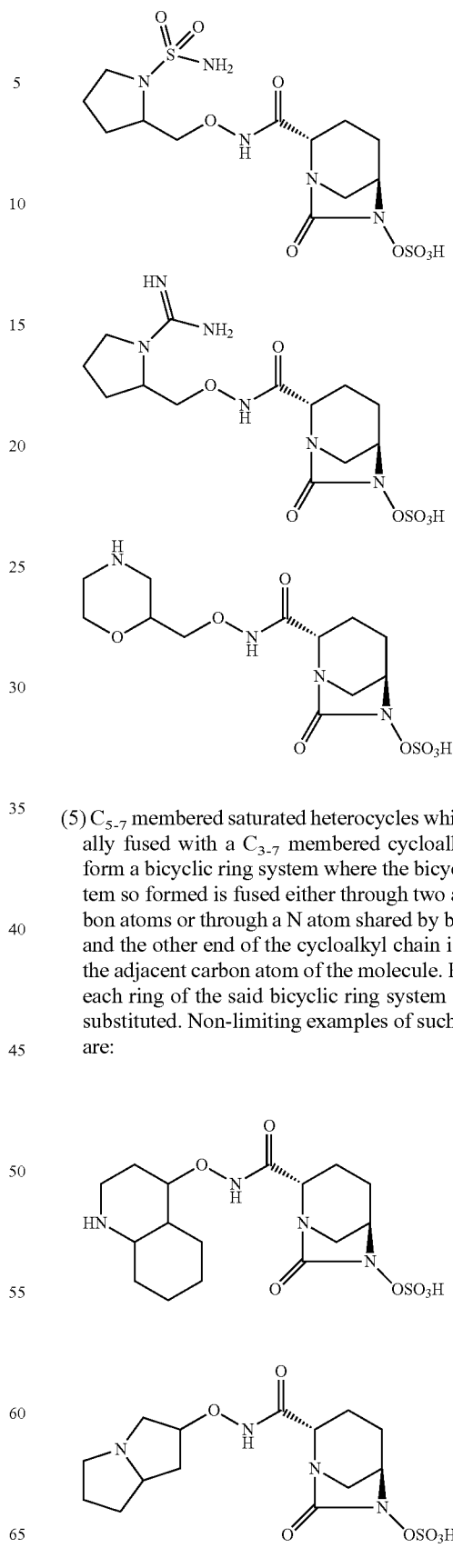

(5) $C_{5-7}$ membered saturated heterocycles which is optionally fused with a $C_{3-7}$ membered cycloalkyl group to form a bicyclic ring system where the bicyclic ring system so formed is fused either through two adjacent carbon atoms or through a N atom shared by both the rings and the other end of the cycloalkyl chain is attached to the adjacent carbon atom of the molecule. Furthermore, each ring of the said bicyclic ring system is optionally substituted. Non-limiting examples of such compounds are:

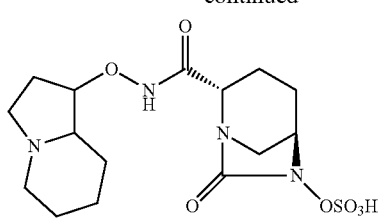

(6) C$_{5-7}$ membered saturated heterocycles which is optionally fused with another C$_{5-7}$ saturated heterocycle to form a bicyclic ring system where the bicyclic ring system so formed is fused either through two adjacent carbon atoms or through a N atom shared by both the rings. Furthermore, each ring of the said bi-cyclic ring system is optionally substituted. Non-limiting examples of such compounds are:

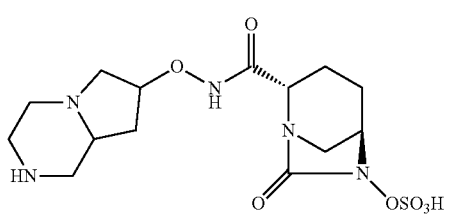

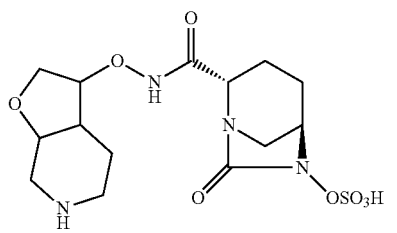

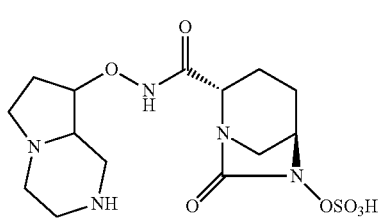

(7) C$_{3-7}$ cycloalkyl which is optionally fused with a C$_{5-7}$ membered saturated heterocycle containing at least one heteroatom selected from O, N and S. Furthermore, the said bicyclic ring is optionally substituted. Non-limiting examples of such compounds are:

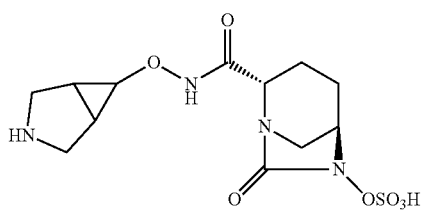

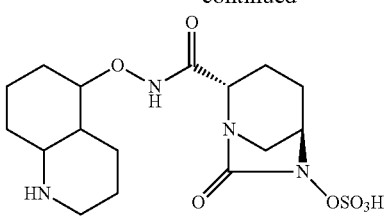

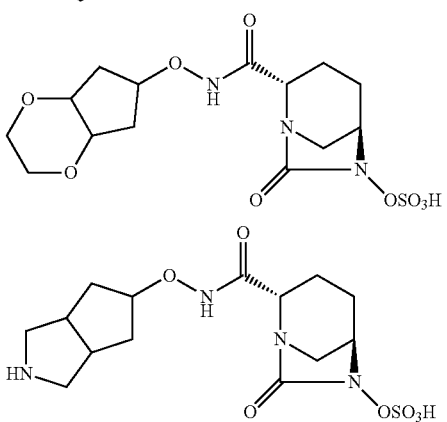

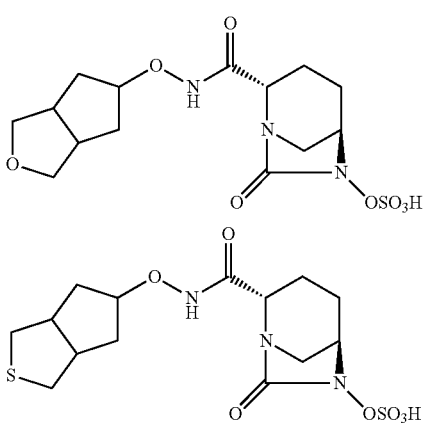

(8) Bridged bicyclic ring system having optionally one or two heteroatoms selected from O, N and S. Furthermore, the bicyclic ring system is optionally substituted either at the carbon atom or at the free N atom present in the ring. Non-limiting examples of such compounds are:

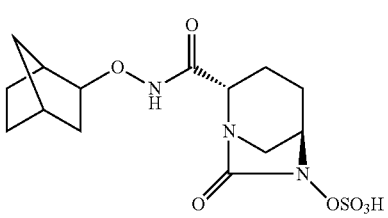

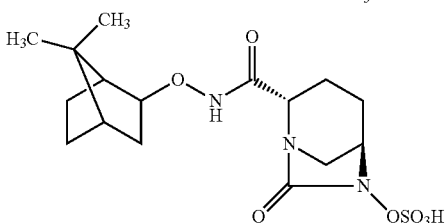

-continued

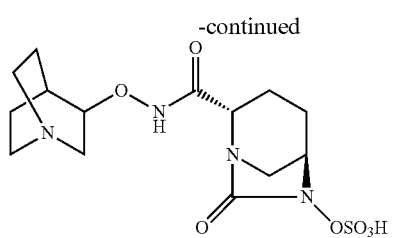
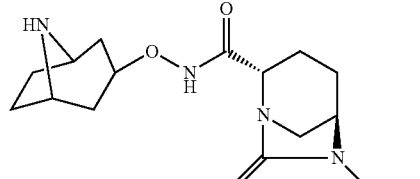
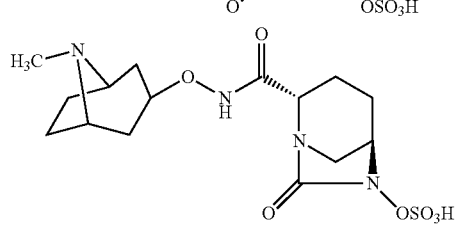

(9) $C_{5-7}$ membered saturated heterocycles which is optionally fused with $C_{5-7}$ membered heteroaryl ring where the bicyclic ring system so formed is fused either through two adjacent carbon atoms or through N atom shared by both the rings. Non-limiting examples of such compounds are:

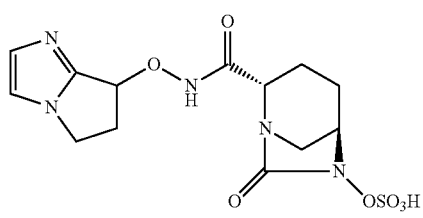
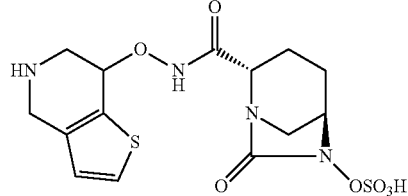
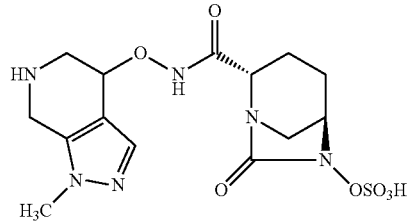
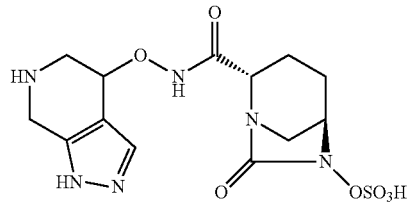

-continued

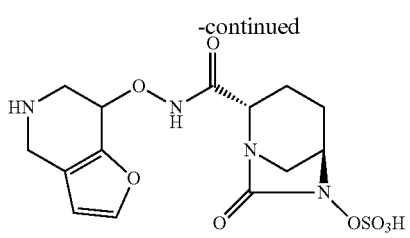

(10) $C_{5-7}$ membered saturated heterocycles which is optionally fused to a $C_{3-6}$ membered ring system through a common carbon atom to form a spiro system optionally containing one heteroatom selected from O, N and S that is present in the spiro ring where the ring S is optionally oxidized to S(O) or S(O)$_2$ and the free N atom present in either ring may optionally take a substituent. Non-limiting examples of such compounds are:

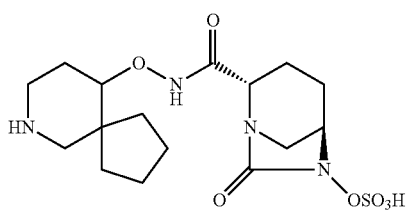
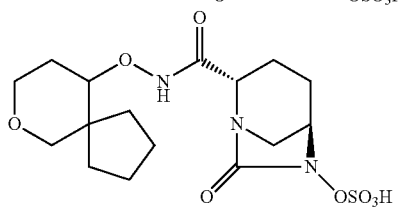

(11) $C_{5-7}$ membered heteroarylalkyl which is optionally substituted. Non-limiting examples of such compounds are:

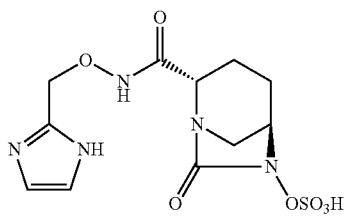
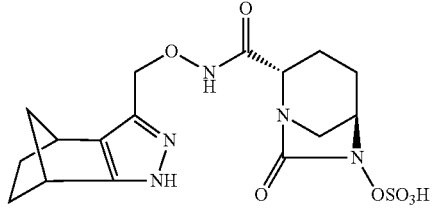
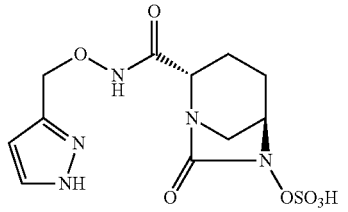

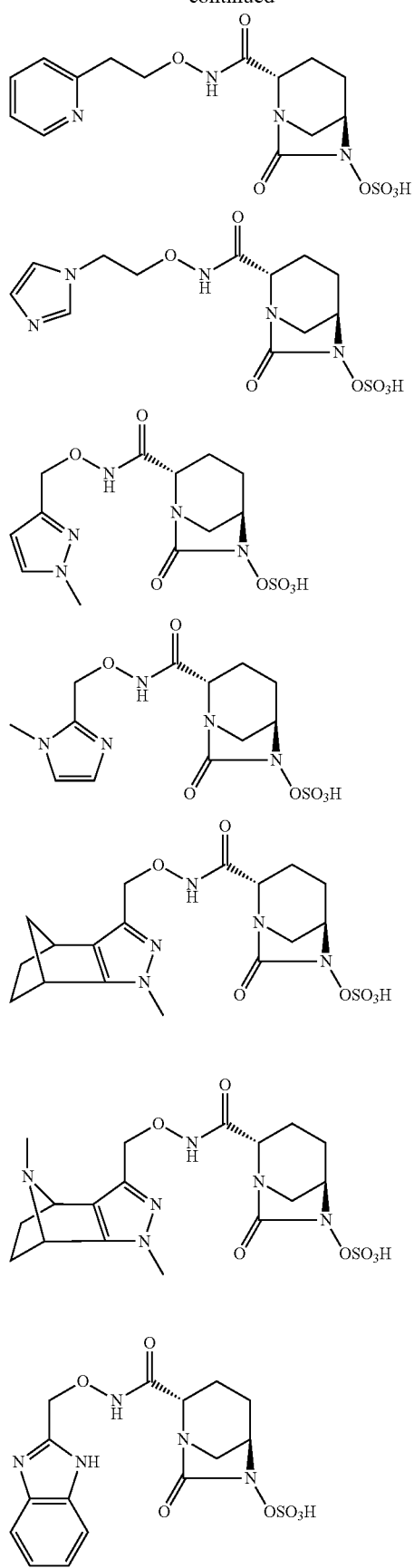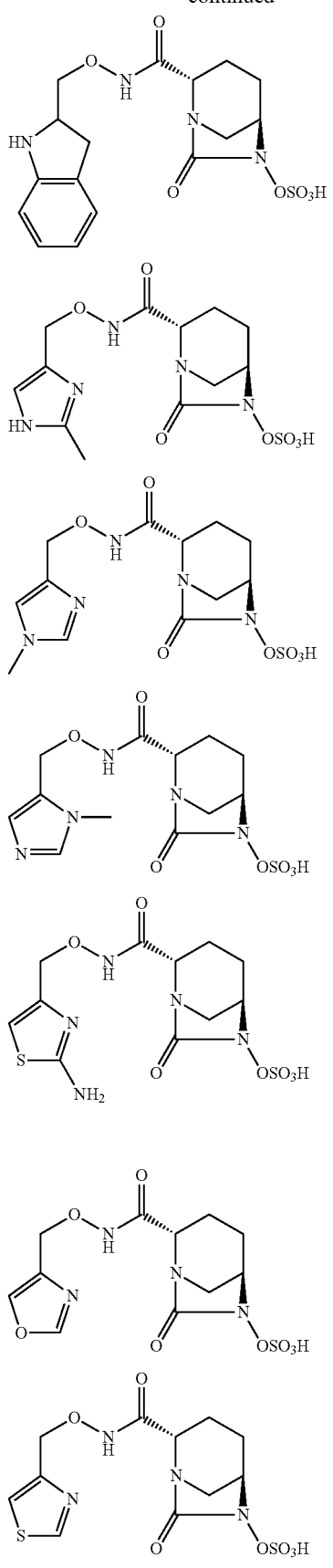

21
-continued
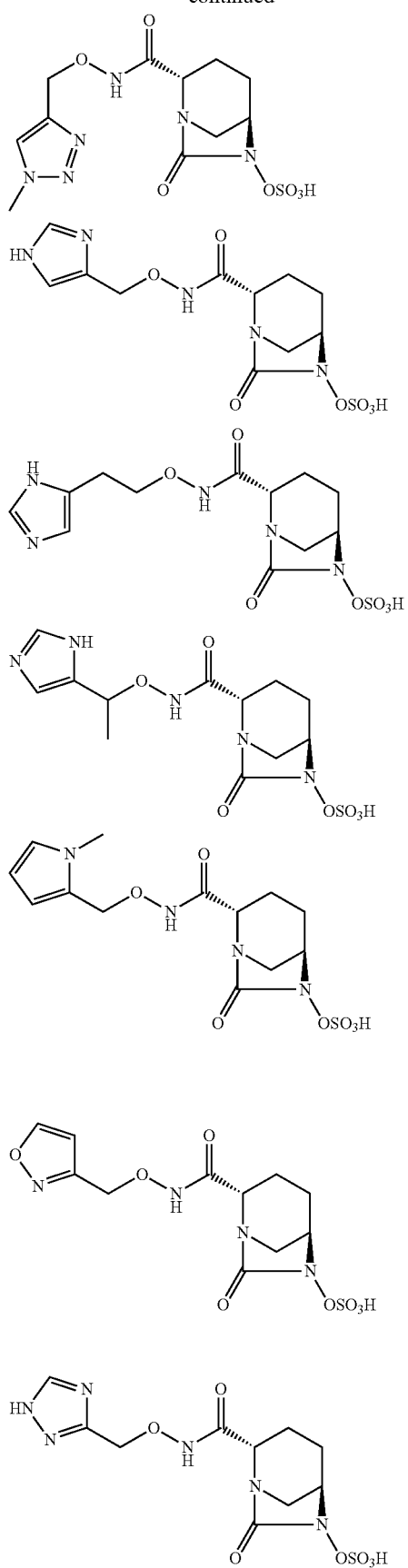
22
-continued
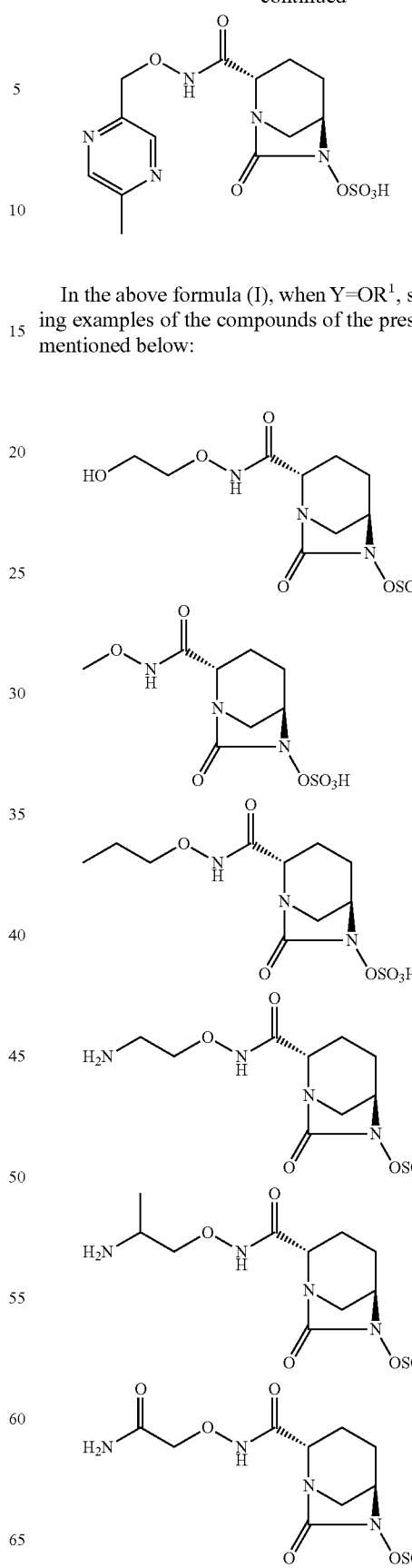
In the above formula (I), when Y=OR¹, several non-limiting examples of the compounds of the present invention are mentioned below:

23
-continued
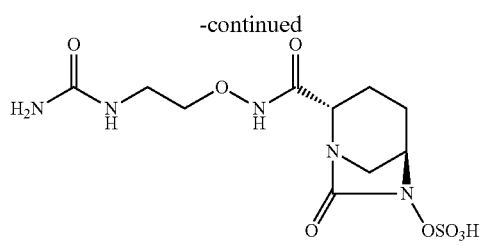
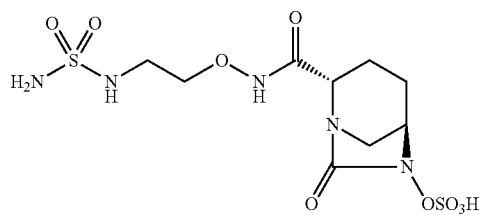
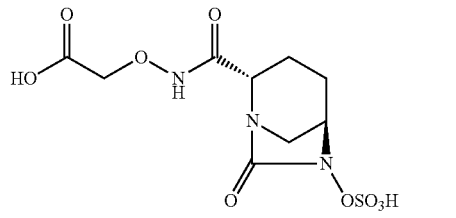
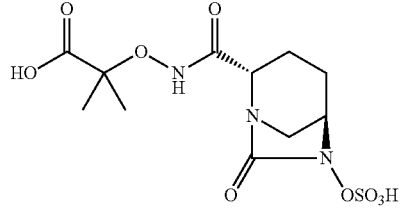
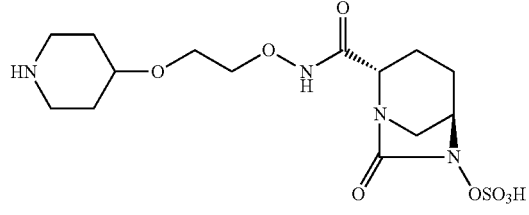
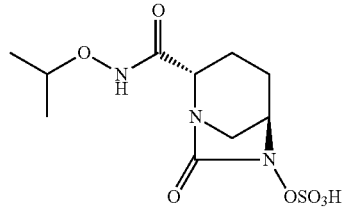
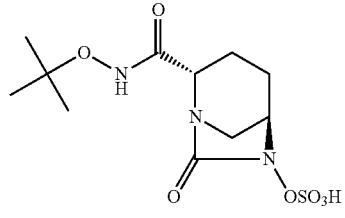
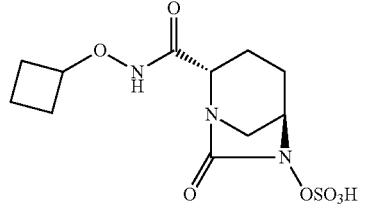
24
-continued
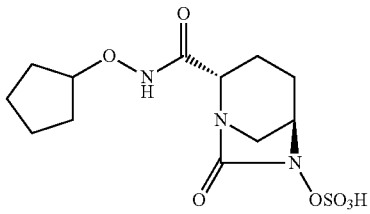
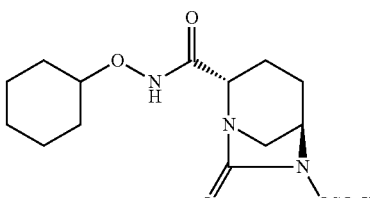
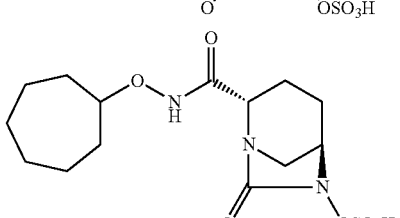
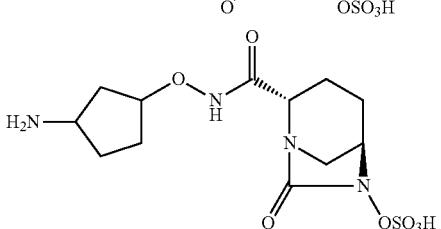
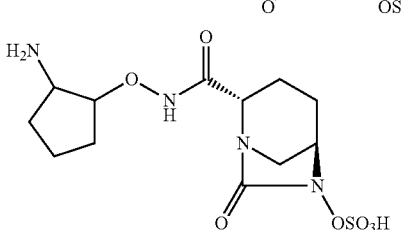
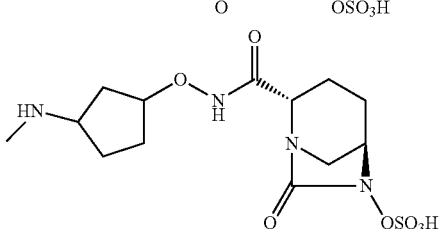
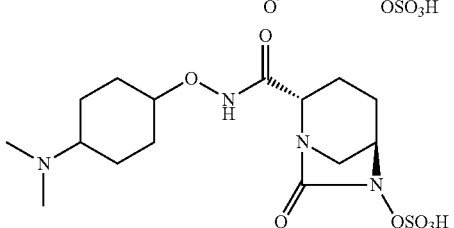
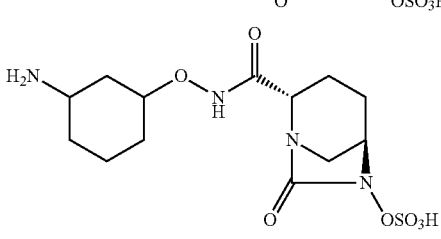

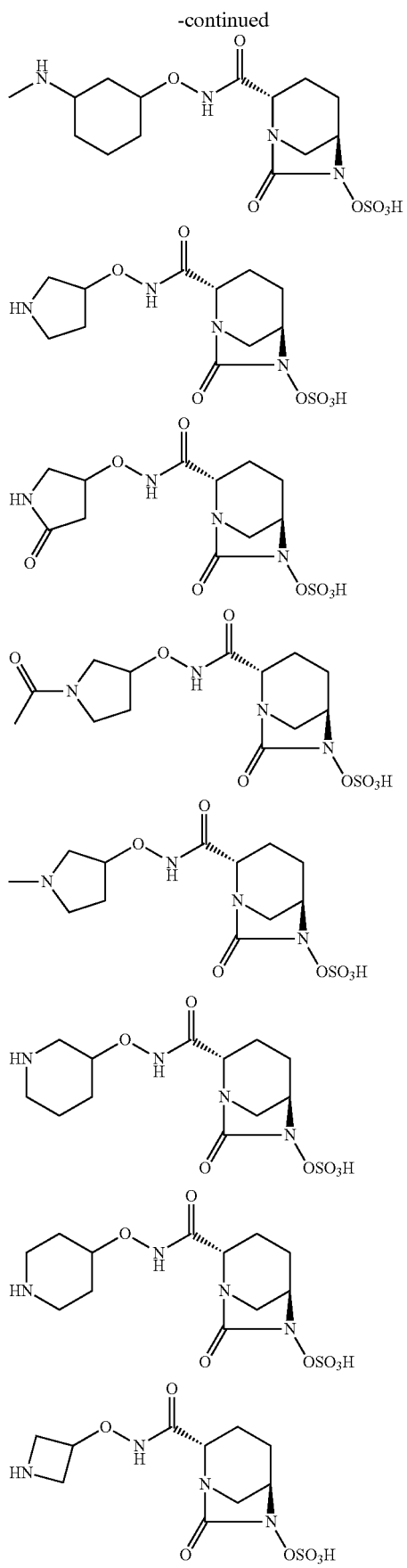
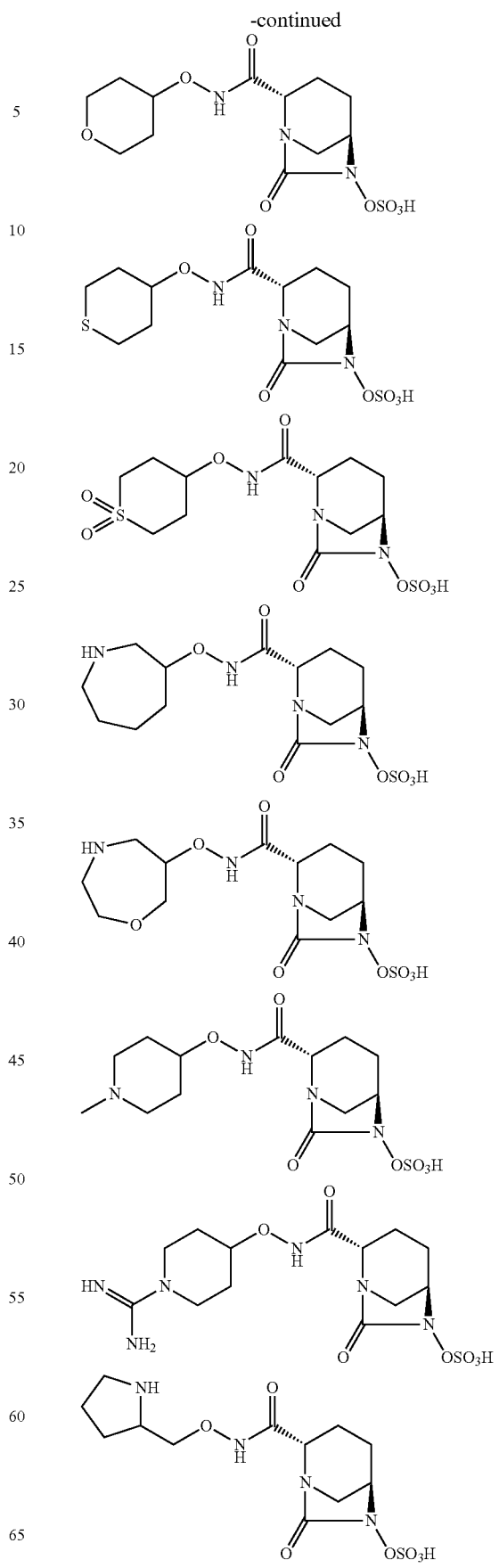

27
-continued
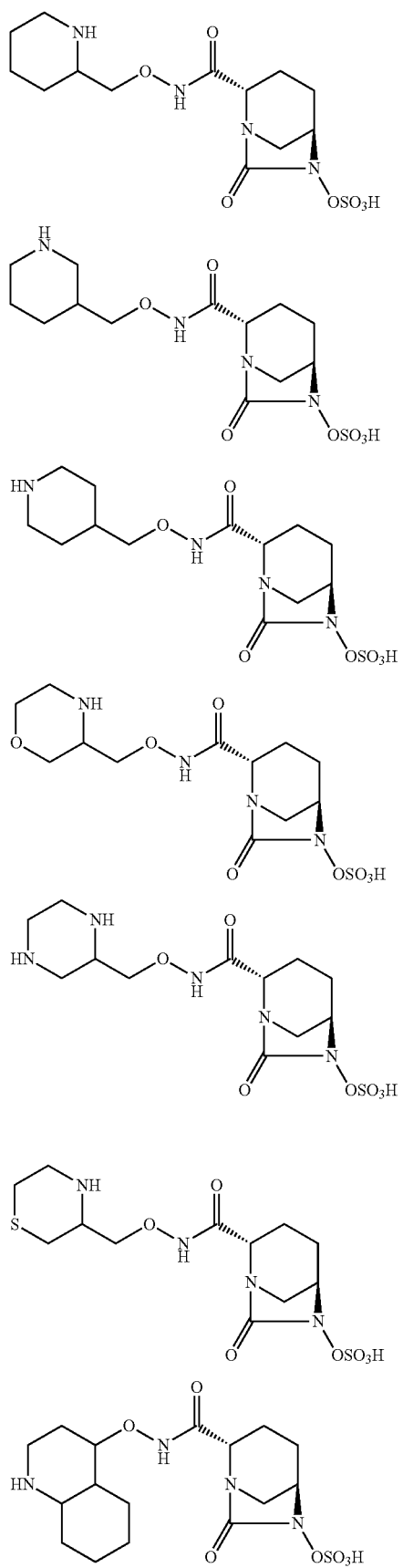
28
-continued
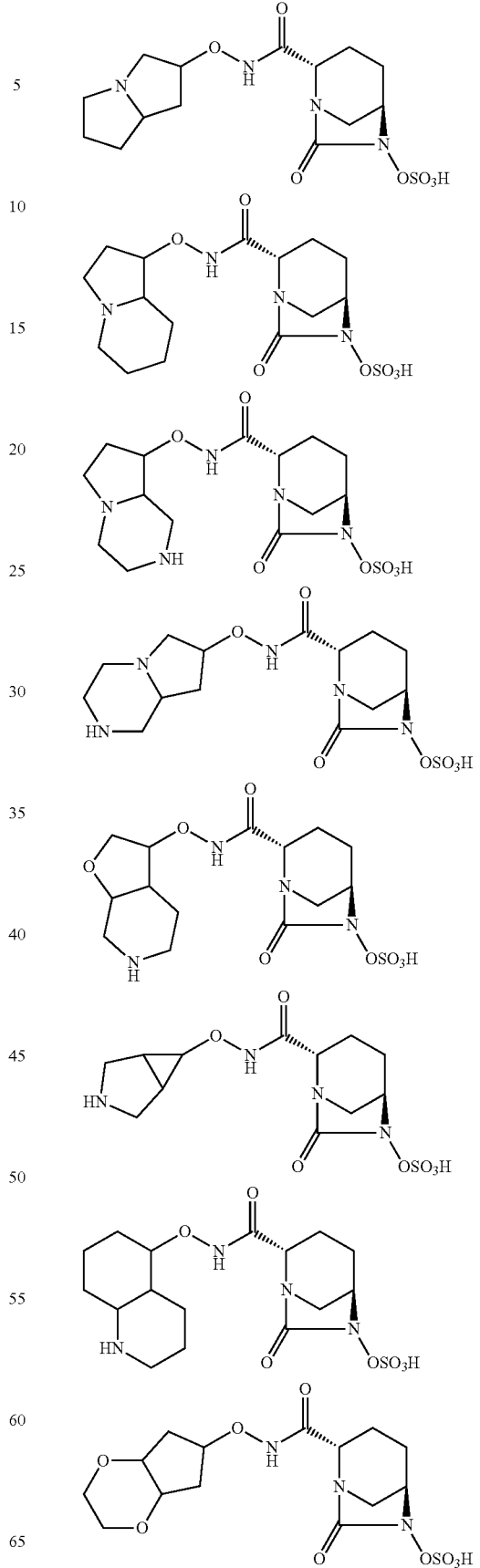

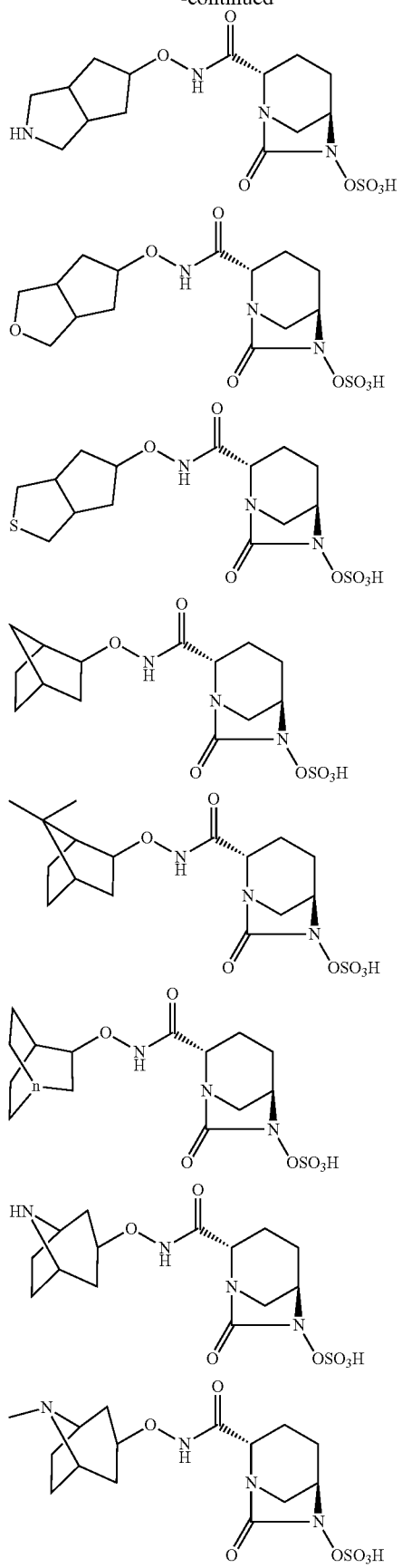
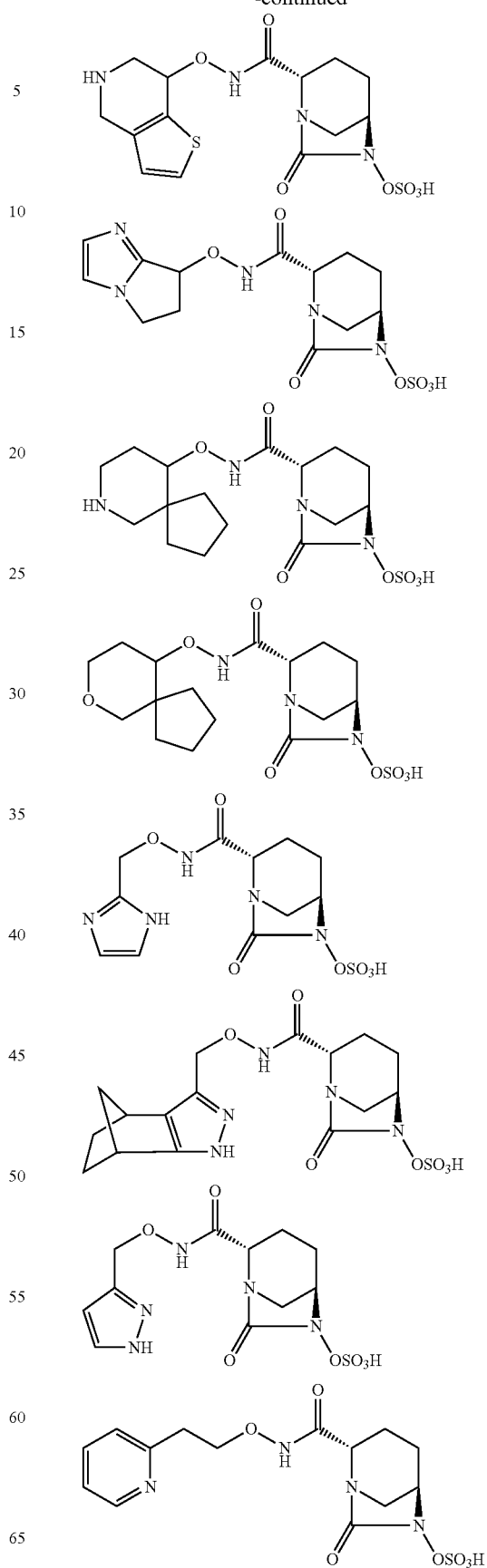

31
-continued

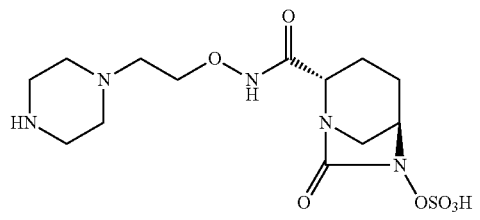
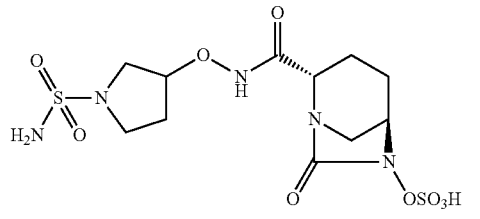
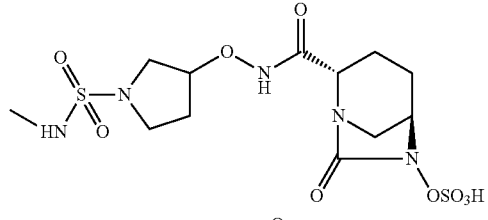
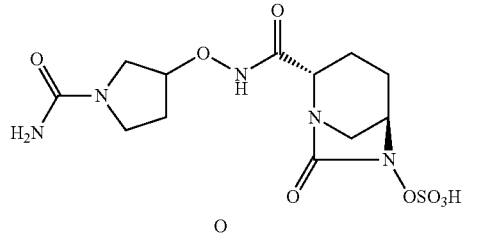
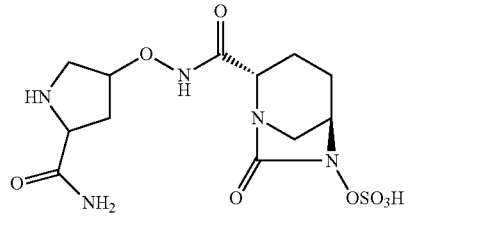
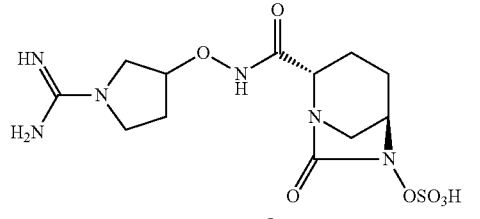
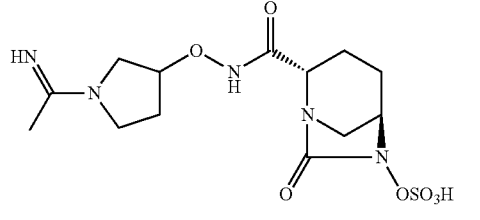
32
-continued
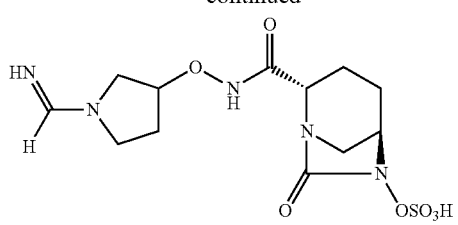
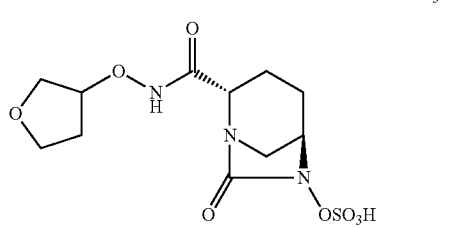
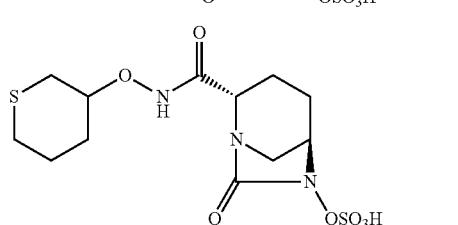
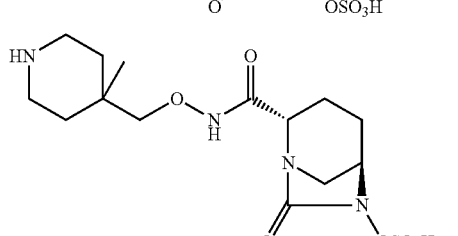
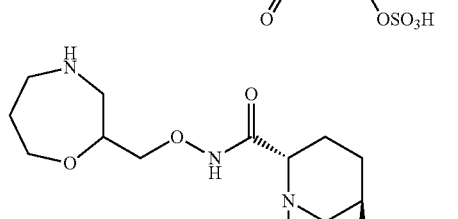
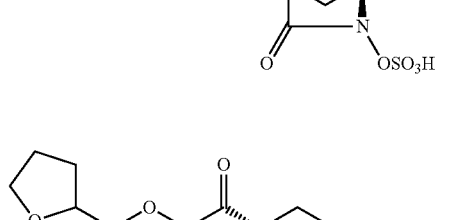
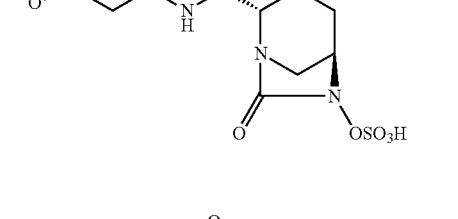
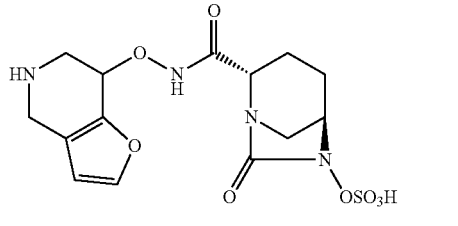

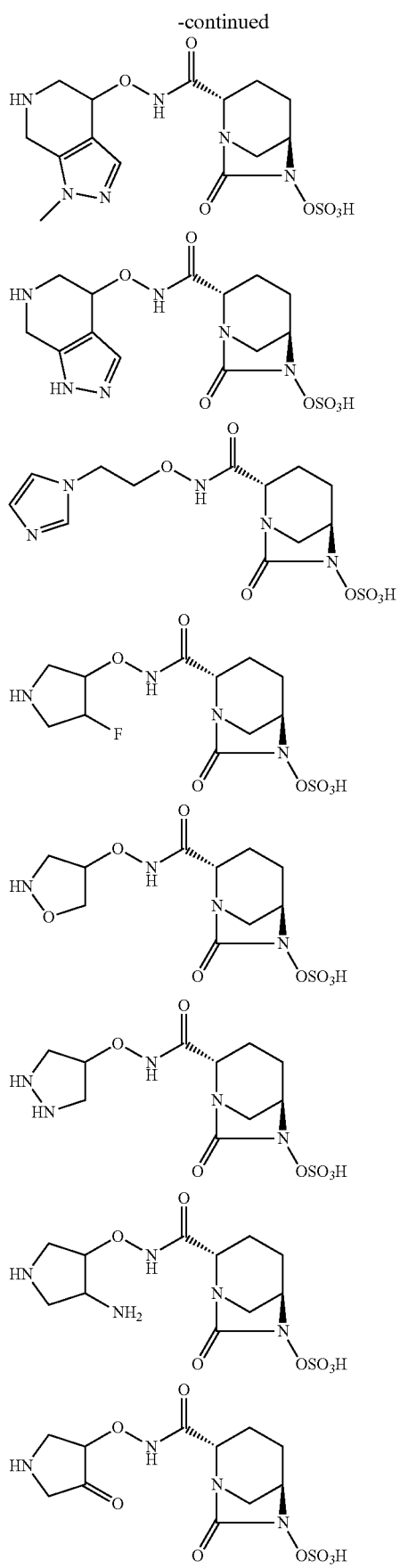

35
-continued
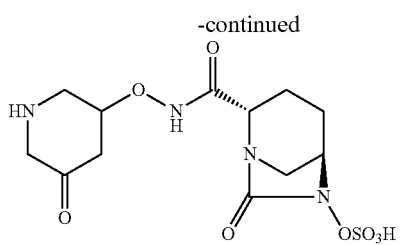
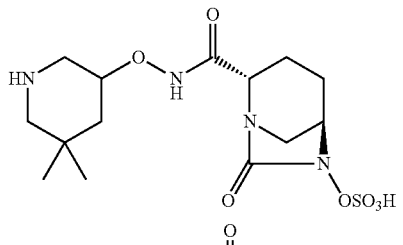
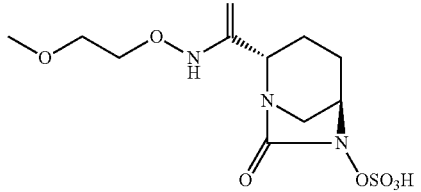
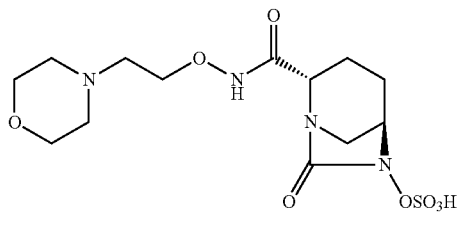
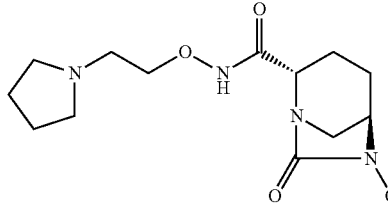
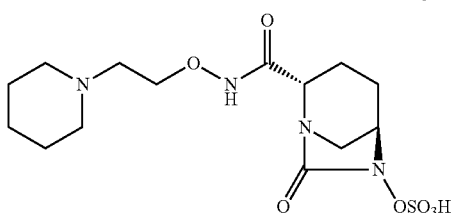
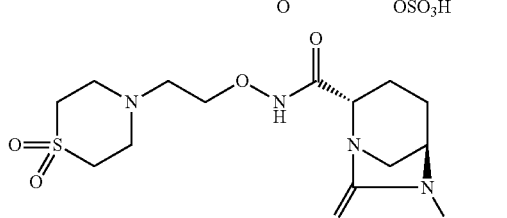
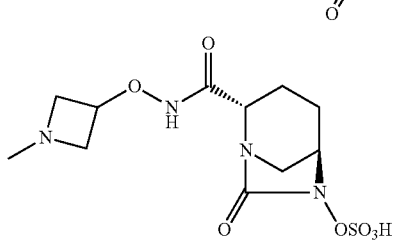
36
-continued
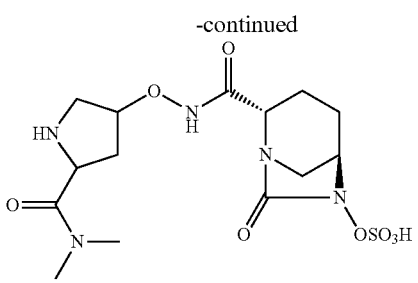
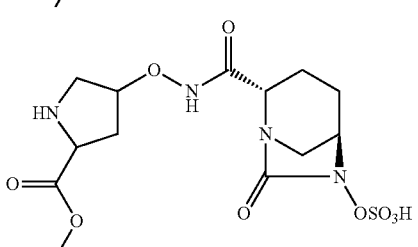
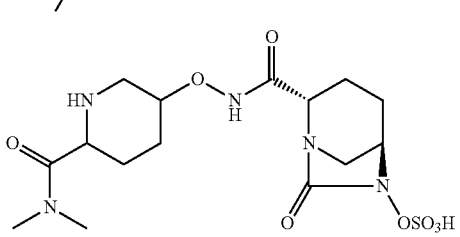

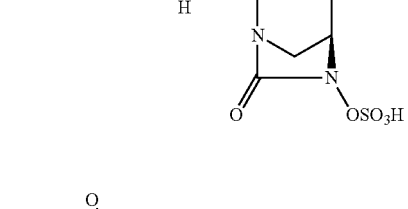
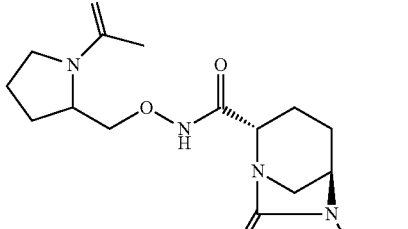
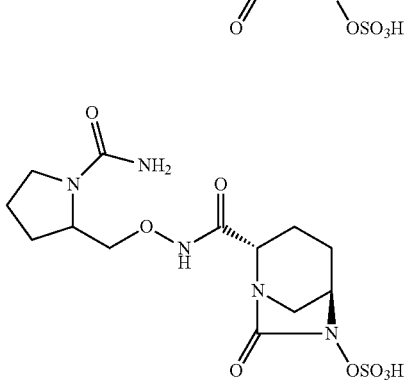

37
-continued
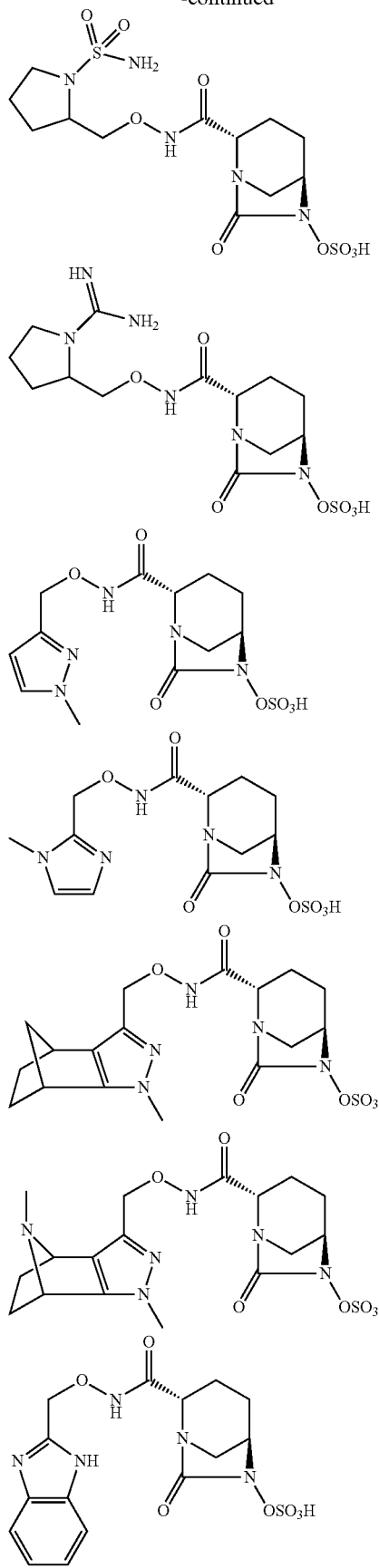
38
-continued
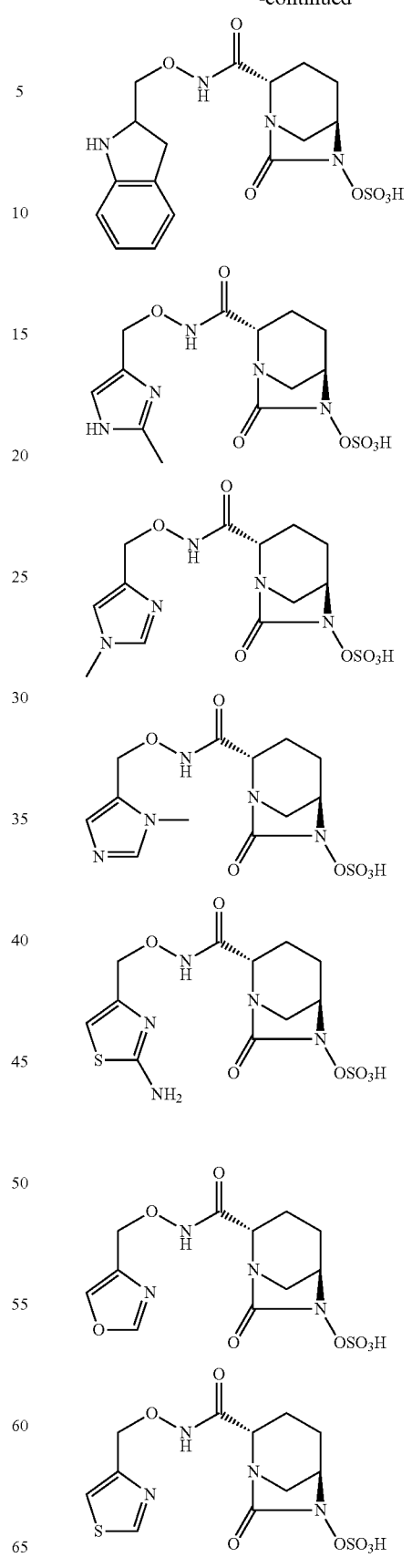

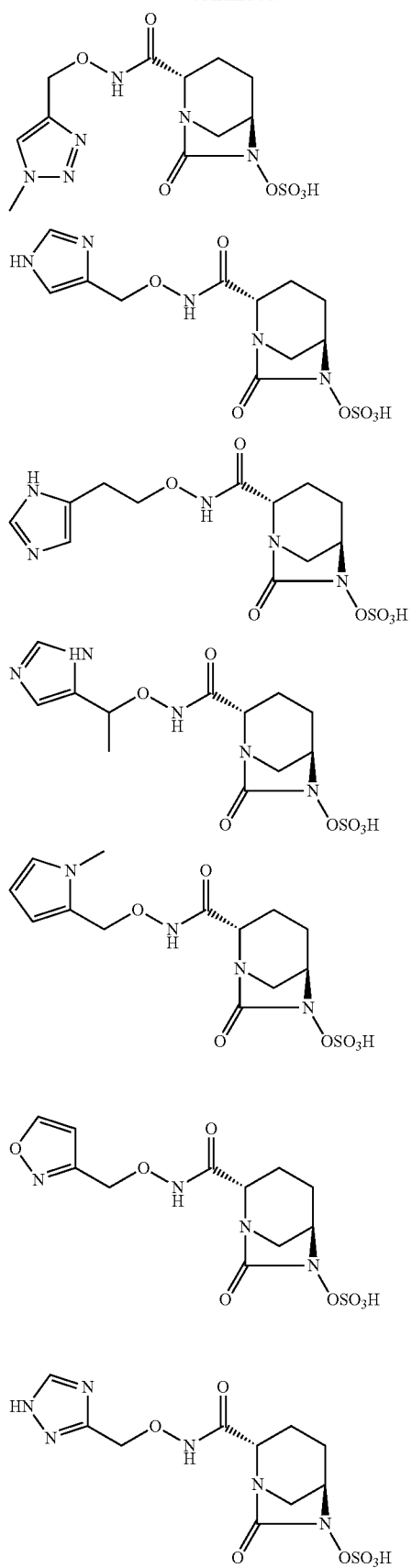

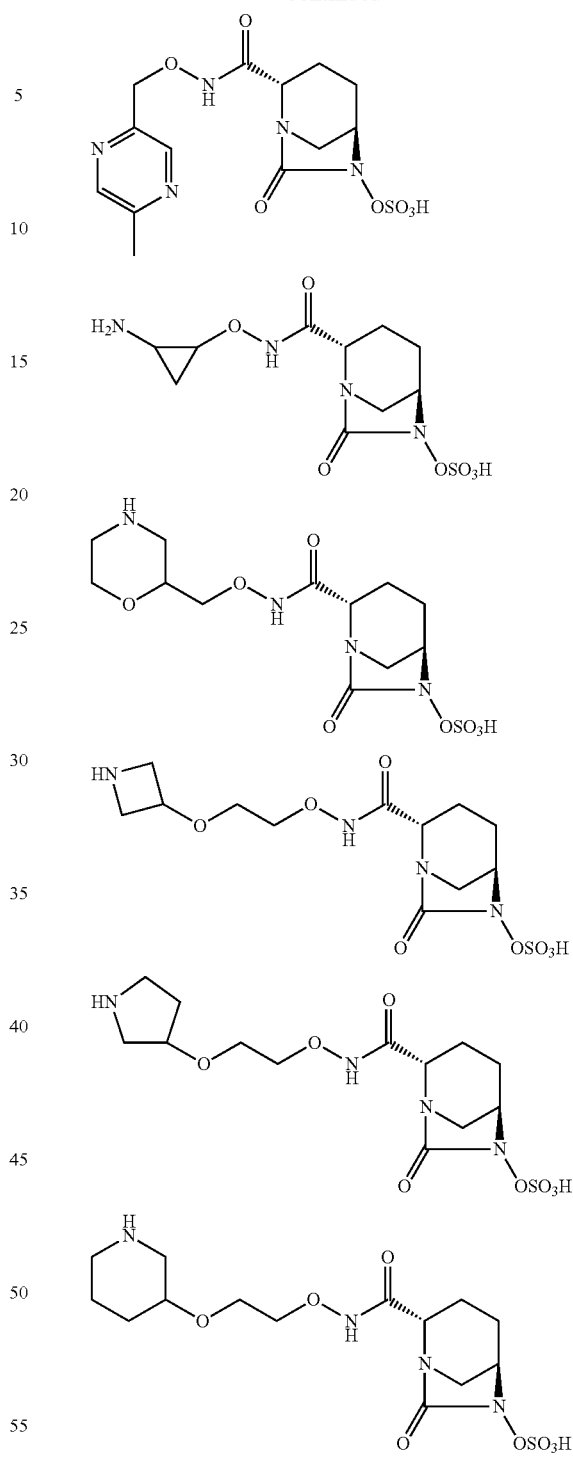

In another embodiment, in the formula (I), Y is $NR^2R^3$.

Wherein, $R^2$ is hydrogen, optionally substituted $C_{1-6}$ lower alkyl, even more preferably $R^2$ is hydrogen;

In the formula (I), when Y=$NR^2R^3$; $R^3$ is a radical selected from any of the following groups:

(1) $C_{1-6}$ straight or branched chain alkyl which is optionally substituted. Non-limiting examples of such compounds are:

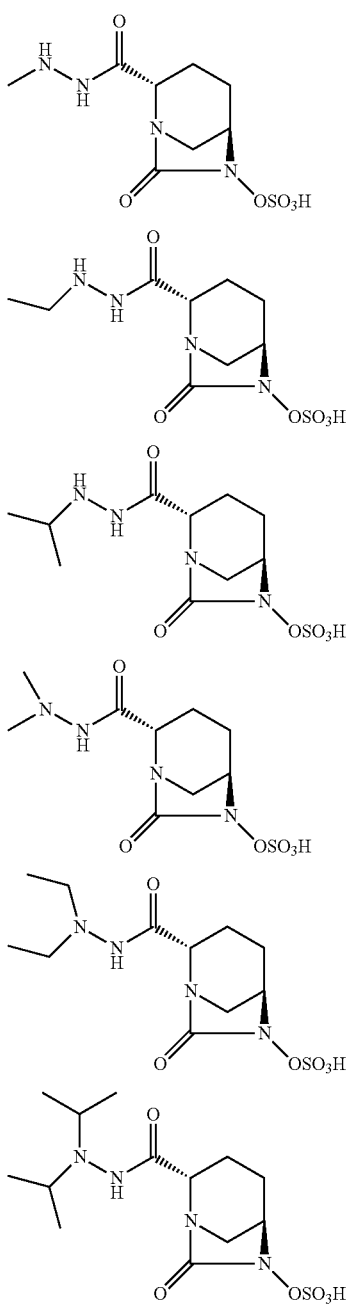

(2) C_{3-7} cycloalkyl which is optionally substituted. Non-limiting examples of such compounds are:

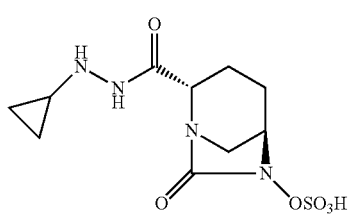

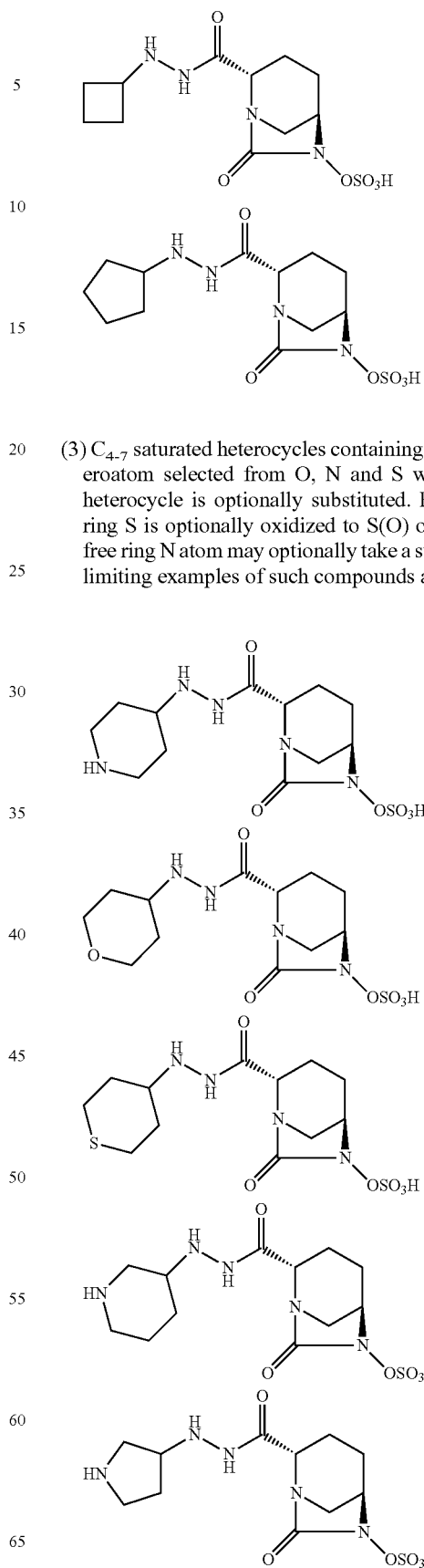

(3) C_{4-7} saturated heterocycles containing at least one heteroatom selected from O, N and S wherein the said heterocycle is optionally substituted. Furthermore the ring S is optionally oxidized to S(O) or S(O)$_2$ and the free ring N atom may optionally take a substituent. Non-limiting examples of such compounds are:

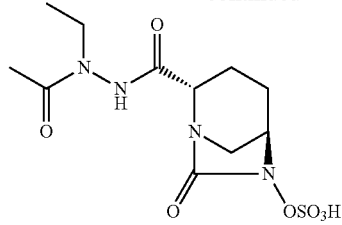
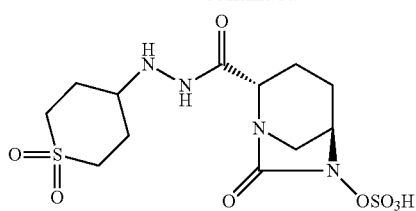
(4) C$_{1-6}$ straight or branched chain alkyl carbonyl which is optionally substituted. Non-limiting examples of such compounds are:
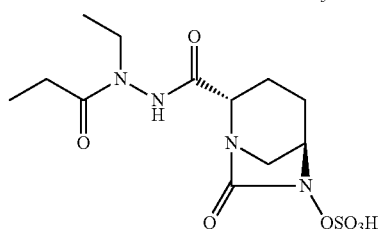
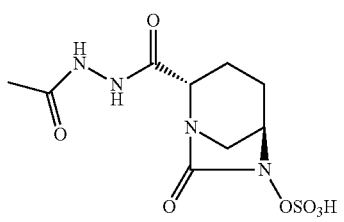
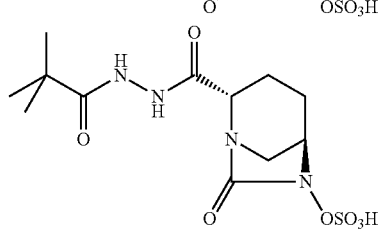
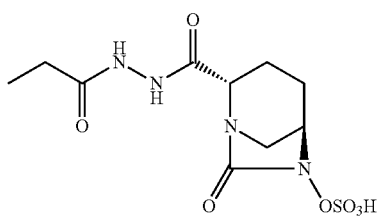
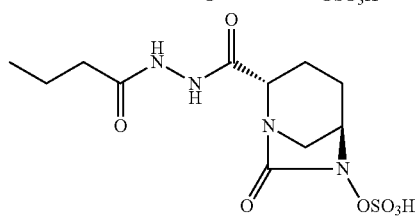
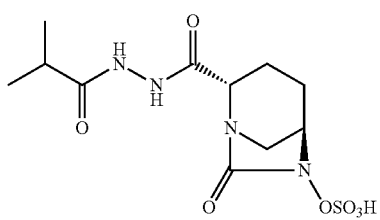
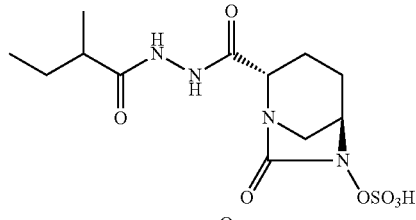
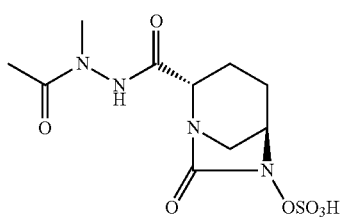
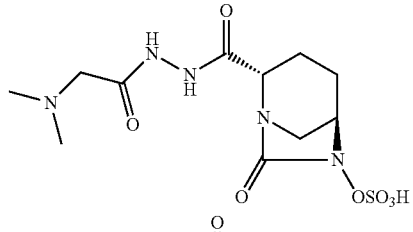
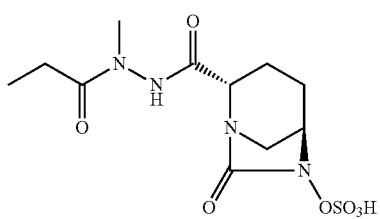
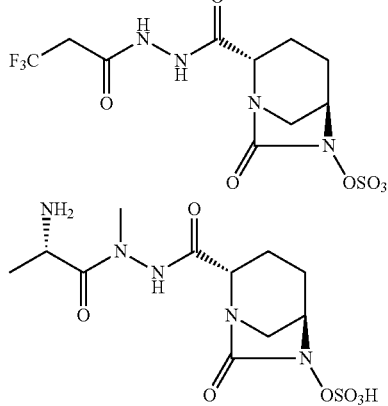
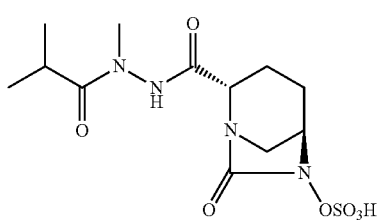

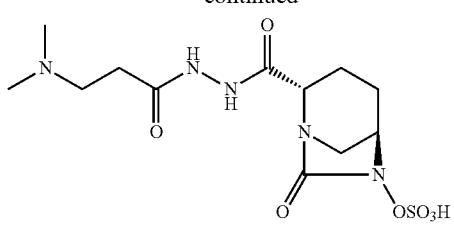
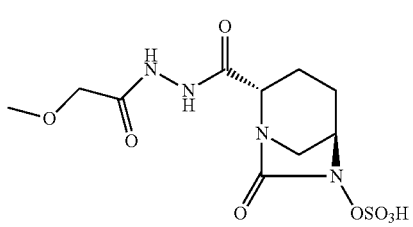
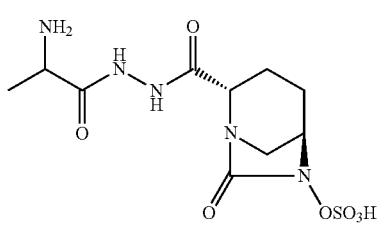
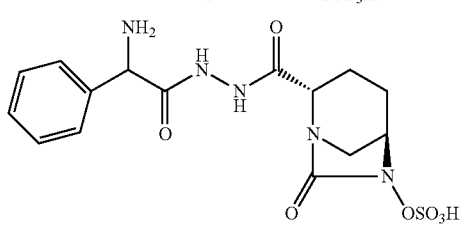
(5) $C_{3-7}$ cycloalkyl carbonyl which is optionally substituted. Non-limiting examples of such compounds are:
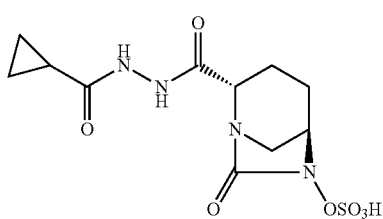
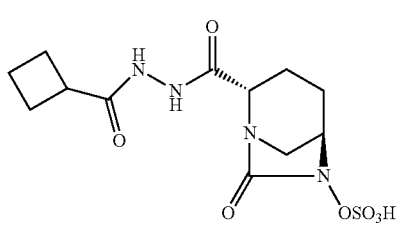
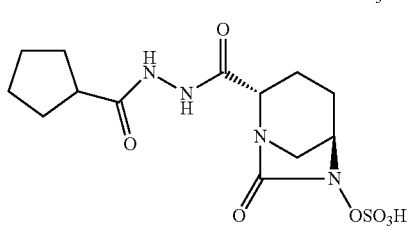
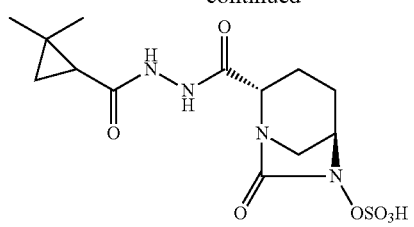
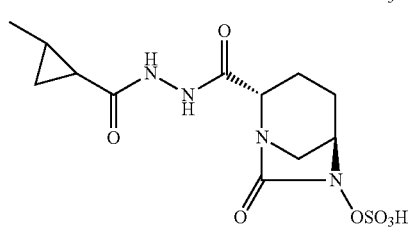
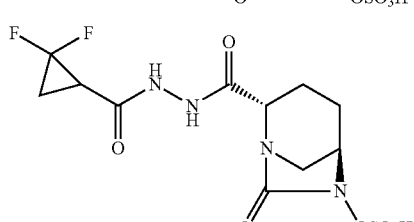
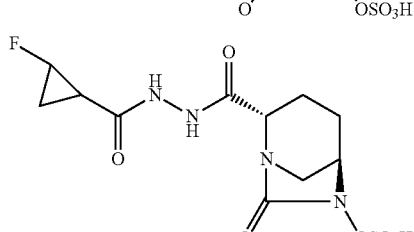
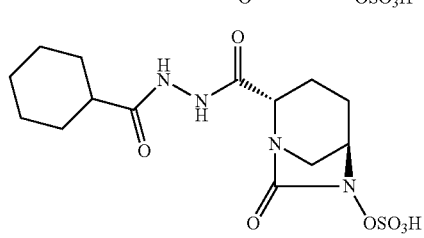
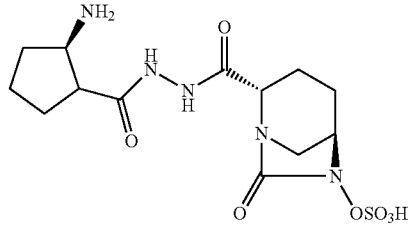
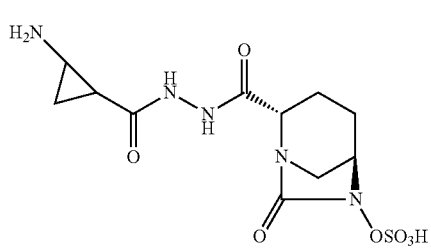

-continued
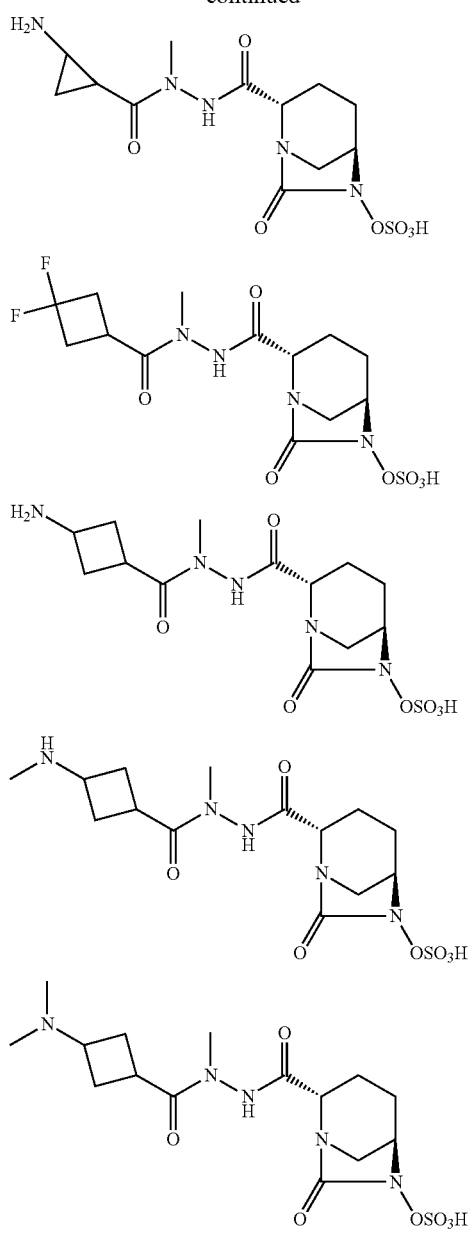
(6) C$_{4-7}$ membered saturated heterocyclyl carbonyl containing at least one heteroatom selected from O, N and S wherein the said heterocycle is optionally substituted.
Furthermore the ring S is optionally oxidized to S(O) or S(O)$_2$ and the free ring N atom may optionally take a substituent. Non-limiting examples of such compounds are:
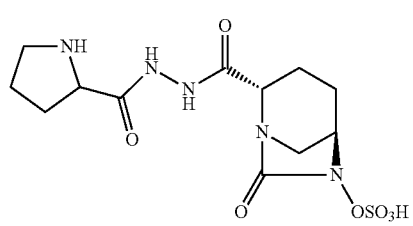
-continued
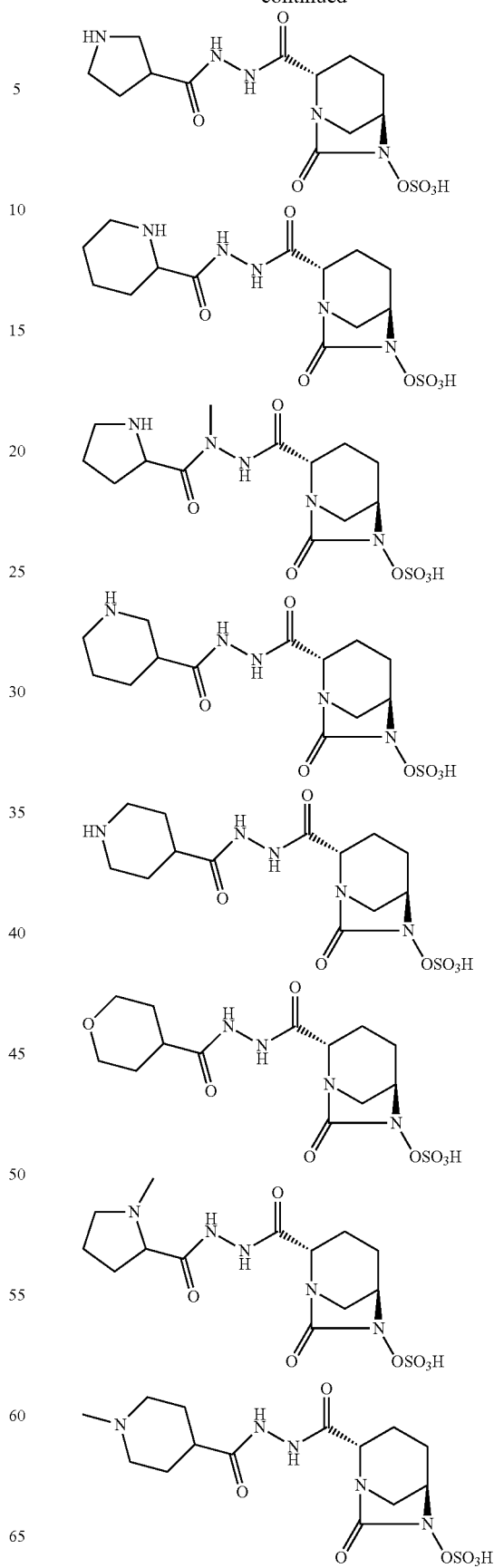

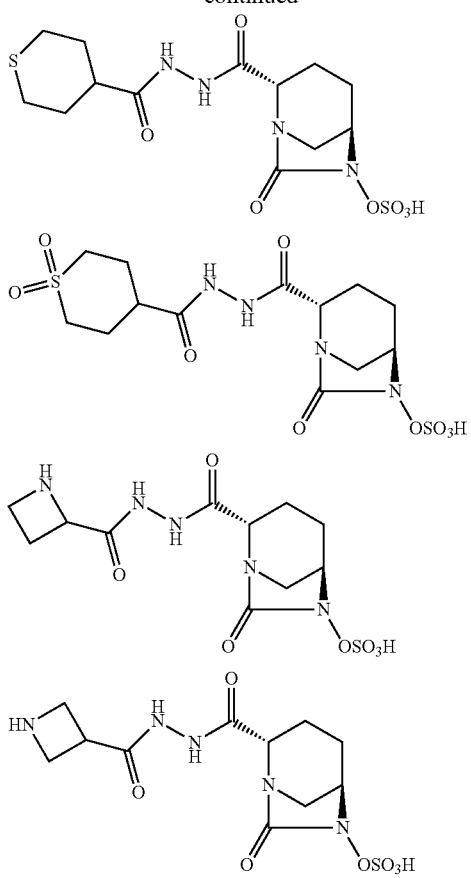
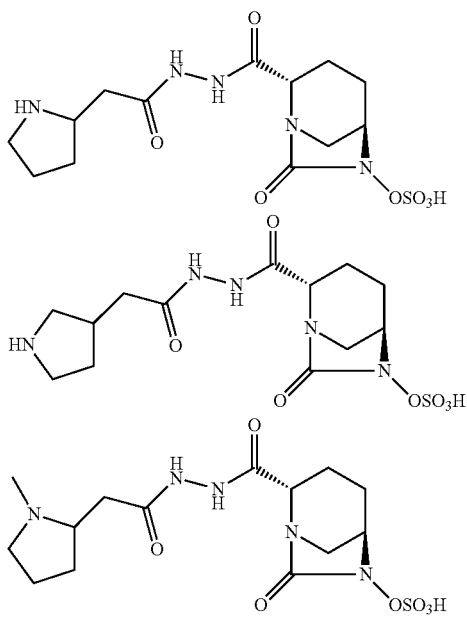
(7) $C_{3-7}$ membered saturated heterocyclyl ($C_{1-6}$) alkyl carbonyl wherein the said heterocycle has the same definition as defined in (6). The free ring N atom may optionally take a substituent. Non-limiting examples of such compounds are:
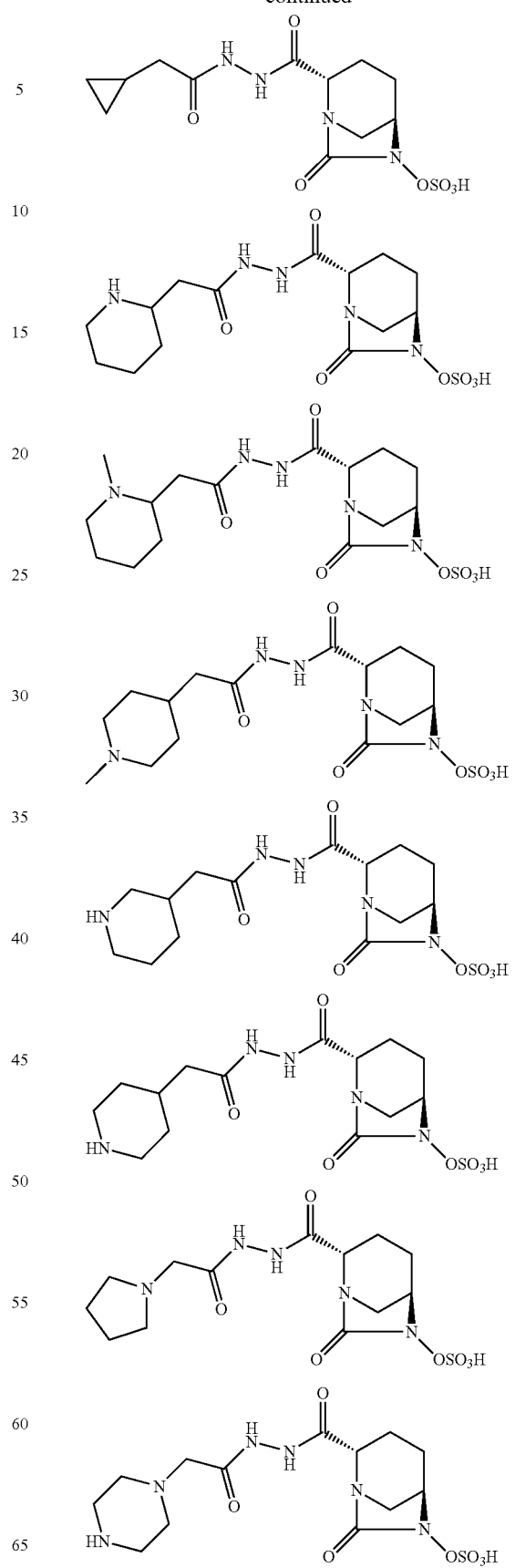

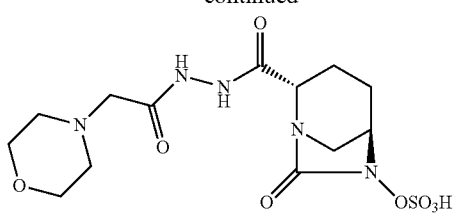

(8) $C_{6-10}$ aryl carbonyl which is optionally substituted. Non-limiting examples of such compounds are:

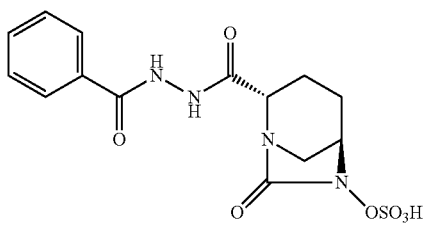

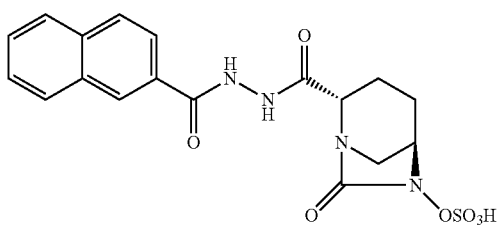

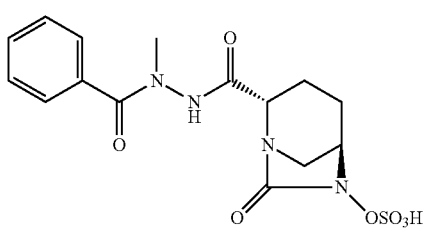

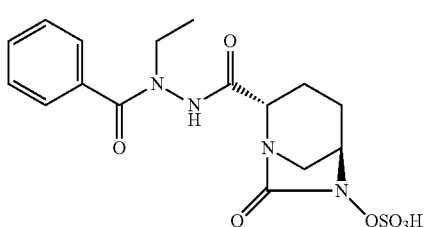

(9) $C_{6-10}$ aryl ($C_{1-6}$) alkyl carbonyl which is optionally substituted. Non-limiting examples of such compounds are:

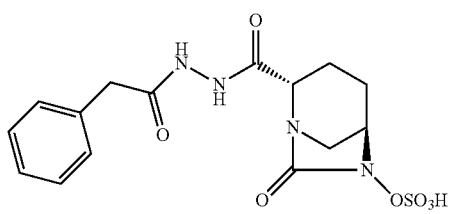

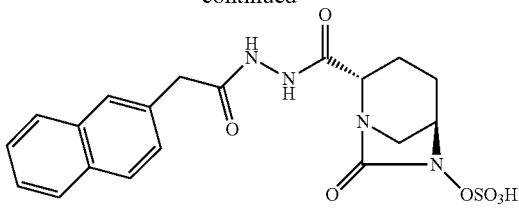

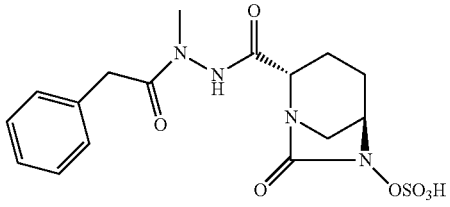

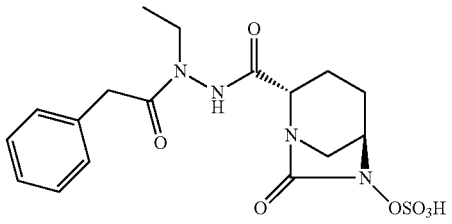

(10) $C_{5-6}$ membered heteroaryl carbonyl containing at least one heteroatom selected from O, S and N wherein the heteroaryl is optionally substituted. Non-limiting examples of such compounds are:

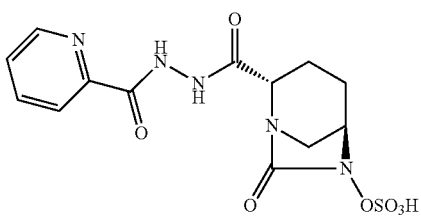

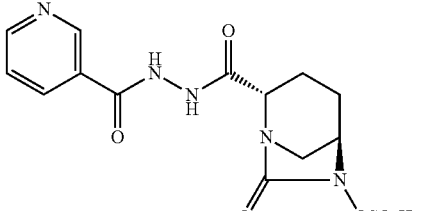

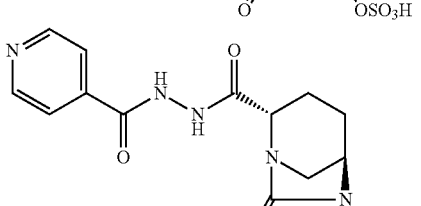

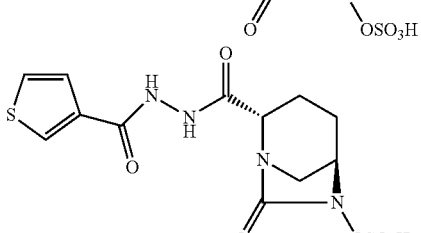

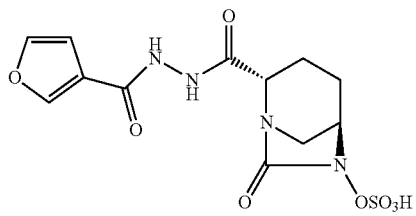
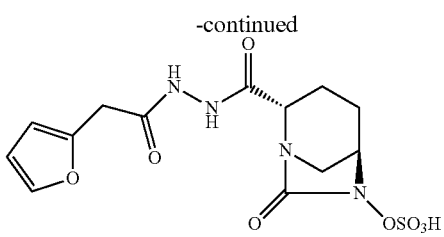
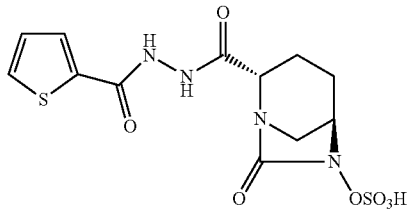
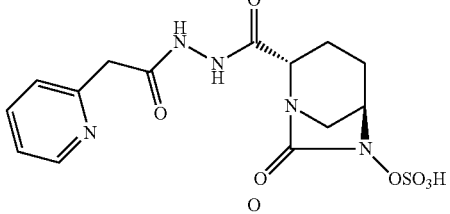
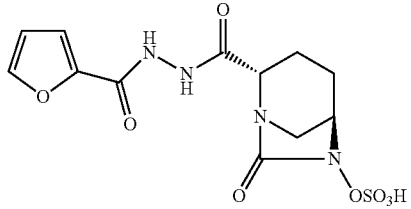
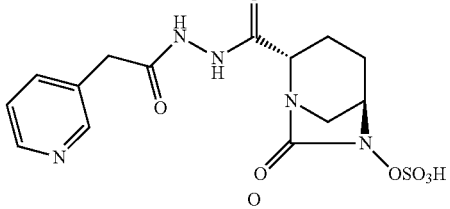
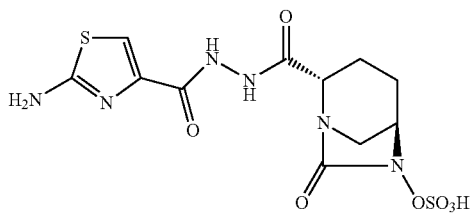
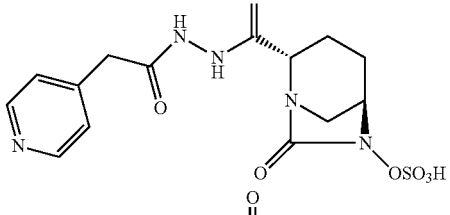
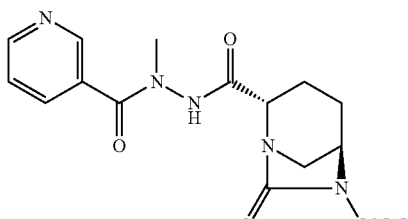
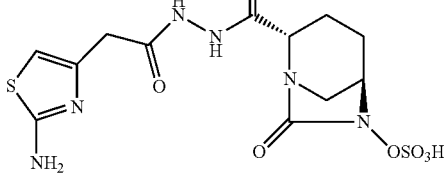
(11) $C_{5-6}$ heteroaryl $(C_{1-6})$ alkyl carbonyl wherein the said heteroaryl has the same definition as defined in (10). Non-limiting examples of such compounds are:
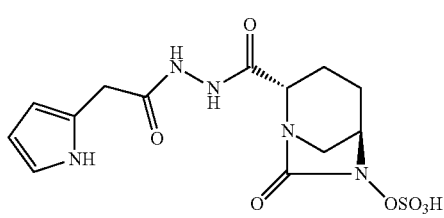
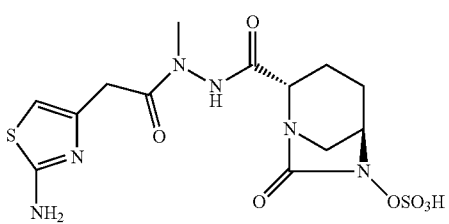
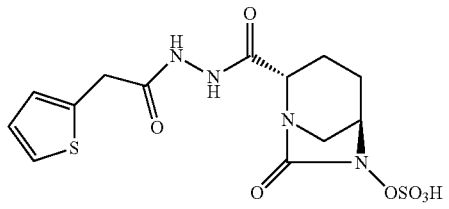
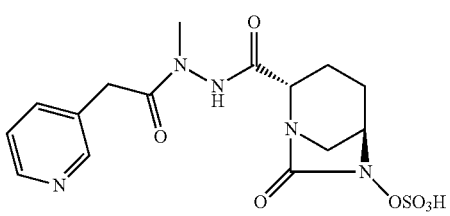
(12) In the formula (I), when $Y=NR^2R^3$; $R^3$ may also be selected from the following groups like $CF_3CO-$, $CH_3SO_2-$, $NH_2CO-$, $NH_2SO_2-$. Non-limiting examples of such compounds are:

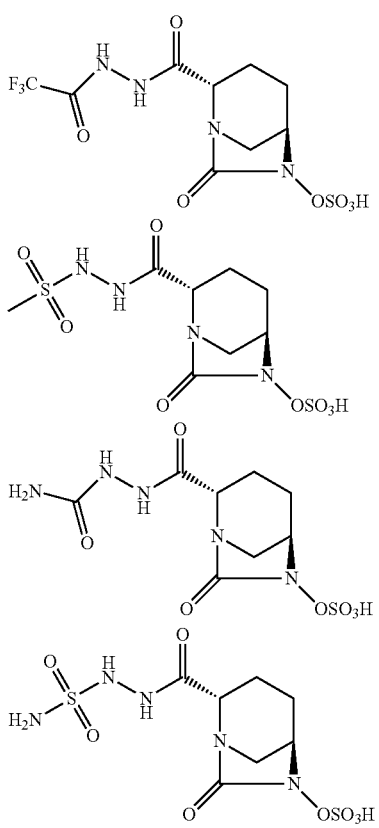

(13) C$_{6-10}$ aryl which is optionally substituted. Non-limiting examples of such compounds are:

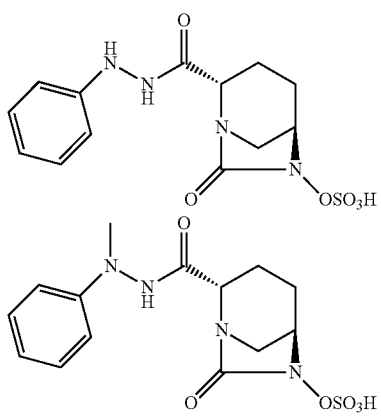

(14) C$_{5-6}$ membered heteroaryl which is optionally substituted. Non-limiting examples of such compounds are:

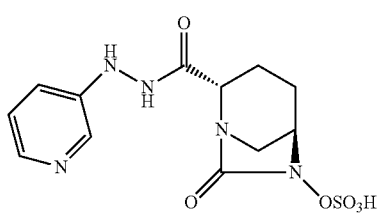

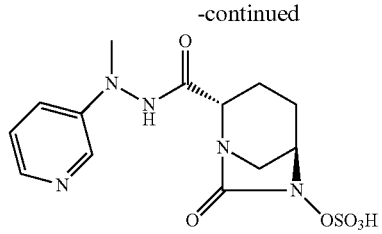

(15) In the formula (I), when Y=NR$^2$R$^3$; R$^2$ and R$^3$ together may form an optionally substituted ring system and the said ring may contain another heteroatom selected from O, N, and S. Furthermore, the ring may be optionally substituted. Non-limiting examples of such compounds are:

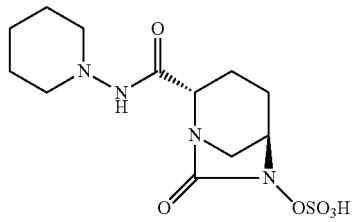

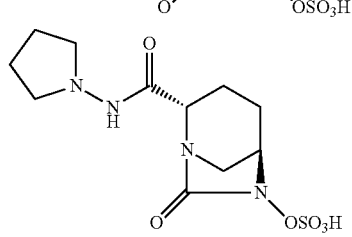

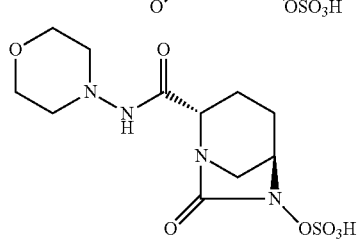

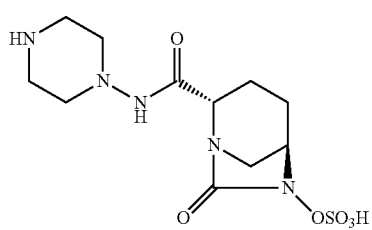

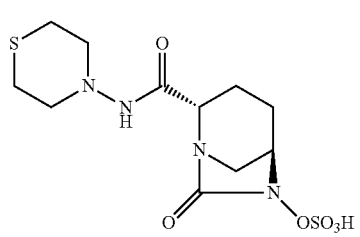

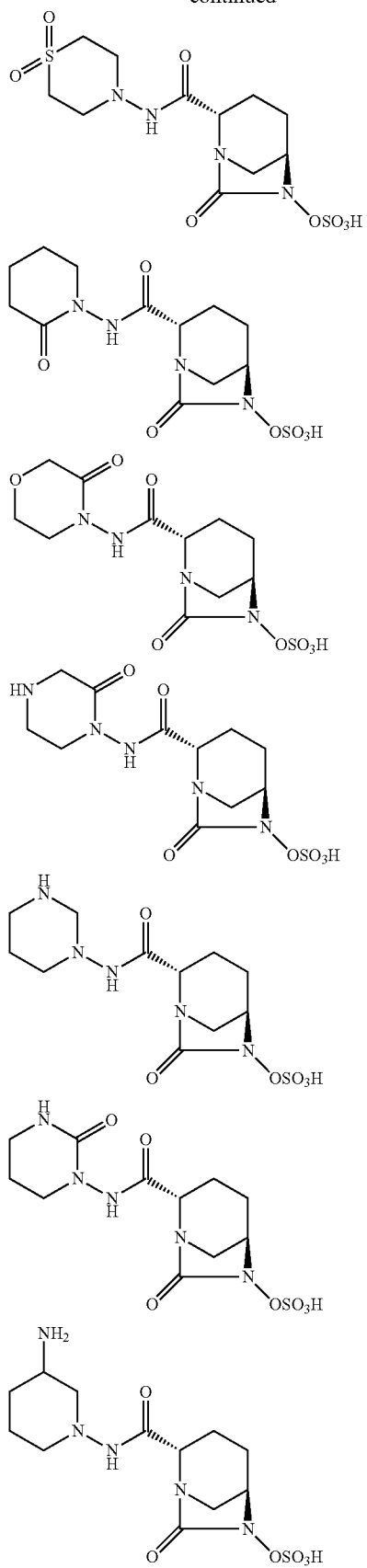
In the above formula (I), when Y=NR²R³, several non-limiting examples of such compounds of the present invention are mentioned below:
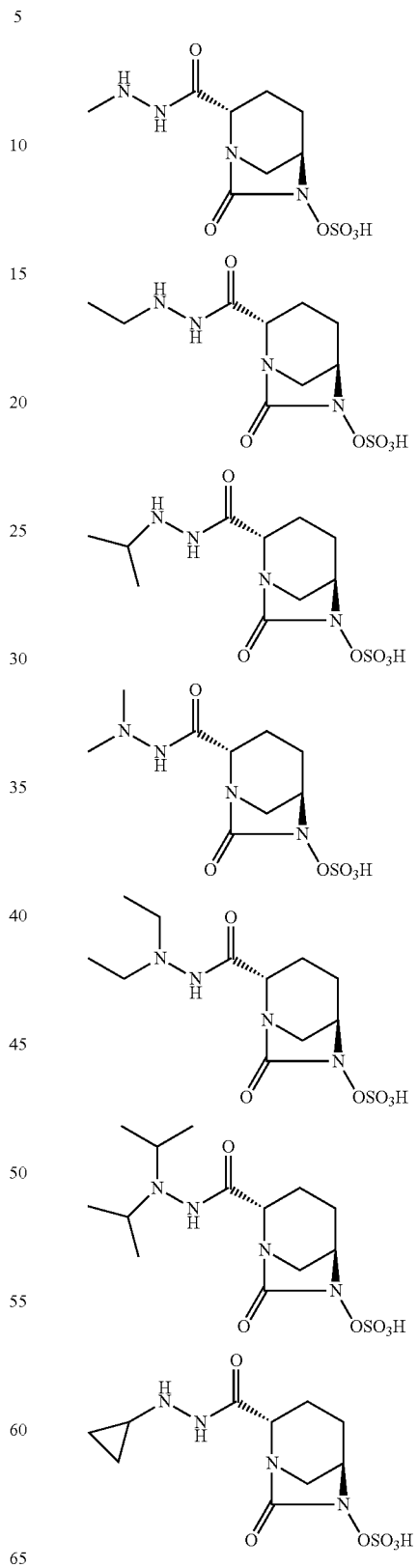

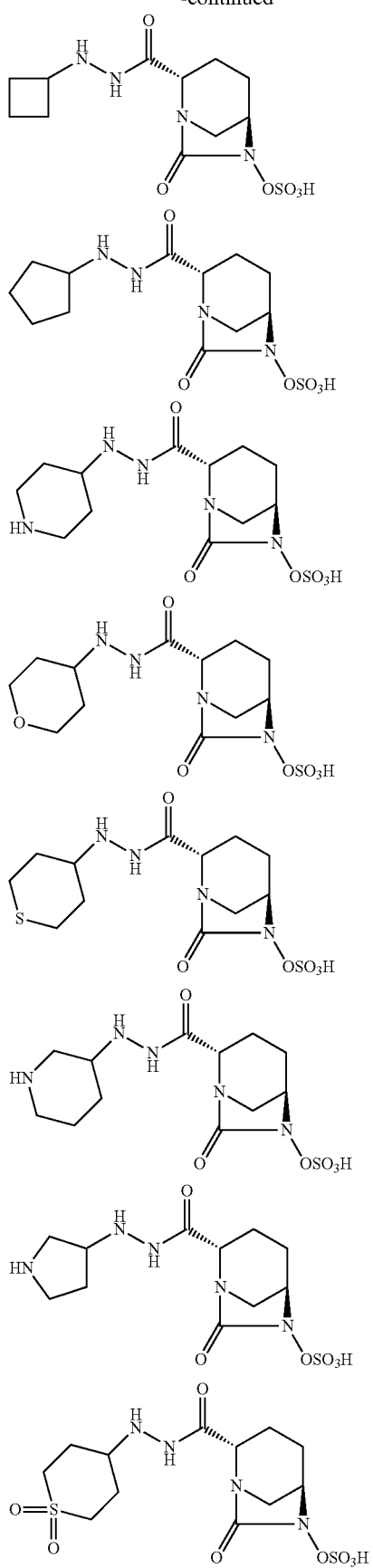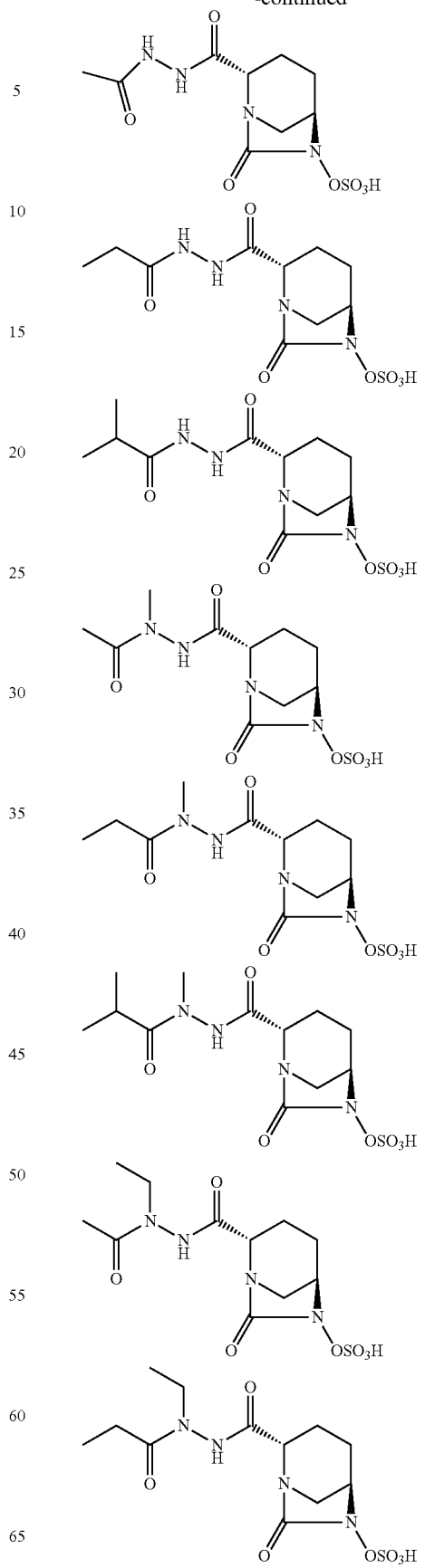

-continued
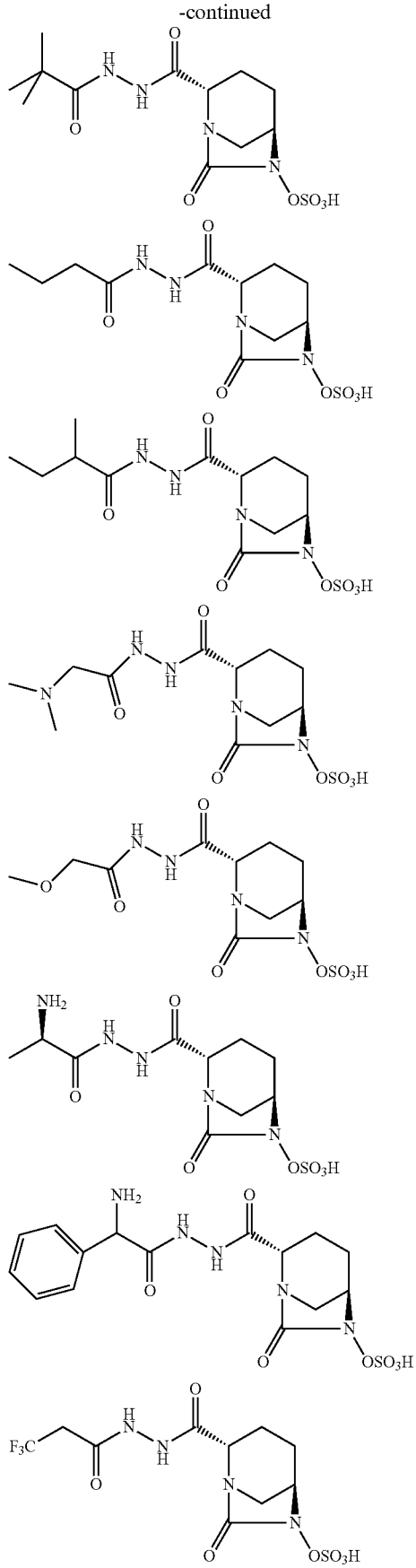
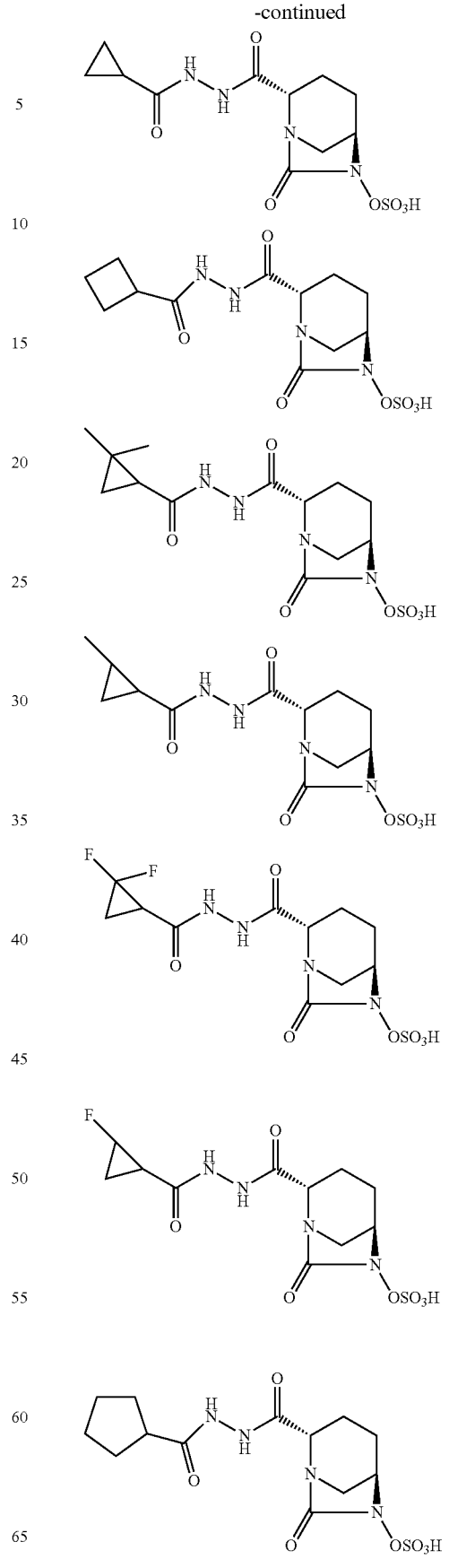

63
-continued
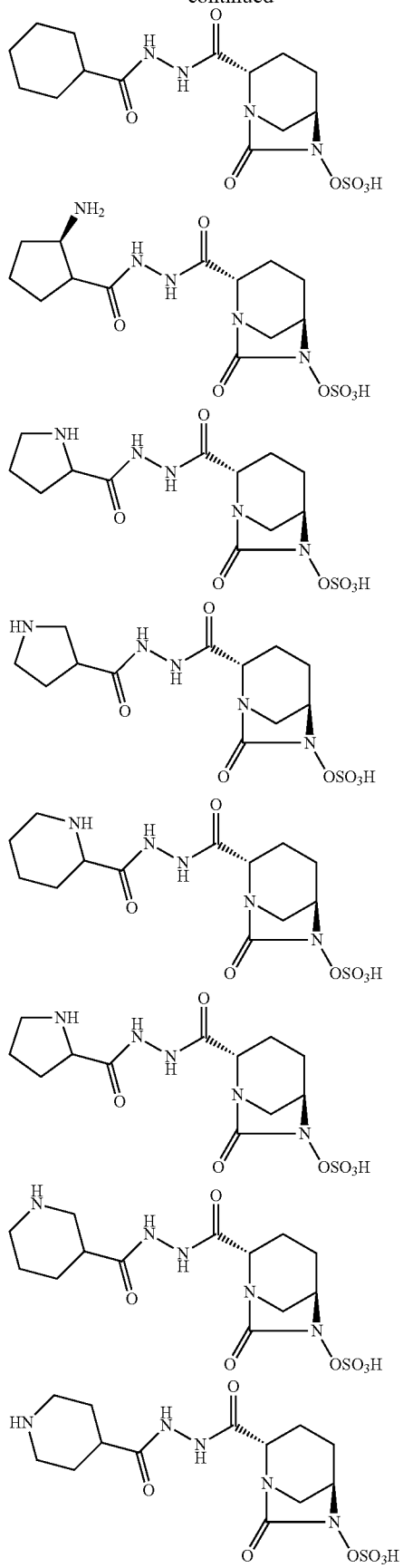
64
-continued
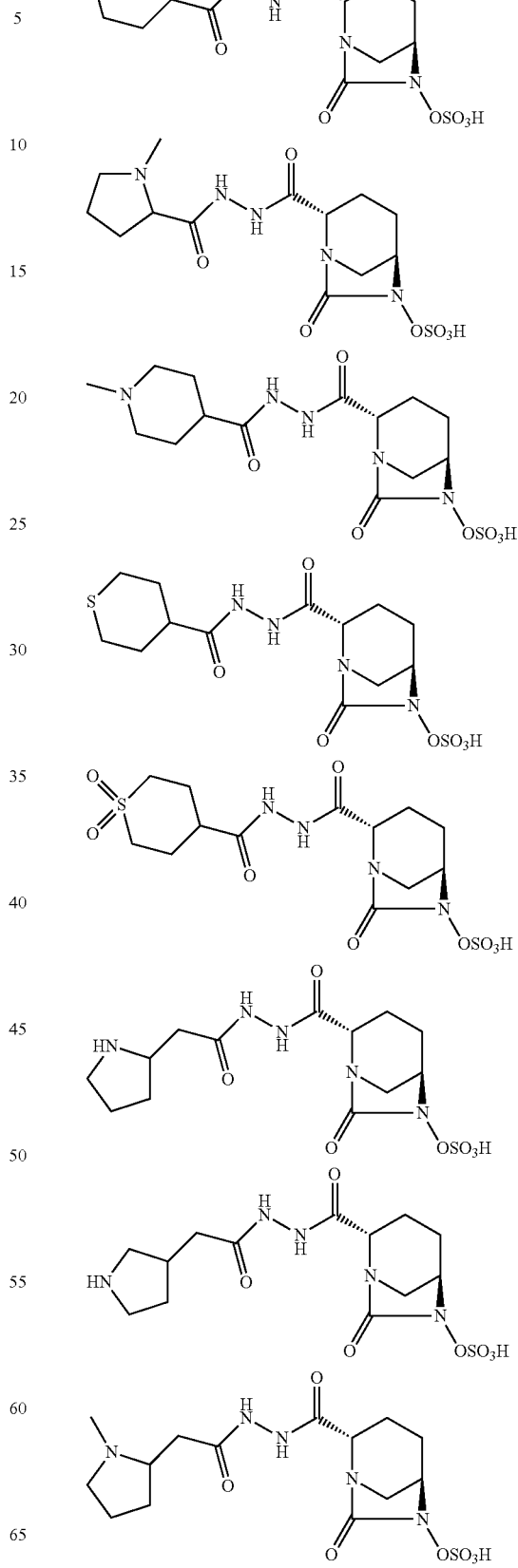

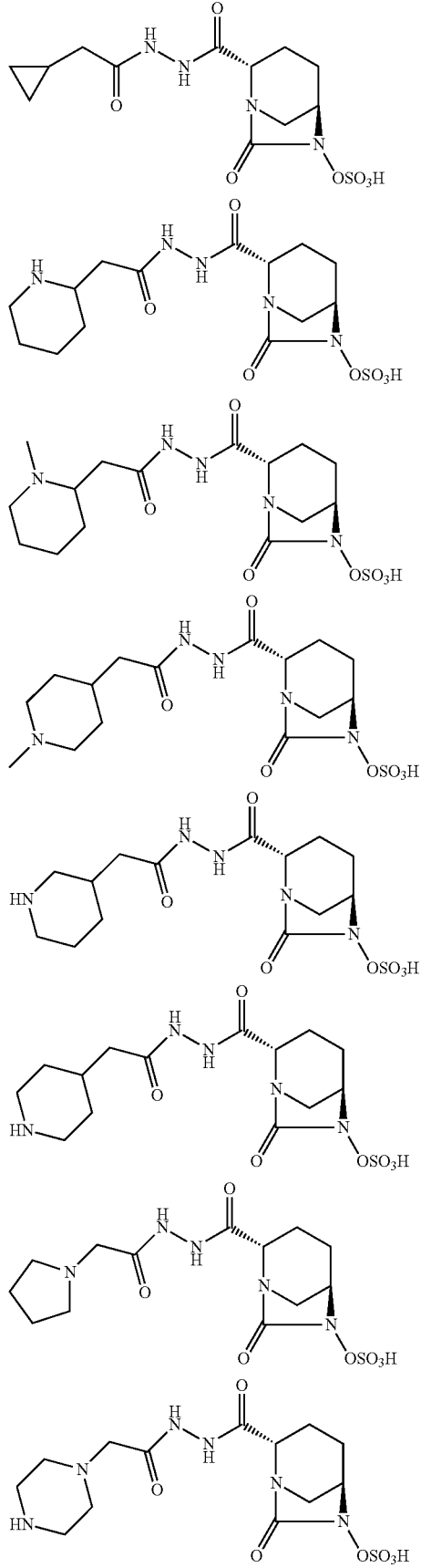
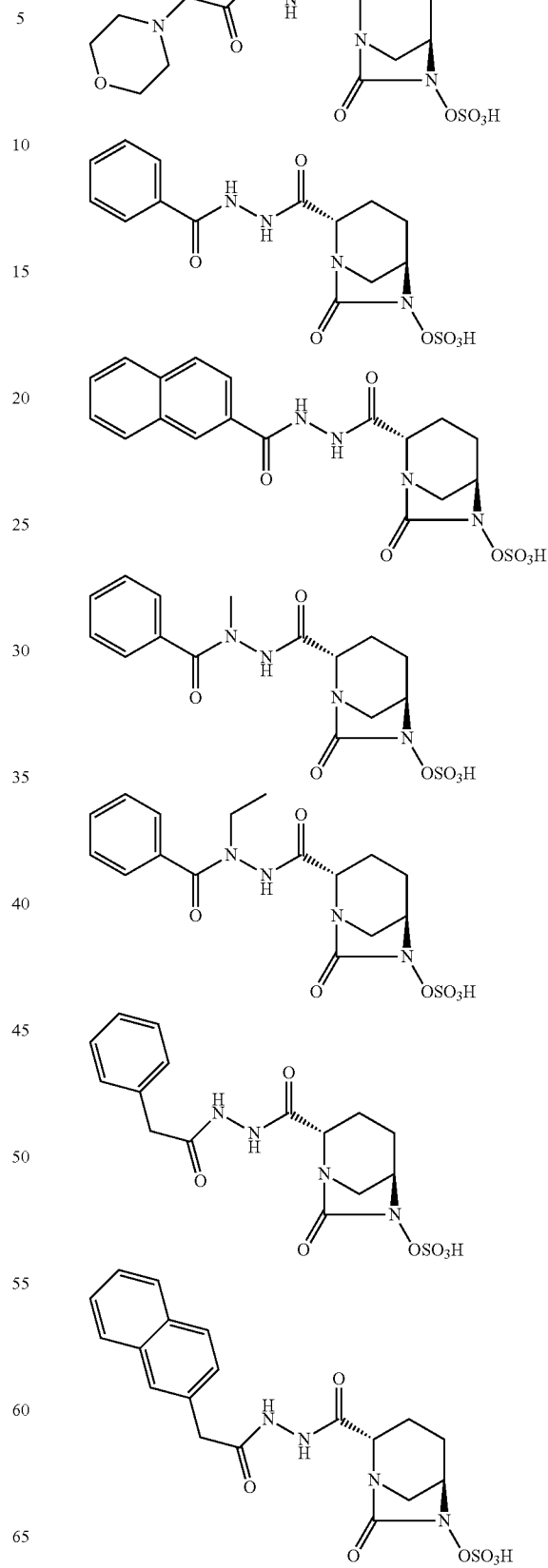

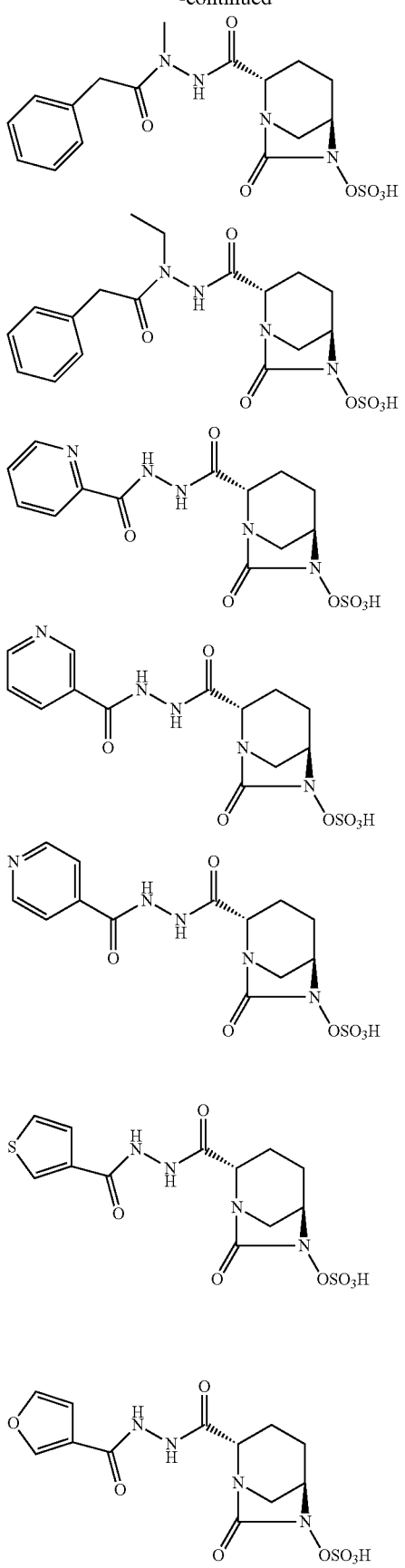
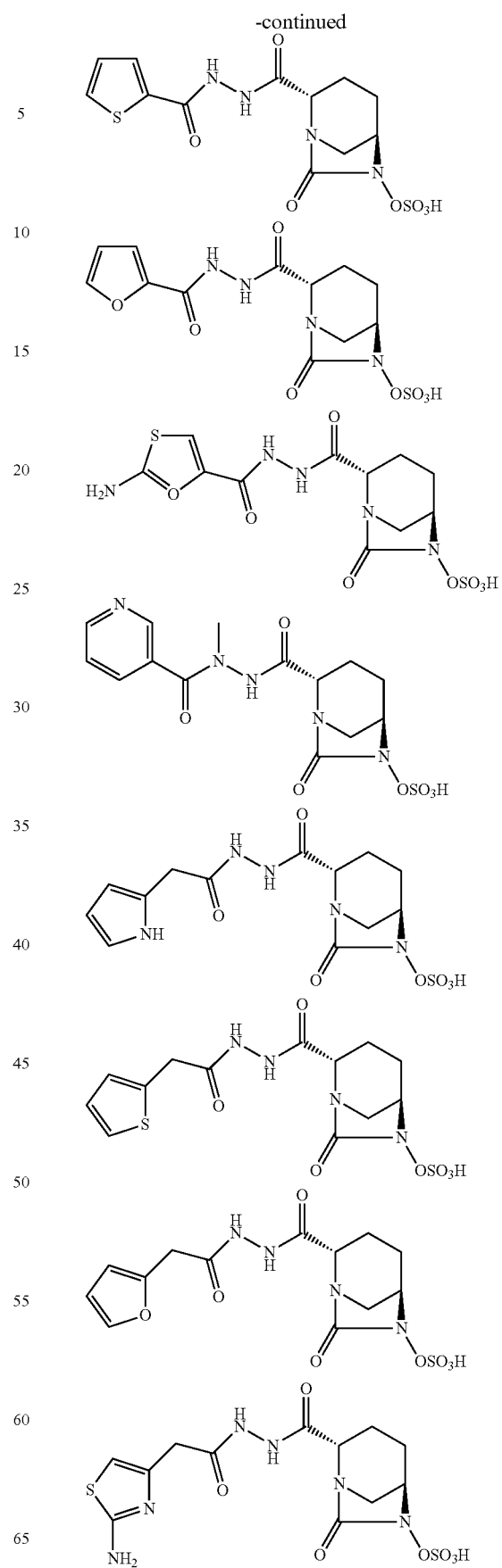

69
-continued
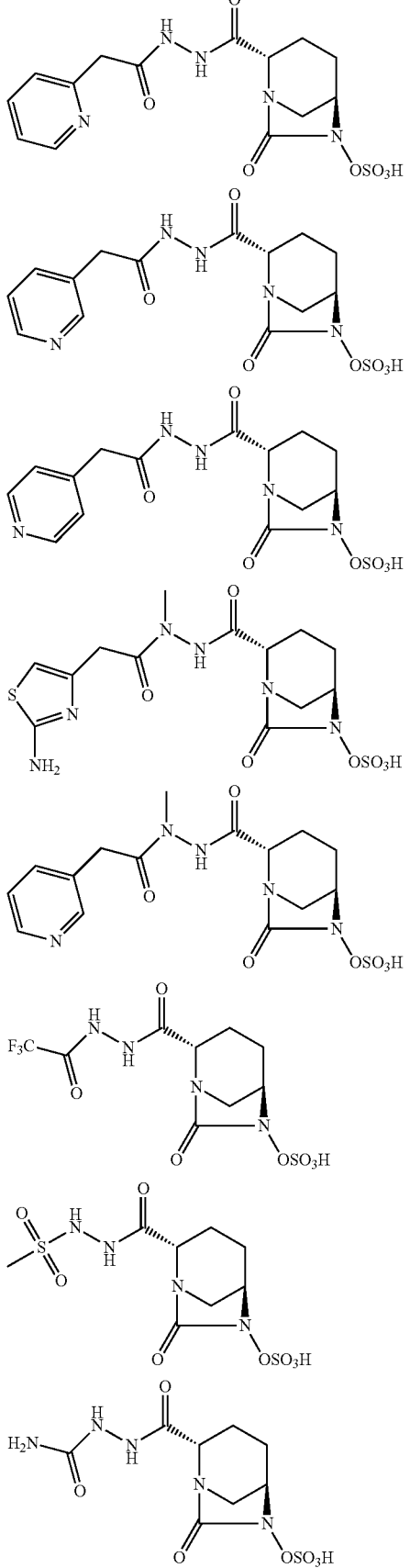
70
-continued
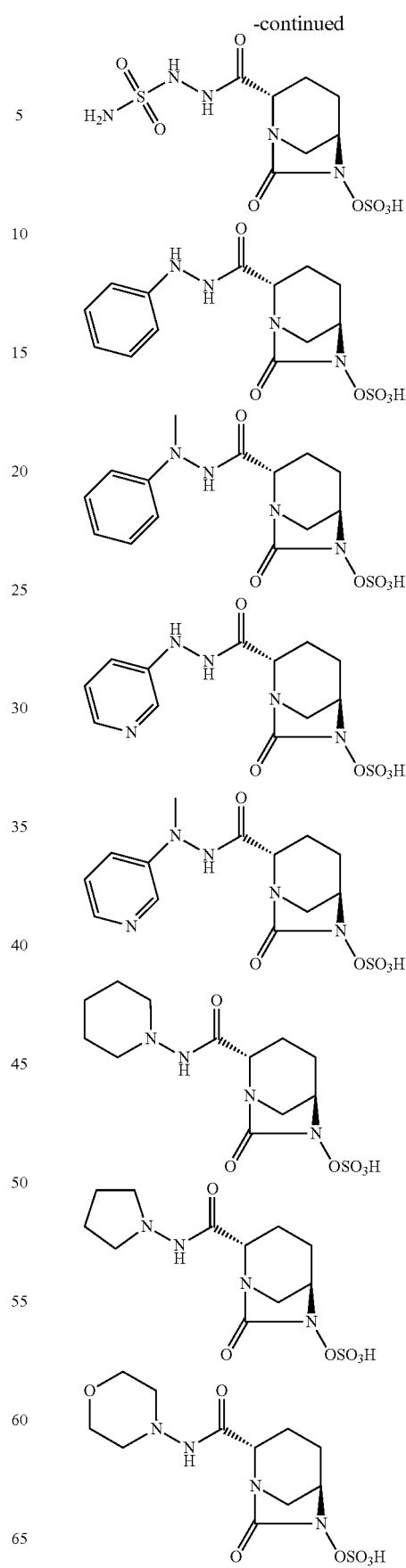

| 71 -continued | 72 -continued |
|---|---|
| 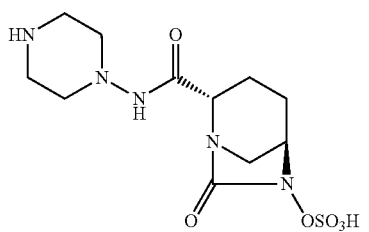 | 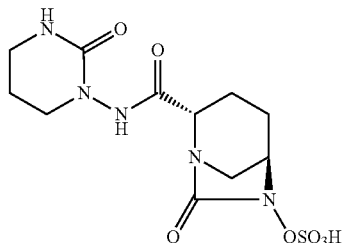 |
| 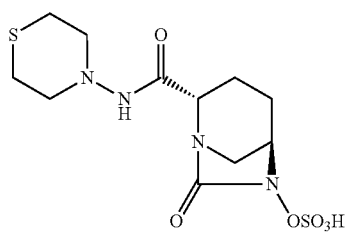 | 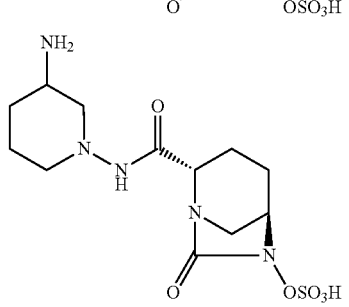 |
| 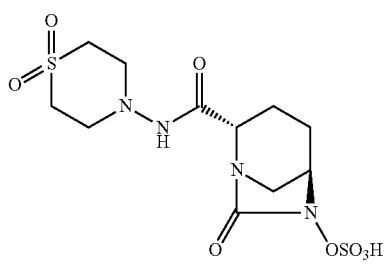 | 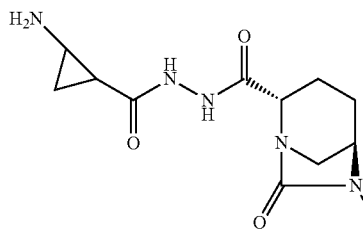 |
| 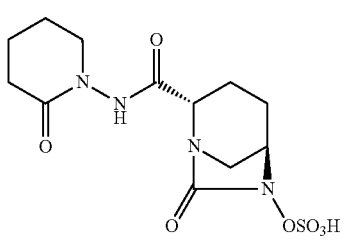 | 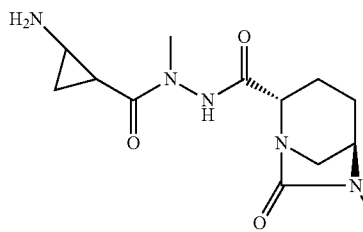 |
| 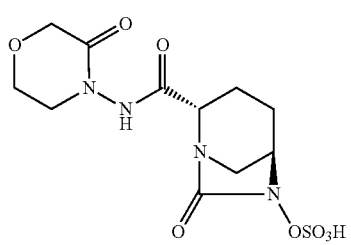 | 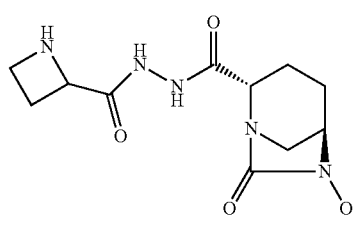 |
| 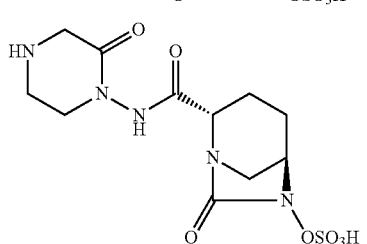 | 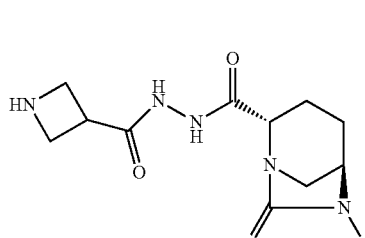 |
| 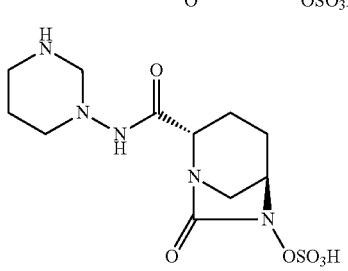 | 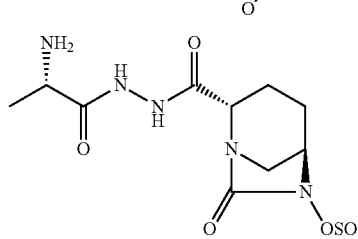 |

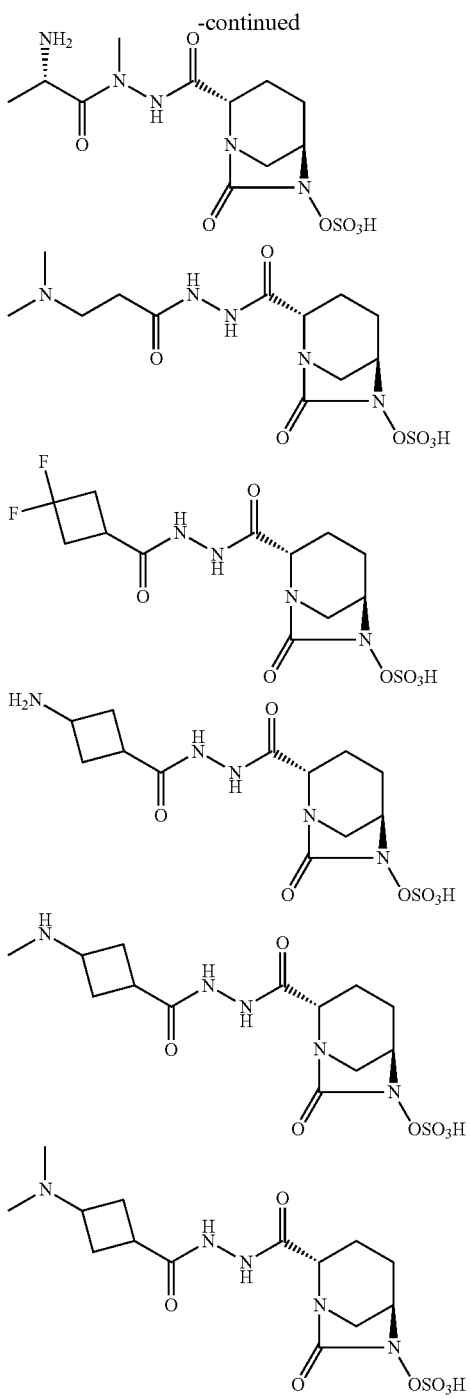

line. Basic amino acids that can form the basic amino acid salts include lysine, arginine, ornithine and histidine. As will be appreciated by one skilled in the art, the compounds of formula (I) containing a basic nitrogen atom are capable of forming acid addition salts. Such salts with pharmaceutically acceptable acids are included in the invention. Examples of such acids are hydrochloric, hydrobromic, phosphoric, sulphuric, citric, oxalic, maleic, fumaric, glycolic, mandelic, tartaric, aspartic, succinic, malic, formic, acetic, trifluoroacetic, methanesulfonic, ethanesulfonic, trifluoromethanesulfonic, benzenesulfonic, p-toluenesulfonic and the like.

Moreover, some compounds of formula (I) when they contain a basic group such as NH, $NH_2$ or pyridine and the like may form an inner, zwitterionic salt with $OSO_3H$; such inner salts are also included in this invention.

Another aspect of the present invention is to include all possible isomers of formula (I). As used herein, the term 'isomers' refers to different compounds that have the same molecular formula but differ in arrangement and configuration of the atoms, such as geometrical isomers and optical isomers. For a given compound of the present invention, it is understood that a substituent may be attached at a chiral center of a carbon atom. Therefore the invention includes enantiomers, diastereoisomers or racemates of the compound. By definition 'enantiomers' are a pair of stereoisomers that are non-superimposable mirror images of each other, and 1:1 mixture of a pair of enantiomers is a racemic mixture. By definition, 'diastereoisomers' are stereoisomers that have at least two asymmetric carbon atoms but which are not mirror-images of each other. When a compound of formula (I) is a pure enantiomer the stereochemistry at each chiral carbon may be specified by either R or S.

Compounds may also exist in several tautomeric forms including the enol form, the keto form, and mixtures of any of the foregoing. Accordingly, the chemical structures depicted herein encompass all possible tautomeric forms of the illustrated compounds.

A variety of protecting groups conventionally used in the β-lactam field to protect a reactive functional group present in the molecule of formula (I) can be used. 'Protecting group' refers to a group of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$, 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of hydroxy protecting groups include, but are not limited to, those where the hydroxyl group is either acylated or alkylated such as benzyl, and trityl ethers as well as alkyl ethers, tetrahydropyranyl ethers, trialkylsilyl ethers, and allyl ethers.

The term 'optionally substituted' refers to unsubstituted or substituted with one or two of the following substituents each of which is independently selected from:
Lower alkyl including from one to six carbon atoms in any arrangement, e.g., methyl, ethyl, i-propyl or t-butyl
Amino
Substituted amino such as $—NHCH_3$, $—N(CH_3)_2$, $—NHCH_2CH_3$, $—NHPr^i$, $—NHBu^t$, Examples of the groups for forming a pharmaceutically acceptable salt represented by M in the formula (I) include: inorganic base salts, ammonium salts, organic base salts, basic amino acid salts, inorganic acid addition salts, and organic acid addition salts. Inorganic bases that can form the inorganic base salts include alkali metals (e.g., sodium, potassium, and lithium) and alkaline earth metals (e.g., calcium and magnesium). Organic bases that can form the organic base salts include n-propylamine, n-butylamine, cyclohexylamine, benzylamine, octylamine, ethanolamine, diethanolamine, diethylamine, triethylamine, dicyclohexylamine, procaine, choline, N-methylglucamine, morpholine, pyrrolidine, piperidine, N-ethylpiperidine and N-methylmorpho-

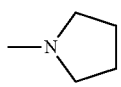

Alkoxy such as —OCH₃, —OC₂H₅, —OPr$^i$ (i.e., isopropyloxy), —OBu$^t$ (i.e., isobutyloxy)
Hydroxyalkyl such as —CH₂OH, —CH₂CH₂OH
Halogen such as F, Cl, Br
Hydroxy
Carboxy
Alkoxycarbonyl such as —COOCH₃, —COOC₂H₅, —COOPr$^i$, and —COOBu$^t$
Haloalkyl such as —CH₂Cl, —CH₂F
Trifluoromethyl
Trifluoromethyloxy
Alkylamine such as —CH₂NH₂, —CH₂CH₂NH₂
Substituted alkylamine such as —CH₂NHCH₃, —CH₂N(CH₃)₂, —CH₂CH₂NHCH₃, —CH₂CH₂N(CH₃)₂,

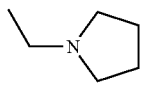

Carboxamide
Thiocarboxamide
Sulfonic acid
Sulfate
Acylamino
Sulfonylamino
Sulfonamide
Substituted sulfonamide such as —SO₂NHCH₃, —SO₂NHCH₂CH₃, —SO₂NHPr$^i$, —SO₂NHBu$^t$,

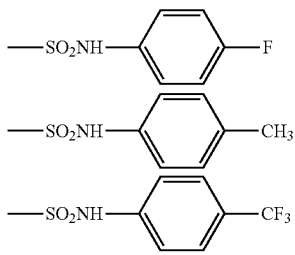

Urea (—NHCONH₂) which may be optionally substituted
Thiourea (—NHCSNH₂) which may be optionally substituted
Sulfonylurea (—NHSO₂NH₂) which may be optionally substituted
Oxo (=O) when oxygen is bonded through double bond to a carbon atom
Oxyimino (=N—O-A) where the nitrogen is bonded through double bond to a carbon atom which is attached to the rest of the molecule and A can be hydrogen, or optionally substituted straight or branched lower alkyl, cycloalkyl, aryl, heteroaryl and heterocyclyl
Hydroxamic acid (—CONHOH)
Acyl (—COCH₃)
Trifluoromethyl carbonyl (—COCF₃)
Cyano (—CN)
Amidino —C(=NH)NH₂ which may be optionally substituted
Guanidino —NHC(=NH)NH₂ which may be optionally substituted
Aryloxy
Heterocyclyl
Heteroaryl
Heterocyclyloxy
Heteroaryloxy
Heterocyclylalkyloxy
Trialkylammonium The substituent mentioned above could be substituted at the carbon atom or at the free N-atom of the molecule as appropriate.

Among the compounds of formula (I), a particular subject of the invention are those in which M is hydrogen or a pharmaceutically acceptable salt forming cation.

A group of preferred examples of compounds of the formula (I), when Y=OR¹, are from the following Table 1.

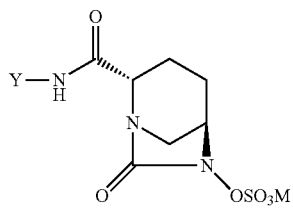

Y=OR¹
*=point of attachment with O

TABLE 1

| Compound No. | M | R¹ |
|---|---|---|
| 1 | H | (S)-pyrrolidin-3-yl (HN-pyrrolidine, wedge bond) |
| 2 | H | (R)-pyrrolidin-3-yl (HN-pyrrolidine, solid wedge) |
| 3 | H | piperidin-3-yl (solid wedge) |
| 4 | H | piperidin-3-yl (hashed wedge) |
| 5 | Na | cyclohexyl |
| 6 | H | piperidin-4-yl |

TABLE 1-continued
List of compounds
| Compound No. | M | R¹ |
|---|---|---|
| 7 | Na | 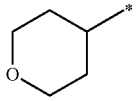 |
| 8 | H |  |
| 9 | H | 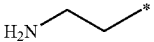 |
| 10 | H | 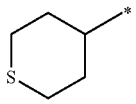 |
| 11 | H | 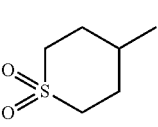 |
| 12 | H |  |
| 13 | Na | 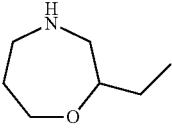 |
| 14 | H | 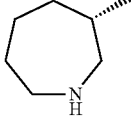 |
| 15 | H | 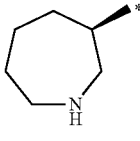 |
| 16 | H | 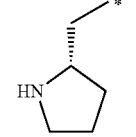 |
| 17 | H | 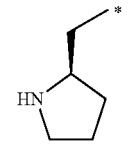 |
| 18 | H | 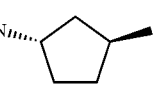 |
TABLE 1-continued
List of compounds
| Compound No. | M | R¹ |
|---|---|---|
| 19 | H | 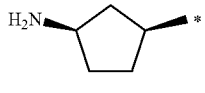 |
| 20 | H | 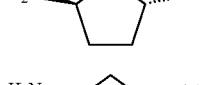 |
| 21 | H | 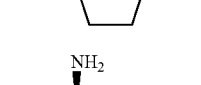 |
| 22 | H | 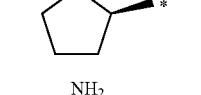 |
| 23 | H | 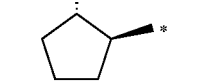 |
| 24 | H | 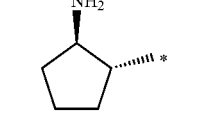 |
| 25 | H | 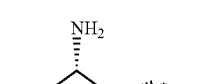 |
| 26 | H |  |
| 27 | H | 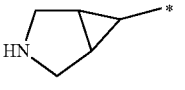 |
| 28 | H | CH₃ |
| 29 | H | 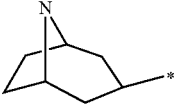 |
| 30 | H | 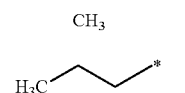 |
| 31 | H | 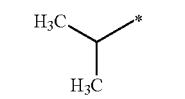 |
| 32 | H |  |

TABLE 1-continued
List of compounds
| Compound No. | M | R¹ |
|---|---|---|
| 33 | H | 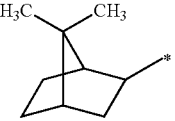 |
| 34 | H | 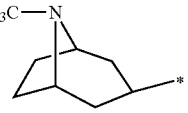 |
| 35 | H | 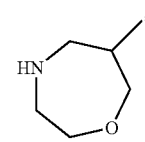 |
| 36 | Na | 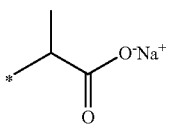 |
| 37 | H | 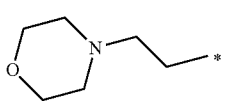 |
| 38 | H | 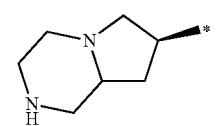 |
| 39 | H | 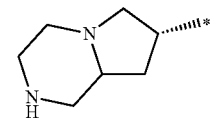 |
| 40 | H | 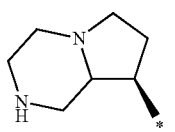 |
| 41 | H | 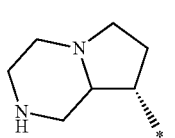 |
| 42 | H | 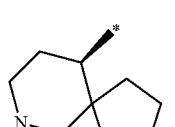 |
| 43 | H | 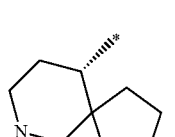 |
TABLE 1-continued
List of compounds
| Compound No. | M | R¹ |
|---|---|---|
| 44 | H | 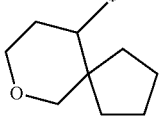 |
| 45 | H | 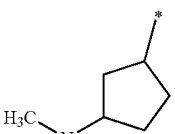 |
| 46 | H | 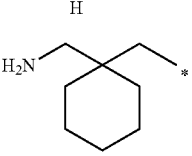 |
| 47 | H | 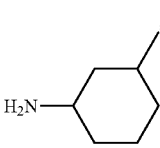 |
| 48 | H | 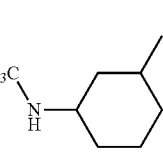 |
| 49 | H | 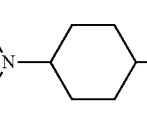 |
| 50 | H | 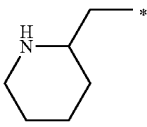 |
| 51 | H | 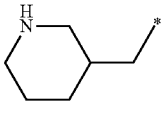 |
| 52 | H | 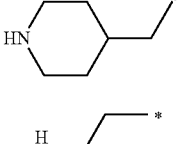 |
| 53 | H | 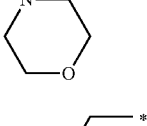 |
| 54 | H | 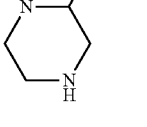 |

TABLE 1-continued

List of compounds

| Compound No. | M | R¹ |
|---|---|---|
| 55 | H | (thiomorpholine-CH2*) |
| 56 | H | (thienopyridine*) |
| 57 | H | (imidazopyrrolidine*) |
| 58 | H | (indolizidine*) |
| 59 | H | (pyrrolizidine*) |
| 60 | H | (decahydroquinoline*) |
| 61 | H | (octahydrofuropyridine*) |
| 62 | H | (decahydroquinoline*) |
| 63 | H | (octahydropyrrolopyrrole*) |
| 64 | H | (hexahydrocyclopenta-dioxine*) |
| 65 | H | (hexahydrocyclopenta-furan*) |
| 66 | H | (hexahydrocyclopenta-thiophene*) |
| 67 | H | (1-methylpiperidin-4-yl*) |
| 68 | H | (tetrahydro-methanoindazole-CH2*) |
| 69 | H | (2-pyridyl-CH2CH2*) |
| 70 | Na | (1-methyl-pyrazolopyridine*) |
| 71 | H | (1H-pyrazol-3-yl-CH2*) |
| 72 | H | (1H-imidazol-2-yl-CH2*) |
| 73 | H | (H2N-C(O)-CH2*) |
| 74 | H | (H2N-CH(CH3)-CH2*) |
| 75 | H | (4-carbamimidoyl-piperidin-1-yl*) |
| 76 | H | (piperidin-4-yloxy-CH2CH2*) |

TABLE 1-continued

List of compounds

| Compound No. | M | R¹ |
|---|---|---|
| 77 | H | (sulfamoylamino-ethyl group: H₂N-S(=O)₂-NH-CH₂CH₂-*) |
| 78 | H | (ureido-ethyl: H₂N-C(=O)-NH-CH₂CH₂-*) |
| 79 | H | (2-hydroxyethyl: HO-CH₂CH₂-*) |
| 80 | H | (amidino-propyl: H₂N-C(=NH)-CH₂CH₂CH₂-*) |
| 81 | H | (guanidino-ethyl: H₂N-C(=NH)-NH-CH₂CH₂-*) |
| 82 | Na | (*-CH₂-C(=O)-O⁻Na⁺) |
| 83 | Na | (*-C(CH₃)₂-C(=O)-O⁻Na⁺) |
| 84 | H | (tert-butyl: (CH₃)₃C-*) |
| 85 | H | (cyclobutyl) |
| 86 | H | (cyclopentyl) |
| 87 | H | (cycloheptyl) |
| 88 | H | (1-sulfamoyl-pyrrolidin-3-yl: H₂N-S(=O)₂-N(pyrrolidine)-*) |
| 89 | H | (1-(N-methylsulfamoyl)-pyrrolidin-3-yl: CH₃-NH-S(=O)₂-N(pyrrolidine)-*) |
| 90 | H | (1-carbamoyl-pyrrolidin-3-yl: H₂N-C(=O)-N(pyrrolidine)-*) |
| 91 | H | (5-carbamoyl-pyrrolidin-3-yl) |
| 92 | H | (1-amidino-pyrrolidin-3-yl: H₂N-C(=NH)-N(pyrrolidine)-*) |
| 93 | H | (1-acetimidoyl-pyrrolidin-3-yl: CH₃-C(=NH)-N(pyrrolidine)-*) |
| 94 | H | (1-formimidoyl-pyrrolidin-3-yl: H-C(=NH)-N(pyrrolidine)-*) |
| 95 | Na | ((S)-tetrahydrofuran-3-yl) |
| 96 | H | (tetrahydrothiopyran-3-yl) |
| 97 | H | (4,5,6,7-tetrahydrofuro[3,2-c]pyridin-7-yl) |
| 98 | H | (4,5,6,7-tetrahydro-1H-pyrazolo[3,4-c]pyridin-4-yl) |
| 99 | H | ((tetrahydrofuran-2-yl)methyl) |
| 100 | Na | (2-(imidazol-1-yl)ethyl) |

TABLE 1-continued
List of compounds
| Compound No. | M | R¹ |
|---|---|---|
| 101 | H | 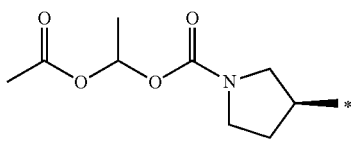 |
| 102 | H | 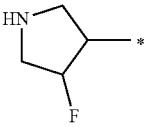 |
| 103 | H | 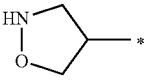 |
| 104 | Na | 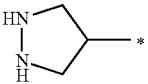 |
| 105 | H | 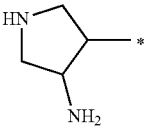 |
| 106 | H | 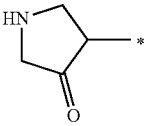 |
| 107 | H | 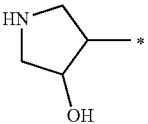 |
| 108 | H | 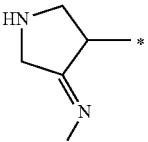 |
| 109 | H | 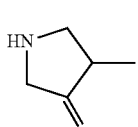 |
| 110 | H | 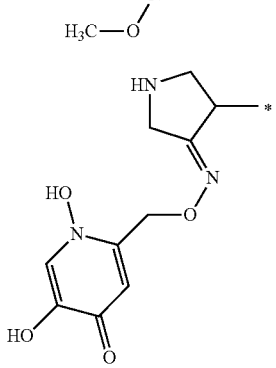 |
| 111 | H | 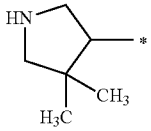 |
| 112 | H | 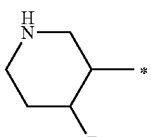 |
| 113 | H | 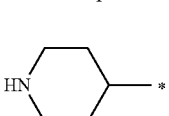 |
| 114 | H | 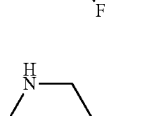 |
| 115 | H | 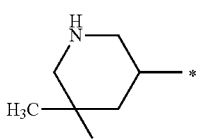 |
| 116 | H | 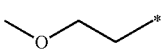 |
| 117 | H | 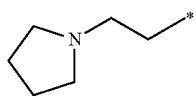 |
| 118 | H | 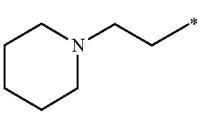 |
| 119 | H | 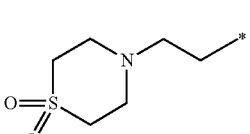 |
| 120 | H | 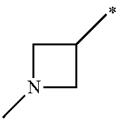 |

TABLE 1-continued
List of compounds
| Compound No. | M | R¹ |
|---|---|---|
| 121 | H | 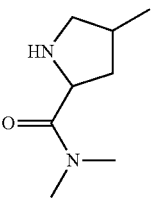 |
| 122 | H | 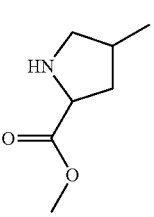 |
| 123 | H | 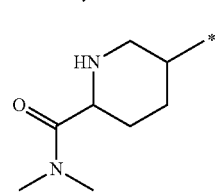 |
| 124 | H | 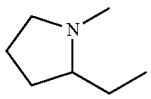 |
| 125 | H | 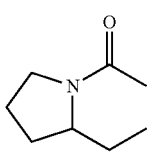 |
| 126 | H | 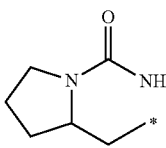 |
| 127 | H | 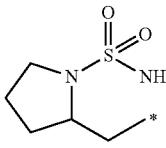 |
| 128 | H | 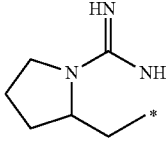 |
| 129 | H | 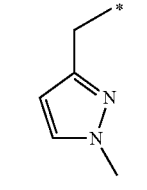 |
| 130 | H | 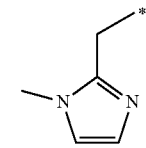 |
| 131 | Na | 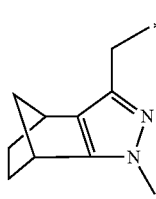 |
| 132 | H | 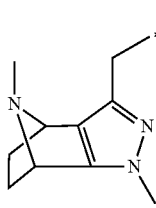 |
| 133 | H | 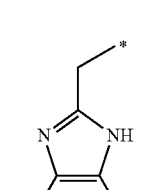 |
| 134 | H | 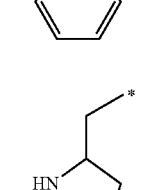 |
| 135 | H | 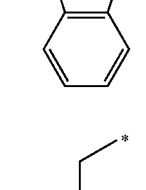 |
| 136 | H | 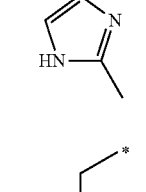 |

TABLE 1-continued
List of compounds
| Compound No. | M | R¹ |
|---|---|---|
| 137 | H | 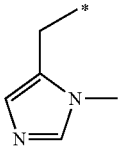 |
| 138 | H | 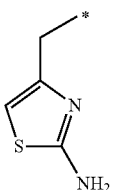 |
| 139 | H | 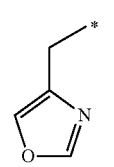 |
| 140 | H | 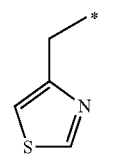 |
| 141 | H | 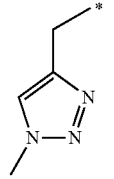 |
| 142 | Na | 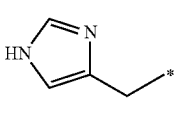 |
| 143 | H | 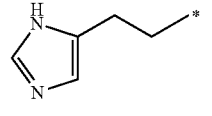 |
| 144 | H | 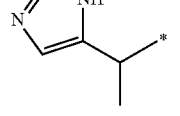 |
| 145 | H | 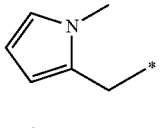 |
| 146 | H | 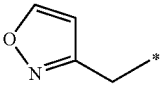 |
| 147 | H | 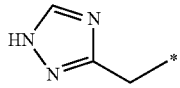 |
| 148 | H | 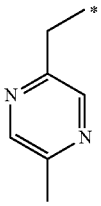 |
| 149 | Na | 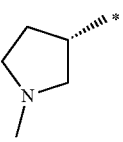 |
| 150 | Na | 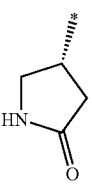 |
| 151 | H | 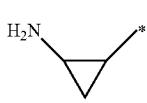 |
| 152 | Na | 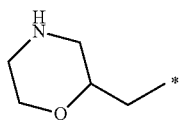 |
| 153 | H | 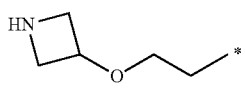 |
| 154 | H | 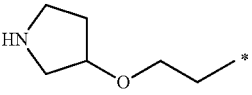 |
| 155 | H |  |
A group of preferred examples of compounds of the formula (I), when Y=NR²R³, are from the following Table 2.

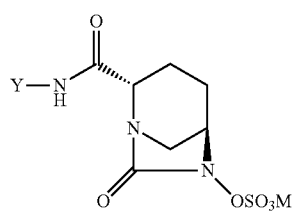

Y=NR²R³
*=point of attachment with N

TABLE 2

List of compounds

| Compound No. | M | R² | R³ |
|---|---|---|---|
| 1 | H | H | H₃C—* |
| 2 | H | H | ethyl-* |
| 3 | H | H | isopropyl-* |
| 4 | H | CH₃ | H₃C—* |
| 5 | H | CH₂CH₃ | ethyl-* |
| 6 | H | CH(CH₃)₂ | isopropyl-* |
| 7 | H | H | cyclopropyl-* |
| 8 | H | H | cyclobutyl-* |
| 9 | H | H | cyclopentyl-* |
| 10 | H | H | piperidin-4-yl-* (HN) |
| 11 | H | H | tetrahydropyran-4-yl-* (O) |
| 12 | H | H | tetrahydrothiopyran-4-yl-* (S) |

TABLE 2-continued

List of compounds

| Compound No. | M | R² | R³ |
|---|---|---|---|
| 13 | H | H | piperidin-3-yl-* (HN) |
| 14 | H | H | pyrrolidin-3-yl-* (HN) |
| 15 | H | H | 1,1-dioxo-tetrahydrothiopyran-4-yl-* |
| 16 | H | H | H₃C-C(=O)-* |
| 17 | H | H | CH₃CH₂-C(=O)-* |
| 18 | H | H | (CH₃)₂CH-C(=O)-* |
| 19 | H | CH₃ | H₃C-C(=O)-* |
| 20 | H | CH₃ | CH₃CH₂-C(=O)-* |
| 21 | H | CH₃ | (CH₃)₂CH-C(=O)-* |
| 22 | H | CH₂CH₃ | H₃C-C(=O)-* |
| 23 | H | CH₂CH₃ | CH₃CH₂-C(=O)-* |
| 24 | H | H | (CH₃)₃C-C(=O)-* |
| 25 | H | H | CH₃CH₂CH₂-C(=O)-* |
| 26 | H | H | CH₃CH₂CH(CH₃)-C(=O)-* |

TABLE 2-continued

List of compounds

| Compound No. | M | $R^2$ | $R^3$ |
|---|---|---|---|
| 27 | H | H | N,N-dimethylaminoacetyl |
| 28 | H | H | trifluoroacetyl (CF₃CH₂C(O)-) |
| 29 | H | H | methoxyacetyl |
| 30 | H | H | L-alanyl (H₂N-CH(CH₃)-C(O)-) |
| 31 | H | H | 2-amino-2-phenylacetyl |
| 32 | H | H | cyclopropanecarbonyl |
| 33 | H | H | cyclobutanecarbonyl |
| 34 | H | H | 2,2-dimethylcyclopropanecarbonyl |
| 35 | H | H | 2-methylcyclopropanecarbonyl |
| 36 | H | H | 2,2-difluorocyclopropanecarbonyl |
| 37 | H | H | 2-fluorocyclopropanecarbonyl |
| 38 | H | H | cyclopentanecarbonyl |
| 39 | H | H | cyclohexanecarbonyl |
| 40 | H | H | 2-aminocyclopentanecarbonyl |
| 41 | H | H | prolyl |
| 42 | H | H | pyrrolidine-3-carbonyl |
| 43 | H | H | piperidine-2-carbonyl |
| 44 | H | CH₃ | prolyl |
| 45 | H | H | piperidine-3-carbonyl |
| 46 | H | H | piperidine-4-carbonyl |
| 47 | H | H | tetrahydropyran-4-carbonyl |
| 48 | H | H | N-methylprolyl |

TABLE 2-continued

List of compounds

| Compound No. | M | R² | R³ |
|---|---|---|---|
| 49 | H | H | 1-methylpiperidine-4-carbonyl |
| 50 | H | H | tetrahydrothiopyran-4-carbonyl |
| 51 | H | H | 1,1-dioxo-tetrahydrothiopyran-4-carbonyl |
| 52 | H | H | (pyrrolidin-2-yl)acetyl |
| 53 | H | H | (pyrrolidin-3-yl)acetyl |
| 54 | H | H | (1-methylpyrrolidin-2-yl)acetyl |
| 55 | H | H | cyclopropylacetyl |
| 56 | H | H | (piperidin-2-yl)acetyl |
| 57 | H | H | (1-methylpiperidin-2-yl)acetyl |
| 58 | H | H | (piperidin-3-yl)acetyl |
| 59 | H | H | (piperidin-4-yl)acetyl |
| 60 | H | H | (1-methylpiperidin-4-yl)acetyl |
| 61 | H | H | (pyrrolidin-1-yl)acetyl |
| 62 | H | H | (piperazin-1-yl)acetyl |
| 63 | H | H | (morpholin-4-yl)acetyl |
| 64 | H | H | benzoyl |
| 65 | H | H | naphthalen-2-ylcarbonyl |
| 66 | H | CH₃ | benzoyl |
| 67 | H | CH₂CH₃ | benzoyl |
| 68 | H | H | phenylacetyl |
| 69 | H | H | naphthalen-2-ylacetyl |

TABLE 2-continued
List of compounds
| Compound No. | M | R² | R³ |
|---|---|---|---|
| 70 | H | CH₃ | 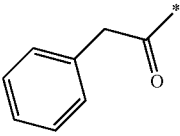 [SMILES: *C(=O)Cc1ccccc1] |
| 71 | H | CH₂CH₃ | 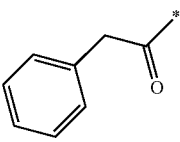 [SMILES: *C(=O)Cc1ccccc1] |
| 72 | H | H | 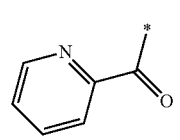 |
| 73 | H | H | 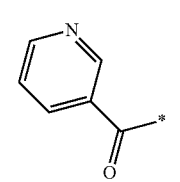 [SMILES: *C(=O)c1cccnc1] |
| 74 | H | H | 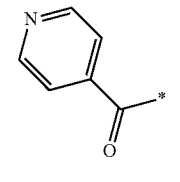 [SMILES: *C(=O)c1ccncc1] |
| 75 | H | H | 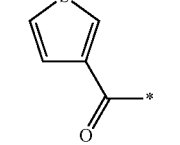 |
| 76 | H | H | 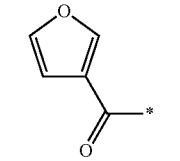 [SMILES: *C(=O)c1ccoc1] |
| 77 | H | H | 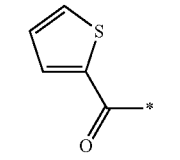 [SMILES: *C(=O)c1cccs1] |
| 78 | H | H | 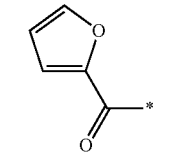 [SMILES: *C(=O)c1ccco1] |
| 79 | H | CH₃ | 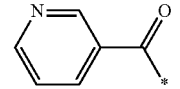 |
| 80 | H | H | 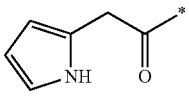 |
| 81 | H | H | 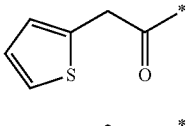 |
| 82 | H | H | 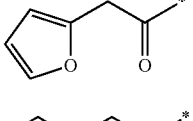 |
| 83 | H | H | 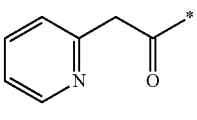 |
| 84 | H | H | 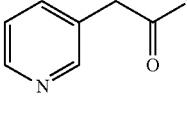 |
| 85 | H | H | 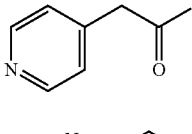 |
| 86 | H | H | 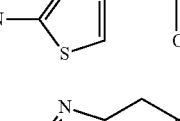 |
| 87 | H | CH₃ | 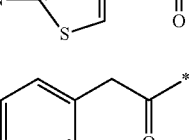 |
| 88 | H | CH₃ | 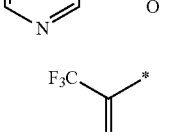 |
| 89 | H | H | 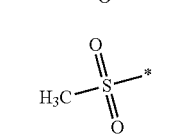 |
| 90 | H | H | 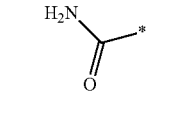 |
| 91 | H | H | 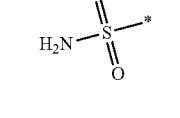 |
| 92 | H | H |  |

TABLE 2-continued

List of compounds

| Compound No. | M | R² | R³ |
|---|---|---|---|
| 93 | H | H | phenyl |
| 94 | H | CH₃ | phenyl |
| 95 | H | H | pyridin-3-yl |
| 96 | H | CH₃ | pyridin-3-yl |
| 97 | H | | -(CH₂)₄- |
| 98 | H | | -(CH₂)₃- |
| 99 | H | | -CH₂-O-CH₂- |
| 100 | H | | -CH₂-NH-CH₂- |
| 101 | H | | -CH₂-S-CH₂- |
| 102 | H | | -CH₂-S(O)₂-CH₂- |
| 103 | H | | -(CH₂)₃-C(=O)- |
| 104 | H | | -CH₂-O-CH₂-C(=O)- |
| 105 | H | | -CH₂-NH-CH₂-C(=O)- |
| 106 | H | | -CH₂CH₂-NH- |
| 107 | H | | -CH₂CH₂-NH-C(=O)- |
| 108 | H | | 3-aminobutyl |
| 109 | H | H | 2-amino-cyclopropanecarbonyl |
| 110 | H | CH₃ | 2-amino-cyclopropanecarbonyl |
| 111 | H | H | azetidine-2-carbonyl |
| 112 | H | H | azetidine-3-carbonyl |
| 113 | H | H | (S)-2-aminopropanoyl |
| 114 | H | CH₃ | (S)-2-aminopropanoyl |
| 115 | H | H | 4-(dimethylamino)butanoyl |
| 116 | H | H | 3,3-difluorocyclobutanecarbonyl |

TABLE 2-continued

List of compounds

| Compound No. | M | R² | R³ |
|---|---|---|---|
| 117 | H | H | H₂N-cyclobutyl-C(=O)-* |
| 118 | H | H | CH₃-NH-cyclobutyl-C(=O)-* |
| 119 | H | H | (CH₃)₂N-cyclobutyl-C(=O)-* |

It is also an object of this invention to provide a combination of a compound of general formula (I) having antibacterial activity with another existing antibacterial agent, thus causing synergistic effect and the use of the same as drugs for the treatment of bacterial infections.

It is another object of the invention to provide methods for preparing the compounds of the invention of formula (I).

It is a further object of the invention to provide pharmaceutical compositions comprising a compound of formula (I) of this invention (some of which directly inhibit β-lactamase enzymatic function and others of which do not directly inhibit β-lactamase's enzymatic function (at pharmaceutically accessible concentrations) as an active ingredient in combination with an antibiotic (e.g., a β-lactam antibiotic or some other non β-lactam antibiotic) and a suitable amount of pharmaceutically acceptable carrier or diluent, so as to provide a form for proper administration to a patient. These compositions can be administered by parenteral, in particular intramuscular route, oral, sublingual, rectal, aerosol or by local route in a topical application on the skin and the mucous membranes. Suitable pharmaceutical vehicles include excipients such as starch, glucose, lactose, sucrose, gelatin, gum arabic, malt, rice, flour, chalk, silica gel, sodium stearate, glycerol monostearate, talc, sodium chloride, dried skim milk, glycerol, propylene glycol, water, ethanol, and the like. Other examples of suitable pharmaceutical vehicles have been described in the art (Remington's Science and Practice of Pharmacy, 21st Edition, 2006). Compositions of the present disclosure, if desired, can also contain minor amounts of wetting, dispersing or emulsifying agents, or pH buffering agents, and preservatives. In addition, auxiliary, stabilizing, thickening, lubricating, and coloring agents can be included. Pharmaceutical compositions can be formulated in a conventional manner. Proper formulation is dependent upon the route of administration chosen. The present pharmaceutical compositions can take the form of injectable preparations, suspensions, emulsions, sugar-coated tablets, pellets, gelatin-capsules, capsules containing liquids, powders, granules, sustained-release formulations, suppositories, aerosols, sprays, ointments, creams or any other form suitable for use.

In another aspect, the present invention also provides for the use, in the manufacture of a medicament, of a compound within formula (I) above as an active ingredient in an antibacterial composition in admixture with a carrier.

In another aspect, the present invention also provides for the use, in the manufacture of a medicament, of a compound within formula (I) above as an active ingredient.

In another aspect, the present invention also provides for the use, in the manufacture of a medicament, of a compound within formula (I) above as an active ingredient, along with one or more antibiotics (e.g., a β-lactam antibiotic or some other non β-lactam antibiotic), in an antibacterial composition in admixture with a carrier.

In another aspect, the present invention also provides for the use, in the manufacture of a medicament, of a compound within formula (I) above as an active ingredient, along with one or more antibiotics (e.g., a β-lactam antibiotic or some other non β-lactam antibiotic).

The parenteral administration which includes intramuscular, intraperitonial, subcutaneous and intravenous use, sterile solutions of the active ingredient are usually prepared and the pH of the solutions are suitably adjusted and buffered. For intravenous use, the total concentration of solutes should be controlled to render the preparation isotonic. Suitable solvents include saline solution (e.g., 0.9% NaCl solution) and apyrogenic sterile water. Pharmaceutical compositions for oral delivery can be, for example, in the form of tablets, lozenges, aqueous or oily suspensions, granules, powders, emulsions, capsules, syrups, or elixirs. Orally administered compositions can contain one or more optional agents, for example, sweetening agents such as fructose, aspartame, or saccharin, flavoring agents such as peppermint, oil of wintergreen, cherry, coloring agents, and preserving agents to provide a pharmaceutically palatable preparation. Moreover, when in tablet form, the compositions can be coated to delay disintegration and absorption in the gastrointestinal tract, thereby providing a sustained action over an extended period of time. Oral compositions can include standard vehicles such as mannitol, lactose, starch, magnesium stearate, sodium saccharin, cellulose, magnesium carbonate, and the like. For oral liquid preparations, for example, suspensions, elixirs, and solutions, suitable carriers, excipients, or diluents include water, saline, alkyleneglycols (e.g. propylene glycol), polyalkylene glycols (e.g., polyethylene glycol), oils, alcohols, slightly acidic buffers ranging from about pH 4 to about pH 6 (e.g., acetate, citrate, ascorbate ranging from about 5 mM to about 50 mM), and the like. Additionally, flavoring agents, preservatives, coloring agents, bile salts, acylcarnitines, and the like can be added.

For topical formulations of compounds of the present invention, creams, gels, ointments or viscous lotions can be used as appropriate delivery forms. Topical delivery systems also include transdermal patches containing at least one compound of formula (I) to be administered. Delivery through the skin can be achieved by diffusion or by more active energy sources such as iontophoresis or electrotransport. Formulations of a compound of the present invention, for topical use, such as in creams, ointments, and gels, can include an oleaginous or water soluble ointment base, for example, topical compositions can include vegetable oils, animal fats, and in certain embodiments, semisolid hydrocarbons obtained from petroleum. Topical compositions can further include white ointment, yellow ointment, cetyl esters wax, oleic acid, olive oil, paraffin, petrolatum, white petrolatum, spermaceti, starch glycerite, white wax, yellow wax, lanolin, and glyceryl monostearate. Various water-soluble ointment bases can also be used, including glycol ethers and derivatives, polyethylene glycols, polyoxyl 40 stearate, and polysorbates.

In a pharmaceutical composition containing a compound of this invention, the weight ratio of active ingredient to carrier will normally be in the range of 1:20 to 20:1. The administered daily dose varies according to the illness treated, and the administration route. However in most instances, an effective dose (e.g., in some instances, a β-lactamase inhibiting dose) of a compound of formula (I) or a pharmaceutically acceptable salt thereof will be a daily dose in the range from about 1 to about 500 mg per kilogram of body weight orally, and from about 1 to about 500 mg per kilogram of body weight parenterally. The weight ratio of the compound of present invention and an antibiotic (if it is being administered with an antibiotic, e.g., a β-lactam antibiotic or some other non β-lactam antibiotic) will normally be in the range from 1:20 to 20:1.

In some aspects of the present invention, an additional object is to provide an improved method for the treatment of bacterial infections caused by β-lactamase producing bacteria in a patient in need of such treatment comprising administering to the patient a therapeutically effective amount of at least one compound chosen from formula (I) or a pharmaceutically acceptable salt thereof in combination with a known β-lactam antibiotic. In such an aspect of the present invention, the compounds increase the antibacterial effectiveness of β-lactamase susceptible β-lactam antibiotics, that is, they increase the effectiveness of the antibiotic against infections caused by β-lactamase producing microorganisms in mammalian subjects, particularly in human. In these aspects of the present invention, this makes the compounds of formula (I) and pharmaceutically acceptable salts thereof, valuable for co-administration with β-lactam antibiotics. In the treatment of a bacterial infection in such aspects of the present invention, said compounds of formula (I) or a pharmaceutically salt thereof can be mixed with the β-lactam antibiotic, and the two agents thereby administered simultaneously. When co-administered with a β-lactam antibiotic in such aspects of the present invention, the combination of the compound of the invention and the antibiotic can provide a synergistic effect. The term 'synergystic effect' refers to the effect produced when two or more agents are co-administered is greater than the effect produced when the agents are administered individually. Alternatively, the compound of formula (I) or a salt thereof can be administered as a separate agent during a course of treatment with the antibiotic.

'Therapeutically effective amount' refers to the amount of a compound that, when administered to a subject for treating a disease, or at least one of the clinical symptoms of a disease, is sufficient to affect such treatment of the disease, disorder, or symptom. The therapeutically effective amount can vary depending, for example, on the compound, the disease, disorder, and/or symptoms of the disease, severity of the disease, disorder, and/or symptoms of the disease, the age, weight, and/or health of the patient to be treated, and the judgement of the prescribing physician.

The term 'β-lactam antibiotic' refers to a compound with antibiotic property that contains a β-lactam functionality. Examples of β-lactam antibiotics which can be used in combination with the compounds of the present invention represented by formula (I) are commonly marketed penicillins, cephalosporins, penems, carbapenems and monobactams.

Examples of β-lactam antibiotics which can be used in combination with the compounds of the present invention represented by formula (I) are commonly used penicillins, such as amoxicillin, ampicillin, azlocillin, mezlocillin, apalcillin, hetacillin, bacampicillin, carbenicillin, sulbenicillin, ticarcillin, piperacillin, methicillin, ciclacillin, talampicillin, oxacillin, cloxacillin, dicloxacillin and commonly used cephalosporins such as cephalothin, cephaloridine, cefaclor, cefadroxil, cefamandole, cefazolin, cephalexin, cephradine, cephapirin, cefuroxime, cefoxitin, cephacetrile, cefotiam, cefotaxime, cefatriazine, cefsulodin, cefoperazone, ceftizoxime, cefmenoxime, cefmetazole, cephaloglycin, cefonicid, cefodizime, cefpirome, cefepime, ceftazidime, cefpiramide, ceftriaxone, cefbuperazone, cefprozil, cefixime, ceftobiprole, ceftaroline, cefalonium, cefminox, ceforanide, cefuzonam, cefoxitin, cefotetan, loracarbef, cefdinir, cefditoren, cefetamet, cefcapene, cefdaloxime, ceftibuten, cefroxadine, latamoxef (moxalactam), and CXA-101. From the carbapenem class of β-lactam antibiotics such as imipenem, meropenem, panipenem, biapenem, doripenem, ertapenem and the like could be used. From monobactam class of β-lactam antibiotics such as aztreonam, carumonam, tigemonam, and the like could be used as the combination partner of antibiotic.

Examples of antibiotics (which are not β-lactam antibiotics) which can be used in combination with the compounds of the present invention (i.e., compounds of formula (I) above, salts thereof, solvates of such compounds and salts, and deuterated compounds of any such compounds) include aminoglycosides, quinolones, tetracyclines, glycylcyclines, glycopeptides, lipopeptides, macrolides, ketolides, lincosamides, streptogramin, oxazolidinones, polymyxins, and other compounds known to have antibacterial properties.

'Pharmaceutically acceptable solvate' refers to a molecular complex of a compound with one or more solvent molecules in a stoichiometric or non-stoichiometric amount. Such solvent molecules are those commonly used in the pharmaceutical art, which are known to be innocuous to recipient, e.g., water, ethanol, and the like. A molecular complex of a compound or moiety of a compound and a solvent can be stabilized by non-covalent intra-molecular forces such as, for example, electrostatic forces, Van der Waals forces or hydrogen bonds. The term hydrate refers to a complex where the one or more solvent molecules are water.

Among the compounds of formula (I), a particular subject of the invention is the compounds with the following names. The following examples illustrate the invention, and are not intended to be limiting of its scope. To the contrary, the claims are intended to cover alternatives, modifications, and equivalents.

The non-limiting examples of the compounds of the present invention are:
(2S,5R)-N-(2-hydroxyethoxy)-7-oxo-6-(sulfooxy)-1,6-diazabicyclo[3.2.1]octane-2-carboxamide
(2S,5R)-N-methoxy-7-oxo-6-(sulfooxy)-1,6-diazabicyclo[3.2.1]octane-2-carboxamide
(2S,5R)-7-oxo-N-propoxy-6-(sulfooxy)-1,6-diazabicyclo[3.2.1]octane-2-carboxamide
(2S,5R)-N-(2-aminoethoxy)-7-oxo-6-(sulfooxy)-1,6-diazabicyclo[3.2.1]octane-2-carboxamide
(2S,5R)-N-(2-aminopropoxy)-7-oxo-6-(sulfooxy)-1,6-diazabicyclo[3.2.1]octane-2-carboxamide
(2S,5R)-N-(2-amino-2-oxoethoxy)-7-oxo-6-(sulfooxy)-1,6-diazabicyclo[3.2.1]octane-2-carboxamide
(2S,5R)-N-[2-(carbamoylamino)ethoxy]-7-oxo-6-(sulfooxy)-1,6-diazabicyclo[3.2.1]octane-2-carboxamide
(2S,5R)-7-oxo-N-[2-(sulfamoylamino)ethoxy]-6-(sulfooxy)-1,6-diazabicyclo[3.2.1]octane-2-carboxamide
[({[(2S,5R)-7-oxo-6-(sulfooxy)-1,6-diazabicyclo[3.2.1]oct-2-yl]carbonyl}amino)oxy]acetic acid
2-methyl-2-[({[(2S,5R)-7-oxo-6-(sulfooxy)-1,6-diazabicyclo[3.2.1]oct-2-yl]carbonyl}amino)oxy]propanoic acid (2S,5R)-7-oxo-N-[2-(piperidin-4-yloxy)ethoxy]-6-(sulfooxy)-1,6-diazabicyclo[3.2.1]octane-2-carboxamide
(2S,5R)-7-oxo-N-(propan-2-yloxy)-6-(sulfooxy)-1,6-diazabicyclo[3.2.1]octane-2-carboxamide
(2S,5R)-N-tert-butoxy-7-oxo-6-(sulfooxy)-1,6-diazabicyclo[3.2.1]octane-2-carboxamide
(2S,5R)-N-(cyclobutyloxy)-7-oxo-6-(sulfooxy)-1,6-diazabicyclo[3.2.1]octane-2-carboxamide
(2S,5R)-N-(cyclopentyloxy)-7-oxo-6-(sulfooxy)-1,6-diazabicyclo[3.2.1]octane-2-carboxamide
(2S,5R)-N-(cyclohexyloxy)-7-oxo-6-(sulfooxy)-1,6-diazabicyclo[3.2.1]octane-2-carboxamide
(2S,5R)-N-(cycloheptyloxy)-7-oxo-6-(sulfooxy)-1,6-diazabicyclo[3.2.1]octane-2-carboxamide
(2S,5R)-N-[(3-aminocyclopentyl)oxy]-7-oxo-6-(sulfooxy)-1,6-diazabicyclo[3.2.1]octane-2-carboxamide
(2S,5R)-N-[(2-aminocyclopentyl)oxy]-7-oxo-6-(sulfooxy)-1,6-diazabicyclo[3.2.1]octane-2-carboxamide
(2S,5R)-N-{[3-(methylamino)cyclopentyl]oxy}-7-oxo-6-(sulfooxy)-1,6-diazabicyclo[3.2.1]octane-2-carboxamide
(2S,5R)-N-{[4-(dimethylamino)cyclohexyl]oxy}-7-oxo-6-(sulfooxy)-1,6-diazabicyclo[3.2.1]octane-2-carboxamide
(2S,5R)-N-[(3-aminocyclohexyl)oxy]-7-oxo-6-(sulfooxy)-1,6-diazabicyclo[3.2.1]octane-2-carboxamide
(2S,5R)-N-{[3-(methylamino)cyclohexyl]oxy}-7-oxo-6-(sulfooxy)-1,6-diazabicyclo[3.2.1]octane-2-carboxamide
(2S,5R)-7-oxo-N-(pyrrolidin-3-yloxy)-6-(sulfooxy)-1,6-diazabicyclo[3.2.1]octane-2-carboxamide
(2S,5R)-7-oxo-N-[(5-oxopyrrolidin-3-yl)oxy]-6-(sulfooxy)-1,6-diazabicyclo[3.2.1]octane-2-carboxamide
(2S,5R)-N-[(1-acetylpyrrolidin-3-yl)oxy]-7-oxo-6-(sulfooxy)-1,6-diazabicyclo[3.2.1]octane-2-carboxamide
(2S,5R)-N-[(1-methylpyrrolidin-3-yl)oxy]-7-oxo-6-(sulfooxy)-1,6-diazabicyclo[3.2.1]octane-2-carboxamide
(2S,5R)-7-oxo-N-(piperidin-3-yloxy)-6-(sulfooxy)-1,6-diazabicyclo[3.2.1]octane-2-carboxamide
(2S,5R)-7-oxo-N-(piperidin-4-yloxy)-6-(sulfooxy)-1,6-diazabicyclo[3.2.1]octane-2-carboxamide
(2S,5R)-N-(azetidin-3-yloxy)-7-oxo-6-(sulfooxy)-1,6-diazabicyclo[3.2.1]octane-2-carboxamide
(2S,5R)-7-oxo-6-(sulfooxy)-N-(tetrahydro-2H-pyran-4-yloxy)-1,6-diazabicyclo[3.2.1]octane-2-carboxamide
(2S,5R)-7-oxo-6-(sulfooxy)-N-(tetrahydro-2H-thiopyran-4-yloxy)-1,6-diazabicyclo[3.2.1]octane-2-carboxamide
(2S,5R)-N-[(1,1-dioxidotetrahydro-2H-thiopyran-4-yl)oxy]-7-oxo-6-(sulfooxy)-1,6-diazabicyclo[3.2.1]octane-2-carboxamide
(2S,5R)-N-(azepan-3-yloxy)-7-oxo-6-(sulfooxy)-1,6-diazabicyclo[3.2.1]octane-2-carboxamide
(2S,5R)-N-(1,4-oxazepan-6-yloxy)-7-oxo-6-(sulfooxy)-1,6-diazabicyclo[3.2.1]octane-2-carboxamide
(2S,5R)-N-[(1-methylpiperidin-4-yl)oxy]-7-oxo-6-(sulfooxy)-1,6-diazabicyclo[3.2.1]octane-2-carboxamide
(2S,5R)-N-[(1-carbamimidoylpiperidin-4-yl)oxy]-7-oxo-6-(sulfooxy)-1,6-diazabicyclo[3.2.1]octane-2-carboxamide
(2S,5R)-7-oxo-N-(pyrrolidin-2-ylmethoxy)-6-(sulfooxy)-1,6-diazabicyclo[3.2.1]octane-2-carboxamide
(2S,5R)-7-oxo-N-(piperidin-2-ylmethoxy)-6-(sulfooxy)-1,6-diazabicyclo[3.2.1]octane-2-carboxamide
(2S,5R)-7-oxo-N-(piperidin-3-ylmethoxy)-6-(sulfooxy)-1,6-diazabicyclo[3.2.1]octane-2-carboxamide
(2S,5R)-7-oxo-N-(piperidin-4-ylmethoxy)-6-(sulfooxy)-1,6-diazabicyclo[3.2.1]octane-2-carboxamide
(2S,5R)-N-(morpholin-3-ylmethoxy)-7-oxo-6-(sulfooxy)-1,6-diazabicyclo[3.2.1]octane-2-carboxamide
(2S,5R)-7-oxo-N-(piperazin-2-ylmethoxy)-6-(sulfooxy)-1,6-diazabicyclo[3.2.1]octane-2-carboxamide
(2S,5R)-7-oxo-6-(sulfooxy)-N-(thiomorpholin-3-ylmethoxy)-1,6-diazabicyclo[3.2.1]octane-2-carboxamide
(2S,5R)-N-(decahydroquinolin-4-yloxy)-7-oxo-6-(sulfooxy)-1,6-diazabicyclo[3.2.1]octane-2-carboxamide
(2S,5R)-N-(hexahydro-1H-pyrrolizin-2-yloxy)-7-oxo-6-(sulfooxy)-1,6-diazabicyclo[3.2.1]octane-2-carboxamide
(2S,5R)-N-(octahydroindolizin-1-yloxy)-7-oxo-6-(sulfooxy)-1,6-diazabicyclo[3.2.1]octane-2-carboxamide
(2S,5R)-N-(octahydropyrrolo[1,2-a]pyrazin-8-yloxy)-7-oxo-6-(sulfooxy)-1,6-diazabicyclo[3.2.1]octane-2-carboxamide
(2S,5R)-N-(octahydropyrrolo[1,2-a]pyrazin-7-yloxy)-7-oxo-6-(sulfooxy)-1,6-diazabicyclo[3.2.1]octane-2-carboxamide
(2S,5R)-N-(octahydrofuro[2,3-c]pyridin-3-yloxy)-7-oxo-6-(sulfooxy)-1,6-diazabicyclo[3.2.1]octane-2-carboxamide
(2S,5R)-N-(3-azabicyclo[3.1.0]hex-6-yloxy)-7-oxo-6-(sulfooxy)-1,6-diazabicyclo[3.2.1]octane-2-carboxamide
(2S,5R)-N-(decahydroquinolin-5-yloxy)-7-oxo-6-(sulfooxy)-1,6-diazabicyclo[3.2.1]octane-2-carboxamide
(2S,5R)-N-(hexahydro-4aH-cyclopenta[b][1,4]dioxin-6-yloxy)-7-oxo-6-(sulfooxy)-1,6-diazabicyclo[3.2.1]octane-2-carboxamide
(2S,5R)-N-(octahydrocyclopenta[c]pyrrol-5-yloxy)-7-oxo-6-(sulfooxy)-1,6-diazabicyclo[3.2.1]octane-2-carboxamide
(2S,5R)-N-(hexahydro-1H-cyclopenta[c]furan-5-yloxy)-7-oxo-6-(sulfooxy)-1,6-diazabicyclo[3.2.1]octane-2-carboxamide
(2S,5R)-N-(hexahydro-1H-cyclopenta[c]thiophen-5-yloxy)-7-oxo-6-(sulfooxy)-1,6-diazabicyclo[3.2.1]octane-2-carboxamide
(2S,5R)-N-(bicyclo[2.2.1]hept-2-yloxy)-7-oxo-6-(sulfooxy)-1,6-diazabicyclo[3.2.1]octane-2-carboxamide
(2S,5R)-N-[(7,7-dimethylbicyclo[2.2.1]hept-2-yl)oxy]-7-oxo-6-(sulfooxy)-1,6-diazabicyclo[3.2.1]octane-2-carboxamide
(2S,5R)-N-(1-azabicyclo[2.2.2]oct-3-yloxy)-7-oxo-6-(sulfooxy)-1,6-diazabicyclo[3.2.1]octane-2-carboxamide
(2S,5R)-N-(8-azabicyclo[3.2.1]oct-3-yloxy)-7-oxo-6-(sulfooxy)-1,6-diazabicyclo[3.2.1]octane-2-carboxamide
(2S,5R)-N-[(8-methyl-8-azabicyclo[3.2.1]oct-3-yl)oxy]-7-oxo-6-(sulfooxy)-1,6-diazabicyclo[3.2.1]octane-2-carboxamide
(2S,5R)-7-oxo-6-(sulfooxy)-N-(4,5,6,7-tetrahydrothieno[3,2-c]pyridin-7-yloxy)-1,6-diazabicyclo[3.2.1]octane-2-carboxamide
(2S,5R)-N-(6,7-dihydro-5H-pyrrolo[1,2-a]imidazol-7-yloxy)-7-oxo-6-(sulfooxy)-1,6-diazabicyclo[3.2.1]octane-2-carboxamide
(2S,5R)-N-(7-azaspiro[4.5]dec-10-yloxy)-7-oxo-6-(sulfooxy)-1,6-diazabicyclo[3.2.1]octane-2-carboxamide
(2S,5R)-N-(7-oxaspiro[4.5]dec-10-yloxy)-7-oxo-6-(sulfooxy)-1,6-diazabicyclo[3.2.1]octane-2-carboxamide
(2S,5R)-N-(1H-imidazol-2-ylmethoxy)-7-oxo-6-(sulfooxy)-1,6-diazabicyclo[3.2.1]octane-2-carboxamide
(2S,5R)-7-oxo-6-(sulfooxy)-N-(4,5,6,7-tetrahydro-1H-4,7-methanoindazol-3-ylmethoxy)-1,6-diazabicyclo[3.2.1]octane-2-carboxamide
(2S,5R)-7-oxo-N-(1H-pyrazol-3-ylmethoxy)-6-(sulfooxy)-1,6-diazabicyclo[3.2.1]octane-2-carboxamide
(2S,5R)-7-oxo-N-[2-(pyridin-2-yl)ethoxy]-6-(sulfooxy)-1,6-diazabicyclo[3.2.1]octane-2-carboxamide
(2S,5R)-7-oxo-N-[2-(piperidin-4-yl)ethoxy]-6-(sulfooxy)-1,6-diazabicyclo[3.2.1]octane-2-carboxamide
(2S,5R)-7-oxo-N-[2-(piperazin-1-yl)ethoxy]-6-(sulfooxy)-1,6-diazabicyclo[3.2.1]octane-2-carboxamide (2S,5R)-7-oxo-N-[(1-sulfamoylpyrrolidin-3-yl)oxy]-6-(sulfooxy)-1,6-diazabicyclo[3.2.1]octane-2-carboxamide
(2S,5R)-N-{[1-(methylsulfamoyl)pyrrolidin-3-yl]oxy}-7-oxo-6-(sulfooxy)-1,6-diazabicyclo[3.2.1]octane-2-carboxamide
(2S,5R)-N-[(1-carbamoylpyrrolidin-3-yl)oxy]-7-oxo-6-(sulfooxy)-1,6-diazabicyclo[3.2.1]octane-2-carboxamide
(2S,5R)-N-[(5-carbamoylpyrrolidin-3-yl)oxy]-7-oxo-6-(sulfooxy)-1,6-diazabicyclo[3.2.1]octane-2-carboxamide
(2S,5R)-N-[(1-carbamimidoylpyrrolidin-3-yl)oxy]-7-oxo-6-(sulfooxy)-1,6-diazabicyclo[3.2.1]octane-2-carboxamide
(2S,5R)-N-[(1-ethanimidoylpyrrolidin-3-yl)oxy]-7-oxo-6-(sulfooxy)-1,6-diazabicyclo[3.2.1]octane-2-carboxamide
(2S,5R)-N-{[1-(iminomethyl)pyrrolidin-3-yl]oxy}-7-oxo-6-(sulfooxy)-1,6-diazabicyclo[3.2.1]octane-2-carboxamide
(2S,5R)-7-oxo-6-(sulfooxy)-N-(tetrahydrofuran-3-yloxy)-1,6-diazabicyclo[3.2.1]octane-2-carboxamide
(2S,5R)-7-oxo-6-(sulfooxy)-N-(tetrahydro-2H-thiopyran-3-yloxy)-1,6-diazabicyclo[3.2.1]octane-2-carboxamide
(2S,5R)-N-[(4-methylpiperidin-4-yl)methoxy]-7-oxo-6-(sulfooxy)-1,6-diazabicyclo[3.2.1]octane-2-carboxamide
(2S,5R)-N-(1,4-oxazepan-2-ylmethoxy)-7-oxo-6-(sulfooxy)-1,6-diazabicyclo[3.2.1]octane-2-carboxamide
(2S,5R)-7-oxo-6-(sulfooxy)-N-(tetrahydrofuran-2-ylmethoxy)-1,6-diazabicyclo[3.2.1]octane-2-carboxamide
(2S,5R)-7-oxo-6-(sulfooxy)-N-(4,5,6,7-tetrahydrofuro[3,2-c]pyridin-7-yloxy)-1,6-diazabicyclo[3.2.1]octane-2-carboxamide
(2S,5R)-N-[(1-methyl-4,5,6,7-tetrahydro-1H-pyrazolo[3,4-c]pyridin-4-yl)oxy]-7-oxo-6-(sulfooxy)-1,6-diazabicyclo[3.2.1]octane-2-carboxamide
(2S,5R)-7-oxo-6-(sulfooxy)-N-(4,5,6,7-tetrahydro-1H-pyrazolo[3,4-c]pyridin-4-yloxy)-1,6-diazabicyclo[3.2.1]octane-2-carboxamide
(2S,5R)-N-[2-(1H-imidazol-1-yl)ethoxy]-7-oxo-6-(sulfooxy)-1,6-diazabicyclo[3.2.1]octane-2-carboxamide
(2S,5R)-N-[(4-fluoropyrrolidin-3-yl)oxy]-7-oxo-6-(sulfooxy)-1,6-diazabicyclo[3.2.1]octane-2-carboxamide
(2S,5R)-N-(1,2-oxazolidin-4-yloxy)-7-oxo-6-(sulfooxy)-1,6-diazabicyclo[3.2.1]octane-2-carboxamide
(2S,5R)-7-oxo-N-(pyrazolidin-4-yloxy)-6-(sulfooxy)-1,6-diazabicyclo[3.2.1]octane-2-carboxamide
(2S,5R)-N-[(4-aminopyrrolidin-3-yl)oxy]-7-oxo-6-(sulfooxy)-1,6-diazabicyclo[3.2.1]octane-2-carboxamide
(2S,5R)-7-oxo-N-[(4-oxopyrrolidin-3-yl)oxy]-6-(sulfooxy)-1,6-diazabicyclo[3.2.1]octane-2-carboxamide
(2S,5R)-N-[(4-hydroxypyrrolidin-3-yl)oxy]-7-oxo-6-(sulfooxy)-1,6-diazabicyclo[3.2.1]octane-2-carboxamide
(2S,5R)-N-{[(4E)-4-(hydroxyimino)pyrrolidin-3-yl]oxy}-7-oxo-6-(sulfooxy)-1,6-diazabicyclo[3.2.1]octane-2-carboxamide
(2S,5R)-N-{[(4E)-4-(methoxyimino)pyrrolidin-3-yl]oxy}-7-oxo-6-(sulfooxy)-1,6-diazabicyclo[3.2.1]octane-2-carboxamide
(2S,5R)-N-{[(4E)-4-{[(1,5-dihydroxy-4-oxo-1,4-dihydropyridin-2-yl)methoxy]imino}pyrrolidin-3-yl]oxy}-7-oxo-6-(sulfooxy)-1,6-diazabicyclo[3.2.1]octane-2-carboxamide
(2S,5R)-N-[(4,4-dimethylpyrrolidin-3-yl)oxy]-7-oxo-6-(sulfooxy)-1,6-diazabicyclo[3.2.1]octane-2-carboxamide
(2S,5R)-N-[(4-fluoropiperidin-3-yl)oxy]-7-oxo-6-(sulfooxy)-1,6-diazabicyclo[3.2.1]octane-2-carboxamide
(2S,5R)-N-[(3-fluoropiperidin-4-yl)oxy]-7-oxo-6-(sulfooxy)-1,6-diazabicyclo[3.2.1]octane-2-carboxamide
(2S,5R)-7-oxo-N-[(5-oxopiperidin-3-yl)oxy]-6-(sulfooxy)-1,6-diazabicyclo[3.2.1]octane-2-carboxamide
(2S,5R)-N-[(5,5-dimethylpiperidin-3-yl)oxy]-7-oxo-6-(sulfooxy)-1,6-diazabicyclo[3.2.1]octane-2-carboxamide
(2S,5R)-N-(2-methoxyethoxy)-7-oxo-6-(sulfooxy)-1,6-diazabicyclo[3.2.1]octane-2-carboxamide
(2S,5R)-N-[2-(morpholin-4-yl)ethoxy]-7-oxo-6-(sulfooxy)-1,6-diazabicyclo[3.2.1]octane-2-carboxamide
(2S,5R)-7-oxo-N-[2-(pyrrolidin-1-yl)ethoxy]-6-(sulfooxy)-1,6-diazabicyclo[3.2.1]octane-2-carboxamide
(2S,5R)-7-oxo-N-[2-(piperidin-1-yl)ethoxy]-6-(sulfooxy)-1,6-diazabicyclo[3.2.1]octane-2-carboxamide
(2S,5R)-N-[2-(1,1-dioxidothiomorpholin-4-yl)ethoxy]-7-oxo-6-(sulfooxy)-1,6-diazabicyclo[3.2.1]octane-2-carboxamide
(2S,5R)-N-[(1-methylazetidin-3-yl)oxy]-7-oxo-6-(sulfooxy)-1,6-diazabicyclo[3.2.1]octane-2-carboxamide
(2S,5R)-N-{[5-(dimethylcarbamoyl)pyrrolidin-3-yl]oxy}-7-oxo-6-(sulfooxy)-1,6-diazabicyclo[3.2.1]octane-2-carboxamide
methyl 4-[({[(2S,5R)-7-oxo-6-(sulfooxy)-1,6-diazabicyclo[3.2.1]oct-2-yl]carbonyl}amino)oxy]prolinate
(2S,5R)-N-{[6-(dimethylcarbamoyl)piperidin-3-yl]oxy}-7-oxo-6-(sulfooxy)-1,6-diazabicyclo[3.2.1]octane-2-carboxamide
(2S,5R)-N-[(1-methylpyrrolidin-2-yl)methoxy]-7-oxo-6-(sulfooxy)-1,6-diazabicyclo[3.2.1]octane-2-carboxamide
(2S,5R)-N-[(1-acetylpyrrolidin-2-yl)methoxy]-7-oxo-6-(sulfooxy)-1,6-diazabicyclo[3.2.1]octane-2-carboxamide
(2S,5R)-N-[(1-carbamoylpyrrolidin-2-yl)methoxy]-7-oxo-6-(sulfooxy)-1,6-diazabicyclo[3.2.1]octane-2-carboxamide
(2S,5R)-7-oxo-N-[(1-sulfamoylpyrrolidin-2-yl)methoxy]-6-(sulfooxy)-1,6-diazabicyclo[3.2.1]octane-2-carboxamide
(2S,5R)-N-[(1-carbamimidoylpyrrolidin-2-yl)methoxy]-7-oxo-6-(sulfooxy)-1,6-diazabicyclo[3.2.1]octane-2-carboxamide
(2S,5R)-N-[(1-methyl-1H-pyrazol-3-yl)methoxy]-7-oxo-6-(sulfooxy)-1,6-diazabicyclo[3.2.1]octane-2-carboxamide
(2S,5R)-N-[(1-methyl-1H-imidazol-2-yl)methoxy]-7-oxo-6-(sulfooxy)-1,6-diazabicyclo[3.2.1]octane-2-carboxamide
(2S,5R)-N-[(1-methyl-4,5,6,7-tetrahydro-1H-4,7-methanoindazol-3-yl)methoxy]-7-oxo-6-(sulfooxy)-1,6-diazabicyclo[3.2.1]octane-2-carboxamide
(2S,5R)-N-[(1,8-dimethyl-4,5,6,7-tetrahydro-1H-4,7-epiminoindazol-3-yl)methoxy]-7-oxo-6-(sulfooxy)-1,6-diazabicyclo[3.2.1]octane-2-carboxamide
(2S,5R)-N-(1H-benzimidazol-2-ylmethoxy)-7-oxo-6-(sulfooxy)-1,6-diazabicyclo[3.2.1]octane-2-carboxamide
(2S,5R)-N-(2,3-dihydro-1H-indol-2-ylmethoxy)-7-oxo-6-(sulfooxy)-1,6-diazabicyclo[3.2.1]octane-2-carboxamide
(2S,5R)-N-[(2-methyl-1H-imidazol-4-yl)methoxy]-7-oxo-6-(sulfooxy)-1,6-diazabicyclo[3.2.1]octane-2-carboxamide
(2S,5R)-N-[(1-methyl-1H-imidazol-4-yl)methoxy]-7-oxo-6-(sulfooxy)-1,6-diazabicyclo[3.2.1]octane-2-carboxamide
(2S,5R)-N-[(1-methyl-1H-imidazol-5-yl)methoxy]-7-oxo-6-(sulfooxy)-1,6-diazabicyclo[3.2.1]octane-2-carboxamide
(2S,5R)-N-[(2-amino-1,3-thiazol-4-yl)methoxy]-7-oxo-6-(sulfooxy)-1,6-diazabicyclo[3.2.1]octane-2-carboxamide
(2S,5R)-N-(1,3-oxazol-4-ylmethoxy)-7-oxo-6-(sulfooxy)-1,6-diazabicyclo[3.2.1]octane-2-carboxamide
(2S,5R)-7-oxo-6-(sulfooxy)-N-(1,3-thiazol-4-ylmethoxy)-1,6-diazabicyclo[3.2.1]octane-2-carboxamide (2S,5R)-N-[(1-methyl-1H-1,2,3-triazol-4-yl)methoxy]-7-oxo-6-(sulfooxy)-1,6-diazabicyclo[3.2.1]octane-2-carboxamide (2S,5R)-N-(1H-imidazol-4-ylmethoxy)-7-oxo-6-(sulfooxy)-1,6-diazabicyclo[3.2.1]octane-2-carboxamide (2S,5R)-N-[2-(1H-imidazol-5-yl)ethoxy]-7-oxo-6-(sulfooxy)-1,6-diazabicyclo[3.2.1]octane-2-carboxamide (2S,5R)-N-[1-(1H-imidazol-5-yl)ethoxy]-7-oxo-6-(sulfooxy)-1,6-diazabicyclo[3.2.1]octane-2-carboxamide (2S,5R)-N-[(1-methyl-1H-pyrrol-2-yl)methoxy]-7-oxo-6-(sulfooxy)-1,6-diazabicyclo[3.2.1]octane-2-carboxamide (2S,5R)-N-(1,2-oxazol-3-ylmethoxy)-7-oxo-6-(sulfooxy)-1,6-diazabicyclo[3.2.1]octane-2-carboxamide (2S,5R)-7-oxo-6-(sulfooxy)-N-(1H-1,2,4-triazol-3-ylmethoxy)-1,6-diazabicyclo[3.2.1]octane-2-carboxamide (2S,5R)-N-[(5-methylpyrazin-2-yl)methoxy]-7-oxo-6-(sulfooxy)-1,6-diazabicyclo[3.2.1]octane-2-carboxamide (2S,5R)-N-[(2-aminocyclopropyl)oxy]-7-oxo-6-(sulfooxy)-1,6-diazabicyclo[3.2.1]octane-2-carboxamide (2S,5R)-N-(morpholin-2-ylmethoxy)-7-oxo-6-(sulfooxy)-1,6-diazabicyclo[3.2.1]octane-2-carboxamide (2S,5R)-N-[2-(azetidin-3-yloxy)ethoxy]-7-oxo-6-(sulfooxy)-1,6-diazabicyclo[3.2.1]octane-2-carboxamide (2S,5R)-7-oxo-N-[2-(pyrrolidin-3-yloxy)ethoxy]-6-(sulfooxy)-1,6-diazabicyclo[3.2.1]octane-2-carboxamide (2S,5R)-7-oxo-N-[2-(piperidin-3-yloxy)ethoxy]-6-(sulfooxy)-1,6-diazabicyclo[3.2.1]octane-2-carboxamide (2S,5R)-N'-methyl-7-oxo-6-(sulfooxy)-1,6-diazabicyclo[3.2.1]octane-2-carbohydrazide (2S,5R)-N'-ethyl-7-oxo-6-(sulfooxy)-1,6-diazabicyclo[3.2.1]octane-2-carbohydrazide (2S,5R)-7-oxo-N'-(propan-2-yl)-6-(sulfooxy)-1,6-diazabicyclo[3.2.1]octane-2-carbohydrazide (2S,5R)-N',N'-dimethyl-7-oxo-6-(sulfooxy)-1,6-diazabicyclo[3.2.1]octane-2-carbohydrazide (2S,5R)-N',N'-diethyl-7-oxo-6-(sulfooxy)-1,6-diazabicyclo[3.2.1]octane-2-carbohydrazide (2S,5R)-7-oxo-N',N'-di(propan-2-yl)-6-(sulfooxy)-1,6-diazabicyclo[3.2.1]octane-2-carbohydrazide (2S,5R)-N'-cyclopropyl-7-oxo-6-(sulfooxy)-1,6-diazabicyclo[3.2.1]octane-2-carbohydrazide (2S,5R)-N'-cyclobutyl-7-oxo-6-(sulfooxy)-1,6-diazabicyclo[3.2.1]octane-2-carbohydrazide (2S,5R)-N'-cyclopentyl-7-oxo-6-(sulfooxy)-1,6-diazabicyclo[3.2.1]octane-2-carbohydrazide (2S,5R)-7-oxo-N'-(piperidin-4-yl)-6-(sulfooxy)-1,6-diazabicyclo[3.2.1]octane-2-carbohydrazide (2S,5R)-7-oxo-6-(sulfooxy)-N'-(tetrahydro-2H-pyran-4-yl)-1,6-diazabicyclo[3.2.1]octane-2-carbohydrazide (2S,5R)-7-oxo-6-(sulfooxy)-N'-(tetrahydro-2H-thiopyran-4-yl)-1,6-diazabicyclo[3.2.1]octane-2-carbohydrazide (2S,5R)-7-oxo-N'-(piperidin-3-yl)-6-(sulfooxy)-1,6-diazabicyclo[3.2.1]octane-2-carbohydrazide (2S,5R)-7-oxo-N'-(pyrrolidin-3-yl)-6-(sulfooxy)-1,6-diazabicyclo[3.2.1]octane-2-carbohydrazide (2S,5R)-N'-(1,1-dioxidotetrahydro-2H-thiopyran-4-yl)-7-oxo-6-(sulfooxy)-1,6-diazabicyclo[3.2.1]octane-2-carbohydrazide (2S,5R)-N'-acetyl-7-oxo-6-(sulfooxy)-1,6-diazabicyclo[3.2.1]octane-2-carbohydrazide (2S,5R)-7-oxo-N'-propanoyl-6-(sulfooxy)-1,6-diazabicyclo[3.2.1]octane-2-carbohydrazide (2S,5R)-N'-(2-methylpropanoyl)-7-oxo-6-(sulfooxy)-1,6-diazabicyclo[3.2.1]octane-2-carbohydrazide (2S,5R)-N'-acetyl-N'-methyl-7-oxo-6-(sulfooxy)-1,6-diazabicyclo[3.2.1]octane-2-carbohydrazide (2S,5R)-N'-methyl-7-oxo-N'-propanoyl-6-(sulfooxy)-1,6-diazabicyclo[3.2.1]octane-2-carbohydrazide (2S,5R)-N'-methyl-N'-(2-methylpropanoyl)-7-oxo-6-(sulfooxy)-1,6-diazabicyclo[3.2.1]octane-2-carbohydrazide (2S,5R)-N'-acetyl-N'-ethyl-7-oxo-6-(sulfooxy)-1,6-diazabicyclo[3.2.1]octane-2-carbohydrazide (2S,5R)-N'-ethyl-7-oxo-N'-propanoyl-6-(sulfooxy)-1,6-diazabicyclo[3.2.1]octane-2-carbohydrazide (2S,5R)-N'-(2,2-dimethylpropanoyl)-7-oxo-6-(sulfooxy)-1,6-diazabicyclo[3.2.1]octane-2-carbohydrazide (2S,5R)-N'-butanoyl-7-oxo-6-(sulfooxy)-1,6-diazabicyclo[3.2.1]octane-2-carbohydrazide (2S,5R)-N'-(2-methylbutanoyl)-7-oxo-6-(sulfooxy)-1,6-diazabicyclo[3.2.1]octane-2-carbohydrazide (2S,5R)-N'-[(dimethylamino)acetyl]-7-oxo-6-(sulfooxy)-1,6-diazabicyclo[3.2.1]octane-2-carbohydrazide (2S,5R)-7-oxo-6-(sulfooxy)-N'-(4,4,4-trifluoropropanoyl)-1,6-diazabicyclo[3.2.1]octane-2-carbohydrazide (2S,5R)-N'-(methoxyacetyl)-7-oxo-6-(sulfooxy)-1,6-diazabicyclo[3.2.1]octane-2-carbohydrazide (2S,5R)-N'-[(2R)-2-aminopropanoyl]-7-oxo-6-(sulfooxy)-1,6-diazabicyclo[3.2.1]octane-2-carbohydrazide (non-preferred name)

(2S,5R)-N'-[amino(phenyl)acetyl]-7-oxo-6-(sulfooxy)-1,6-diazabicyclo[3.2.1]octane-2-carbohydrazide (2S,5R)-N'-(cyclopropylcarbonyl)-7-oxo-6-(sulfooxy)-1,6-diazabicyclo[3.2.1]octane-2-carbohydrazide (2S,5R)-N'-(cyclobutylcarbonyl)-7-oxo-6-(sulfooxy)-1,6-diazabicyclo[3.2.1]octane-2-carbohydrazide (2S,5R)-N'-[(2,2-dimethylcyclopropyl)carbonyl]-7-oxo-6-(sulfooxy)-1,6-diazabicyclo[3.2.1]octane-2-carbohydrazide (2S,5R)-N'-[(2-methylcyclopropyl)carbonyl]-7-oxo-6-(sulfooxy)-1,6-diazabicyclo[3.2.1]octane-2-carbohydrazide (2S,5R)-N'-[(2,2-difluorocyclopropyl)carbonyl]-7-oxo-6-(sulfooxy)-1,6-diazabicyclo[3.2.1]octane-2-carbohydrazide (2S,5R)-N'-[(2-fluorocyclopropyl)carbonyl]-7-oxo-6-(sulfooxy)-1,6-diazabicyclo[3.2.1]octane-2-carbohydrazide (2S,5R)-N'-(cyclopentylcarbonyl)-7-oxo-6-(sulfooxy)-1,6-diazabicyclo[3.2.1]octane-2-carbohydrazide (2S,5R)-N'-(cyclohexylcarbonyl)-7-oxo-6-(sulfooxy)-1,6-diazabicyclo[3.2.1]octane-2-carbohydrazide (2S,5R)-N'-{[(2R)-2-aminocyclopentyl]carbonyl}-7-oxo-6-(sulfooxy)-1,6-diazabicyclo[3.2.1]octane-2-carbohydrazide (2S,5R)-7-oxo-N'-(pyrrolidin-2-ylcarbonyl)-6-(sulfooxy)-1,6-diazabicyclo[3.2.1]octane-2-carbohydrazide (2S,5R)-7-oxo-N'-(pyrrolidin-3-ylcarbonyl)-6-(sulfooxy)-1,6-diazabicyclo[3.2.1]octane-2-carbohydrazide (2S,5R)-7-oxo-N'-(piperidin-2-ylcarbonyl)-6-(sulfooxy)-1,6-diazabicyclo[3.2.1]octane-2-carbohydrazide (2S,5R)-N'-methyl-7-oxo-N'-(pyrrolidin-2-ylcarbonyl)-6-(sulfooxy)-1,6-diazabicyclo[3.2.1]octane-2-carbohydrazide (2S,5R)-7-oxo-N'-(piperidin-3-ylcarbonyl)-6-(sulfooxy)-1,6-diazabicyclo[3.2.1]octane-2-carbohydrazide (2S,5R)-7-oxo-N'-(piperidin-4-ylcarbonyl)-6-(sulfooxy)-1,6-diazabicyclo[3.2.1]octane-2-carbohydrazide (2S,5R)-7-oxo-6-(sulfooxy)-N'-(tetrahydro-2H-pyran-4-ylcarbonyl)-1,6-diazabicyclo[3.2.1]octane-2-carbohydrazide (2S,5R)-N'-[(1-methylpyrrolidin-2-yl)carbonyl]-7-oxo-6-(sulfooxy)-1,6-diazabicyclo[3.2.1]octane-2-carbohydrazide (2S,5R)-N'-[(1-methylpiperidin-4-yl)carbonyl]-7-oxo-6-(sulfooxy)-1,6-diazabicyclo[3.2.1]octane-2-carbohydrazide (2S,5R)-7-oxo-6-(sulfooxy)-N'-(tetrahydro-2H-thiopyran-4-ylcarbonyl)-1,6-diazabicyclo[3.2.1]octane-2-carbohydrazide (2S,5R)-N'-[(1,1-dioxidotetrahydro-2H-thiopyran-4-yl)carbonyl]-7-oxo-6-(sulfooxy)-1,6-diazabicyclo[3.2.1]octane-2-carbohydrazide (2S,5R)-7-oxo-N'-(pyrrolidin-2-ylacetyl)-6-(sulfooxy)-1,6-diazabicyclo[3.2.1]octane-2-carbohydrazide (2S,5R)-7-oxo-N'-(pyrrolidin-3-ylacetyl)-6-(sulfooxy)-1,6-diazabicyclo[3.2.1]octane-2-carbohydrazide (2S,5R)-N'-[(1-methylpyrrolidin-2-yl)acetyl]-7-oxo-6-(sulfooxy)-1,6-diazabicyclo[3.2.1]octane-2-carbohydrazide (2S,5R)-N'-(cyclopropylacetyl)-7-oxo-6-(sulfooxy)-1,6-diazabicyclo[3.2.1]octane-2-carbohydrazide (2S,5R)-7-oxo-N'-(piperidin-2-ylacetyl)-6-(sulfooxy)-1,6-diazabicyclo[3.2.1]octane-2-carbohydrazide (2S,5R)-N'-[(1-methylpiperidin-2-yl)acetyl]-7-oxo-6-(sulfooxy)-1,6-diazabicyclo[3.2.1]octane-2-carbohydrazide (2S,5R)-7-oxo-N'-(piperidin-3-ylacetyl)-6-(sulfooxy)-1,6-diazabicyclo[3.2.1]octane-2-carbohydrazide (2S,5R)-7-oxo-N'-(piperidin-4-ylacetyl)-6-(sulfooxy)-1,6-diazabicyclo[3.2.1]octane-2-carbohydrazide (2S,5R)-N'-[(1-methylpiperidin-4-yl)acetyl]-7-oxo-6-(sulfooxy)-1,6-diazabicyclo[3.2.1]octane-2-carbohydrazide (2S,5R)-7-oxo-N'-(pyrrolidin-1-ylacetyl)-6-(sulfooxy)-1,6-diazabicyclo[3.2.1]octane-2-carbohydrazide (2S,5R)-7-oxo-N'-(piperazin-1-ylacetyl)-6-(sulfooxy)-1,6-diazabicyclo[3.2.1]octane-2-carbohydrazide (2S,5R)-N'-(morpholin-4-ylacetyl)-7-oxo-6-(sulfooxy)-1,6-diazabicyclo[3.2.1]octane-2-carbohydrazide (2S,5R)-7-oxo-N'-(phenylcarbonyl)-6-(sulfooxy)-1,6-diazabicyclo[3.2.1]octane-2-carbohydrazide (2S,5R)-N'-(naphthalen-2-ylcarbonyl)-7-oxo-6-(sulfooxy)-1,6-diazabicyclo[3.2.1]octane-2-carbohydrazide (2S,5R)-N'-methyl-7-oxo-N'-(phenylcarbonyl)-6-(sulfooxy)-1,6-diazabicyclo[3.2.1]octane-2-carbohydrazide (2S,5R)-N'-ethyl-7-oxo-N'-(phenylcarbonyl)-6-(sulfooxy)-1,6-diazabicyclo[3.2.1]octane-2-carbohydrazide (2S,5R)-7-oxo-N'-(phenylacetyl)-6-(sulfooxy)-1,6-diazabicyclo[3.2.1]octane-2-carbohydrazide (2S,5R)-N'-(naphthalen-2-ylacetyl)-7-oxo-6-(sulfooxy)-1,6-diazabicyclo[3.2.1]octane-2-carbohydrazide (2S,5R)-N'-methyl-7-oxo-N'-(phenylacetyl)-6-(sulfooxy)-1,6-diazabicyclo[3.2.1]octane-2-carbohydrazide (2S,5R)-N'-ethyl-7-oxo-N'-(phenylacetyl)-6-(sulfooxy)-1,6-diazabicyclo[3.2.1]octane-2-carbohydrazide (2S,5R)-7-oxo-N'-(pyridin-2-ylcarbonyl)-6-(sulfooxy)-1,6-diazabicyclo[3.2.1]octane-2-carbohydrazide (2S,5R)-7-oxo-N'-(pyridin-3-ylcarbonyl)-6-(sulfooxy)-1,6-diazabicyclo[3.2.1]octane-2-carbohydrazide (2S,5R)-7-oxo-N'-(pyridin-4-ylcarbonyl)-6-(sulfooxy)-1,6-diazabicyclo[3.2.1]octane-2-carbohydrazide (2S,5R)-7-oxo-6-(sulfooxy)-N'-(thiophen-3-ylcarbonyl)-1,6-diazabicyclo[3.2.1]octane-2-carbohydrazide (2S,5R)-N'-(furan-3-ylcarbonyl)-7-oxo-6-(sulfooxy)-1,6-diazabicyclo[3.2.1]octane-2-carbohydrazide (2S,5R)-7-oxo-6-(sulfooxy)-N'-(thiophen-2-ylcarbonyl)-1,6-diazabicyclo[3.2.1]octane-2-carbohydrazide (2S,5R)-N'-(furan-2-ylcarbonyl)-7-oxo-6-(sulfooxy)-1,6-diazabicyclo[3.2.1]octane-2-carbohydrazide (2S,5R)-N'-methyl-7-oxo-N'-(pyridin-3-ylcarbonyl)-6-(sulfooxy)-1,6-diazabicyclo[3.2.1]octane-2-carbohydrazide (2S,5R)-7-oxo-N'-(1H-pyrrol-2-ylacetyl)-6-(sulfooxy)-1,6-diazabicyclo[3.2.1]octane-2-carbohydrazide (2S,5R)-7-oxo-6-(sulfooxy)-N'-(thiophen-2-ylacetyl)-1,6-diazabicyclo[3.2.1]octane-2-carbohydrazide (2S,5R)-N'-[(2-amino-1,3-thiazol-4-yl)carbonyl]-7-oxo-6-(sulfooxy)-1,6-diazabicyclo[3.2.1]octane-2-carbohydrazide (2S,5R)-N'-(furan-2-ylacetyl)-7-oxo-6-(sulfooxy)-1,6-diazabicyclo[3.2.1]octane-2-carbohydrazide (2S,5R)-7-oxo-N'-(pyridin-2-ylacetyl)-6-(sulfooxy)-1,6-diazabicyclo[3.2.1]octane-2-carbohydrazide (2S,5R)-7-oxo-N'-(pyridin-3-ylacetyl)-6-(sulfooxy)-1,6-diazabicyclo[3.2.1]octane-2-carbohydrazide (2S,5R)-7-oxo-N'-(pyridin-4-ylacetyl)-6-(sulfooxy)-1,6-diazabicyclo[3.2.1]octane-2-carbohydrazide (2S,5R)-N'-[(2-amino-1,3-thiazol-4-yl)acetyl]-7-oxo-6-(sulfooxy)-1,6-diazabicyclo[3.2.1]octane-2-carbohydrazide (2S,5R)-N'-[(2-amino-1,3-thiazol-4-yl)acetyl]-N'-methyl-7-oxo-6-(sulfooxy)-1,6-diazabicyclo[3.2.1]octane-2-carbohydrazide (2S,5R)-N'-methyl-7-oxo-N'-(pyridin-3-ylacetyl)-6-(sulfooxy)-1,6-diazabicyclo[3.2.1]octane-2-carbohydrazide (2S,5R)-7-oxo-6-(sulfooxy)-N'-(trifluoroacetyl)-1,6-diazabicyclo[3.2.1]octane-2-carbohydrazide (2S,5R)-N'-(methylsulfonyl)-7-oxo-6-(sulfooxy)-1,6-diazabicyclo[3.2.1]octane-2-carbohydrazide 2-{[(2S,5R)-7-oxo-6-(sulfooxy)-1,6-diazabicyclo[3.2.1]oct-2-yl]carbonyl}hydrazinecarboxamide 2-{[(2S,5R)-7-oxo-6-(sulfooxy)-1,6-diazabicyclo[3.2.1]oct-2-yl]carbonyl}hydrazinesulfonamide (2S,5R)-7-oxo-N'-phenyl-6-(sulfooxy)-1,6-diazabicyclo[3.2.1]octane-2-carbohydrazide (2S,5R)-N'-methyl-7-oxo-N'-phenyl-6-(sulfooxy)-1,6-diazabicyclo[3.2.1]octane-2-carbohydrazide (2S,5R)-7-oxo-N'-(pyridin-3-yl)-6-(sulfooxy)-1,6-diazabicyclo[3.2.1]octane-2-carbohydrazide (2S,5R)-N'-methyl-7-oxo-N'-(pyridin-3-yl)-6-(sulfooxy)-1,6-diazabicyclo[3.2.1]octane-2-carbohydrazide (2S,5R)-7-oxo-N-(piperidin-1-yl)-6-(sulfooxy)-1,6-diazabicyclo[3.2.1]octane-2-carboxamide (2S,5R)-7-oxo-N-(pyrrolidin-1-yl)-6-(sulfooxy)-1,6-diazabicyclo[3.2.1]octane-2-carboxamide (2S,5R)-N-(morpholin-4-yl)-7-oxo-6-(sulfooxy)-1,6-diazabicyclo[3.2.1]octane-2-carboxamide (2S,5R)-7-oxo-N-(piperazin-1-yl)-6-(sulfooxy)-1,6-diazabicyclo[3.2.1]octane-2-carboxamide (2S,5R)-7-oxo-6-(sulfooxy)-N-(thiomorpholin-4-yl)-1,6-diazabicyclo[3.2.1]octane-2-carboxamide (2S,5R)-N-(1,1-dioxidothiomorpholin-4-yl)-7-oxo-6-(sulfooxy)-1,6-diazabicyclo[3.2.1]octane-2-carboxamide (2S,5R)-7-oxo-N-(2-oxopiperidin-1-yl)-6-(sulfooxy)-1,6-diazabicyclo[3.2.1]octane-2-carboxamide (2S,5R)-7-oxo-N-(3-oxomorpholin-4-yl)-6-(sulfooxy)-1,6-diazabicyclo[3.2.1]octane-2-carboxamide (2S,5R)-7-oxo-N-(2-oxopiperazin-1-yl)-6-(sulfooxy)-1,6-diazabicyclo[3.2.1]octane-2-carboxamide (2S,5R)-7-oxo-6-(sulfooxy)-N-(tetrahydropyrimidin-1(2H)-yl)-1,6-diazabicyclo[3.2.1]octane-2-carboxamide (2S,5R)-7-oxo-N-(2-oxotetrahydropyrimidin-1(2H)-yl)-6-(sulfooxy)-1,6-diazabicyclo[3.2.1]octane-2-carboxamide (2S,5R)-N-(3-aminopiperidin-1-yl)-7-oxo-6-(sulfooxy)-1,6-diazabicyclo[3.2.1]octane-2-carboxamide (2S,5R)-N'-[(2-aminocyclopropyl)carbonyl]-7-oxo-6-(sulfooxy)-1,6-diazabicyclo[3.2.1]octane-2-carbohydrazide (2S,5R)-N'-[(2-aminocyclopropyl)carbonyl]-N'-methyl-7-oxo-6-(sulfooxy)-1,6-diazabicyclo[3.2.1]octane-2-carbohydrazide (2S,5R)-N'-(azetidin-2-ylcarbonyl)-7-oxo-6-(sulfooxy)-1,6-diazabicyclo[3.2.1]octane-2-carbohydrazide (2S,5R)-N'-(azetidin-3-ylcarbonyl)-7-oxo-6-(sulfooxy)-1,6-diazabicyclo[3.2.1]octane-2-carbohydrazide (2S,5R)-N'-[(2S)-2-aminopropanoyl]-7-oxo-6-(sulfooxy)-1,6-diazabicyclo[3.2.1]octane-2-carbohydrazide (2S,5R)-N-[(2S)-2-aminopropanoyl]-N'-methyl-7-oxo-6-(sulfooxy)-1,6-diazabicyclo[3.2.1]octane-2-carbohydrazide (2S,5R)-N'-[3-(dimethylamino)propanoyl]-7-oxo-6-(sulfooxy)-1,6-diazabicyclo[3.2.1]octane-2-carbohydrazide (2S,5R)-N'-[(3,3-difluorocyclobutyl)carbonyl]-7-oxo-6-(sulfooxy)-1,6-diazabicyclo[3.2.1]octane-2-carbohydrazide (2S,5R)-N'-[(3-aminocyclobutyl)carbonyl]-7-oxo-6-(sulfooxy)-1,6-diazabicyclo[3.2.1]octane-2-carbohydrazide (2S,5R)-N'-{[3-(methylamino)cyclobutyl]carbonyl}-7-oxo-6-(sulfooxy)-1,6-diazabicyclo[3.2.1]octane-2-carbohydrazide (2S,5R)-N'-{[3-(dimethylamino)cyclobutyl]carbonyl}-7-oxo-6-(sulfooxy)-1,6-diazabicyclo[3.2.1]octane-2-carbohydrazide The compounds of the present invention of formula (I, when Y=OR$^1$) can be readily prepared by the following reaction Scheme 2 and examples using readily available starting materials, reagents and conventional synthesis procedures known to those of ordinary skill in this art. The methods differ according to the kind of substituted hydroxylamines of general formula (V) used to prepare the bicyclic diazaoctane derivatives. The bicyclic intermediate acid (VI) may be prepared following the patent literature WO 2009/091856.

Compounds of general formula (I, Y=OR$^1$, M=H) can be prepared by coupling an appropriately substituted hydroxylamine (V) with the bicyclic acid (VI) in presence of a suitable coupling reagent to give the desired intermediate (VII). The coupling reagents useful for carrying out this step include, but are not limited to, EDCI, HOBT-DCC, HATU, HOBT, PyBop and the like. The organic solvents useful in the reaction are not particularly limited and include any of those which do not adversely affect the coupling reaction. Typical solvents include DCM, chloroform, dimethylformamide, dimethylacetamide, tetrahydrofuran, acetonitrile, dimethylsulfoxide, acetonitrile, and the like. The reaction is normally carried out at a temperature of from about 0° C. to about 30° C. and preferably at room temperature under nitrogen. After completion of the reaction the desired product can be easily separated by conventional methods such as column chromatography, crystallization or similar methods.

In the following step, the intermediate (VII) could be converted to compound (VIII) under an atmosphere of hydrogen or hydrogen mixed with an inert diluent such as nitrogen or argon in the presence of a hydrogenation catalyst. The catalysts used in this hydrogenation reaction are the type of agents known in the art for this kind of deprotection and typical examples are the noble metals, such as nickel, palladium, platinum and rhodium. Examples of the catalysts are platinum, platinum oxide, palladium, palladium oxide and the like. The catalyst is usually present in the amount from about 1 to about 50 weight percent and preferably from about 5 to about 10 weight percent based on the compound of formula (I). It is often convenient to suspend the catalyst on an inert support. A particularly convenient catalyst is palladium suspended on an inert support such as carbon, e.g 10% by weight palladium on carbon. This reaction may be conveniently effected at ambient temperature at 40 psi until reaction is complete (2 to 12 hours). Suitable solvents for this reaction are those which substantially dissolve the starting material of the formula (VII), are sufficiently volatile to be removed by evaporation and do not themselves suffer hydrogenation. Examples of such solvents include methanol, ethanol, dioxane, ethyl acetate, tetrahydrofuran or a mixture of these solvents. Upon completion, the hydroxy intermediate (VIII) can be purified by silica gel column chromatography or in many cases can be directly carried out to the next step without further purification.

Sulfation of the intermediate (VIII) can be achieved using a sulfating reagent (e.g., pyridine-SO$_3$ complex, ClSO$_3$H and DMF-SO$_3$ complex) in an appropriate solvent (e.g., pyridine or 2-picoline), e.g., as described in the literature (U.S. Pat. No. 4,337,197 A1, *J. Am. Chem. Soc.*, 1982, 104, 6053-6060). Thus, SO$_3$-Py complex can be added to a solution of the intermediate (VIII) in a solvent in excess amount, if desired, to force the reaction to completion. The organic solvents useful for this transformation are not particularly limited and include those which do not adversely affect the reaction. Typical solvents include, but not limited to, pyridine, dimethyl formamide, dimethylacetamide, acetonitrile, DCM, and the like. The transformation can be carried out at from 10° C. to 40° C., and more preferably at room temperature. The product (IX) can be isolated by standard procedure that is by filtering the reaction mixture, concentrating the filtrate, suspending the concentrate in a saturated aqueous potassium dihydrogenphosphate solution, washing the aqueous layer with ethyl acetate, adding excess amount of tetrabutylammonium hydrogen sulfate to the aqueous layer, extracting the mixture with organic solvent, such as ethyl acetate, combining the organic layers, drying and concentrating to provide the tetrabutylammonium salt intermediate. Treating the intermediate (IX) with an acid to obtain a compound of formula (Ia, M=H), wherein R$^1$ has the same definition as in formula (I). Suitable organic acids include trifluoroacetic acid, methanesulfonic acid, trifluoromethane sulfonic acid, and formic acid. The treatment is suitably conducted at a temperature in a range from about −10° C. to about 30° C. and is typically conducted at a temperature in a range of from about 0° C. to about 10° C.

The substituted hydroxylamines (V) used in the invention can be prepared by a two steps procedure using the methods well known in the art. Thus, the alcohol (II) is reacted with N-hydroxyphthalimide (III) in presence of PPh$_3$ under Mitsunobu conditions to provide the intermediate (IV). Treating (IV) with hydrazine hydrate in presence of a solvent provides the desired substituted hydroxylamine (V) which can be used without further purification (Scheme 1).

Similarly, compounds of general formula (I, Y=NR$^2$R$^3$, M=H) can be prepared by coupling an appropriately substituted hydrazine (Va) with the bicyclic acid (VI) in presence of a suitable coupling reagent to give the desired intermediate (VIIa). Utilizing the intermediate (VIIa) and carrying out similar sets of experiments as described for (Ia), the desired compounds (Ib, M=H) of the present invention can be obtained as shown in Scheme 3. The substituted hydrazines (Va) used in the present invention can be obtained from the commercial source or can be prepared by the known literature procedure.

Scheme 1

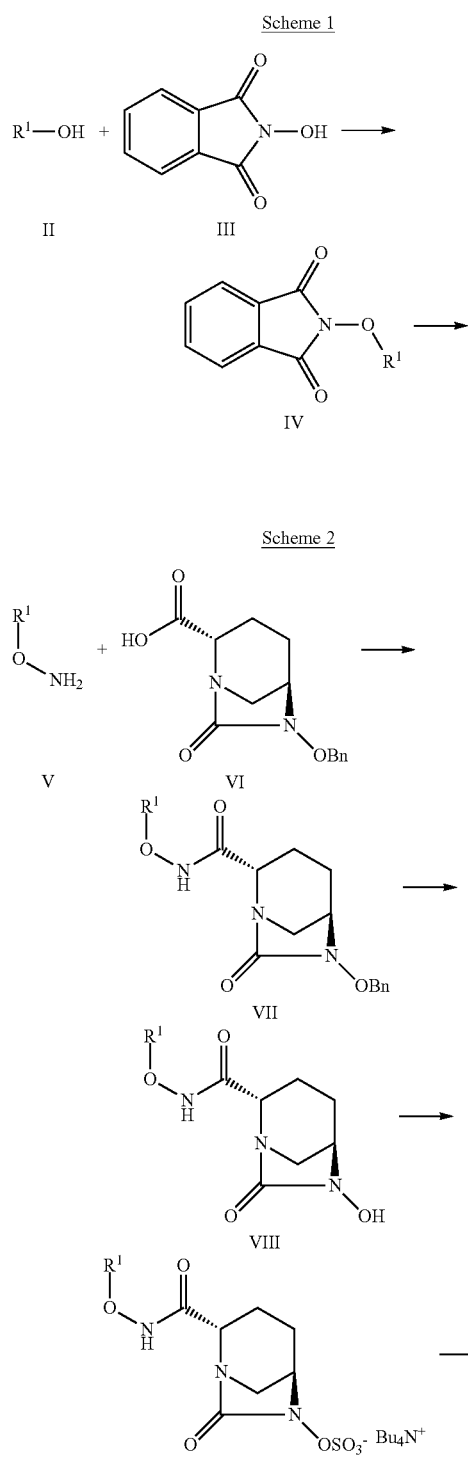

Scheme 2

Scheme 3

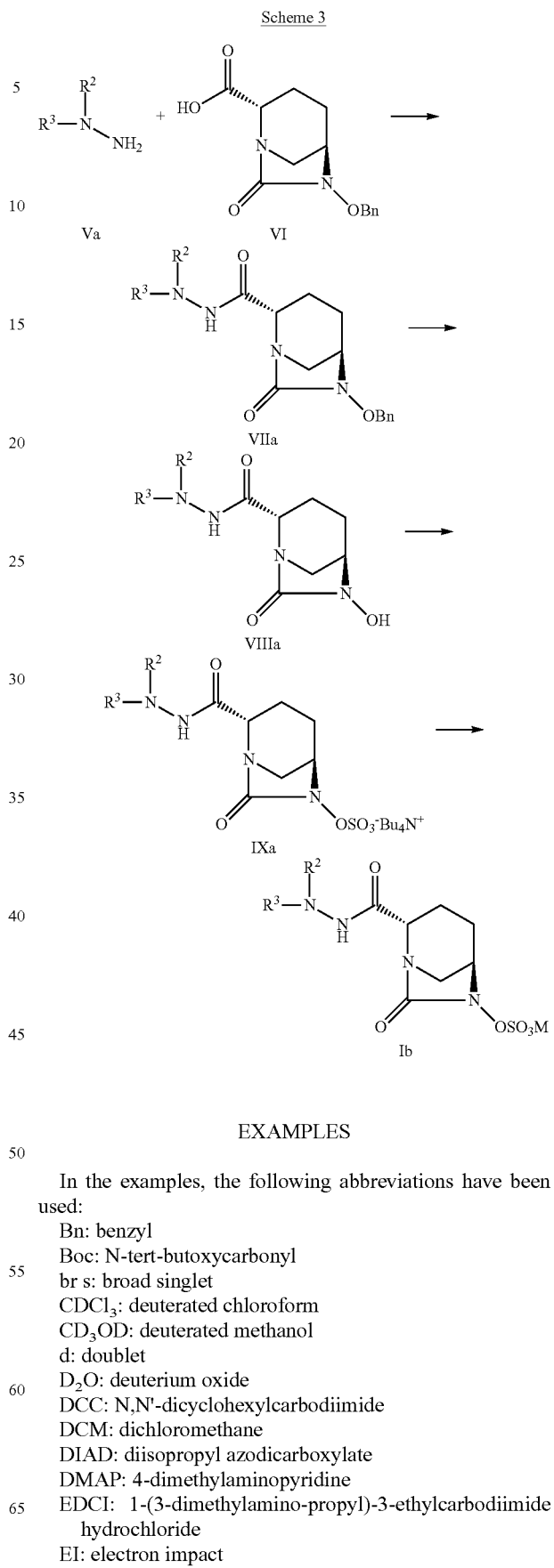

EXAMPLES

In the examples, the following abbreviations have been used:
Bn: benzyl
Boc: N-tert-butoxycarbonyl
br s: broad singlet
$CDCl_3$: deuterated chloroform
$CD_3OD$: deuterated methanol
d: doublet
$D_2O$: deuterium oxide
DCC: N,N'-dicyclohexylcarbodiimide
DCM: dichloromethane
DIAD: diisopropyl azodicarboxylate
DMAP: 4-dimethylaminopyridine
EDCI: 1-(3-dimethylamino-propyl)-3-ethylcarbodiimide hydrochloride
EI: electron impact ES: electron spray
FAB: fast atom bombardment
g: gram(s)
h: hour(s)
HOBT: N-hydroxybenzotriazole
HATU: 2-(7-aza-1H-benzotriazol-1-yl)-1,1,3,3-tetramethyluronium hexafluorophosphate
HPLC: high-performance liquid chromatography
Hz: Hertz
J: coupling constant
m: multiplet
mL: milliliter(s)
mmol: millimole(s)
MHz: megahertz
MS: mass spectrometry
m/z: mass-to-charge ratio
NMR: nuclear magnetic resonance
Pd/C: palladium on carbon
PyBop: (benzotriazol-1-yloxy)tripyrrolidinophosphonium hexafluorophosphate
s: singlet
t: triplet
TFA: trifluoroacetic acid
THF: tertrahydrofuran
δ: chemical shift in parts per million (ppm) by frequency Example 1

(2S,5R)-7-Oxo-N-[(3R)-pyrrolidin-3-yloxy]-6-(sulfooxy)-1,6-diazabicyclo[3.2.1]octane-2-carboxamide (Compound 1, Table 1)

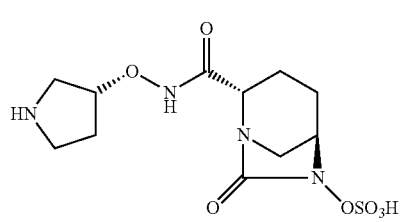

Step 1. tert-Butyl (3R)-3-[({[(2S,5R)-6-(benzyloxy)-7-oxo-1,6-diazabicyclo[3.2.1]oct-2-yl]carbonyl}amino)oxy]pyrrolidine-1-carboxylate (3)

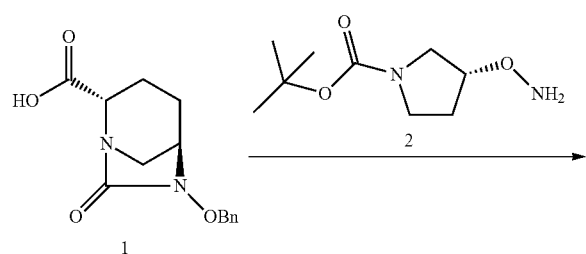

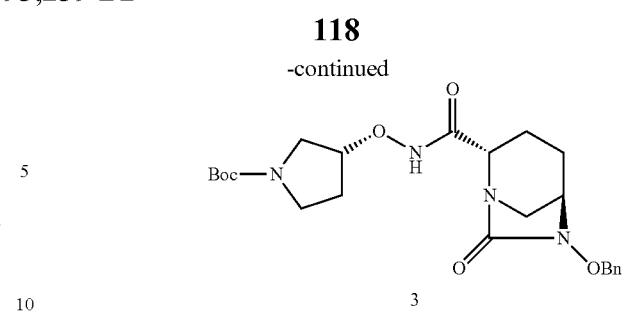

To a solution of (2S,5R)-6-(benzyloxy)-7-oxo-1,6-diazabicyclo[3.2.1]octane-2-carboxylic acid 1 (0.15 g, 0.54 mmol) in dry DCM (20 mL) were added tert-butyl (3R)-3-(aminooxy)pyrrolidine-1-carboxylate 2 (0.17 g, 0.81 mmol, *J. Med. Chem.* 2008, 51, 4601-4608), 1-hydroxybenzotriazole (0.11 g, 0.81 mmol) and 1-ethyl-(3-dimethylaminopropyl)carbodiimide hydrochloride (0.16 g, 0.81 mmol) at room temperature. The reaction mixture was stirred at room temperature overnight, and then concentrated under vacuum. The residue was purified by column chromatography to give compound tert-butyl (3R)-3-[({[(2S,5R)-6-(benzyloxy)-7-oxo-1,6-diazabicyclo[3.2.1]oct-2-yl]carbonyl}amino)oxy]pyrrolidine-1-carboxylate 3 (0.23 g, 93%) as a clear thick oil.

$^1$H NMR (400 MHz, CDCl$_3$): δ 1.26 (9H, s), 1.62 (1H, m), 1.96 (3H, m), 2.17 (1H, m), 2.28 (1H, m), 2.75 (1H, d, J=11.6 Hz), 3.01 (1H, d, J=12.0 Hz), 3.31-3.66 (5H, m), 3.96 (1H, m), 4.64 (1H, m), 4.89 (1H, d, J=11.2 Hz), 5.04 (1H, d, J=11.6 Hz), 7.41 (5H, m), 9.16 (1H, br s).

Step 2. tert-Butyl (3R)-3-[({[(2S,5R)-6-hydroxy-7-oxo-1,6-diazabicyclo[3.2.1]oct-2-yl]carbonyl}amino)oxy]pyrrolidine-1-carboxylate (4)

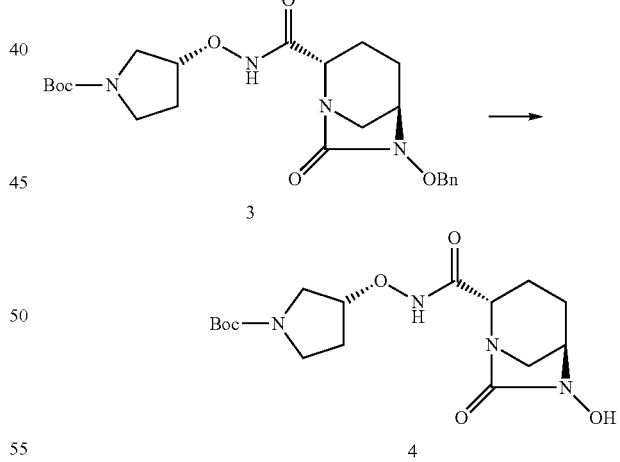

To a solution of tert-butyl (3R)-3-[({[(2S,5R)-6-(benzyloxy)-7-oxo-1,6-diazabicyclo[3.2.1]oct-2-yl]carbonyl}amino)oxy]pyrrolidine-1-carboxylate 3 (0.23 g, 050 mmol) in methanol (15 mL) was added 5% Pd/C (0.3 g). The mixture was hydrogenated at 35 psi hydrogen atmosphere at room temperature for 1 h. The catalyst was filtered out through Celite, and the filtrate was evaporated to give tert-butyl (3R)-3-[({[(2S,5R)-6-hydroxy-7-oxo-1,6-diazabicyclo[3.2.1]oct-2-yl]carbonyl}amino)oxy]pyrrolidine-1-carboxylate 4 (0.18 g, 93%) as a colorless foam.

$^1$H NMR (400 MHz, CD$_3$OD): δ 1.43 (9H, s), 1.68-2.09 (4H, m), 2.20 (2H, m), 3.03 (1H, d, J=12.0 Hz), 3.20 (3H, m), 3.60 (1H, d, J=12.0 Hz), 3.70 (1H, s), 3.86 (1H, d, J=7.2 Hz), 4.60 (1H, m), 2 protons were not observed in CD$_3$OD.

Step 3. tert-Butyl (3R)-3-[({[(2S,5R)-7-oxo-6-(sulfooxy)-1,6-diazabicyclo[3.2.1]oct-2-yl]carbonyl}amino)oxy]pyrrolidine-1-carboxylate pyridine salt (5)

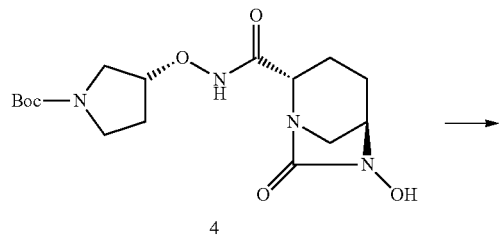

4

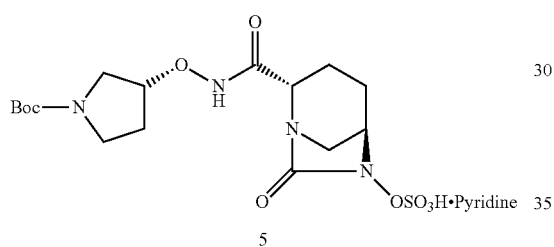

5

To a solution of tert-butyl (3R)-3-[({[(2S,5R)-6-hydroxy-7-oxo-1,6-diazabicyclo[3.2.1]oct-2-yl]carbonyl}amino)oxy]pyrrolidine-1-carboxylate 4 (0.18 g, 0.486 mmol) in dry pyridine (7 mL) under nitrogen atmosphere was added sulfur trioxide pyridine complex (0.31 g, 1.94 mmol). The mixture was stirred at room temperature for 20 h, filtered and evaporated to give tert-butyl (3R)-3-[({[(2S,5R)-7-oxo-6-(sulfooxy)-1,6-diazabicyclo[3.2.1]oct-2-yl]carbonyl}amino)-oxy]pyrrolidine-1-carboxylate pyridine salt 5 (0.22 g crude) which was used in the next step without purification.

Step 4. N,N,N-Tributylbutan-1-aminium({[(2S,5R)-2-({[(3R)-1-(tert-butoxycarbonyl)pyrrolidin-3-yl]oxy}carbamoyl)-7-oxo-1,6-diazabicyclo[3.2.1]oct-6-yl]oxy}sulfonyl)oxidanide (6)

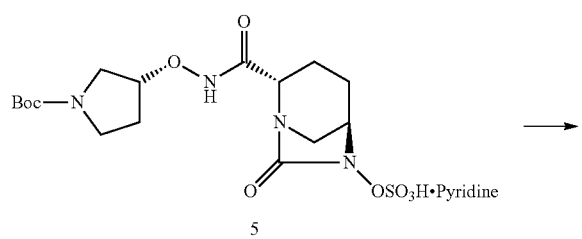

5

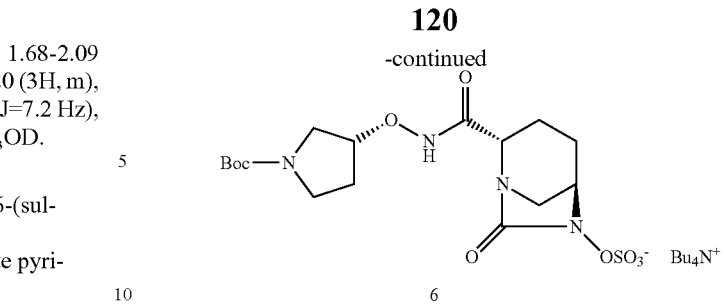

6 tert-Butyl (3R)-3-[({[(2S,5R)-7-oxo-6-(sulfooxy)-1,6-diazabicyclo[3.2.1]oct-2-yl]carbonyl}-amino)oxy]pyrrolidine-1-carboxylate pyridine salt 5 (0.22 g, 0.48 mmol) was introduced into a concentrated aqueous solution of monosodium dihydrogen phosphate solution (7 mL) so as to obtain a pH of 4. The mixture was washed with ethyl acetate, then added tetrabutyl ammonium hydrogen sulfate (0.10 g, 0.30 mmol) and stirred at room temperature for 10 min. The mixture was extracted with ethyl acetate (3×10 mL), and the extracts were combined, dried over sodium sulfate and evaporated to give N,N,N-tributylbutan-1-aminium({[(2S,5R)-2-({[(3R)-1-(tert-butoxycarbonyl)pyrrolidin-3-yl]oxy}carbamoyl)-7-oxo-1,6-diazabicyclo[3.2.1]-oct-6-yl]oxy}sulfonyl)oxidanide 6 (0.245 g, 80%) as a white solid.

$^1$H NMR (400 MHz, CDCl$_3$): δ 1.00 (12H, t, J=7.2 Hz), 1.43 (17H, m), 1.65 (8H, m), 1.90 (3H, m), 2.18 (2H, m), 2.34 (1H, m), 2.82 (1H, d, J=12 Hz), 3.28 (8H, m), 3.30-3.66 (5H, m), 3.94 (1H, d, J=7.6 Hz), 4.35 (1H, m), 4.66 (1H, s), 9.17 (1H, br s).

Step 5. (2S,5R)-7-Oxo-N-[(3R)-pyrrolidin-3-yloxy]-6-(sulfooxy)-1,6-diazabicyclo[3.2.1]octane-2-carboxamide (Compound 1, Table 1)

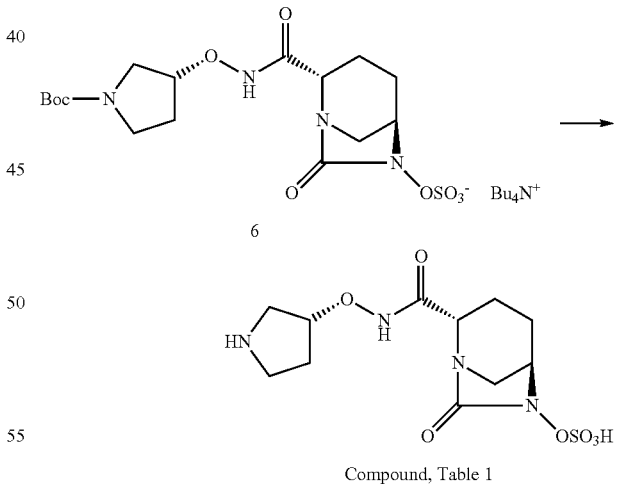

Compound, Table 1

To a solution of N,N,N-tributylbutan-1-aminium({[(2S,5R)-2-({[(3R)-1-(tert-butoxycarbonyl)pyrrolidin-3-yl]oxy}carbamoyl)-7-oxo-1,6-diazabicyclo[3.2.1]oct-6-yl]oxy}sulfonyl)oxidanide 6 (0.245 g, 0.35 mmol) in DCM (14 mL) was added trifluoroacetic acid (0.70 mL, 9.08 mmol) dropwise at 0° C. The reaction mixture was stirred for 1 h, then evaporated. Ether was added to the residue and the resulting white precipitate was collected by centrifugation. The solid was triturated with acetonitrile (2×) and the white solid was collected by centrifugation. The white solid was purified by HPLC on a prep-X Bridge-19×250 mm column and freeze-dried to give (2S,5R)-7-oxo-N-[(3R)-pyrrolidin-3-yloxy]-6-(sulfooxy)-1,6-diazabicyclo[3.2.1]octane-2-carboxamide Compound 1 (Table 1) (0.03 g, 25%) as a white solid.

$^1$H NMR (400 MHz, D$_2$O): δ 1.73 (1H, m), 1.87 (1H, m), 1.95-2.13 (3H, m), 2.16-2.40 (2H, m), 2.99 (1H, d, J=12.4 Hz), 3.19 (1H, d, J=11.6 Hz), 3.26-3.90 (3H, m), 3.46 (1H, d, J=13.2 Hz). 3.96 (1H, d, J=7.2 Hz), 4.08 (1H, s), 3 protons were not observed in D$_2$O.

HPLC: 97.24%
MS (ES$^-$): m/z: [M]$^-$=348.89

Example 2

(2S,5R)-7-Oxo-N-[(3S)-pyrrolidin-3-yloxy]-6-(sulfooxy)-1,6-diazabicyclo[3.2.1]octane-2-carboxamide (Compound 2, Table 1)

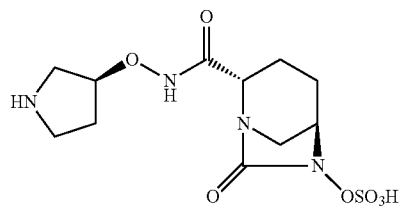

Step 1. tert-Butyl (3S)-3-[({[(2S,5R)-6-(benzyloxy)-7-oxo-1,6-diazabicyclo[3.2.1]oct-2-yl]carbonyl}amino)oxy]pyrrolidine-1-carboxylate (8)

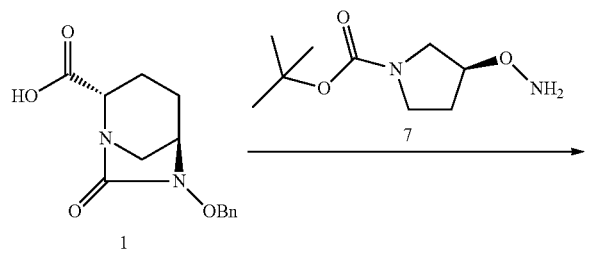

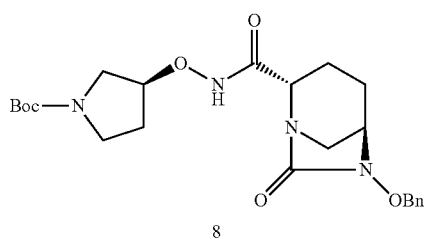

To a mixture of (2S,5R)-6-(benzyloxy)-7-oxo-1,6-diazabicyclo[3.2.1]octane-2-carboxylic acid 1 (0.150 g, 0.543 mmol, US 2005/20572 A1) in DCM (4.0 mL) were added tert-butyl (3S)-3-(aminooxy)pyrrolidine-1-carboxylate 7 (0.164 g, 0.814 mmol, WO 2008/67481 A1), 1-hydroxybenzotriazole (0.110 g, 0.814 mmol) and 1-ethyl-(3-dimethylaminopropyl) carbodiimide hydrochloride (0.156 g, 0.814 mmol) sequentially at room temperature. The mixture was stirred at room temperature overnight, diluted with DCM and concentrated to provide a residue which was subjected to chromatography to give 8 (0.22 g, 88%) as a white foam.

$^1$H NMR (400 MHz, CDCl$_3$): δ 1.46 (9H, s), 1.61 (1H, m), 1.93 (3H, m), 2.17 (1H, m), 2.30 (1H, m), 2.72 (1H, d, J=11.6 Hz), 2.99 (1H, m), 3.45 (5H, m), 3.99 (1H, m), 4.60 (1H, m), 4.92 (1H, d, J=11.6 Hz), 5.04 (1H, d, J=11.6 Hz), 7.42 (5H, m), 9.00 (1H, br s).

MS (ES$^-$) m/z: [M–H]$^-$ calcd for C$_{23}$H$_{31}$N$_4$O$_6$. 459.22. Found: 459.08.

Step 2. tert-Butyl (3S)-3-[({[(2S,5R)-6-hydroxy-7-oxo-1,6-diazabicyclo[3.2.1]oct-2-yl]carbonyl}amino)oxy]pyrrolidine-1-carboxylate (9)

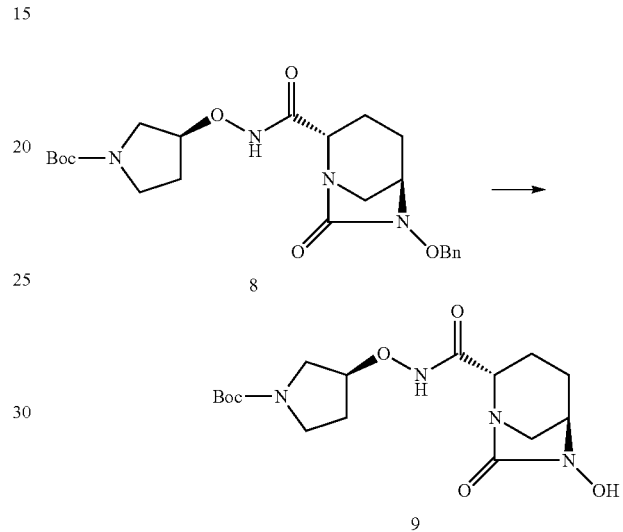

A mixture of tert-butyl (3S)-3-[({[(2S,5R)-6-(benzyloxy)-7-oxo-1,6-diazabicyclo[3.2.1]oct-2-yl]carbonyl}amino)oxy]pyrrolidine-1-carboxylate 8 (0.22 g, 0.48 mmol) and Pd/C (0.070 g) in methanol (10 mL) was hydrogenated at 1 atm at room temperature for 3 h. The mixture was filtered through Celite pad and concentrated to provide 9 (0.19 g, quant. yield) as a light yellow foam.

$^1$H NMR (400 MHz, CD$_3$OD): δ 1.46 (9H, m), 1.75-2.20 (6H, m), 3.03 (1H, d, J=11.6 Hz), 3.17 (1H, m), 3.44 (3H, m), 3.63 (1H, d, J=13.2 Hz), 3.69 (1H, m), 3.86 (1H, d, J=7.2 Hz), 4.58 (1H, t, J=3.6 Hz). 2 protons were not observed in CD$_3$OD.

MS (ES$^-$): m/z [M–H]$^-$ calcd for C$_{16}$H$_{25}$N$_4$O$_6$: 369.18. Found: 369.06.

Step 3. tert-Butyl (3S)-3-[({[(2S,5R)-7-oxo-6-(sulfooxy)-1,6-diazabicyclo[3.2.1]oct-2-yl]carbonyl}amino)oxy]pyrrolidine-1-carboxylate (10)

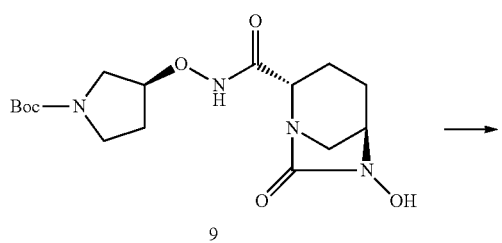

123
-continued

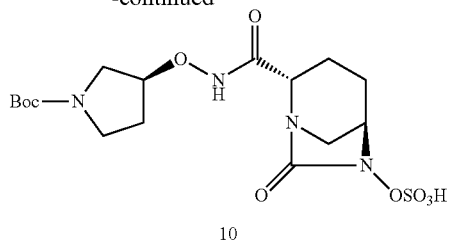

10

To a mixture of tert-butyl (3S)-3-[({[(2S,5R)-6-hydroxy-7-oxo-1,6-diazabicyclo[3.2.1]oct-2-yl]carbonyl}amino)oxy]pyrrolidine-1-carboxylate 9 (0.19 g, 0.51 mmol) in pyridine (7.0 mL) was added sulfur trioxide pyridine complex (0.326 g, 2.05 mmol). The mixture was stirred at room temperature for 23 h and concentrated to provide a residue which was subjected to chromatography to give 10 (0.11 g, 48%) as a white solid.

$^1$H NMR (400 MHz, CD$_3$OD): δ 1.47 (9H, s), 1.80-2.20 (6H, m), 3.07 (1H, d, J=12 Hz), 3.27 (1H, m), 3.44 (3H, m), 3.60 (1H, m), 3.92 (1H, d, J=11.6 Hz), 4.14 (1H, m), 4.59 (1H, m). 2 protons were not observed in CD$_3$OD.

MS (ES$^-$): m/z [M–H]$^-$ calcd for C$_{16}$H$_{25}$N$_4$O$_9$S: 449.13. Found: 448.99.

Step 4. (2S,5R)-7-Oxo-N-[(3S)-pyrrolidin-3-yloxy]-6-(sulfooxy)-1,6-diazabicyclo[3.2.1]octane-2-carboxamide (Compound 2, Table 1)

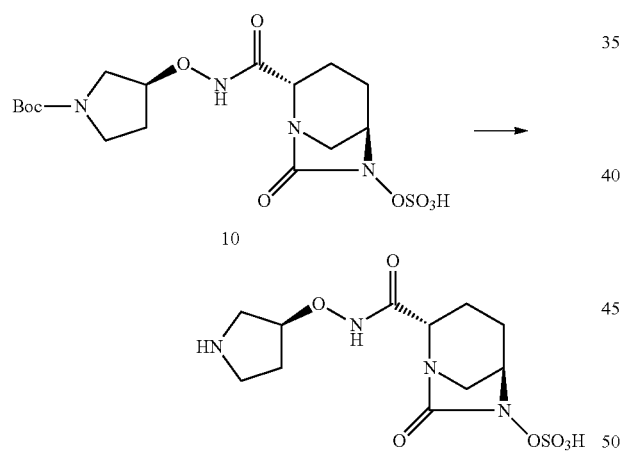

Compound 2,, Table 1

To a mixture of tert-butyl (3S)-3-[({[(2S,5R)-7-oxo-6-(sulfooxy)-1,6-diazabicyclo[3.2.1]oct-2-yl]carbonyl}amino)oxy]pyrrolidine-1-carboxylate 10 (0.11 g, 0.24 mmol) in DCM (4.0 mL) was added trifluoroacetic acid (0.20 mL) at 0° C. The mixture was stirred at 0° C. for 1 h, concentrated and washed with ether. The white solid was collected by centrifugation. The crude product was purified by preparative HPLC to provide Compound 2 (Table 1)(30.4 mg, 36%) as a white solid.

$^1$H NMR (400 MHz, D$_2$O): δ 1.74-1.83 (2H, m), 1.91-2.11 (3H, m), 2.18-2.22 (1H, m), 2.98 (1H, d, J=12 Hz), 3.17 (1H, m), 3.27-3.34 (3H, m), 3.45 (1H, dd, J=0.8 Hz, 13.6 Hz), 3.94 (1H, m), 4.06 (1H, m), 4.71 (1H, m). 3 protons were not observed in D$_2$O.

124

HPLC: 96.77%

MS (ES$^-$): m/z [M–H]$^-$ calcd for C$_{11}$H$_{17}$N$_4$O$_7$S: 349.08. Found: 348.95.

Example 3

(2S,5R)-7-Oxo-N-[(3R)-piperidin-3-yloxy]-6-(sulfooxy)-1,6-diazabicyclo[3.2.1]octane-2-carboxamide (Compound 3, Table 1)

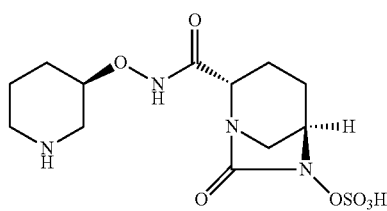

Step 1. tert-Butyl (3R)-3-[({[(2S,5R)-6-(benzyloxy)-7-oxo-1,6-diazabicyclo[3.2.1]oct-2-yl]carbonyl}amino)oxy]piperidine-1-carboxylate (12)

To a solution of (2S,5R)-6-(benzyloxy)-7-oxo-1,6-diazabicyclo[3.2.1]octane-2-carboxylic acid 1 (0.20 g, 0.72 mmol) in dry DCM (20 mL) were added tert-butyl (3R)-3-(aminooxy)piperidine-1-carboxylate 11 (0.19 g, 0.86 mmol, J. Med. Chem. 2008, 51, 4601-4608), 1-hydroxybenzotriazole (0.14 g, 1.03 mmol) and 1-ethyl-(3-dimethylaminopropyl)carbodiimide hydrochloride (0.20 g, 1.03 mmol) at room temperature. The reaction mixture was stirred at room temperature overnight, and then concentrated under vacuum. The residue was purified by column chromatography to give tert-butyl (3R)-3-[({[(2S,5R)-6-(benzyloxy)-7-oxo-1,6-diazabicyclo[3.2.1]oct-2-yl]carbonyl}amino)oxy]piperidine-1-carboxylate 12 (0.28 g, 82%) as a white solid.

$^1$H NMR (400 MHz, CDCl$_3$): δ 1.46 (9H, s), 1.61 (1H, m), 1.83 (2H, m), 2.01 (4H, m), 2.31 (1H, m), 2.79 (1H, d, J=11.2

Hz), 2.99 (3H, m), 3.30 (1H, s), 3.60-4.11 (4H, m), 4.88 (1H, d, J=11.6 Hz), 5.05 (1H, d, J=11.6 Hz), 7.39 (5H, m), 9.96 (1H, br s).

Step 2. tert-Butyl (3R)-3-[({[(2S,5R)-6-hydroxy-7-oxo-1,6-diazabicyclo[3.2.1]oct-2-yl]carbonyl}amino)oxy]piperidine-1-carboxylate (13)

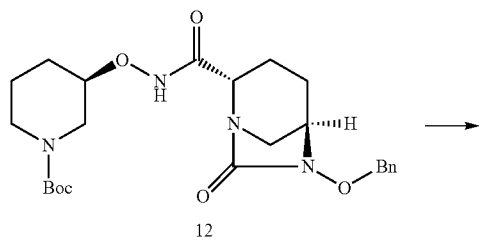

12

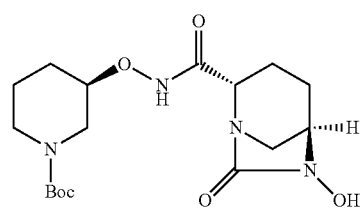

13

To a solution of tert-butyl (3R)-3-[({[(2S,5R)-6-(benzyloxy)-7-oxo-1,6-diazabicyclo[3.2.1]oct-2-yl]carbonyl}amino)oxy]piperidine-1-carboxylate 12 (0.28 g, 0.59 mmol) in methanol (20 mL) was added 5% Pd/C (0.25 g). The mixture was hydrogenated at 35 psi hydrogen atmosphere at room temperature for 1 h. The catalyst was filtered out through Celite, and the filtrate was evaporated to give tert-butyl (3R)-3-[({[(2S,5R)-6-hydroxy-7-oxo-1,6-diazabicyclo[3.2.1]oct-2-yl]carbonyl}amino)oxy]piperidine-1-carboxylate 13 (0.21 g, 91%) as a white solid.

$^1$H NMR (400 MHz, CD$_3$OD): δ 1.45 (9H, s), 1.68-1.98 (6H, m), 2.05 (1H, m), 2.22 (1H, m), 3.03 (1H, d, J=12.0 Hz), 3.13 (1H, d, J=11.6 Hz), 3.28-3.59 (4H, m), 3.71 (1H, s), 3.87 (2H, m), 2 protons were not observed in CD$_3$OD.

Step 3. tert-Butyl (3R)-3-[({[(2S,5R)-7-oxo-6-(sulfooxy)-1,6-diazabicyclo[3.2.1]oct-2-yl]carbonyl}amino)oxy]piperidine-1-carboxylate pyridine salt (14)

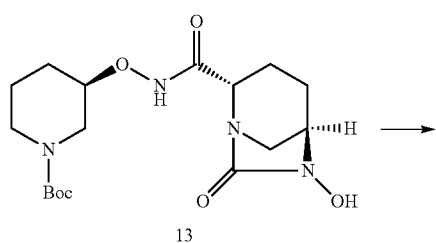

13

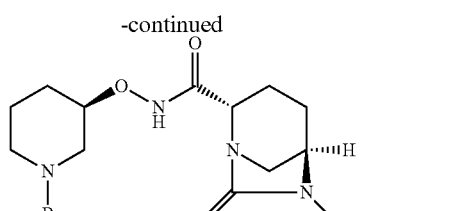

14

To a solution of tert-butyl (3R)-3-[({[(2S,5R)-6-hydroxy-7-oxo-1,6-diazabicyclo[3.2.1]oct-2-yl]carbonyl}amino)oxy]piperidine-1-carboxylate 13 (0.21 g, 0.55 mmol) in dry pyridine (8 mL) under nitrogen atmosphere was added sulfur trioxide pyridine complex (0.35 g, 2.20 mmol). The mixture was stirred at room temperature for 20 h, filtered and evaporated to give tert-butyl (3R)-3-[({[(2S,5R)-7-oxo-6-(sulfooxy)-1,6-diazabicyclo[3.2.1]oct-2-yl]carbonyl}amino)oxy]piperidine-1-carboxylate pyridine salt 14 (0.30 g crude) which was used in the next step without purification.

Step 4. N,N,N-Tributylbutan-1-aminium({[(2S,5R)-2-({[(3R)-1-(tert-butoxycarbonyl)piperidin-3-yl]oxy}carbamoyl)-7-oxo-1,6-diazabicyclo[3.2.1]oct-6-yl]oxy}sulfonyl)oxidanide (15)

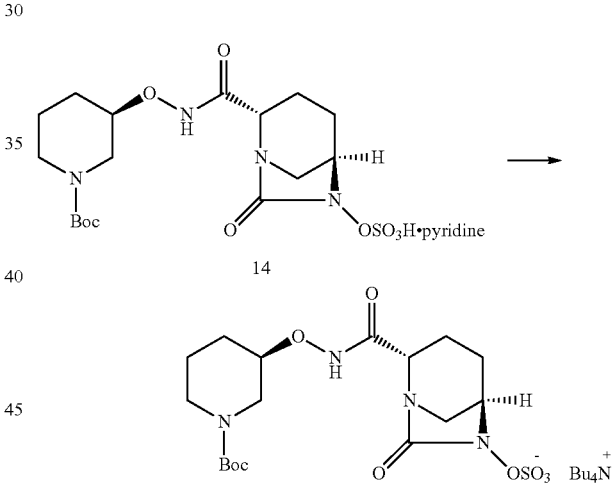

tert-Butyl (3R)-3-[({[(2S,5R)-7-oxo-6-(sulfooxy)-1,6-diazabicyclo[3.2.1]oct-2-yl]carbonyl}amino)oxy]piperidine-1-carboxylate pyridine salt 14 (0.30 g, 0.55 mmol) was introduced into a concentrated aqueous solution of monosodium dihydrogen phosphate solution (8 mL) so as to obtain a pH of 4. The mixture was washed with ethyl acetate, then added tetrabutyl ammonium hydrogen sulfate (0.117 g, 0.34 mmol) and stirred at room temperature for 10 min. The mixture was extracted with ethyl acetate (3×20 mL), and the extracts were combined, dried over sodium sulfate and evaporated to give N,N,N-tributylbutan-1-aminium ({[(2S,5R)-2-({[(3R)-1-(tert-butoxycarbonyl)piperidin-3-yl]oxy}carbamoyl)-7-oxo-1,6-diazabicyclo[3.2.1]oct-6-yl]oxy}sulfonyl)oxidanide 15 (0.3 g, 77%) as a white solid.

$^1$H NMR (400 MHz, CDCl$_3$): δ 0.98 (12H, t, J=7.2 Hz), 1.42 (17H, m), 1.65 (8H, m), 1.77 (4H, m), 2.05 (3H, m), 2.33

(1H, m), 2.85 (1H, d, J=11.6 Hz), 2.96 (2H, m), 3.24 (9H, m), 3.65 (1H, m), 3.95 (2H, m), 4.10 (1H, m), 4.13 (1H, s), 10.00 (1H, br s).

Step 5. (2S,5R)-7-Oxo-N-[(3R)-piperidin-3-yloxy]-6-(sulfooxy)-1,6-diazabicyclo[3.2.1]octane-2-carboxamide (Compound 3, Table 1)

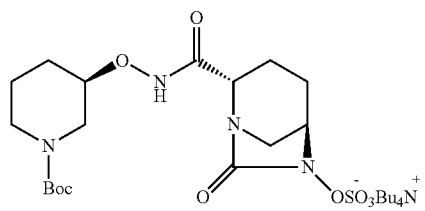

15

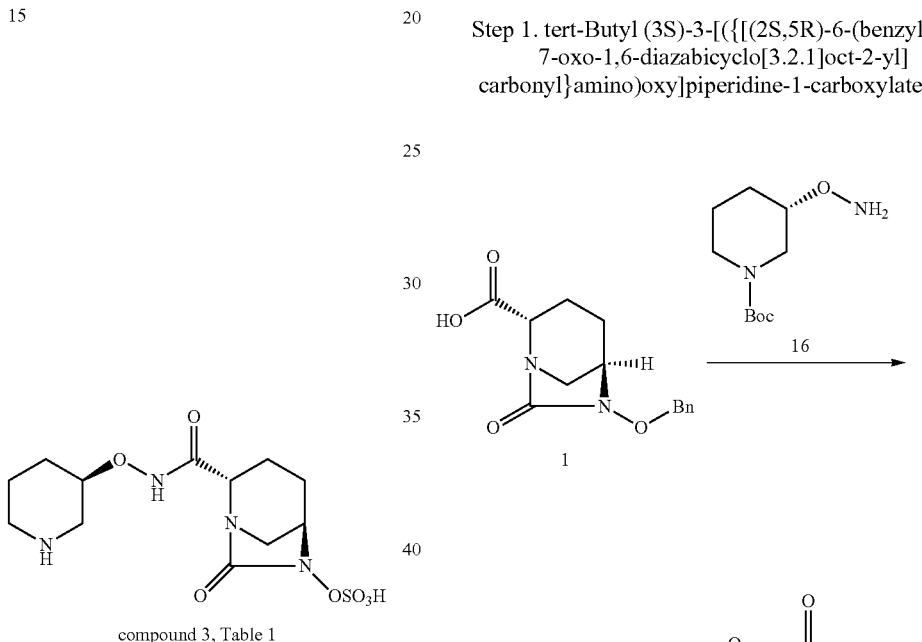

compound 3, Table 1

To a solution of N,N,N-tributylbutan-1-aminium({[(2S,5R)-2-({[(3R)-1-(tert-butoxycarbonyl)piperidin-3-yl]oxy}carbamoyl)-7-oxo-1,6-diazabicyclo[3.2.1]oct-6-yl]oxy}sulfonyl)oxidanide 15 (0.30 g, 0.42 mmol) in DCM (17 mL) was added trifluoroacetic acid (0.84 mL, 10.9 mmol) dropwise at 0° C. The reaction mixture was stirred for 1 h, then evaporated. Ether was added to the residue and the resulting white precipitate was collected by centrifugation. The solid was triturated with acetonitrile (2×) and the white solid was collected by centrifugation. The white solid was purified by HPLC and freeze-dried to give (2S,5R)-7-oxo-N-[(3R)-piperidin-3-yloxy]-6-(sulfooxy)-1,6-diazabicyclo[3.2.1]octane-2-carboxamide Compound 3 (Table 1) (0.045 g, 29.41%) as a white solid.

$^1$H NMR (400 MHz, CD$_3$OD): δ 1.60-1.78 (3H, m), 1.80-2.08 (5H, m), 2.92-3.04 (2H, m), 3.14-3.26 (2H, m), 3.30 (1H, d, J=13.2 Hz), 3.94-4.02 (2H, m), 4.08 (1H, d, s), 4.18 (1H, s), 3 protons were not observed in CD$_3$OD.

HPLC: 95.81%

MS (ES$^-$): m/z: [M]$^-$=363.02

Example 4

(2S,5R)-7-Oxo-N-[(3S)-piperidin-3-yloxy]-6-(sulfooxy)-1,6-diazabicyclo[3.2.1]octane-2-carboxamide (Compound 4, Table 1)

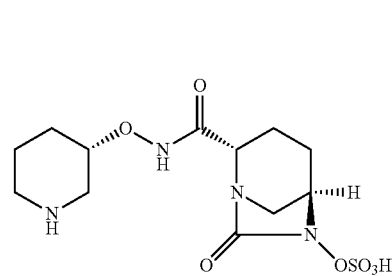

Step 1. tert-Butyl (3S)-3-[({[(2S,5R)-6-(benzyloxy)-7-oxo-1,6-diazabicyclo[3.2.1]oct-2-yl]carbonyl}amino)oxy]piperidine-1-carboxylate (17)

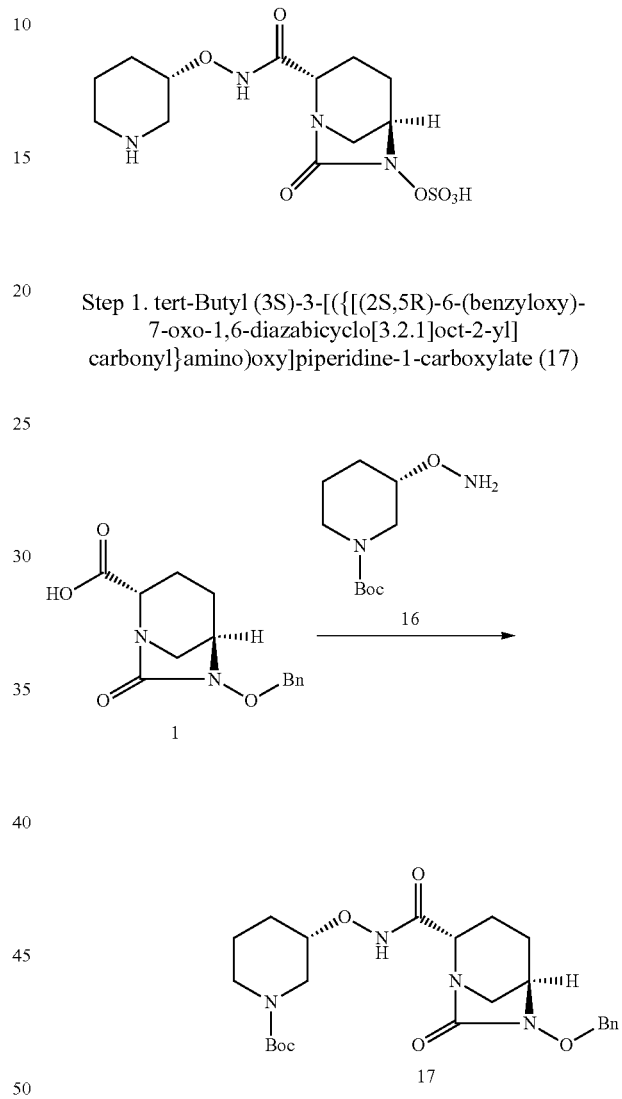

To a solution of (2S,5R)-6-(benzyloxy)-7-oxo-1,6-diazabicyclo[3.2.1]octane-2-carboxylic acid 1 (0.20 g, 0.72 mmol) in dry DCM (20 mL) were added tert-butyl (3S)-3-(aminooxy)piperidine-1-carboxylate 16 (0.19 g, 0.86 mmol, J. Med. Chem. 2008, 51, 4601-4608), 1-hydroxybenzotriazole (0.14 g, 1.03 mmol) and 1-ethyl-(3-dimethylaminopropyl)carbodiimide hydrochloride (0.20 g, 1.03 mmol) at room temperature. The reaction mixture was stirred at room temperature overnight and concentrated under vacuum. The residue was purified by column chromatography to give tert-butyl (3S)-3-[({[(2S,5R)-6-(benzyloxy)-7-oxo-1,6-diazabicyclo[3.2.1]oct-2-yl]carbonyl}amino)oxy]piperidine-1-carboxylate 17 (0.28 g, 82%) as a white solid.

$^1$H NMR (400 MHz, CDCl$_3$): δ 1.46 (9H, s), 1.61 (1H, m), 1.83 (2H, m), 2.01 (4H, m), 2.31 (1H, m), 2.79 (1H, d, J=11.2

Hz), 2.99 (3H, m), 3.30 (1H, s), 3.60-4.11 (4H, m), 4.88 (1H, d, J=11.6 Hz), 5.05 (1H, d, J=11.6 Hz), 7.39 (5H, m), 9.96 (1H, br s).

Step 2. tert-Butyl (3S)-3-[({[(2S,5R)-6-hydroxy-7-oxo-1,6-diazabicyclo[3.2.1]oct-2-yl]carbonyl}amino)oxy]piperidine-1-carboxylate (18)

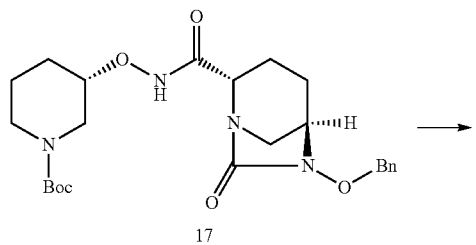

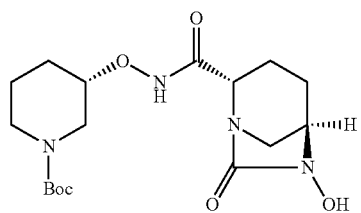

To a solution of tert-butyl (3S)-3-[({[(2S,5R)-6-(benzyloxy)-7-oxo-1,6-diazabicyclo[3.2.1]oct-2-yl]carbonyl}amino)oxy]piperidine-1-carboxylate 17 (0.28 g, 0.59 mml) in methanol (20 mL) was added 5% Pd/C (0.25 g). The mixture was hydrogenated at 35 psi hydrogen atmosphere at room temperature for 1 h. The catalyst was filtered out through Celite, and the filtrate was evaporated to give tert-butyl (3S)-3-[({[(2S,5R)-6-hydroxy-7-oxo-1,6-diazabicyclo[3.2.1]oct-2-yl]carbonyl}amino)oxy]piperidine-1-carboxylate 18 (0.22 g, 97%) as a white solid.

$^1$H NMR (400 MHz, CDCl$_3$): δ 1.45 (9H, s), 1.68-1.98 (6H, m), 2.05 (1H, m), 2.22 (1H, m), 3.03 (1H, d, J=12.0 Hz), 3.13 (1H, d, J=11.6 Hz), 3.28-3.59 (4H, m), 3.71 (1H, s), 3.87 (2H, m), 2 protons were not observed in CD$_3$OD.

Step 3. tert-Butyl (3S)-3-[({[(2S,5R)-7-oxo-6-(sulfooxy)-1,6-diazabicyclo[3.2.1]oct-2-yl]carbonyl}amino)oxy]piperidine-1-carboxylate pyridine salt (19)

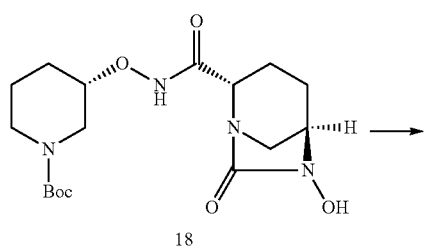

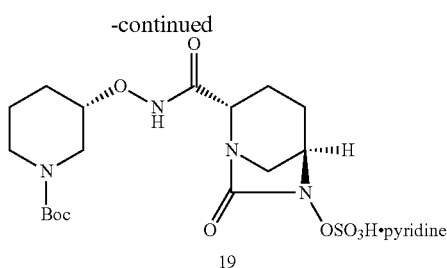

To a solution of tert-butyl (3S)-3-[({[(2S,5R)-6-hydroxy-7-oxo-1,6-diazabicyclo[3.2.1]oct-2-yl]carbonyl}amino)oxy]piperidine-1-carboxylate 18 (0.22 g, 0.57 mmol) in dry pyridine (8 mL) under nitrogen atmosphere was added sulfur trioxide pyridine complex (0.40 g, 2.51 mmol). The mixture was stirred at room temperature for 20 h, filtered and evaporated to give tert-butyl (3S)-3-[({[(2S,5R)-7-oxo-6-(sulfooxy)-1,6-diazabicyclo[3.2.1]oct-2-yl]carbonyl}amino)oxy]piperidine-1-carboxylate pyridine salt 19 (0.23 g crude) which was used in the next step without purification.

Step 4. N,N,N-Tributylbutan-1-aminium({[(2S,5R)-2-({[(3S)-1-(tert-butoxycarbonyl)piperidin-3-yl]oxy}carbamoyl)-7-oxo-1,6-diazabicyclo[3.2.1]oct-6-yl]oxy}sulfonyl)oxidanide (20)

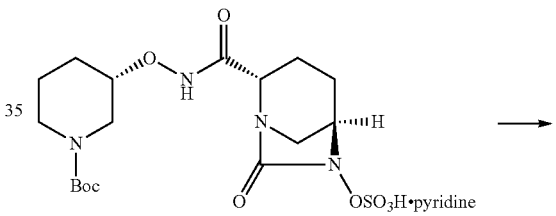

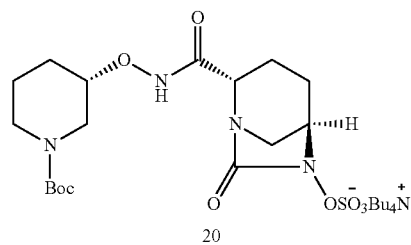

tert-Butyl (3S)-3-[({[(2S,5R)-7-oxo-6-(sulfooxy)-1,6-diazabicyclo[3.2.1]oct-2-yl]carbonyl}amino)oxy]piperidine-1-carboxylate pyridine salt 19 (0.23 g, 0.42 mmol) was introduced into a concentrated aqueous solution of monosodium dihydrogen phosphate solution (8 mL) so as to obtain a pH of 4. The mixture was washed with ethyl acetate, then added tetrabutyl ammonium hydrogen sulfate (0.088 g, 0.26 mmol) and stirred at room temperature for 10 min. The mixture was extracted with ethyl acetate (3×20 mL), and the extracts were combined, dried over sodium sulfate and evaporated to give N,N,N-tributylbutan-1-aminium ({[(2S,5R)-2-({[(3S)-1-(tert-butoxycarbonyl)piperidin-3-yl]oxy}carbamoyl)-7-oxo-1,6-diazabicyclo[3.2.1]oct-6-yl]oxy}sulfonyl)oxidanide 20 (0.23 g, 52.5%) as a white solid.

$^1$H NMR (400 MHz, CDCl$_3$): δ 0.98 (12H, t, J=7.2 Hz), 1.42 (17H, m), 1.65 (8H, m), 1.77 (4H, m), 2.05 (3H, m), 2.33

(1H, m), 2.85 (1H, d, J=11.6 Hz), 2.96 (2H, m), 3.24 (9H, m), 3.65 (1H, m), 3.95 (2H, m), 4.10 (1H, m), 4.13 (1H, s), 10.00 (1H, br s).

Step 5. (2S,5R)-7-Oxo-N-[(3S)-piperidin-3-yloxy]-6-(sulfooxy)-1,6-diazabicyclo[3.2.1]octane-2-carboxamide (Compound 4, Table 1)

compound 4, Table 1

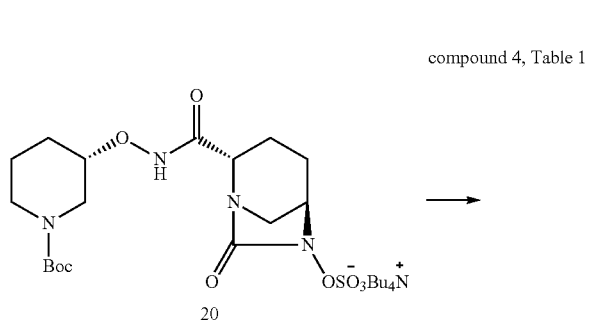

To a solution of N,N,N-tributylbutan-1-aminium({[(2S,5R)-2-({[(3S)-1-(tert-butoxycarbonyl)piperidin-3-yl]oxy}carbamoyl)-7-oxo-1,6-diazabicyclo[3.2.1]oct-6-yl]oxy}sulfonyl)oxidanide 20 (0.23 g, 0.32 mmol) in DCM (15 mL) was added trifluoroacetic acid (0.64 mL, 8.32 mmol) dropwise at 0° C. The reaction mixture was stirred for 1 h, then evaporated. Ether was added to the residue and the resulting white precipitate was collected by centrifugation. The solid was triturated with acetonitrile (2×) and the white solid was collected by centrifugation. The white solid was purified by HPLC and freeze-dried to give (2S,5R)-7-oxo-N-[(3S)-piperidin-3-yloxy]-6-(sulfooxy)-1,6-diazabicyclo[3.2.1]octane-2-carboxamide Compound 4 (Table 1) (0.008 g, 6.8%) as a white solid.

$^1$H NMR (400 MHz, CD$_3$OD): δ 1.60-1.78 (3H, m), 1.80-2.08 (5H, m), 2.92-3.04 (2H, m), 3.14-3.26 (2H, m), 3.30 (1H, d, J=13.2 Hz), 3.94-4.02 (2H, m), 4.08 (1H, d, s), 4.18 (1H, s), 3 protons were not observed in CD$_3$OD.

HPLC: 97.05%

MS (ES$^-$): m/z [M]$^-$=363.02

Example 5

Sodium[({(2S,5R)-2-[(cyclohexyloxy)carbamoyl]-7-oxo-1,6-diazabicyclo[3.2.1]oct-6-yl}oxy)sulfonyl]oxidanide (Compound 5, Table 1)

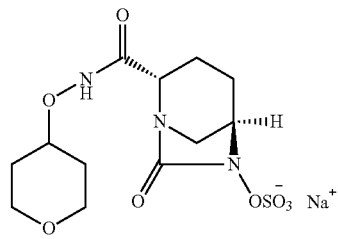

Step 1. (2S,5R)-6-(Benzyloxy)-N-(cyclohexyloxy)-7-oxo-1,6-diazabicyclo[3.2.1]octane-2-carboxamide (22)

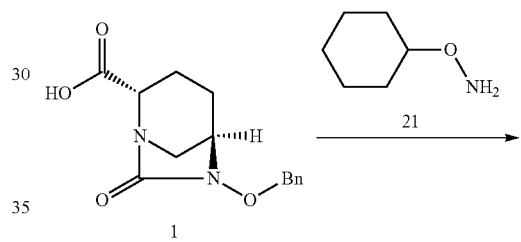

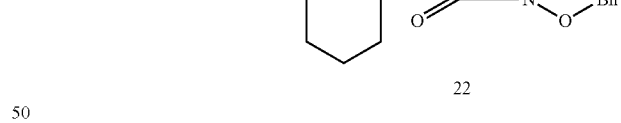

To a solution of (2S,5R)-6-(benzyloxy)-7-oxo-1,6-diazabicyclo[3.2.1]octane-2-carboxylic acid 1 (0.2 g, 0.72 mmol) in dry DCM (20 mL) were added (aminooxy)cyclohexane 21 (0.1 g, 0.86 mmol, US 2008/146625 A1), 1-hydroxybenzotriazole (0.14 g, 1.1 mmol) and 1-ethyl-(3-dimethylaminopropyl)carbodiimide hydrochloride (0.2 g, 1.1 mmol) at room temperature. The reaction mixture was stirred at room temperature overnight, and then concentrated under vacuum. The residue was purified by column chromatography to give (2S,5R)-6-(benzyloxy)-N-(cyclohexyloxy)-7-oxo-1,6-diazabicyclo[3.2.1]octane-2-carboxamide 22 (0.24 g, 89.5%) as a clear thick oil.

$^1$H NMR (400 MHz, CDCl$_3$): δ 1.23 (3H, m), 1.42 (2H, m), 1.54 (1H, m), 1.68 (1H, m), 1.76 (2H, m), 2.02 (4H, m), 2.36 (1H, m), 2.80 (1H, d, J=11.6 Hz), 2.99 (1H, d, J=12.0 Hz), 3.30 (1H, s), 3.86 (1H, m), 3.96 (1H, d, J=7.2 Hz), 4.89 (1H, d, J=11.2 Hz), 5.04 (1H, d, J=12.0 Hz), 7.39 (5H, m), 8.92 (1H, br s).

Step 2. (2S,5R)-N-(Cyclohexyloxy)-6-hydroxy-7-oxo-1,6-diazabicyclo[3.2.1]octane-2-carboxamide (23)

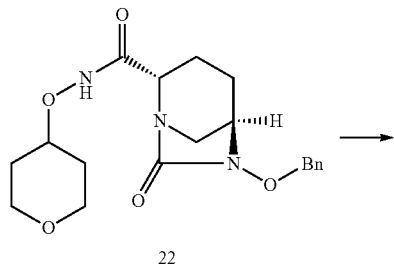

22

To a solution of (2S,5R)-6-(benzyloxy)-N-(cyclohexyloxy)-7-oxo-1,6-diazabicyclo[3.2.1]octane-2-carboxamide 22 (0.24 g, 0.64 mml) in methanol (20 mL) was added 5% Pd/C (0.30 g). The mixture was hydrogenated at 35 psi hydrogen atmosphere at room temperature for 1 h. The catalyst was filtered out through Celite, and the filtrate was evaporated to give (2S,5R)-N-(cyclohexyloxy)-6-hydroxy-7-oxo-1,6-diazabicyclo[3.2.1]octane-2-carboxamide 23 (0.155 g, 85%) as a colorless foam.

¹H NMR (400 MHz, CD₃OD): δ 1.32 (3H, m), 1.44 (2H, m), 1.55 (1H, m), 1.79 (3H, m), 1.87 (3H, m), 2.06 (1H, m), 2.16 (1H, m), 3.10 (2H, m), 3.70 (1H, s), 3.80 (2H, m), 2 protons were not observed in CD₃OD.

Step 3. (2S,5R)-N-(Cyclohexyloxy)-7-oxo-6-(sulfooxy)-1,6-diazabicyclo[3.2.1]octane-2-carboxamide pyridine salt (24)

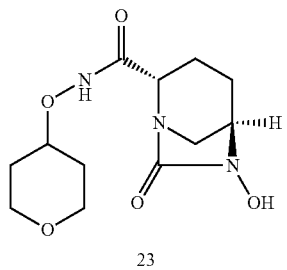

23

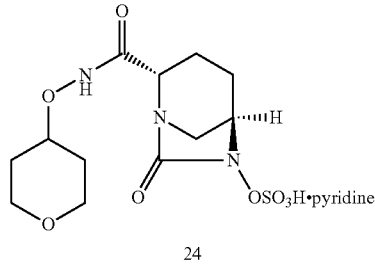

24

To a solution of (2S,5R)-N-(cyclohexyloxy)-6-hydroxy-7-oxo-1,6-diazabicyclo[3.2.1]octane-2-carboxamide 23 (0.155 g, 0.55 mmol) in dry pyridine (7 mL) under nitrogen atmosphere was added sulfur trioxide pyridine complex (0.40 g, 2.51 mmol). The mixture was stirred at room temperature for 20 h, filtered and evaporated to give (2S,5R)-N-(cyclohexyloxy)-7-oxo-6-(sulfooxy)-1,6-diazabicyclo[3.2.1]octane-2-carboxamide pyridine salt 24 (0.21 g crude) which was used in the next step without purification.

Step 4. N,N,N-Tributylbutan-1-aminium[({(2S,5R)-2-[(cyclohexyloxy)carbamoyl]-7-oxo-1,6-diazabicyclo[3.2.1]oct-6-yl}oxy)sulfonyl]oxidanide (25)

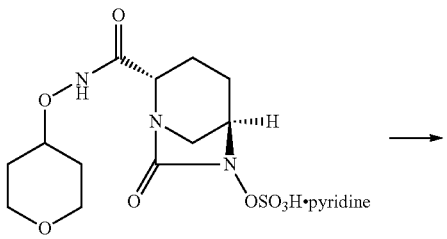

24

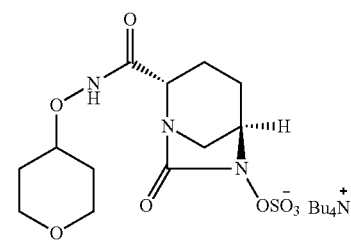

25

(2S,5R)-N-(Cyclohexyloxy)-7-oxo-6-(sulfooxy)-1,6-diazabicyclo[3.2.1]octane-2-carboxamide pyridine salt 24 (0.21 g, 0.47 mmol) was introduced into a concentrated aqueous solution of monosodium dihydrogen phosphate solution (8 mL) so as to obtain a pH of 4. The mixture was washed with ethyl acetate, then added tetrabutyl ammonium hydrogen sulfate (0.11 g, 0.32 mmol) and stirred at room temperature for 10 min. The mixture was extracted with ethyl acetate (3×20 mL), and the extracts were combined, dried over sodium sulfate and evaporated to give N,N,N-tributylbutan-1-aminium[({(2S,5R)-2-[(cyclohexyloxy)carbamoyl]-7-oxo-1,6-diazabicyclo[3.2.1]oct-6-yl}oxy)sulfonyl]oxidanide 25 (0.16 g, 56%) as a white solid.

¹H NMR (400 MHz, CDCl₃): δ 1.00 (12H, t, J=7.2 Hz), 1.18 (3H, m), 1.46 (12H, m), 1.66 (12H, m), 1.94 (2H, m), 2.15 (1H, m), 2.38 (1H, m), 2.84 (1H, d, J=11.2 Hz), 3.29 (8H, m), 3.87 (1H, m), 3.93 (1H, d, J=8.0 Hz), 4.35 (1H, s), 8.98 (1H, br s).

Step 5. Sodium[({(2S,5R)-2-[(cyclohexyloxy)carbamoyl]-7-oxo-1,6-diazabicyclo[3.2.1]oct-6-yl}oxy)sulfonyl]oxidanide (Compound 5, Table 1)

compound 5, Table 1

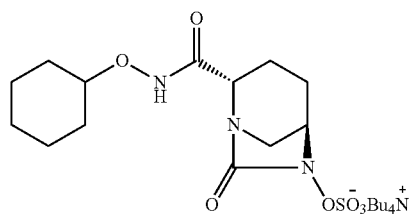

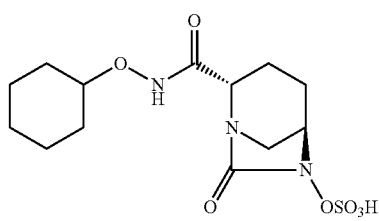

To a suspension of N,N,N-tributylbutan-1-aminium[({(2S,5R)-2-[(cyclohexyloxy)carbamoyl]-7-oxo-1,6-diazabicyclo[3.2.1]oct-6-yl}oxy)sulfonyl]oxidanide 25 (0.16 g, 0.26 mmol) in water (20 mL) was added DOWEX 50WX4 (2 g). The mixture was stirred at room temperature for 2 h, and then filtered. The filtrate was freeze-dried to give a yellow solid which was purified by HPLC and freeze-dried to give sodium [({(2S,5R)-2-[(cyclohexyloxy)carbamoyl]-7-oxo-1,6-diazabicyclo[3.2.1]oct-6-yl}oxy)sulfonyl]oxidanide Compound 5 (Table 1) (0.05 g, 50%) as a white solid.

$^1$H NMR (400 MHz, CD$_3$OD): δ 1.22-1.35 (3H, m), 1.38-1.45 (2H, m), 1.55 (1H, m), 1.78-1.89 (4H, m), 1.91-1.97 (3H, m), 2.07 (1H, m), 2.10 (1H, m), 3.10 (1H, d, J=11.6 Hz), 3.80 (1H, m), 3.90 (1H, d, J=6.8 Hz), 4.15 (1H, m), 1 proton was not observed in CD$_3$OD.

HPLC: 96.82%

MS (ES$^-$): m/z [M−Na]$^-$=362.08

Example 6

(2S,5R)-7-Oxo-N-(piperidin-4-yloxy)-6-(sulfooxy)-1,6-diazabicyclo[3.2.1]octane-2-carboxamide (Compound 6, Table 1)

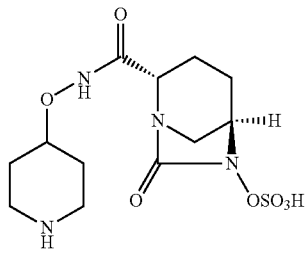

Step 1. tert-Butyl 4-[({[(2S,5R)-6-(benzyloxy)-7-oxo-1,6-diazabicyclo[3.2.1]oct-2-yl]carbonyl}amino)oxy]piperidine-1-carboxylate (27)

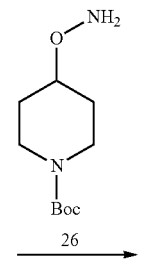

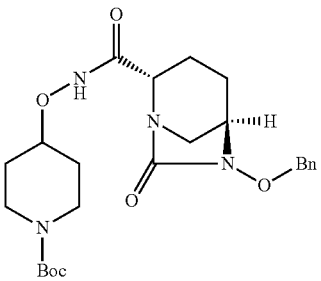

To a solution of (2S,5R)-6-(benzyloxy)-7-oxo-1,6-diazabicyclo[3.2.1]octane-2-carboxylic acid 1 (0.3 g, 1.085 mmol) in dry DCM (20 mL) were added tert-butyl 4-(aminooxy)piperidine-1-carboxylate 26 (0.29 g, 1.302 mmol, *J. Med. Chem.* 2008, 51, 4601-4608), 1-hydroxybenzotriazole (0.22 g, 1.63 mmol) and 1-ethyl-(3-dimethylaminopropyl)carbodiimide hydrochloride (0.31 g, 1.63 mmol) at room temperature. The reaction mixture was stirred at room temperature overnight and concentrated under vacuum. The residue was purified by column chromatography to give tert-butyl 4-[({[(2S,5R)-6-(benzyloxy)-7-oxo-1,6-diazabicyclo[3.2.1]oct-2-yl]carbonyl}amino)oxy]piperidine-1-carboxylate 27 (0.5 g, 98%) as a clear thick oil.

¹H NMR (400 MHz, CDCl₃): δ 1.45 (9H, s), 1.64 (4H, m), 1.93 (3H, m), 2.34 (1H, m), 2.75 (1H, d, J=11.6 Hz), 3.00 (1H, d, J=11.6 Hz), 3.13 (2H, m), 3.31 (1H, s), 3.77 (2H, m), 3.96 (1H, d, J=7.2 Hz), 4.04 (1H, m), 4.92 (1H, d, J=11.6 Hz), 5.05 (1H, d, J=11.6 Hz), 7.41 (5H, m), 8.99 (1H, br s).

Step 2. tert-Butyl 4-[({[(2S,5R)-6-hydroxy-7-oxo-1,6-diazabicyclo[3.2.1]oct-2-yl]carbonyl}amino)oxy]piperidine-1-carboxylate (28)

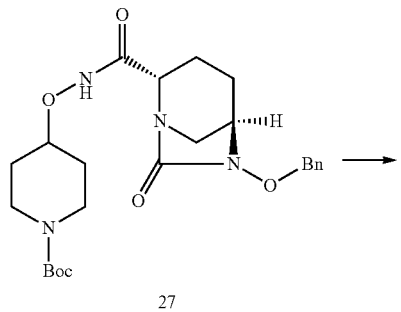

27

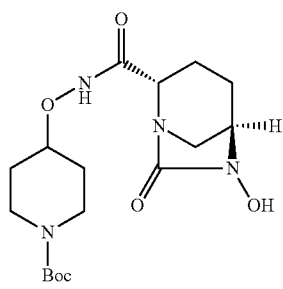

28

To a solution of tert-butyl 4-[({[(2S,5R)-6-(benzyloxy)-7-oxo-1,6-diazabicyclo[3.2.1]oct-2-yl]carbonyl}amino)oxy]piperidine-1-carboxylate 27 (0.5 g, 1.05 mml) in methanol (30 mL) was added 5% Pd/C (0.5 g). The mixture was hydrogenated under 35 psi hydrogen atmosphere at room temperature for 1 h. The catalyst was filtered out through Celite, and the filtrate was evaporated to give tert-butyl 4-[({[(2S,5R)-6-hydroxy-7-oxo-1,6-diazabicyclo[3.2.1]oct-2-yl]carbonyl}amino)oxy]piperidine-1-carboxylate 28 (0.395 g, 98%) as a colorless foam.

¹H NMR (400 MHz, CD₃OD): δ 1.45 (9H, s), 1.60 (2H, m), 1.85 (4H, m), 2.06 (1H, m), 2.18 (1H, m), 3.25 (4H, m), 3.73 (3H, m), 3.84 (1H, d, J=7.2 Hz), 4.00 (1H, m), 2 protons were not observed in CD₃OD.

Step 3. tert-Butyl 4-[({[(2S,5R)-7-oxo-6-(sulfooxy)-1,6-diazabicyclo[3.2.1]oct-2-yl]carbonyl}amino)oxy]piperidine-1-carboxylate pyridine salt (29)

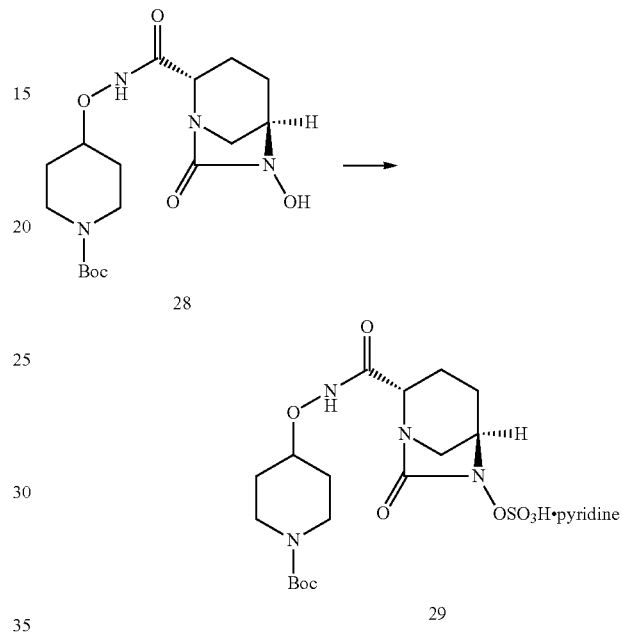

To a solution of tert-butyl 4-[({[(2S,5R)-6-hydroxy-7-oxo-1,6-diazabicyclo[3.2.1]oct-2-yl]carbonyl}amino)oxy]piperidine-1-carboxylate 28 (0.395 g, 1.03 mmol) in dry pyridine (15 mL) under nitrogen atmosphere was added sulfur trioxide pyridine complex (0.8 g, 4.86 mmol). The mixture was stirred at room temperature for 20 h, filtered and evaporated to give tert-butyl 4-[({[(2S,5R)-7-oxo-6-(sulfooxy)-1,6-diazabicyclo[3.2.1]oct-2-yl]carbonyl}amino)oxy]piperidine-1-carboxylate pyridine salt 29 (0.49 g crude) which was used in the next step without purification.

Step 4. N,N,N-Tributylbutan-1-aminium({[(2S,5R)-2-({[1-(tert-butoxycarbonyl)piperidin-4-yl]oxy}carbamoyl)-7-oxo-1,6-diazabicyclo[3.2.1]oct-6-yl]oxy}sulfonyl)oxidanide (30)

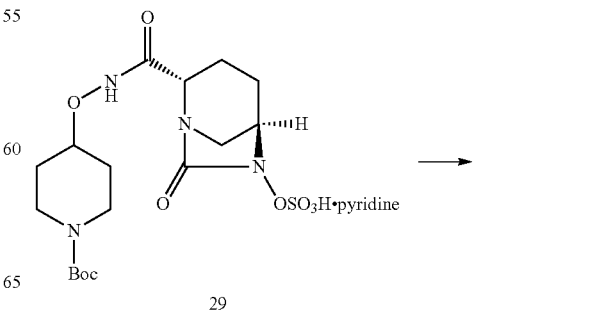

29

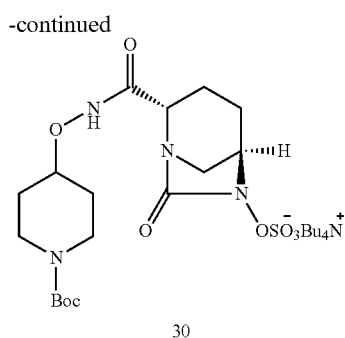

30 tert-Butyl 4-[({[(2S,5R)-7-oxo-6-(sulfooxy)-1,6-diazabicyclo[3.2.1]oct-2-yl]carbonyl}amino)oxy]piperidine-1-carboxylate pyridine salt 29 (0.49 g, 1.02 mmol) was introduced into a concentrated aqueous solution of monosodium dihydrogen phosphate solution (11 mL) so as to obtain a pH of 4. The mixture was washed with ethyl acetate, then added tetrabutyl ammonium hydrogen sulfate (0.31 g, 0.91 mmol) and stirred at room temperature for 10 min. The mixture was extracted with ethyl acetate (3×40 mL), and the extracts were combined, dried over sodium sulfate and evaporated to give N,N,N-tributylbutan-1-aminium ({[(2S,5R)-2-({[1-(tert-butoxycarbonyl)piperidin-4-yl]oxy}carbamoyl)-7-oxo-1,6-diazabicyclo[3.2.1]oct-6-yl]oxy}sulfonyl)oxidanide 30 (0.64 g, 87%) as a white solid.

$^1$H NMR (400 MHz, CDCl$_3$): δ 1.00 (12H, t, J=7.2 Hz), 1.43 (17H, m), 1.67 (11H, m), 1.88 (3H, m), 2.19 (1H, m), 2.36 (1H, m), 2.82 (1H, d, J=11.6), 3.17 (2H, m), 3.29 (9H, m), 3.78 (2H, m), 3.94 (1H, d, J=8.0 Hz), 4.06 (1H, m), 4.35 (1H, s), 9.06 (1H, br s).

Step 5. (2S,5R)-7-Oxo-N-(piperidin-4-yloxy)-6-(sulfooxy)-1,6-diazabicyclo[3.2.1]octane-2-carboxamide (Compound 6, Table 1)

compound 6, Table 1

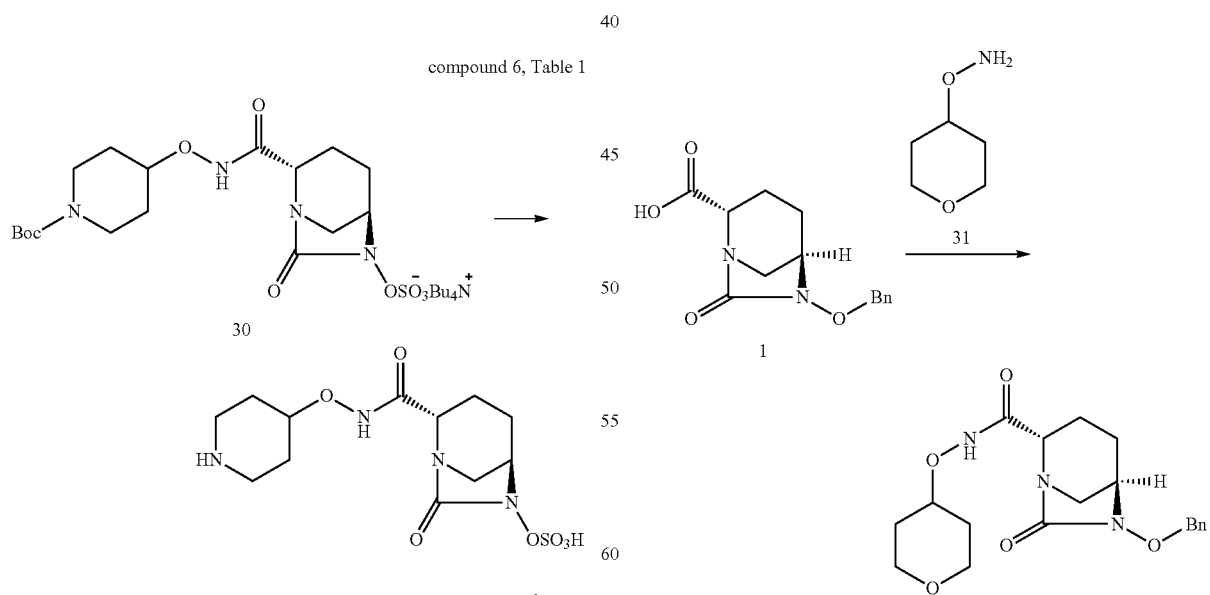

To a solution of N,N,N-tributylbutan-1-aminium({[(2S,5R)-2-({[1-(tert-butoxycarbonyl)piperidin-4-yl]oxy}carbamoyl)-7-oxo-1,6-diazabicyclo[3.2.1]oct-6-yl]oxy}sulfonyl)oxidanide 30 (0.64 g, 0.89 mmol) in DCM (36 mL) was added trifluoroacetic acid (1.78 mL, 23.1 mmol) dropwise at 0° C. The reaction mixture was stirred for 1 h, then evaporated. Ether was added to the residue and the resulting white precipitate was collected by centrifugation. The solid was triturated with acetonitrile (2×) and the white solid was collected by centrifugation. The white solid was purified by HPLC and freeze-dried to give (2S,5R)-7-oxo-N-(piperidin-4-yloxy)-6-(sulfooxy)-1,6-diazabicyclo[3.2.1]octane-2-carboxamide Compound 6 (Table 1) (0.08 g, 25%) as a white solid.

$^1$H NMR (400 MHz, CD$_3$OD): δ1.68 (1H, m), 1.70-1.87 (3H, m), 1.90-2.01 (4H, m), 2.94-3.04 (3H, m), 3.16 (1H, m), 3.25 (2H, m), 3.92 (1H, d, J=6.4 Hz), 4.07 (2H, m), 3 protons were not observed in CD$_3$OD.

HPLC: 98.21%

MS (ES$^-$): m/z [M]$^-$=362.92

Example 7

Sodium[({(2S,5R)-7-oxo-2-[(tetrahydro-2H-pyran-4-yloxy)carbamoyl]-1,6-diazabicyclo[3.2.1]oct-6-yl}oxy)sulfonyl]oxidanide (Compound 7, Table 1)

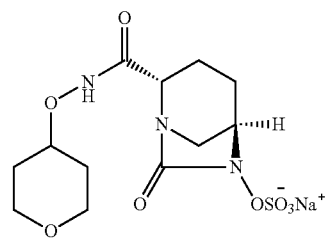

Step 1. (2S,5R)-6-(Benzyloxy)-7-oxo-N-(tetrahydro-2H-pyran-4-yloxy)-1,6-diazabicyclo[3.2.1]octane-2-carboxamide (32)

To a solution of (2S,5R)-6-(benzyloxy)-7-oxo-1,6-diazabicyclo[3.2.1]octane-2-carboxylic acid 1 (0.204 g, 0.74 mmol) in dry DCM (20 mL) were added 4-(aminooxy)tetrahydro-2H-pyran 31 (0.131 g, 1.11 mmol, *J. Med. Chem.* 2008, 51, 4601-4608), 1-hydroxybenzotriazole (0.142 g, 1.11 mmol) and 1-ethyl-(3-dimethylaminopropyl)carbodiimide hydrochloride (0.201 g, 1.11 mmol) at room temperature. The reaction mixture was stirred at room temperature overnight and concentrated under vacuum. The residue was purified by column chromatography to give (2S,5R)-6-(benzyloxy)-7-oxo-N-(tetrahydro-2H-pyran-4-yloxy)-1,6-diazabicyclo[3.2.1]octane-2-carboxamide 32 (0.26 g, 93%) as a clear thick oil.

$^1$H NMR (400 MHz, CDCl$_3$): δ 1.69 (4H, m), 1.97 (3H, m), 2.32 (1H, m), 2.75 (1H, d, J=11.2 Hz), 3.00 (1H, d, J=11.6 Hz), 3.31 (1H, s), 3.99 (3H, m), 4.06 (1H, m), 4.89 (1H, d, J=11.2 Hz), 5.04 (1H, d, J=11.6 Hz), 7.41 (5H, m), 8.94 (1H, br s).

Step 2. (2S,5R)-6-Hydroxy-7-oxo-N-(tetrahydro-2H-pyran-4-yloxy)-1,6-diazabicyclo[3.2.1]octane-2-carboxamide (33)

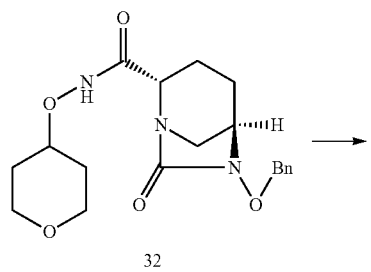

32

To a solution of (2S,5R)-6-(benzyloxy)-7-oxo-N-(tetrahydro-2H-pyran-4-yloxy)-1,6-diazabicyclo[3.2.1]octane-2-carboxamide 32 (0.26 g, 0.69 mml) in methanol (20 mL) was added 5% Pd/C (0.30 g). The mixture was hydrogenated under 35 psi hydrogen atmosphere at room temperature for 1 h. The catalyst was filtered out through Celite, and the filtrate was evaporated to give (2S,5R)-6-hydroxy-7-oxo-N-(tetrahydro-2H-pyran-4-yloxy)-1,6-diazabicyclo[3.2.1]octane-2-carboxamide 33 (0.19 g, 99%) as a colorless foam.

$^1$H NMR (400 MHz, CD$_3$OD): δ 1.65 (2H, m), 1.81 (1H, m), 1.95 (3H, m), 2.08 (1H, m), 2.15 (1H, m), 3.05 (2H, m), 3.45 (2H, m), 3.70 (1H, s), 3.84 (1H, d, J=7.2 Hz), 3.91 (2H, m), 4.04 (1H, m), 2 protons were not observed in CD$_3$OD.

Step 3. (2S,5R)-7-Oxo-6-(sulfooxy)-N-(tetrahydro-2H-pyran-4-yloxy)-1,6-diazabicyclo[3.2.1]octane-2-carboxamide pyridine salt (34)

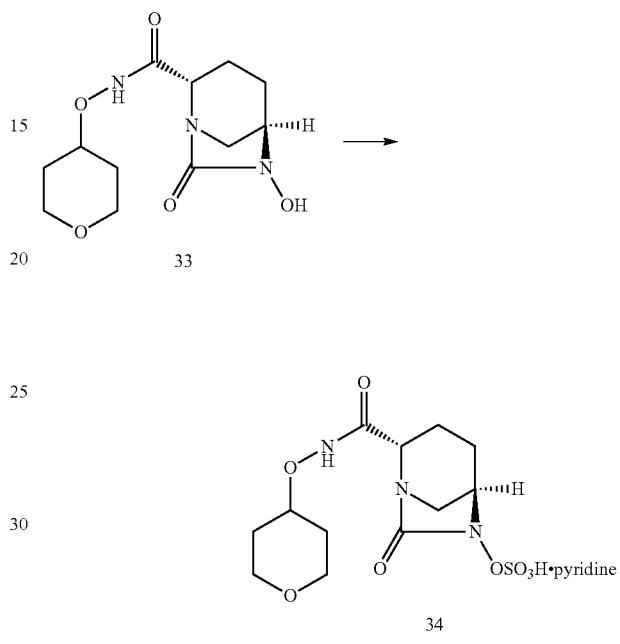

To a solution of (2S,5R)-6-hydroxy-7-oxo-N-(tetrahydro-2H-pyran-4-yloxy)-1,6-diazabicyclo[3.2.1]octane-2-carboxamide 33 (0.197 g, 0.69 mmol) in dry pyridine (7 mL) under nitrogen atmosphere was added sulfur trioxide pyridine complex (0.44 g, 2.76 mmol). The mixture was stirred at room temperature for 20 h, filtered and evaporated to give (2S,5R)-7-oxo-6-(sulfooxy)-N-(tetrahydro-2H-pyran-4-yloxy)-1,6-diazabicyclo[3.2.1]octane-2-carboxamide pyridine salt 34 (0.28 g crude) which was used in the next step without purification.

Step 4. N,N,N-Tributylbutan-1-aminium[({(2S,5R)-7-oxo-2-[(tetrahydro-2H-pyran-4-yloxy)carbamoyl]-1,6-diazabicyclo[3.2.1]oct-6-yl}oxy)sulfonyl]oxidanide (35)

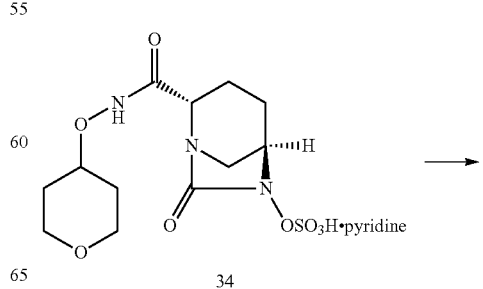

34

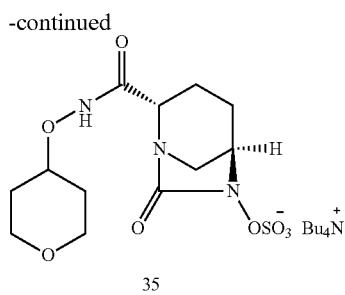

35

(2S,5R)-7-Oxo-6-(sulfooxy)-N-(tetrahydro-2H-pyran-4-yloxy)-1,6-diazabicyclo[3.2.1]octane-2-carboxamide pyridine salt 34 (0.28 g, 0.63 mmol) was introduced into a concentrated aqueous solution of monosodium dihydrogen phosphate solution (9 mL) so as to obtain a pH of 4. The mixture was washed with ethyl acetate, then added tetrabutyl ammonium hydrogen sulfate (0.13 g, 0.38 mmol) and stirred at room temperature for 10 min. The mixture was extracted with ethyl acetate (3×20 mL), and the extracts were combined, dried over sodium sulfate and evaporated to give N,N,N-tributylbutan-1-aminium[({(2S,5R)-7-oxo-2-[(tetrahydro-2H-pyran-4-yloxy)carbamoyl]-1,6-diazabicyclo[3.2.1]oct-6 yl}oxy)sulfonyl]oxidanide 35 (0.21 g, 55%) as a white solid.

¹H NMR (400 MHz, CDCl₃): δ 1.00 (12H, t, J=7.2 Hz), 1.47 (8H, m), 1.69 (11H, m), 1.88 (3H, m), 2.17 (1H, m), 2.35 (1H, m), 2.86 (1H, d, J=11.2 Hz), 3.31 (8H, m), 3.46 (1H, m), 3.99 (2H, m), 4.12 (1H, m), 4.32 (1H, s), 9.17 (1H, br s).

Step 5. Sodium[({(2S,5R)-7-oxo-2-[(tetrahydro-2H-pyran-4-yloxy)carbamoyl]-1,6-diazabicyclo[3.2.1]oct-6-yl}oxy)sulfonyl]oxidanide (Compound 7, Table 1)

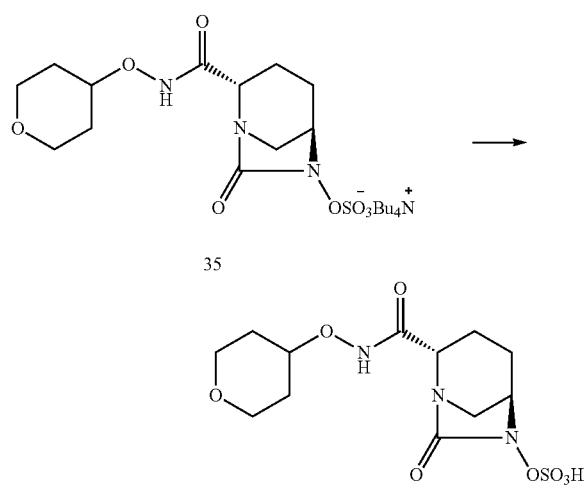

compound 7, Table 1

To a suspension of N,N,N-tributylbutan-1-aminium[({(2S,5R)-7-oxo-2-[(tetrahydro-2H-pyran-4-yloxy)carbamoyl]-1,6-diazabicyclo[3.2.1]oct-6-yl}oxy)sulfonyl]oxidanide 35 (0.21 g, 0.34 mmol) in water (20 mL) was added DOWEX 50WX4 (2 g). The mixture was stirred at room temperature for 2 h and filtered. The filtrate was freeze-dried to give a yellow solid which was purified by HPLC and freeze-dried again to give sodium[({(2S,5R)-7-oxo-2-[(tetrahydro-2H-pyran-4-yloxy)carbamoyl]-1,6-diazabicyclo[3.2.1]oct-6-yl}oxy)sulfonyl]oxidanide Compound 7 (Table 1) (0.07 g, 46%) as a white solid.

¹H NMR (400 MHz, CD₃OD): δ 1.65 (2H, m), 1.81-1.98 (4H, m), 2.09 (1H, m), 2.19 (1H, m), 3.10 (1H, d, J=11.6 Hz), 3.24 (1H, d, J=12.0 Hz), 3.47 (2H, m), 3.95 (3H, m), 4.15 (1H, m), 1 proton was not observed in CD₃OD.

HPLC: 98.88%

MS (ES⁻): m/z [M]⁻=364.02

Example 8

(2S,5R)-N-(Azetidin-3-yloxy)-7-oxo-6-(sulfooxy)-1,6-diazabicyclo[3.2.1]octane-2-carboxamide (Compound 8, Table 1)

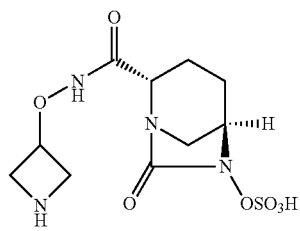

Step 1. tert-Butyl 3-[({[(2S,5R)-6-(benzyloxy)-7-oxo-1,6-diazabicyclo[3.2.1]oct-2-yl]carbonyl}amino)oxy]azetidine-1-carboxylate (37)

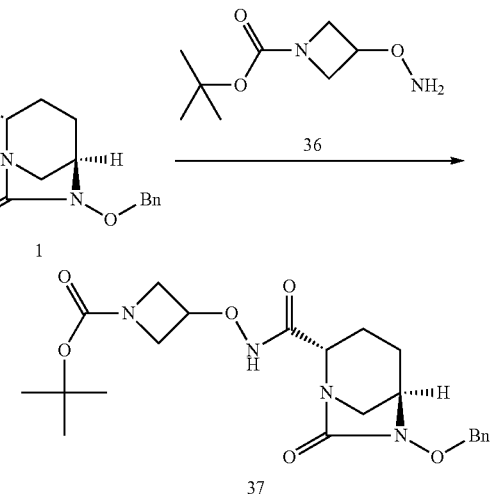

To a solution of compound (2S,5R)-6-(benzyloxy)-7-oxo-1,6-diazabicyclo[3.2.1]octane-2-carboxylic acid 1 (0.193 g, 0.70 mmol) in dry DCM (20 mL) were added tert-butyl 3-(aminooxy)azetidine-1-carboxylate 36 (0.198 g, 1.05 mmol, J. Med. Chem. 2008, 51, 4601-4608), 1-hydroxybenzotriazole (0.142 g, 1.05 mmol) and 1-ethyl-(3-dimethylaminopropyl)carbodiimide hydrochloride (0.201 g, 1.05 mmol) at room temperature. The reaction mixture was stirred at room temperature overnight, and then concentrated under vacuum. The residue was purified by column chromatography to give tert-butyl 3-[({[(2S,5R)-6-(benzyloxy)-7-oxo-1, 6-diazabicyclo[3.2.1]oct-2-yl]carbonyl}amino)oxy]azetidine-1-carboxylate 37 (0.15 g, 48%) as a clear thick oil.

¹H NMR (400 MHz, CDCl₃): δ 1.42 (9H, s), 1.65 (1H, m), 1.99 (2H, m), 2.32 (1H, m), 2.37 (1H, d, J=11.6 Hz), 2.99 (1H, d, J=12.0 Hz), 3.32 (1H, s), 3.99 (3H, m), 4.09 (2H, m), 4.72 (1H, m), 4.88 (1H, d, J=11.6 Hz), 5.05 (1H, d, J=11.6 Hz), 7.37 (5H, m), 9.03 (1H, br s).

Step 2. tert-Butyl 3-[({[(2S,5R)-6-hydroxy-7-oxo-1,6-diazabicyclo[3.2.1]oct-2-yl]carbonyl}amino)oxy]azetidine-1-carboxylate (38)

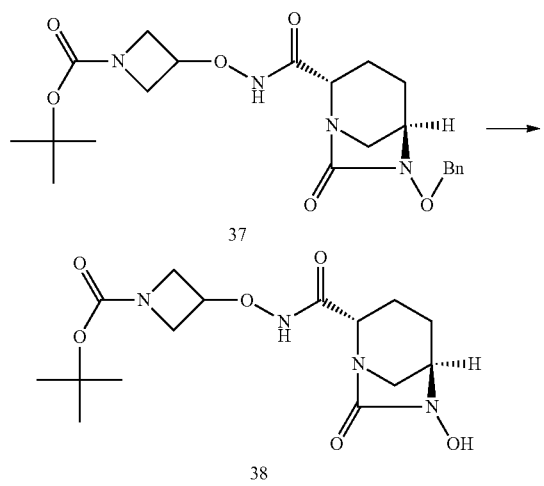

To a solution of tert-butyl 3-[({[(2S,5R)-6-(benzyloxy)-7-oxo-1,6-diazabicyclo[3.2.1]oct-2-yl]carbonyl}amino)oxy]azetidine-1-carboxylate 37 (0.15 g, 0.34 mml) in methanol (15 mL) was added 5% Pd/C (0.3 g). The mixture was hydrogenated under 35 psi hydrogen atmosphere at room temperature for 1 h. The catalyst was filtered out through Celite, and the filtrate was evaporated to give tert-butyl 3-[({[(2S,5R)-6-hydroxy-7-oxo-1,6-diazabicyclo[3.2.1]oct-2-yl]carbonyl}amino)oxy]azetidine-1-carboxylate 38 (0.11 g, 91%) as a colorless foam.

¹H NMR (400 MHz, CD₃OD): δ 1.44 (9H, s), 1.78 (1H, m), 1.91 (1H, m), 2.08 (1H, m), 2.21 (1H, m), 2.98 (1H, d, J=12 Hz), 3.11 (1H, d, J=12 Hz), 3.70 (1H, S), 3.85 (1H, d, J=7.6 Hz), 3.95 (2H, m), 4.10 (2H, m), 4.74 (1H, m), 2 protons were not observed in CD₃OD.

Step 3. tert-Butyl 3-[({[(2S,5R)-7-oxo-6-(sulfooxy)-1,6-diazabicyclo[3.2.1]oct-2-yl]carbonyl}amino)oxy]azetidine-1-carboxylate pyridine salt (39)

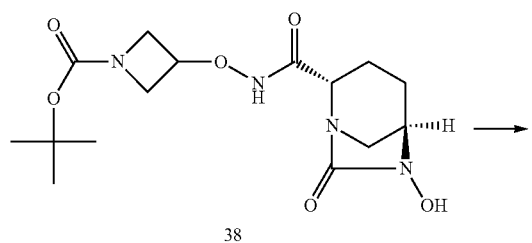

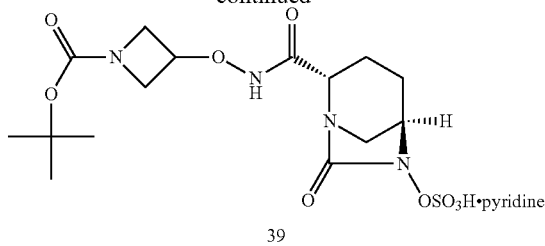

To a solution of tert-butyl 3-[({[(2S,5R)-6-hydroxy-7-oxo-1,6-diazabicyclo[3.2.1]oct-2-yl]carbonyl}amino)oxy]azetidine-1-carboxylate 38 (0.11 g, 0.31 mmol) in dry pyridine (6 mL) under nitrogen atmosphere was added sulfur trioxide pyridine complex (0.197 g, 1.24 mmol). The mixture was stirred at room temperature for 20 h, filtered and evaporated to give tert-butyl 3-[({[(2S,5R)-7-oxo-6-(sulfooxy)-1,6-diazabicyclo[3.2.1]oct-2-yl]carbonyl}amino)oxy]azetidine-1-carboxylate pyridine salt 39 (0.10 g crude) which was used in the next step without purification.

Step 4. N,N,N-Tributylbutan-1-aminium({[(2S,5R)-2-({[1-(tert-butoxycarbonyl)azetidin-3-yl]oxy}carbamoyl)-7-oxo-1,6-diazabicyclo[3.2.1]oct-6-yl]oxy}sulfonyl)oxidanide (40)

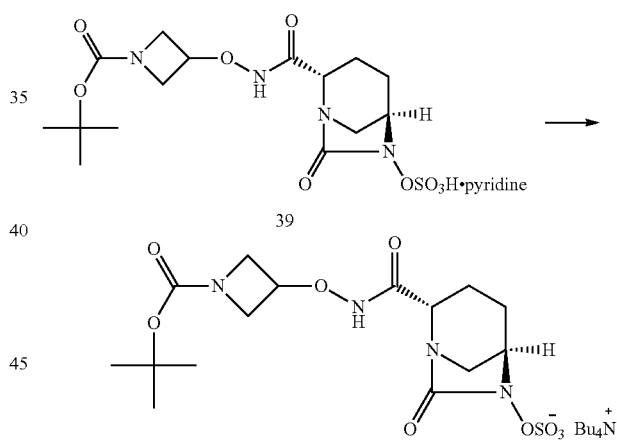

tert-Butyl 3-[({[(2S,5R)-7-oxo-6-(sulfooxy)-1,6-diazabicyclo[3.2.1]oct-2-yl]carbonyl}amino)oxy]azetidine-1-carboxylate pyridine salt 39 (0.13 g, 0.31 mmol) was introduced into a concentrated aqueous solution of monosodium dihydrogen phosphate solution (6 mL) so as to obtain a pH of 4. The mixture was washed with ethyl acetate, then added tetrabutyl ammonium hydrogen sulfate (0.1 g, 0.29 mmol) and stirred at room temperature for 10 min. The mixture was extracted with ethyl acetate (3×10 mL), and the extracts were combined, dried over sodium sulfate and evaporated to give N,N,N-tributylbutan-1-aminium({[(2S,5R)-2-({[1-(tert-butoxycarbonyl)azetidin-3-yl]oxy}carbamoyl)-7-oxo-1,6-diazabicyclo[3.2.1]oct-6-yl]oxy}sulfonyl)oxidanide 40 (0.1 g, 51%) as a white solid.

¹H NMR (400 MHz, CDCl₃): δ 0.98 (12H, t, J=7.2 Hz), 1.39 (17H, m), 1.70 (8H, m), 1.90 (1H, m), 2.05 (1H, m), 2.20

(1H, m), 2.35 (1H, m), 2.78 (1H, d, J=12 Hz), 3.00 (8H, m), 3.33 (1H, m), 4.00 (5H, m), 4.36 (1H, m), 5.01 (1H, m), 9.20 (1H, br s).

Step 5. (2S,5R)-N-(Azetidin-3-yloxy)-7-oxo-6-(sulfooxy)-1,6-diazabicyclo[3.2.1]octane-2-carboxamide (Compound 8, Table 1)

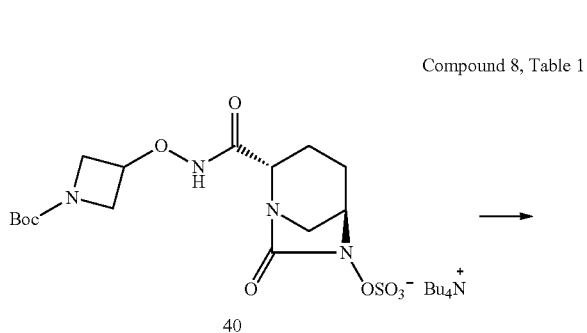

To a solution of N,N,N-tributylbutan-1-aminium({[(2S,5R)-2-({[1-(tert-butoxycarbonyl)azetidin-3-yl]oxy}carbamoyl)-7-oxo-1,6-diazabicyclo[3.2.1]oct-6-yl]oxy}sulfonyl)oxidanide 40 (0.1 g, 0.15 mmol) in DCM (8.8 mL) was added trifluoroacetic acid (0.44 mL, 5.7 mmol) dropwise at 0° C. The reaction mixture was stirred for 1 h, then evaporated. Ether was added to the residue and the resulting white precipitate was collected by centrifugation. The solid was triturated with acetonitrile (2×) and the white solid was collected by centrifugation. The white solid was purified by HPLC and freeze-dried to give (2S,5R)-N-(azetidin-3-yloxy)-7-oxo-6-(sulfooxy)-1,6-diazabicyclo[3.2.1]octane-2-carboxamide Compound 8 (Table 1) (0.01 g, 20%) as a white solid.

$^1$H NMR (400 MHz, D$_2$O): δ 1.65-2.08 (4H, m), 2.98 (1H, d, J=12.4 Hz), 3.18 (1H, d, J=11.6 Hz), 3.96 (1H, d, J=6.8 Hz), 4.09 (3H, m), 4.28 (2H, m), 4.80 (1H, m), 3 protons were not observed in D$_2$O.

HPLC: 92.34%

MS (ES$^-$): m/z [M]$^-$=334.92

Example 9

(2S,5R)-N-(2-Aminoethoxy)-7-oxo-6-(sulfooxy)-1,6-diazabicyclo[3.2.1]octane-2-carboxamide (Compound 9, Table 1)

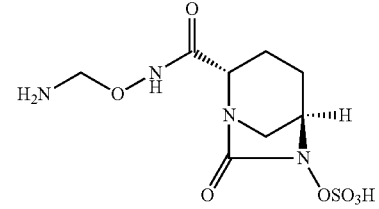

Step 1. tert-Butyl {2-[({[(2S,5R)-6-(benzyloxy)-7-oxo-1,6-diazabicyclo[3.2.1]oct-2-yl]carbonyl}amino)oxy]ethyl}carbamate (42)

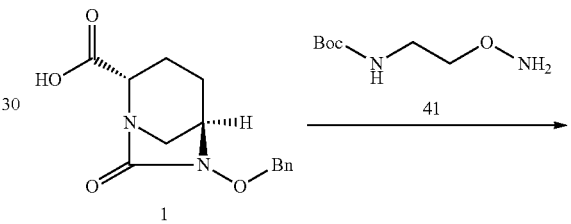

To a mixture of (2S,5R)-6-(benzyloxy)-7-oxo-1,6-diazabicyclo[3.2.1]octane-2-carboxylic acid 1 (0.150 g, 0.543 mmol, US 2005/20572 A1) in DCM (4.0 mL) was added tert-butyl[2-(aminooxy)ethyl]carbamate 41 (0.143 g, 0.814 mmol, US 2005/54701 A1), 1-hydroxybenzotriazole (0.110 g, 0.814 mmol), 1-ethyl-(3-dimethylamino propyl) carbodiimide hydrochloride (0.156 g, 0.814 mmol) and DMAP (0.100 g, 0.814 mmol) sequentially at room temperature. The mixture was stirred at room temperature overnight, diluted with DCM and concentrated to provide a residue which was subjected to chromatography to give 42 (0.21 g, 89%) as a white foam.

$^1$H NMR (400 MHz, CDCl$_3$): δ 1.44 (9H, s), 1.65 (1H, m), 1.93 (2H, m), 2.31 (1H, m), 2.76 (1H, d, J=12 Hz), 3.04 (1H, d, J=11.2 Hz), 3.26 (2H, m), 3.38 (1H, m), 3.91 (2H, m), 3.98 (1H, d, J=12 Hz), 4.89 (1H, d, J=11.2 Hz), 5.07 (1H, d, J=11.2 Hz), 5.41 (1H, br s), 7.41 (5H, m), 9.30 (1H, br s).

MS (ES⁺): m/z [M+H]⁺ calcd for $C_{21}H_{31}N_4O_6$. 435.22. Found: 435.02.

Step 2. tert-Butyl {2-[({[(2S,5R)-6-hydroxy-7-oxo-1,6-diazabicyclo[3.2.1]oct-2-yl]carbonyl}amino)oxy]ethyl}carbamate (43)

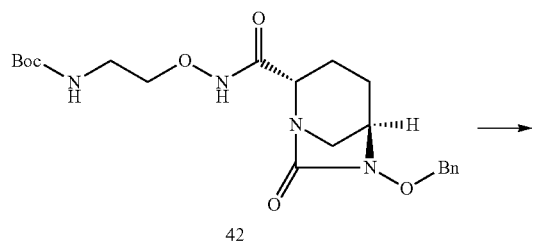
42

↓

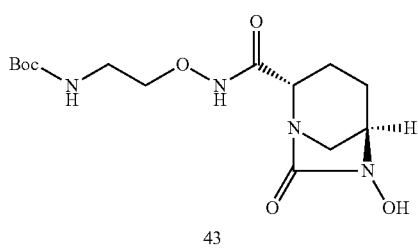
43

A mixture of tert-Butyl {2-[({[(2S,5R)-6-(benzyloxy)-7-oxo-1,6-diazabicyclo[3.2.1]oct-2-yl]carbonyl}amino)oxy]ethyl}carbamate 42 (0.21 g, 0.48 mmol) and Pd/C (0.063 g) in methanol (10 mL) was hydrogenated at 1 atm at room temperature for 3 h. The mixture was filtered through celite pad and concentrated to provide 43 (0.17 g, quant. yield) as a light yellow foam.

¹H NMR (400 MHz, CD₃OD): δ 1.44 (9H, s), 1.75 (1H, m), 1.92 (1H, m), 2.05 (1H, m), 2.23 (1H, m), 3.04 (1H, d, J=12 Hz), 3.12 (2H, m), 3.69 (1H, s), 3.89 (3H, m), 6.74 (1H, br s). 3 protons were not observed in CD₃OD.

MS (ES⁻): m/z [M–H]⁻ calcd for $C_{14}H_{23}N_4O_6$: 343.16. Found: 343.00.

Step 3. tert-Butyl {2-[({[(2S,5R)-7-oxo-6-(sulfooxy)-1,6-diazabicyclo[3.2.1]oct-2-yl]carbonyl}amino)oxy]ethyl}carbamate (44)

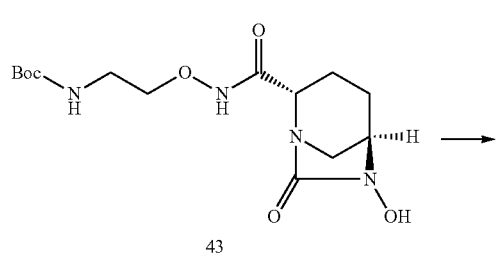
43

↓

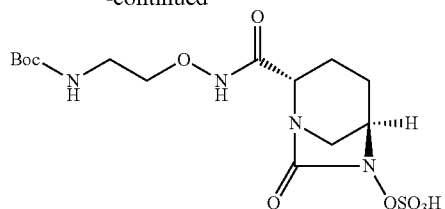
44

To a mixture of tert-butyl {2-[({[(2S,5R)-6-hydroxy-7-oxo-1,6-diazabicyclo[3.2.1]oct-2-yl]carbonyl}amino)oxy]ethyl}carbamate 43 (0.17 g, 0.49 mmol) in pyridine (7.0 mL) was added sulfur trioxide pyridine complex (0.314 g, 1.98 mmol). The mixture was stirred at room temperature for 23 h and concentrated to provide a residue which was subjected to chromatography to give 44 (0.19 g, 92%) as a white solid.

¹H NMR (400 MHz, CD₃OD): δ 1.44 (9H, s), 1.80 (1H, m), 1.92 (1H, m), 2.07 (1H, m), 2.20 (1H, m), 3.06 (1H, d, J=12 Hz), 3.28 (2H, m), 3.88 (4H, m), 4.15 (1H, m). 3 protons were not observed in CD₃OD.

MS (ES⁻): m/z [M–H]⁻ calcd for $C_{14}H_{23}N_4O_9S$: 423.12. Found: 422.93.

Step 4. (2S,5R)-N-(2-aminoethoxy)-7-oxo-6-(sulfooxy)-1,6-diazabicyclo[3.2.1]octane-2-carboxamide (Compound 9, Table 1)

compound 9, Table 1

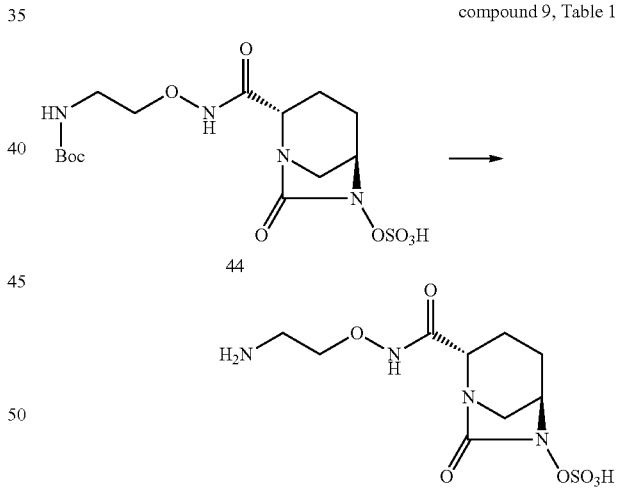

To a mixture of tert-butyl {2-[({[(2S,5R)-7-oxo-6-(sulfooxy)-1,6-diazabicyclo[3.2.1]oct-2-yl]carbonyl}amino)oxy]ethyl}carbamate 44 (0.19 g, 0.45 mmol) in DCM (6.0 mL) was added trifluoroacetic acid (0.30 mL) at 0° C. The mixture was stirred at 0° C. for 1 h, concentrated and washed with ether. The white solid was collected by centrifugation. The crude product was purified by preparative HPLC to provide Compound 9 (Table 1) (44 mg) as a white solid.

¹H NMR (400 MHz, D₂O): δ 1.75 (1H, m), 1.86 (1H, m), 1.95 (1H, m), 2.04 (1H, m), 3.03 (1H, d, J=12 Hz), 3.19 (3H, m), 3.98 (1H, d, J=6.8 Hz), 4.08 (3H, m). 4 protons were not observed in D₂O.

HPLC: 90.18%.

MS (ES−): m/z [M−H]− calcd for $C_9H_{15}N_4O_7S$: 323.07. Found: 322.95.

Example 10

(2S,5R)-N-(8-Azabicyclo[3.2.1]oct-3-yloxy)-7-oxo-6-(sulfooxy)-1,6-diazabicyclo[3.2.1]octane-2-carboxamide (Compound 27, Table 1)

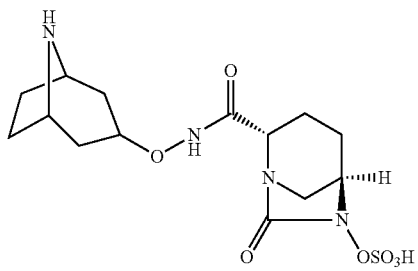

Step 1. tert-Butyl 3-[({[(2S,5R)-6-(benzyloxy)-7-oxo-1,6-diazabicyclo[3.2.1]oct-2-yl]carbonyl}amino)oxy]-8-azabicyclo[3.2.1]octane-8-carboxylate (46)

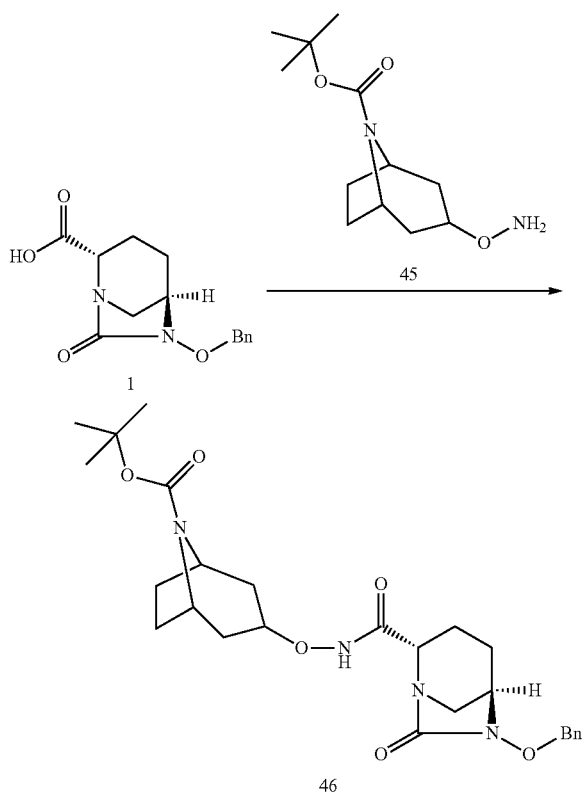

To a solution of (2S,5R)-6-(benzyloxy)-7-oxo-1,6-diazabicyclo[3.2.1]octane-2-carboxylic acid 1 (0.15 g, 0.54 mmol) in dry DCM (20 mL) were added tert-butyl 3-(aminooxy)-8-azabicyclo[3.2.1]octane-8-carboxylate 45 (0.15 g, 0.62 mmol, *J. Med. Chem.* 2008, 51, 4601-4608), 1-hydroxybenzotriazole (0.11 g, 0.81 mmol) and 1-ethyl-(3-dimethylaminopropyl)carbodiimide hydrochloride (0.16 g, 0.81 mmol) at room temperature. The reaction mixture was stirred at room temperature overnight and concentrated under vacuum. The residue was purified by column chromatography to give tert-butyl 3-[({[(2S,5R)-6-(benzyloxy)-7-oxo-1,6-diazabicyclo[3.2.1]oct-2-yl]carbonyl}amino)oxy]-8-azabicyclo[3.2.1]octane-8-carboxylate 46 (0.26 g, 96%) as a white solid.

$^1$H NMR (400 MHz, CDCl$_3$): δ 1.46 (9H, s), 1.50-1.80 (7H, m), 1.83-2.04 (5H, m), 2.32 (1H, m), 2.72 (1H, d, J=11.6 Hz), 2.99 (1H, d, J=11.2 Hz), 3.29 (1H, m), 3.95 (1H, d, J=7.2 Hz), 4.20-4.38 (2H, m), 4.89 (1H, d, J=11.2 Hz), 5.05 (1H, d, J=11.6 Hz), 7.39 (5H, m), 8.90 (1H, br s).

Step 2. tert-Butyl 3-[({[(2S,5R)-6-hydroxy-7-oxo-1,6-diazabicyclo[3.2.1]oct-2-yl]carbonyl}amino)oxy]-8-azabicyclo[3.2.1]octane-8-carboxylate (47)

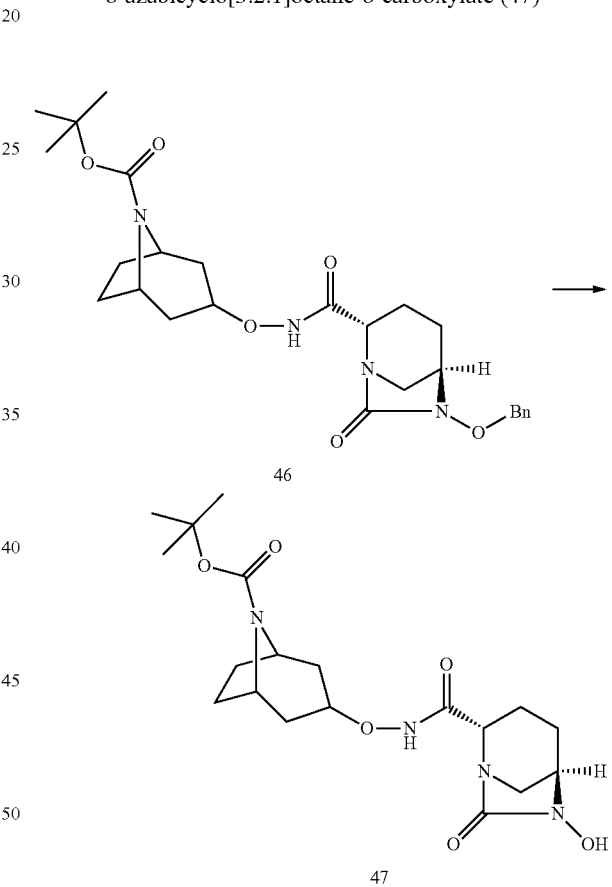

To a solution of tert-butyl 3-[({[(2S,5R)-6-(benzyloxy)-7-oxo-1,6-diazabicyclo[3.2.1]oct-2-yl]carbonyl}amino)oxy]-8-azabicyclo[3.2.1]octane-8-carboxylate 46 (0.26 g, 0.52 mml) in methanol (20 mL) was added 5% Pd/C (0.3 g). The mixture was hydrogenated under 35 psi hydrogen atmosphere at room temperature for 1 h. The catalyst was filtered out through Celite, and the filtrate was evaporated to give tert-butyl 3-[({[(2S,5R)-6-hydroxy-7-oxo-1,6-diazabicyclo[3.2.1]oct-2-yl]carbonyl}amino)oxy]-8-azabicyclo[3.2.1]octane-8-carboxylate 47 (0.14 g, 66%) as a white solid.

$^1$H NMR (400 MHz, CD$_3$OD): δ 1.48 (9H, s), 1.62-1.76 (4H, m), 1.79-1.85 (1H, m), 1.89-2.00 (3H, m), 2.02-2.11 (3H, m), 2.15-2.20 (1H, m), 3.04-3.17 (2H, m), 3.69 (1H, s), 3.83 (1H, d, J=7.2 Hz), 4.24 (2H, m), 4.35 (1H, m), 2 protons were not observed in CD₃OD.

Step 3. tert-Butyl 3-[({[(2S,5R)-7-oxo-6-(sulfooxy)-1,6-diazabicyclo[3.2.1]oct-2-yl]carbonyl}amino)oxy]-8-azabicyclo[3.2.1]octane-8-carboxylate (48)

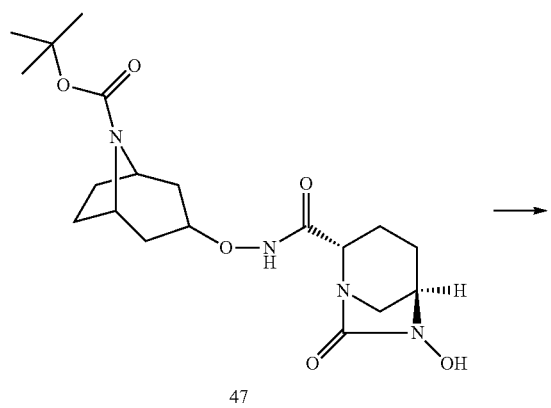

47

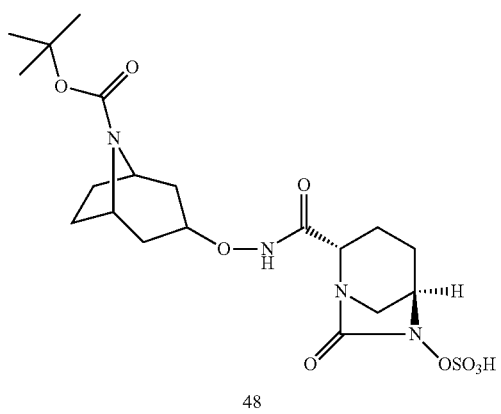

48

To a solution of tert-butyl 3-[({[(2S,5R)-6-hydroxy-7-oxo-1,6-diazabicyclo[3.2.1]oct-2-yl]carbonyl}amino)oxy]-8-azabicyclo[3.2.1]octane-8-carboxylate 47 (0.14 g, 0.34 mmol) in dry pyridine (6 mL) under nitrogen atmosphere was added sulfur trioxide pyridine complex (0.22 g, 1.36 mmol). The mixture was stirred at room temperature for 20 h, filtered and evaporated. The crude compound was suspended in aqueous acid (a mixture of NaH₂PO₄ and H₃PO₄ to pH 3) and extracted with ethyl acetate (30 mL×2). The organic extracts were combined, washed with brine, dried over sodium sulfate and evaporated to give tert-butyl 3-[({[(2S,5R)-7-oxo-6-(sulfooxy)-1,6-diazabicyclo[3.2.1]oct-2-yl]carbonyl}amino)oxy]-8-azabicyclo[3.2.1]octane-8-carboxylate 48 (0.077 g) which was used in the next step without purification.

Step 4. (2S,5R)-N-(8-Azabicyclo[3.2.1]oct-3-yloxy)-7-oxo-6-(sulfooxy)-1,6-diazabicyclo[3.2.1]octane-2-carboxamide (Compound 27, Table 1)

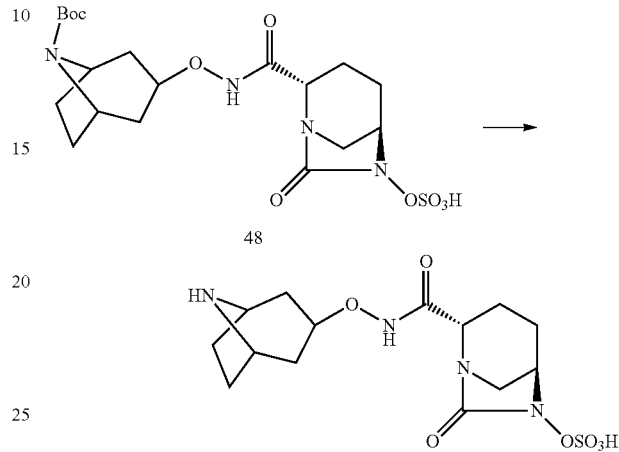

compound 27, Table 1

To a solution of tert-butyl 3-[({[(2S,5R)-7-oxo-6-(sulfooxy)-1,6-diazabicyclo[3.2.1]oct-2-yl]carbonyl}amino)oxy]-8-azabicyclo[3.2.1]octane-8-carboxylate 48 (0.077 g, 0.17 mmol) in DCM (7 mL) was added trifluoroacetic acid (0.34 mL, 4.42 mmol) dropwise at 0° C. The reaction mixture was stirred for 1 h, then evaporated. Ether was added to the residue and the resulting white precipitate was collected by centrifugation. The solid was triturated with acetonitrile (2×) and the white solid was collected by centrifugation. The white solid was purified by HPLC and freeze-dried to give (2S,5R)-N-(8-azabicyclo[3.2.1]oct-3-yloxy)-7-oxo-6-(sulfooxy)-1,6-diazabicyclo[3.2.1]octane-2-carboxamide Compound 27 (Table 1) (0.003 g, 7%) as a white solid.

¹H NMR (400 MHz, CD₃OD): δ 1.70-2.14 (9H, m), 2.16-2.58 (3H, m), 3.07 (1H, d, J=11.2 Hz), 3.25 (1H, d, J=11.6 Hz), 3.91 (1H, d, J=7.2 Hz), 4.00 (2H, m), 4.16 (1H, m), 4.26 (1H, m), 3 protons were not observed in CD₃OD.
HPLC: 81.82%
MS (ES⁻): m/z [M−H]⁻=388.96

Example 11

(2S,5R)-N-[(1-Methylpiperidin-4-yl)oxy]-7-oxo-6-(sulfooxy)-1,6-diazabicyclo[3.2.1]octane-2-carboxamide (Compound 67 Table 1)

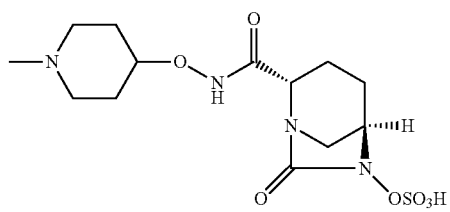

Step 1. 4-(Aminooxy)-1-methylpiperidine (50)

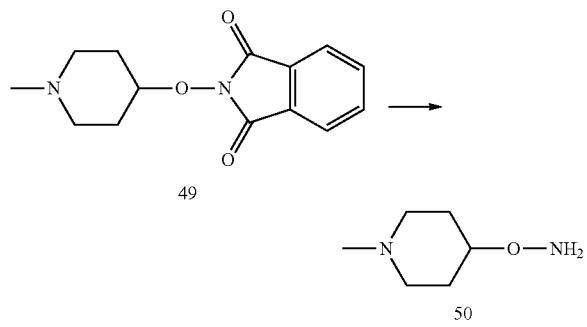

To a solution of 2-[(1-methylpiperidin-4-yl)oxy]-1H-isoindole-1,3(2H)-dione 49 (1.18 g, 4.53 mmol) in a mixture of ethanol (3 mL) and DCM (18 mL) was added hydrazine hydrate (0.268 g, 4.53 mmol). The reaction mixture was stirred at room temperature for 4.5 h. Precipitate was filtered off. The filtrate was evaporated and sonicated in ethyl acetate (20 mL). Solid was filtered off and filtrate was evaporated to give the residue which was subjected to chromatography to give 50 (0.15 g, 25%) as a colorless oil.

$^1$H NMR (400 MHz, CD$_3$OD): δ 1.60-1.70 (2H, m), 1.88-1.97 (2H, m), 2.23-2.33 (5H, m), 2.64-2.74 (2H, m), 3.51-3.59 (1H, m), 2 protons were not observed in CD$_3$OD.

Step 2. (2S,5R)-6-(Benzyloxy)-N-[(1-methylpiperidin-4-yl)oxy]-7-oxo-1,6-diazabicyclo[3.2.1]octane-2-carboxamide (51)

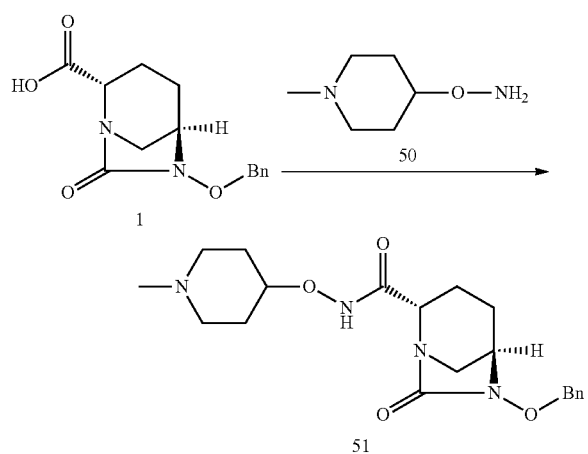

To a mixture of (2S,5R)-6-(benzyloxy)-7-oxo-1,6-diazabicyclo[3.2.1]octane-2-carboxylic acid 1 (0.150 g, 0.543 mmol, US 2005/20572 A1) in DCM (10 mL) were added 4-(aminooxy)-1-methylpiperidine 50 (0.129 g, 0.99 mmol), 1-hydroxybenzotriazole (0.110 g, 0.814 mmol) and 1-ethyl-(3-dimethylaminopropyl) carbodiimide hydrochloride (0.156 g, 0.814 mmol) sequentially at room temperature. The mixture was stirred at room temperature for 16 h, diluted with DCM, washed with water, brine, dried over sodium sulfate and concentrated to provide a residue which was subjected to chromatography to give 51 (0.065 g, 31%) as a yellow oil.

$^1$H NMR (400 MHz, CD$_3$OD): δ 1.64-2.02 (7H, m), 2.11-2.19 (1H, m), 2.20-2.38 (5H, m), 2.62-2.80 (2H, m), 3.00 (2H, s), 3.58 (1H, s), 3.80-3.90 (2H, m), 4.91 (2H, q, J=11.2 Hz), 7.30-7.50 (5H, m), one proton was not observed in CD$_3$OD.

MS (ES$^+$): m/z [M+H]$^+$ calcd for C$_{20}$H$_{28}$N$_4$O$_4$: 389.47. Found: 389.02.

Step 3. (2S,5R)-6-Hydroxy-N-[(1-methylpiperidin-4-yl)oxy]-7-oxo-1,6-diazabicyclo[3.2.1]octane-2-carboxamide (52)

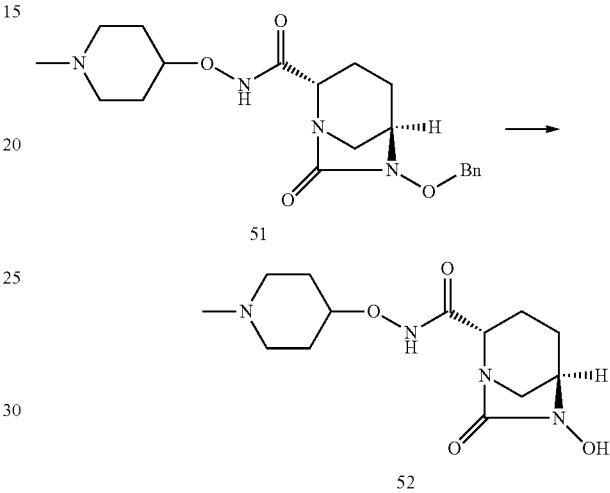

A mixture of (2S,5R)-6-(benzyloxy)-N-[(1-methylpiperidin-4-yl)oxy]-7-oxo-1,6-diazabicyclo[3.2.1]octane-2-carboxamide 51 (0.065 g, 0.167 mmol) and Pd/C (0.060 g) in methanol (30 mL) was hydrogenated at 35 psi at room temperature for 2 h. The mixture was filtered through a Celite pad and concentrated to provide 52 (0.050 g, quantitative) as a light yellow solid.

$^1$H NMR (400 MHz, CD$_3$OD): δ 1.76-2.21 (8H, m), 2.37 (3H, s), 2.39-2.48 (2H, m), 2.80-2.90 (2H, m), 3.00-3.17 (2H, m), 3.68-3.72 (1H, m), 3.85 (1H, d, J=7.6 Hz), 3.91-3.98 (1H, m), 2 protons were not observed in CD$_3$OD.

MS (ES$^-$): m/z [M+H]$^+$ calcd for C$_{13}$H$_{22}$N$_4$O$_4$: 299.34. Found 299.0.

Step 4. (2S,5R)-N-[(1-Methylpiperidin-4-yl)oxy]-7-oxo-6-(sulfooxy)-1,6-diazabicyclo[3.2.1]octane-2-carboxamide (Compound 67, Table 1)

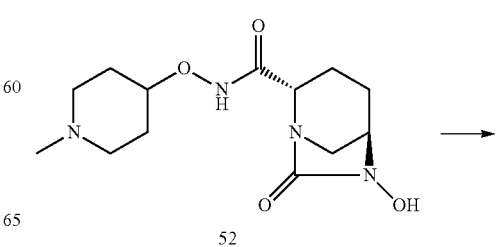

-continued

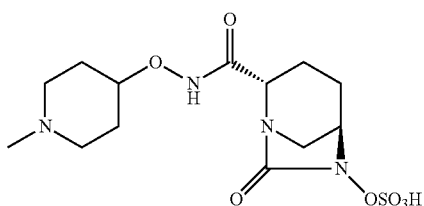

Compound 67, Table 1

To a mixture of (2S,5R)-6-hydroxy-N-[(1-methylpiperidin-4-yl)oxy]-7-oxo-1,6-diazabicyclo[3.2.1]octane-2-carboxamide 52 (0.047 g, 0.517 mmol) in pyridine (1.5 mL) was added sulfur trioxide pyridine complex (0.070 g, 1.438 mmol). The mixture was stirred at room temperature for 16 h, evaporated to dryness. The residue was sonicated in ethyl acetate (5 mL), solid was obtained and subjected to chromatography to give Compound 67 (Table 1) (0.024 g, 40%) as a white solid.

$^1$H NMR (400 MHz, CD$_3$OD): δ 1.78-2.37 (8H, m), 2.90 (3H, s), 3.07-3.16 (2H, m), 3.20-3.41 (3H, m), 3.55-3.65 (1H, m), 3.92-3.98 (1H, m), 4.12-4.22 (2H, m), 2 protons were not observed in CD$_3$OD.

HPLC: 96.05%

MS (ES$^+$): m/z [M+H]$^+$ calcd for C$_{13}$H$_{22}$N$_4$O$_7$S: 379.41. Found: 378.93.

Example 12

(2S,5R)-N-(2-Amino-2-oxoethoxy)-7-oxo-6-(sulfooxy)-1,6-diazabicyclo[3.2.1]octane-2-carboxamide (Compound 73, Table 1)

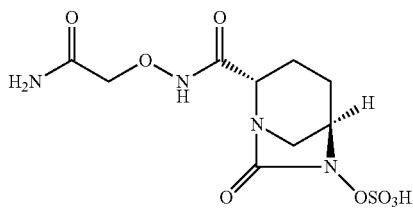

Step 1. (2S,5R)-N-(2-Amino-2-oxoethoxy)-6-(benzyloxy)-7-oxo-1,6-diazabicyclo[3.2.1]octane-2-carboxamide (54)

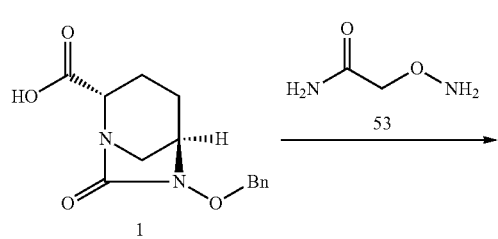

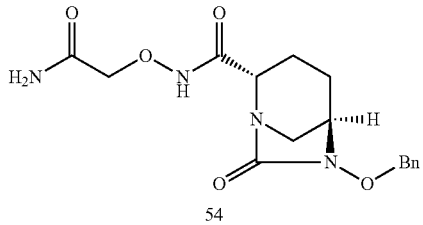

To a mixture of (2S,5R)-6-(benzyloxy)-7-oxo-1,6-diazabicyclo[3.2.1]octane-2-carboxylic acid 1 (0.200 g, 0.723 mmol, US 2005/20572 A1) in DCM (6.0 mL) were added 2-(aminooxy) acetamide 53 (0.098 g, 1.086 mmol), 1-hydroxybenzotriazole (0.147 g, 1.086 mmol) and 1-ethyl-(3-dimethylaminopropyl) carbodiimide hydrochloride (0.208 g, 1.086 mmol) sequentially at room temperature. The mixture was stirred at room temperature overnight, diluted with DCM and concentrated to provide a residue which was subjected to chromatography to give 54 (0.203 g, 81%) as a white solid.

$^1$H NMR (400 MHz, CD$_3$OD): δ 1.70 (1H, m), 1.90 (1H, m), 2.00 (1H, m), 2.15 (1H, m), 2.96 (2H, m), 3.56 (1H, m), 3.89 (1H, d), 4.33 (2H, s), 4.98 (2H, ABq), 7.36 (3H, m), 7.46 (2H, m). 3 protons were not observed in CD$_3$OD.

MS (ES$^+$): m/z [M+H]$^+$ calcd for C$_{16}$H$_{21}$N$_4$O$_5$: 349.15. Found: 349.39.

Step 2. (2S,5R)-N-(2-Amino-2-oxoethoxy)-6-hydroxy-7-oxo-1,6-diazabicyclo[3.2.1]octane-2-carboxamide (55)

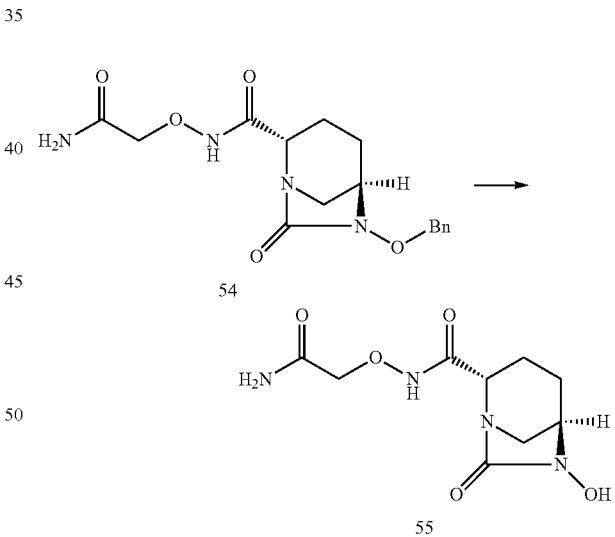

A mixture of (2S,5R)-N-(2-amino-2-oxoethoxy)-6-(benzyloxy)-7-oxo-1,6-diazabicyclo[3.2.1]octane-2-carboxamide 54 (0.11 g, 0.40 mmol) and Pd/C (0.040 g) in methanol (10 mL) was hydrogenated at 1 atm at room temperature for 3 h. The mixture was filtered through Celite pad and concentrated to provide 55 (0.10 g, 98%) as a white solid.

$^1$H NMR (400 MHz, CD$_3$OD): δ 1.76 (1H, m), 1.92 (1H, m), 2.07 (1H, m), 2.19 (1H, m), 2.98 (1H, d, J=11.6 Hz), 3.11 (1H, m), 3.69 (1H, m), 3.88 (1H, d, J=7.6 Hz), 4.35 (2H, s). 4 protons were not observed in CD$_3$OD.

MS (ES⁻): m/z [M−H]⁻ calcd for $C_9H_{13}N_4O_5$: 257.09. Found: 257.44.

Step 3. (2S,5R)-N-(2-Amino-2-oxoethoxy)-7-oxo-6-(sulfooxy)-1,6-diazabicyclo[3.2.1]octane-2-carboxamide (Compound 73, Table 1)

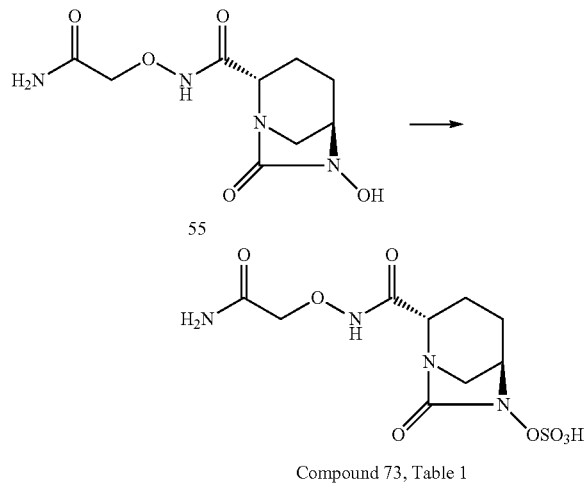

Compound 73, Table 1

To a mixture of (2S,5R)-N-(2-amino-2-oxoethoxy)-6-hydroxy-7-oxo-1,6-diazabicyclo[3.2.1]octane-2-carboxamide 55 (0.11 g, 0.43 mmol) in pyridine (4.0 mL) was added sulfur trioxide pyridine complex (0.27 g, 1.70 mmol). The mixture was stirred at room temperature overnight and concentrated to provide a residue which was dissolved in $KH_2PO_4$ (7 mL), extracted with ethyl acetate and freeze-dried to give a white solid which was purified by HPLC to provide Compound 73 (Table 1) (3.6 mg) as a white solid.

¹H NMR (400 MHz, D₂O): δ 1.73 (1H, m), 1.82 (1H, m), 1.95 (1H, m), 2.03 (1H, m), 3.02 (1H, d, J=12.0 Hz), 3.18 (1H, m), 3.95 (1H, d, J=6.4 Hz), 4.08 (1H, m), 4.38 (2H, s). 4 protons were not observed in D₂O.

HPLC: 88.53

MS (ES⁻): m/z [M−H]⁻ calcd for $C_9H_{13}N_4O_8S$: 337.05. Found: 336.90.

Example 13

(2S,5R)-N-{[(2S)-2-Aminopropyl]oxy}-7-oxo-6-(sulfooxy)-1,6-diazabicyclo[3.2.1]octane-2-carboxamide (Compound 74, Table 1)

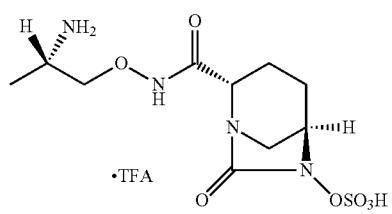

Step 1. tert-Butyl [(1S)-2-hydroxy-1-methylethyl]carbamate (57)

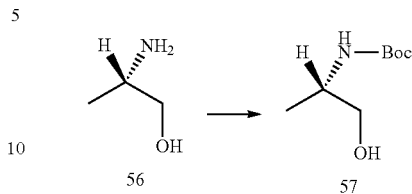

To a mixture of (S)-(+)-2 amino-1-propanol 56 (3.76 g, 50 mmol) and triethylamine (6.97 mL, 50 mmol) in THF (70 mL) at 0° C. under nitrogen was added dropwise di-tert-butyl dicarbonate (10.91 g, 50 mmol) in THF (30 mL). The mixture was stirred at room temperature for 2 h. Solvent was evaporated off. Residue was dissolved in ethyl acetate, washed with water, brine, dried over sodium sulfate, filtered and evaporated to provide 57 (crude, 8.29 g, 95%) as a white solid which was used in the next step without purification.

¹H NMR (400 MHz, CDCl₃): δ 1.15 (3H, d, J=6.8 Hz), 1.46 (9H, s), 3.42-3.61 (3H, m), 3.75 (1H, br s), 4.94 (1H, br s).

MS (ES⁺): m/z [M+H]⁺ calcd for $C_8H_{17}NO_3$: 176.23. Found: 175.96.

Step 2. tert-Butyl {(1S)-2-[(1,3-dioxo-1,3-dihydro-2H-isoindol-2-yl)oxy]-1-methylethyl}carbamate (58)

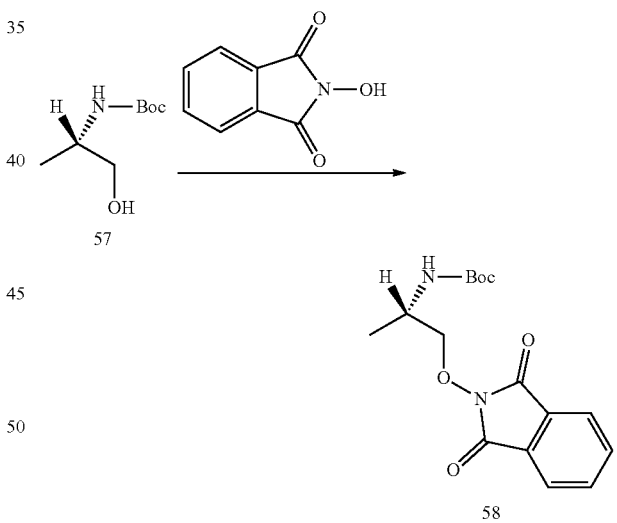

To a mixture of tert-butyl [(1S)-2-hydroxy-1-methylethyl]carbamate 57 (4.03 g, 23.0 mmol), N-hydroxyphthalimide (5.63 g, 34.5 mmol) and triphenylphosphine (9.05 g, 34.5 mmol) in anhydrous THF (172 mL) at 0° C. under nitrogen was added DIAD (6.69 mL, 34.5 mmol) in anhydrous THF (40 mL) over 15 minutes. The mixture was stirred at 0° C. for 30 min and at room temperature for 2.5 h. Solvent was evaporated off and the residue was subjected to chromatography to give a white solid 58 (7.38 g).

¹H NMR (400 MHz, CDCl₃): δ 1.26 (3H, d, J=6.8 Hz), 1.43 (9H, s), 3.90-4.03 (1H, m), 4.12-4.30 (2H, m), 5.20 (1H, br s), 7.71-7.88 (4H, m).

MS (ES⁺): m/z [M+H]⁺ calcd for $C_{16}H_{20}N_2O_5$: 321.35. Found: 320.89.

Step 3. tert-Butyl [(1S)-2-(aminooxy)-1-methylethyl]carbamate (59)

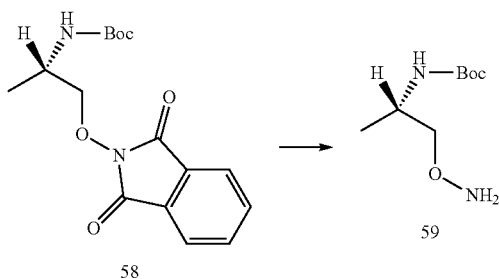 [SMILES: C[C@@H](CON1C(=O)c2ccccc2C1=O)NC(=O)OC(C)(C)C ; C[C@@H](CON)NC(=O)OC(C)(C)C]

To a solution of tert-butyl {(1S)-2-[(1,3-dioxo-1,3-dihydro-2H-isoindol-2-yl)oxy]-1-methylethyl}carbamate 58 (1.2 g, 3.74 mmol) in a mixture of ethanol (3 mL) and DCM (20 mL) was added hydrazine hydrate (0.215 mL, 3.74 mmol). The reaction mixture was stirred at room temperature for 6 h. Precipitate was filtered off, the filtrate was evaporated and the residue was subjected to chromatography to give 59 (0.55 g, 77%) as a white solid.

¹H NMR (400 MHz, $CD_3OD$): δ 1.03 (3H, d, J=6.8 Hz), 1.36 (9H, s), 3.38-3.42 (1H, m), 3.53-3.56 (1H, m), 3.89 (1H, br s), 4.79 (1H, br s), 5.54 (2H, br s).

Step 4. tert-Butyl {(2S)-1-[({[(2S,5R)-6-(benzyloxy)-7-oxo-1,6-diazabicyclo[3.2.1]oct-2-yl]carbonyl}amino)oxy]propan-2-yl}carbamate (60)

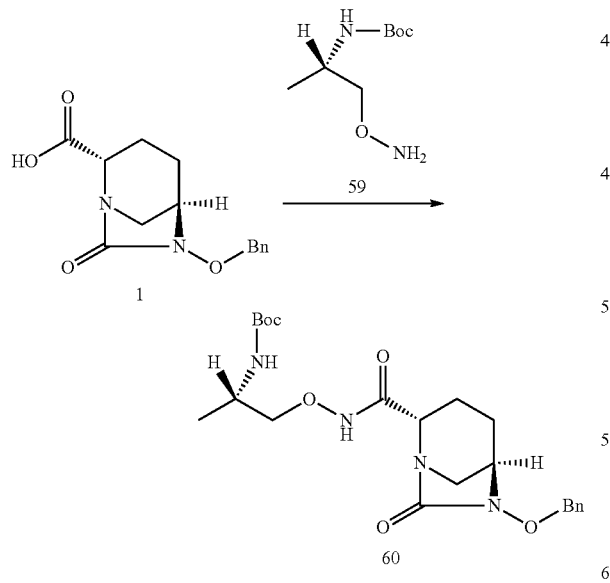

To a mixture of (2S,5R)-6-(benzyloxy)-7-oxo-1,6-diazabicyclo[3.2.1]octane-2-carboxylic acid 1 (0.150 g, 0.543 mmol) in DCM (15 mL) were added tert-butyl [(1S)-2-(aminooxy)-1-methylethyl]carbamate 59 (0.176 g, 0.923 mmol), 1-hydroxybenzotriazole (0.110 g, 0.814 mmol) and 1-ethyl-(3-dimethylaminopropyl) carbodiimide hydrochloride (0.156 g, 0.814 mmol) sequentially at room temperature. The mixture was stirred at room temperature for 18 h, diluted with DCM, washed with water and brine, dried over sodium sulfate and concentrated to provide a residue which was subjected to chromatography to give 60 (0.237 g, 97%) as a white solid.

¹H NMR (400 MHz, $CDCl_3$): δ 1.67 (3H, d, J=6.8 Hz), 1.42 (9H, s), 1.63-1.69 (1H, m), 1.91-2.05 (2H, m), 2.28-2.33 (1H, m), 2.81 (1H, d, J=12.0 Hz), 3.04-3.07 (1H, m), 3.29 (1H, s), 3.66-3.70 (1H, m), 3.87-3.96 (3H, m), 4.83-5.07 (3H, m), 7.32-7.42 (5H, m), 9.72 (1H, br s).

MS (ES⁻): m/z [M–H]⁻ calcd for $C_{22}H_{32}N_4O_6$: 447.52. Found: 447.47.

Step 5. tert-Butyl {(2S)-1-[({[(2S,5R)-6-hydroxy-7-oxo-1,6-diazabicyclo[3.2.1]oct-2-yl]carbonyl}amino)oxy]propan-2-yl}carbamate (61)

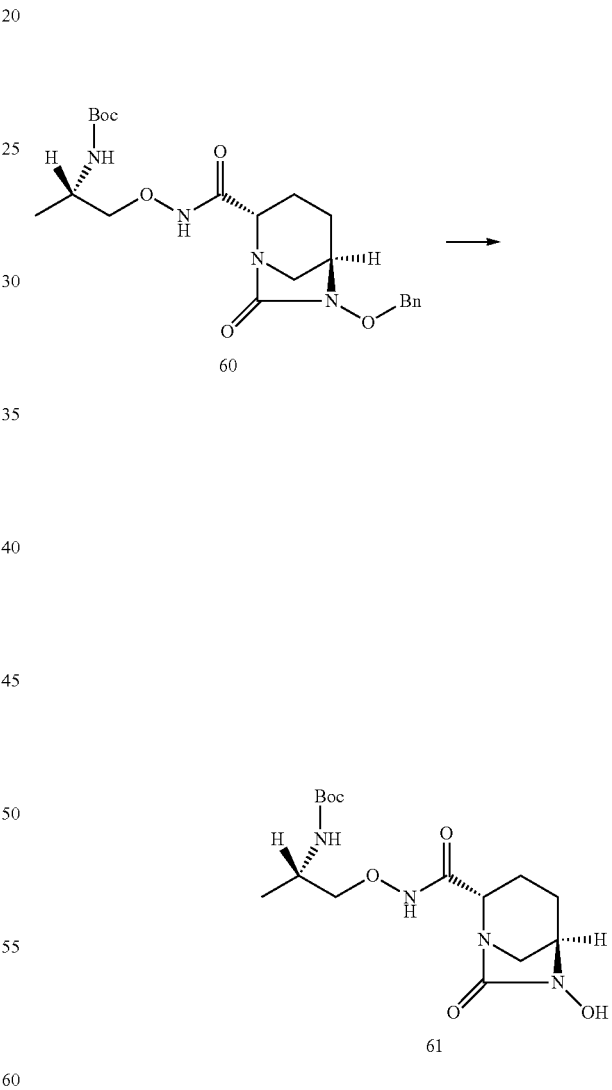

A mixture of tert-butyl {(2S)-1-[({[(2S,5R)-6-(benzyloxy)-7-oxo-1,6-diazabicyclo[3.2.1]oct-2-yl]carbonyl}amino)oxy]propan-2-yl}carbamate 60 (0.237 g, 0.528 mmol) and Pd/C (0.200 g) in methanol (20 mL) was hydrogenated at 35 psi at room temperature for 2 h. The mixture was filtered through a Celite pad and concentrated to provide 61 (crude, 0.189 g, quant.) as a colorless foam which was used in the next step without purification.

Step 6. tert-Butyl {(2S)-1-[({[(2S,5R)-7-oxo-6-(sulfooxy)-1,6-diazabicyclo[3.2.1]oct-2-yl]carbonyl}amino)oxy]propan-2-yl}carbamate (62)

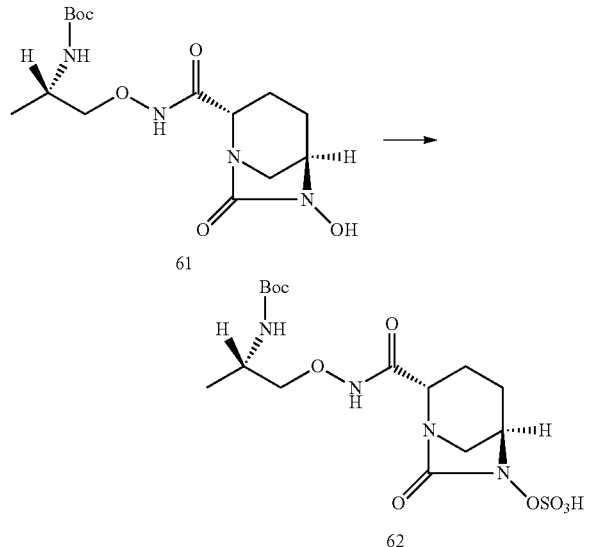

To a mixture of tert-butyl {(2S)-1-[({[(2S,5R)-6-hydroxy-7-oxo-1,6-diazabicyclo[3.2.1]oct-2-yl]carbonyl}amino)oxy]propan-2-yl}carbamate 61 (0.189 g, 0.527 mmol) in pyridine (5.0 mL) was added sulfur trioxide pyridine complex (0.233 g, 1.466 mmol). The mixture was stirred at room temperature for 20 h. Solid was filtered off. The filtrate was evaporated to provide a residue which was subjected to chromatography to give 62 (0.214 g, 93%) as a light yellow foam.

$^1$H NMR (400 MHz, CDCl$_3$): δ 1.20 (3H, d, J=6.0 Hz), 1.42 (9H, m), 1.80-2.27 (4H, m), 3.03 (1H, d, J=12.0 Hz), 3.27-3.35 (1H, m), 3.90-3.97 (3H, m), 4.26 (1H, s), 5.13 (1H, br s), 3 protons were not observed in moisture-containing CDCl$_3$.

MS (ES$^-$): m/z [M–H]$^-$ calcd for C$_{15}$H$_{26}$N$_4$O$_9$S: 437.46. Found: 437.38.

Step 7. (2S,5R)-N-{[(2S)-2-Aminopropyl]oxy}-7-oxo-6-(sulfooxy)-1,6-diazabicyclo[3.2.1]octane-2-carboxamide (Compound 74, Table 1)

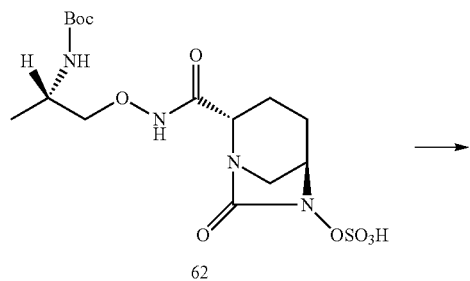

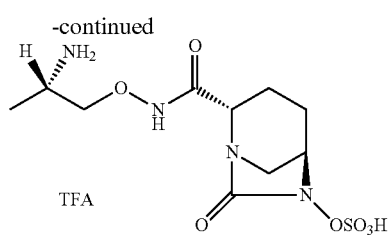

Compound 74, Table 1

To a mixture of tert-butyl {(2S)-1-[({[(2S,5R)-7-oxo-6-(sulfooxy)-1,6-diazabicyclo[3.2.1]oct-2-yl]carbonyl}amino)oxy]propan-2-yl}carbamate 62 (0.214 g, 0.488 mmol) in DCM (9.0 mL) was added trifluoroacetic acid (0.44 mL) at 0° C. The mixture was stirred at 0° C. for 1 h, concentrated and washed with ether. The white solid was collected by centrifugation. The crude product was purified by preparative HPLC to provide Compound 74 (Table 1) (27 mg) as a light yellow solid.

$^1$H NMR (400 MHz, CD$_3$OD): δ 1.27 (3H, d, J=6.8 Hz), 1.78-2.25 (4H, m), 3.03 (1H, d, J=12.0 Hz), 3.22-3.30 (1H, m), 3.51-3.60 (1H, m), 3.82-3.90 (1H, m), 3.96-4.07 (2H, m), 4.12-4.18 (1H, m), 4 protons were not observed in CD$_3$OD.

HPLC: 83.80

MS (ES$^-$) m/z: [M–H]$^-$ calcd for C$_{10}$H$_{18}$N$_4$O$_7$S: 337.34. Found: 336.96.

Example 14

(2S,5R)-N-[(1-Carbamimidoylpiperidin-4-yl)oxy]-7-oxo-6-(sulfooxy)-1,6-diazabicyclo[3.2.1]octane-2-carboxamide (Compound 75, Table 1)

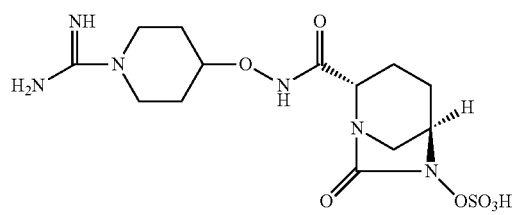

Step 1. Di-tert-butyl [{4-[(1,3-dioxo-1,3-dihydro-2H-isoindol-2-yl)oxy]piperidin-1-yl}methylylidene]biscarbamate (64)

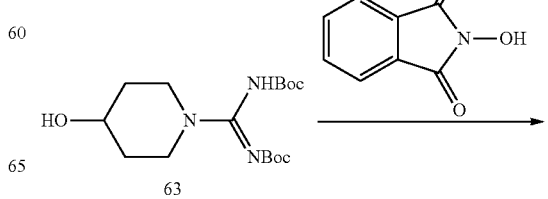

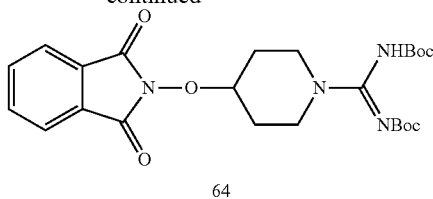

64

To a mixture of N-hydroxyphthalimide (1.89 g, 11.62 mmol), di-tert-butyl [(4-hydroxypiperidin-1-yl)methylylidene]biscarbamate 63 (2.00 g, 5.81 mmol, US 2004/209921 A1) and triphenylphosphine (3.05 g, 11.62 mmol) in THF (100 mL) was added diisopropyl azodicarboxylate (2.47 mL, 12.78 mmol) slowly at room temperature. The resulting mixture was stirred at room temperature overnight and concentrated to provide a residue which was subjected to chromatography to give 64 (0.9 g) as a white solid.

$^1$H NMR (400 MHz, CDCl$_3$): δ 1.49 (18H, s), 2.04 (4H, m), 3.57 (2H, br s), 3.89 (2H, br s), 4.50 (1H, m), 7.76 (2H, m), 7.85 (2H, m), 10.20 (1H, br s).

MS (ES$^+$): m/z [M+H]$^+$ calcd for $C_{24}H_{33}N_4O_7$: 489.23. Found: 489.07.

Step 2. Di-tert-butyl {[4-(aminooxy)piperidin-1-yl]methylylidene}biscarbamate (65)

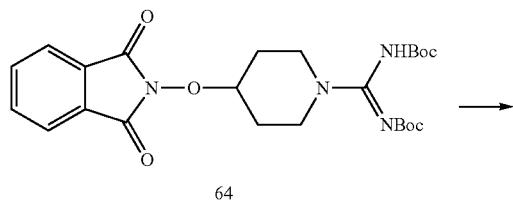

64

↓

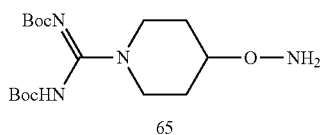

65

To a mixture di-tert-butyl [{4-[(1,3-dioxo-1,3-dihydro-2H-isoindol-2-yl)oxy]piperidin-1-yl}methylylidene]biscarbamate 64 (2.30 g, 4.71 mmol) in a solution of DCM (40 mL) and ethanol (6 mL) was added hydrazine hydrate (0.270 mL, 4.71 mmol) at room temperature. The mixture was stirred at room temperature overnight, filtered and concentrated to provide a residue which was subjected to chromatography to give 65 (0.72 g, 43%) as a white foam.

$^1$H NMR (400 MHz, CDCl$_3$): δ 1.47 (9H, s), 1.50 (9H, s), 1.72 (2H, m), 1.95 (2H, m), 3.38 (2H, m), 3.77 (3H, m), 5.30 (2H, s), 10.15 (1H, s).

MS (ES$^+$): m/z [M+H]$^+$ calcd for $C_{16}H_{31}N_4O_5$: 359.23. Found: 359.07.

Step 3. Di-tert-butyl [{4-[({[(2S,5R)-6-(benzyloxy)-7-oxo-1,6-diazabicyclo[3.2.1]oct-2-yl]carbonyl}amino)oxy]piperidin-1-yl}methylylidene]biscarbamate (66)

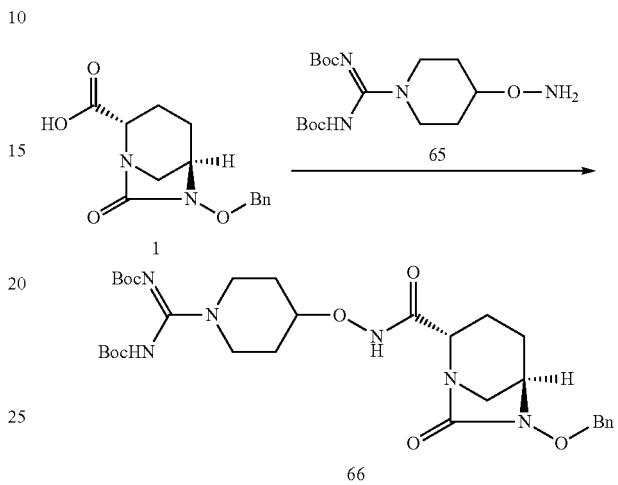

To a mixture of (2S,5R)-6-(benzyloxy)-7-oxo-1,6-diazabicyclo[3.2.1]octane-2-carboxylic acid 1 (0.200 g, 0.723 mmol, US 2005/20572 A1) in DCM (6.0 mL) was added di-tert-butyl {[4-(aminooxy)piperidin-1-yl]methylylidene}biscarbamate 65 (0.389 g, 1.086 mmol), 1-hydroxybenzotriazole (0.147 g, 1.086 mmol) and 1-ethyl-(3-dimethylaminopropyl) carbodiimide hydrochloride (0.208 g, 1.086 mmol) sequentially at room temperature. The mixture was stirred at room temperature overnight, diluted with DCM and concentrated to provide a residue which was subjected to chromatography to give 66 (0.33 g, 74%) as a white solid.

$^1$H NMR (400 MHz, CDCl$_3$): δ 1.48 (18H, m), 1.62 (2H, m), 1.82 (2H, m), 2.01 (4H, m), 2.32 (1H, m), 2.77 (1H, d, J=11.6 Hz), 3.03 (1H, d, J=11.2 Hz), 3.32 (1H, s), 3.43 (2H, br s), 3.78 (2H, br s), 3.95 (1H, d, J=7.6 Hz), 4.09 (1H, m), 4.92 (2H, ABq), 7.41 (5H, m), 8.95 (1H, s).

MS (ES$^+$): m/z [M+H]$^+$ calcd for $C_{30}H_{45}N_6O_8$: 617.33. Found: 617.18.

Step 4. Di-tert-butyl [{4-[({[(2S,5R)-6-hydroxy-7-oxo-1,6-diazabicyclo[3.2.1]oct-2-yl]carbonyl}amino)oxy]piperidin-1-yl}methylylidene]biscarbamate (67)

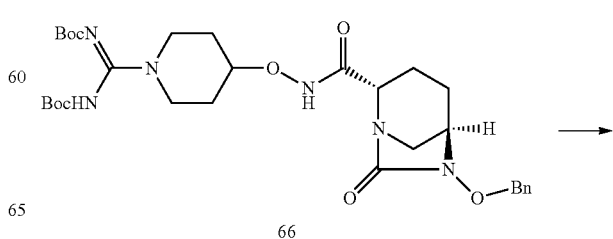

66

→

-continued

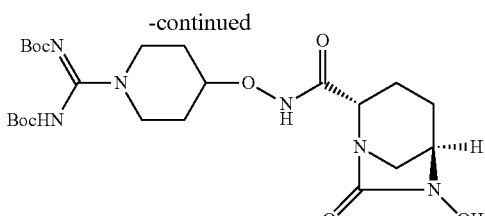
67

A mixture of di-tert-butyl [{4-[({[(2S,5R)-6-(benzyloxy)-7-oxo-1,6-diazabicyclo[3.2.1]oct-2-yl]carbonyl}amino)oxy]piperidin-1-yl}methylylidene]biscarbamate 66 (0.26 g, 0.42 mmol) and Pd/C (0.080 g) in methanol (10 mL) was hydrogenated at 1 atm at room temperature for 3 h. The mixture was filtered through Celite pad and concentrated to provide 67 (0.21 g, 98%) as a white solid.

$^1$H NMR (400 MHz, CD$_3$OD): δ 1.51 (18H, s), 1.60 (1H, m), 1.96 (3H, m), 2.06 (3H, m), 2.17 (1H, m), 3.04 (1H, d, J=11.6 Hz), 3.12 (1H, m), 3.64 (2H, m), 3.71 (1H, m), 3.84 (3H, m), 4.18 (1H, m). 3 protons were not observed in CD$_3$OD.

MS (ES$^+$): m/z [M+H]$^+$ calcd for C$_{23}$H$_{39}$N$_6$O$_8$: 527.28. Found: 527.09.

Step 5. Di-tert-butyl [{4-[({[(2S,5R)-7-oxo-6-(sulfooxy)-1,6-diazabicyclo[3.2.1]oct-2-yl]carbonyl}amino)oxy]piperidin-1-yl}methylylidene]biscarbamate (68)

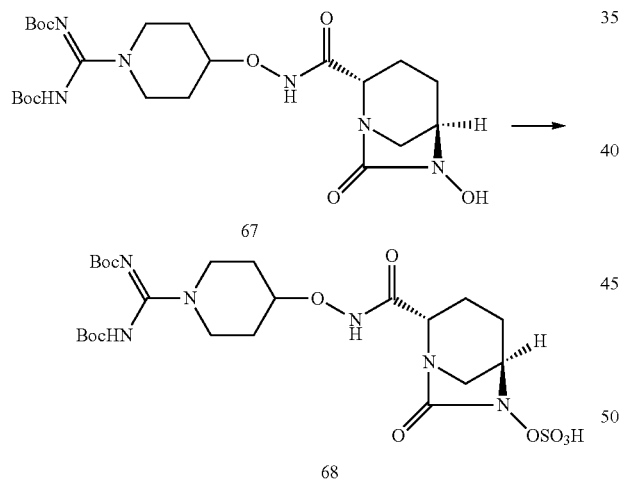

To a mixture of di-tert-butyl [{4-[({[(2S,5R)-6-hydroxy-7-oxo-1,6-diazabicyclo[3.2.1]oct-2-yl]carbonyl}amino)oxy]piperidin-1-yl}methylylidene]biscarbamate 67 (0.26 g, 0.50 mmol) in pyridine (8.0 mL) was added sulfur trioxide pyridine complex (0.23 g, 1.49 mmol). The mixture was stirred at room temperature overnight and concentrated to provide a residue which was subjected to chromatography to give 68 (0.20 g, 67%) as a white solid.

$^1$H NMR (400 MHz, CD$_3$OD): δ 1.47 (18H, s), 1.80 (3H, m), 1.94 (3H, m), 2.10 (1H, m), 2.20 (1H, m), 3.10 (1H, d, J=11.6 Hz), 3.25 (1H, m), 3.43 (2H, m), 3.75 (2H, m), 3.92 (1H, d, J=6.0 Hz), 4.14 (2H, m), 3 protons were not observed in CD$_3$OD.

MS (ES$^-$) m/z: [M−H]$^-$ calcd for C$_{23}$H$_{37}$N$_6$O$_{11}$S: 605.22. Found: 605.03.

Step 6. (2S,5R)-N-[(1-Carbamimidoylpiperidin-4-yl)oxy]-7-oxo-6-(sulfooxy)-1,6-diazabicyclo[3.2.1]octane-2-carboxamide (Compound 75, Table 1)

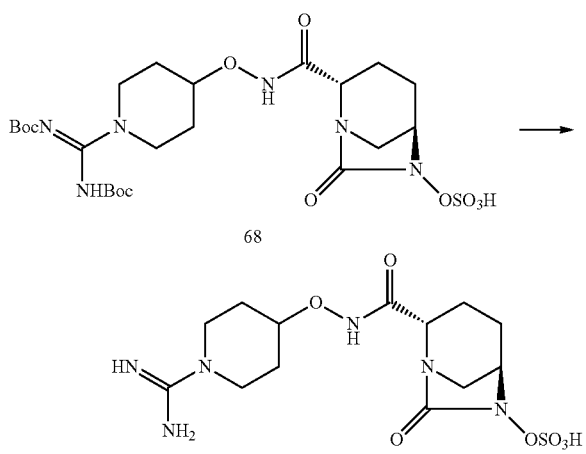
Compound 75, Table 1

To a mixture of di-tert-butyl [{4-[({[(2S,5R)-7-oxo-6-(sulfooxy)-1,6-diazabicyclo[3.2.1]oct-2-yl]carbonyl}amino)oxy]piperidin-1-yl}methylylidene]biscarbamate 68 (0.15 g, 0.25 mmol) in DCM (5.0 mL) was added trifluoroacetic acid (1.0 mL) at 0° C. The mixture was stirred at 0° C. for 0.5 h and at room temperature for 2 h, concentrated and washed with ether. The white solid was collected by centrifugation. The crude product was purified by preparative HPLC to provide Compound 75 (Table 1) (40 mg) as a white solid.

$^1$H NMR (400 MHz, D$_2$O): δ 1.60-2.10 (8H, m), 3.01 (1H, d, J=12 Hz), 3.22 (3H, m), 3.56 (2H, m), 3.96 (1H, d, J=6.8 Hz), 4.09 (2H, m). 5 protons were not observed in D$_2$O.

HPLC: 95.56%

MS (ES$^-$): m/z [M−H]$^-$ calcd for C$_{13}$H$_{21}$N$_6$O$_7$S: 405.12. Found: 404.93.

Example 15

(2S,5R)-7-Oxo-N-[2-(piperidin-4-yloxy)ethoxy]-6-(sulfooxy)-1,6-diazabicyclo[3.2.1]octane-2-carboxamide (Compound 76, Table 1)

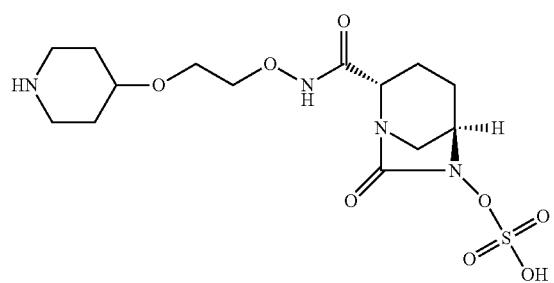 [SMILES: O=C(NOCCOC1CCNCC1)[C@@H]1CC[C@@H]2CN1C(=O)N2OS(=O)(=O)O]

Step 1. tert-Butyl 4-{2-[(1,3-dioxo-1,3-dihydro-2H-isoindol-2-yl)oxy]ethoxy}piperidine-1-carboxylate (70)

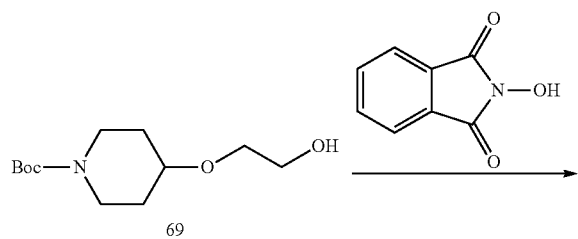

To a solution of tert-butyl 4-(2-hydroxyethoxy)piperidine-1-carboxylate 69 (0.9 g, 3.67 mmol, WO 2009/87649 A1) in THF (28 mL) were added N-hydroxyphthalimide (0.9 g, 5.51 mmol), triphenylphosphine (1.44 g, 5.51 mmol) and DIAD (1.07 mL, 5.51 mmol) sequentially at 0° C. under nitrogen. The mixture was stirred at 0° C. for 30 min and at room temperature for 16 h. Solvent was evaporated off and the residue was subjected to chromatography to give 70 (0.69 g, 48%) as a white solid.

$^1$H NMR (400 MHz, CDCl$_3$): δ 1.27-1.40 (11H, m), 1.67-1.75 (2H, m), 2.95-3.00 (2H, m), 3.42-3.46 (1H, m), 3.56-3.59 (2H, m), 3.76-3.80 (2H, m), 4.29-4.31 (2H, m), 7.67-7.78 (4H, m).

MS (ES$^+$): m/z [M+H]$^+$ calcd for C$_{20}$H$_{26}$N$_2$O$_6$: 391.44. Found: 391.02.

Step 2. tert-Butyl 4-[2-(aminooxy)ethoxy]piperidine-1-carboxylate (71)

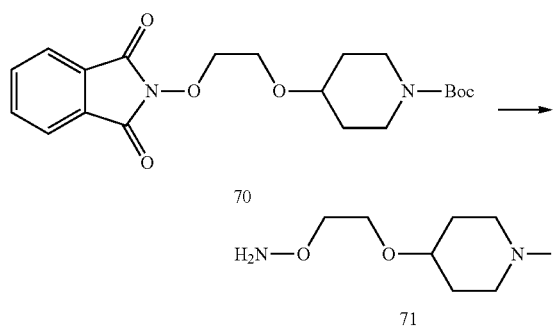

To a solution of tert-butyl 4-{2-[(1,3-dioxo-1,3-dihydro-2H-isoindol-2-yl)oxy]ethoxy}piperidine-1-carboxylate 70 (0.57 g, 1.46 mmol) in a mixture of ethanol (1 mL) and DCM (6 mL) was added hydrazine hydrate (0.086 g, 1.46 mmol). The reaction mixture was stirred at room temperature for 16 h. Precipitate was filtered off. The filtrate was evaporated and the residue was subjected to chromatography to give 71 (0.327 g, 86%) as a colorless oil.

$^1$H NMR (400 MHz, CD$_3$OD): δ 1.45-1.57 (11H, m), 1.80-1.90 (2H, m), 3.00-3.19 (2H, m), 3.45-3.51 (2H, m), 3.62-3.68 (1H, m), 3.75-3.85 (4H, m), 5.50 (2H, br s).

MS (ES$^+$): m/z [M+H]$^+$ calcd for C$_{12}$H$_{24}$N$_2$O$_4$: 261.34. Found: 261.04.

Step 3. tert-Butyl 4-{2-[({[(2S,5R)-6-(benzyloxy)-7-oxo-1,6-diazabicyclo[3.2.1]oct-2-yl]carbonyl}amino)oxy]ethoxy}piperidine-1-carboxylate (72)

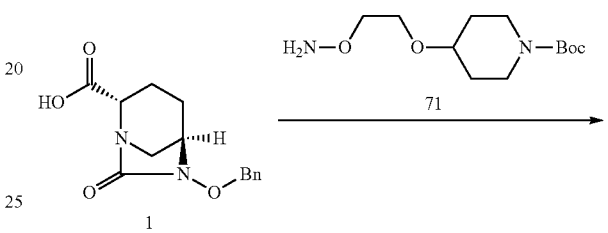

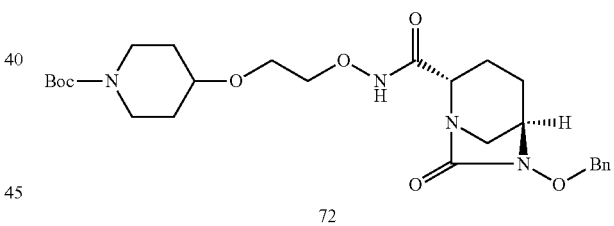

To a mixture of (2S,5R)-6-(benzyloxy)-7-oxo-1,6-diazabicyclo[3.2.1]octane-2-carboxylic acid 1 (0.150 g, 0.543 mmol, US 2005/20572 A1) in DCM (4.0 mL) were added tert-butyl 4-[2-(aminooxy)ethoxy]piperidine-1-carboxylate 71 (0.240 g, 0.543 mmol), 1-hydroxybenzotriazole (0.110 g, 0.814 mmol) and 1-ethyl-(3-dimethylamino-propyl) carbodiimide hydrochloride (0.156 g, 0.814 mmol) sequentially at room temperature. The mixture was stirred at room temperature for 16 h, diluted with DCM, washed with water, brine, dried over sodium sulfate and concentrated to provide a residue which was subjected to chromatography to give 72 (0.276 g, 98%) as a colorless foam.

$^1$H NMR (400 MHz, CDCl$_3$): δ 1.46-1.67 (12H, m), 1.84-2.04 (4H, m), 2.30-2.35 (1H, m), 2.77 (1H, d, J=11.6 Hz), 2.98-3.09 (3H, m), 3.31 (1H, s), 3.45-3.53 (1H, m), 3.64-3.85 (4H, m), 3.94 (1H, d, J=7.6 Hz), 4.05-4.11 (2H, m), 4.90 (1H, d, J=11.2 Hz), 5.05 (1H, d, J=12.0 Hz), 7.35-7.46 (5H, m), 1 proton was not observed in moisture-containing CDCl$_3$.

MS (ES⁻): m/z [M–H]⁻ calcd for $C_{26}H_{38}N_4O_7$: 517.62. Found: 517.13.

Step 4. tert-Butyl 4-{2-[({[(2S,5R)-6-hydroxy-7-oxo-1,6-diazabicyclo[3.2.1]oct-2-yl]carbonyl}amino)oxy]ethoxy}piperidine-1-carboxylate (73)

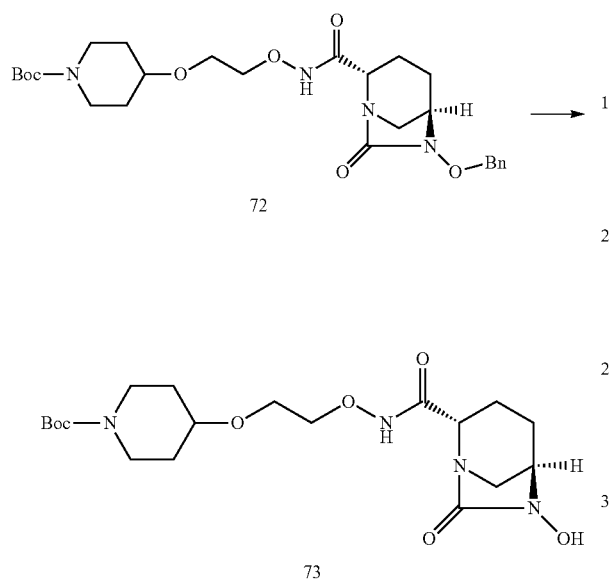

A mixture of tert-butyl 4-{2-[({[(2S,5R)-6-(benzyloxy)-7-oxo-1,6-diazabicyclo[3.2.1]oct-2-yl]carbonyl}amino)oxy]ethoxy}piperidine-1-carboxylate 72 (0.270 g, 0.521 mmol) and Pd/C (0.270 g) in methanol (25 mL) was hydrogenated at 35 psi at room temperature for 2 h. The mixture was filtered through a Celite pad and concentrated to provide 73 (0.221 g, 99%) as a light grey solid.

¹H NMR (400 MHz, CDCl₃): δ 1.45-1.58 (11H, m), 1.70-2.05 (4H, m), 2.11-2.20 (1H, m), 2.33-2.42 (1H, m), 2.90-3.20 (4H, m), 3.46-3.60 (2H, m), 3.68-3.85 (6H, m), 3.90-3.96 (1H, m), 4.05-4.18 (1H, m), 9.61 (1H, br s).

MS (ES⁻): m/z [M–H]⁻ calcd for $C_{19}H_{32}N_4O_7$: 427.49. Found: 426.98.

Step 5. tert-Butyl 4-{2-[({[(2S,5R)-7-oxo-6-(sulfooxy)-1,6-diazabicyclo[3.2.1]oct-2-yl]carbonyl}amino)oxy]ethoxy}piperidine-1-carboxylate (74)

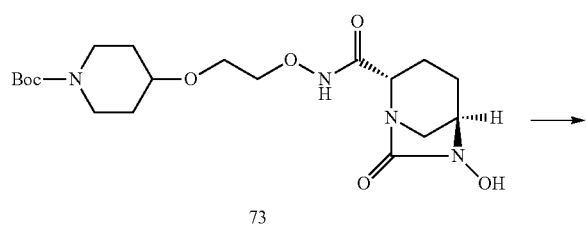

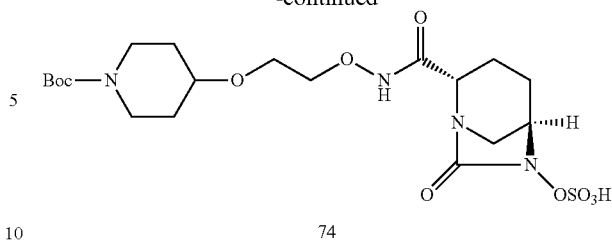

To a mixture of tert-butyl 4-{2-[({[(2S,5R)-6-hydroxy-7-oxo-1,6-diazabicyclo[3.2.1]oct-2-yl]carbonyl}amino)oxy]ethoxy}piperidine-1-carboxylate 73 (0.221 g, 0.516 mmol) in pyridine (5.0 mL) was added sulfur trioxide pyridine complex (0.228 g, 1.434 mmol). The mixture was stirred at room temperature for 20 h. Solid was filtered off. The filtrate was evaporated to provide a residue which was subjected to chromatography to give 74 (0.197 g, 75%) as a light yellow solid.

¹H NMR (400 MHz, CD₃OD): δ 1.40-1.53 (11H, m), 1.79-1.97 (4H, m), 2.05-2.09 (1H, m), 2.19-2.24 (1H, m), 3.05-3.18 (3H, m), 3.21-3.28 (1H, m), 3.53-3.61 (1H, m), 3.68-3.78 (4H, m), 3.92 (1H, d, J=6.8 Hz), 4.00-4.06 (2H, m), 4.12-4.18 (1H, m).

MS (ES⁻): m/z [M–H]⁻ calcd for $C_{19}H_{32}N_4O_{10}S$: 507.55. Found: 506.92.

Step 6. (2S,5R)-7-Oxo-N-[2-(piperidin-4-yloxy)ethoxy]-6-(sulfooxy)-1,6-diazabicyclo[3.2.1]octane-2-carboxamide (Compound 76, Table 1)

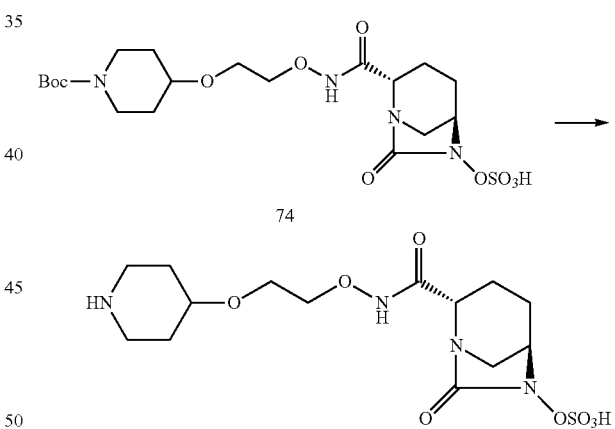

Compound 76, Table 1

To a mixture of tert-butyl 4-{2-[({[(2S,5R)-7-oxo-6-(sulfooxy)-1,6-iazabicyclo[3.2.1]oct-2-yl]carbonyl}amino)oxy]ethoxy}piperidine-1-carboxylate 74 (0.195 g, 0.386 mmol) in DCM (9.0 mL) was added trifluoroacetic acid (0.44 mL) at 0° C. The mixture was stirred at 0° C. for 1 h, concentrated and washed with ether. The white solid was collected by centrifugation. The crude product was purified by preparative HPLC to provide Compound 76 (Table 1) (25 mg) as a white solid.

¹H NMR (400 MHz, CD₃OD): δ 1.80-2.01 (6H, m), 2.06-2.15 (1H, m), 2.18-2.22 (1H, m), 3.04-3.12 (4H, m), 3.24-3.27 (1H, m), 3.72-3.78 (4H, m), 3.90 (1H, d, J=6.0 Hz), 4.02-4.06 (2H, m), 4.15 (1H, d, J=3.2 Hz), 3 protons were not observed in CD₃OD.

HPLC: 92.51%

MS (ES⁻): m/z [M−H]⁻ calcd for $C_{14}H_{24}N_4O_8S$: 407.45. Found: 406.93.

Example 16

(2S,5R)-7-Oxo-N-[2-(sulfamoylamino)ethoxy]-6-(sulfooxy)-1,6-diazabicyclo[3.2.1]octane-2-carboxamide (Compound 77, Table 1)

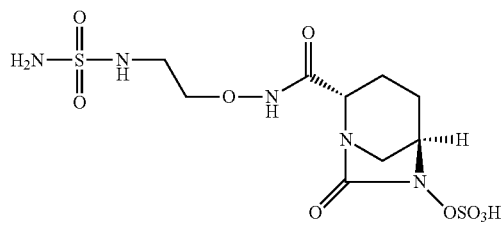

Step 1. tert-Butyl ({2-[(1,3-dioxo-1,3-dihydro-2H-isoindol-2-yl)oxy]ethyl}sulfamoyl)carbamate (77)

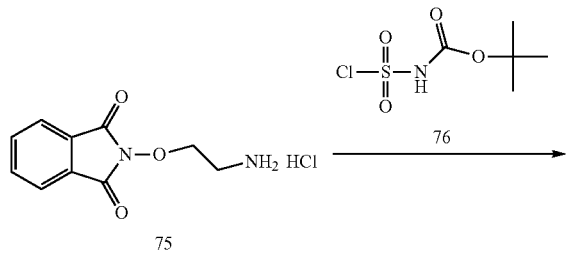

To a mixture of 2-(2-aminoethoxy)-1H-isoindole-1,3(2H)-dione hydrochloride 75 (0.53 g, 2.19 mmol, EP 16744522 A1, 2006), tert-butyl (chlorosulfonyl)carbamate 76 (0.71 g, 3.28 mmol, WO 2006/84281 A1) in DCM (10 mL) was added triethylamine (0.92 mL, 6.57 mmol) slowly at 0° C. The resulting mixture was stirred at room temperature for 7 h and concentrated to provide a residue which was subjected to chromatography to give 77 (0.63 g, 74%) as a white foam.

¹H NMR (400 MHz, CDCl₃): δ 1.50 (9H, s), 3.49 (2H, m), 4.36 (2H, t, J=4.8 Hz), 6.28 (1H, t, J=4.8 Hz), 7.11 (1H, s), 7.79 (2H, m), 7.86 (2H, m).

MS (ES⁻): m/z [M−H]⁻ calcd for $C_{15}H_{18}N_3O_7S$: 384.09. Found: 383.94.

Step 2. tert-Butyl {[2-(aminooxy)ethyl]sulfamoyl}carbamate (78)

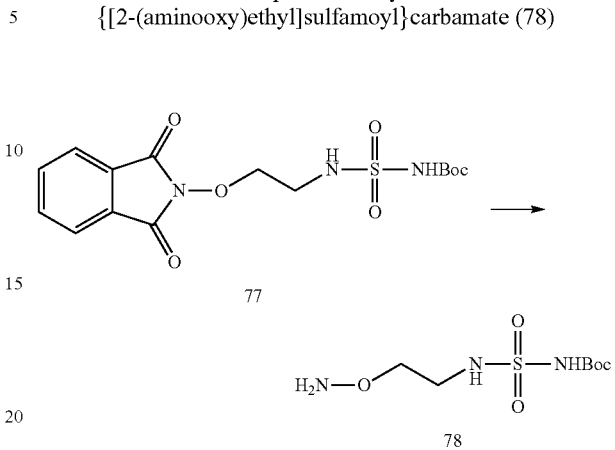

To a mixture of tert-butyl ({2-[(1,3-dioxo-1,3-dihydro-2H-isoindol-2-yl)oxy]ethyl}sulfamoyl)carbamate 77 (0.62 g, 1.61 mmol) in a solution of DCM (10 mL) and ethanol (2 mL) was added hydrazine hydrate (0.092 mL, 1.61 mmol) at room temperature. The mixture was stirred at room temperature overnight, filtered and concentrated to provide a residue which was subjected to chromatography to give 78 (0.18 g, 44%) as a white solid.

¹H NMR (400 MHz, CDCl₃): δ 1.49 (9H, s), 3.33 (2H, m), 3.81 (2H, m), 5.28 (2H, br s), 5.93 (1H, br s), 7.24 (1H, br s).

MS (ES⁺): m/z [M+H]⁺ calcd for $C_7H_{18}N_3O_5S$: 256.10. Found: 255.91.

Step 3. tert-Butyl ({2-[({[(2S,5R)-6-(benzyloxy)-7-oxo-1,6-diazabicyclo[3.2.1]oct-2-yl]carbonyl}amino)oxy]ethyl}sulfamoyl)carbamate (79)

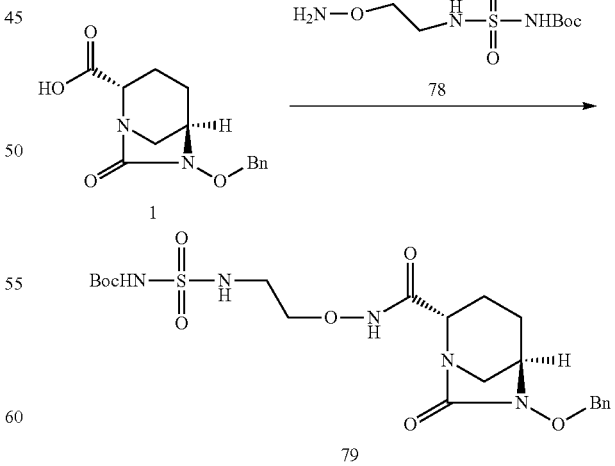

To a mixture of (2S,5R)-6-(benzyloxy)-7-oxo-1,6-diazabicyclo[3.2.1]octane-2-carboxylic acid 1 (0.200 g, 0.723 mmol) in DCM (6.0 mL) was added tert-butyl {[2-(aminooxy)ethyl]sulfamoyl}carbamate 78 (0.276 g, 1.085 mmol), 1-hydroxybenzotriazole (0.147 g, 1.086 mmol) and 1-ethyl-(3-dimethylaminopropyl) carbodiimide hydrochloride (0.208 g, 1.086 mmol) sequentially at room temperature. The mixture was stirred at room temperature overnight, diluted with DCM and concentrated to provide a residue which was subjected to chromatography to give 79 (0.35 g, 93%) as a white solid.

$^1$H NMR (400 MHz, CDCl$_3$): δ 1.48 (9H, m), 1.64 (1H, m), 1.95 (2H, m), 2.33 (1H, m), 2.76 (1H, d, J=11.2 Hz), 3.01 (1H, d, J=12.0 Hz), 3.32 (1H, s), 3.38 (2H, br s), 3.95 (1H, d, J=7.2 Hz), 4.03 (2H, m), 4.92 (2H, ABq), 6.38 (1H, br s), 7.26 (1H, m), 7.41 (5H, m), 9.20 (1H, s).

MS (ES$^+$): m/z [M+H]$^+$ calcd for C$_{21}$H$_{32}$N$_5$O$_8$S: 514.20. Found: 514.00.

Step 4. tert-Butyl ({2-[({[(2S,5R)-6-hydroxy-7-oxo-1,6-diazabicyclo[3.2.1]oct-2-yl]carbonyl}amino)oxy]ethyl}sulfamoyl)carbamate (80)

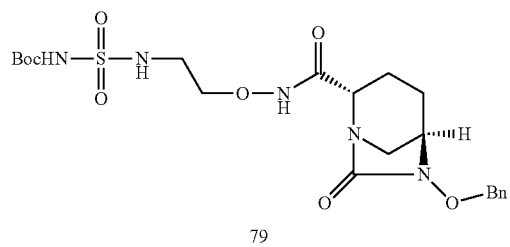

79

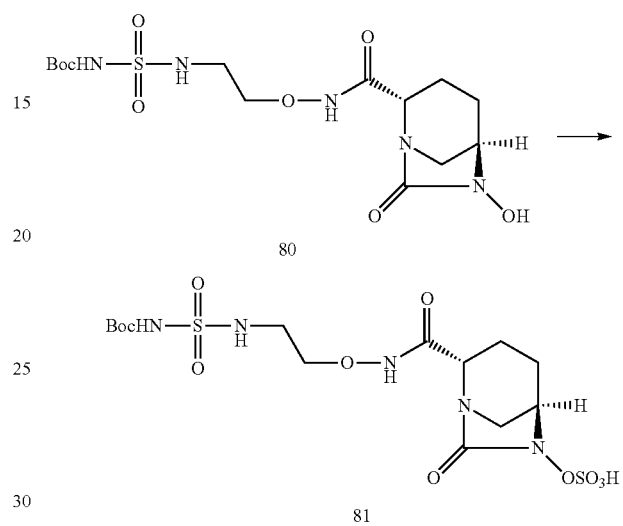

A mixture of tert-butyl ({2-[({[(2S,5R)-6-(benzyloxy)-7-oxo-1,6-diazabicyclo[3.2.1]oct-2-yl]carbonyl}amino)oxy]ethyl}sulfamoyl)carbamate 79 (0.35 g, 0.67 mmol) and Pd/C (10%, 0.12 g) in methanol (10 mL) was hydrogenated at 1 atm at room temperature for 3 h. The mixture was filtered through Celite pad and concentrated to provide 80 (0.25 g, 88%) as a white foam.

$^1$H NMR (400 MHz, CD$_3$OD): δ 1.48 (9H, s), 1.80 (1H, m), 1.96 (1H, m), 2.06 (1H, m), 2.20 (1H, m), 3.03 (1H, d, J=11.6 Hz), 3.12 (1H, m), 3.28 (2H, m), 3.70 (1H, m), 3.84 (1H, d, J=8.0 Hz), 3.98 (2H, t, J=5.6 Hz). 4 protons were not observed in CD$_3$OD.

MS (ES$^+$): m/z [M+H]$^+$ calcd for C$_{14}$H$_{26}$N$_5$O$_8$S: 424.15. Found: 423.97.

Step 5. tert-Butyl ({2-[({[(2S,5R)-7-oxo-6-(sulfooxy)-1,6-diazabicyclo[3.2.1]oct-2-yl]carbonyl}amino)oxy]ethyl}sulfamoyl)carbamate (81)

To a mixture of tert-butyl ({2-[({[(2S,5R)-6-hydroxy-7-oxo-1,6-diazabicyclo[3.2.1]oct-2-yl]carbonyl}amino)oxy]ethyl}sulfamoyl)carbamate 80 (0.25 g, 0.59 mmol) in pyridine (10.0 mL) was added sulfur trioxide pyridine complex (0.28 g, 1.77 mmol). The mixture was stirred at room temperature overnight and concentrated to provide a residue which was subjected to chromatography to give 81 (0.20 g, 67%) as a white solid.

$^1$H NMR (400 MHz, CD$_3$OD): δ 1.48 (9H, s), 1.83 (1H, m), 1.91 (1H, m), 2.06 (1H, m), 2.21 (1H, m), 3.08 (1H, d, J=11.6 Hz), 3.24 (1H, m), 3.28 (2H, m), 3.91 (1H, d, J=7.2 Hz), 3.98 (2H, t, J=5.6 Hz), 4.15 (1H, m). 4 protons were not observed in CD$_3$OD.

MS (ES$^-$): m/z [M−H]$^-$ calcd for C$_{14}$H$_{24}$N$_5$O$_{11}$S$_2$: 502.09. Found: 501.97.

Step 6. (2S,5R)-7-Oxo-N-[2-(sulfamoylamino)ethoxy]-6-(sulfooxy)-1,6-diazabicyclo[3.2.1]octane-2-carboxamide (Compound 77, Table 1)

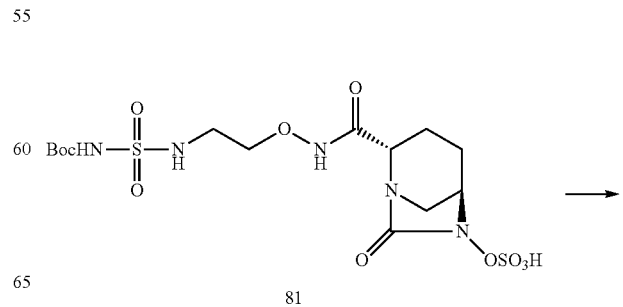

81

-continued

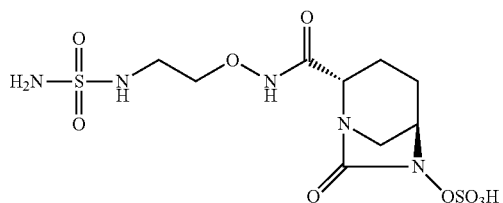

Compound 77, Table 1

To a mixture of tert-butyl ({2-[({[(2S,5R)-7-oxo-6-(sulfooxy)-1,6-diazabicyclo[3.2.1]oct-2-yl]carbonyl}amino)oxy]ethyl}sulfamoyl)carbamate 81 (0.20 g, 0.40 mmol) in DCM (5.0 mL) was added trifluoroacetic acid (1.0 mL) at 0° C. The mixture was stirred at 0° C. for 0.5 h and at room temperature for 2 h, concentrated and washed with ether. The white solid was collected by centrifugation. The crude product was purified by preparative HPLC to provide Compound 77 (Table 1) (37 mg, 23%) as a white solid.

¹H NMR (400 MHz, D₂O): δ 1.68-2.06 (4H, m), 3.00 (1H, d, J=12.0 Hz), 3.17-3.22 (3H, m), 3.94 (3H, m), 4.07 (1H, d, J=2.8 Hz). 5 protons were not observed in D₂O.

HPLC: 95.56%

MS (ES⁻) m/z: [M−H]⁻ calcd for C₉H₁₆N₅O₉S₂: 402.04. Found: 401.99.

Example 17

(2S,5R)-N-[2-(Carbamoylamino)ethoxy]-7-oxo-6-(sulfooxy)-1,6-diazabicyclo[3.2.1]octane-2-carboxamide (Compound 78, Table 1)

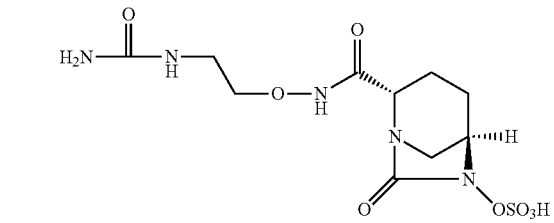

Step 1. tert-Butyl ({2-[(1,3-dioxo-1,3-dihydro-2H-isoindol-2-yl)oxy]ethyl}carbamoyl)carbamate (83)

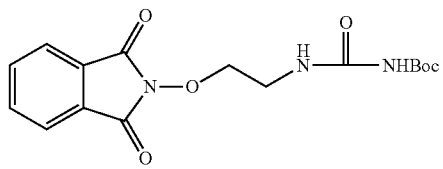

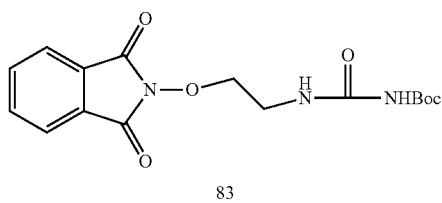

To a mixture of 2-(2-aminoethoxy)-1H-isoindole-1,3(2H)-dione hydrochloride 75 (0.40 g, 1.65 mmol, EP 1674452 A1, 2006), tert-butyl (chlorocarbonyl)carbamate 82 (1.70 g crude, US 2005/187277 A1) in DCM (10 mL) was added triethylamine (0.69 mL, 4.95 mmol) slowly at 0° C. The resulting mixture was stirred at room temperature overnight and concentrated to provide a residue which was subjected to chromatography to give 83 (0.56 g, 96%) as a white solid.

¹H NMR (400 MHz, CDCl₃): δ 1.50 (9H, s), 3.64 (2H, m), 4.30 (2H, t, J=5.2 Hz), 6.91 (1H, br s), 7.75 (2H, m), 7.87 (2H, m), 8.45 (1H, m).

Step 2. tert-Butyl {[2-(aminooxy)ethyl]carbamoyl}carbamate (84)

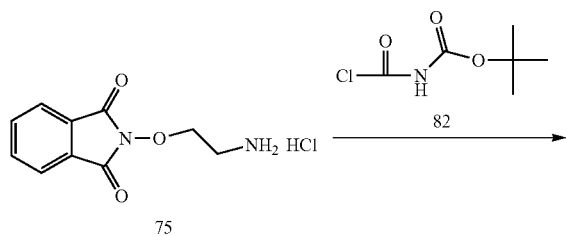

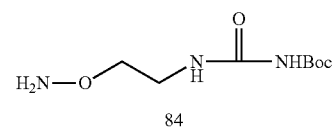

To a mixture of tert-butyl ({2-[(1,3-dioxo-1,3-dihydro-2H-isoindol-2-yl)oxy]ethyl}carbamoyl)carbamate 83 (0.56 g, 1.59 mmol) in a solution of DCM (10 mL) and ethanol (2 mL) was added hydrazine hydrate (0.091 mL, 1.59 mmol) at room temperature. The mixture was stirred at room temperature overnight, filtered and concentrated to provide a residue which was subjected to chromatography to give 84 (0.25 g, 72%) as a white solid.

¹H NMR (400 MHz, CDCl₃): δ 1.49 (9H, s), 3.53 (2H, q, J=5.2 Hz), 3.76 (2H, t, J=5.2 Hz), 5.51 (2H, br s), 6.83 (1H, br s), 7.80 (1H, br s).

Step 3. tert-Butyl ({2-[({[(2S,5R)-6-(benzyloxy)-7-oxo-1,6-diazabicyclo[3.2.1]oct-2-yl]carbonyl}amino)oxy]ethyl}carbamoyl)carbamate (85)

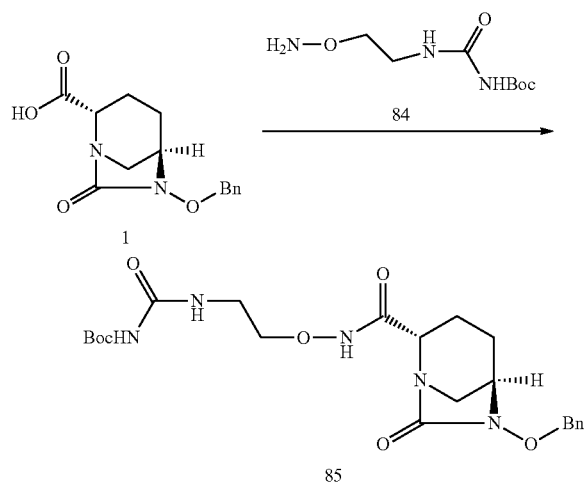

To a mixture of (2S,5R)-6-(benzyloxy)-7-oxo-1,6-diazabicyclo[3.2.1]octane-2-carboxylic acid 1 (0.210 g, 0.760 mmol, US 2005/20572 A1) in DCM (6.0 mL) were added tert-butyl {[2-(aminooxy)ethyl]carbamoyl}carbamate 84 (0.250 g, 1.140 mmol), 1-hydroxybenzotriazole (0.154 g, 1.140 mmol) and 1-ethyl-(3-dimethylaminopropyl) carbodiimide hydrochloride (0.218 g, 1.140 mmol) sequentially at room temperature. The mixture was stirred at room temperature overnight, diluted with DCM and concentrated to provide a residue which was subjected to chromatography to give 85 (0.31 g, 85%) as a white solid.

¹H NMR (400 MHz, CDCl₃): δ 1.48 (9H, m), 1.64 (2H, m), 1.98 (2H, m), 2.34 (1H, m), 2.77 (1H, d, J=11.2 Hz), 3.02 (1H, m), 3.28 (1H, m), 3.47 (1H, m), 3.63 (1H, m), 3.97 (2H, m), 4.90 (2H, ABq), 6.79 (1H, br s), 7.39 (5H, m), 8.11 (1H, m), 9.77 (1H, s).

MS (ES⁺) m/z: [M+H]⁺ calcd for C₂₂H₃₂N₅O₇: 478.23. Found: 478.10.

Step 4. tert-Butyl ({2-[({[(2S,5R)-6-hydroxy-7-oxo-1,6-diazabicyclo[3.2.1]oct-2-yl]carbonyl}amino)oxy]ethyl}carbamoyl)carbamate (86)

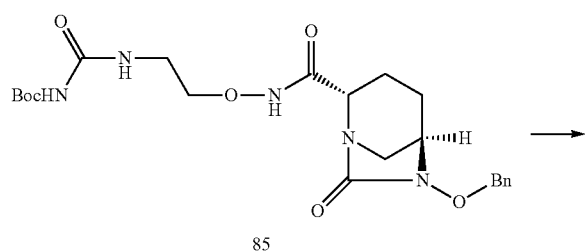

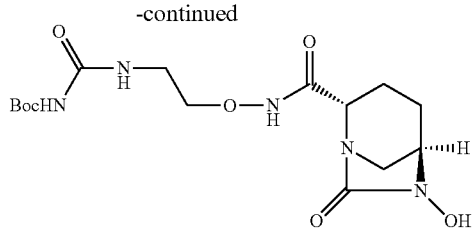

A mixture of tert-butyl ({2-[({[(2S,5R)-6-(benzyloxy)-7-oxo-1,6-diazabicyclo[3.2.1]oct-2-yl]carbonyl}amino)oxy]ethyl}carbamoyl)carbamate 85 (0.31 g, 0.64 mmol) and Pd/C (10%, 0.11 g) in methanol (10 mL) was hydrogenated at 1 atm at room temperature for 3 h. The mixture was filtered through Celite pad and concentrated to provide 86 (0.25 g, quantitative) as a white foam.

¹H NMR (400 MHz, CD₃OD): δ 1.48 (9H, s), 1.80 (1H, m), 1.92 (1H, m), 2.05 (1H, m), 2.20 (1H, m), 3.02 (1H, d, J=11.6 Hz), 3.15 (1H, m), 3.51 (2H, t, J=5.6 Hz), 3.70 (1H, m), 3.85 (1H, d, J=7.2 Hz), 3.94 (2H, t, J=5.6 Hz). 4 protons were not observed in CD₃OD.

MS (ES⁻) m/z: [M−H]⁻ calcd for C₁₅H₂₄N₅O₇: 386.17. Found: 386.07.

Step 5. tert-Butyl ({2-[({[(2S,5R)-7-oxo-6-(sulfooxy)-1,6-diazabicyclo[3.2.1]oct-2-yl]carbonyl}amino)oxy]ethyl}carbamoyl)carbamate (87)

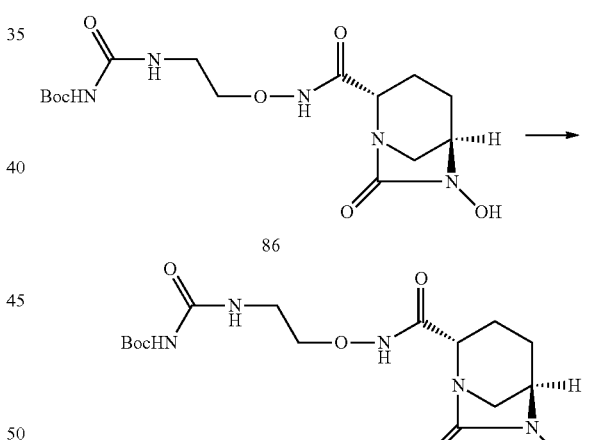

To a mixture of tert-butyl ({2-[({[(2S,5R)-6-hydroxy-7-oxo-1,6-diazabicyclo[3.2.1]oct-2-yl]carbonyl}amino)oxy]ethyl}carbamoyl)carbamate 86 (0.25 g, 0.65 mmol) in pyridine (10.0 mL) was added sulfur trioxide pyridine complex (0.30 g, 1.94 mmol). The mixture was stirred at room temperature overnight and concentrated to provide a residue which was subjected to chromatography to give 87 (0.25 g, 83%) as a white solid.

¹H NMR (400 MHz, CD₃OD): δ 1.49 (9H, s), 1.83 (1H, m), 1.93 (1H, m), 2.07 (1H, m), 2.21 (1H, m), 3.07 (1H, d, J=21.0 Hz), 3.27 (1H, m), 3.51 (2H, t, J=5.2 Hz), 3.92 (1H, m), 3.95 (2H, t, J=5.2 Hz), 4.15 (1H, m). 4 protons were not observed in CD₃OD.

MS (ES⁻) m/z: [M−H]⁻ calcd for $C_{15}H_{24}N_5O_{10}S$: 466.12. Found: 466.01.

Step 6. (2S,5R)-N-[2-(Carbamoylamino)ethoxy]-7-oxo-6-(sulfooxy)-1,6-diazabicyclo[3.2.1]octane-2-carboxamide (Compound 78, Table 1)

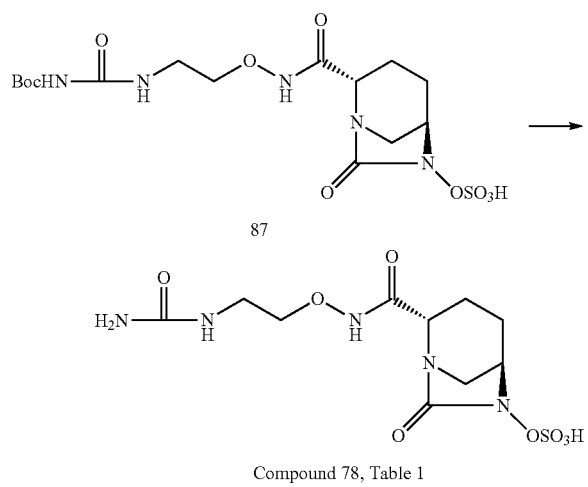

Compound 78, Table 1

To a mixture of tert-butyl ({2-[({[(2S,5R)-7-oxo-6-(sulfooxy)-1,6-diazabicyclo[3.2.1]oct-2-yl]carbonyl}amino)oxy]ethyl}carbamoyl)carbamate 87 (0.25 g, 0.54 mmol) in DCM (5.0 mL) was added trifluoroacetic acid (1.0 mL) at 0° C. The mixture was stirred at 0° C. for 0.5 h and at room temperature for 2 h, concentrated and washed with ether. The white solid was collected by centrifugation. The crude product was purified by preparative HPLC to provide Compound 78 (Table 1) (11 mg, 5.6%) as a white solid.

¹H NMR (400 MHz, D₂O): δ 1.69-1.88 (2H, m), 1.90-2.09 (2H, m), 2.98 (1H, d, J=12.0 Hz), 3.17-3.21 (1H, m), 3.24 (2H, t, J=5.2 Hz), 3.84 (2H, t, J=5.2 Hz), 3.93 (1H, d, J=7.6 Hz), 4.07 (1H, s). 5 protons were not observed in D₂O.

HPLC: 85.17%

MS (ES⁻) m/z: [M−H]⁻ calcd for $C_{10}H_{16}N_5O_8S$: 366.07. Found: 365.96.

Example 18

Disodium[({[(2S,5R)-7-oxo-6-(sulfonatooxy)-1,6-diazabicyclo[3.2.1]oct-2-yl]carbonyl}amino)oxy]acetate (Compound 82, Table 1)

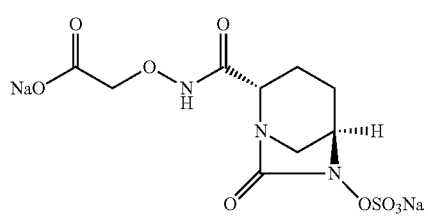

Step 1. tert-Butyl [({[(2S,5R)-6-(benzyloxy)-7-oxo-1,6-diazabicyclo[3.2.1]oct-2-yl]carbonyl}amino)oxy]acetate (89)

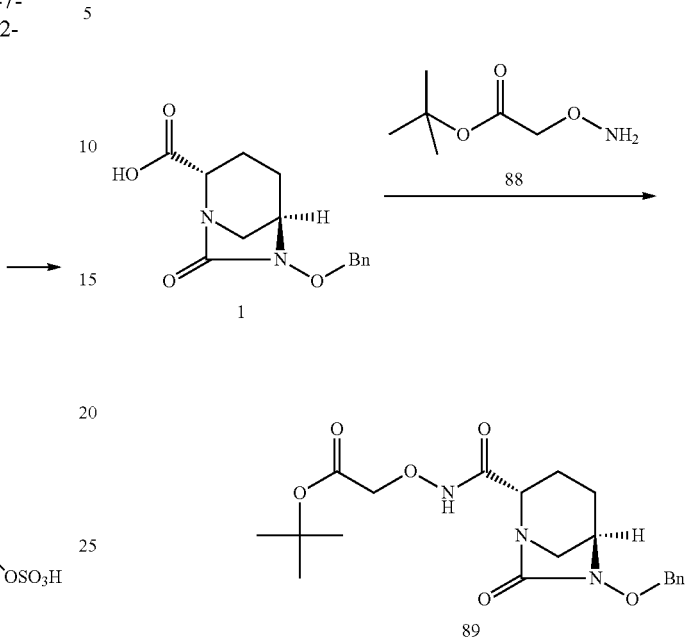

To a solution of (2S,5R)-6-(benzyloxy)-7-oxo-1,6-diazabicyclo[3.2.1]octane-2-carboxylic acid 1 (0.20 g, 0.72 mmol) in dry DCM (20 mL) were added tert-butyl (aminooxy)acetate 88 (0.13 g, 0.86 mmol, Organic Letters, 2002, 4(6) 869-872), 1-hydroxybenzotriazole (0.15 g, 1.11 mmol) and 1-ethyl-(3-dimethylaminopropyl)carbodiimide hydrochloride (0.21 g, 1.10 mmol) at room temperature. The reaction mixture was stirred at room temperature overnight and concentrated under vacuum. The residue was purified by column chromatography to give tert-butyl [({[(2S,5R)-6-(benzyloxy)-7-oxo-1,6-diazabicyclo[3.2.1]oct-2-yl]carbonyl}amino)oxy]acetate 89 (0.23 g, 79%) as a white solid.

¹H NMR (400 MHz, CDCl₃): δ 1.49 (9H, s), 1.65 (1H, m), 1.98 (2H, m), 2.33 (1H, m), 2.72 (1H, d, J=11.6 Hz), 2.99 (1H, d, J=11.2 Hz), 3.30 (1H, s), 3.95 (1H, d, J=7.2 Hz), 4.34 (2H, m), 4.89 (1H, d, J=11.2 Hz), 5.04 (1H, d, J=12.0 Hz), 7.39 (5H, m), 9.68 (1H, br s).

Step 2. tert-Butyl [({[(2S,5R)-6-hydroxy-7-oxo-1,6-diazabicyclo[3.2.1]oct-2-yl]carbonyl}amino)oxy]acetate (90)

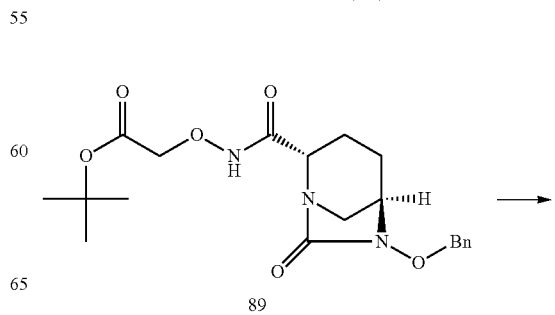

-continued

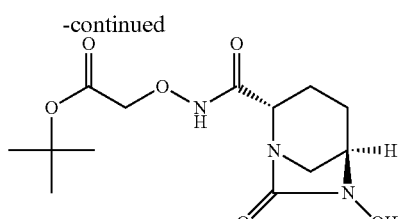

90

To a solution of tert-butyl [({[(2S,5R)-6-(benzyloxy)-7-oxo-1,6-diazabicyclo[3.2.1]oct-2-yl]carbonyl}amino)oxy]acetate 89 (0.23 g, 0.57 mml) in methanol (20 mL) was added 5% Pd/C (0.30 g). The mixture was hydrogenated under 35 psi hydrogen atmosphere at room temperature for 1 h. The catalyst was filtered out through Celite, and the filtrate was evaporated to give tert-butyl [({[(2S,5R)-6-hydroxy-7-oxo-1,6-diazabicyclo[3.2.1]oct-2-yl]carbonyl}amino)oxy]acetate 90 (0.16 g, 89%) as a clear thick oil.

$^1$H NMR (400 MHz, CD$_3$OD): δ 1.48 (9H, s), 1.77 (1H, m), 1.90 (1H, m), 2.06 (1H, m), 2.20 (1H, m), 3.10 (2H, m), 3.70 (1H, m), 3.84 (1H, d, J=7.2 Hz), 4.35 (2H, m), 2 protons were not observed in CD$_3$OD.

Step 3. tert-Butyl [({[(2S,5R)-7-oxo-6-(sulfooxy)-1,6-diazabicyclo[3.2.1]oct-2-yl]carbonyl}amino)oxy] acetate pyridine salt (91)

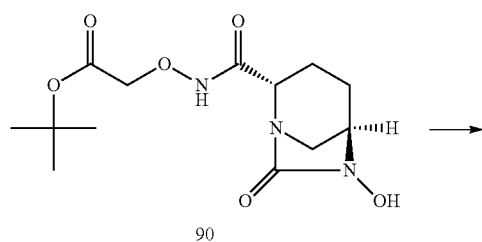

90

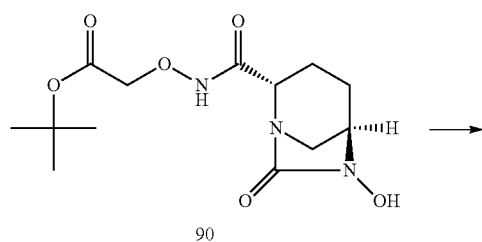

91

To a solution of tert-butyl [({[(2S,5R)-6-hydroxy-7-oxo-1,6-diazabicyclo[3.2.1]oct-2-yl]carbonyl}amino)oxy]acetate 90 (0.16 g, 0.51 mmol) in dry pyridine (7 mL) under nitrogen atmosphere was added sulfur trioxide pyridine complex (0.325 g, 2.04 mmol). The mixture was stirred at room temperature for 20 h, filtered and evaporated to give tert-butyl [({[(2S,5R)-7-oxo-6-(sulfooxy)-1,6-diazabicyclo[3.2.1]oct-2-yl]carbonyl}amino)oxy]acetate pyridine salt 91 (0.20 g crude) which was used in the next step without purification.

Step 4. N,N,N-Tributylbutan-1-aminium[({(2S,5R)-2-[(2-tert-butoxy-2-oxoethoxy)carbamoyl]-7-oxo-1,6-diazabicyclo[3.2.1]oct-6-yl}oxy)sulfonyl]oxidanide (92)

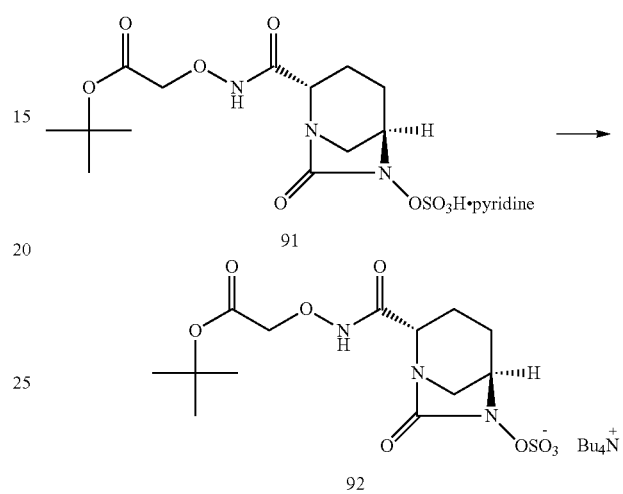

tert-Butyl [({[(2S,5R)-7-oxo-6-(sulfooxy)-1,6-diazabicyclo[3.2.1]oct-2-yl]carbonyl}amino)oxy]acetate pyridine salt 91 (0.20 g, 0.51 mmol) was introduced into a concentrated aqueous solution of monosodium dihydrogen phosphate solution (8 mL) so as to obtain a pH of 4. The mixture was washed with ethyl acetate, then added tetrabutyl ammonium hydrogen sulfate (0.10 g, 0.29 mmol) and stirred at room temperature for 10 min. The mixture was extracted with ethyl acetate (3×10 mL), and the extracts were combined, dried over sodium sulfate and evaporated to give N,N,N-tributylbutan-1-aminium[({(2S,5R)-2-[(2-tert-butoxy-2-oxoethoxy)carbamoyl]-7-oxo-1,6-diazabicyclo[3.2.1]oct-6-yl}oxy)sulfonyl]oxidanide 92 (0.15 g, 46% in 2 steps) as a white solid.

$^1$H NMR (400 MHz, CDCl$_3$): δ 1.01 (12H, t, J=7.2 Hz), 1.42 (17H, m), 1.65 (9H, m), 1.90 (1H, m), 2.18 (1H, m), 2.34 (1H, m), 2.76 (1H, d, J=11.6), 3.29 (9H, m), 3.91 (1H, d, J=7.2 Hz), 4.34 (3H, m), 9.78 (1H, br s).

Step 5. Disodium[({[(2S,5R)-7-oxo-6-(sulfonatooxy)-1,6-diazabicyclo[3.2.1]oct-2-yl] carbonyl}amino)oxy]acetate (Compound 82, Table 1)

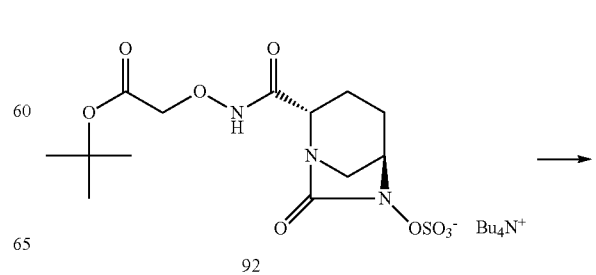

92

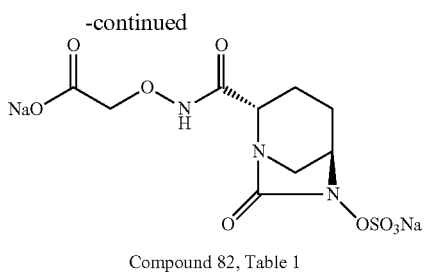

Compound 82, Table 1

To a solution of N,N,N-tributylbutan-1-aminium[({(2S,5R)-2-[(2-tert-butoxy-2-oxoethoxy)carbamoyl]-7-oxo-1,6-diazabicyclo[3.2.1]oct-6-yl}oxy)sulfonyl]oxidanide 92 (0.15 g, 0.24 mmol) in DCM (2 mL) was added trifluoroacetic acid (0.50 mL, 6.49 mmol) dropwise at 0° C. The reaction mixture was stirred for 1 h, then evaporated. The residue after washing with ether (3×) was suspended in water (5 mL) and DOWEX 50WX4 (1 g) was added. The mixture was stirred at room temperature for 1 h, and then filtered. The filtrate was freeze-dried, purified by HPLC and freeze-dried again to give disodium[({[(2S,5R)-7-oxo-6-(sulfonatooxy)-1,6-diazabicyclo[3.2.1]oct-2-yl]carbonyl}amino)oxy]acetate Compound 82 (Table 1) (0.012 g, 15%) as a white solid.

$^1$H NMR (400 MHz, CD$_3$OD): δ 1.82 (1H, m), 1.91 (1H, m), 2.06 (1H, m), 2.22 (1H, m), 3.09 (1H, d, J=12.0 Hz), 3.24 (1H, d, J=10.8 Hz), 3.92 (1H, d, J=7.6 Hz), 4.14 (1H, m), 4.25 (2H, m), 1 proton was not observed in CD$_3$OD.

HPLC 95.36%

MS (ES$^-$): m/z [M−2Na+H]$^-$=337.86.

Example 19

(2S,5R)-7-Oxo-N-[(2S)-pyrrolidin-2-ylmethoxy]-6-(sulfooxy)-1,6-diazabicyclo[3.2.1]octane-2-carboxamide (Compound 16, Table 1)

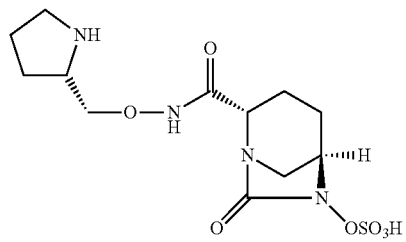

Step 1. tert-Butyl (2S)-2-{[({[(2S,5R)-6-(Benzyloxy)-7-oxo-1,6-diazabicyclo[3.2.1]oct-2-yl]carbonyl}amino)oxy]methyl}pyrrolidine-1-carboxylate (94)

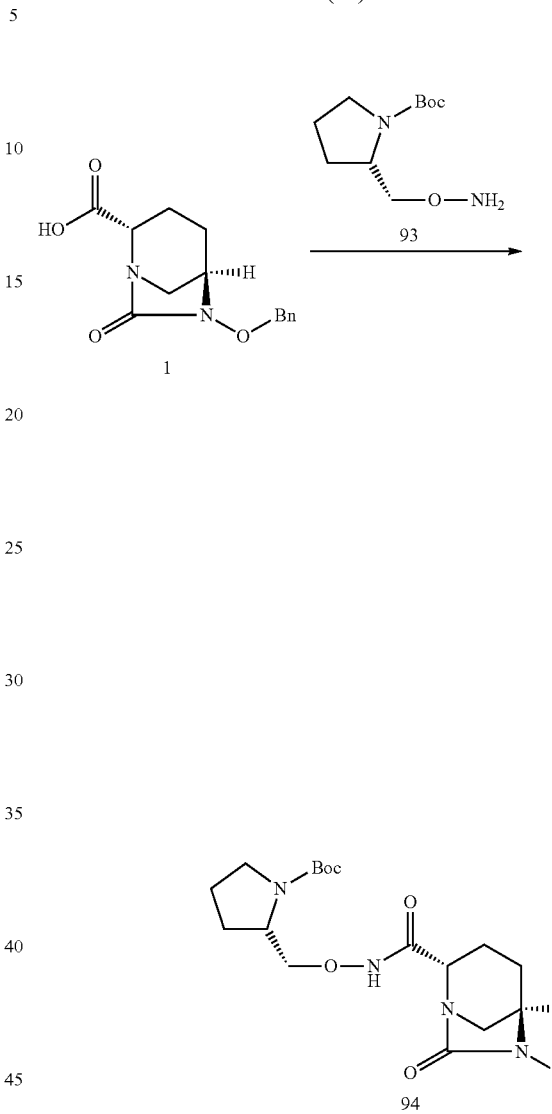

To a mixture of (2S,5R)-6-(benzyloxy)-7-oxo-1,6-diazabicyclo[3.2.1]octane-2-carboxylic acid 1 (0.200 g, 0.720 mmol, US 2005/20572 A1) in DCM (6.0 mL) were added tert-butyl (2S)-2-[(aminooxy)methyl]pyrrolidine-1-carboxylate 93 (0.234 g, 1.085 mmol, US 2007/118830 A1), 1-hydroxybenzotriazole (0.147 g, 1.085 mmol) and 1-ethyl-(3-dimethylamino propyl) carbodiimide hydrochloride (0.208 g, 1.085 mmol) sequentially at room temperature. The mixture was stirred at room temperature overnight, diluted with DCM and concentrated to provide a residue which was subjected to chromatography to give 94 (0.30 g, 88%) as a white foam.

$^1$H NMR (400 MHz, CDCl$_3$): δ 1.47 (9H, s), 1.70 (1H, m), 1.94 (5H, m), 2.29 (1H, m), 2.89 (1H, d, J=12 Hz), 3.03 (1H, m), 3.27 (1H, m), 3.36 (2H, m), 3.73 (1H, m), 3.83 (1H, m), 3.93 (1H, m), 4.12 (1H, m), 4.89 (1H, d, J=11.2 Hz), 5.07 (1H, d, J=11.2 Hz), 7.41 (5H, m), 10.12 (1H, br s). One proton was not observed in moisture-containing CDCl$_3$.

MS (ES⁺): m/z [M+H]⁺ calcd for $C_{24}H_{35}N_4O_6$: 475.26. Found: 475.38.

Step 2. tert-Butyl (2S)-2-{[({[(2S,5R)-6-hydroxy-7-oxo-1,6-diazabicyclo[3.2.1]oct-2-yl]carbonyl}amino)oxy]methyl}pyrrolidine-1-carboxylate (95)

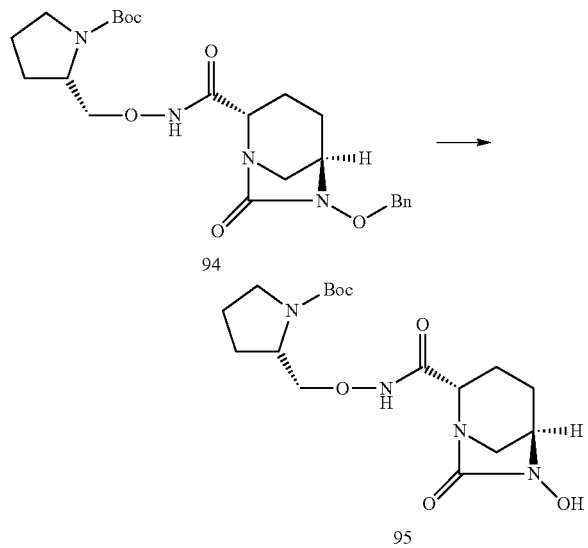

A mixture of tert-butyl (2S)-2-{[({[(2S,5R)-6-(benzyloxy)-7-oxo-1,6-diazabicyclo[3.2.1]oct-2-yl]carbonyl}amino)oxy]methyl}pyrrolidine-1-carboxylate 94 (0.30 g, 0.63 mmol) and Pd/C (0.10 g) in methanol (10 mL) was hydrogenated at 1 atm at room temperature for 3 h. The mixture was filtered through Celite pad and concentrated to provide 95 (0.26 g, quant. yield) as a white foam.

¹H NMR (400 MHz, CD₃OD): δ 1.46 (9H, s), 1.72-2.22 (7H, m), 3.06 (1H, m), 3.12 (1H, m), 3.30 (3H, m), 3.69 (1H, m), 3.37-4.05 (4H, m). 2 protons were not observed in CD₃OD.

MS (ES⁺) m/z: [M+H]⁺ calcd for $C_{17}H_{29}N_4O_6$: 385.21. Found: 385.33.

Step 3. tert-Butyl (2S)-2-{[({[(2S,5R)-7-Oxo-6-(sulfooxy)-1,6-diazabicyclo[3.2.1]oct-2-yl]carbonyl}amino)oxy]methyl}pyrrolidine-1-carboxylate (96)

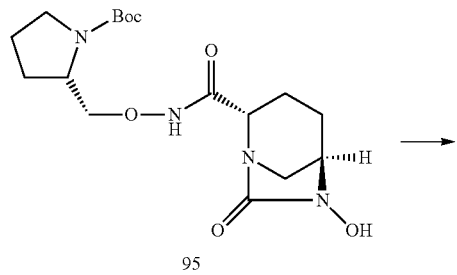

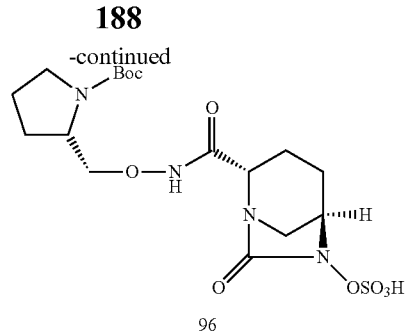

To a mixture of tert-butyl (2S)-2-{[({[(2S,5R)-6-hydroxy-7-oxo-1,6-diazabicyclo[3.2.1]oct-2-yl]carbonyl}amino)oxy]methyl}pyrrolidine-1-carboxylate 95 (0.26 g, 0.67 mmol) in pyridine (10.0 mL) was added sulfur trioxide pyridine complex (0.32 g, 2.03 mmol). The mixture was stirred at room temperature for 23 h and concentrated to provide a residue which was subjected to chromatography to give 96 (0.20 g, 64%) as a white solid.

¹H NMR (400 MHz, CD₃OD): δ 1.46 (9H, s), 1.83-2.18 (7H, m), 3.10 (2H, m), 3.27 (2H, m), 3.72-4.10 (5H, m), 4.15 (1H, m). 2 protons were not observed in CD₃OD.

MS (ES⁻): m/z [M–H]⁻ calcd for $C_{17}H_{27}N_4O_9S$: 463.15. Found: 463.22.

Step 4. (2S,5R)-7-Oxo-N-[(2S)-pyrrolidin-2-ylmethoxy]-6-(sulfooxy)-1,6-diazabicyclo[3.2.1]octane-2-carboxamide (Compound 16, Table 1)

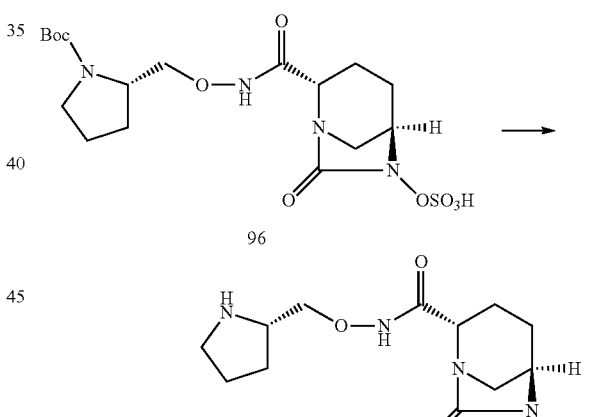

compound 16, Table 1

To a mixture of tert-butyl (2S)-2-{[({[(2S,5R)-7-oxo-6-(sulfooxy)-1,6-diazabicyclo[3.2.1]oct-2-yl]carbonyl}amino)oxy]methyl}pyrrolidine-1-carboxylate 96 (0.20 g, 0.43 mmol) in DCM (4.0 mL) was added trifluoroacetic acid (0.20 mL) at 0° C. The mixture was stirred at 0° C. for 1 h and at room temperature for 2 h, concentrated and washed with ether. The white solid was collected by centrifugation. Half of the crude product was purified by preparative HPLC (3% MeOH in water) to provide Compound 16 (Table 1) (12 mg) as a white solid.

¹H NMR (400 MHz, D₂O): δ 1.60-2.05 (8H, m), 3.03-3.15 (2H, m), 3.20 (2H, m), 3.78-3.90 (3H, m), 4.00-4.05 (2H, m). 3 protons were not observed in D₂O.

HPLC: 96.10%

MS (ES⁻): m/z [M−H]⁻ calcd for $C_{12}H_{19}N_4O_7S$: 363.10. Found: 363.16.

Example 20

(2S,5R)-N-Methoxy-7-oxo-6-(sulfooxy)-1,6-diazabicyclo[3.2.1]octane-2-carboxamide (Compound 28, Table 1)

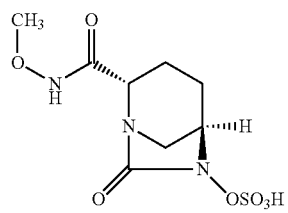

Step 1. (2S,5R)-6-(Benzyloxy)-N-methoxy-7-oxo-1,6-diazabicyclo[3.2.1]octane-2-carboxamide (98)

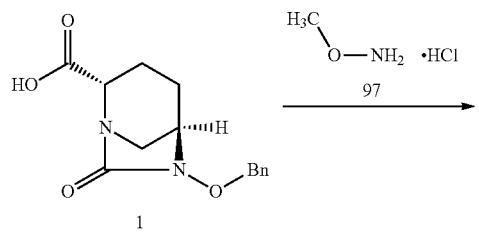

To a mixture of (2S,5R)-6-(benzyloxy)-7-oxo-1,6-diazabicyclo[3.2.1]octane-2-carboxylic acid 1 (0.334 g, 1.21 mmol) in DCM (25.0 mL) were added O-methylhydroxylamine 97 (0.193 g, 2.31 mmol), 1-hydroxybenzotriazole (0.25 g, 1.85 mmol), 1-ethyl-(3-dimethylaminopropyl) carbodiimide hydrochloride (0.35 g, 1.82 mmol) and 4-di(methylamino) pyridine (0.34 g, 2.78 mmol) sequentially at room temperature. The mixture was stirred at room temperature overnight, diluted with DCM and concentrated to provide a residue, which was subjected to chromatography to give (2S,5R)-6-(benzyloxy)-N-methoxy-7-oxo-1,6-diazabicyclo[3.2.1]octane-2-carboxamide 98 (0.17 g, 46%) as a white foam.

¹H NMR (400 MHz, CDCl₃): δ 1.67 (1H, m), 1.99 (2H, m), 2.30 (1H, m), 2.80 (1H, d, J=11.6 Hz), 3.01 (1H, m), 3.33 (1H, m), 3.77 (3H, s), 3.92 (1H, d, J=7.6 Hz), 4.87 (1H, d, J=11.6 Hz), 4.98 (1H, d, J=11.6 Hz), 7.36 (5H, m), 9.34 (1H, br s).

Step 2. (2S,5R)-6-hydroxy-N-methoxy-7-oxo-1,6-diazabicyclo[3.2.1]octane-2-carboxamide (99)

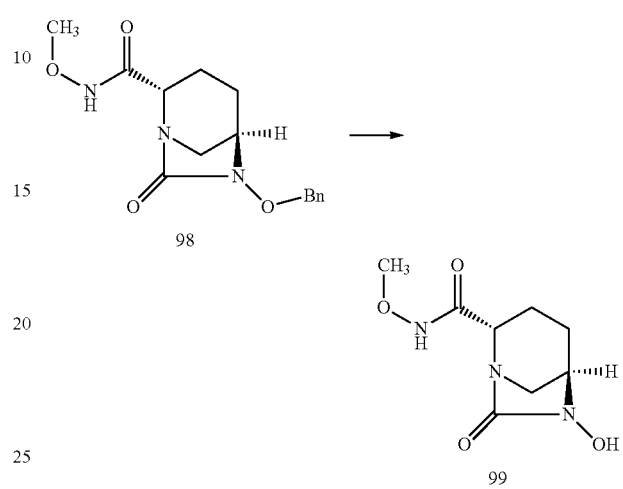

A mixture of (2S,5R)-6-(benzyloxy)-N-methoxy-7-oxo-1,6-diazabicyclo[3.2.1]octane-2-carboxamide 98 (0.17 g, 0.56 mmol) and 5% Pd/C (0.2 g) in methanol (15 mL) was hydrogenated at 10 psi for 1 h. The mixture was filtered through Celite pad and concentrated to provide (2S,5R)-6-hydroxy-N-methoxy-7-oxo-1,6-diazabicyclo[3.2.1]octane-2-carboxamide 99 (0.12 g, quant. yield) as a white foam.

¹H NMR (400 MHz, CD₃OD): δ 1.78-2.23 (4H, m), 3.03 (1H, d, J=12.0 Hz), 3.11 (1H, m), 3.50 (4H, m), 3.81 (1H, d, J=7.6 Hz). 2 protons were not observed in CD₃OD.

Step 3. (2S,5R)-N-methoxy-7-oxo-6-(sulfooxy)-1,6-diazabicyclo[3.2.1]octane-2-carboxamide (Compound 28, Table 1)

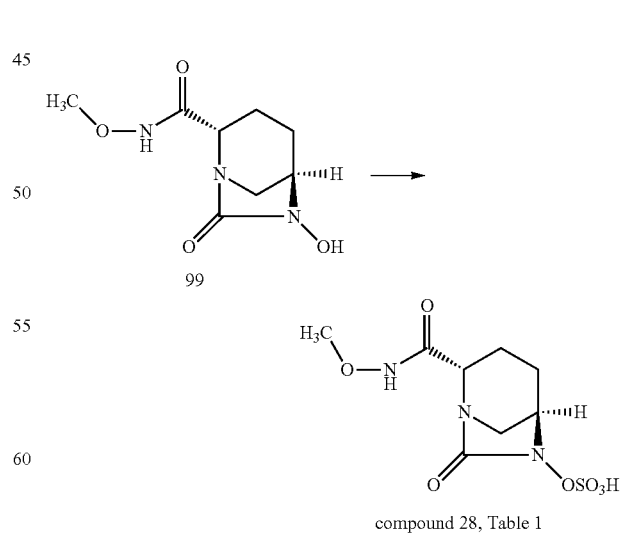

compound 28, Table 1

To a mixture of (2S,5R)-6-hydroxy-N-methoxy-7-oxo-1,6-diazabicyclo[3.2.1]octane-2-carboxamide 99 (0.12 g, 0.55 mmol) in pyridine (7.0 mL) was added sulfur trioxide pyridine complex (0.35 g, 2.20 mmol). The mixture was stirred at room temperature for 23 h and concentrated to provide a residue, which was purified by chromatography and again purified by HPLC and freeze-dried to give (2S,5R)-N-methoxy-7-oxo-6-(sulfooxy)-1,6-diazabicyclo[3.2.1]octane-2-carboxamide compound 28 (Table 1) (0.02 g, 12%) as a white solid.

$^1$H NMR (400 MHz, CD$_3$OD): δ 1.81-1.96 (2H, m), 2.09 (1H, m), 2.21 (1H, m), 3.09 (1H, d, J=11.6 Hz), 3.24 (1H, m), 3.71 (3H, s), 3.90 (1H, d, J=6.8 Hz), 4.14 (1H, m). 2 protons were not observed in CD$_3$OD.

HPLC 96.87%

MS (ES$^-$): m/z [M−H]$^-$=293.89

Example 21

(2S,5R)-N-[(1-methyl-1H-imidazol-5-yl)methoxy]-7-oxo-6-(sulfooxy)-1,6-diazabicyclo[3.2.1]octane-2-carboxamide (Compound 137, Table 1)

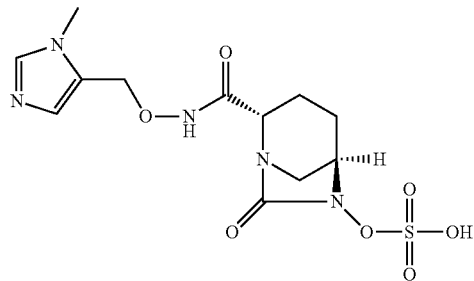 [SMILES: Cn1cncc1CONC(=O)[C@@H]1CC[C@@H]2CN1C(=O)N2OS(=O)(=O)O]

Step 1. (2S,5R)-6-(benzyloxy)-N-[(1-methyl-1H-imidazol-5-yl)methoxy]-7-oxo-1,6-diazabicyclo[3.2.1]octane-2-carboxamide (101)

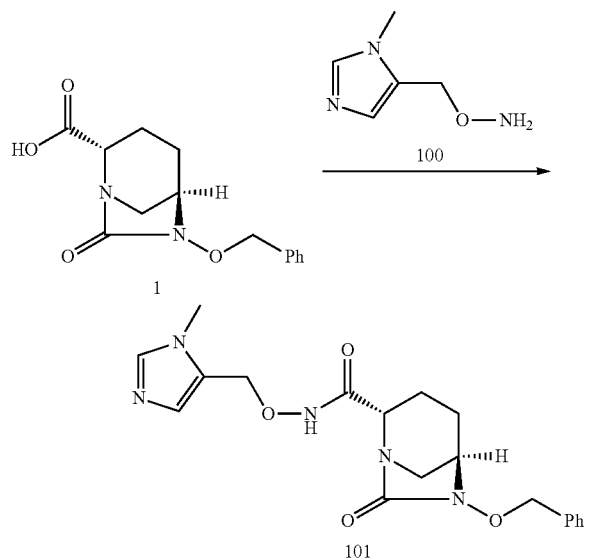

To a mixture of (2S,5R)-6-(benzyloxy)-7-oxo-1,6-diazabicyclo[3.2.1]octane-2-carboxylic acid 1 (0.250 g, 0.905 mmol) in DCM (10.0 mL) was added 5-[(aminooxy)methyl]-1-methyl-1H-imidazole 100 (0.172 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 101 (0.40 g, quantitative yield) as a white foam.

$^1$H NMR (400 MHz, CDCl$_3$): δ 1.56 (1H, m), 1.91 (2H, m), 2.21 (1H, m), 2.65 (1H, d, J=12.0 Hz), 2.95 (1H, d, J=11.6 Hz), 3.30 (1H, s), 3.82 (3H, s), 3.91 (1H, d, J=11.2 Hz), 4.84 (3H, m), 5.04 (1H, d, J=11.6 Hz), 7.05 (1H, s), 7.33 (5H, m), 7.62 (1H, s).

MS (ES$^+$) m/z: [M+H]$^+$ calcd for C$_{19}$H$_{24}$N$_5$O$_4$: 386.2. Found: 386.1.

Step 2. (2S,5R)-6-hydroxy-N-[(1-methyl-1H-imidazol-5-yl)methoxy]-7-oxo-1,6-diazabicyclo[3.2.1]octane-2-carboxamide (102)

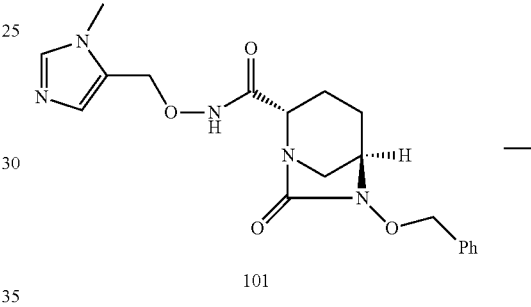

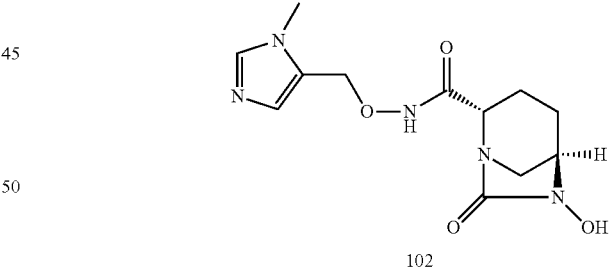

A mixture of (2S,5R)-6-(benzyloxy)-N-[(1-methyl-1H-imidazol-5-yl)methoxy]-7-oxo-1,6-diazabicyclo[3.2.1]octane-2-carboxamide 101 (0.40 g, 0.90 mmol) and Pd/C (0.13 g) in methanol (20 mL) was hydrogenated at 1 atm at room temperature for 3 h. The mixture was filtered through Celite pad and concentrated to give a residue which was subjected to chromatography to give 102 (0.21 g, 75%) as a white foam.

$^1$H NMR (400 MHz, CD$_3$OD): δ 1.74 (1H, m), 1.89 (1H, m), 2.04 (1H, m), 2.15 (1H, m), 2.91 (1H, d, J=12.0 Hz), 3.09 (1H, m), 3.67 (1H, s), 3.79 (1H, d, J=6.8 Hz), 3.85 (3H, s), 4.92 (2H, m), 7.07 (1H, s), 7.73 (1H, s). 2 protons were not observed in CD$_3$OD.

MS (ES⁺) m/z: [M+H]⁺ calcd for $C_{12}H_{18}N_5O_4$: 296.13. Found: 296.10.

Step 3. (2S,5R)-N-[(1-methyl-1H-imidazol-5-yl)methoxy]-7-oxo-6-(sulfooxy)-1,6-diazabicyclo[3.2.1]octane-2-carboxamide (Compound 137, Table 1).

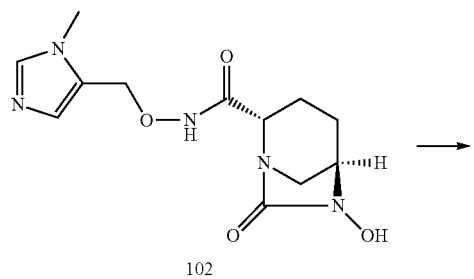

102

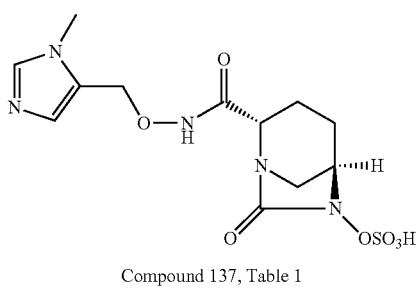

Compound 137, Table 1

To a mixture of (2S,5R)-6-hydroxy-N-[(1-methyl-1H-imidazol-5-yl)methoxy]-7-oxo-1,6-diazabicyclo[3.2.1]octane-2-carboxamide 102 (0.21 g, 0.71 mmol) in pyridine (6 mL) was added sulfur trioxide pyridine complex (0.33 g, 2.13 mmol). The mixture was stirred at room temperature for 23 h and concentrated to provide a residue which was subjected to flash chromatography to give Compound 137 (Table 1) (64 mg) as a white solid.

¹H NMR (400 MHz, D₂O): δ 1.62 (1H, m), 1.75 (1H, m), 1.91 (2H, m), 2.82 (1H, d, J=11.6 Hz), 3.13 (1H, d, J=11.2 Hz), 3.86 (3H, s), 3.89 (1H, s), 4.05 (1H, s), 4.93 (2H, s), 7.49 (1H, s), 8.61 (1H, s). Two protons were not observed in D₂O.

HPLC: 98.14%
MS (ES⁻) m/z: [M−H]⁻ calcd for $C_{12}H_{16}N_5O_7S$: 374.1. Found: 373.9.

Example 22

1-(Acetyloxy)ethyl (3S)-3-[({[(2S,5R)-7-oxo-6-(sulfooxy)-1,6-diazabicyclo[3.2.1]oct-2-yl]carbonyl}amino)oxy]pyrrolidine-1-carboxylate (Compound 101, Table 1)

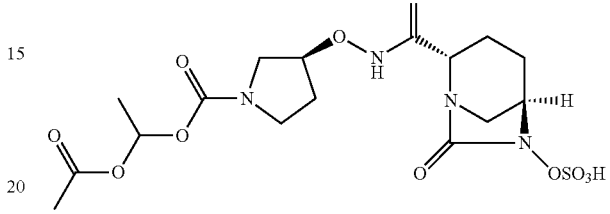

Step 1. 1-(Acetyloxy)ethyl (3S)-3-[({[(2S,5R)-7-oxo-6-(sulfooxy)-1,6-diazabicyclo[3.2.1]oct-2-yl]carbonyl}amino)oxy]pyrrolidine-1-carboxylate (Compound 101, Table 1)

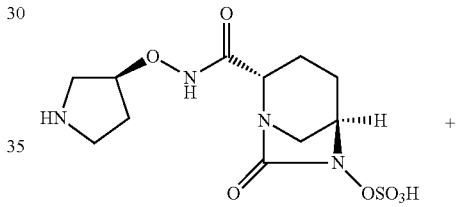

compound 2, Table 1

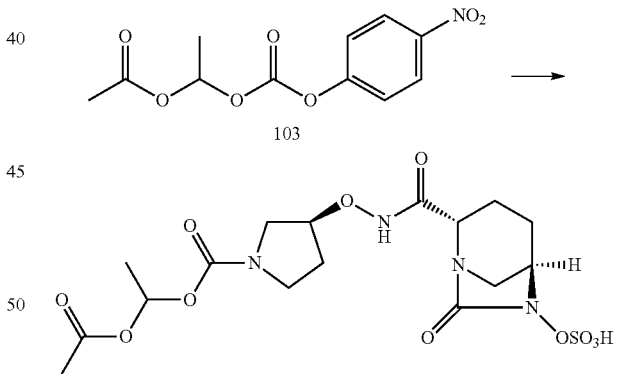

103 compound 101, Table 1

To a mixture of (2S,5R)-7-oxo-N-[(3S)-pyrrolidin-3-yloxy]-6-(sulfooxy)-1,6-diazabicyclo[3.2.1]octane-2-carboxamide Compound 2 (Table 1) (0.030 g, 0.086 mmol, Example 2) in DMF (dimethyl formamide) (1.5 mL) was added 1-{[(4-nitrophenoxy)carbonyl]oxy}ethyl acetate 103 (0.027 g, 0.102 mmol, J. Med. Chem., 1988, vol 31, 2, p318-322) and triethylamine (0.023 mL, 0.171 mmol) sequentially at room temperature. The mixture was stirred at room temperature overnight, diluted with DCM and concentrated to provide a residue, which was subjected to chromatography and preparative HPLC to give Compound 101 (Table 1) (0.011 g) as a white solid.

¹H NMR (400 MHz, CD₃OD): δ 1.47 (3H, m), 1.82-2.00 (2H, m), 2.04-2.06 (3H, m), 2.10 (1H, m), 2.27 (2H, m), 3.08 (1H, dd, J=4.2, 12.0 Hz), 3.24-3.30 (2H, m), 3.41-3.53 (3H, m), 3.65 (1H, m), 3.94 (1H, d, J=7.6 Hz), 4.15 (1H, s), 4.62 (1H, s), 6.76 (1H, m).

2 protons were not observed in CD₃OD.

HPLC: 86.89%

MS (ES⁻): m/z [M−H]⁻ calcd for $C_{16}H_{23}N_4O_{11}S$: 479.11. Found: 479.04.

Example 23

(2S,5R)-7-oxo-N-(piperidin-2-ylmethoxy)-6-(sulfooxy)-1,6-diazabicyclo[3.2.1]octane-2-carboxamide trifluoroacetate (Compound 50, Table 1)

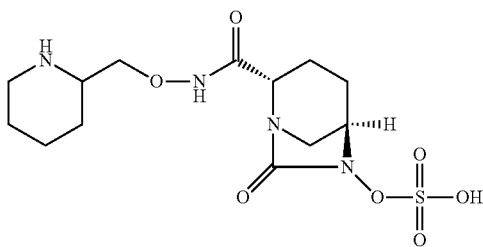 [SMILES: O=C(NOCC1CCCCN1)[C@@H]1CC[C@@H]2CN1C(=O)N2OS(=O)(=O)O]

Step 1. tert-butyl 2-[(aminooxy)methyl]piperidine-1-carboxylate (105)

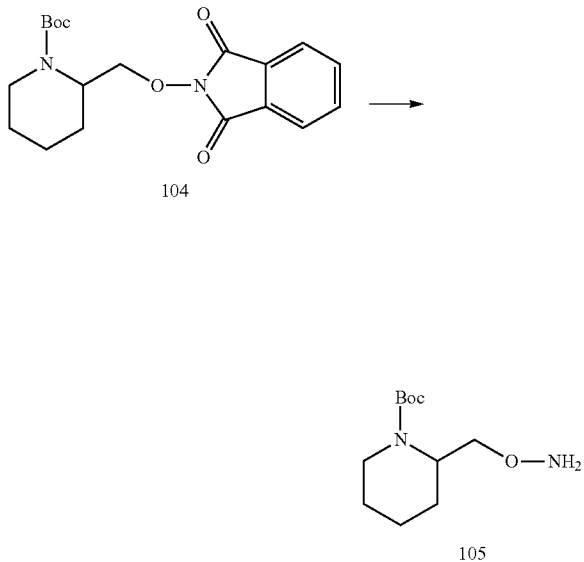

To a mixture of tert-butyl 2-{[(1,3-dioxo-1,3-dihydro-2H-isoindol-2-yl)oxy]methyl}piperidine-1-carboxylate 104 (1.50 g, 4.16 mmol) in a solution of methanol (20 mL) was added methylhydrazine hydrate (4.16 mmol) at room temperature. The mixture was stirred at room temperature overnight, filtered and concentrated to provide a residue which was subjected to chromatography to give 105 (0.50 g, 53%) as a white solid.

¹H NMR (400 MHz, CDCl₃): δ 1.36-1.60 (15H, m), 2.75 (1H, m), 3.53 (1H, m), 3.91 (2H, m), 4.57 (1H, br s), 5.70 (2H, br s).

Step 2. tert-butyl 2-{[({[(2S,5R)-6-(benzyloxy)-7-oxo-1,6-diazabicyclo[3.2.1]oct-2-yl] carbonyl}amino)oxy]methyl}piperidine-1-carboxylate (106)

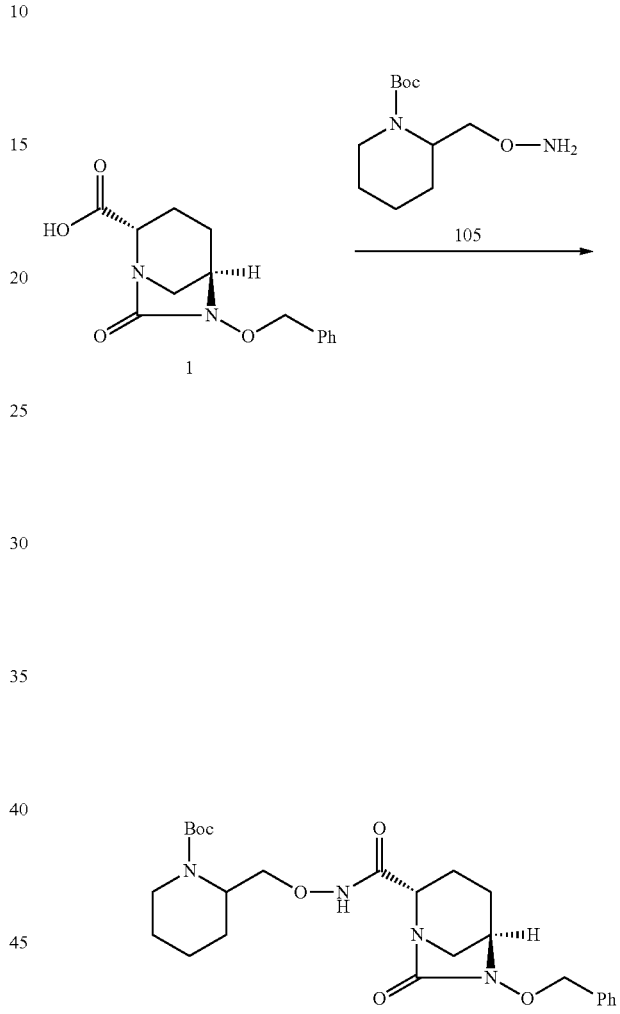

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added tert-butyl 2-[(aminooxy)methyl]piperidine-1-carboxylate 105 (0.312 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 106 (0.40 g, 91%) as a white foam.

¹H NMR (400 MHz, CDCl₃): δ 1.41 (9H, m), 1.61 (6H, m), 1.97 (2H, m), 2.29 (1H, m), 2.78 (3H, m), 2.97 (1H, m), 3.26 (1H, m), 3.70 (1H, m), 3.99 (2H, m), 4.15 (1H, m), 4.51 (1H, m), 4.88 (1H, d, J=11.6 Hz), 5.06 (1H, m), 7.42 (5H, m). One proton was not observed in moisture containing CDCl₃.

MS (ES⁻) m/z: [M−H]⁻ calcd for C₂₅H₃₅N₄O₈: 487.2. Found: 487.1.

Step 3. tert-butyl 2-{[({[(2S,5R)-6-hydroxy-7-oxo-1,6-diazabicyclo[3.2.1]oct-2-yl]carbonyl}amino)oxy]methyl}piperidine-1-carboxylate (107)

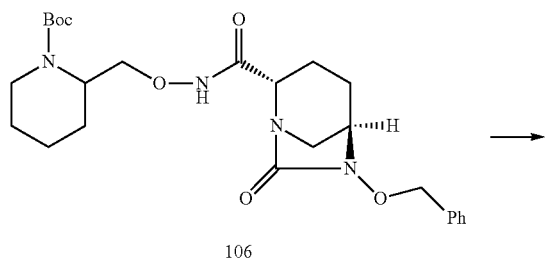

106

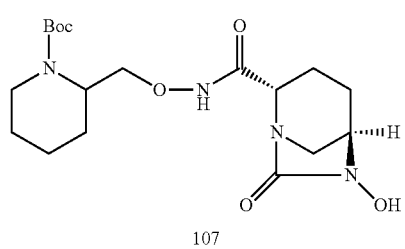

107

A mixture of tert-butyl 2-{[({[(2S,5R)-6-(benzyloxy)-7-oxo-1,6-diazabicyclo[3.2.1]oct-2-yl]carbonyl}amino)oxy]methyl}piperidine-1-carboxylate 106 (0.40 g, 0.82 mmol) and Pd/C (0.13 g) in methanol (20 mL) was hydrogenated at 1 atm at room temperature for 3 h. The mixture was filtered through Celite pad and concentrated to give 107 (0.33 g, quantitative yield) as a white foam.

¹H NMR (400 MHz, CD₃OD): δ 1.45 (9H, s), 1.60 (5H, m), 1.80 (2H, m), 1.93 (1H, m), 2.04 (1H, m), 2.21 (1H, m), 2.84 (1H, m), 2.99 (1H, m), 3.31 (1H, m), 3.68 (1H, s), 3.89 (1H, s), 4.02 (3H, m), 4.47 (1H, m). Two protons were not observed in CD₃OD.

MS (ES⁺) m/z: [M+H]⁺ calcd. For C₁₈H₃₁N₄O₆: 399.2. Found: 399.1.

Step 4. tert-butyl 2-{[({[(2S,5R)-7-oxo-6-(sulfooxy)-1,6-diazabicyclo[3.2.1]oct-2-yl]carbonyl}amino)oxy]methyl}piperidine-1-carboxylate (108)

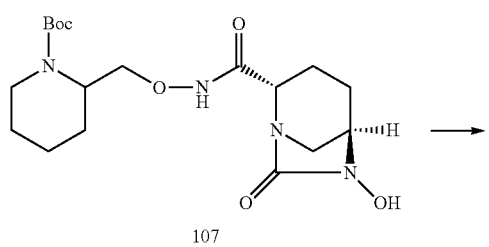

107

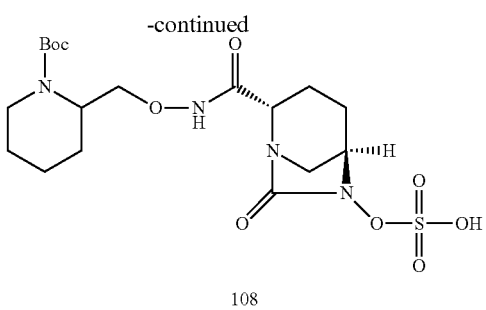

108

To a mixture of tert-butyl 2-{[({[(2S,5R)-6-hydroxy-7-oxo-1,6-diazabicyclo[3.2.1]oct-2-yl]carbonyl}amino)oxy]methyl}piperidine-1-carboxylate 107 (0.33 g, 0.83 mmol) in pyridine (4.0 mL) was added sulfur trioxide pyridine complex (0.38 g, 2.48 mmol). The mixture was stirred at room temperature for 23 h and concentrated to provide a residue which was subjected to chromatography to give 108 (0.27 g, 69%) as a white foam.

¹H NMR (400 MHz, CD₃OD): δ 1.45 (10H, m), 1.63 (4H, m), 1.84 (2H, m), 1.92 (1H, m), 2.06 (1H, m), 2.21 (1H, m), 2 87 (1H, m), 3.09 (1H, m), 3.24 (2H, m), 3.91 (2H, m), 4.03 (1H, m), 4.11 (1H, m), 4.46 (1H, m). Two protons were not observed in CD₃OD.

Step 5. (2S,5R)-7-oxo-N-(piperidin-2-ylmethoxy)-6-(sulfooxy)-1,6-diazabicyclo[3.2.1]octane-2-carboxamide trifluoroacetate (Compound 50, Table 1)

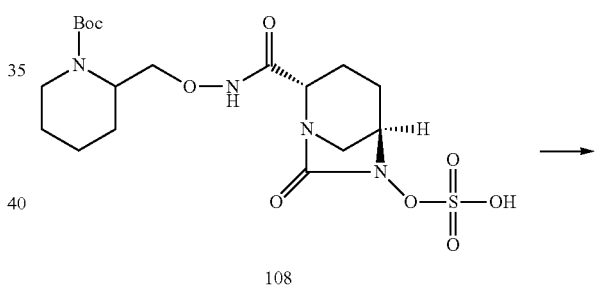

108

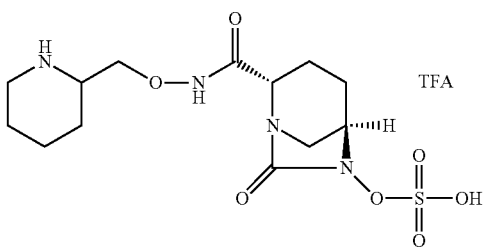

Compound 50, Table 1

To a mixture of tert-butyl 2-{[({[(2S,5R)-7-oxo-6-(sulfooxy)-1,6-diazabicyclo[3.2.1]oct-2-yl]carbonyl}amino)oxy]methyl}piperidine-1-carboxylate 108 (0.27 g, 0.58 mmol) in DCM (8.0 mL) was added trifluoroacetic acid (0.40 mL) at 0° C. The mixture was stirred at 0° C. for 3 h, concentrated and washed with ether, EtOAc and DCM to give TFA salt of Compound 50 (Table 1) (61 mg) as a white solid as a pair of diastereomers.

¹H NMR (400 MHz, D₂O): δ 1.38 (2H, m), 1.54 (1H, m), 1.75 (5H, m), 2.01 (2H, m), 2.85 (1H, m), 3.00 (1H, m), 3.21 (1H, m), 3.36 (2H, m), 3.91 (3H, m), 4.08 (1H, s). Three protons were not observed in D₂O.

HPLC: 95.23%

MS (ES⁻) m/z: [M–H]⁻ calcd for $C_{13}H_{21}N_4O_7S$: 377.1. Found: 377.0.

Example 24

Sodium({[(2S,5R)-2-({[(3S)-1-methylpyrrolidin-3-yl]oxy}carbamoyl)-7-oxo-1,6-diazabicyclo[3.2.1]oct-6-yl]oxy}sulfonyl)oxidanide (Compound 149, Table 1)

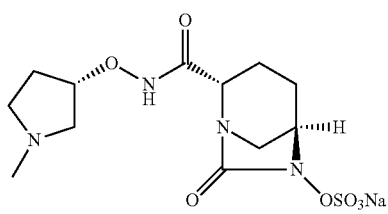

Step 1. (2S,5R)-6-(benzyloxy)-N-{[(3S)-1-methylpyrrolidin-3-yl]oxy}-7-oxo-1,6-diazabicyclo[3.2.1]octane-2-carboxamide (110)

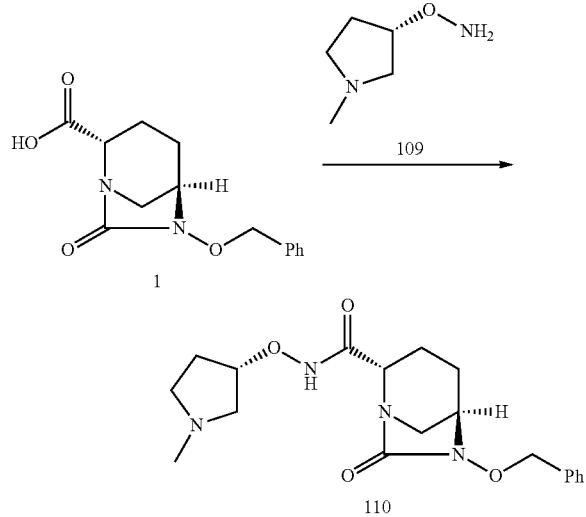

To a mixture of (2S,5R)-6-(benzyloxy)-7-oxo-1,6-diazabicyclo[3.2.1]octane-2-carboxylic acid 1 (0.25 g, 0.90 mmol, US2005/20572 A1, 2005) in DCM (20 mL) was added (3S)-3-(aminooxy)-1-methylpyrrolidine 109 (0.32 g, 1.39 mmol, J. Med. Chem., 2008, 51, 4601-4608), 1-hydroxybenzotriazole (0.18 g, 1.33 mmol), and 1-ethyl-(3-dimethylaminopropyl)carbodiimide hydrochloride (0.26 g, 1.36 mmol) sequentially at room temperature. The mixture was stirred at room temperature overnight, then concentrated in vacuo to provide a residue, which was subjected to chromatography to give 110 (0.26 g, 77%) as a yellow foam.

¹H NMR (400 MHz, CDCl₃): δ 1.60 (1H, m), 2.00 (4H, m), 2.26 (4H, m), 2.71 (1H, d, J=11.7 Hz), 2.84 (1H, m), 2.93 (4H, m), 3.12 (1H, m), 3.30 (1H, m), 3.97 (1H, d, J=6.3 Hz), 4.74 (1H, br s), 4.90 (1H, d, J=11.3 Hz), 5.04 (1H, d, J=11.3 Hz), 7.39 (5H, m).

MS (ES⁺) m/z: [M+H]⁺ calcd for $C_{19}H_{27}N_4O_4$: 375.20. Found: 375.21

Step 2. (2S,5R)-6-hydroxy-N-{[(3S)-1-methylpyrrolidin-3-yl]oxy}-7-oxo-1,6-diazabicyclo[3.2.1]octane-2-carboxamide (111)

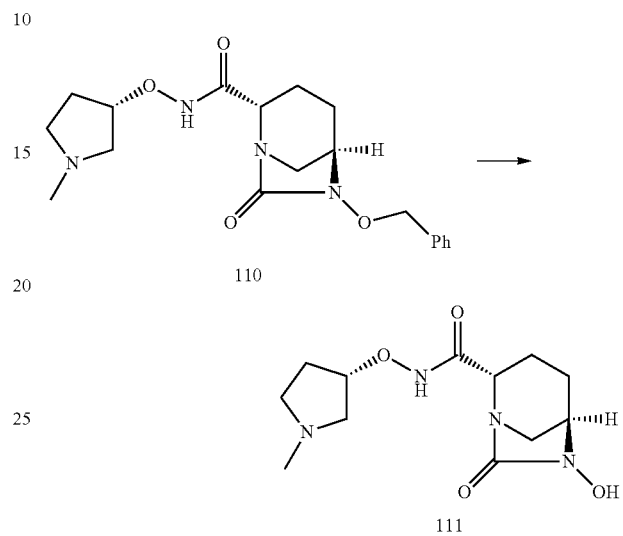

A mixture of (2S,5R)-6-(benzyloxy)-N-{[(3S)-1-methylpyrrolidin-3-yl]oxy}-7-oxo-1,6-diazabicyclo[3.2.1]octane-2-carboxamide 110 (0.26 g, 0.69 mmol) and Pd/C (0.50 g) in methanol (25 mL) was hydrogenated at 20 psi at room temperature for 2 hours. The mixture was filtered through a Celite pad and concentrated to provide 111 (0.20 g) as a white foam.

¹H NMR (400 MHz, CD₃OD): δ 1.99 (3H, m), 2.29 (3H, m), 2.99 (3H, s), 3.03 (1H, d, J=11.7 Hz), 3.15 (1H, m), 3.41 (2H, m), 3.66 (2H, d, J=13.3 Hz), 3.71 (1H, br s), 3.89 (1H, d, J=7.8 Hz), 4.74 (1H, m). 2 protons were not observed in CD₃OD.

MS (ES⁺) m/z: [M+H]⁺ calcd for $C_{12}H_{21}N_4O_4$: 285.16. Found: 285.19.

Step 3. Sodium({[(2S,5R)-2-({[(3S)-1-methylpyrrolidin-3-yl]oxy}carbamoyl)-7-oxo-1,6-diazabicyclo[3.2.1]oct-6-yl]oxy}sulfonyl)oxidanide (Compound 149, Table 1)

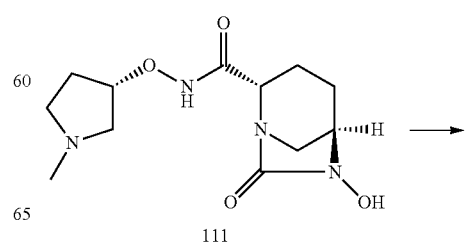

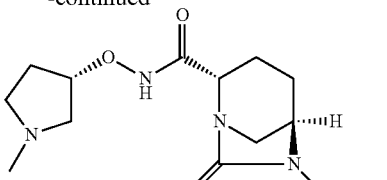

Compound 149, Table 1

To a mixture of (2S,5R)-6-hydroxy-N-{[(3S)-1-methylpyrrolidin-3-yl]oxy}-7-oxo-1,6-diazabicyclo[3.2.1]octane-2-carboxamide 111 (0.21 g, 0.74 mmol) in pyridine (5 mL) was added sulfur trioxide pyridine complex (0.24 g, 1.51 mmol). The mixture was stirred at room temperature overnight. The mixture was concentrated in vacuo, then diluted with toluene and concentrated in vacuo (repeated twice). The residue was washed with DCM, then the organics were decanted off to give a sticky residue (repeat twice). The residue was dried to give an off white solid. The crude product was passed through a resin column (DOWEX 50WX4) eluting with water, then lyophilized to afford Compound 149 (Table 1) (0.017 g, 8%, over 2 steps) as sodium salt as a white solid.

$^1$H NMR (400 MHz, D$_2$O): δ 1.76 (2H, m), 1.97 (2H, m), 2.15 (1H, m), 2.28 (1H, m), 2.84 (3H, s), 2.99 (1H, d, J=12.1 Hz), 3.16 (1H, d, J=12.5 Hz), 3.30 (2H, br m), 3.54 (2H, br s), 3.92 (1H, d, J=5.5 Hz), 4.05 (1H, d, J=3.1 Hz), 4.65 (1H, m), 2 protons were not observed in D$_2$O.

HPLC: 93.67%.

MS (ES$^-$) m/z: [M−H]$^-$ calcd for C$_{12}$H$_{19}$N$_4$O$_7$S: 363.10. Found: 363.05.

Example 25

(2S,5R)-N-{[trans-3-(methylamino)cyclopentyl]oxy}-7-oxo-6-(sulfooxy)-1,6-diazabicyclo[3.2.1]octane-2-carboxamide (Compound 45, Table 1)

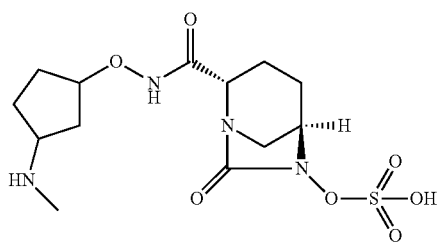 [SMILES: CNC1CCC(ONC(=O)[C@@H]2CC[C@@H]3CN2C(=O)N3OS(=O)(=O)O)C1]

Step 1. cis-3-(methylamino)cyclopentanol (113)

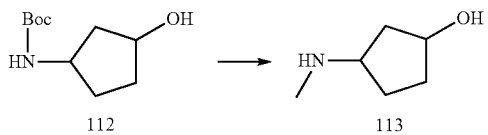

To an ice-cold mixture of tert-butyl [cis (1R,3R)-3-hydroxycyclopentyl]carbamate 112 (0.32 g, 1.59 mmol, US2005/54658 A1, 2005) in tetrahydrofuran (10 mL) was added lithium aluminum hydride (1 M solution in tetrahydrofuran, 3.2 mL, 3.2 mmol). The mixture was refluxed for 4 hours, cooled to room temperature then quenched with a minimum amount of saturated sodium sulfate solution. Solid sodium sulfate was added to the mixture to give a suspension. The mixture was filtered through a pad of Celite, and the filtrate was concentrated in vacuo to afford 113 as colorless oil. The oil was used in the next step without further purification.

$^1$H NMR (400 MHz, CDCl$_3$): δ 1.54 (1H, m), 1.66 (1H, m), 1.83 (4H, m), 2.38 (3H, s), 3.21 (1H, m), 4.24 (1H, m).

MS (ES$^+$) m/z: [M+H]$^+$ calcd for C$_6$H$_{14}$NO: 116.11. Found: 116.05.

Step 2. tert-butyl (cis-3-hydroxycyclopentyl)methylcarbamate (114)

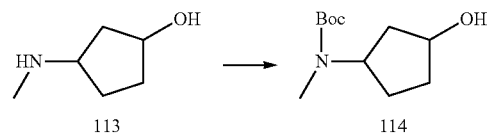

To a mixture of cis-3-(methylamino)cyclopentanol 113 (1.59 mmol) in DCM (20 mL) was added di-tert-butyldicarbonate (0.35 g, 1.59 mmol) followed by triethylamine (0.45 mL, 3.23 mmol). The mixture was stirred at room temperature overnight, then concentrated in vacuo to give a yellow oil which was purified by chromatography to give 114 (0.18 g, 52%, over 2 steps) as a white foam.

$^1$H NMR (400 MHz, CDCl$_3$): δ 1.46 (9H, s), 1.64 (2H, m), 1.79 (2H, m), 1.94 (1H, m), 2.18 (1H, ddd, J=15.1, 9.2, 5.9 Hz), 2.83 (3H, s), 4.23 (2H, m). 1 proton was not observed in CDCl$_3$.

MS (ES$^+$) m/z: [M+H]$^+$ calcd for C$_{11}$H$_{21}$NO$_3$: 216.16. Found: 216.15.

Step 3. tert-butyl {trans-3-[(1,3-dioxo-1,3-dihydro-2H-isoindol-2-yl)oxy]cyclopentyl}methylcarbamate (115)

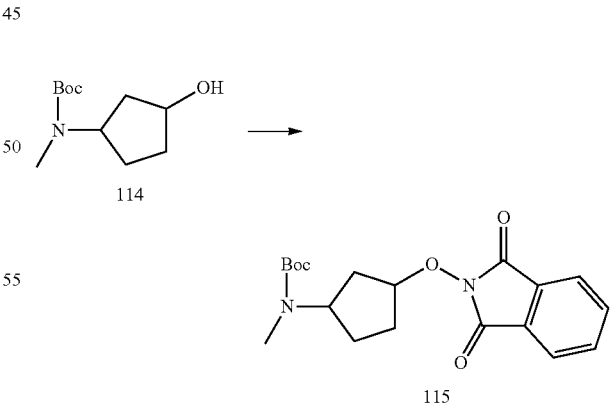

An ice-cold mixture of tert-butyl (cis-3-hydroxycyclopentyl)methylcarbamate 114 (0.19 g, 0.88 mmol), N-hydroxyphthalimide (0.29 g, 1.78 mmol), and triphenylphosphine (0.46 g, 1.75 mmoL) in tetrahydrofuran (10 mL) was treated with diisopropylazodicarboxylate (0.40 g, 1.98 mmol). The mixture was stirred at room temperature overnight, then concentrated in vacuo to a yellow foam which was purified by chromatography to give 115 (0.19 g, containing DIAD byproduct) as a yellow oil. The mixture was used in the next step without further purification.

$^1$H NMR (400 MHz, CDCl$_3$): δ 1.69 (2H, m), 2.04 (2H, m), 2.20 (2H, m), 2.77 (3H, s), 4.95 (2H, m), 7.76 (2H, m), 7.85 (2H, m).

MS (ES$^+$) m/z: [M+H]$^+$ calcd for C$_{19}$H$_{25}$N$_2$O$_5$: 361.18. Found: 361.15.

Step 4. tert-butyl [trans-3-(aminooxy)cyclopentyl]methylcarbamate (116)

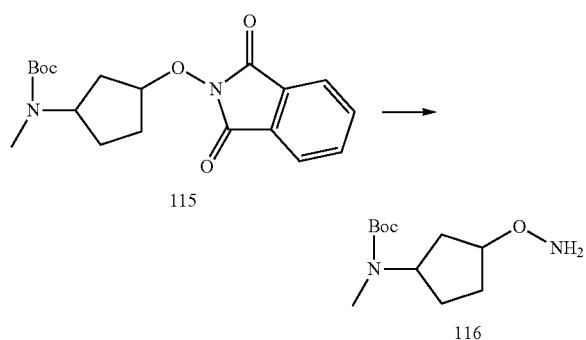

A mixture of tert-butyl {trans-3-[(1,3-dioxo-1,3-dihydro-2H-isoindol-2-yl)oxy]cyclopentyl}methylcarbamate 115 (0.19 g, 0.53 mmol) was treated with hydrazine hydrate (0.03 g, 0.60 mmol). The mixture was stirred at room temperature for 2 hours. The solid was filtered off and the filtrate was concentrated in vacuo. The residue was diluted with DCM, and the insoluble solid was filtered off. The filtrate was concentrated in vacuo to give an oil which was purified by chromatography to give 116 (0.09 g, 44% over 2 steps) as a light yellow oil.

$^1$H NMR (400 MHz, CDCl$_3$): δ 1.46 (9H, s), 1.53 (1H, m), 1.68 (2H, m), 1.95 (3H, m), 2.72 (3H, s), 4.20 (1H, m), 4.60 (1H, br s), 5.28 (2H, br s).

MS (ES$^+$) m/z: [M+H]$^+$ calcd for C$_{11}$H$_{22}$N$_2$O$_3$: 231.17. Found: 231.15.

Step 5. tert-butyl {trans-3-[({[(2S,5R)-6-(benzyloxy)-7-oxo-1,6-diazabicyclo[3.2.1]oct-2-yl]carbonyl}amino)oxy]cyclopentyl}methylcarbamate (117)

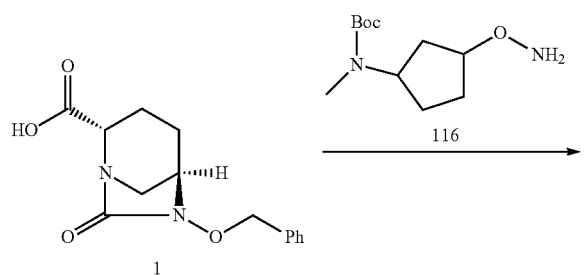

-continued

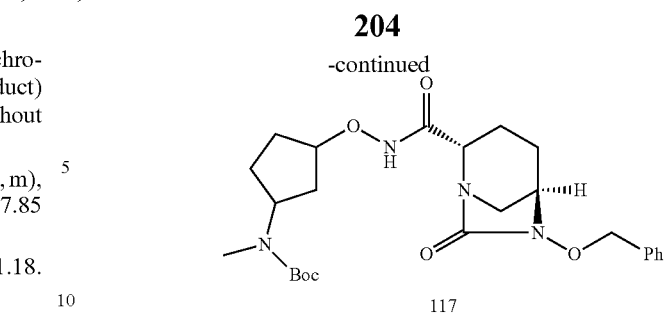

To a mixture of (2S,5R)-6-(benzyloxy)-7-oxo-1,6-diazabicyclo[3.2.1]octane-2-carboxylic acid 1 (0.25 g, 0.90 mmol, US2005/20572 A1, 2005) in DCM (20 mL) was added tert-butyl [trans-3-(aminooxy)cyclopentyl]methylcarbamate 116 (0.32 g, 1.39 mmol), 1-hydroxybenzotriazole (0.18 g, 1.33 mmol), and 1-ethyl-(3-dimethylamino propyl) carbodiimide hydrochloride (0.26 g, 1.36 mmol) sequentially at room temperature. The mixture was stirred at room temperature for 6 hours, then concentrated in vacuo to provide a residue which was subjected to chromatography to give 117 (0.45 g, contains some byproduct) as a white foam.

$^1$H NMR (400 MHz, CDCl$_3$): δ 1.45 (9H, s), 1.77 (10H, m), 2.31 (1H, m), 2.72 (3H, s), 2.78 (1H, dd, J=11.3, 3.1 Hz), 3.15 (1H, br d, J=14.1 Hz), 3.30 (1H, br s), 3.96 (1H, br d, J=7.4 Hz), 4.60 (2H, m), 4.90 (1H, d, J=11.3 Hz), 5.05 (1H, d, J=11.3 Hz), 7.40 (5H, m).

MS (ES$^+$) m/z: [M+H]$^+$ calcd for C$_{25}$H$_{37}$N$_4$O$_6$: 489.27. Found: 489.20.

Step 6. tert-butyl {trans-3-[({[(2S,5R)-6-hydroxy-7-oxo-1,6-diazabicyclo[3.2.1]oct-2-yl]carbonyl}amino)oxy]cyclopentyl}methylcarbamate (118)

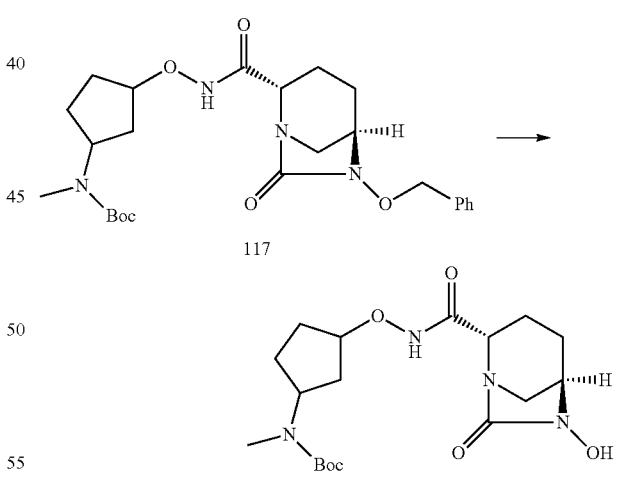

A mixture of tert-butyl {trans-3-[({[(2S,5R)-6-(benzyloxy)-7-oxo-1,6-diazabicyclo[3.2.1]oct-2-yl]carbonyl}amino)oxy]cyclopentyl}methylcarbamate 117 (0.90 mmol) and Pd/C (0.50 g) in methanol (20 mL) was hydrogenated at 30 psi at room temperature for 1 hour. The mixture was filtered through a Celite pad and concentrated to provide 118 (0.40 g) as a white foam.

$^1$H NMR (400 MHz, CD$_3$OD): δ 1.46 (9H, s), 1.80 (9H, m), 2.20 (1H, m), 2.74 (3H, s), 3.11 (2H, m), 3.70 (1H, br s), 3.83

(1H, d, J=7.4 Hz), 4.50 (1H, br s), 4.67 (1H, m). 2 protons were not observed in CD$_3$OD.

MS (ES$^+$) m/z: [M+H]$^+$ calcd for C$_{18}$H$_{30}$N$_4$O$_6$: 399.22. Found: 399.15.

Step 7. tert-butyl methyl{trans-3-[({[(2S,5R)-7-oxo-6-(sulfooxy)-1,6-diazabicyclo[3.2.1]oct-2-yl]carbonyl}amino)oxy]cyclopentyl}carbamate (119)

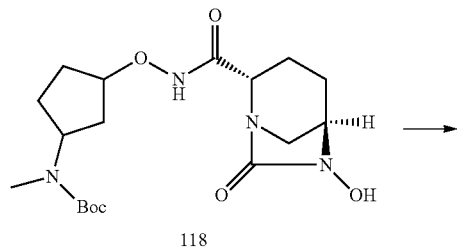

118

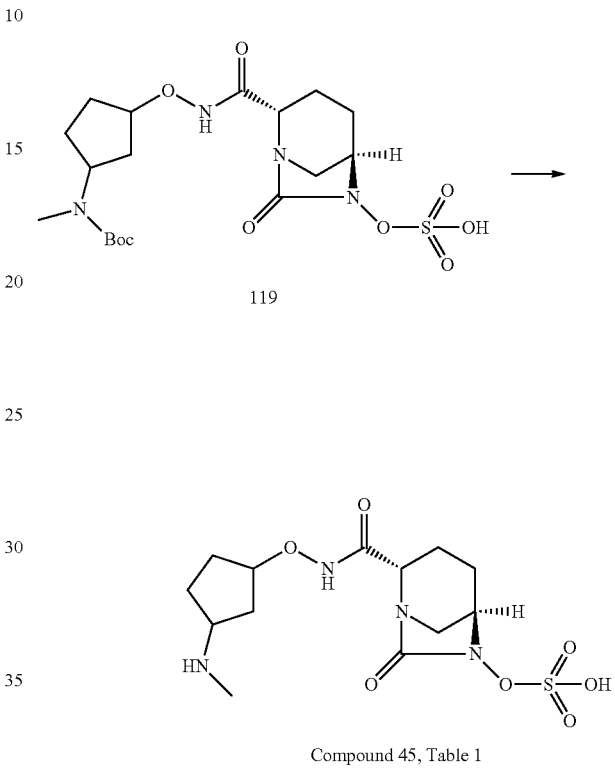

119

To a mixture of tert-butyl {trans-3-[({[(2S,5R)-6-hydroxy-7-oxo-1,6-diazabicyclo[3.2.1]oct-2-yl]carbonyl}amino)oxy]cyclopentyl}methylcarbamate 118 (0.40 g, 1.00 mmol) in pyridine (10 mL) was added sulfur trioxide pyridine complex (0.24 g, 1.50 mmol). The mixture was stirred at room temperature for 3 days. The reaction showed little conversion to the product by $^1$H NMR. Additional sulfur trioxide pyridine complex (0.46 g, 2.90 mmol) and pyridine (5 mL) were added to the mixture, and stirring was continued for 1 day. Conversion was 50% by $^1$H NMR, so more sulfur trioxide pyridine complex (0.62 g, 3.90 mmol) and pyridine (10 mL) were added, and stirring was continued for 1 day. The solid was filtered off and the filtrate was concentrated in vacuo. The residue was diluted with DCM and the solid was filtered off again. The filtrate was concentrated in vacuo, then subjected to chromatography to give 119 (0.20 g, 47%, over 3 steps) as a pale yellow solid.

$^1$H NMR (400 MHz, CD$_3$OD): δ 1.46 (9H, s), 1.87 (9H, m), 2.19 (1H, m), 2.74 (3H, s), 3.10 (1H, d, J=11.7 Hz), 3.27 (1H, m), 3.91 (1H, d, J=7.0 Hz), 4.15 (1H, br s), 4.51 (1H, br s), 4.79 (1H, m). 2 protons were not observed in CD$_3$OD.

MS (ES$^-$) m/z: [M–H]$^-$ calcd for C$_{18}$H$_{29}$N$_4$O$_9$S: 477.17. Found: 477.04.

Step 8. (2S,5R)-N-{[trans-3-(methylamino)cyclopentyl]oxy}-7-oxo-6-(sulfooxy)-1,6-diazabicyclo[3.2.1]octane-2-carboxamide (Compound 45, Table 1)

Compound 45, Table 1

To a mixture of tert-butyl methyl{trans-3-[({[(2S,5R)-7-oxo-6-(sulfooxy)-1,6-diazabicyclo[3.2.1]oct-2-yl]carbonyl}amino)oxy]cyclopentyl}carbamate 119 (0.20 g, 0.42 mmol) in DCM (4.0 mL) was added trifluoroacetic acid (0.20 mL) at 0° C. The mixture was stirred at 0° C. for 30 minutes, then at room temperature for 2 hours. The mixture was concentrated in vacuo to give a yellow oil, then diluted with diethyl ether and sonicated. The suspension was filtered to give an off-white solid. The solid was purified by trituating with methanol and diethyl ether to give a white suspension. The white solid was collected by vacuum filtration (hygroscopic) to give a residue on the filter paper. The residue was washed with methanol and diethyl ether, and the washings were discarded. The residue was dissolved in water and the aqueous solution was lyophilized to a white solid to afford Compound 45 (Table 1) (45 mg, 22%, as a mixture of diastereoisomers, trifluoroacetate salt) as a white solid.

$^1$H NMR (400 MHz, D$_2$O): δ 1.72 (6H, m), 1.98 (3H, m), 2.17 (1H, m), 2.28 (1H, m), 2.57 (3H, s), 2.98 (1H, dd, d, J=12.1, 4.7 Hz), 3.19 (1H, d, J=11.7 Hz), 3.63 (1H, m), 3.94 (1H, d, J=7.4 Hz), 4.07 (1H, d, J=3.1), 4.50 (1H, d, J=2.0 Hz). 2 protons were not observed in D$_2$O.

$^{19}$F NMR (376 MHz, D$_2$O): δ –76.05.

HPLC: 90.9%

MS (ES$^-$) m/z: [M–H]$^-$ calcd for C$_{13}$H$_{22}$N$_4$O$_7$S: 377.11. Found: 377.05.

Example 26

Sodium[({(2S,5R)-2-[(1H-imidazol-4-ylmethoxy)carbamoyl]-7-oxo-1,6-diazabicyclo[3.2.1]oct-6-yl}oxy)sulfonyl]oxidanide (Compound 142, Table 1)

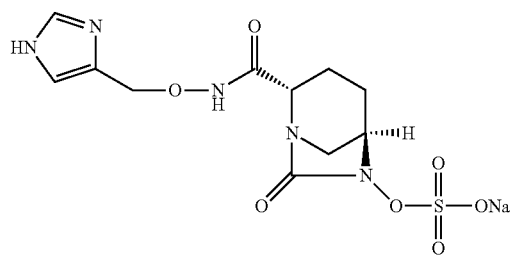

Step 1. tert-butyl 4-{[(1,3-dioxo-1,3-dihydro-2H-isoindol-2-yl)oxy]methyl}-1H-imidazole-1-carboxylate (121)

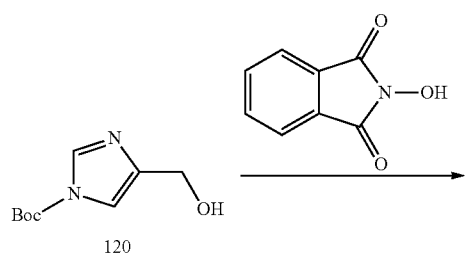

To a mixture of 2-hydroxy-1H-isoindole-1,3(2H)-dione (2.70 g, 16.6 mmol), tert-butyl 4-(hydroxymethyl)-1H-imidazole-1-carboxylate 120 (*Bull. Chem. Soc., Japan,* 2002, Vol 75, No 11, 2517-2526, 1.64 g, 8.27 mmol) and triphenylphosphine (4.34 g, 16.6 mmol) in THF (100 mL) was added DIAD (3.52 mL, 18.2 mmol) slowly at room temperature. The resulting mixture was stirred at room temperature overnight and concentrated to provide a residue which was subjected to chromatography to give 121 (1.7 g, 61%) as a white foam.

$^1$H NMR (400 MHz, CDCl$_3$): δ 1.61 (9H, s), 5.17 (2H, m), 7.56 (1H, s), 7.64 (2H, m), 7.82 (2H, m), 8.01 (1H, s).

MS (ES$^+$) m/z: [M+H]$^+$ calcd for C$_{17}$H$_{18}$N$_3$O$_5$: 344.13. Found: 344.08.

Step 2. tert-butyl 4-[(aminooxy)methyl]-1H-imidazole-1-carboxylate (122)

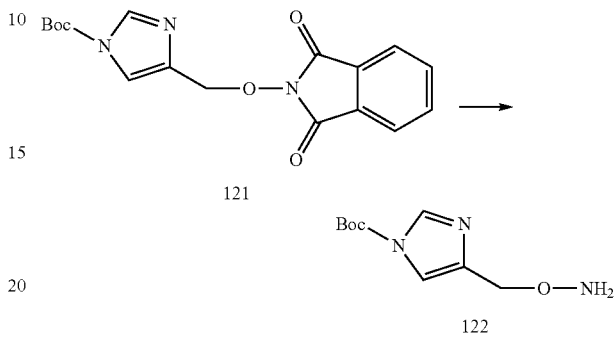

To a mixture of tert-butyl 4-{[(1,3-dioxo-1,3-dihydro-2H-isoindol-2-yl)oxy]methyl}-1H-imidazole-1-carboxylate 121 (1.72 g, 5.00 mmol) in a solution of DCM (20 mL) and ethanol (4 mL) was added hydrazine hydrate (0.287 mL, 5.00 mmol) at room temperature. The mixture was stirred at room temperature overnight, filtered and concentrated to provide a residue which was washed with ether and methanol to give 122 (0.54 g, 51%) as a white solid.

$^1$H NMR (400 MHz, CDCl$_3$): δ 1.62 (9H, m), 4.64 (2H, s), 5.51 (2H, br s), 7.38 (1H, s), 8.06 (1H, s).

MS (ES$^+$) m/z: [M+H]$^+$ calcd for C$_9$H$_{16}$N$_3$O$_3$: 214.12. Found: 214.09.

Step 3. tert-butyl 4-{[({[(2S,5R)-6-(benzyloxy)-7-oxo-1,6-diazabicyclo[3.2.1]oct-2-yl]carbonyl}amino)oxy]methyl}-1H-imidazole-1-carboxylate (123)

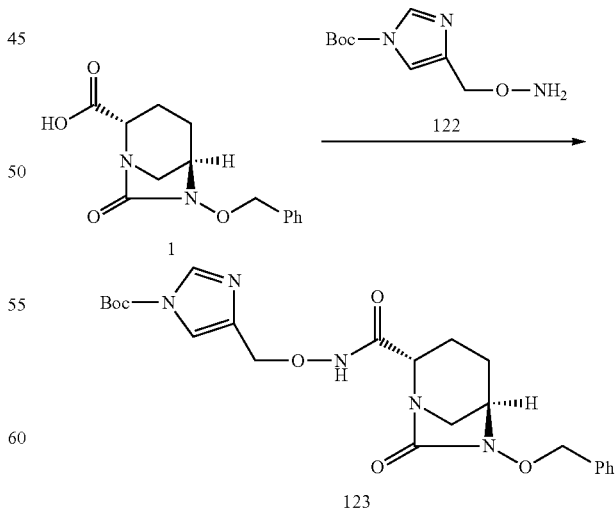

To a mixture of (2S,5R)-6-(benzyloxy)-7-oxo-1,6-diazabicyclo[3.2.1]octane-2-carboxylic acid 1 (0.250 g, 0.905 mmol) in DCM (10.0 mL) was added tert-butyl 4-[(aminooxy)methyl]-1H-imidazole-1-carboxylate 122 (0.289 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 123 (0.40 g, 94%) as a colorless oil.

$^1$H NMR (400 MHz, CDCl$_3$): δ 1.62 (9H, s), 1.95 (3H, m), 2.34 (1H, dd, J=6.0, 14.4 Hz), 2.76 (1H, d, J=11.6 Hz), 3.00 (1H, m), 3.29 (1H, s), 3.93 (1H, d, J=6.8 Hz), 4.86 (3H, m), 5.06 (1H, d, J=11.6 Hz), 7.40 (6H, m), 8.10 (1H, s). One proton was not observed in moisture-containing CDCl$_3$.

MS (ES$^+$) m/z: [M+H]$^+$ calcd for $C_{23}H_{30}N_5O_6$: 472.22. Found: 472.11.

Step 4. tert-butyl 4-{[({[(2S,5R)-6-hydroxy-7-oxo-1,6-diazabicyclo[3.2.1]oct-2-yl]carbonyl}amino)oxy]methyl}-1H-imidazole-1-carboxylate (124)

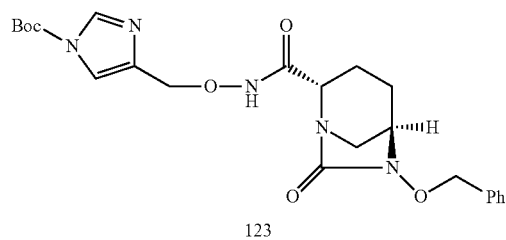

123

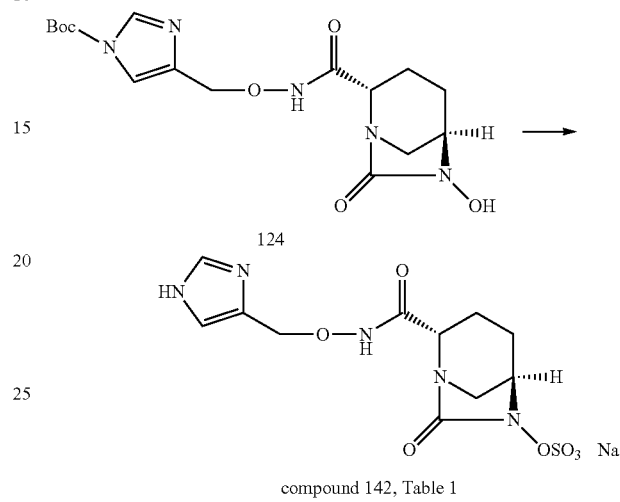

124

A mixture of tert-butyl 4-{[({[(2S,5R)-6-(benzyloxy)-7-oxo-1,6-diazabicyclo[3.2.1]oct-2-yl]carbonyl}amino)oxy]methyl}-1H-imidazole-1-carboxylate 123 (0.40 g, 0.85 mmol) and Pd/C (0.10 g) in methanol (15 mL) was hydrogenated at 1 atm at room temperature for 13 h. The mixture was filtered through Celite pad and concentrated to provide 124 (0.33 g, quantitative) as a white foam.

$^1$H NMR (400 MHz, CD$_3$OD): δ 1.63 (9H, s), 1.80-2.20 (4H, m), 3.08 (2H, m), 3.69 (1H, s), 3.82 (1H, d, J=7.6 Hz), 4.80 (2H, s), 7.64 (1H, s), 8.19 (1H, s). 2 protons were not observed in CD$_3$OD.

MS (ES$^+$) m/z: [M+H]$^+$ calcd for $C_{16}H_{24}N_5O_6$: 382.17. Found: 382.10.

Step 5. sodium[({[(2S,5R)-2-[(1H-imidazol-4-yl-methoxy)carbamoyl]-7-oxo-1,6-diazabicyclo[3.2.1]oct-6-yl}oxy)sulfonyl]oxidanide (Compound 142, Table 1)

compound 142, Table 1

To a mixture of tert-butyl 4-{[({[(2S,5R)-6-hydroxy-7-oxo-1,6-diazabicyclo[3.2.1]oct-2-yl]carbonyl}amino)oxy]methyl}-1H-imidazole-1-carboxylate 124 (0.33 g, 0.86 mmol) in pyridine (10.0 mL) was added sulfur trioxide pyridine complex (0.40 g, 2.60 mmol). The mixture was stirred at room temperature for 3 days and concentrated to provide a residue, which was subjected to chromatography to give a yellow solid which was purified by ion-exchange resin (Dowex50 Na$^+$ form, water) to give Compound 142 (Table 1) (10.7 mg) as a white solid.

$^1$H NMR (400 MHz, D$_2$O): δ1.57-1.76 (2H, m), 1.86-1.99 (2H, m), 2.79 (1H, d, J=12.4 Hz), 2.06 (1H, d, J=12.4 Hz), 3.83 (1H, d, J=7.2 Hz), 3.99 (1H, m), 4.72 (2H, s), 7.14 (1H, s), 7.69 (1H, s). 3 protons were not observed in D$_2$O.

HPLC: 87%.

MS (ES$^-$) m/z: [M−Na]$^-$ calcd for $C_{11}H_{14}N_5O_7$SNa: 360.06. Found: 359.97.

Example 27

(2S,5R)-7-oxo-N-[2-(pyridin-2-yl)ethoxy]-6-(sulfooxy)-1,6-diazabicyclo[3.2.1]octane-2-carboxamide (Compound 69, Table 1)

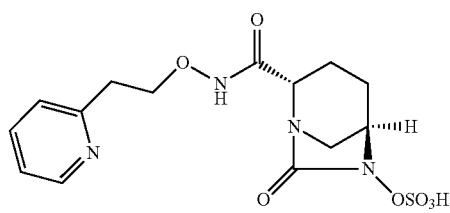

Step 1. (2S,5R)-6-(benzyloxy)-7-oxo-N-[2-(pyridin-2-yl)ethoxy]-1,6-diazabicyclo[3.2.1]octane-2-carboxamide (126)

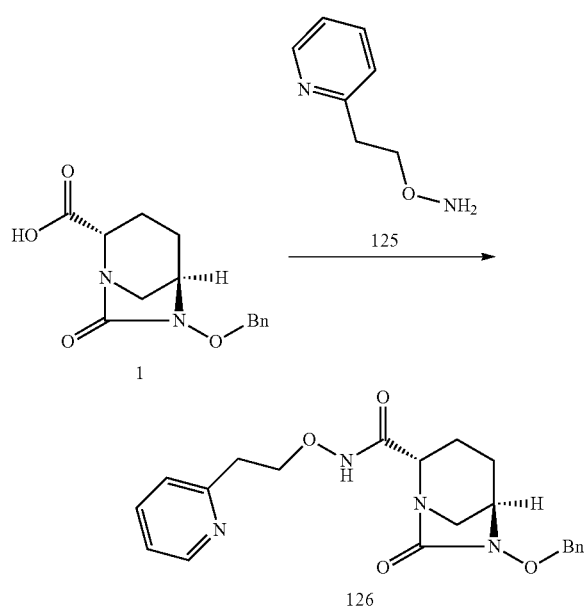

To a solution of (2S,5R)-6-(benzyloxy)-7-oxo-1,6-diazabicyclo[3.2.1]octane-2-carboxylic acid 1 (0.20 g, 0.72 mmol) in dry DCM (20 mL) were added 2-[2-(aminooxy)ethyl]pyridine 125 (0.12 g, 0.86 mmol, *J. Med. Chem.* 1997, 40(15), 2363-2373), 1-hydroxybenzotriazole (0.14 g, 1.10 mmol) and 1-ethyl-(3-dimethylaminopropyl)carbodiimide hydrochloride (0.20 g, 1.10 mmol) at room temperature. The reaction mixture was stirred at room temperature overnight, and then concentrated under vacuum. The residue was purified by column chromatography to give (2S,5R)-6-(benzyloxy)-7-oxo-N-[2-(pyridin-2-yl)ethoxy]-1,6-diazabicyclo[3.2.1]octane-2-carboxamide 126 (0.26 g, 91%) as a clear thick oil.

$^1$H NMR (400 MHz, CDCl$_3$): δ 1.62 (1H, m), 1.95 (2H, m), 2.30 (1H, m), 2.75 (1H, d, J=11.6 Hz), 2.92 (1H, d, J=11.2 Hz), 3.24 (3H, m), 3.95 (1H, d, J=7.6 Hz), 4.27 (2H, m), 4.87 (1H, d, J=11.2 Hz), 5.02 (1H, d, J=11.2 Hz), 7.34 (6H, m), 7.70 (1H, d, J=8.0 Hz), 7.79 (2H, m), 8.53 (1H, br s).

Step 2. (2S,5R)-6-hydroxy-7-oxo-N-[2-(pyridin-2-yl)ethoxy]-1,6-diazabicyclo[3.2.1]octane-2-carboxamide (127)

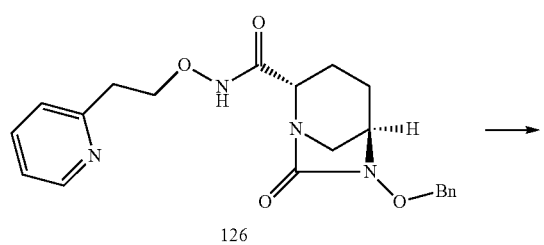

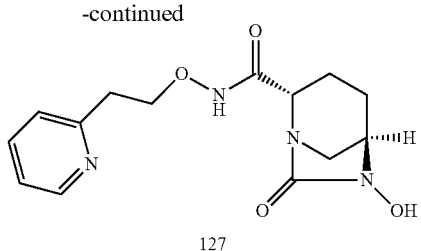

To a solution of (2S,5R)-6-(benzyloxy)-7-oxo-N-[2-(pyridin-2-yl)ethoxy]-1,6-diazabicyclo[3.2.1]octane-2-carboxamide 126 (0.26 g, 0.65 mml) in methanol (20 mL) was added 5% Pd/C (0.25 g). The mixture was hydrogenated at 10 psi hydrogen atmosphere at room temperature for 1 h. The catalyst was filtered out through Celite, and the filtrate was evaporated to give (2S,5R)-6-hydroxy-7-oxo-N-[2-(pyridin-2-yl)ethoxy]-1,6-diazabicyclo[3.2.1]octane-2-carboxamide 127 (0.10 g, 50%) as a white foam.

$^1$H NMR (400 MHz, CDCl$_3$): δ 1.78 (1H, m), 1.97 (1H, m), 2.11 (1H, m), 2.28 (1H, m), 2.91 (1H, d, J=12.0 Hz), 3.20 (2H, m), 3.70 (1H, s), 3.97 (1H, d, J=7.6 Hz), 4.26 (2H, m), 7.30 (2H, m), 7.72 (2H, m), 8.47 (1H, s), 1 proton was not observed.

Step 3. (2S,5R)-7-oxo-N-[2-(pyridin-2-yl)ethoxy]-6-(sulfooxy)-1,6-diazabicyclo[3.2.1]octane-2-carboxamide (Compound 69, Table 1)

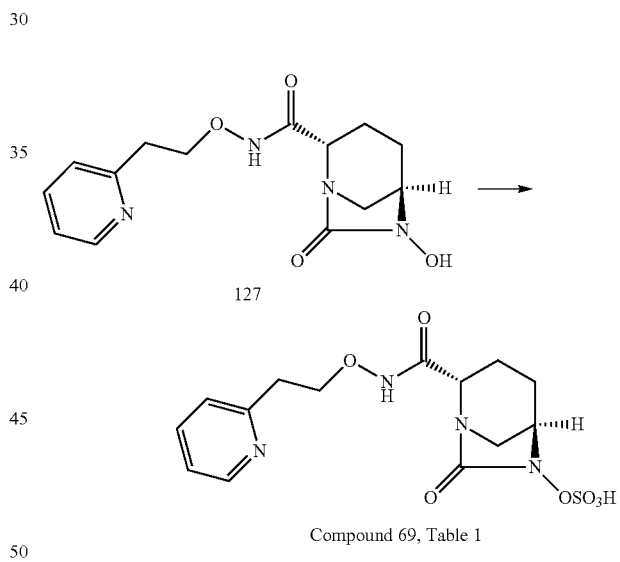

Compound 69, Table 1

To a solution of (2S,5R)-6-hydroxy-7-oxo-N-[2-(pyridin-2-yl)ethoxy]-1,6-diazabicyclo[3.2.1]octane-2-carboxamide 127 (0.10 g, 0.33 mmol) in dry pyridine (7 mL) under nitrogen atmosphere was added sulfur trioxide pyridine complex (0.30 g, 1.88 mmol). The mixture was stirred at room temperature for 20 h, filtered and evaporated. The residue was purified by HPLC and freeze dried to give (2S,5R)-7-oxo-N-[2-(pyridin-2-yl)ethoxy]-6-(sulfooxy)-1,6-diazabicyclo[3.2.1]octane-2-carboxamide Compound 69 (Table 1) (0.0025 g, 2%) as a white solid.

$^1$H NMR (400 MHz, CD$_3$OD): δ 1.83 (1H, m), 1.91 (1H, m), 2.08 (1H, m), 2.21 (1H, m), 3.06 (1H, d, J=12.0 Hz), 3.13 (2H, t, J=6.4 Hz), 3.25 (1H, m), 3.86 (1H, d, J=7.2 Hz), 4.14 (1H, s), 4.23 (2H, t, J=6.4 Hz), 7.27 (1H, m), 7.46 (1H, d, J=8.0 Hz), 7.76 (1H, m), 8.45 (1H, d, J=2.4 Hz), 2 protons were of observed in CD$_3$OD.

HPLC: 76.3%
MS (ES⁻): m/z: [M]⁻=385.06

Example 28 sodium({[(2S,5R)-7-oxo-2-{[(5-oxopyrrolidin-3-yl)oxy]carbamoyl}-1,6-diazabicyclo[3.2.1]oct-6-yl]oxy}sulfonyl)oxidanide (Compound 150, Table 1)

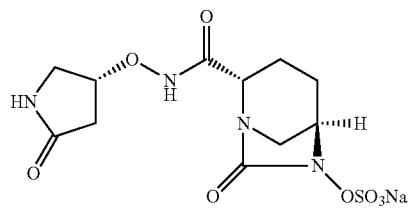

Step 1. (2S,5R)-6-(benzyloxy)-7-oxo-N-{[(3R)-5-oxopyrrolidin-3-yl]oxy}-1,6-diazabicyclo[3.2.1]octane-2-carboxamide (129)

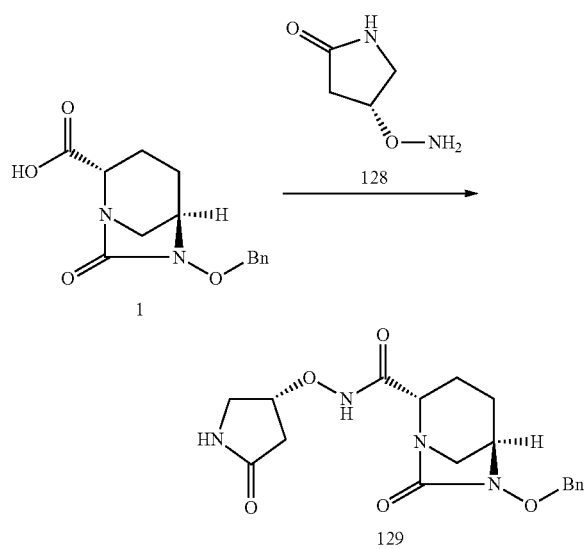

To solution of (2S,5R)-6-(benzyloxy)-7-oxo-1,6-diazabicyclo[3.2.1]octane-2-carboxylic acid 1 (0.20 g, 0.72 mmol) in dry DCM (25 mL) were added (4R)-4-(aminooxy)pyrrolidin-2-one 128 (0.12 g, 0.86 mmol, J. Med. Chem. 1997, 40(15), 2363-2373), 1-hydroxybenzotriazole (0.14 g, 1.10 mmol), 1-ethyl-(3-dimethylaminopropyl)carbodiimide hydrochloride (0.20 g, 1.10 mmol) and 4-dimethylaminopyridine (0.13 g, 1.08 mmol) at room temperature. The reaction mixture was stirred at room temperature overnight, and then concentrated under vacuum. The residue was purified by column chromatography to give (2S,5R)-6-(benzyloxy)-7-oxo-N-{[(3R)-5-oxopyrrolidin-3-yl]oxy}-1,6-diazabicyclo[3.2.1]octane-2-carboxamide 129 (0.22 g, 82%) as a white solid.

¹H NMR (400 MHz, CDCl₃): δ 1.66 (1H, m), 1.96 (2H, m), 2.29 (1H, m), 3.56 (2H, m), 2.78 (1H, d, J=12.0 Hz), 3.00 (1H, d, J=12.0 Hz), 3.33 (1H, s), 3.58 (2H, m), 3.93 (1H, d, J=7.6 Hz), 3.93 (1H, m), 4.84 (1H, m), 4.88 (1H, d, J=12.0 Hz), 5.03 (1H, d, J=11.2 Hz), 6.15 (1H, br s), 7.41 (5H, m), 9.63 (1H, br s).

Step 2. (2S,5R)-6-hydroxy-7-oxo-N-{[(3R)-5-oxopyrrolidin-3-yl]oxy}-1,6-diazabicclo[3.2.1]octane-2-carboxamide (130)

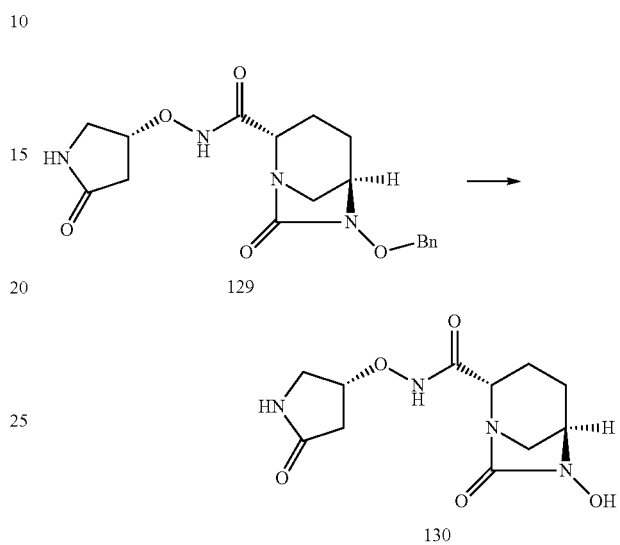

To a solution of (2S,5R)-6-(benzyloxy)-7-oxo-N-{[(3R)-5-oxopyrrolidin-3-yl]oxy}-1,6-diazabicyclo[3.2.1]octane-2-carboxamide 129 (0.22 g, 0.59 mml) in methanol (20 mL) was added 5% Pd/C (0.30 g). The mixture was hydrogenated at 10 psi hydrogen atmosphere at room temperature for 1 h. The catalyst was filtered out through Celite, and the filtrate was evaporated to give (2S,5R)-6-hydroxy-7-oxo-N-{[(3R)-5-oxopyrrolidin-3-yl]oxy}-1,6-diazabicyclo[3.2.1]octane-2-carboxamide 130 (0.156 g, 93%) as a white foam.

¹H NMR (400 MHz, CD₃OD): δ 1.79 (1H, m), 1.97 (1H, m), 2.09 (1H, m), 2.22 (1H, m), 2.46 (1H, d, J=16.4 Hz), 2.64 (1H, dd, 6.8 Hz, 18.0 Hz), 3.01 (1H, d, J=11.6 Hz), 3.12 (1H, m), 3.59 (3H, m), 3.85 (1H, d, J=7.2 Hz), 4.74 (1H, m), 3 protons were not observed in CD₃OD.

Step 3. sodium({[(2S,5R)-7-oxo-2-{[(5-oxopyrrolidin-3-yl)oxy]carbamoyl}-1,6-diazabicyclo[3.2.1]oct-6-yl]oxy}sulfonyl)oxidanide (Compound 150, Table 1)

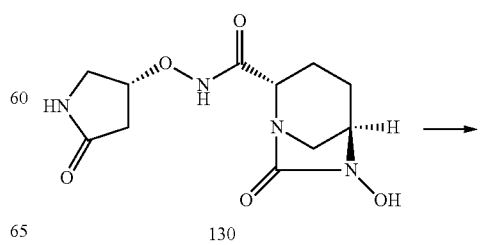

215
-continued

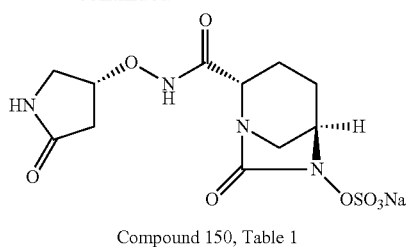

Compound 150, Table 1

To a solution of (2S,5R)-6-hydroxy-7-oxo-N-{[(3R)-5-oxopyrrolidin-3-yl]oxy}-1,6-diazabicyclo[3.2.1]octane-2-carboxamide 130 (0.156 g, 0.55 mmol) in dry pyridine (9 mL) under nitrogen atmosphere was added sulfur trioxide pyridine complex (0.40 g, 2.51 mmol). The mixture was stirred at room temperature for 20 h, then filtered and evaporated. Ether was added to the residue and the resulting white precipitate was collected by centrifugation. The white solid was purified by resin DOWEX 50WX4 column using water as eluent and freeze dried to give sodium({[(2S,5R)-7-oxo-2-{[(5-oxopyrrolidin-3-yl)oxy]carbamoyl}-1,6-diazabicyclo[3.2.1]oct-6-yl]oxy}sulfonyl)oxidanide Compound 150 (Table 1) (0.025 g, 12%) as a white solid.

$^1$H NMR (400 MHz, CD$_3$OD): δ 1.84 (1H, m), 1.93 (1H, m), 2.07 (1H, m), 2.20 (1H, m), 2.47 (1H, d, J=18.0 Hz), 2.65 (1H, dd, J=6.4 Hz and 18.0 Hz), 3.05 (1H, d, J=11.6 Hz), 3.24 (1H, m), 3.59 (2H, m), 3.92 (1H, d, J=6.8 Hz), 4.14 (1H, m), 4.75 (1H, m), 2 protons were not observed in CD$_3$OD.

HPLC: 97.3%

MS (ES$^-$): m/z: [M]$^-$=362.97

Example 29

Sodium[({(2S,5R)-2-[(1,4-oxazepan-2-ylmethoxy)carbamoyl]-7-oxo-1,6-diazabicyclo[3.2.1]oct-6-yl}oxy)sulfonyl]oxidanide (Compound 13, Table 1)

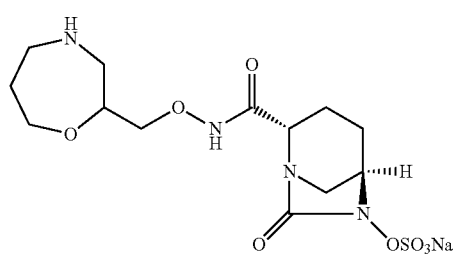

216

Step 1. tert-butyl 2-{[({[(2S,5R)-6-(benzyloxy)-7-oxo-1,6-diazabicyclo[3.2.1]oct-2-yl]carbonyl}amino)oxy]methyl}-1,4-oxazepane-4-carboxylate (132)

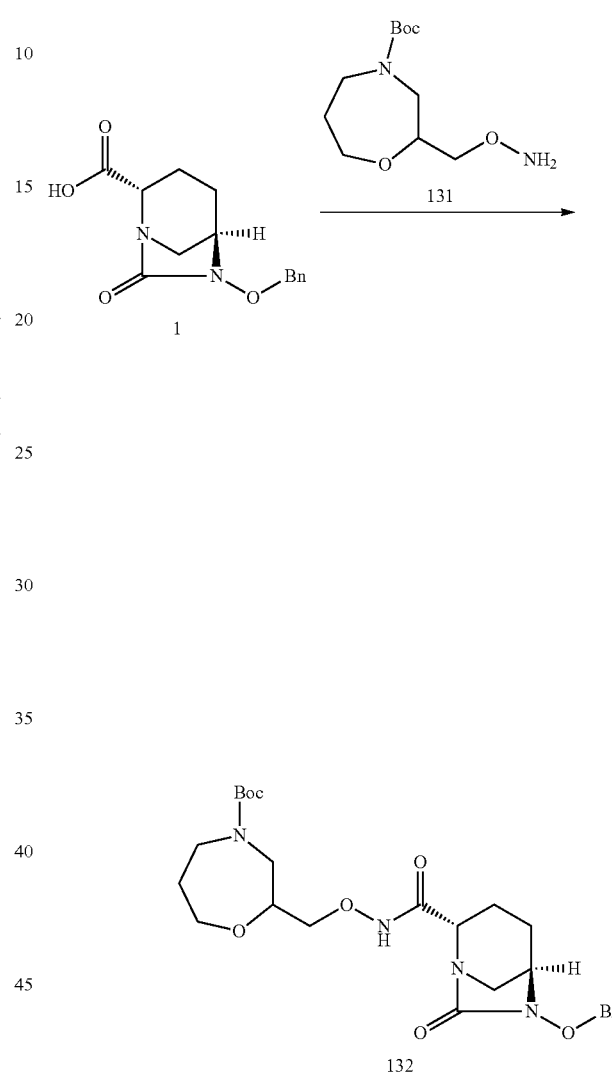

To a solution of (2S,5R)-6-(benzyloxy)-7-oxo-1,6-diazabicyclo[3.2.1]octane-2-carboxylic acid 1 (0.22 g, 0.80 mmol) in dry DCM (20 mL) were added tert-butyl 2-[(aminooxy)methyl]-1,4-oxazepane-4-carboxylate 131 (0.23 g, 0.93 mmol, US 2010/0168080 and J. Med. Chem. 2008, 51, 4601-4608), 1-hydroxybenzotriazole (0.15 g, 1.12 mmol) and 1-ethyl-(3-dimethylaminopropyl)carbodiimide hydrochloride (0.21 g, 1.12 mmol) at room temperature. The reaction mixture was stirred at room temperature overnight and concentrated under vacuum. The residue was purified by column chromatography to give tert-butyl 2-{[({[(2S,5R)-6-(benzyloxy)-7-oxo-1,6-diazabicyclo[3.2.1]oct-2-yl]carbonyl}amino)oxy]methyl}-1,4-oxazepane-4-carboxylate 132 (0.32 g, 80%) as a clear thick oil.

$^1$H NMR (400 MHz, CDCl$_3$): δ 1.46 (9H, s), 1.62 (2H, m), 2.01 (4H, m), 2.34 (1H, m), 2.77 (1H, m), 3.03 (2H, m), 3.30

(2H, m), 3.49 (1H, m), 3.57-4.00 (5H, m), 4.11 (1H, m), 4.89 (1H, d, J=11.6 Hz), 5.04 (1H, d, J=11.6 Hz), 7.39 (5H, m), 9.39 (1H, m).

Step 2. tert-butyl 2-{[({[(2S,5R)-6-hydroxy-7-oxo-1,6-diazabicyclo[3.2.1]oct-2-yl]carbonyl}amino)oxy]methyl}-1,4-oxazepane-4-carboxylate (133)

$^1$H NMR (400 MHz, CD$_3$OD): δ 1.47 (9H, s), 1.70-1.98 (4H, m), 2.05 (1H, m), 2.18 (1H, m), 3.08 (2H, m), 3.41-4.00 (10H, m), 4.06 (1H, m), 2 protons were not observed in CD$_3$OD.

Step 3. tert-butyl 2-{[({[(2S,5R)-7-oxo-6-(sulfooxy)-1,6-diazabicyclo[3.2.1]oct-2-yl]carbonyl}amino)oxy]methyl}-1,4-oxazepane-4-carboxylate pyridine salt (134)

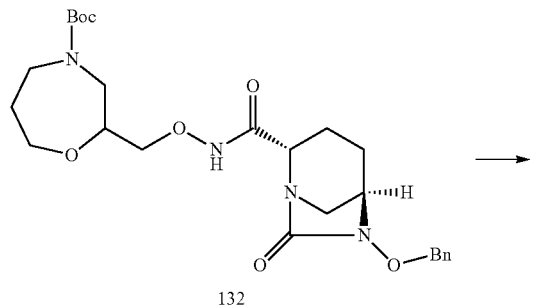

To a solution of tert-butyl 2-{[({[(2S,5R)-6-(benzyloxy)-7-oxo-1,6-diazabicyclo[3.2.1]oct-2-yl]carbonyl}amino)oxy]methyl}-1,4-oxazepane-4-carboxylate 132 (0.32 g, 0.63 mmol) in methanol (20 mL) was added 5% Pd/C (0.30 g). The mixture was hydrogenated at 15 psi hydrogen atmosphere at room temperature for 1 h. The catalyst was filtered out through Celite, and the filtrate was evaporated to give tert-butyl 2-{[({[(2S,5R)-6-hydroxy-7-oxo-1,6-diazabicyclo[3.2.1]oct-2-yl]carbonyl}amino)oxy]methyl}-1,4-oxazepane-4-carboxylate 133 (0.205 g, 78%) as a colorless foam.

To a solution of tert-butyl 2-{[({[(2S,5R)-6-hydroxy-7-oxo-1,6-diazabicyclo[3.2.1]oct-2-yl]carbonyl}amino)oxy]methyl}-1,4-oxazepane-4-carboxylate 133 (0.20 g, 0.48 mmol) in dry pyridine (6 mL) under nitrogen atmosphere was added sulfur trioxide pyridine complex (0.34 g, 2.14 mmol). The mixture was stirred at room temperature for 20 h, then filtered and evaporated. The residue was washed 4 times with ether to give tert-butyl 2-{[({[(2S,5R)-7-oxo-6-(sulfooxy)-1,6-diazabicyclo[3.2.1]oct-2-yl]carbonyl}amino)oxy]methyl}-1,4-oxazepane-4-carboxylate pyridine salt 134 (0.16 g) which was used in the next step without purification.

Step 4. sodium[({(2S,5R)-2-[(1,4-oxazepan-2-yl-methoxy)carbamoyl]-7-oxo-1,6-diazabicyclo[3.2.1]oct-6-yl}oxy)sulfonyl]oxidanide (Compound 13, Table 1)

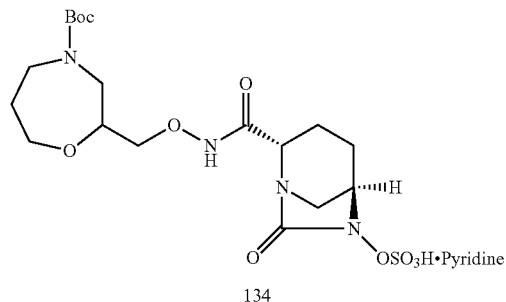

134

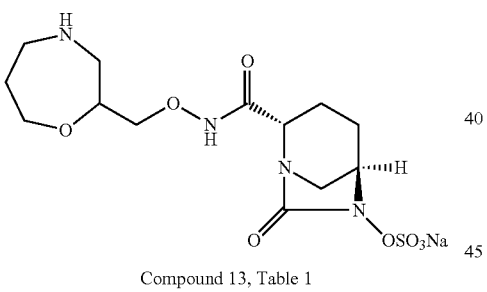

Compound 13, Table 1

To a solution of tert-butyl 2-{[({[(2S,5R)-7-oxo-6-(sulfooxy)-1,6-diazabicyclo[3.2.1]oct-2-yl]carbonyl}amino)oxy]methyl}-1,4-oxazepane-4-carboxylate pyridine salt 134 (0.16 g, 0.28 mmol) in DCM (5 mL) was added trifluoroacetic acid (0.30 mL, 3.89 mmol) dropwise at 0° C. The reaction mixture was stirred for 1 h then evaporated. Ether was added to the residue and the resulting white precipitate was collected by centrifugation. The white solid was purified by resin DOWEX 50WX4 column using water as eluent and freeze dried to give sodium[({(2S,5R)-2-[(1,4-oxazepan-2-yl-methoxy)carbamoyl]-7-oxo-1,6-diazabicyclo[3.2.1]oct-6-yl}oxy)sulfonyl]oxidanide Compound 13 (Table 1) (0.04 g, 34%) as a white solid.

$^1$H NMR (400 MHz, D$_2$O): δ 1.68 (1H, m), 1.79 (1H, m), 1.93 (4H, m), 2.97 (1H, d, J=11.2 Hz), 3.13 (2H, m), 3.24 (2H, m), 3.32 (1H, m), 3.61 (1H, m), 3.78-3.99 (4H, m), 4.04 (2H, m), 2 protons were not observed in D$_2$O.

HPLC: 97.4%

MS (ES$^-$) m/z: [M]$^-$=393.04

Example 30

Sodium[({(2S,5R)-2-[(1,4-oxazepan-6-yloxy)carbamoyl]-7-oxo-1,6-diazabicyclo[3.2.1]oct-6-yl}oxy)sulfonyl]oxidanide (Compound 35, Table 1)

Using the similar procedures as described earlier but using tert-butyl 6-(aminooxy)-1,4-oxazepane-4-carboxylate, Compound 35 (Table 1) was prepared as a diastereoisomeric mixture as a white solid in 20% yield.

$^1$H NMR (400 MHz, CD$_3$OD): δ 1.82 (1H, m), 1.94 (1H, m), 2.07 (1H, m), 2.23 (1H, m), 3.00 (1H, d, J=12.0 Hz), 3.09 (1H, d, J=12.0 Hz), 3.21 (1H, m), 3.44 (2H, m), 3.63 (1H, m), 3.85-4.04 (5H, m), 4.15 (1H, s), 4.36 (1H, m), 2 protons were not observed in CD$_3$OD.

HPLC: 95.5%

MS (ES$^-$): m/z: [M]$^-$=379.01

Example 31

Sodium({[(2S,5R)-2-{[2-(1H-imidazol-1-yl)ethoxy]carbamoyl}-7-oxo-1,6-diazabicyclo[3.2.1]oct-6-yl]oxy}sulfonyl)oxidanide (Compound 100, Table 1)

Using the similar procedures as describe earlier but using O-(2-(1H-imidazol-1-yl)ethyl)hydroxylamine, Compound 100 (Table 1) was prepared as a white solid.

$^1$H NMR (400 MHz, D$_2$O): δ 1.64-1.90 (4H, m), 2.90 (1H, d, J=12.0 Hz), 3.06 (1H, d, J=12.0 Hz), 3.78 (1H, d, J=6.8 Hz), 4.00 (1H, m), 4.06 (2H, m), 4.15 (2H, m), 6.89 (1H, s), 7.09 (1H, s), 7.67 (1H, s). 2 protons were not observed in D$_2$O.

HPLC: 87.4%,

MS (ES$^-$) m/z: [M-Na]$^-$ calcd for C$_{12}$H$_{16}$N$_5$O$_7$S: 374.08. Found: 374.01.

Example 32

Sodium({[(2S,5R)-7-oxo-2-{[(3R)-tetrahydrofuran-3-yloxy]carbamoyl}-1,6-diazabicyclo[3.2.1]oct-6-yl]oxy}sulfonyl)oxidanide (Compound 95, Table 1)

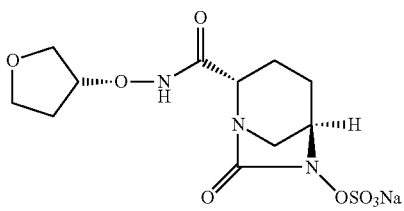

Using the similar procedures as describe earlier but using O-[(3R)-tetrahydrofuran-3-yl]hydroxylamine, Compound 95 (Table 1) was prepared as a white solid.

$^1$H NMR (400 MHz, D$_2$O): δ 1.62-1.83 (2H, m), 1.90-2.03 (4H, m), 2.94 (1H, d, J=12.8 Hz), 3.14 (1H, d, J=12.8 Hz), 3.60-3.73 (2H, m), 3.75-3.93 (3H, m), 4.04 (1H, m), 4.60 (1H, m). 2 protons were not observed in D$_2$O.

HPLC: 95.2%,

MS (ES$^-$) m/z: [M−Na]$^-$ calcd for C$_{11}$H$_{16}$N$_3$O$_8$S: 350.07. Found: 349.99.

Example 33

Sodium({[(2S,5R)-2-{[(1-methyl-4,5,6,7-tetrahydro-1H-pyrazolo[3,4-c]pyridin-4-yl)oxy]carbamoyl}-7-oxo-1,6-diazabicyclo[3.2.1]oct-6-yl]oxy}sulfonyl)oxidanide (Compound 70, Table 1)

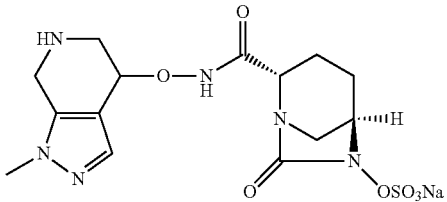

Step 1. tert-butyl 4-[(1,3-dioxo-1,3-dihydro-2H-isoindol-2-yl)oxy]-1-methyl-1,4,5,7-tetrahydro-6H-pyrazolo[3,4-c]pyridine-6-carboxylate (136)

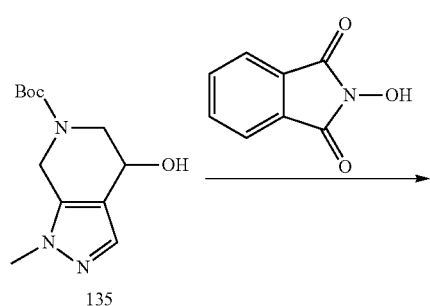

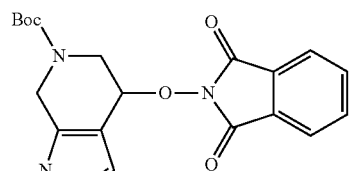

To a mixture of 2-hydroxy-1H-isoindole-1,3(2H)-dione (2.95 g, 18.1 mmol), tert-butyl 4-hydroxy-1-methyl-1,4,5,7-tetrahydro-6H-pyrazolo[3,4-c]pyridine-6-carboxylate 135 (US2005/245505 A1, 2.29 g, 9.04 mmol) and triphenylphosphine (4.74 g, 18.1 mmol) in THF (100 mL) was added DIAD (3.85 mL, 19.9 mmol) slowly at room temperature. The resulting mixture was stirred at room temperature overnight and concentrated to provide a residue which was subjected to chromatography to give 136 (2.5 g, 35%) as a yellow solid.

$^1$H NMR (400 MHz, CDCl$_3$): δ 1.52 (9H, s), 3.29 (2H, m), 3.76 (3H, s), 4.25-5.16 (2H, m), 5.44 (1H, m), 7.80 (5H, m).

MS (ES$^+$) m/z: [M+H]$^+$ calcd for C$_{20}$H$_{23}$N$_4$O$_5$: 399.17. Found: 399.11.

Step 2. tert-butyl 4-(aminooxy)-1-methyl-1,4,5,7-tetrahydro-6H-pyrazolo[3,4-c]pyridine-6-carboxylate (137)

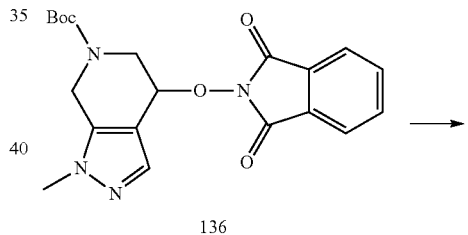

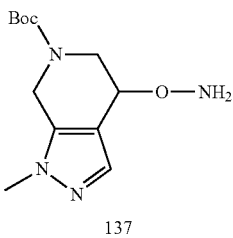

To a mixture of tert-butyl 4-[(1,3-dioxo-1,3-dihydro-2H-isoindol-2-yl)oxy]-1-methyl-1,4,5,7-tetrahydro-6H-pyrazolo[3,4-c]pyridine-6-carboxylate 136 (2.50 g, 6.27 mmol) in a solution of DCM (20 mL) and ethanol (4 mL) was added hydrazine hydrate (0.360 mL, 6.27 mmol) at room temperature. The mixture was stirred at room temperature overnight, filtered and concentrated to provide a residue which was washed with ether and methanol to give 137 (1.06 g, 62%) as a white foam.

$^1$H NMR (400 MHz, CDCl$_3$): δ 1.50 (9H, s), 2.88 (1H, m), 3.76 (3H, s), 4.05 (1H, m), 4.57 (1H, m), 4.78-5.10 (2H, m), 5.47 (2H, m), 7.51 (1H, s).

MS (ES+) m/z: [M+H]+ calcd for $C_{12}H_{21}N_4O_3$: 269.16. Found: 269.10.

Step 3. tert-butyl 4-[({[(2S,5R)-6-(benzyloxy)-7-oxo-1,6-diazabicyclo[3.2.1]oct-2-yl]carbonyl}amino)oxy]-1-methyl-1,4,5,7-tetrahydro-6H-pyrazolo[3,4-c]pyridine-6-carboxylate (138)

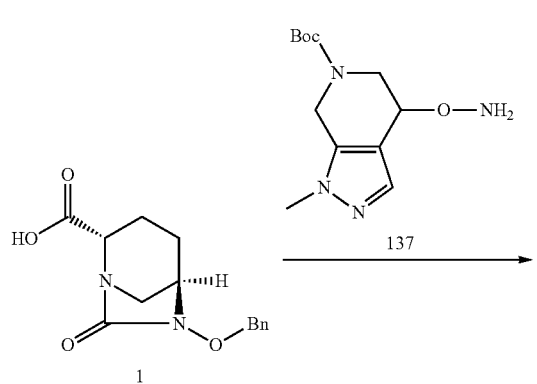

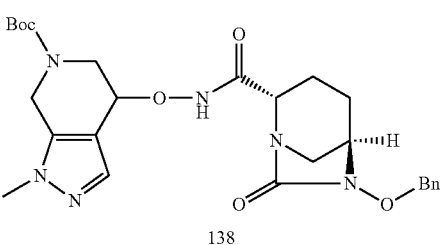

To a mixture of (2S,5R)-6-(benzyloxy)-7-oxo-1,6-diazabicyclo[3.2.1]octane-2-carboxylic acid 1 (0.250 g, 0.905 mmol) in DCM (10.0 mL) were added tert-butyl 4-(aminooxy)-1-methyl-1,4,5,7-tetrahydro-6H-pyrazolo[3,4-c]pyridine-6-carboxylate 137 (0.360 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 138 (0.42 g, 89%) as a white foam.

$^1$H NMR (400 MHz, CDCl$_3$): δ 1.50 (9H, s), 1.62 (1H, m), 2.00 (2H, m), 2.32 (1H, m), 2.70-3.10 (3H, m), 3.29 (1H, s), 3.76 (3H, s), 4.06 (2H, m), 4.58 (1H, m), 4.88 (1H, d, J=11.6 Hz), 4.99 (2H, m), 5.04 (1H, d, J=11.6 Hz), 7.42 (5H, m), 7.60 (1H, s). One proton was not observed.

MS (ES+) m/z: [M+H]+ calcd for $C_{26}H_{35}N_6O_6$: 527.26. Found: 527.17.

Step 4. tert-butyl 4-[({[(2S,5R)-6-hydroxy-7-oxo-1,6-diazabicyclo[3.2.1]oct-2-yl]carbonyl}amino)oxy]-1-methyl-1,4,5,7-tetrahydro-6H-pyrazolo[3,4-c]pyridine-6-carboxylate (139).

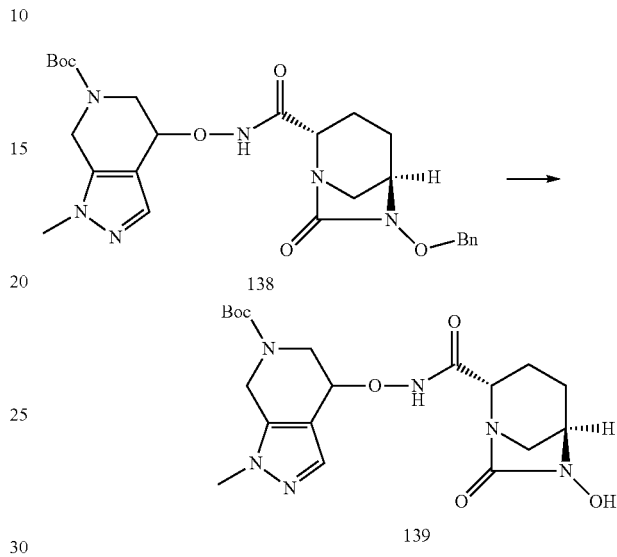

A mixture of tert-butyl 4-[({[(2S,5R)-6-(benzyloxy)-7-oxo-1,6-diazabicyclo[3.2.1]oct-2-yl]carbonyl}amino)oxy]-1-methyl-1,4,5,7-tetrahydro-6H-pyrazolo[3,4-c]pyridine-6-carboxylate 138 (0.42 g, 0.80 mmol) and Pd/C (0.13 g) in methanol (20 mL) was hydrogenated at one atm. at room temperature for 13 h. The mixture was filtered through Celite pad and concentrated to give a residue which was subjected to chromatography to provide 139 (0.33 g, 94%) as a white solid.

$^1$H NMR (400 MHz, CD$_3$OD): δ 1.51 (9H, s), 1.80-2.30 (4H, m), 3.07 (3H, m), 3.70 (1H, m), 3.77 (3H, s), 3.90 (1H, m), 4.23 (1H, br s), 4.45 (1H, br s), 4.98 (2H, d, J=8.4 Hz), 7.58 (1H, br s). 2 protons were not observed in CD$_3$OD.

MS (ES−) m/z: [M−H]− calcd for $C_{19}H_{27}N_6O_6$: 435.20. Found: 435.11.

Step 5. tert-butyl 1-methyl-4-[({[(2S,5R)-7-oxo-6-(sulfooxy)-1,6-diazabicyclo[3.2.1]oct-2-yl]carbonyl}amino)oxy]-1,4,5,7-tetrahydro-6H-pyrazolo[3,4-c]pyridine-6-carboxylate (140)

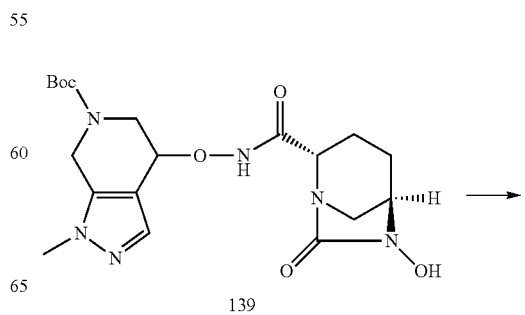

225
-continued

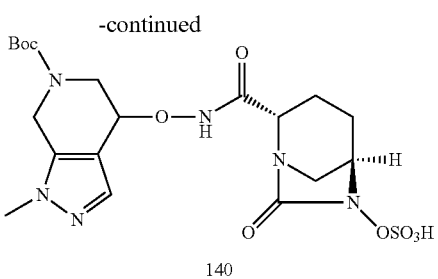

140

To a mixture of tert-butyl 4-[({[(2S,5R)-6-hydroxy-7-oxo-1,6-diazabicyclo[3.2.1]oct-2-yl]carbonyl}amino)oxy]-1-methyl-1,4,5,7-tetrahydro-6H-pyrazolo[3,4-c]pyridine-6-carboxylate 139 (0.33 g, 0.76 mmol) in pyridine (10.0 mL) was added sulfur trioxide pyridine complex (0.35 g, 2.27 mmol). The mixture was stirred at room temperature for 23 h and concentrated to provide a residue which was subjected to chromatography to give 140 (0.35 g, 90%) as a light yellow foam.

$^1$H NMR (400 MHz, CD$_3$OD): δ 1.50 (9H, s), 1.80-2.00 (4H, m), 3.12 (1H, d, J=11.2 Hz), 3.27 (2H, m), 3.77 (3H, s), 3.96 (1H, m), 4.16 (1H, m), 4.30 (1H, m), 4.50 (1H, m), 5.00 (2H, m), 7.58 (1H, br s). 2 protons were not observed in CD$_3$OD.

MS (ES$^-$) m/z: [M−H]$^-$ calcd for C$_{19}$H$_{27}$N$_6$O$_9$S: 515.16. Found: 515.04.

Step 6. sodium({[(2S,5R)-2-{[(1-methyl-4,5,6,7-tetrahydro-1H-pyrazolo[3,4-c]pyridin-4-yl)oxy]carbamoyl}-7-oxo-1,6-diazabicyclo[3.2.1]oct-6-yl]oxy}sulfonyl) oxidanide (Compound 70, Table 1)

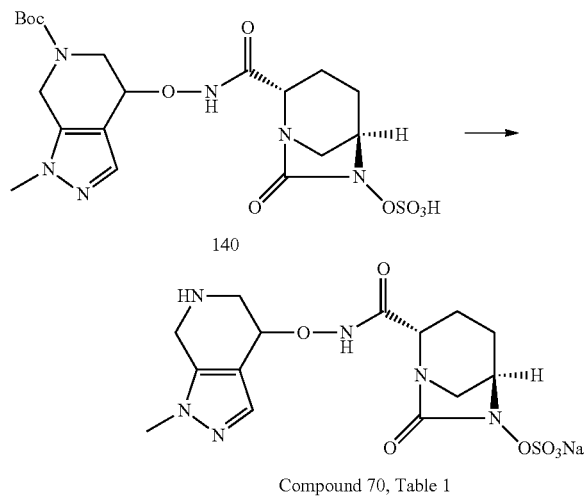

Compound 70, Table 1

To a mixture of tert-butyl 1-methyl-4-[({[(2S,5R)-7-oxo-6-(sulfooxy)-1,6-diazabicyclo[3.2.1]oct-2-yl]carbonyl}amino)oxy]-1,4,5,7-tetrahydro-6H-pyrazolo[3,4-c]pyridine-6-carboxylate 140 (0.35 g, 0.68 mmol) in DCM (8.0 mL) was added trifluoroacetic acid (0.40 mL) at 0° C. The mixture was stirred at 0° C. for 1 h, concentrated and washed with ether. The white solid was collected by centrifugation. The crude product was purified by ion-exchange resin (Dowex50 Na$^+$ form, water) to give Compound 70 (Table 1) (30 mg) as a white solid as a pair of diastereoisomers.

226

$^1$H NMR (400 MHz, D$_2$O): δ 1.67-1.82 (2H, m), 1.90-2.02 (2H, m), 2.72 (1H, m), 2.86-2.95 (1H, m), 3.13 (1H, m), 3.28 (1H, d, J=14.4 Hz), 3.56 (3H, s), 3.72 (1H, d, J=16.0 Hz), 3.87-4.10 (3H, m), 4.82 (1H, s), 7.46 (1H, s). 3 protons were not observed in D$_2$O.

HPLC: 94.1%

MS (ES$^-$) m/z: [M−Na]$^-$ calcd for C$_{14}$H$_{19}$N$_6$O$_7$S: 415.11. Found: 415.03.

Example 34

Sodium[({(2S,5R)-7-oxo-2-[(pyrazolidin-4-yloxy)carbamoyl]-1,6-diazabicyclo[3.2.1]oct-6-yl}oxy)sulfonyl]oxidanide (Compound 104, Table 1)

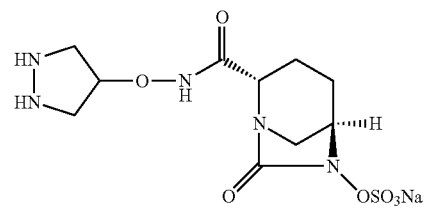

Step 1. di-tert-butyl 4-[(1,3-dioxo-1,3-dihydro-2H-isoindol-2-yl)oxy]pyrazolidine-1,2-dicarboxylate (142)

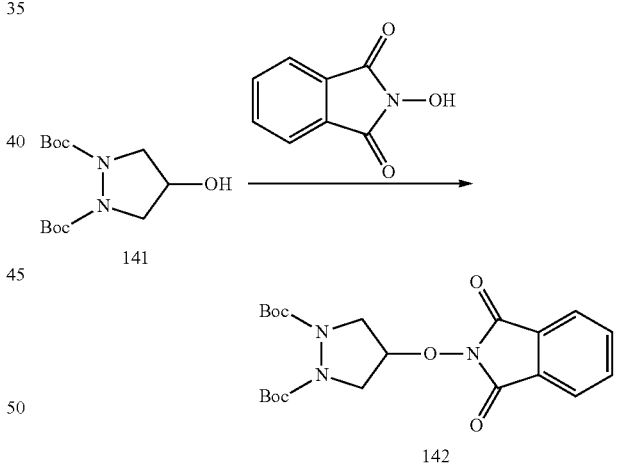

To a mixture of 2-hydroxy-1H-isoindole-1,3(2H)-dione (1.72 g, 10.541 mmol), di-tert-butyl 4-hydroxypyrazolidine-1,2-dicarboxylate 141 (*Journal of Antibiotics*, 1993, Vol 46, (12), 1866-1882, 1.52 g, 5.27 mmol) and triphenylphosphine (2.76 g, 10.54 mmol) in THF (50 mL) was added DIAD (2.24 mL, 11.59 mmol) slowly at room temperature. The resulting mixture was stirred at room temperature overnight and concentrated to provide a residue, which was subjected to chromatography to give 142 (1.8 g, 79%) as a white foam.

$^1$H NMR (400 MHz, CDCl$_3$): δ 1.48 (9H, s), 1.52 (9H, s), 3.30 (1H, dd, J=4.0, 13.6 Hz), 3.71 (1H, d, J=14.0 Hz), 4.11 (1H, m), 4.50 (1H, d, J=13.2 Hz), 5.13 (1H, br s), 7.77 (2H, m), 7.87 (2H, m).

MS (ES+) m/z: [M+H]+ calcd for $C_{21}H_{28}N_3O_7$: 434.19. Found: 434.10.

Step 2. di-tert-butyl 4-(aminooxy)pyrazolidine-1,2-dicarboxylate (143)

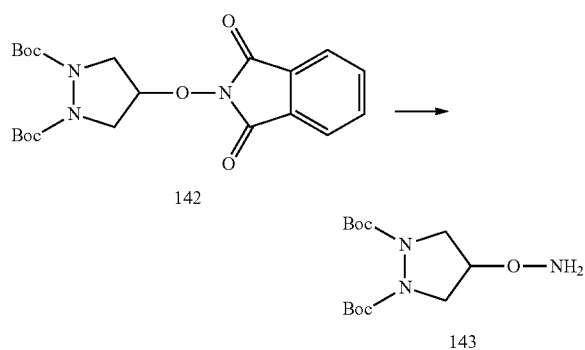

To a mixture of di-tert-butyl 4-[(1,3-dioxo-1,3-dihydro-2H-isoindol-2-yl)oxy]pyrazolidine-1,2-dicarboxylate 142 (1.81 g, 4.18 mmol) in a solution of DCM (20 mL) and ethanol (4 mL) was added hydrazine hydrate (0.240 mL, 4.18 mmol) at room temperature. The mixture was stirred at room temperature overnight, filtered and concentrated to provide a residue which was subjected to chromatography to give 143 (1.04 g, 83%) as a white foam.

$^1$H NMR (400 MHz, CDCl$_3$): δ 1.48 (18H, m), 2.99 (1H, m), 3.62 (1H, m), 3.78 (1H, dd, J=5.6 Hz and 12.0 Hz), 4.43 (2H, m), 5.38 (2H, br s).

MS (ES+) m/z: [M+H]+ calcd for $C_{13}H_{26}N_3O_5$: 304.19. Found: 304.15.

Step 3. di-tert-butyl 4-[({[(2S,5R)-6-(benzyloxy)-7-oxo-1,6-diazabicyclo[3.2.1]oct-2-yl]carbonyl}amino)oxy]pyrazolidine-1,2-dicarboxylate (144)

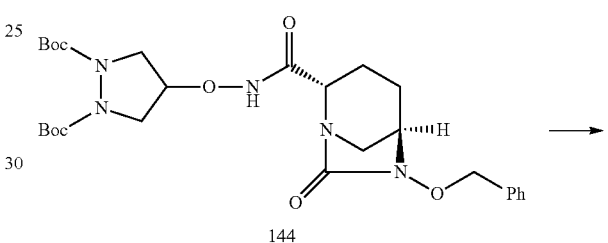

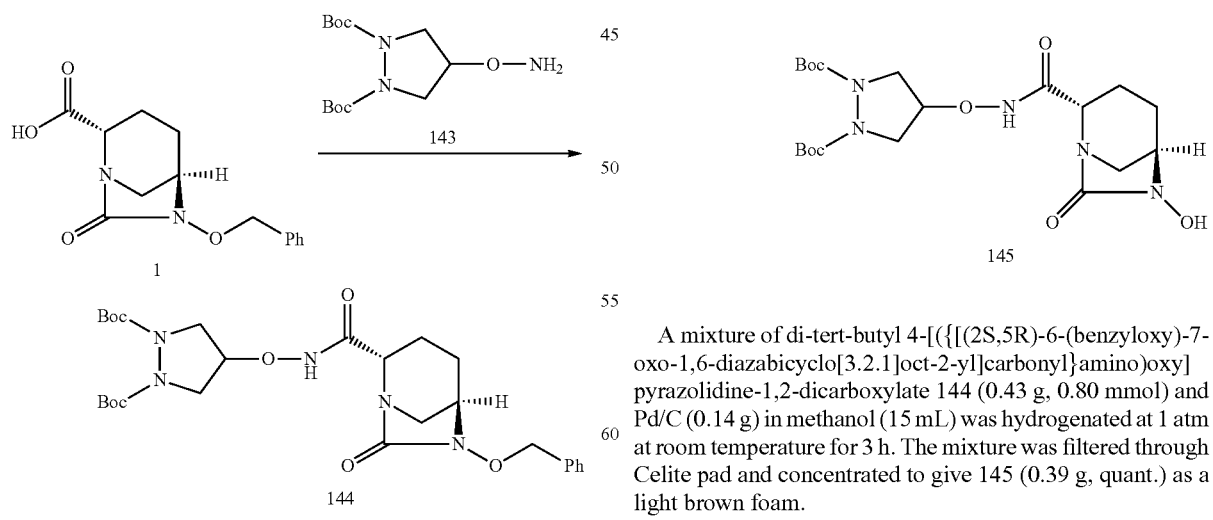

To a mixture of (2S,5R)-6-(benzyloxy)-7-oxo-1,6-diazabicyclo[3.2.1]octane-2-carboxylic acid 1 (0.250 g, 0.905 mmol) in DCM (10.0 mL) were added di-tert-butyl 4-(aminooxy)pyrazolidine-1,2-dicarboxylate 143 (0.411 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 144 (0.43 g, 85%) as a white foam.

$^1$H NMR (400 MHz, CDCl$_3$): δ 1.46 (18H, s), 1.62 (1H, m), 2.00 (2H, m), 2.30 (1H, m), 2.68 (1H, m), 3.00 (2H, m), 3.29 (1H, s), 3.51 (1H, m), 3.86 (1H, m), 3.98 (1H, m), 4.42 (1H, m), 4.86 (1H, m), 4.88 (1H, d, J=11.2 Hz), 5.04 (1H, d, J=11.2 Hz), 7.42 (5H, m), 9.14 (1H, m).

MS (ES+) m/z: [M+H]+ calcd for $C_{27}H_{40}N_5O_8$: 562.29. Found: 562.22.

Step 4. di-tert-butyl 4-[({[(2S,5R)-6-hydroxy-7-oxo-1,6-diazabicyclo[3.2.1]oct-2-yl]carbonyl}amino)oxy]pyrazolidine-1,2-dicarboxylate (145)

A mixture of di-tert-butyl 4-[({[(2S,5R)-6-(benzyloxy)-7-oxo-1,6-diazabicyclo[3.2.1]oct-2-yl]carbonyl}amino)oxy]pyrazolidine-1,2-dicarboxylate 144 (0.43 g, 0.80 mmol) and Pd/C (0.14 g) in methanol (15 mL) was hydrogenated at 1 atm at room temperature for 3 h. The mixture was filtered through Celite pad and concentrated to give 145 (0.39 g, quant.) as a light brown foam.

$^1$H NMR (400 MHz, CD$_3$OD): δ 1.48 (18H, s), 1.80-2.20 (4H, m), 3.02-3.13 (3H, m), 3.55 (1H, m), 3.70 (1H, m), 3.86 (1H, m), 3.93 (1H, m), 4.24 (1H, m), 4.79 (1H, m). 2 protons were not observed in CD$_3$OD.

MS (ES⁻) m/z: [M−H]⁻ calcd for $C_{20}H_{32}N_5O_8$: 470.22. Found: 470.14.

Step 5. di-tert-butyl 4-[({[(2S,5R)-7-oxo-6-(sulfooxy)-1,6-diazabicyclo[3.2.1]oct-2-yl]carbonyl}amino)oxy]pyrazolidine-1,2-dicarboxylate (146)

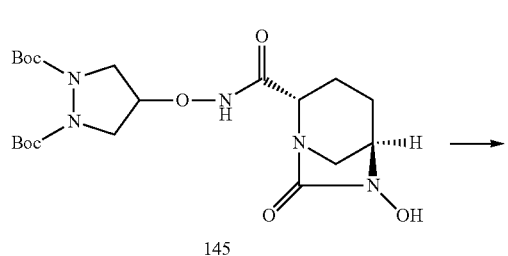

145

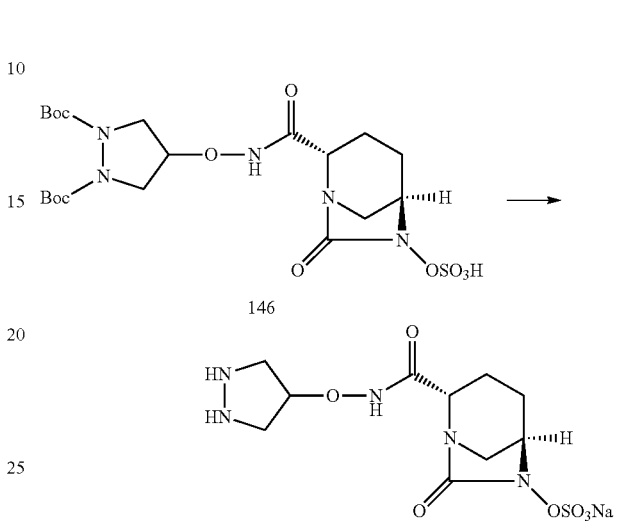

146

To a mixture of di-tert-butyl 4-[({[(2S,5R)-6-hydroxy-7-oxo-1,6-diazabicyclo[3.2.1]oct-2-yl]carbonyl}amino)oxy]pyrazolidine-1,2-dicarboxylate 145 (0.39 g, 0.82 mmol) in pyridine (10.0 mL) was added sulfur trioxide pyridine complex (0.39 g, 2.48 mmol). The mixture was stirred at room temperature for 23 h and concentrated to provide a residue which was subjected to chromatography to give 146 (0.31 g, 68%) as a white foam.

¹H NMR (400 MHz, CD₃OD): δ 1.48 (18H, s), 1.80-2.20 (4H, m), 3.07 (1H, d, J=12.4 Hz), 3.23 (2H, m), 3.55 (1H, m), 3.93 (2H, m), 4.14 (1H, m), 4.25 (1H, d, J=12.4 Hz), 4.81 (1H, t, J=5.6 Hz). 2 protons were not observed in CD₃OD.

MS (ES⁻) m/z: [M−H]⁻ calcd for $C_{20}H_{32}N_5O_{11}S$: 550.18. Found: 550.05.

Step 6. sodium[({(2S,5R)-7-oxo-2-[(pyrazolidin-4-yloxy)carbamoyl]-1,6-diazabicyclo[3.2.1]oct-6-yl}oxy)sulfonyl]oxidanide (Compound 104, Table 1)

Compound 104, Table 1

To a mixture of di-tert-butyl 4-[({[(2S,5R)-7-oxo-6-(sulfooxy)-1,6-diazabicyclo[3.2.1]oct-2-yl]carbonyl}amino)oxy]pyrazolidine-1,2-dicarboxylate 146 (0.33 g, 0.60 mmol) in DCM (5.0 mL) was added trifluoroacetic acid (0.60 mL) at 0° C. The mixture was stirred at 0° C. for 0.5 h and at room temperature for 5.5 h, concentrated and washed with ether. The white solid was collected by centrifugation. The crude product was purified by ion-exchange resin (Dowex50 Na⁺ form, water) to give Compound 104 (Table 1) (22.5 mg) as a white solid.

¹H NMR (400 MHz, D₂O): δ 1.60-1.82 (2H, m), 1.87-2.02 (2H, m), 2.92 (1H, d, J=11.6 Hz), 3.08-3.15 (3H, m), 3.25 (2H, d, J=13.6 Hz), 3.90 (1H, d, J=6.4 Hz), 4.01 (1H, m), 4.79 (1H, m). 4 protons were not observed in D₂O.

HPLC: 93.18%,

MS (ES⁻) m/z: [M−Na]⁻ calcd for $C_{10}H_{16}N_5O_7SNa$: 350.08. Found: 349.99.

Example 35

Sodium({[(2S,5R)-2-{[(1-methyl-4,5,6,7-tetrahydro-1H-4,7-methanoindazol-3-yl)methoxy]carbamoyl}-7-oxo-1,6-diazabicyclo[3.2.1]oct-6-yl]oxy}sulfonyl)oxidanide (Compound 131, Table, 1)

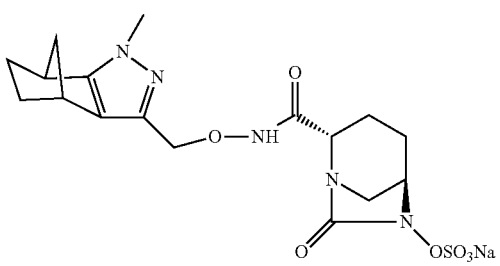

Step 1. 2-[(1-methyl-4,5,6,7-tetrahydro-1H-4,7-methanoindazol-3-yl)methoxy]-1H-isoindole-1,3(2H)-dione (148)

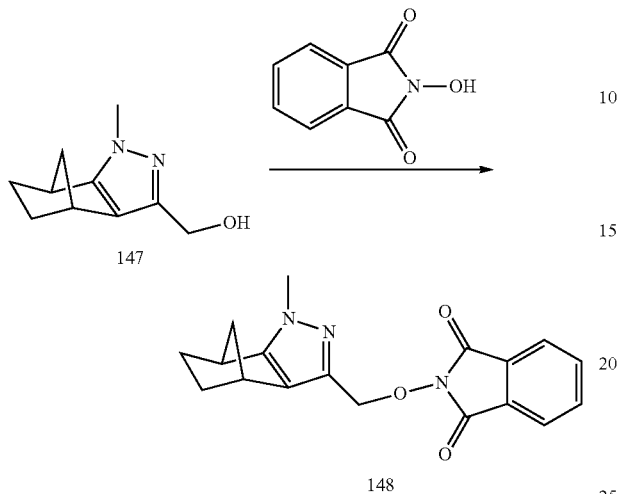

To a mixture of 2-hydroxy-1H-isoindole-1,3(2H)-dione (4.10 g, 25.2 mmol), (1-methyl-4,5,6,7-tetrahydro-1H-4,7-methanoindazol-3-yl)methanol 147 (2.24 g, 12.6 mmol) and triphenylphosphine (6.59 g, 25.2 mmol) in THF (100 mL) was added DIAD (5.35 mL, 27.6 mmol) slowly at room temperature. The resulting mixture was stirred at room temperature overnight and concentrated to provide a residue, which was subjected to chromatography to give 148 (1.80 g, 62%) as a yellow solid.

$^1$H NMR (400 MHz, CDCl$_3$): δ 1.10 (1H, m), 1.24 (1H, m), 1.61 (1H, d, J=10 Hz), 1.87 (3H, m), 3.33 (1H, s), 3.42 (1H, s), 3.71 (3H, s), 5.12 (2H, m), 7.17 (2H, m), 7.81 (2H, m).

MS (ES$^+$) m/z: [M+H]$^+$ calcd for C$_{18}$H$_{18}$N$_3$O$_3$: 324.13. Found: 324.08.

Step 2. 3-[(aminooxy)methyl]-1-methyl-4,5,6,7-tetrahydro-1H-4,7-methanoindazole (149)

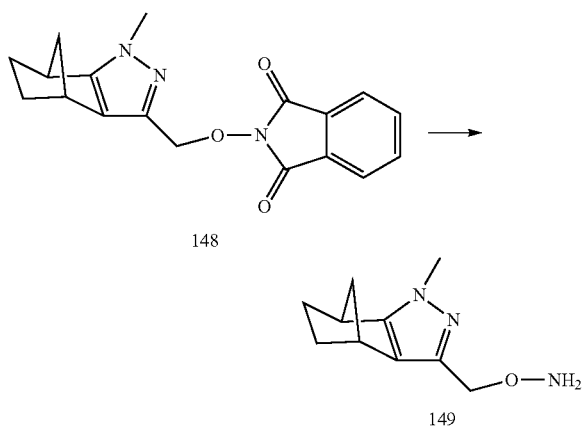

To a mixture of 2-[(1-methyl-4,5,6,7-tetrahydro-1H-4,7-methanoindazol-3-yl)methoxy]-1H-isoindole-1,3(2H)-dione 148 (1.80 g, 5.57 mmol) in a solution of DCM (20 mL) and ethanol (4 mL) was added hydrazine hydrate (0.32 mL, 5.57 mmol) at room temperature. The mixture was stirred at room temperature overnight, filtered and concentrated to provide a residue which was subjected to chromatography to give 149 (0.68 g, 64%) as a colorless oil.

$^1$H NMR (400 MHz, CDCl$_3$): δ 1.09 (1H, m), 1.26 (1H, d, J=6.0 Hz), 1.64 (1H, d, J=8.8 Hz), 1.88 (2H, m), 1.99 (1H, m), 3.35 (2H, d, J=8.4 Hz), 3.79 (3H, s), 4.65 (2H, ABq), 5.24 (2H, br s).

MS (ES$^+$) m/z: [M+H]$^+$ calcd for C$_{10}$H$_{16}$N$_3$O: 194.13. Found: 194.08.

Step 3. (2S,5R)-6-(benzyloxy)-N-[(1-methyl-4,5,6,7-tetrahydro-1H-4,7-methanoindazol-3-yl)methoxy]-7-oxo-1,6-diazabicyclo[3.2.1]octane-2-carboxamide (150)

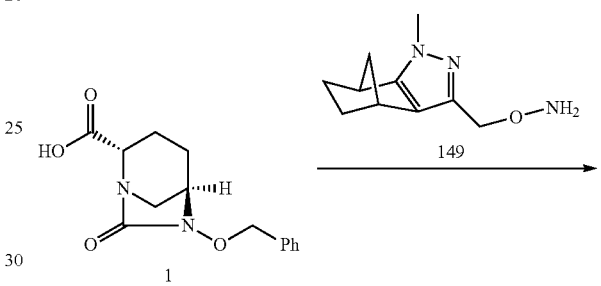

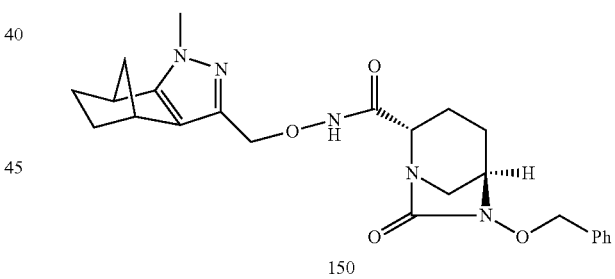

To a mixture of (2S,5R)-6-(benzyloxy)-7-oxo-1,6-diazabicyclo[3.2.1]octane-2-carboxylic acid 1 (0.250 g, 0.905 mmol) in DCM (10.0 mL) were added 3-[(aminooxy)methyl]-1-methyl-4,5,6,7-tetrahydro-1H-4,7-methanoindazole 149 (0.172 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 150 (0.34 g, 83%) as a white foam.

$^1$H NMR (400 MHz, CDCl$_3$): δ 1.08 (2H, m), 1.25 (1H, d, J=6.4 Hz), 1.63 (2H, m), 1.95 (5H, m), 2.38 (1H, m), 2.80 (1H, m), 2.92 (1H, m), 3.30 (1H, s), 3.36 (2H, s), 3.78 (3H, s), 3.94 (1H, d, J=7.6 Hz), 4.85 (3H, m), 5.03 (1H, d, J=11.2 Hz), 7.41 (5H, m), 9.10 (1H, s).

MS (ES⁺) m/z: [M+H]⁺ calcd for $C_{24}H_{29}N_5O_4$: 452.23. Found: 452.15.

Step 4. (2S,5R)-6-hydroxy-N-[(1-methyl-4,5,6,7-tetrahydro-1H-4,7-methanoindazol-3-yl)methoxy]-7-oxo-1,6-diazabicyclo[3.2.1]octane-2-carboxamide (151)

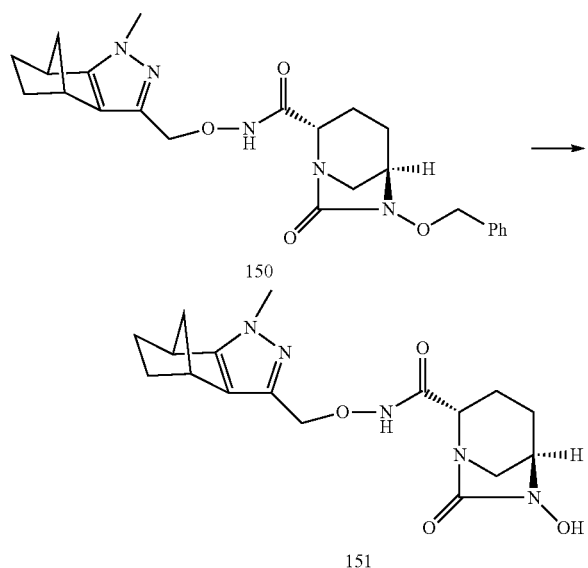

A mixture of (2S,5R)-6-(benzyloxy)-N-[(1-methyl-4,5,6,7-tetrahydro-1H-4,7-methanoindazol-3-yl)methoxy]-7-oxo-1,6-diazabicyclo[3.2.1]octane-2-carboxamide 150 (0.34 g, 0.75 mmol) and Pd/C (0.12 g) in methanol (15 mL) was hydrogenated at 1 atm at room temperature for 3 h. The mixture was filtered through Celite pad and concentrated to give 151 (0.27 g, quantitative yield) as a white foam.

¹H NMR (400 MHz, CD₃OD): δ 1.14 (2H, m), 1.23 (1H, d, J=6.4 Hz), 1.66 (1H, d, J=8.0 Hz), 1.85 (4H, m), 2.03 (1H, m), 2.21 (1H, m), 3.02 (2H, m), 3.42 (1H, s), 3.45 (1H, s), 3.68 (1H, s), 3.76 (3H, s), 3.80 (1H, d, J=7.2 Hz), 4.71 (2H, m). 2 protons were not observed in CD₃OD.

MS (ES⁺) m/z: [M+H]⁺ calcd for $C_{17}H_{24}N_5O_4$: 262.18. Found: 262.12.

Step 5. sodium({[(2S,5R)-2-{[(1-methyl-4,5,6,7-tetrahydro-1H-4,7-methanoindazol-3-yl)methoxy]carbamoyl}-7-oxo-1,6-diazabicyclo[3.2.1]oct-6-yl]oxy}sulfonyl)oxidanide (Compound 131, Table 1)

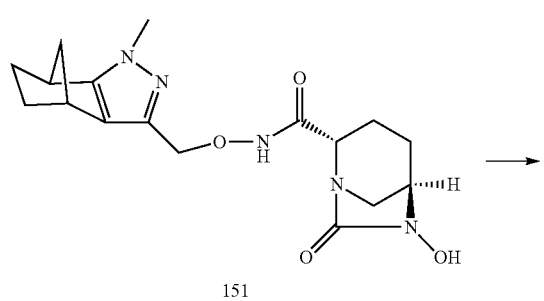

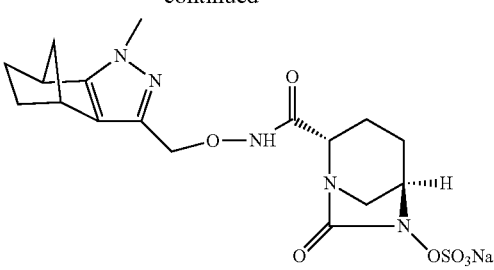

Compound 131, Table 1

To a mixture of (2S,5R)-6-hydroxy-N-[(1-methyl-4,5,6,7-tetrahydro-1H-4,7-methanoindazol-3-yl)methoxy]-7-oxo-1,6-diazabicyclo[3.2.1]octane-2-carboxamide 151 (0.27 g, 0.75 mmol) in pyridine (10.0 mL) was added sulfur trioxide pyridine complex (0.35 g, 2.24 mmol). The mixture was stirred at room temperature for 23 h and concentrated to provide a residue which was subjected to ion-exchange resin column (Dowex50 Na⁺ form, water) to give Compound 131 (Table 1) (177 mg, 51%) as a white solid.

¹H NMR (400 MHz, CD₃OD): δ 1.12 (2H, m), 1.67 (1H, d, J=8.8 Hz), 1.80 (1H, m), 1.91 (4H, m), 2.08 (1H, m), 2.20 (1H, m), 3.05 (1H, t, J=12.4 Hz), 3.17 (1H, m), 3.24 (1H, s), 3.45 (1H, s), 3.77 (3H, s), 3.87 (1H, d, J=5.6 Hz), 4.13 (1H, s), 4.78 (2H, m). One proton was not observed in D₂O.

HPLC: 91.05%,

MS (ES⁻) m/z: [M−Na]⁻ calcd for $C_{17}H_{22}N_5O_4SNa$: 440.12. Found: 440.00.

Example 36

(2S,5R)-N-[(1-methyl-1H-imidazol-5-yl)methoxy]-7-oxo-6-(sulfooxy)-1,6-diazabicyclo[3.2.1]octane-2-carboxamide (Compound 51, Table 1)

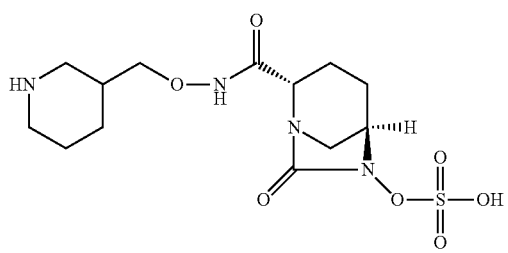 [SMILES: O=C(NOCC1CCCNC1)[C@@H]1CC[C@@H]2CN1C(=O)N2OS(=O)(=O)O]

235

Step 1. Step1: tert-butyl 3-{[({[(2S,5R)-6-(benzyloxy)-7-oxo-1,6-diazabicyclo[3.2.1]oct-2-yl]carbonyl}amino)oxy]methyl}piperidine-1-carboxylate (153)

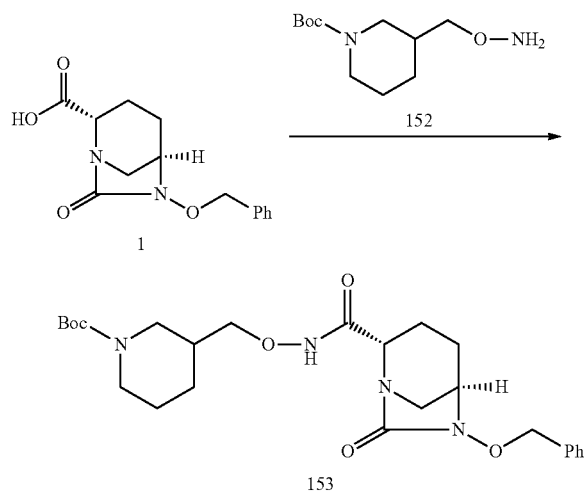

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added tert-butyl 3-[(aminooxy)methyl]piperidine-1-carboxylate 152 (0.312 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 153 (0.37 g, 84%) as a white foam.

$^1$H NMR (400 MHz, CDCl$_3$): δ 1.45 (9H, m), 1.53 (5H, m), 190 (3H, m), 2.31 (1H, m), 2.77 (3H, m), 2.97 (1H, m), 3.30 (1H, m), 3.70 (5H, m), 4.88 (1H, d, J=11.6 Hz), 5.06 (1H, d, J=11.6 Hz), 7.42 (5H, m). One proton was not observed in moisture containing CDCl$_3$.

MS (ES$^+$) m/z: [M+H]$^+$ calcd for C$_{25}$H$_{37}$N$_4$O$_8$: 489.2. Found: 489.2.

Step 2. Step2: tert-butyl 3-{[({[(2S,5R)-6-hydroxy-7-oxo-1,6-diazabicyclo[3.2.1]oct-2-yl]carbonyl}amino)oxy]methyl}piperidine-1-carboxylate (154)

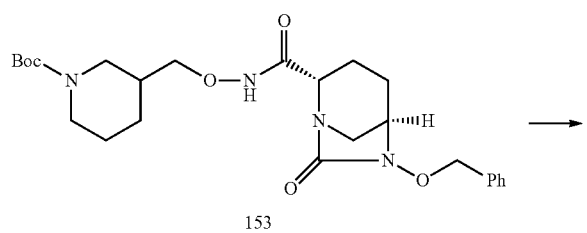

236

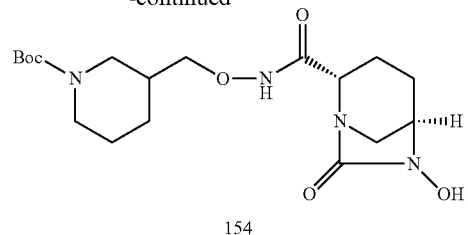

A mixture of tert-butyl 3-{[({[(2S,5R)-6-(benzyloxy)-7-oxo-1,6-diazabicyclo[3.2.1]oct-2-yl]carbonyl}amino)oxy]methyl}piperidine-1-carboxylate 153 (0.40 g, 0.82 mmol) and Pd/C (0.13 g) in methanol (20 mL) was hydrogenated at 1 atm at room temperature for 3 h. The mixture was filtered through Celite pad and concentrated to give 154 (0.33 g, quantitative yield) as a white foam.

$^1$H NMR (400 MHz, CD$_3$OD): δ 1.28 (1H, m), 1.45 (10H, m), 1.68 (1H, m), 1.80 (4H, m), 2.04 (1H, m), 2.20 (1H, m), 2.75 (1H, m), 2.84 (1H, m), 3.10 (2H, m), 3.74 (5H, s), 4.02 (1H, m). Two protons were not observed in CD$_3$OD.

MS (ES$^+$) m/z: [M+H]$^+$ calcd for C$_{18}$H$_{31}$N$_4$O$_6$: 399.2. Found: 399.1.

Step 3. Step 3. tert-butyl 3-{[({[(2S,5R)-7-oxo-6-(sulfooxy)-1,6-diazabicyclo[3.2.1]oct-2-yl]carbonyl}amino)oxy]methyl}piperidine-1-carboxylate (155)

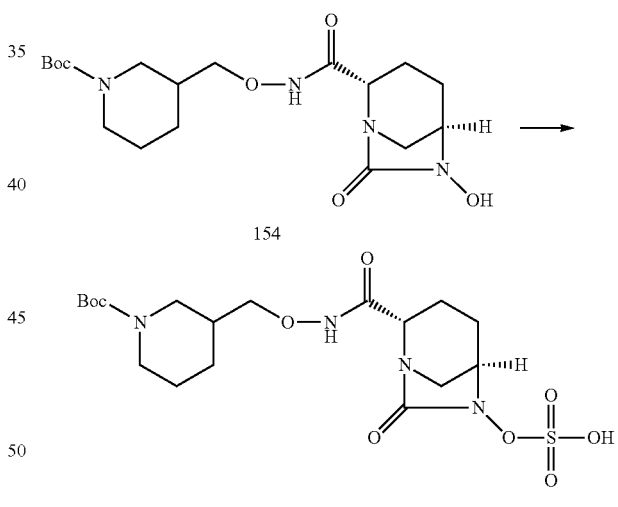

To a mixture of tert-butyl 3-{[({[(2S,5R)-6-hydroxy-7-oxo-1,6-diazabicyclo[3.2.1]oct-2-yl]carbonyl}amino)oxy]methyl}piperidine-1-carboxylate 154 (0.33 g, 0.83 mmol) in pyridine (4.0 mL) was added sulfur trioxide pyridine complex (0.38 g, 2.48 mmol). The mixture was stirred at room temperature for 23 h and concentrated to provide a residue which was subjected to chromatography to give 155 (0.33 g, 83%) as a white foam.

$^1$H NMR (400 MHz, CD$_3$OD): δ 1.30 (1H, m), 1.42 (10H, m), 1.67 (1H, m), 1.90 (4H, m), 2.08 (1H, m), 2.20 (1H, m), 2.70 (1H, m), 2 85 (1H, m), 3.10 (1H, d, J=12.0 Hz), 3.26 (1H, m), 3.74 (2H, m), 3.88 (2H, m), 4.15 (2H, m). Two protons were not observed in CD$_3$OD.

MS (ES⁻) m/z: [M−H]⁻ calcd for $C_{18}H_{29}N_4O_9S$: 477.2. Found: 477.1.

Step 4. Step 4 (2S,5R)-N-[(1-methyl-1H-imidazol-5-yl)methoxy]-7-oxo-6-(sulfooxy)-1,6-diazabicyclo[3.2.1]octane-2-carboxamide (Compound 51, Table 1).

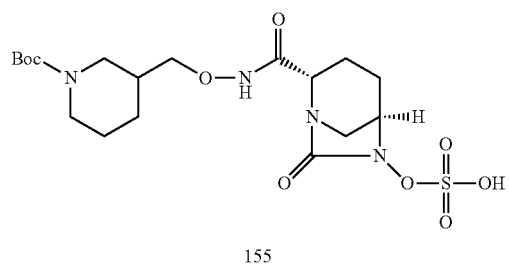

155

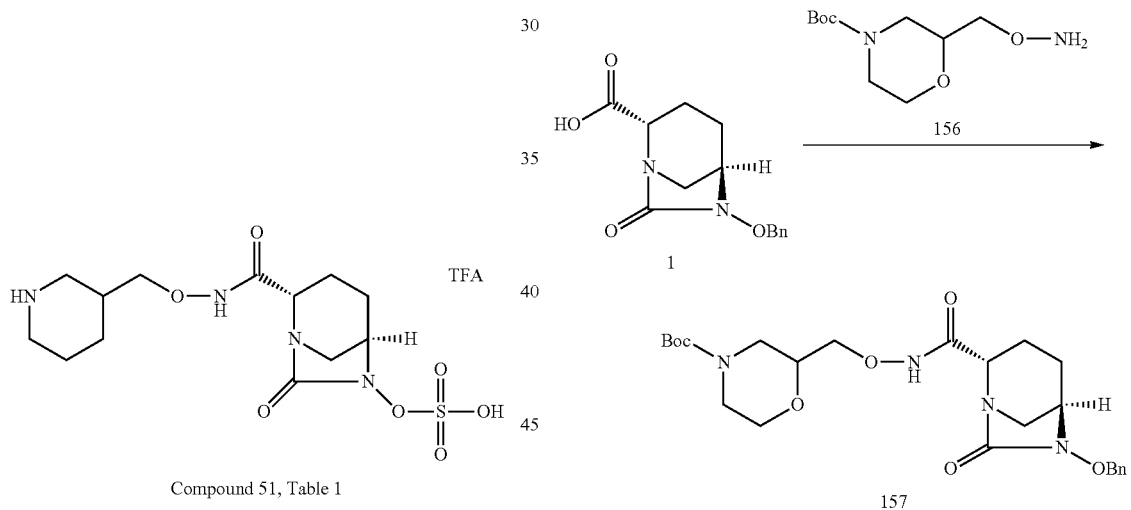

Compound 51, Table 1

To a mixture of tert-butyl 3-{[({[(2S,5R)-7-oxo-6-(sulfooxy)-1,6-diazabicyclo[3.2.1]oct-2-yl]carbonyl}amino)oxy]methyl}piperidine-1-carboxylate 155 (0.33 g, 0.69 mmol) in DCM (8.0 mL) was added trifluoroacetic acid (0.40 mL) at 0° C. The mixture was stirred at 0° C. for 3 h, concentrated and washed with ether, EtOAc and DCM to give TFA salt of Compound 51 (Table 1) (62 mg) as a white solid as a pair of diastereomers.

¹H NMR (400 MHz, D₂O): δ 1.21 (1H, m), 1.58-2.06 (8H, m), 2.72 (1H, t, J=12.0 Hz), 2.80 (1H, t, J=12.0 Hz), 2.98 (1H, d, J=11.2 Hz), 3.21 (2H, m), 3.40 (1H, d, J=11.6 Hz), 3.72 (1H, m), 3.79 (1H, m), 3.93 (1H, d, J=7.2 Hz), 4.08 (1H, s). Three protons were not observed in D₂O.

HPLC: 92.31%

MS (ES⁻) m/z: [M−H]⁻ calcd for $C_{13}H_{21}N_4O_7S$: 377.1. Found: 377.0.

Example 37

Sodium(2S,5R)-N-(morpholin-2-ylmethoxy)-7-oxo-6-(sulfooxy)-1,6-diazabicyclo[3.2.1]octane-2-carboxamide (Compound 152, Table 1)

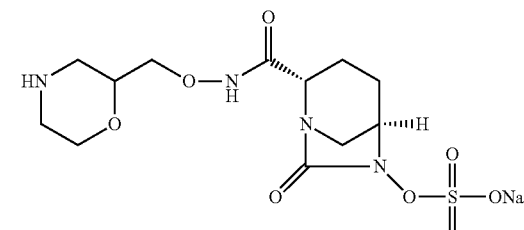

Step 1. tert-butyl 2-{[({[(2S,5R)-6-(benzyloxy)-7-oxo-1,6-diazabicyclo[3.2.1]oct-2-yl]carbonyl}amino)oxy]methyl}morpholine-4-carboxylate (157)

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added tert-butyl 2-[(aminooxy)methyl]morpholine-4-carboxylate 156 (0.317 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 157 (0.35 g, 79%) as a colorless oil.

¹H NMR (400 MHz, CDCl₃): δ 1.45 (9H, m), 1.60 (1H, m), 1.90 (2H, m), 2.30 (1H, m), 2.78 (2H, m), 3.00 (2H, m), 3.30 (1H, m), 3.56 (1H, m), 3.70 (1H, m), 3.87 (6H, m), 4.92 (1H, d, J=11.6 Hz), 5.06 (1H, d, J=11.6 Hz), 7.42 (5H, m), 9.36 (1H, s).

MS (ES⁻) m/z: [M−H]⁻ calcd for $C_{24}H_{33}N_4O_7$: 489.2. Found: 489.2.

Step 2. tert-butyl 2-{[({[(2S,5R)-6-hydroxy-7-oxo-1,6-diazabicyclo[3.2.1]oct-2-yl]carbonyl}amino)oxy]methyl}morpholine-4-carboxylate (158)

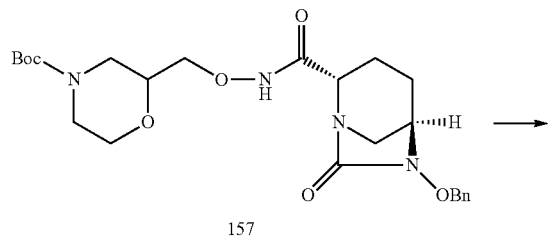

157

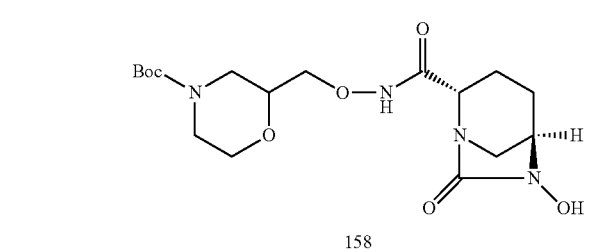

158

A mixture of tert-butyl 2-{[({[(2S,5R)-6-(benzyloxy)-7-oxo-1,6-diazabicyclo[3.2.1]oct-2-yl]carbonyl}amino)oxy]methyl}morpholine-4-carboxylate 157 (0.35 g, 0.71 mmol) and Pd/C (0.12 g) in methanol (20 mL) was hydrogenated at 1 atm at room temperature for 3 h. The mixture was filtered through Celite pad and concentrated to give 158 (0.29 g, quantitative yield) as a white foam.

¹H NMR (400 MHz, CD₃OD): δ 1.46 (9H, m), 1.79 (1H, m), 1.92 (1H, m), 2.04 (1H, m), 2.19 (1H, m), 2.80 (1H, m), 2.90 (1H, m), 3.08 (2H, m), 3.49 (1H, m), 3.68 (2H, m), 3.90 (6H, m). 2 protons were not observed in CD₃OD.

MS (ES⁺) m/z: [M+H]⁺ calcd for $C_{17}H_{29}N_4O_7$: 401.2. Found: 401.2.

Step 3. tert-butyl 2-{[({[(2S,5R)-7-oxo-6-(sulfooxy)-1,6-diazabicyclo[3.2.1]oct-2-yl]carbonyl}amino)oxy]methyl}morpholine-4-carboxylate (159)

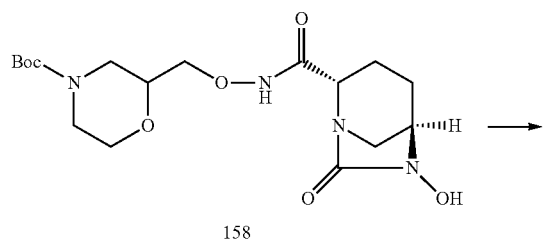

158

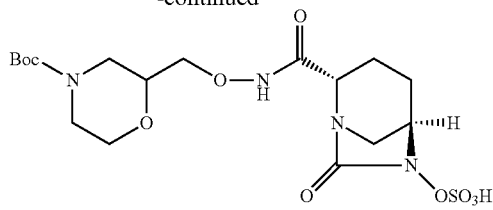

159

To a mixture of tert-butyl 2-{[({[(2S,5R)-6-hydroxy-7-oxo-1,6-diazabicyclo[3.2.1]oct-2-yl]carbonyl}amino)oxy]methyl}morpholine-4-carboxylate 158 (0.29 g, 0.72 mmol) in pyridine (5.0 mL) was added sulfur trioxide pyridine complex (0.34 g, 2.17 mmol). The mixture was stirred at room temperature for 23 h and concentrated to provide a residue which was subjected to chromatography to give 159 (0.29 g, 83%) as a white foam.

¹H NMR (400 MHz, CD₃OD): δ 1.46 (9H, s), 1.82 (1H, m), 1.90 (1H, m), 2.09 (1H, m), 2.22 (1H, m), 2.78 (1H, m), 2.90 (1H, m), 3.10 (1H, d, J=11.6 Hz), 3.22 (1H, m), 3.50 (1H, m), 3.68 (1H, m), 3.90 (6H, m), 4.14 (1H, m). Two protons were not observed in CD₃OD.

MS (ES⁻) m/z: [M−H]⁻ calcd for $C_{17}H_{27}N_4O_{10}S$: 479.2. Found: 479.1.

Step 4. Sodium(2S,5R)-N-(morpholin-2-ylmethoxy)-7-oxo-6-(sulfooxy)-1,6-diazabicyclo[3.2.1]octane-2-carboxamide (Compound 152, Table 1)

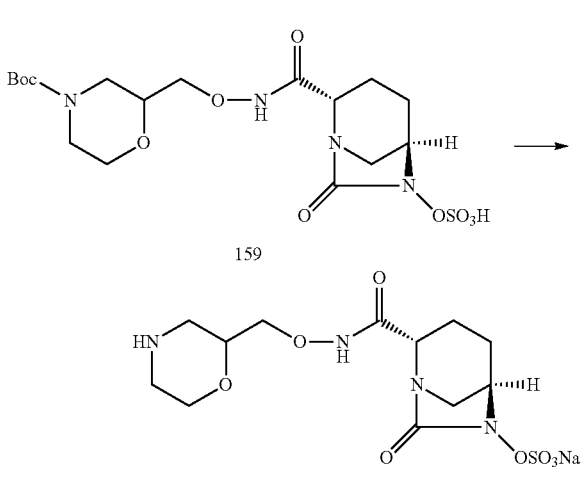

Compound 152, Table 1

To a mixture tert-butyl 2-{[({[(2S,5R)-7-oxo-6-(sulfooxy)-1,6-diazabicyclo[3.2.1]oct-2-yl]carbonyl}amino)oxy]methyl}morpholine-4-carboxylate 159 (0.29 g, 0.60 mmol) in DCM (8.0 mL) was added trifluoroacetic acid (0.40 mL) at 0° C. The mixture was stirred at 0° C. for 3 h, concentrated and washed with ether to give Compound 152 (Table 1) as a TFA salt, which was converted to sodium salt by treating with Dowex 50 to give the corresponding sodium salt (74 mg) as a white solid as a pair of diastereomers.

¹H NMR (400 MHz, D₂O): δ 1.60-2.10 (4H, m), 2.98-3.18 (3H, m), 3.20-3.35 (3H, m), 3.80 (1H, t, J=12.1 Hz), 3.90-4.18 (6H, m). Three protons were not observed in D₂O.

HPLC: 98.23%

MS (ES⁻) m/z: [M−Na]⁻ calcd for $C_{12}H_{19}N_4O_8SNa$: 379.1. Found: 379.0.

Example 38

(2S,5R)-7-oxo-N-(piperidin-2S-ylmethoxy)-6-(sulfooxy)-1,6-diazabicyclo[3.2.1]octane-2-carboxamide

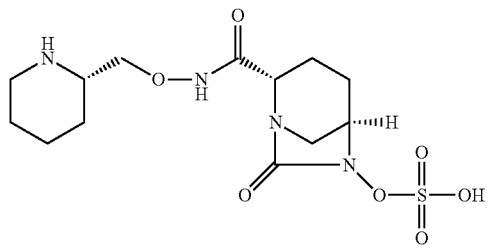 [SMILES: O=C(NOC[C@@H]1CCCCN1)[C@@H]1CC[C@@H]2CN1C(=O)N2OS(=O)(=O)O]

Step 1. tert-butyl 2S-{[({[(2S,5R)-6-(benzyloxy)-7-oxo-1,6-diazabicyclo[3.2.1]oct-2-yl]carbonyl}amino)oxy]methyl}piperidine-1-carboxylate (161)

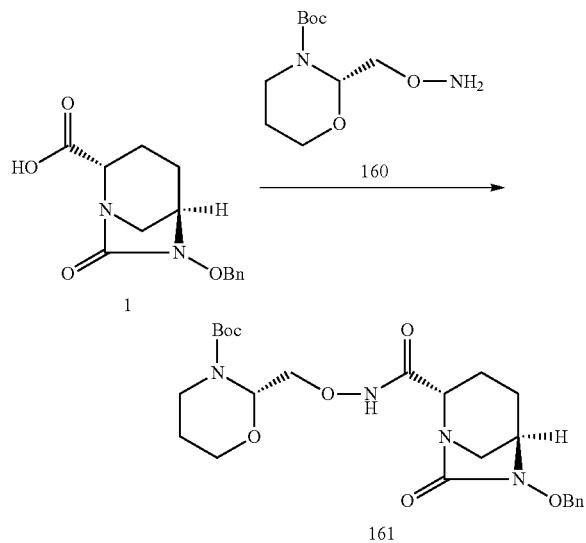

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added tert-butyl 2S-[(aminooxy)methyl]piperidine-1-carboxylate 160 (0.312 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 161 (0.35 g, 80%) as a white foam.

¹H NMR (400 MHz, CDCl₃): δ 1.41 (9H, m), 1.61 (6H, m), 1.97 (2H, m), 2.29 (1H, m), 2.78 (3H, m), 2.97 (1H, m), 3.26 (1H, m), 3.70 (1H, m), 3.99 (2H, m), 4.15 (1H, m), 4.51 (1H, m), 4.88 (1H, d, J=11.6 Hz), 5.06 (1H, m), 7.42 (5H, m). One proton was not observed in moisture containing CDCl₃.

MS (ES⁻) m/z: [M−H]⁻ calcd for $C_{25}H_{35}N_4O_8$: 487.2. Found: 487.1.

Step 2. tert-butyl 2S-{[({[(2S,5R)-6-hydroxy-7-oxo-1,6-diazabicyclo[3.2.1]oct-2-yl]carbonyl}amino)oxy]methyl}piperidine-1-carboxylate (162)

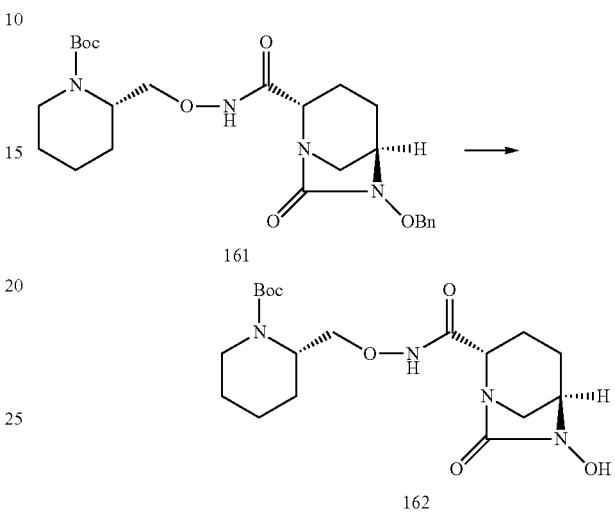

A mixture of tert-butyl 2S-{[({[(2S,5R)-6-(benzyloxy)-7-oxo-1,6-diazabicyclo[3.2.1]oct-2-yl]carbonyl}amino)oxy]methyl}piperidine-1-carboxylate 161 (0.40 g, 0.82 mmol) and Pd/C (0.13 g) in methanol (20 mL) was hydrogenated at 1 atm at room temperature for 3 h. The mixture was filtered through Celite pad and concentrated to give 162 (0.27 g, quantitative yield) as a white foam.

¹H NMR (400 MHz, CD₃OD): δ 1.45 (9H, s), 1.60 (5H, m), 1.80 (2H, m), 1.93 (1H, m), 2.04 (1H, m), 2.21 (1H, m), 2.84 (1H, m), 2.99 (1H, m), 3.31 (1H, m), 3.68 (1H, s), 3.89 (1H, s), 4.02 (3H, m), 4.47 (1H, m). Two protons were not observed in CD₃OD.

MS (ES⁺) m/z: [M+H]⁺ calcd for $C_{18}H_{31}N_4O_6$: 399.2. Found: 399.1.

Step 3. tert-butyl 2S-{[({[(2S,5R)-7-oxo-6-(sulfooxy)-1,6-diazabicyclo[3.2.1]oct-2-yl]carbonyl}amino)oxy]methyl}piperidine-1-carboxylate (163)

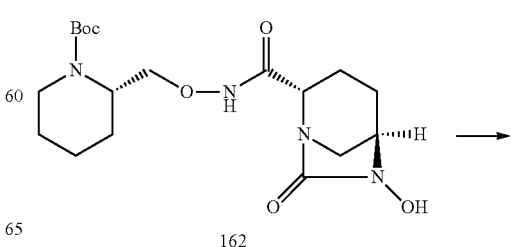

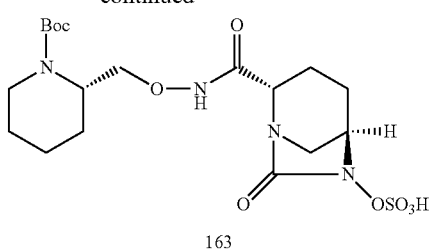

163

To a mixture of tert-butyl 2S-{[({[(2S,5R)-6-hydroxy-7-oxo-1,6-diazabicyclo[3.2.1]oct-2-yl]carbonyl}amino)oxy]methyl}piperidine-1-carboxylate 162 (0.33 g, 0.83 mmol) in pyridine (4.0 mL) was added sulfur trioxide pyridine complex (0.38 g, 2.48 mmol). The mixture was stirred at room temperature for 23 h and concentrated to provide a residue which was subjected to chromatography to give 163 (0.24 g, 69%) as a white foam.

$^1$H NMR (400 MHz, CD$_3$OD): δ 1.45 (10H, m), 1.63 (4H, m), 1.84 (2H, m), 1.92 (1H, m), 2.06 (1H, m), 2.21 (1H, m), 2 87 (1H, m), 3.09 (1H, m), 3.24 (2H, m), 3.91 (2H, m), 4.03 (1H, m), 4.11 (1H, m), 4.46 (1H, m). Two protons were not observed in CD$_3$OD.

Step 4. (2S,5R)-7-oxo-N-(piperidin-2S-ylmethoxy)-6-(sulfooxy)-1,6-diazabicyclo[3.2.1]octane-2-carboxamide (164)

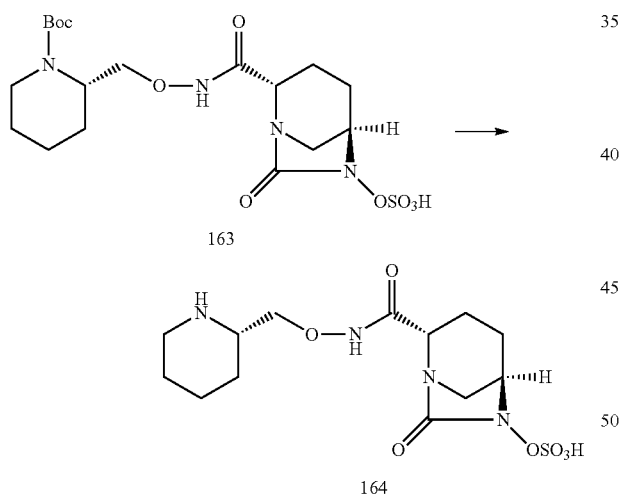

To a mixture of tert-butyl 2-{[({[(2S,5R)-7-oxo-6-(sulfooxy)-1,6-diazabicyclo[3.2.1]oct-2-yl]carbonyl}amino)oxy]methyl}piperidine-1-carboxylate 163 (0.27 g, 0.58 mmol) in DCM (8.0 mL) was added trifluoroacetic acid (0.40 mL) at 0° C. The mixture was stirred at 0° C. for 3 h, concentrated and washed with ether, EtOAc and DCM to give 164 (53 mg) as a white foam.

$^1$H NMR (400 MHz, D$_2$O): δ 1.20 (2H, m), 1.36 (1H, m), 1.60 (5H, m), 1.77 (2H, m), 1.90 (1H, m), 2.65 (1H, m), 2.82 (1H, m), 3.00 (1H, m), 3.15 (2H, m), 3.70 (1H, m), 3.80 (2H, m), 3.90 (1H, s). Three protons were not observed in D$_2$O.

HPLC: 95.22%
MS (ES$^-$) m/z: [M–H]$^-$ calcd for C$_{13}$H$_{21}$N$_4$O$_7$S: 377.1. Found: 377.0.

Example 39

(2S,5R)-7-oxo-N-(piperidin-2R-ylmethoxy)-6-(sulfooxy)-1,6-diazabicyclo[3.2.1]octane-2-carboxamide

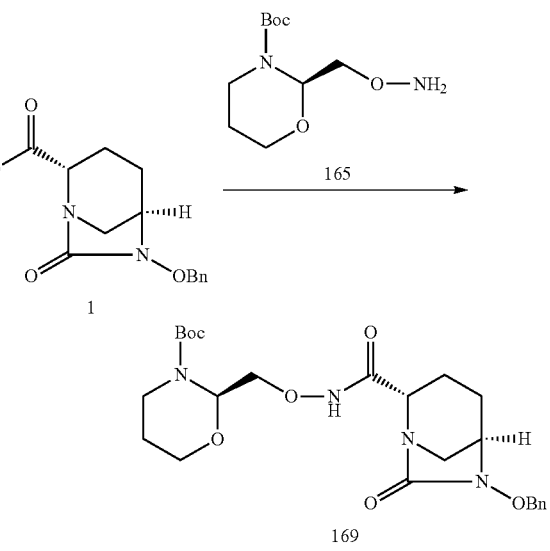

Step 1. tert-butyl 2S-{[({[(2S,5R)-6-(benzyloxy)-7-oxo-1,6-diazabicyclo[3.2.1]oct-2-yl]carbonyl}amino)oxy]methyl}piperidine-1-carboxylate (166)

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added tert-butyl 2S-[(aminooxy)methyl]piperidine-1-carboxylate 165 (0.312 g, 1.358 mmol), 1-hydroxybenzotriazole (0.183 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 169 (0.35 g, 80%) as a white foam.

$^1$H NMR (400 MHz, CDCl$_3$): δ 1.41 (9H, m), 1.61 (6H, m), 1.97 (2H, m), 2.29 (1H, m), 2.78 (3H, m), 2.97 (1H, m), 3.26 (1H, m), 3.70 (1H, m), 3.99 (2H, m), 4.15 (1H, m), 4.51 (1H, m), 4.88 (1H, d, J=11.6 Hz), 5.06 (1H, m), 7.42 (5H, m). One proton was not observed in moisture containing CDCl$_3$.

MS (ES⁻) m/z: [M−H]⁻ calcd for C₂₅H₃₅N₄O₈: 487.2. Found: 487.1.

Step 2. tert-butyl 2S-{[({[(2S,5R)-6-hydroxy-7-oxo-1,6-diazabicyclo[3.2.1]oct-2-yl]carbonyl}amino)oxy]methyl}piperidine-1-carboxylate (170)

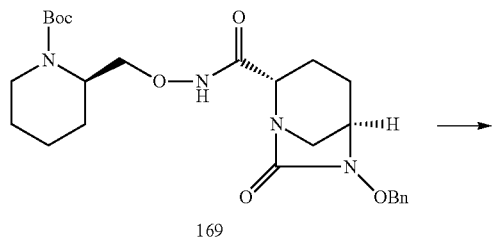

169

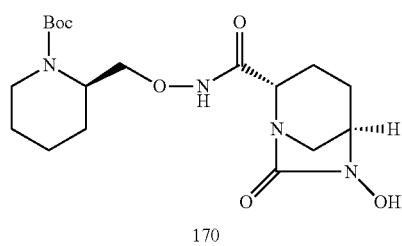

170

A mixture of tert-butyl 2S-{[({[(2S,5R)-6-(benzyloxy)-7-oxo-1,6-diazabicyclo[3.2.1]oct-2-yl]carbonyl}amino)oxy]methyl}piperidine-1-carboxylate 169 (0.40 g, 0.82 mmol) and Pd/C (0.13 g) in methanol (20 mL) was hydrogenated at 1 atm at room temperature for 3 h. The mixture was filtered through Celite pad and concentrated to give 170 (0.27 g, quantitative yield) as a white foam.

¹H NMR (400 MHz, CD₃OD): δ 1.45 (9H, s), 1.60 (5H, m), 1.80 (2H, m), 1.93 (1H, m), 2.04 (1H, m), 2.21 (1H, m), 2.84 (1H, m), 2.99 (1H, m), 3.31 (1H, m), 3.68 (1H, s), 3.89 (1H, s), 4.02 (3H, m), 4.47 (1H, m). Two protons were not observed in CD₃OD.

MS (ES⁺) m/z: [M+H]⁺ calcd for C₁₈H₃₁N₄O₆: 399.2. Found: 399.1.

Step 3. tert-butyl 2S-{[({[(2S,5R)-7-oxo-6-(sulfooxy)-1,6-diazabicyclo[3.2.1]oct-2-yl]carbonyl}amino)oxy]methyl}piperidine-1-carboxylate (171)

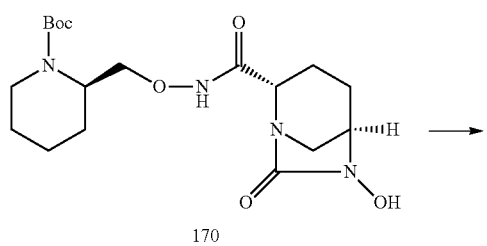

170

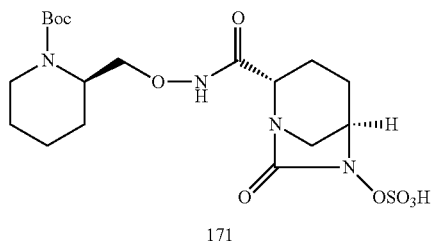

171

To a mixture of tert-butyl 2S-{[({[(2S,5R)-6-hydroxy-7-oxo-1,6-diazabicyclo[3.2.1]oct-2-yl]carbonyl}amino)oxy]methyl}piperidine-1-carboxylate 170 (0.33 g, 0.83 mmol) in pyridine (4.0 mL) was added sulfur trioxide pyridine complex (0.38 g, 2.48 mmol). The mixture was stirred at room temperature for 23 h and concentrated to provide a residue which was subjected to chromatography to give 171 (0.24 g, 69%) as a white foam.

¹H NMR (400 MHz, CD₃OD): δ 1.45 (10H, m), 1.63 (4H, m), 1.84 (2H, m), 1.92 (1H, m), 2.06 (1H, m), 2.21 (1H, m), 2 87 (1H, m), 3.09 (1H, m), 3.24 (2H, m), 3.91 (2H, m), 4.03 (1H, m), 4.11 (1H, m), 4.46 (1H, m). Two protons were not observed in CD₃OD.

Step 4. (2S,5R)-7-oxo-N-(piperidin-2R-ylmethoxy)-6-(sulfooxy)-1,6-diazabicyclo[3.2.1]octane-2-carboxamide (172)

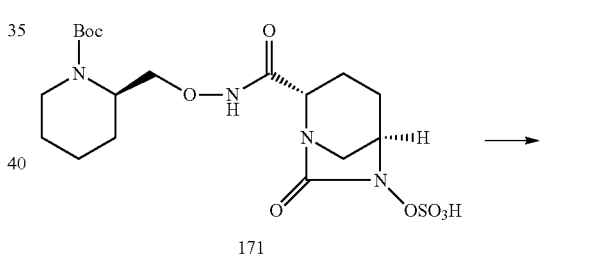

171

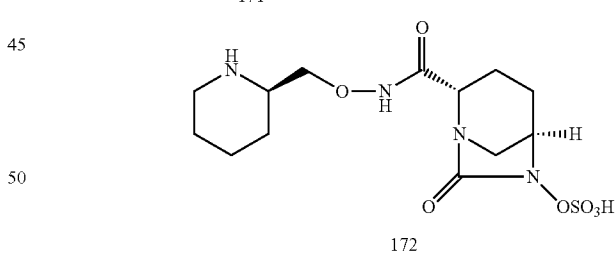

172

To a mixture of tert-butyl 2-{[({[(2S,5R)-7-oxo-6-(sulfooxy)-1,6-diazabicyclo[3.2.1]oct-2-yl]carbonyl}amino)oxy]methyl}piperidine-1-carboxylate 171 (0.27 g, 0.58 mmol) in DCM (8.0 mL) was added trifluoroacetic acid (0.40 mL) at 0° C. The mixture was stirred at 0° C. for 3 h, concentrated and washed with ether, EtOAc and DCM to give 172 (53 mg) as a white solid.

¹H NMR (400 MHz, D₂O): δ 1.38 (2H, m), 1.54 (1H, m), 1.75 (5H, m), 2.01 (2H, m), 2.85 (1H, m), 3.00 (1H, m), 3.21 (1H, m), 3.36 (2H, m), 3.91 (3H, m), 4.08 (1H, s). Three protons were not observed in D₂O.

HPLC: 95.22%

MS (ES⁻) m/z: [M−H]⁻ calcd for $C_{13}H_{21}N_4O_7S$: 377.1. Found: 377.0.

Example 40

(2S,5R)-N'-acetyl-7-oxo-6-(sulfooxy)-1,6-diazabicyclo[3.2.1]octane-2-carbohydrazide (Compound 16, Table 2)

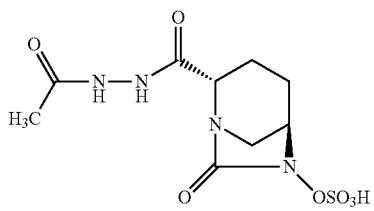

Step 1. (2S,5R)-N'-Acetyl-6-(benzyloxy)-7-oxo-1,6-diazabicyclo[3.2.1]octane-2-carbohydrazide (174)

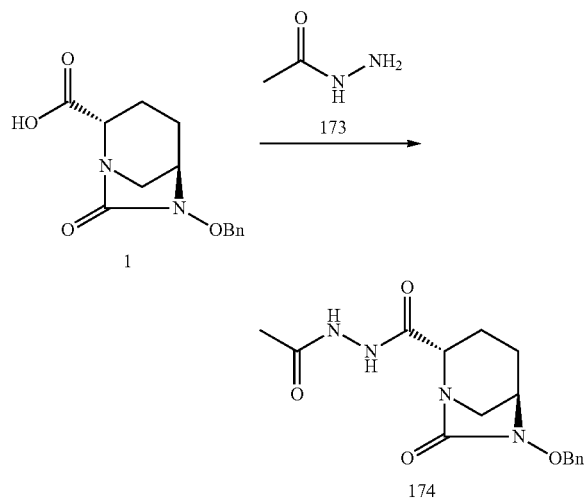

To a mixture of (2S,5R)-6-(benzyloxy)-7-oxo-1,6-diazabicyclo[3.2.1]octane-2-carboxylic acid 1 (0.200 g, 0.720 mmol, US2005/20572 A1) in DCM (6.0 mL) were added acetohydrazide 173 (0.090 g, 1.085 mmol), 1-hydroxybenzotriazole (0.147 g, 1.085 mmol), 1-ethyl-(3-dimethylamino propyl) carbodiimide hydrochloride (0.208 g, 1.085 mmol) and N,N-dimethylaminopyridine sequentially at room temperature. The mixture was stirred at room temperature overnight, diluted with DCM and concentrated to provide a residue, which was subjected to chromatography to give 174 (0.14 g, 60%) as a white foam.

¹H NMR (400 MHz, CDCl₃): δ 1.60 (1H, m), 1.96 (2H, m), 2.06 (3H, s), 2.34 (1H, m), 3.09 (1H, m), 3.15 (1H, d, J=12 Hz), 3.32 (1H, m), 4.01 (1H, d, J=8.4 Hz), 4.90 (1H, d, J=11.2 Hz), 5.07 (1H, d, J=11.2 Hz), 7.26-7.44 (5H, m), 7.74 (1H, br s), 8.54 (1H, br s).

MS (ES⁺): m/z [M+H]⁺ calcd for $C_{16}H_{21}N_4O_4$: 333.16. Found: 333.21.

Step 2. (2S,5R)-N'-Acetyl-6-hydroxy-7-oxo-1,6-diazabicyclo[3.2.1]octane-2-carbohydrazide (175)

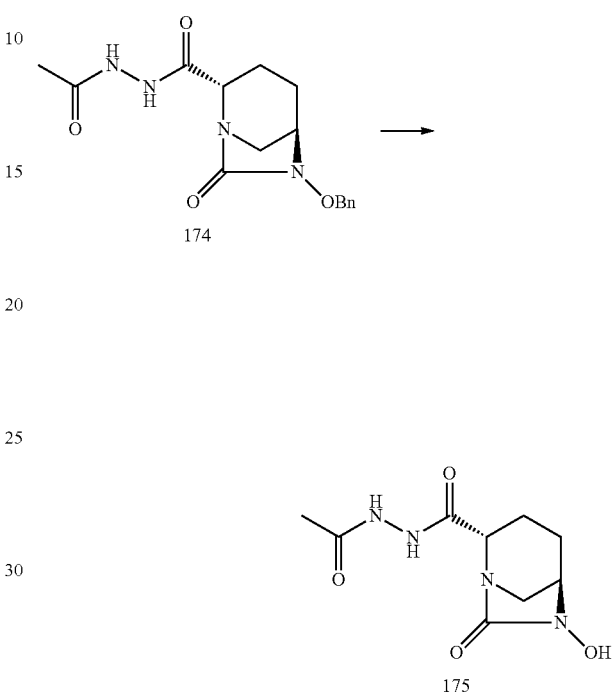

A mixture of (2S,5R)-N'-acetyl-6-(benzyloxy)-7-oxo-1,6-diazabicyclo[3.2.1]octane-2-carbohydrazide 174 (0.14 g, 0.43 mmol) and Pd/C (0.070 g) in methanol (10 mL) was hydrogenated at 1 atm at room temperature for 3 h. The mixture was filtered through Celite pad and concentrated to provide 175 (0.10 g, 95%) as a white foam.

¹H NMR (400 MHz, CD₃OD): δ 1.71-1.78 (1H, m), 1.88-1.93 (1H, m), 2.04 (3H, s), 2.06-2.09 (1H, m), 2.24-2.29 (1H, m), 3.13 (1H, m), 3.22 (1H, d, J=12 Hz), 3.69 (1H, m), 3.93 (1H, d, J=8.4 Hz). 3 protons were not observed in CD₃OD.

MS (ES⁺): m/z [M+H]⁺ calcd for $C_9H_{15}N_4O_4$: 243.11. Found: 243.18.

Step 3. (2S,5R)-N'-Acetyl-7-oxo-6-(sulfooxy)-1,6-diazabicyclo[3.2.1]octane-2-carbohydrazide (Compound 16, Table 2)

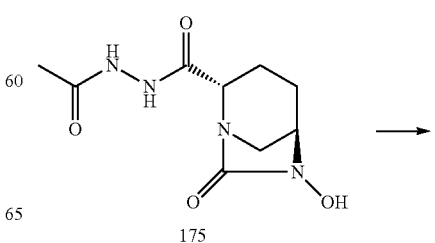

249
-continued

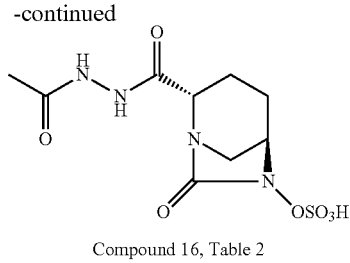

Compound 16, Table 2

To a mixture of (2S,5R)-N'-acetyl-6-hydroxy-7-oxo-1,6-diazabicyclo[3.2.1]octane-2-carbohydrazide 175 (0.10 g, 0.41 mmol) in pyridine (5.0 mL) was added sulfur trioxide pyridine complex (0.19 g, 1.24 mmol). The mixture was stirred at room temperature for 23 h and concentrated to provide a residue which was subjected to chromatography to give Compound 16 (Table 2) (0.040 g, 30%) as a light yellow solid.

$^1$H NMR (400 MHz, D$_2$O): δ 1.64-1.69 (1H, m), 1.76-1.81 (1H, m), 1.88-1.98 (4H, m), 2.03-2.09 (1H, m), 3.03 (1H, d, J=12.0 Hz), 3.20 (1H, m), 4.00 (1H, m), 4.05 (1H, m). 3 protons were not observed in D$_2$O.

HPLC: 89.2%

MS (ES$^-$): m/z [M−H]$^-$ calcd for C$_9$H$_{13}$N$_4$O$_7$S: 321.05. Found: 321.05.

The corresponding sodium salt of compound 16 (Table 2) was prepared in the following manner:

To a mixture of (2S,5R)-N-acetyl-6-hydroxy-7-oxo-1,6-diazabicyclo[3.2.1]octane-2-carbohydrazide 175 (0.20 g, 0.78 mmol) in pyridine (10.0 mL) was added sulfur trioxide pyridine complex (0.37 g, 2.35 mmol). The mixture was stirred at room temperature for 24 h and concentrated to provide a residue which was subjected to purification by ion-exchange resin (Dowex50 Na$^+$ form, water) and reverse phase column to give sodium salt of Compound 16 (Table 2) (42 mg) as a white solid.

$^1$H NMR (400 MHz, D$_2$O): δ 1.64-1.69 (1H, m), 1.76-1.81 (1H, m), 1.88-1.98 (4H, m), 2.03-2.09 (1H, m), 3.03 (1H, d, J=12.0 Hz), 3.20 (1H, m), 4.00 (1H, m), 4.05 (1H, m). 3 protons were not observed in D$_2$O.

HPLC: 96.5%

MS (ES$^-$) m/z: [M−Na]$^-$ calcd for C$_9$H$_{13}$N$_4$O$_7$SNa: 321.05. Found: 321.05.

Example 41

(2S,5R)-N'-methyl-7-oxo-6-(sulfooxy)-1,6-diazabicyclo[3.2.1]octane-2-carbohydrazide (Compound 1, Table 2)

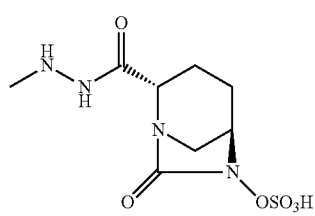

250

Step 1. tert-butyl 2-{[(2S,5R)-6-(benzyloxy)-7-oxo-1,6-diazabicyclo[3.2.1]oct-2-yl]carbonyl}-1-methyl-hydrazinecarboxylate (177)

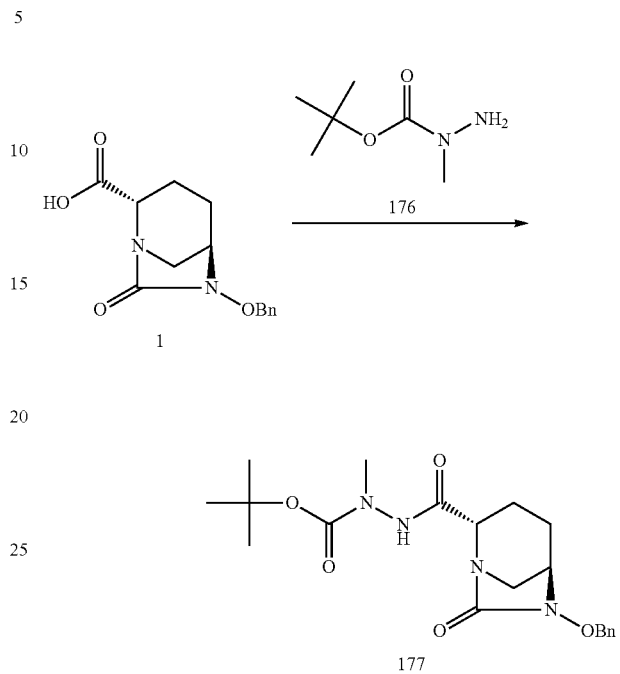

To a solution of (2S,5R)-6-(benzyloxy)-7-oxo-1,6-diazabicyclo[3.2.1]octane-2-carboxylic acid 1 (0.2 g, 0.72 mmol) in dry DCM (10 mL) were added tert-butyl 1-methylhydrazinecarboxylate 176 (0.16 g, 1.08 mmol), 1-hydroxybenzotriazole (0.15 g, 1.08 mmol), 1-ethyl-(3-dimethylaminopropyl)carbodiimide hydrochloride (0.21 g, 1.08 mmol) and 4-dimethylaminopyridine (0.13 g, 1.08 mmol) at room temperature. The reaction mixture was stirred at room temperature overnight, and then concentrated under vacuum. The residue was purified by column chromatography to give tert-butyl 2-{[(2S,5R)-6-(benzyloxy)-7-oxo-1,6-diazabicyclo[3.2.1]oct-2-yl]carbonyl}-1-methylhydrazinecarboxylate 177 (0.25 g, 86%) as a clear thick oil.

$^1$H NMR (400 MHz, CDCl$_3$): δ 1.46 (9H, s), 1.58 (1H, m), 1.97 (2H, m), 2.37 (1H, m), 3.04-3.16 (5H, m), 3.29 (1H, m), 3.96 (1H, d, J=6.8 Hz), 4.90 (1H, d, J=11.2 Hz), 5.05 (1H, d, J=11.6 Hz), 7.38 (5H, m), 8.32 (1H, br s).

Step 4. tert-butyl 2-{[(2S,5R)-6-hydroxy-7-oxo-1,6-diazabicyclo[3.2.1]oct-2-yl]carbonyl}-1-methylhydrazinecarboxylate (178)

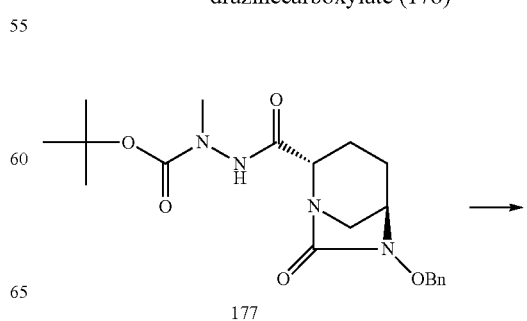

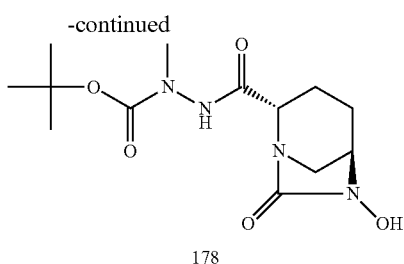

178

To a solution of tert-butyl 2-{[(2S,5R)-6-(benzyloxy)-7-oxo-1,6-diazabicyclo[3.2.1]oct-2-yl]carbonyl}-1-methylhydrazinecarboxylate 177 (0.29 g, 0.72 mml) in methanol (15 mL) was added 5% Pd/C (0.3 g). The mixture was hydrogenated under 10 psi hydrogen atmosphere at room temperature for 1 h. The catalyst was filtered out through Celite, and the filtrate was evaporated to give tert-butyl 2-{[(2S,5R)-6-hydroxy-7-oxo-1,6-diazabicyclo[3.2.1]oct-2-yl]carbonyl}-1-methylhydrazinecarboxylate 178 (0.22 g, 98%) as a colorless foam.

$^1$H NMR (400 MHz, CD$_3$OD): δ 1.46 (9H, s), 1.74 (1H, m), 1.92 (1H, m), 2.07 (1H, m), 2.26 (1H, m), 3.01-3.22 (5H, m), 3.71 (1H, m), 3.88 (1H, m), 2 protons were not observed in CD$_3$OD.

Step 5. tert-butyl 1-methyl-2-{[(2S,5R)-7-oxo-6-(sulfooxy)-1,6-diazabicyclo[3.2.1]oct-2-yl]carbonyl}hydrazinecarboxylate pyridine salt (179)

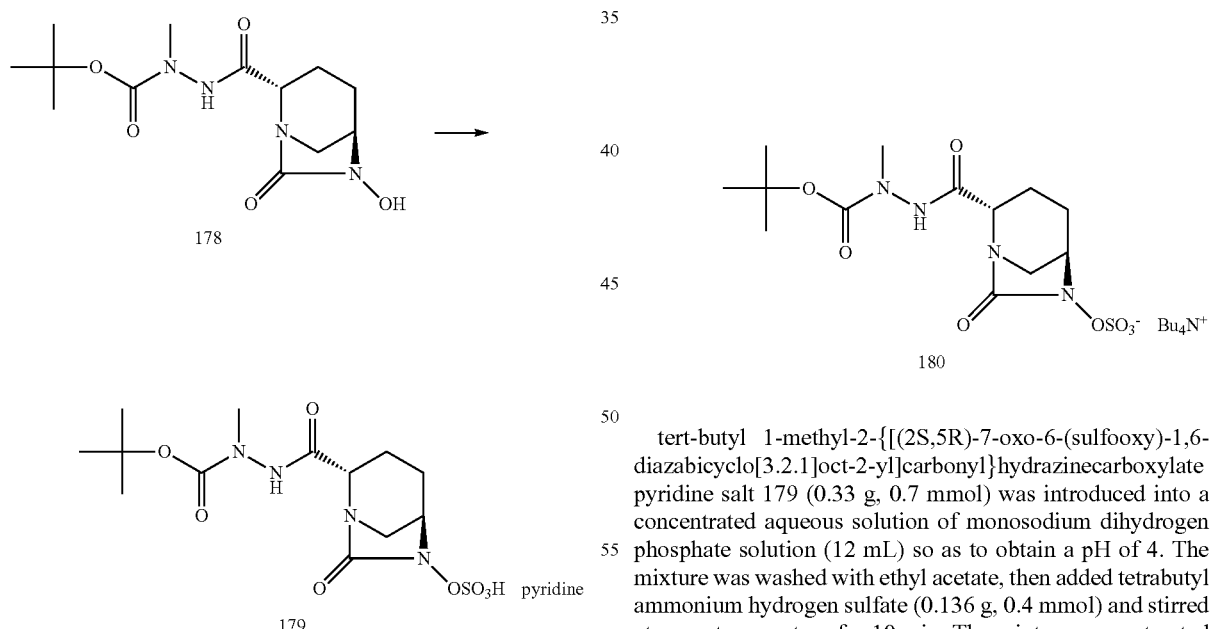

To a solution of tert-butyl 2-{[(2S,5R)-6-hydroxy-7-oxo-1,6-diazabicyclo[3.2.1]oct-2-yl]carbonyl}-1-methylhydrazinecarboxylate 178 (0.22 g, 0.7 mmol) in dry pyridine (10 mL) under nitrogen atmosphere was added sulfur trioxide pyridine complex (0.56 g, 3.5 mmol). The mixture was stirred at room temperature for 20 h, filtered and evaporated to give tert-butyl 1-methyl-2-{[(2S,5R)-7-oxo-6-(sulfooxy)-1,6-diazabicyclo[3.2.1]oct-2-yl]carbonyl}hydrazinecarboxylate pyridine salt 179 (0.33 g crude) which was used in the next step without purification.

Step 6. N,N,N-tributylbutan-1-aminium({[(2S,5R)-2-{[2-(tert-butoxycarbonyl)-2-methylhydrazinyl]carbonyl}-7-oxo-1,6-diazabicyclo[3.2.1]oct-6-yl]oxy}sulfonyl)oxidanide (180)

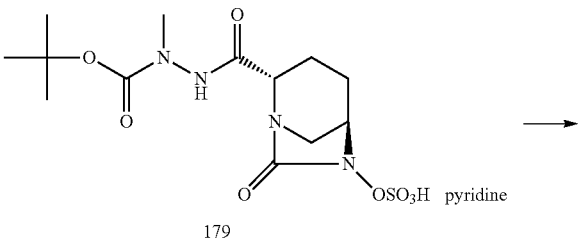

179

180 tert-butyl 1-methyl-2-{[(2S,5R)-7-oxo-6-(sulfooxy)-1,6-diazabicyclo[3.2.1]oct-2-yl]carbonyl}hydrazinecarboxylate pyridine salt 179 (0.33 g, 0.7 mmol) was introduced into a concentrated aqueous solution of monosodium dihydrogen phosphate solution (12 mL) so as to obtain a pH of 4. The mixture was washed with ethyl acetate, then added tetrabutyl ammonium hydrogen sulfate (0.136 g, 0.4 mmol) and stirred at room temperature for 10 min. The mixture was extracted with ethyl acetate (3×20 mL), and the extracts were combined, dried over sodium sulfate and evaporated to give N,N,N-tributylbutan-1-aminium({[(2S,5R)-2-{[2-(tert-butoxycarbonyl)-2-methylhydrazinyl]carbonyl}-7-oxo-1,6-diazabicyclo[3.2.1]oct-6-yl]oxy}sulfonyl)oxidanide 180 (0.31 g, 70%) as a white solid.

$^1$H NMR (400 MHz, CDCl$_3$): δ 1.00 (12H, t, J=7.2 Hz), 1.18 (3H, m), 1.46 (12H, m), 1.66 (12H, m), 1.94 (2H, m), 2.15 (1H, m), 2.38 (1H, m), 2.84 (1H, d, J=11.2 Hz), 3.29 (8H, m), 3.87 (1H, m), 3.93 (1H, d, J=8.0 Hz), 4.35 (1H, s), 8.98 (1H, br s).

Step 7. (2S,5R)-N'-methyl-7-oxo-6-(sulfooxy)-1,6-diazabicyclo[3.2.1]octane-2-carbohydrazide (Compound 1, Table 2)

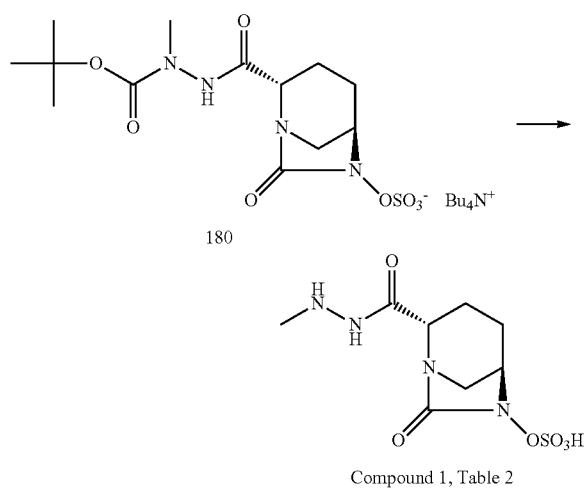

Compound 1, Table 2

To a solution of N,N,N-tributylbutan-1-aminium({[(2S,5R)-2-{[2-(tert-butoxycarbonyl)-2-methylhydrazinyl]carbonyl}-7-oxo-1,6-diazabicyclo[3.2.1]oct-6-yl]oxy}sulfonyl)oxidanide 180 (0.31 g, 0.49 mmol) in DCM (20 mL) was added trifluoroacetic acid (1.2 mL, 15.55 mmol) dropwise at 0° C. The reaction mixture was stirred for 2 h, then evaporated. Ether was added to the residue and the resulting white precipitate was collected by centrifugation. The solid was triturated with acetonitrile (2×) and the white solid was collected by centrifugation. The white solid was purified by HPLC and freeze-dried to give (2S,5R)-N-methyl-7-oxo-6-(sulfooxy)-1,6-diazabicyclo[3.2.1]octane-2-carbohydrazide Compound 1 (Table 2) (0.01 g, 6.9%) as a white solid.

$^1$H NMR (400 MHz, CD$_3$OD): δ 1.77 (2H, m), 1.95 (1H, m), 2.05 (1H, m), 2.97 (5H, m), 3.16 (1H, d, J=12.0 Hz), 3.26 (4H, m), 3.89 (1H, d, J=7.6 Hz), 4.06 (1H, m), 3 protons were not observed in CD$_3$OD.

MS (ES$^-$): m/z [M−H]$^-$=293.04

Example 42

(2R,5S)-7-oxo-N'-(phenylcarbonyl)-6-(sulfooxy)-1,6-diazabicyclo[3.2.1]octane-2-carbohydrazide (Compound 64, Table 2)

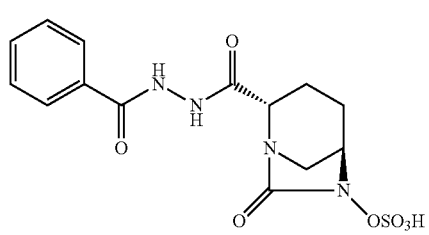

Step 1. (2R,5R)-6-(benzyloxy)-7-oxo-N'-(phenylcarbonyl)-1,6-diazabicyclo[3.2.1]octane-2-carbohydrazide (182)

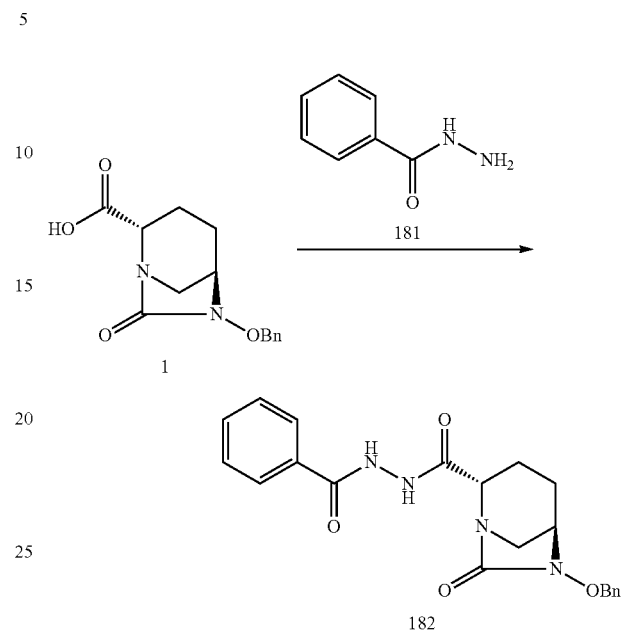

To solution of (2S,5R)-6-(benzyloxy)-7-oxo-1,6-diazabicyclo[3.2.1]octane-2-carboxylic acid 1 (0.25 g, 0.90 mmol) in dry DCM (20 mL) were added benzohydrazide 181 (0.118 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight, and then concentrated under vacuum. The residue was purified by column chromatography to give (2R,5R)-6-(benzyloxy)-7-oxo-N'-(phenylcarbonyl)-1,6-diazabicyclo[3.2.1]octane-2-carbohydrazide 182 (0.35 g, 98%) as a white solid.

$^1$H NMR (400 MHz, CDCl$_3$): δ 1.58-1.74 (1H, m), 2.02 (2H, m), 2.36 (1H, m), 3.11 (1H, d, J=12.0 Hz), 3.22 (1H, d, J=12.0 Hz), 3.32 (1H, s), 4.05 (1H, d, J=7.2 Hz), 4.90 (1H, d, J=11.2 Hz), 5.04 (1H, d, J=11.6 Hz), 7.41 (7H, m), 7.51 (1H, m), 7.79 (2H, d, J=8.4 Hz), 8.74 (1H, br s), 8.79 (1H, br s).

Step 2. (2R,5R)-6-hydroxy-7-oxo-N'-(phenylcarbonyl)-1,6-diazabicyclo[3.2.1]octane-2-carbohydrazide (183)

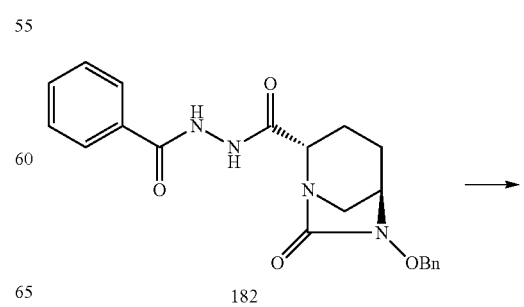

-continued

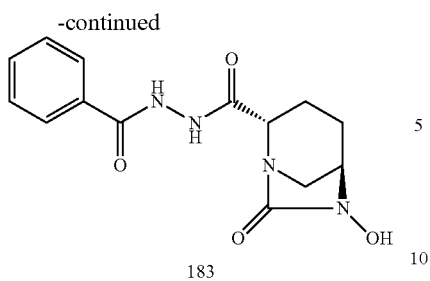

To a solution of (2R,5R)-6-(benzyloxy)-7-oxo-N'-(phenylcarbonyl)-1,6-diazabicyclo[3.2.1]octane-2-carbohydrazide 182 (0.33 g, 0.88 mml) in methanol (20 mL) was added 5% Pd/C (0.40 g). The mixture was hydrogenated under 10 psi hydrogen atmosphere at room temperature for 1 h. The catalyst was filtered out through Celite, and the filtrate was evaporated to give (2R,5R)-6-hydroxy-7-oxo-N'-(phenylcarbonyl)-1,6-diazabicyclo[3.2.1]octane-2-carbohydrazide 183 (0.19 g, 89%) as a colorless foam.

$^1$H NMR (400 MHz, CD$_3$OD): δ 1.80 (1H, m), 1.98 (1H, m), 2.07 (1H, m), 2.33 (1H, m), 3.20 (1H, d, J=11.6 Hz), 3.35 (1H, m), 3.74 (1H, s), 4.02 (1H, d, J=7.6 Hz), 7.47 (2H, m), 7.57 (1H, m), 7.86 (2H, m), 3 protons were not observed in CD$_3$OD.

Step 3. (2R,5S)-7-oxo-N'-(phenylcarbonyl)-6-(sulfooxy)-1,6-diazabicyclo[3.2.1]octane-2-carbohydrazide (Compound 64, Table 2)

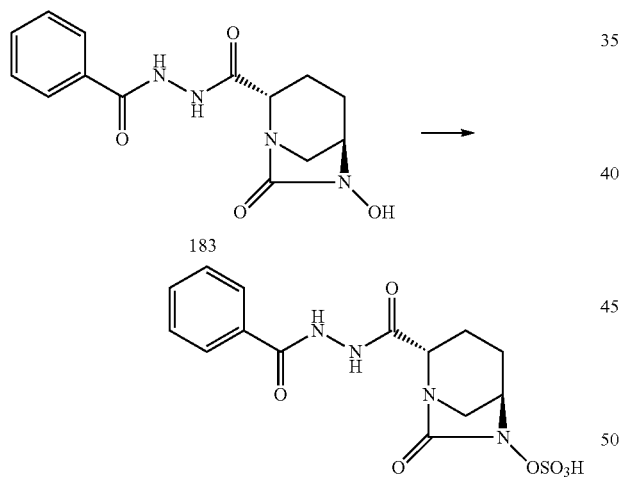

Compound 64, Table 2

To a solution of (2R,5R)-6-hydroxy-7-oxo-N'-(phenylcarbonyl)-1,6-diazabicyclo[3.2.1]octane-2-carbohydrazide 183 (0.197 g, 0.69 mmol) in dry pyridine (7 mL) under nitrogen atmosphere was added sulfur trioxide pyridine complex (0.44 g, 2.76 mmol). The mixture was stirred at room temperature for 20 h, filtered and evaporated. The residue was purified by column chromatography followed by HPLC on a prep-X Bridge-30×100 mm column and freeze-dried to give (2R,5S)-7-oxo-N'-(phenylcarbonyl)-6-(sulfooxy)-1,6-diazabicyclo[3.2.1]octane-2-carbohydrazide Compound 64 (Table 2) (0.05 g, 16.7%) as a white solid.

$^1$H NMR (400 MHz, CD$_3$OD): δ 1.83 (1H, m), 1.99 (1H, m), 2.10 (1H, m), 2.33 (1H, m), 3.29-3.39 (2H, m), 4.09 (1H, d, J=7.2 Hz), 4.19 (1H, s), 7.49 (2H, m), 7.56 (1H, m), 7.89 (2H, m), 3 protons were not observed in CD$_3$OD.

HPLC: 98.2%

MS (ES$^-$) m/z: [M]$^-$=383

Example 43

(2R,5S)-7-oxo-6-(sulfooxy)-N'-(trifluoroacetyl)-1,6-diazabicyclo[3.2.1]octane-2-carbohydrazide (Compound 89, Table 2)

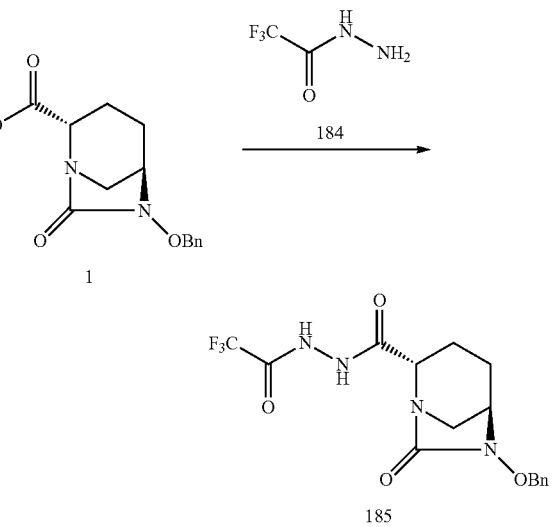

Step 1. (2R,5R)-6-(benzyloxy)-7-oxo-N'-(trifluoroacetyl)-1,6-diazabicyclo[3.2.1]octane-2-carbohydrazide (185)

To solution of (2S,5R)-6-(benzyloxy)-7-oxo-1,6-diazabicyclo[3.2.1]octane-2-carboxylic acid 1 (0.25 g, 0.90 mmol) in dry DCM (20 mL) were added 2,2,2-trifluoroacetohydrazide 184 (0.17 g, 1.35 mmol, Aldrich), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight and concentrated under vacuum. The residue was purified by column chromatography to give (2R,5R)-6-(benzyloxy)-7-oxo-N'-(trifluoroacetyl)-1,6-diazabicyclo[3.2.1]octane-2-carbohydrazide 185 (0.224 g, 65%) as a white solid.

$^1$H NMR (400 MHz, CDCl$_3$): δ 1.62 (1H, m), 2.01 (2H, m), 2.33 (1H, m), 2.99 (1H, d, J=12.0 Hz), 3.07 (1H, d, J=12.0

Hz), 3.34 (1H, s), 4.03 (1H, d, J=7.2 Hz), 4.90 (1H, d, J=11.2 Hz), 5.04 (1H, d, J=11.6 Hz), 7.39 (5H, m), 8.59 (1H, br s), 8.68 (1H, br s).

Step 2. (2R,5R)-6-hydroxy-7-oxo-N'-(trifluoroacetyl)-1,6-diazabicyclo[3.2.1]octane-2-carbohydrazide (186)

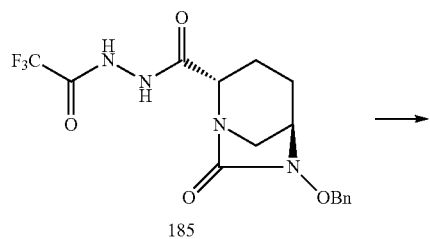
185

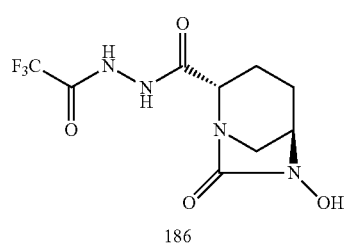
186

To a solution of (2R,5R)-6-(benzyloxy)-7-oxo-N'-(trifluoroacetyl)-1,6-diazabicyclo[3.2.1]octane-2-carbohydrazide 185 (0.224 g, 0.58 mml) in methanol (20 mL) was added 5% Pd/C (0.30 g). The mixture was hydrogenated under 10 psi hydrogen atmosphere at room temperature for 1 h. The catalyst was filtered out through Celite and the filtrate was evaporated to give (2R,5R)-6-hydroxy-7-oxo-N'-(trifluoroacetyl)-1,6-diazabicyclo[3.2.1]octane-2-carbohydrazide 186 (0.15 g, 88%) as a colorless foam.

$^1$H NMR (400 MHz, CD$_3$OD): δ 1.77 (1H, m), 1.95 (1H, m), 2.06 (1H, m), 2.30 (1H, m), 3.17 (1H, m), 3.33 (1H, m), 3.73 (1H, s), 3.97 (1H, d, J=7.2 Hz), 3 protons were not observed in CD$_3$OD.

Step 3. (2R,5S)-7-oxo-6-(sulfooxy)-N'-(trifluoroacetyl)-1,6-diazabicyclo[3.2.1]octane-2-carbohydrazide (Compound 89, Table 2)

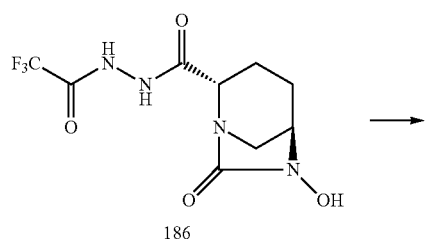
186

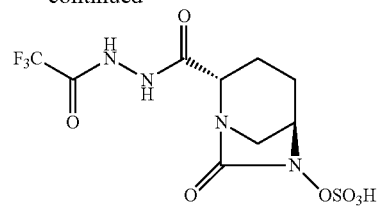
Compound 89, Table 2

To a solution of (2R,5R)-6-hydroxy-7-oxo-N'-(trifluoroacetyl)-1,6-diazabicyclo[3.2.1]octane-2-carbohydrazide 186 (0.15 g, 0.51 mmol) in dry pyridine (9 mL) under nitrogen atmosphere was added sulfur trioxide pyridine complex (0.38 g, 2.37 mmol). The mixture was stirred at room temperature for 20 h, filtered and evaporated. The residue was purified by column chromatography followed by HPLC on a prep-X Bridge-30×100 mm column and freeze-dried to give (2R,5S)-7-oxo-6-(sulfooxy)-N'-(trifluoroacetyl)-1,6-diazabicyclo [3.2.1]octane-2-carbohydrazide Compound 89 (Table 2) (0.02 g, 10.5%) as a white solid.

$^1$H NMR (400 MHz, CD$_3$OD): δ 1.81 (1H, m), 1.96 (1H, m), 2.06 (1H, m), 2.32 (1H, m), 3.05 (1H, d, J=11.6 Hz), 3.31 (1H, m), 4.01 (1H, d, J=8.0 Hz), 4.16 (1H, s), 3 protons were not observed in CD$_3$OD.

HPLC: 92.6%

MS (ES$^-$) m/z: [M]$^-$=375

Example 44

(2R,5S)-N'-(methylsulfonyl)-7-oxo-6-(sulfooxy)-1,6-diazabicyclo[3.2.1]octane-2-carbohydrazide (Compound 90, Table 2)

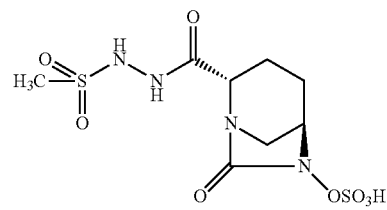

Step 1. (2R,5R)-6-(benzyloxy)-N'-(methylsulfonyl)-7-oxo-1,6-diazabicyclo[3.2.1]octane-2-carbohydrazide (188)

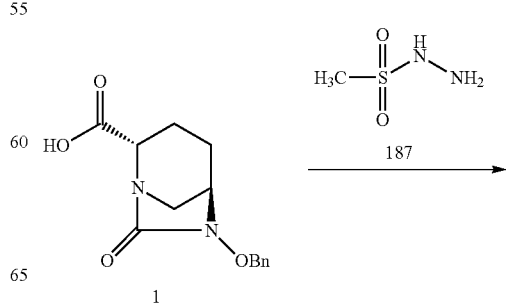
1        187

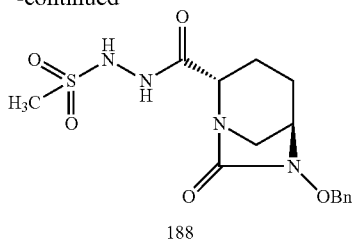

188

To solution of (2S,5R)-6-(benzyloxy)-7-oxo-1,6-diazabicyclo[3.2.1]octane-2-carboxylic acid 1 (0.67 g, 2.42 mmol) in dry DCM (60 mL) were added methanesulfonohydrazide 187 (0.40 g, 3.63 mmol), 1-hydroxybenzotriazole (0.44 g, 3.63 mmol), 1-ethyl-(3-dimethylaminopropyl)carbodiimide hydrochloride (0.72 g, 3.63 mmol) and 4-(dimethylamino)pyridine (0.44 g, 3.63 mmol) at room temperature. The reaction mixture was stirred at room temperature overnight and concentrated under vacuum. The residue was purified by column chromatography to give (2R,5R)-6-(benzyloxy)-N'-(methylsulfonyl)-7-oxo-1,6-diazabicyclo[3.2.1]octane-2-carbohydrazide 188 (0.37 g, 42%) as a white solid.

$^1$H NMR (400 MHz, CDCl$_3$): δ 1.67 (1H, m), 2.02 (2H, m), 2.26 (1H, m), 2.79 (1H, d, J=11.6 Hz), 3.02 (3H, s), 3.09 (1H, d, J=12.8 Hz), 3.32 (1H, s), 4.12 (1H, d, J=6.8 Hz), 4.89 (1H, d, J=11.2 Hz), 5.03 (1H, d, J=11.2 Hz), 7.16 (1H, br s), 7.39 (5H, m), 9.08 (1H, br s).

Step 2. (2R,5R)-6-hydroxy-N'-(methylsulfonyl)-7-oxo-1,6-diazabicyclo[3.2.1]octane-2-carbohydrazide (189)

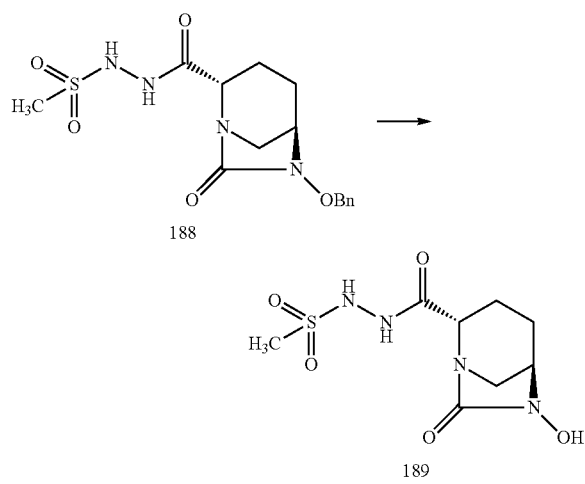

189

To a solution of (2R,5R)-6-(benzyloxy)-N'-(methylsulfonyl)-7-oxo-1,6-diazabicyclo[3.2.1]octane-2-carbohydrazide 188 (0.37 g, 1.044 mml) in methanol (35 mL) was added 5% Pd/C (0.40 g). The mixture was hydrogenated under 10 psi hydrogen atmosphere at room temperature for 1 h. The catalyst was filtered through Celite and the filtrate was evaporated to give (2R,5R)-6-hydroxy-N'-(methylsulfonyl)-7-oxo-1,6-diazabicyclo[3.2.1]octane-2-carbohydrazide 189 (0.276 g, 99%) as a colorless foam.

$^1$H NMR (400 MHz, CD$_3$OD): δ 1.78 (1H, m), 1.95 (1H, m), 2.06 (1H, m), 2.24 (1H, m), 3.01 (3H, s), 3.03 (1H, d, J=12.0 Hz), 3.14 (1H, d, J=11.6 Hz), 3.69 (1H, s), 3.91 (1H, d, J=7.6 Hz), 3 protons were not observed in CD$_3$OD.

Step 3. (2R,5S)-N'-(methylsulfonyl)-7-oxo-6-(sulfooxy)-1,6-diazabicyclo[3.2.1]octane-2-carbohydrazide (Compound 90, Table 2)

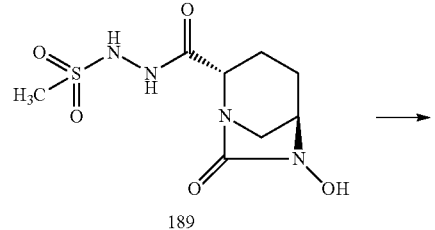

189

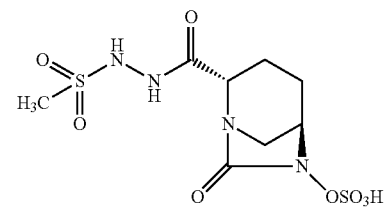

Compound 90, Table 2

To a solution of (2R,5R)-6-hydroxy-N'-(methylsulfonyl)-7-oxo-1,6-diazabicyclo[3.2.1]octane-2-carbohydrazide 189 (0.276 g, 0.99 mmol) in dry pyridine (18 mL) under nitrogen atmosphere was added sulfur trioxide pyridine complex (0.70 g, 4.37 mmol). The mixture was stirred at room temperature for 20 h, filtered and evaporated. The residue was purified by column chromatography followed by trituration with a mixture of MeOH:DCM:Ether (1:1:1) (4×) to give (2R,5S)-N'-(methylsulfonyl)-7-oxo-6-(sulfooxy)-1,6-diazabicyclo[3.2.1]octane-2-carbohydrazide Compound 90 (Table 2) (0.12 g, 34%) as a white solid.

$^1$H NMR (400 MHz, CD$_3$OD): δ 1.81 (1H, m), 1.96 (1H, m), 2.06 (1H, m), 2.32 (1H, m), 3.05 (1H, d, J=11.6 Hz), 3.31 (1H, m), 4.01 (1H, d, J=8.0 Hz), 4.16 (1H, s), 3 protons were not observed in CD$_3$OD.

HPLC: 91.8%

MS (ES$^-$) m/z: [M]$^-$=357

Example 45

(2S,5R)-N'-(cyclopentylcarbonyl)-7-oxo-6-(sulfooxy)-1,6-diazabicyclo[3.2.1]octane-2-carbohydrazide (Compound 38, Table 2)

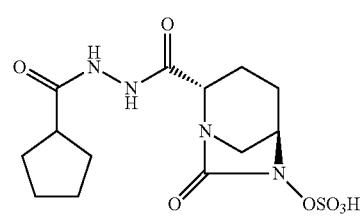

261

Step 1. (2S,5R)-6-(benzyloxy)-N'-(cyclopentylcarbonyl)-7-oxo-1,6-diazabicyclo[3.2.1]octane-2-carbohydrazide (191)

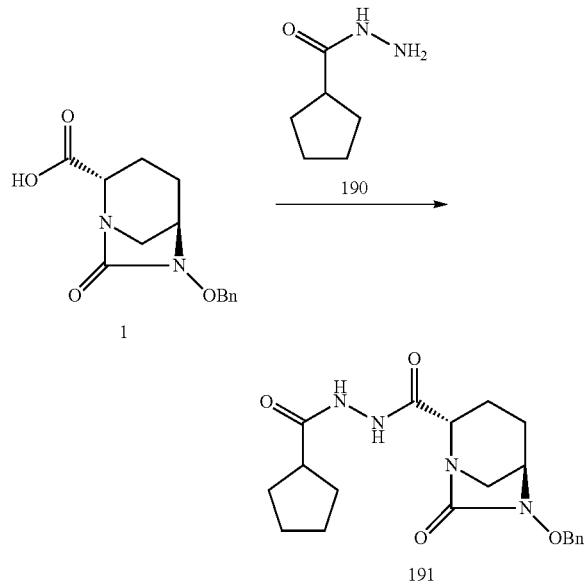

To a solution of (2S,5R)-6-(benzyloxy)-7-oxo-1,6-diazabicyclo[3.2.1]octane-2-carboxylic acid 1 (0.25 g, 0.90 mmol) in dry DCM (20 mL) were added cyclopentanecarboxyhydrazide 190 (0.173 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight, and then concentrated under vacuum. The residue was purified to give (2S,5R)-6-(benzyloxy)-N'-(cyclopentylcarbonyl)-7-oxo-1,6-diazabicyclo[3.2.1]octane-2-carbohydrazide 191 (0.33 g, 94%) as a white solid.

$^1$H NMR (400 MHz, CDCl$_3$): δ 1.50-2.00 (11H, m), 2.23-2.38 (1H, m), 2.60-2.70 (1H, m), 3.05 (1H, d, J=12.0 Hz), 3.20 (1H, d, J=12.0 Hz), 3.30 (1H, s), 3.98 (1H, m), 4.90 (1H, d, J=11.2 Hz), 5.04 (1H, d, J=11.6 Hz), 7.30-7.48 (5H, m), 7.85 (1H, br s), 8.60 (1H, br s).

MS (ES$^+$) m/z: [M]$^+$=387

Step 2. (2S,5R)-N'-(cyclopentylcarbonyl)-6-hydroxy-7-oxo-1,6-diazabicyclo[3.2.1]octane-2-carbohydrazide (192)

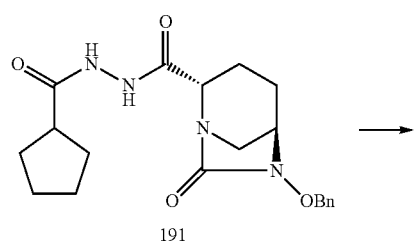

262

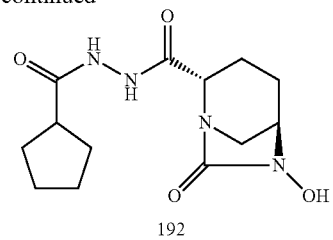

To a solution of (2S,5R)-6-(benzyloxy)-N'-(cyclopentylcarbonyl)-7-oxo-1,6-diazabicyclo[3.2.1]octane-2-carbohydrazide 191 (0.33 g, 0.84 ml) in methanol (20 mL) was added 10% Pd/C (0.30 g). The mixture was hydrogenated under 15 psi hydrogen atmosphere at room temperature for 1 h. The catalyst was filtered through Celite, and the filtrate was evaporated to give (2S,5R)-N'-(cyclopentylcarbonyl)-6-hydroxy-7-oxo-1,6-diazabicyclo[3.2.1]octane-2-carbohydrazide 192 (0.24 g, 98%) as a colorless foam.

$^1$H NMR (400 MHz, CD$_3$OD): δ 1.50-2.12 (10H, m), 2.21-2.33 (1H, m), 2.63-2.80 (1H, m), 3.10-3.38 (3H, m), 3.70 (1H, s), 3.98 (1H, d, J=7.6 Hz), 3 protons were not observed in CD$_3$OD.

Step 3. (2S,5R)-N'-(cyclopentylcarbonyl)-7-oxo-6-(sulfooxy)-1,6-diazabicyclo[3.2.1]octane-2-carbohydrazide (Compound 38, Table 2)

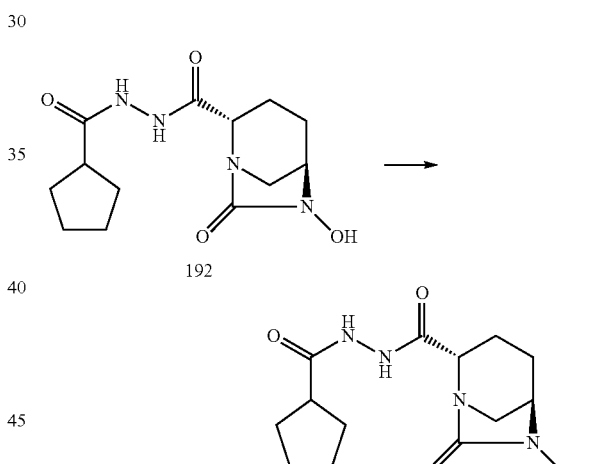

Compound 38, Table 2

To a solution of (2S,5R)-N'-(cyclopentylcarbonyl)-6-hydroxy-7-oxo-1,6-diazabicyclo[3.2.1]octane-2-carbohydrazide 192 (0.24 g, 0.81 mmol) in dry pyridine (7 mL) under nitrogen atmosphere was added sulfur trioxide pyridine complex (0.36 g, 2.25 mmol). The mixture was stirred at room temperature for 72 h, filtered and evaporated. The residue was purified by column chromatography followed by HPLC on a prep-X Bridge-30×100 mm column and freeze-dried to give (2S,5R)-N'-(cyclopentylcarbonyl)-7-oxo-6-(sulfooxy)-1,6-diazabicyclo[3.2.1]octane-2-carbohydrazide Compound 38 (Table 2) (0.12 g, 40%) as a light brown solid.

$^1$H NMR (400 MHz, CD$_3$OD): δ 1.60-1.99 (10H, m), 2.06-2.10 (1H, m), 2.25-2.31 (1H, m), 2.68-2.74 (1H, m), 3.26-3.33 (2H, m), 4.02 (1H, d, J=7.6 Hz), 4.15 (1H, br s). 3 protons were not observed in CD$_3$OD.

HPLC: 92.01%

MS (ES$^-$) m/z: [M]$^-$=375

Example 46

(2R,5S)-N'-(2-methylpropanoyl)-7-oxo-6-(sulfooxy)-1,6-diazabicyclo[3.2.1]octane-2-carbohydrazide (Compound 18, Table 2)

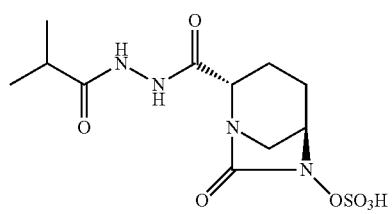

Step 1. (2R,5S)-6-(benzyloxy)-N'-(2-methylpropanoyl)-7-oxo-1,6-diazabicyclo[3.2.1]octane-2-carbohydrazide (194)

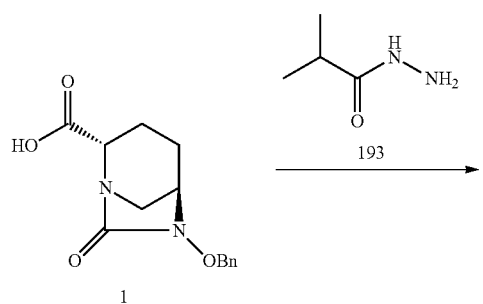

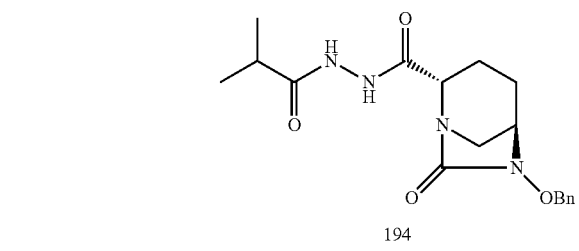

To a solution of (2S,5R)-6-(benzyloxy)-7-oxo-1,6-diazabicyclo[3.2.1]octane-2-carboxylic acid 1 (0.25 g, 0.90 mmol) in dry DCM (20 mL) were added 2-methylpropanehydrazide 193 (0.14 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight, and then concentrated under vacuum. The residue was purified by column chromatography to give (2R,5S)-6-(benzyloxy)-N'-(2-methylpropanoyl)-7-oxo-1,6-diazabicyclo[3.2.1]octane-2-carbohydrazide 194 (0.30 g, 92.6%) as a white solid.

$^1$H NMR (400 MHz, CDCl$_3$): δ 1.12 (6H, m), 1.60 (1H, m), 1.94 (2H, m), 2.29 (1H, m), 2.47 (1H, q, J=6.8 Hz), 3.06 (1H, d, J=12.0 Hz), 3.18 (1H, d, J=11.6 Hz), 3.30 (1H, s), 3.99 (1H, d, J=7.2 Hz), 4.90 (1H, d, J=10.8 Hz), 5.04 (1H, d, J=11.2 Hz), 7.40 (5H, m), 8.07 (1H, br s), 8.61 (1H, br s).

Step 2. (2R,5S)-6-hydroxy-N'-(2-methylpropanoyl)-7-oxo-1,6-diazabicyclo[3.2.1]octane-2-carbohydrazide (195)

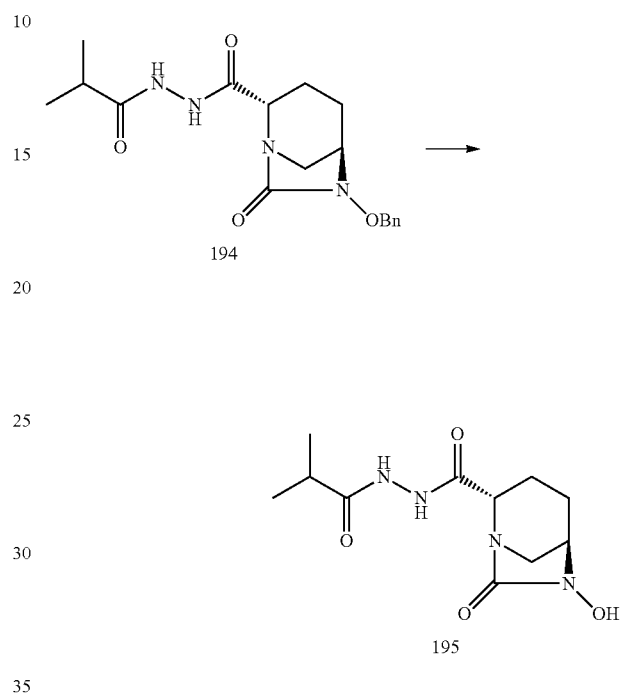

To a solution of (2R,5S)-6-(benzyloxy)-N-(2-methylpropanoyl)-7-oxo-1,6-diazabicyclo[3.2.1]octane-2-carbohydrazide 194 (0.30 g, 0.83 mml) in methanol (20 mL) was added 5% Pd/C (0.40 g). The mixture was hydrogenated under 10 psi hydrogen atmosphere at room temperature for 1 h. The catalyst was filtered out through Celite, and the filtrate was evaporated to give (2R,5S)-6-hydroxy-N'-(2-methylpropanoyl)-7-oxo-1,6-diazabicyclo[3.2.1]octane-2-carbohydrazide 195 (0.21 g, 95%) as a colorless foam.

$^1$H NMR (400 MHz, CD$_3$OD): δ 1.16 (6H, m), 1.74 (1H, m), 1.94 (1H, m), 2.02 (1H, m), 2.29 (1H, m), 2.53 (1H, m), 3.14 (1H, d, J=12.0 Hz), 3.26 (1H, m), 3.70 (1H, s), 3.94 (1H, d, J=7.2 Hz), 3 protons were not observed in CD$_3$OD.

Step 3. (2R,5S)-N'-(2-methylpropanoyl)-7-oxo-6-(sulfooxy)-1,6-diazabicyclo[3.2.1]octane-2-carbohydrazide (Compound 18, Table 2)

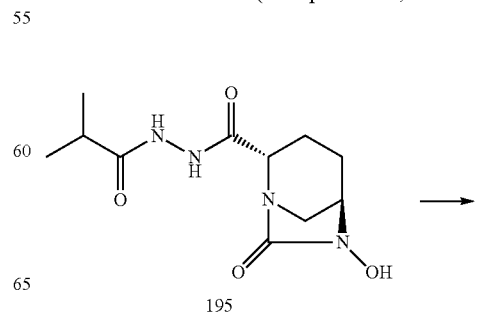

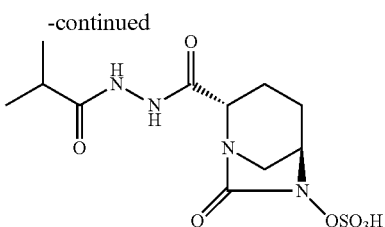

Compound 18, Table 2

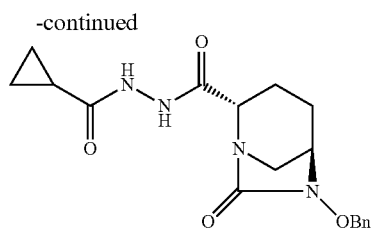

197

To a solution of (2R,5S)-6-hydroxy-N'-(2-methylpropanoyl)-7-oxo-1,6-diazabicyclo[3.2.1]octane-2-carbohydrazide 195 (0.21 g, 0.78 mmol) in dry pyridine (7 mL) under nitrogen atmosphere was added sulfur trioxide pyridine complex (0.70 g, 4.40 mmol). The mixture was stirred at room temperature for 20 h, filtered and evaporated. The residue was purified first by column chromatography followed by HPLC on a prep-X Bridge-30×100 mm column and freeze-dried to give (2R,5S)-N'-(2-methylpropanoyl)-7-oxo-6-(sulfooxy)-1,6-diazabicyclo[3.2.1]octane-2-carbohydrazide Compound 18 (Table 2) (0.03 g, 11%) as a grey solid.

$^1$H NMR (400 MHz, CD$_3$OD): δ 1.64 (6H, m), 1.80 (1H, m), 1.94 (1H, m), 2.07 (1H, m), 2.29 (1H, m), 2.53 (1H, m), 3.30 (2H, m), 4.01 (1H, d, J=7.6 Hz), 4.15 (1H, s), 3 protons were not observed in CD$_3$OD.

HPLC: 97.5%

MS (ES$^-$) m/z: [M]$^-$=349

Example 47

(2R,5S)-N'-(cyclopropylcarbonyl)-7-oxo-6-(sulfooxy)-1,6-diazabicyclo[3.2.1]octane-2-carbohydrazide (Compound 32, Table 2)

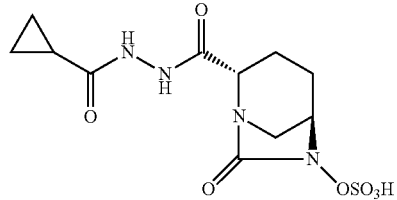

Step 1. (2R,5S)-6-(benzyloxy)-N'-(cyclopropylcarbonyl)-7-oxo-1,6-diazabicyclo[3.2.1]octane-2-carbohydrazide (197)

To a solution of (2S,5R)-6-(benzyloxy)-7-oxo-1,6-diazabicyclo[3.2.1]octane-2-carboxylic acid 1 (0.25 g, 0.90 mmol) in dry DCM (30 mL) were added cyclopropanecarbohydrazide 196 (0.135 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight, and concentrated under vacuum. The residue was purified by column chromatography to give (2R,5S)-6-(benzyloxy)-N'-(cyclopropylcarbonyl)-7-oxo-1,6-diazabicyclo[3.2.1]octane-2-carbohydrazide 197 (0.27 g, 84%) as a white solid.

$^1$H NMR (400 MHz, CDCl$_3$): δ 0.83 (2H, m), 1.04 (2H, m), 1.62 (2H, m), 2.02 (2H, m), 2.34 (1H, m), 3.04 (1H, d, J=12.0 Hz), 3.15 (1H, d, J=12.0 Hz), 3.29 (1H, s), 4.00 (1H, d, J=7.6 Hz), 4.89 (1H, d, J=11.2 Hz), 5.03 (1H, d, J=11.2 Hz), 7.38 (5H, m), 8.29 (1H, br s), 8.57 (1H, br s).

Step 2. (2R,5S)-N'-(cyclopropylcarbonyl)-6-hydroxy-7-oxo-1,6-diazabicyclo[3.2.1]octane-2-carbohydrazide (198)

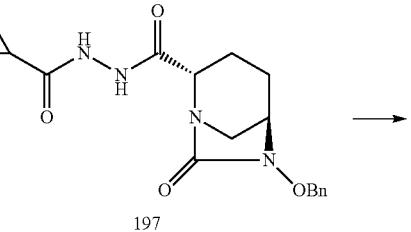

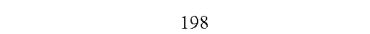

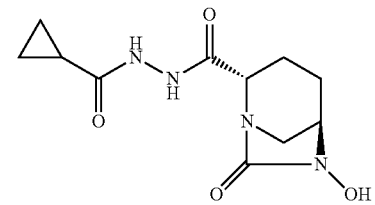

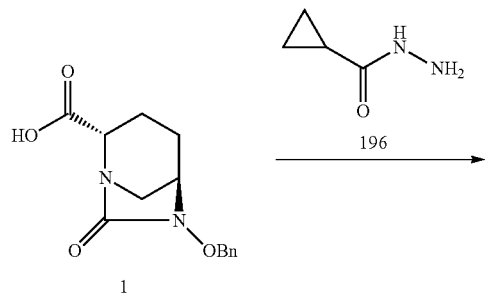

To a solution of (2R,5S)-6-(benzyloxy)-N'-(cyclopropylcarbonyl)-7-oxo-1,6-diazabicyclo[3.2.1]octane-2-carbohydrazide 197 (0.27 g, 0.75 mml) in methanol (20 mL) was added 5% Pd/C (0.30 g). The mixture was hydrogenated under 10 psi hydrogen atmosphere at room temperature for 1 h. The catalyst was filtered out through Celite, and the filtrate was evaporated to give (2R,5S)—N'-(cyclopropylcarbonyl)-6-hydroxy-7-oxo-1,6-diazabicyclo[3.2.1]octane-2-carbohydrazide 198 (0.20 g, 98%) as a colorless foam.

$^1$H NMR (400 MHz, CD$_3$OD): δ 0.86 (2H, m), 0.91 (2H, m), 1.65 (1H, m), 1.76 (1H, m), 1.94 (1H, m), 2.04 (1H, m), 2.26 (1H, m), 3.13 (1H, d, J=13.2 Hz), 3.23 (1H, d, J=12.0 Hz), 3.70 (1H, s), 3.94 (1H, d, J=7.2 Hz), 3 protons were not observed in CD$_3$OD.

Step 3. (2R,5S)-N'-(cyclopropylcarbonyl)-7-oxo-6-(sulfooxy)-1,6-diazabicyclo[3.2.1]octane-2-carbohydrazide (Compound 32, Table 2)

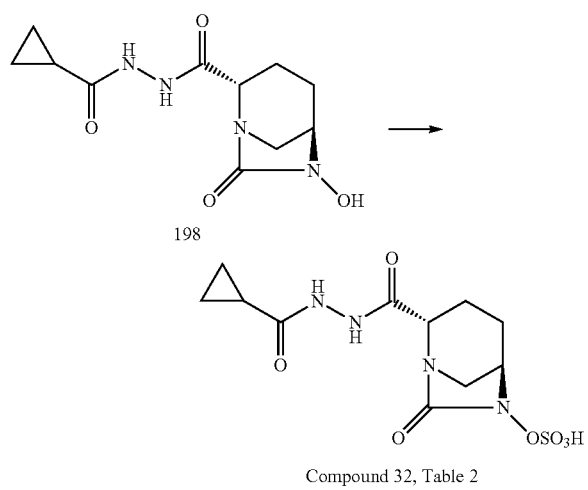

Compound 32, Table 2

To a solution of (2R,5S)-N'-(cyclopropylcarbonyl)-6-hydroxy-7-oxo-1,6-diazabicyclo[3.2.1]octane-2-carbohydrazide 198 (0.20 g, 0.75 mmol) in dry pyridine (7 mL) under nitrogen atmosphere was added sulfur trioxide pyridine complex (0.70 g, 4.40 mmol). The mixture was stirred at room temperature for 20 h, filtered and evaporated. The residue was purified first by column chromatography followed by HPLC on a prep-X Bridge-30×100 mm column and freeze-dried to give (2R,5S)—N'-(cyclopropylcarbonyl)-7-oxo-6-(sulfooxy)-1,6-diazabicyclo[3.2.1]octane-2-carbohydrazide Compound 32 (Table 2) (0.035 g) as a grey solid.

$^1$H NMR (400 MHz, CD$_3$OD): δ 0.83 (2H, m), 0.90 (2H, m), 1.66 (1H, m), 1.78 (1H, m), 1.94 (1H, m), 2.06 (1H, m), 2.28 (1H, m), 3.30 (2H, m), 4.01 (1H, d, J=7.6 Hz), 4.14 (1H, s), 3 protons were not observed in CD$_3$OD.

HPLC: 98.4%

MS (ES$^-$) m/z: [M]$^-$=347

Example 48

(2S,5R)-N'-(cyclobutylcarbonyl)-7-oxo-6-(sulfooxy)-1,6-diazabicyclo[3.2.1]octane-2-carbohydrazide (Compound 33, Table 2)

Step 1. (2S,5R)-6-(benzyloxy)-N'-(cyclobutylcarbonyl)-7-oxo-1,6-diazabicyclo[3.2.1]octane-2-carbohydrazide (200)

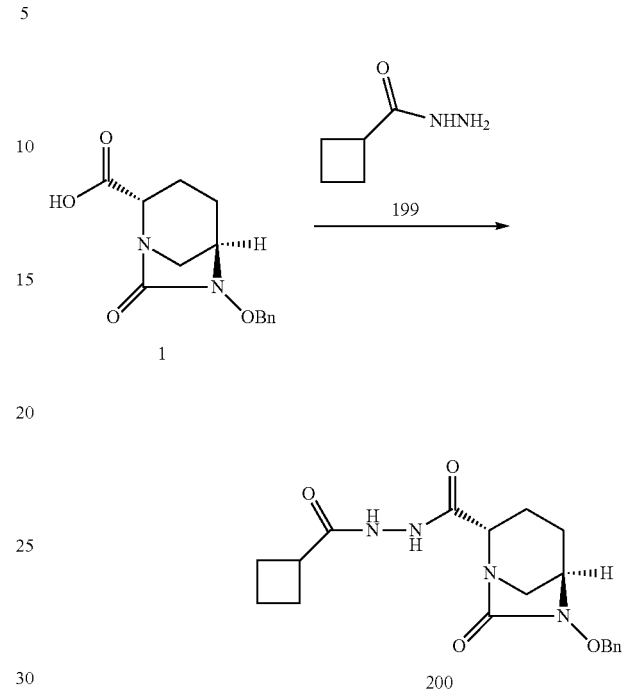

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added cyclobutanecarbohydrazide 199 (0.155 g, 1.358 mmol), 1-hydroxybenzotriazole (0.186 g, 1.358 mmol) and 1-ethyl-(3-dimethylamino propyl) carbodiimide hydrochloride (0.260 g, 1.358 mmol) sequentially at room temperature. The mixture was stirred at room temperature overnight, diluted with DCM and concentrated to provide a residue, which was subjected to chromatography to give 200 (0.34 g, quant. yield) as a white foam.

$^1$H NMR (400 MHz, CDCl$_3$): δ 1.60 (1H, m), 1.90 (4H, m), 2.21 (2H, m), 2.30 (3H, m), 3.10 (3H, m), 3.30 (1H, m), 3.40 (2H, br s), 4.00 (1H, d, J=7.4 Hz), 4.90 (1H, d, J=11.2 Hz), 5.07 (1H, d, J=11.2 Hz), 7.26-7.44 (5H, m).

MS (ES$^+$) m/z: [M+H]$^+$ calcd for C$_{19}$H$_{25}$N$_4$O$_4$: 373.2. Found: 373.2.

Step 2. (2S,5R)-N'-(cyclobutylcarbonyl)-6-hydroxy-7-oxo-1,6-diazabicyclo[3.2.1]octane-2-carbohydrazide (201)

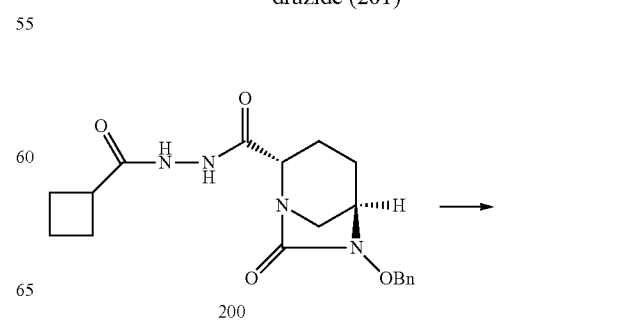

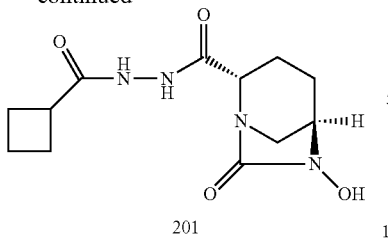

201

A mixture of (2S,5R)-6-(benzyloxy)-N'-(cyclobutylcarbonyl)-7-oxo-1,6-diazabicyclo[3.2.1]octane-2-carbohydrazide 200 (0.34 g, 0.91 mmol) and Pd/C (0.12 g) in methanol (20 mL) was hydrogenated at 1 atm at room temperature for 3 h. The mixture was filtered through Celite and concentrated to provide 201 (0.30 g, quant. yield) as a white foam.

$^1$H NMR (400 MHz, CD$_3$OD): δ 1.86 (1H, m), 1.90 (3H, m), 2.00 (2H, m), 2.09 (2H, m), 2.10 (3H, m), 3.20 (2H, m), 3.71 (1H, s), 3.94 (1H, d, J=7.4 Hz). 3 protons were not observed in CD$_3$OD.

MS (ES$^-$) m/z: [M–H]$^-$ calcd for C$_{12}$H$_{17}$N$_4$O$_4$: 281.1. Found: 281.0.

Step 3. (2S,5R)-N'-(cyclobutylcarbonyl)-7-oxo-6-(sulfooxy)-1,6-diazabicyclo[3.2.1]octane-2-carbohydrazide (Compound 33, Table 2)

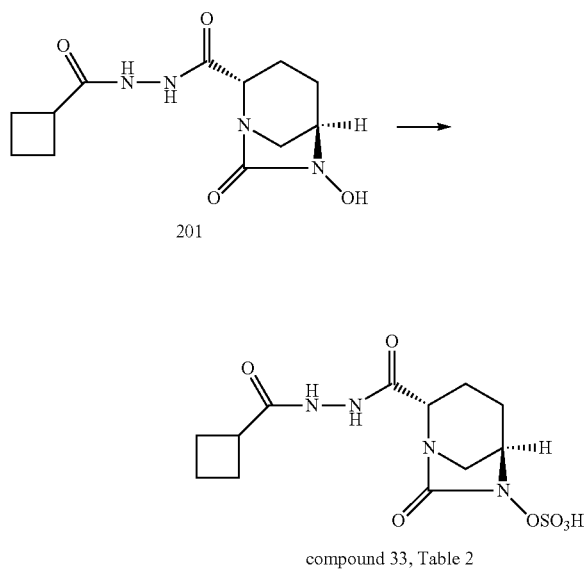

compound 33, Table 2

To a mixture of (2S,5R)-N'-(cyclobutylcarbonyl)-6-hydroxy-7-oxo-1,6-diazabicyclo[3.2.1]octane-2-carbohydrazide 201 (0.91 mmol) in pyridine (5.0 mL) was added sulfur trioxide pyridine complex (0.52 g, 3.33 mmol). The mixture was stirred at room temperature for 3 days and concentrated to provide a residue which was subjected to chromatography and HPLC purification to give Compound 33 (Table 2) (29 mg, 9% yield) as a white solid.

$^1$H NMR (400 MHz, D$_2$O): δ 1.60-2.10 (8H, m), 3.05-3.13 (2H, m), 3.16-3.25 (1H, m), 4.00 (1H, d, J=7.4 Hz), 4.08 (1H, s). 3 protons were not observed in D$_2$O.

HPLC: 98.31%

MS (ES$^-$) m/z: [M–H]$^-$ calcd for C$_{12}$H$_{17}$N$_4$O$_9$S: 361.1. Found: 361.0.

Example 49

(2S,5R)-7-oxo-N'-propanoyl-6-(sulfooxy)-1,6-diazabicyclo[3.2.1]octane-2-carbohydrazide (Compound 17, Table 2)

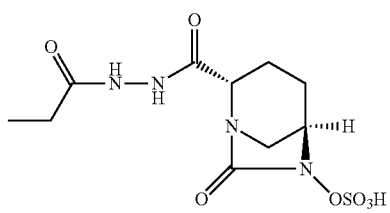

Step 1. (2S,5R)-6-(benzyloxy)-7-oxo-N'-propanoyl-1,6-diazabicyclo[3.2.1]octane-2-carbohydrazide (203)

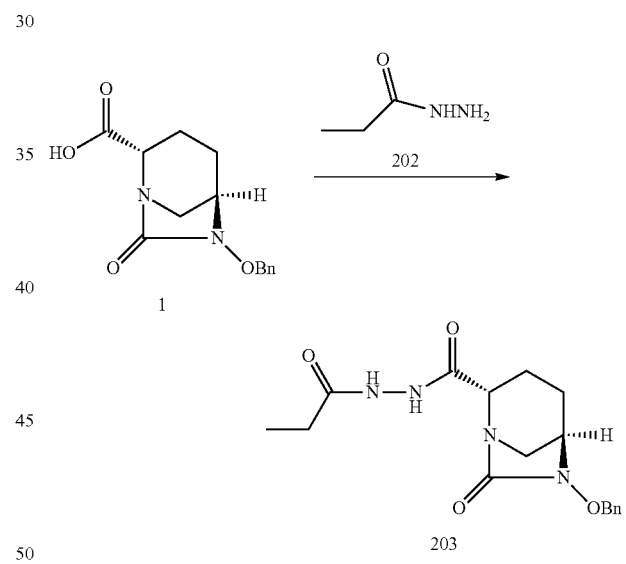

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added propanehydrazide 202 (0.120 g, 1.358 mmol), 1-hydroxybenzotriazole (0.186 g, 1.358 mmol) and 1-ethyl-(3-dimethylamino propyl) carbodiimide hydrochloride (0.260 g, 1.358 mmol) sequentially at room temperature. The mixture was stirred at room temperature overnight, diluted with DCM and concentrated to provide a residue which was subjected to chromatography to give 203 (0.31 g, 99%) as a white foam.

$^1$H NMR (400 MHz, CDCl$_3$): δ 1.20 (3H, t, J=7.4 Hz), 1.62 (1H, m), 1.98 (2H, m), 2.12 (1H, m), 2.38 (2H, m), 3.10 (1H, d, J=12.1 Hz), 3.19 (1H, d, J=12.1 Hz), 3.30 (1H, s), 3.90 (2H, br s), 4.02 (1H, d, J=7.4 Hz), 4.90 (1H, d, J=11.3 Hz), 5.05 (1H, d, J=11.3 Hz), 7.42 (5H, m).

MS (ES+) m/z: [M+H]+ calcd for $C_{11}H_{23}N_4O_4$: 347.2. Found: 347.2.

Step 2. (2S,5R)-6-hydroxy-7-oxo-N'-propanoyl-1,6-diazabicyclo[3.2.1]octane-2-carbohydrazide (204)

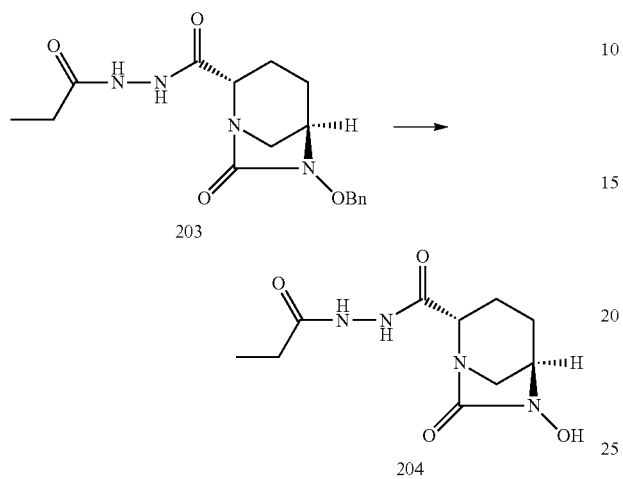

A mixture of (2S,5R)-6-(benzyloxy)-7-oxo-N'-propanoyl-1,6-diazabicyclo[3.2.1]octane-2-carbohydrazide 203 (0.31 g, 0.89 mmol) and Pd/C (0.12 g) in methanol (20 mL) was hydrogenated at 1 atm at room temperature for 16 h. The mixture was filtered through Celite and concentrated to provide 204 (0.24 g, quant. yield) as a white foam.

$^1$H NMR (400 MHz, CD$_3$OD): δ 1.18 (3H, t, J=7.4 Hz), 1.75 (1H, m), 1.85 (1H, m), 1.96 (1H, m), 2.08 (1H, m), 2.30 (2H, m), 3.18 (1H, m), 3.30 (1H, m), 3.70 (1H, br s), 3.95 (1H, d, J=7.4 Hz). 3 protons were not observed in CD$_3$OD.

MS (ES−) m/z: [M−H]− calcd for $C_{10}H_{14}N_4O_4$: 255.1. Found: 255.0.

Step 3. (2S,5R)-7-oxo-N'-propanoyl-6-(sulfooxy)-1,6-diazabicyclo[3.2.1]octane-2-carbohydrazide (Compound 17, Table 2)

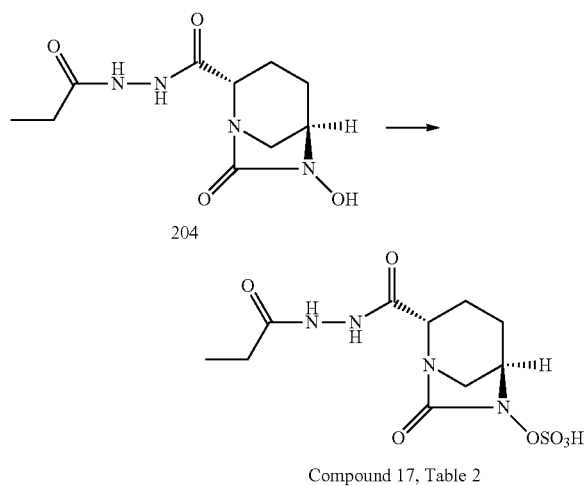

To a mixture of (2S,5R)-6-hydroxy-7-oxo-N'-propanoyl-1,6-diazabicyclo[3.2.1]octane-2-carbohydrazide 204 (0.24 g, 0.93 mmol) in pyridine (5.0 mL) was added sulfur trioxide pyridine complex (0.44 g, 2.81 mmol). The mixture was stirred at room temperature for 23 h and concentrated to provide a residue which was subjected to chromatography and HPLC purification to give Compound 17 (Table 2) (0.053 g, 17%) as a white solid.

$^1$H NMR (400 MHz, D$_2$O): δ 0.98 (3H, t, J=7.8 Hz), 1.65 (1H, m), 1.80 (1H, m), 1.95 (1H, m), 2.05 (1H, m), 2.18 (2H, q, J=7.8 Hz), 3.05 (1H, d, J=12.1 Hz), 3.18 (1H, d, J=12.9 Hz), 4.00 (1H, d, J=7.8 Hz), 4.05 (1H, m). 3 protons were not observed in D$_2$O.

HPLC: 97.12%

MS (ES−) m/z: [M−H]− calcd for $C_{10}H_{15}N_4O_7S$: 335.1. Found: 335.0.

Example 50

(2S,5R)-7-oxo-N-(piperazin-1-yl)-6-(sulfooxy)-1,6-diazabicyclo[3.2.1]octane-2-carboxamide (Compound 100, Table 2)

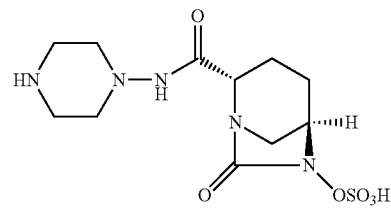

Step 1. tert-butyl 4-({[(2S,5R)-6-(benzyloxy)-7-oxo-1,6-diazabicyclo[3.2.1]oct-2-yl]carbonyl}amino)piperazine-1-carboxylate (206)

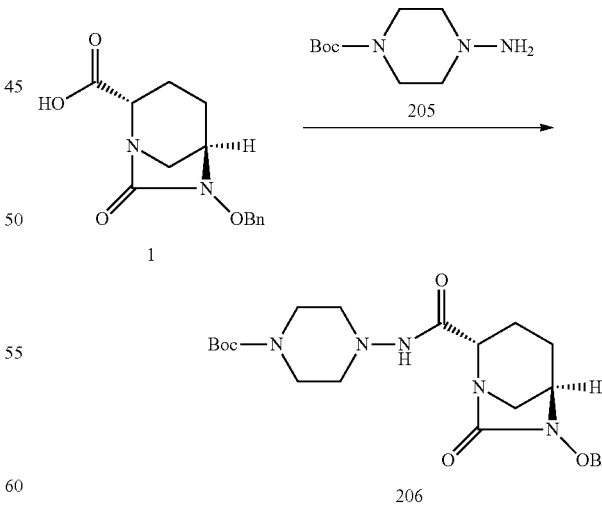

To a solution of (2S,5R)-6-(benzyloxy)-7-oxo-1,6-diazabicyclo[3.2.1]octane-2-carboxylic acid 1 (0.17 g, 0.615 mmol) in dry DCM (10 mL) were added tert-butyl 4-aminopiperazine-1-carboxylate 205 (0.19 g, 0.923 mmol), 1-hydroxybenzotriazole (0.125 g, 0.923 mmol), 1-ethyl-(3-dimethylaminopropyl)carbodiimide hydrochloride (0.177 g, 0.923 mmol) and 4-dimethylaminopyridine (0.113 g, 0.923 mmol) at room temperature. The reaction mixture was stirred at room temperature overnight, and then concentrated under vacuum. The residue was purified by column chromatography to give tert-butyl 4-({[(2S,5R)-6-(benzyloxy)-7-oxo-1,6-diazabicyclo[3.2.1]oct-2-yl]carbonyl}amino)piperazine-1-carboxylate 206 (0.25 g, 88%) as a clear thick oil.

$^1$H NMR (400 MHz, CDCl$_3$): δ 1.46 (9H, s), 1.62 (1H, m), 1.95 (2H, m), 2.38 (1H, m), 2.70 (1H, d, J=12.0 Hz), 2.76 (4H, m), 2.99 (1H, d, J=12.0 Hz), 3.30 (1H, m), 3.57 (4H, m), 3.89 (1H, d, J=8.0 Hz), 4.90 (1H, d, J=11.6 Hz), 5.04 (1H, d, J=12.0 Hz), 7.21 (5H, m), 8.90 (1H, br s).

Step 2. tert-Butyl 4-({[(2S,5R)-6-hydroxy-7-oxo-1,6-diazabicyclo[3.2.1]oct-2-yl]carbonyl}amino)piperazine-1-carboxylate (207)

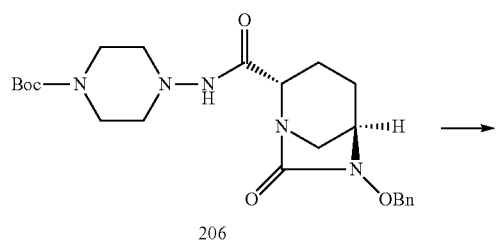

206

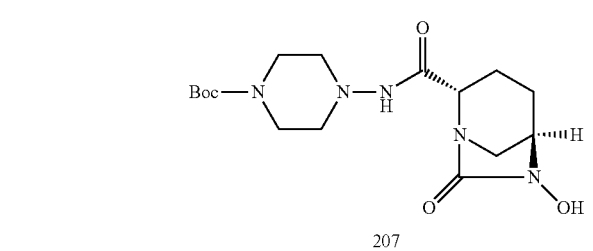

207

To a solution of tert-butyl 4-({[(2S,5R)-6-(benzyloxy)-7-oxo-1,6-diazabicyclo[3.2.1]oct-2-yl]carbonyl}amino)piperazine-1-carboxylate 206 (0.25 g, 0.54 mml) in methanol (15 mL) was added 10% Pd/C (0.3 g). The mixture was hydrogenated under 35 psi hydrogen atmosphere at room temperature for 2 h. The catalyst was filtered out through Celite, and the filtrate was evaporated to give tert-butyl 4-({[(2S,5R)-6-hydroxy-7-oxo-1,6-diazabicyclo[3.2.1]oct-2-yl]carbonyl}amino)piperazine-1-carboxylate 207 (0.20 g, 99%) as a colorless foam.

$^1$H NMR (400 MHz, CD$_3$OD): δ 1.48 (9H, s), 1.78 (1H, m), 1.88 (1H, m), 2.07 (1H, m), 2.20 (1H, m), 2.75 (4H, m), 2.99 (1H, d, J=12.0 Hz), 3.11 (1H, d, J=11.6 Hz), 3.53 (4H, m), 3.70 (1H, m), 3.80 (1H, d, J=7.2 Hz), 2 protons were not observed in CD$_3$OD.

Step 3. tert-Butyl 4-({[(2S,5R)-7-oxo-6-(sulfooxy)-1,6-diazabicyclo[3.2.1]oct-2-yl]carbonyl}amino)piperazine-1-carboxylate (208)

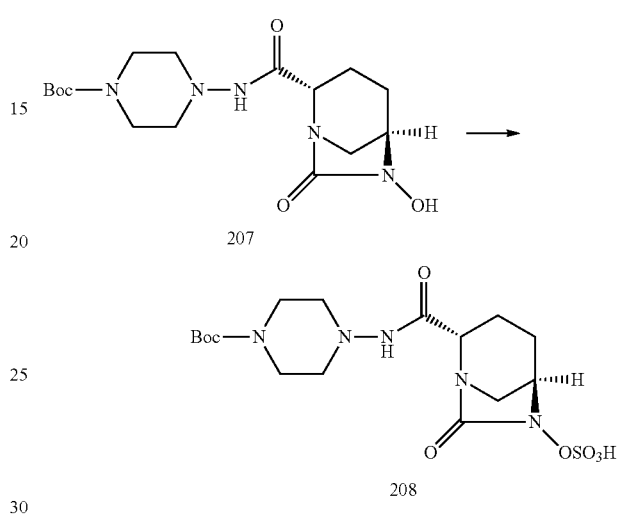

207

208

To a solution of tert-butyl 4-({[(2S,5R)-6-hydroxy-7-oxo-1,6-diazabicyclo[3.2.1]oct-2-yl]carbonyl}amino)piperazine-1-carboxylate 207 (0.20 g, 0.54 mmol) in dry pyridine (7 mL) under nitrogen atmosphere was added sulfur trioxide pyridine complex (0.34 g, 2.16 mmol). The mixture was stirred at room temperature for 20 h, filtered and evaporated. The residue was purified by column chromatography to give tert-butyl 4-({[(2S,5R)-7-oxo-6-(sulfooxy)-1,6-diazabicyclo[3.2.1]oct-2-yl]carbonyl}amino)piperazine-1-carboxylate 208 (0.12 g, 49.6%) as a white solid.

$^1$H NMR (400 MHz, CD$_3$OD): δ 1.45 (9H, s), 1.86 (2H, m), 2.07 (1H, m), 2.23 (1H, m), 2.75 (4H, m), 3.03 (1H, d, J=11.2 Hz), 3.21 (1H, m), 3.52 (4H, m), 3.85 (1H, d, J=11.2 Hz), 4.14 (1H, m), 2 protons were not observed in CD$_3$OD.

Step 4. (2S,5R)-7-oxo-N-(piperazin-1-yl)-6-(sulfooxy)-1,6-diazabicyclo[3.2.1]octane-2-carboxamide (Compound 100, Table 2)

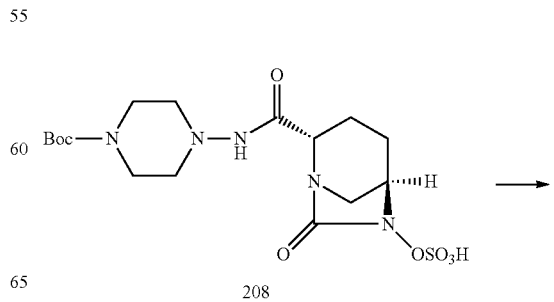

208

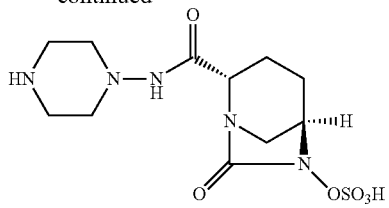

Compound 100, Table 2

To a solution of tert-butyl 4-({[(2S,5R)-7-oxo-6-(sulfooxy)-1,6-diazabicyclo[3.2.1]oct-2-yl]carbonyl}amino)piperazine-1-carboxylate 208 (0.12 g, 0.27 mmol) in DCM (12.5 mL) was added trifluoroacetic acid (1.0 mL, 12.96 mmol) dropwise at 0° C. The reaction mixture was stirred for 1 h, then evaporated. Ether was added to the residue and the resulting white precipitate was collected by centrifugation. The solid was triturated with acetonitrile (2×) and the white solid was collected by centrifugation. This white solid was purified by HPLC on a prep-X Bridge-19×250 mm column and freeze-dried to give (2S,5R)-7-oxo-N-(piperazin-1-yl)-6-(sulfooxy)-1,6-diazabicyclo[3.2.1]octane-2-carboxamide Compound 100 (Table 2) (0.11 g, 88%) as a white solid.

$^1$H NMR (400 MHz, CD$_3$OD): δ 1.77 (2H, m), 1.95 (1H, m), 2.05 (1H, m), 2.97 (5H, m), 3.16 (1H, d, J=12.0 Hz), 3.26 (4H, m), 3.89 (1H, d, J=7.6 Hz), 4.06 (1H, m), 3 protons were not observed in CD$_3$OD.

HPLC: 81.5%
MS (ES$^-$) m/z: [M]$^-$=348.01

Example 51

(2S,5R)-N-(morpholin-4-yl)-7-oxo-6-(sulfooxy)-1,6-diazabicyclo[3.2.1]octane-2-carboxamide (Compound 99, Table 2)

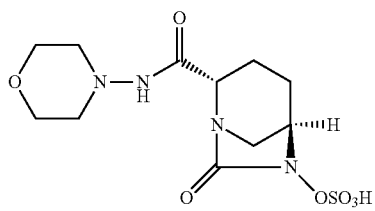

Step 1. (2S,5R)-6-(benzyloxy)-N-(morpholin-4-yl)-7-oxo-1,6-diazabicyclo[3.2.1]octane-2-carboxamide (210)

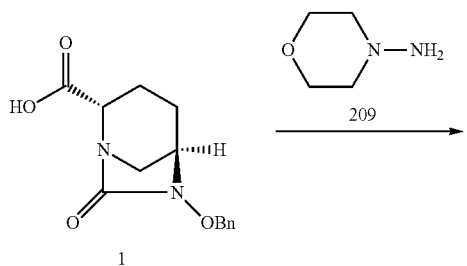

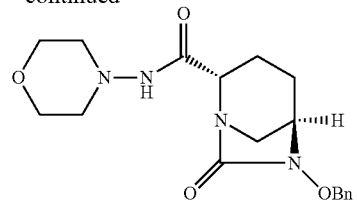

210

To a solution of (2S,5R)-6-(benzyloxy)-7-oxo-1,6-diazabicyclo[3.2.1]octane-2-carboxylic acid 1 (0.23 g, 0.83 mmol) in dry DCM (15 mL) were added morpholin-4-amine 209 (0.13 g, 1.25 mmol), 1-hydroxybenzotriazole (0.19 g, 1.41 mmol), 1-ethyl-(3-dimethylaminopropyl)carbodiimide hydrochloride (0.24 g, 1.25 mmol) and 4-dimethylaminopyridine (0.15 g, 1.23 mmol) at room temperature. The reaction mixture was stirred at room temperature overnight and concentrated under vacuum. The residue was purified by column chromatography to give (2S,5R)-6-(benzyloxy)-N-(morpholin-4-yl)-7-oxo-1,6-diazabicyclo[3.2.1]octane-2-carboxamide 210 (0.255 g, 85%) as a clear thick oil.

$^1$H NMR (400 MHz, CDCl$_3$): δ 1.62 (1H, m), 1.97 (2H, m), 2.38 (1H, m), 2.71 (1H, d, J=11.6 Hz), 2.82 (4H, m), 3.00 (1H, d, J=11.2 Hz), 3.30 (1H, s), 3.8 (4H, m), 3.90 (1H, d, J=8.0 Hz), 4.90 (1H, d, J=11.2 Hz), 5.04 (1H, d, J=12.0 Hz), 7.37 (5H, m), 8.90 (1H, br s).

Step 2. (2S,5R)-6-hydroxy-N-(morpholin-4-yl)-7-oxo-1,6-diazabicyclo[3.2.1]octane-2-carboxamide (211)

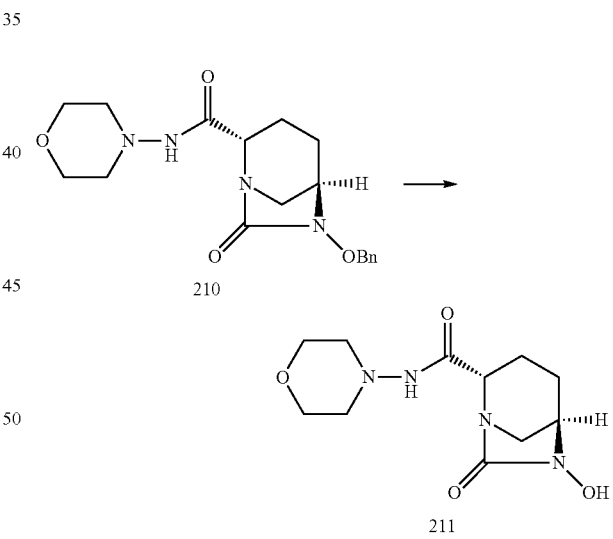

To a solution of (2S,5R)-6-(benzyloxy)-N-(morpholin-4-yl)-7-oxo-1,6-diazabicyclo[3.2.1]octane-2-carboxamide 210 (0.255 g, 0.71 mml) in methanol (15 mL) was added 10% Pd/C (0.5 g). The mixture was hydrogenated under 35 psi hydrogen atmosphere at room temperature for 2 h. The catalyst was filtered out through Celite, and the filtrate was evaporated to give (2S,5R)-6-hydroxy-N-(morpholin-4-yl)-7-oxo-1,6-diazabicyclo[3.2.1]octane-2-carboxamide 211 (0.19 g, quantitative yield) as a colorless foam.

$^1$H NMR (400 MHz, CD$_3$OD): δ 1.77 (1H, m), 1.95 (1H, m), 2.06 (1H, m), 2.20 (1H, m), 2.81 (4H, m), 3.00 (1H, d,

J=11.2 Hz), 3.11 (1H, d, J=11.6 Hz), 3.69 (1H, m), 3.76 (4H, m), 3.80 (1H, d, J=7.2 Hz), 2 protons was not observed in CD₃OD.

Step 3. (2S,5R)-N-(morpholin-4-yl)-7-oxo-6-(sulfooxy)-1,6-diazabicyclo[3.2.1]octane-2-carboxamide (Compound 99, Table 2)

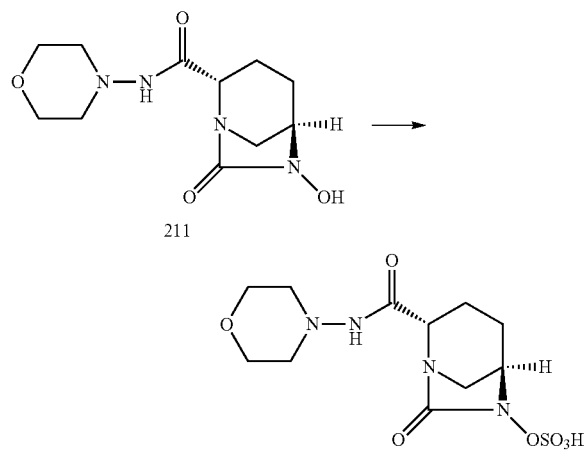

Compound 99, Table 2

To a solution of (2S,5R)-6-hydroxy-N-(morpholin-4-yl)-7-oxo-1,6-diazabicyclo[3.2.1]octane-2-carboxamide 211 (0.19 g, 0.71 mmol) in dry pyridine (7 mL) under nitrogen atmosphere was added sulfur trioxide pyridine complex (0.29 g, 1.82 mmol). The mixture was stirred at room temperature for 20 h, filtered and evaporated. The residue was purified by HPLC on Prep_30×100 mm_5 µm column and freeze-dried to give (2S,5R)-N-(morpholin-4-yl)-7-oxo-6-(sulfooxy)-1,6-diazabicyclo[3.2.1]octane-2-carboxamide Compound 99 (Table 2) (0.005 g, 2%) as a white solid.

¹H NMR (400 MHz, CD₃OD): δ 1.82 (2H, m), 2.07 (1H, m), 2.21 (1H, m), 2.80 (4H, m), 3.05 (1H, d, J=11.2 Hz), 3.20 (1H, m), 3.80 (4H, m), 3.89 (1H, d, J=11.2 Hz), 4.16 (1H, s), 2 protons were not observed in CD₃OD.

MS (ES⁻) m/z: [M]⁻=348.89

Example 52

(2R,5S)-N'-acetyl-N'-methyl-7-oxo-6-(sulfooxy)-1,6-diazabicyclo[3.2.1]octane-2-carbohydrazide (Compound 19, Table 2)

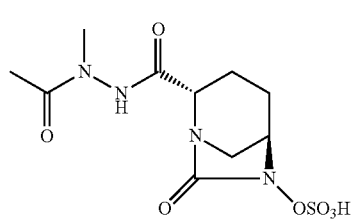

Step 1. (2R,5S)-N'-acetyl-6-(benzyloxy)-N'-methyl-7-oxo-1,6-diazabicyclo[3.2.1]octane-2-carbohydrazide (213)

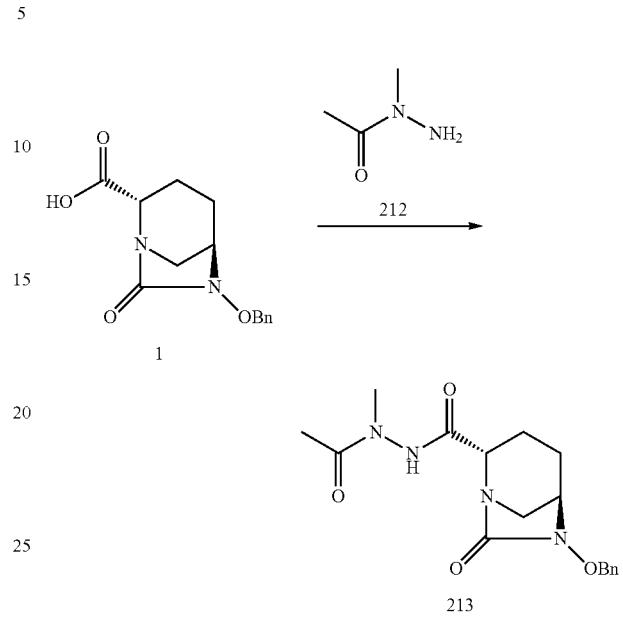

To a solution of (2S,5R)-6-(benzyloxy)-7-oxo-1,6-diazabicyclo[3.2.1]octane-2-carboxylic acid 1 (0.25 g, 0.90 mmol) in dry DCM (30 mL) were added N-methylacetohydrazide 212 (0.14 g, 1.59 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight and concentrated under vacuum. The residue was purified by column chromatography to give (2R,5S)-N'-acetyl-6-(benzyloxy)-N'-methyl-7-oxo-1,6-diazabicyclo[3.2.1] octane-2-carbohydrazide 213 (0.20 g, 64%) as a white solid.

¹H NMR (400 MHz, CDCl₃): δ 1.65 (1H, m), 1.83-2.12 (5H, m), 2.32 (1H, m), 2.70 (1H, d, J=12.0 Hz), 3.05-3.37 (5H, m), 4.01 (1H, m), 4.88-5.07 (2H, m), 7.41 (5H, m), 8.55 (0.5H, br s), 8.76 (0.5H, br s).

Step 2. (2R,5S)-N'-acetyl-6-hydroxy-N'-methyl-7-oxo-1,6-diazabicyclo[3.2.1]octane-2-carbohydrazide (214)

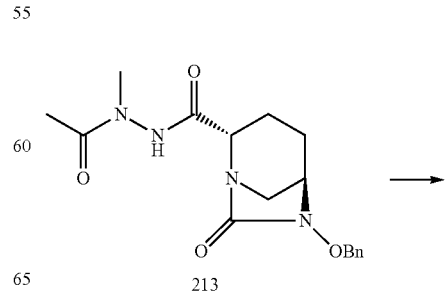

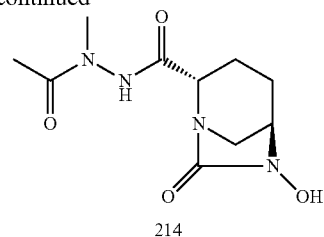

To a solution of (2R,5S)-N'-acetyl-6-(benzyloxy)-N'-methyl-7-oxo-1,6-diazabicyclo[3.2.1]octane-2-carbohydrazide 213 (0.20 g, 0.57 mml) in methanol (20 mL) was added 5% Pd/C (0.30 g). The mixture was hydrogenated under 10 psi hydrogen atmosphere at room temperature for 1 h. The catalyst was filtered out through Celite, and the filtrate was evaporated to give (2R,5S)-N'-acetyl-6-hydroxy-N'-methyl-7-oxo-1,6-diazabicyclo[3.2.1]octane-2-carbohydrazide 214 (0.15 g, 99%) as a colorless foam.

$^1$H NMR (400 MHz, CD$_3$OD): δ 1.82 (1H, m), 1.89-2.10 (5H, m), 2.25 (1H, m), 2.93 (1H, d, J=12.0 Hz), 3.11-3.26 (4H, m), 3.72 (1H, s), 3.95 (1H, d, J=7.2 Hz), 2 protons were not observed in CD$_3$OD.

Step 3. (2R,5S)-N'-acetyl-N'-methyl-7-oxo-6-(sulfooxy)-1,6-diazabicyclo[3.2.1]octane-2-carbohydrazide (Compound 19, Table 2)

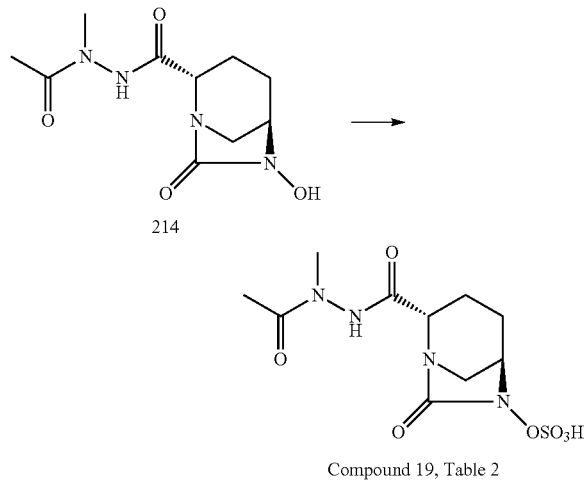

Compound 19, Table 2

To a solution of (2R,5S)-N'-acetyl-6-hydroxy-N'-methyl-7-oxo-1,6-diazabicyclo[3.2.1]octane-2-carbohydrazide 214 (0.15 g, 0.58 mmol) in dry pyridine (8 mL) under nitrogen atmosphere was added sulfur trioxide pyridine complex (0.70 g, 4.40 mmol). The mixture was stirred at room temperature for 40 h, filtered and evaporated. The residue was purified by column chromatography followed by HPLC on a prep-X Bridge-30×100 mm column and freeze-dried to give (2R,5S)-N'-acetyl-N'-methyl-7-oxo-6-(sulfooxy)-1,6-diazabicyclo[3.2.1]octane-2-carbohydrazide Compound 19 (Table 2) (0.030 g, 15%) as a grey solid.

$^1$H NMR (400 MHz, CD$_3$OD): δ 1.82 (1H, m), 1.96 (1H, m), 2.02 (3H, s), 2.11 (1H, m), 2.26 (1H, m), 2.99 (1H, d, J=12.4 Hz), 3.11 (3H, s), 3.34 (1H, m), 4.02 (1H, d, J=8.0 Hz), 4.16 (1H, s), 2 protons were not observed in CD$_3$OD.

HPLC: 95.4%

MS (ES$^-$) m/z: [M]$^-$=335

Example 53

(2S,5R)-7-oxo-N'-(pyridin-2-ylcarbonyl)-6-(sulfooxy)-1,6-diazabicyclo[3.2.1]octane-2-carbohydrazide (Compound 72, Table 2)

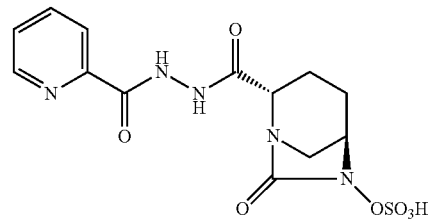

Step 1. (2S,5R)-6-(benzyloxy)-7-oxo-N'-picolinoyl-1,6-diazabicyclo[3.2.1]octane-2-carbohydrazide (216)

To a solution of (2S,5R)-6-(benzyloxy)-7-oxo-1,6-diazabicyclo[3.2.1]octane-2-carboxylic acid 1 (0.276 g, 1.0 mmol) in dry DCM (30 mL) were added 215 (0.206 g, 1.5 mmol), 1-hydroxybenzotriazole (0.211 g, 1.5 mmol), 1-ethyl-(3-dimethylaminopropyl)carbodiimide hydrochloride (0.292 g, 1.5 mmol) and 4-(dimethylamino)pyridine (0.178 g, 1.5 mmol) at room temperature. The reaction mixture was stirred at room temperature overnight, and concentrated under vacuum. The residue was purified by column chromatography to give 216 (0.36 g, 90%) as a white solid.

$^1$H NMR (400 MHz, CDCl$_3$): δ 1.65 (1H, m), 2.01 (2H, m), 2.42 (1H, m), 3.13 (1H, d, J=12.0 Hz), 3.19 (1H, d, J=12 Hz), 3.33 (1H, s), 4.11 (1H, d, J=7.2 Hz), 4.92 (1H, d, J=11.6 Hz), 5.063 (1H, d, J=11.2 Hz), 7.42 (6H, m), 7.85 (1H, t, J=8.6 Hz), 8.12 (1H, d, J=9.6 Hz), 8.58 (1H, d, J=7.2 Hz), 8.67 (1H, br s), 9.75 (1H, br s).

Step 2. (2S,5R)-6-hydroxy-7-oxo-N'-picolinoyl-1,6-diazabicyclo[3.2.1]octane-2-carbohydrazide (217)

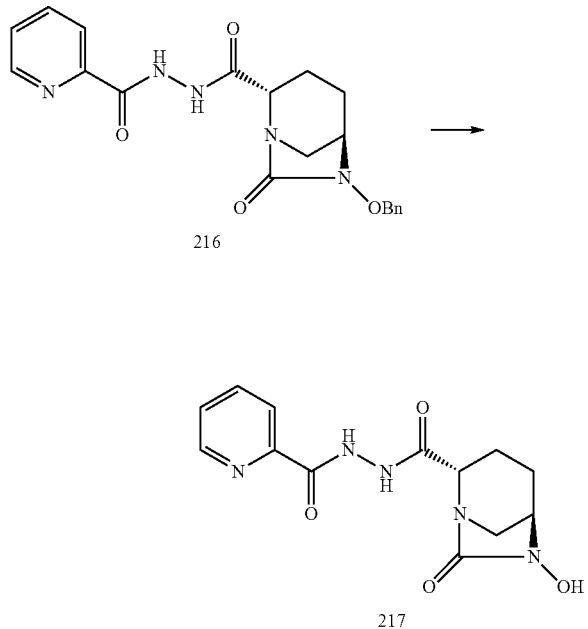

A mixture of (2S,5R)-6-(benzyloxy)-7-oxo-N'-picolinoyl-1,6-diazabicyclo[3.2.1]octane-2-carbohydrazide 216 (0.30 g, 0.76 mmol) and Pd/C (0.40 g) in methanol (100 mL) was hydrogenated at 1 atm at room temperature for 3 h. The mixture was filtered through Celite pad and concentrated to provide 217 (0.23 g, quant. yield) as a white foam.

$^1$H NMR (400 MHz, CD$_3$OD): δ 1.50-2.40 (4H, m), 1.75 (1H, m), 3.20 (1H, m), 3.35 (1H, m), 3.71 (1H, m), 4.05 (1H, m), 7.60 (1H, m), 8.00 (1H, m), 8.18 (1H, m), 8.70 (1H, m). 3 protons were not observed in CD$_3$OD.

MS (ES$^-$) m/z: [M+H]$^-$ calcd for C$_{13}$H$_{16}$N$_5$O$_4$: 306.2. Found: 306.1.

Step 3. (2S,5R)-7-oxo-N'-(pyridin-2-ylcarbonyl)-6-(sulfooxy)-1,6-diazabicyclo[3.2.1]octane-2-carbohydrazide (Compound 72, Table 2)

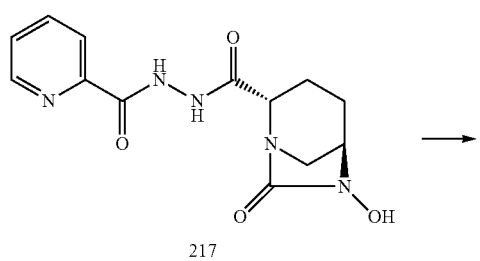

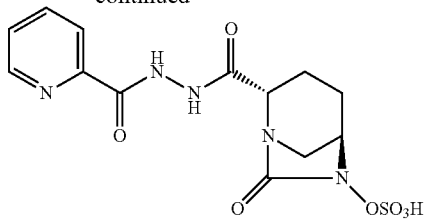

Compound 72, Table 2

To a mixture of (2S,5R)-6-hydroxy-7-oxo-N'-picolinoyl-1,6-diazabicyclo[3.2.1]octane-2-carbohydrazide 217 (0.23 g, 0.75 mmol) in pyridine (10 mL) was added sulfur trioxide pyridine complex (0.35 g, 2.26 mmol). The mixture was stirred at room temperature for 24 h. NMR showed no reaction, additional sulfur trioxide pyridine complex (0.70 g, 4.52 mmol) was added, and the mixture was stirred at room temperature for 4 days. The reaction mixture was concentrated and subjected to chromatography to give 140 mg off-white solid; 80 mg of this product was further purified by HPLC to give Compound 72 (Table 2) (0.030 g, 20%) as a white solid.

$^1$H NMR (400 MHz, D$_2$O): δ 1.68 (1H, m), 1.82 (1H, m), 1.93 (1H, m), 2.08 (1H, m), 3.13 (1H, d, J=12.1 Hz), 3.22 (1H, d, J=12.1 Hz), 4.07 (2H, m), 7.46 (1H, m), 7.86 (2H, m), 8.46 (1H, d, J=4.69 Hz). 3 protons were not observed in D$_2$O.

HPLC: 91.81%.

MS (ES$^-$) m/z: [M−H]$^-$ calcd for C$_{13}$H$_{14}$N$_5$O$_7$S: 384.3. Found: 384.0.

Example 54

(2S,5R)-N'-(methoxyacetyl)-7-oxo-6-(sulfooxy)-1,6-diazabicyclo[3.2.1]octane-2-carbohydrazide (Example 29, Table 2)

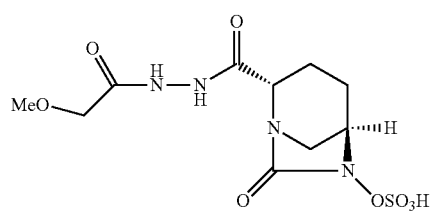

Step 1. (2S,5R)-6-(benzyloxy)-N'-(methoxyacetyl)-7-oxo-1,6-diazabicyclo[3.2.1]octane-2-carbohydrazide (219)

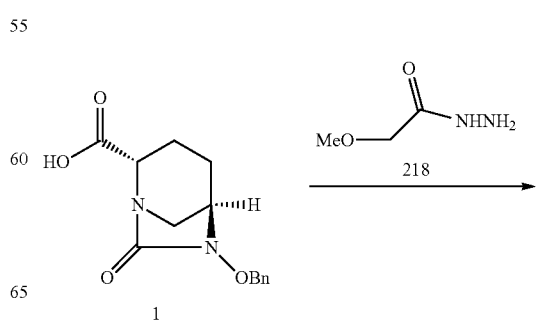

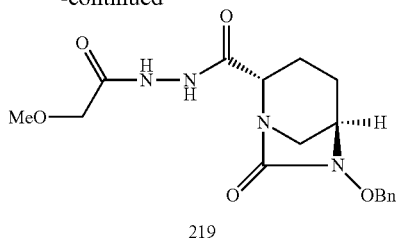

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added 2-methoxyacetohydrazide 218 (0.141 g, 1.358 mmol), 1-hydroxybenzotriazole (0.186 g, 1.358 mmol) and 1-ethyl-(3-dimethylamino propyl)carbodiimide hydrochloride (0.260 g, 1.358 mmol) sequentially at room temperature. The mixture was stirred at room temperature overnight, diluted with DCM and concentrated to provide a residue, which was subjected to chromatography to give 219 (0.27 g, 82%) as a white foam.

$^1$H NMR (400 MHz, CDCl$_3$): δ 1.60 (1H, m), 1.99 (2H, m), 2.40 (1H, m), 3.10 (2H, s), 3.32 (1H, s), 3.46 (3H, s), 3.04 (2H, s), 4.06 (1H, m), 4.90 (1H, d, J=11.2 Hz), 5.05 (1H, d, J=11.2 Hz), 7.42 (5H, m).

MS (ES$^-$) m/z: [M–H]$^-$ calcd for C$_{10}$H$_{15}$N$_4$O$_6$: 347.2. Found: 361.1.

Step 2. (2S,5R)-6-hydroxy-N'-(methoxyacetyl)-7-oxo-1,6-diazabicyclo[3.2.1]octane-2-carbohydrazide (220)

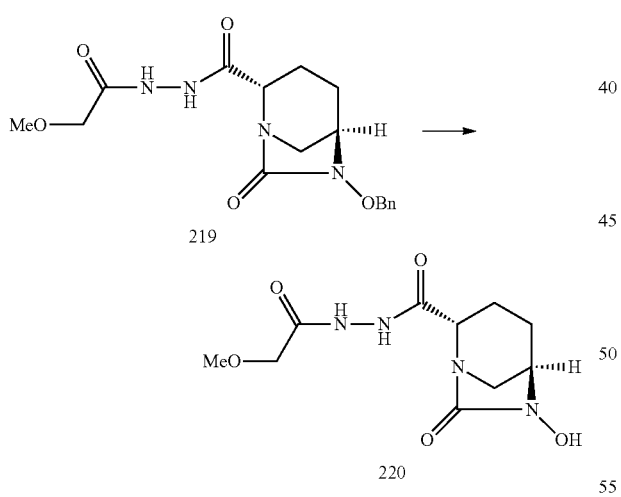

A mixture of (2S,5R)-6-(benzyloxy)-N'-(methoxyacetyl)-7-oxo-1,6-diazabicyclo[3.2.1]octane-2-carbohydrazide 219 (0.27 g, 0.74 mmol) and Pd/C (0.10 g) in methanol (20 mL) was hydrogenated at 1 atm at room temperature for 3 h. The mixture was filtered through Celite and concentrated to provide 220 (0.19 g, 90%) as a white foam.

$^1$H NMR (400 MHz, CD$_3$OD): δ 1.75 (1H, m), 1.90 (1H, m), 1.96 (1H, m), 2.08 (1H, m), 2.28 (1H, m), 3.17 (1H, m), 3.30 (1H, m), 3.44 (3H, s), 3.70 (1H, br s), 3.95 (1H, d, J=7.6 Hz), 4.03 (2H, s). 3 protons were not observed in CD$_3$OD.

MS (ES$^-$) m/z: [M–H]$^-$ calcd for C$_{10}$H$_{15}$N$_4$O$_5$: 271.1. Found: 271.1.

Step 3. (2S,5R)-N'-(methoxyacetyl)-7-oxo-6-(sulfooxy)-1,6-diazabicyclo[3.2.1]octane-2-carbohydrazide (Compound 29, Table 2)

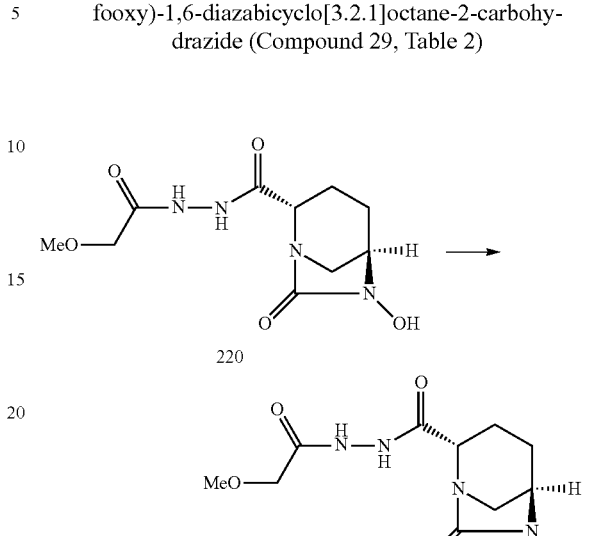

Compound 29, Table 2

To a mixture of (2S,5R)-6-hydroxy-N'-(methoxyacetyl)-7-oxo-1,6-diazabicyclo[3.2.1]octane-2-carbohydrazide 220 (0.19 g, 0.70 mmol) in pyridine (5.0 mL) was added sulfur trioxide pyridine complex (0.32 g, 2.10 mmol). The mixture was stirred at room temperature for 2 days and concentrated to provide a residue, which was subjected to chromatography followed by HPLC separation to give Compound 29 (Table 2) (9 mg) as a white solid.

$^1$H NMR (400 MHz, D$_2$O): δ 1.67 (1H, m), 1.82 (1H, m), 1.92 (1H, m), 3.05 (1H, d, J=12.4 Hz), 3.20 (1H, m), 3.30 (3H, s), 4.00 (2H, s), 4.04 (2H, m). 3 protons were not observed in D$_2$O.

HPLC: 91.84%

MS (ES$^-$) m/z: [M–H]$^-$ calcd for C$_{10}$H$_{15}$N$_4$O$_8$S: 351.1. Found: 351.0.

Example 55

(2S,5R)-7-oxo-N'-(pyrrolidin-3-ylcarbonyl)-6-(sulfooxy)-1,6-diazabicyclo[3.2.1]octane-2-carbohydrazide trifluoroacetate (Example 42, Table 2)

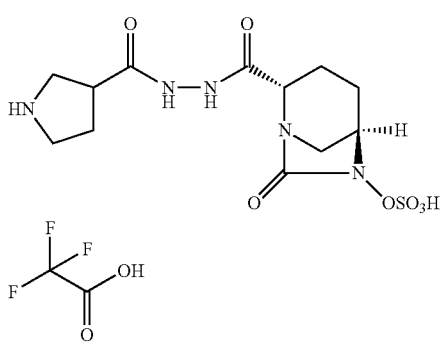

Step 1. tert-butyl 3-[(2-{[(2S,5R)-6-(benzyloxy)-7-oxo-1,6-diazabicyclo[3.2.1]oct-2-yl]carbonyl}hydrazinyl)carbonyl]pyrrolidine-1-carboxylate (222)

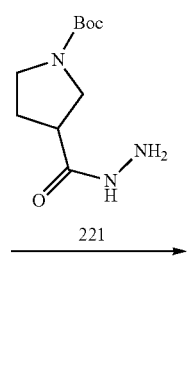

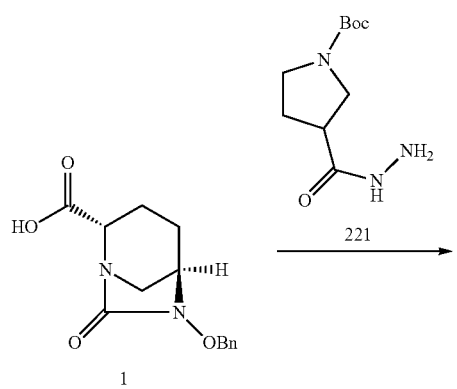

To a mixture of (2S,5R)-6-(benzyloxy)-7-oxo-1,6-diazabicyclo[3.2.1]octane-2-carboxylic acid 1 (0.304 g, 1.10 mmol) in DCM (20.0 mL) were added tert-butyl 3-(hydrazinecarbonyl)pyrrolidine-1-carboxylate 221 (0.380 g, 1.65 mmol), 1-hydroxybenzotriazole (0.223 g, 1.65 mmol) and 1-ethyl-(3-dimethylaminopropyl) carbodiimide hydrochloride (0.315 g, 1.65 mmol) sequentially at room temperature. The mixture was stirred at room temperature overnight, concentrated to provide a residue which was subjected to chromatography to give 222 (0.48 g, slightly impure) as a white foam.

Step 2. tert-butyl 3-[(2-{[(2S,5R)-6-hydroxy-7-oxo-1,6-diazabicyclo[3.2.1]oct-2-yl]carbonyl}hydrazinyl)carbonyl]pyrrolidine-1-carboxylate (223)

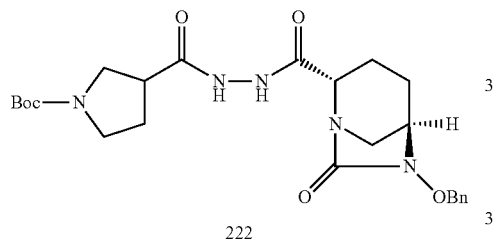

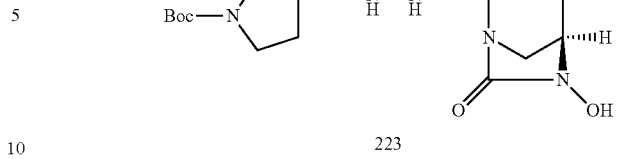

A mixture of tert-butyl 2-(2-((2S,5R)-6-(benzyloxy)-7-oxo-1,6-diazabicyclo[3.2.1]-octane-2-carbonyl)hydrazinecarbonyl)pyrrolidine-1-carboxylate 222 (0.48 g, 0.984 mmol) and Pd/C (0.60 g) in methanol (100 mL) was hydrogenated at 1 atm at room temperature for 1.5 h. The mixture was filtered through Celite pad and concentrated to give 223 (0.39 g, slightly impure) as an off-white foam.

Step 3. tert-butyl 3-[(2-{[(2S,5R)-7-oxo-6-(sulfooxy)-1,6-diazabicyclo[3.2.1]oct-2-yl]carbonyl}hydrazinyl)carbonyl]pyrrolidine-1-carboxylate (224)

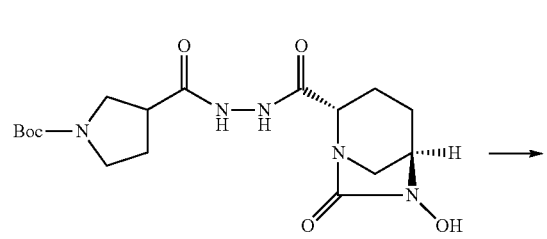

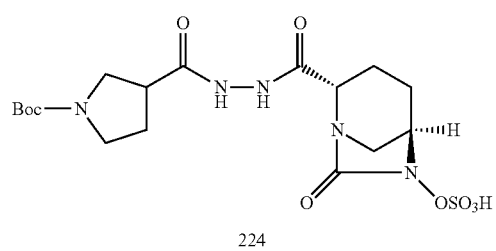

To a mixture of tert-butyl 2-(2-((2S,5R)-6-hydroxy-7-oxo-1,6-diazabicyclo[3.2.1]-octane-2-carbonyl)hydrazinecarbonyl)pyrrolidine-1-carboxylate 223 (0.390 g, 0.984 mmol) in pyridine (15 mL) was added sulfur trioxide pyridine complex (0.461 g, 2.952 mmol). The mixture was stirred at room temperature for 23 h. Additional sulfur trioxide pyridine complex (0.461 g, 2.952 mmol) was added. The mixture was stirred at room temperature over the weekend and concentrated to provide a residue which was subjected to chromatography to give 224 (0.245 g, 52%) as an off-white solid.

$^1$H NMR (400 MHz, D$_2$O): δ 1.25 (9H, s), 1.66 (1H, m), 1.84 (1H, m), 1.95 (2H, m), 2.10 (2H, m), 3.04 (2H, m), 3.10-3.60 (5H, m), 4.05 (2H, m). Three protons were not observed in CD$_3$OD.

Step 4. (2S,5R)-7-oxo-N'-(pyrrolidin-3-ylcarbonyl)-6-(sulfooxy)-1,6-diazabicyclo[3.2.1]octane-2-carbohydrazide trifluoroacetate (Compound 42, Table 2)

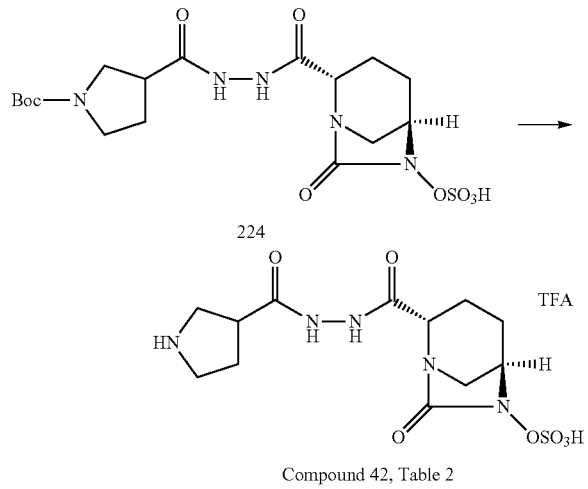

Compound 42, Table 2

To a mixture of tert-butyl 2-(2-(((2S,5R)-7-oxo-6-(sulfooxy)-1,6-diazabicyclo[3.2.1]-octane-2-carbonyl)hydrazinecarbonyl)pyrrolidine-1-carboxylate 224 (0.20 g, 0.42 mmol) in DCM (8.0 mL) was added trifluoroacetic acid (0.40 mL) at 0° C. The mixture was stirred at 0° C. for 1 h, concentrated and washed with ether and MeOH to give Compound 42 (Table 2) (90 mg) as a white solid as a pair of diastereomers.

$^1$H NMR (400 MHz, D$_2$O): δ 1.63 (1H, m), 1.76 (1H, m), 1.88 (1H, m), 2.01 (2H, m), 2.23 (1H, m), 3.00 (1H, m), 3.19 (4H, m), 3.35 (2H, m), 4.00 (2H, m). Four protons were not observed in D$_2$O.

$^{19}$F NMR (376.5 MHz, D$_2$O): δ −75.79

HPLC: 62.09% and 34.89%. (Two isomers).

MS (ES$^-$) m/z: [M+H]$^+$ calcd for C$_{12}$H$_{20}$N$_5$O$_7$S: 378.4. Found: 378.1.

Example 56

(2R,5S)-N'-methyl-7-oxo-N'-propanoyl-6-(sulfooxy)-1,6-diazabicyclo[3.2.1]octane-2-carbohydrazide (Compound 20, Table 2)

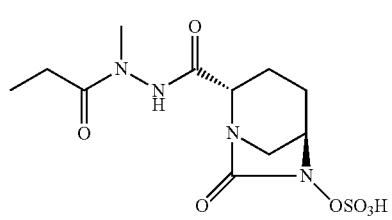

MS (ES$^-$) m/z: [M−H]$^-$ calcd for C$_{17}$H$_{26}$N$_5$O$_9$S: 476.5. Found: 476.1.

Step 1. (2R,5S)-6-(benzyloxy)-N'-methyl-7-oxo-N'-propanoyl-1,6-diazabicyclo[3.2.1]octane-2-carbohydrazide (226)

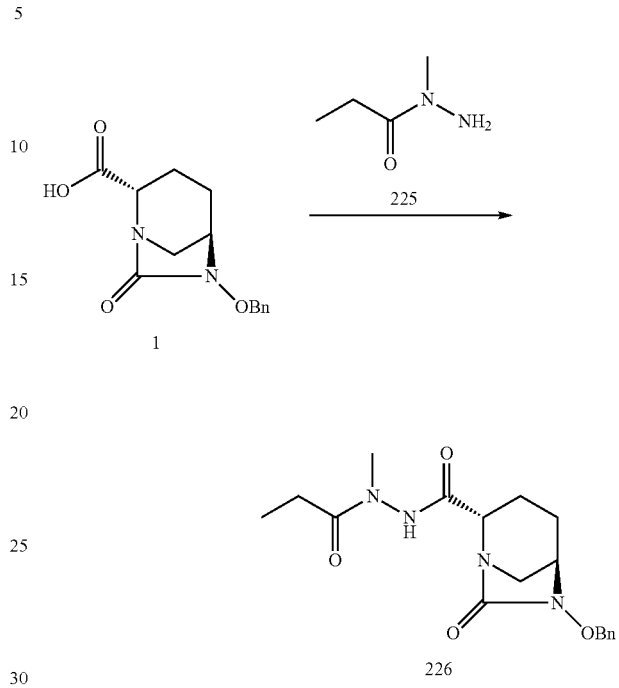

To a solution of (2S,5R)-6-(benzyloxy)-7-oxo-1,6-diazabicyclo[3.2.1]octane-2-carboxylic acid 1 (0.25 g, 0.90 mmol) in dry DCM (30 mL) were added N-methylpropanehydrazide 225 (0.14 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight and concentrated under vacuum. The residue was purified by column chromatography to give (2R,5S)-6-(benzyloxy)-N'-methyl-7-oxo-N'-propanoyl-1,6-diazabicyclo[3.2.1]octane-2-carbohydrazide 226 (0.19 g, 59%) as a white solid.

$^1$H NMR (400 MHz, CDCl$_3$): δ 1.04-1.18 (3H, m), 1.65 (1H, m), 1.98 (2H, m), 2.10-2.20 (3H, m), 2.68-3.32 (6H, m), 3.72-4.02 (1H, m), 4.80-5.05 (2H, m), 7.41 (5H, m), 8.54 (0.5H, br s), 8.63 (0.5H, br s).

Step 2. (2R,5S)-6-hydroxy-N'-methyl-7-oxo-N'-propanoyl-1,6-diazabicyclo[3.2.1]octane-2-carbohydrazide (227)

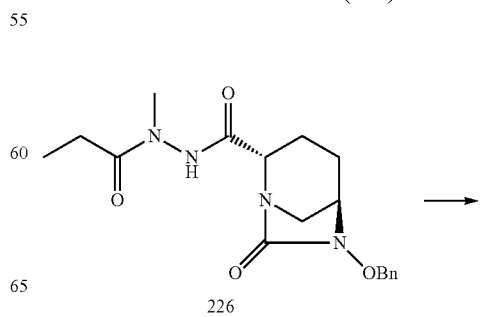

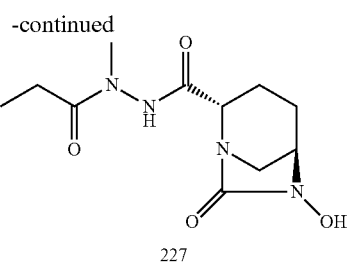

To a solution of (2R,5S)-6-(benzyloxy)-N'-methyl-7-oxo-N'-propanoyl-1,6-diazabicyclo[3.2.1]octane-2-carbohydrazide 226 (0.19 g, 0.52 mml) in methanol (20 mL) was added 5% Pd/C (0.20 g). The mixture was hydrogenated under 10 psi hydrogen atmosphere at room temperature for 1 h. The catalyst was filtered through Celite, and the filtrate was evaporated to give (2R,5S)-6-hydroxy-N'-methyl-7-oxo-N'-propanoyl-1,6-diazabicyclo[3.2.1]octane-2-carbohydrazide 227 (0.11 g, 79%) as a brown foam.

$^1$H NMR (400 MHz, CD$_3$OD): δ 1.04-1.14 (3H, m), 1.69-1.80 (2H, m), 1.85-2.14 (2H, m), 2.22-2.40 (2H, m), 2.90-3.34 (5H, m), 3.73 (1H, s), 3.95 (1H, d, J=7.2 Hz), 2 protons were not observed in CD$_3$OD.

Step 3. (2R,5S)-N'-methyl-7-oxo-N'-propanoyl-6-(sulfooxy)-1,6-diazabicyclo[3.2.1]octane-2-carbohydrazide (Compound 20, Table 2)

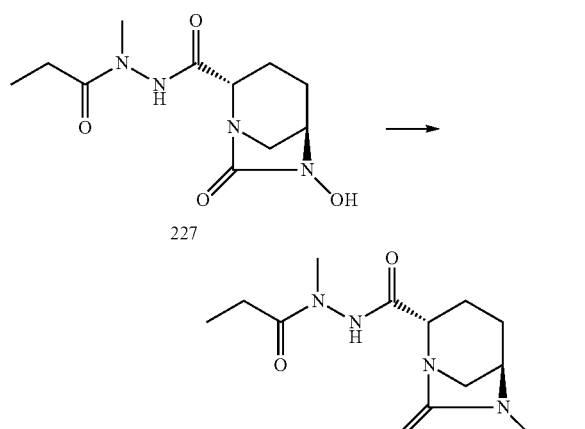

Compound 20, Table 2

To a solution of (2R,5S)-6-hydroxy-N'-methyl-7-oxo-N'-propanoyl-1,6-diazabicyclo[3.2.1]octane-2-carbohydrazide 227 (0.11 g, 0.41 mmol) in dry pyridine (6 mL) under nitrogen atmosphere was added sulfur trioxide pyridine complex (0.60 g, 3.80 mmol). The mixture was stirred at room temperature for 40 h, filtered and evaporated. The residue was purified first by column chromatography followed by washing several times with a mixture of methanol and diethyl ether (1:9) to give (2R,5S)-N'-methyl-7-oxo-N'-propanoyl-6-(sulfooxy)-1, 6-diazabicyclo[3.2.1]octane-2-carbohydrazide Compound 20 (Table 2) (0.015 g, 10.5%) as a white solid.

$^1$H NMR (400 MHz, CD$_3$OD): δ 1.05 (3H, t, J=7.4 Hz), 1.81 (1H, m), 1.94 (1H, m), 2.08 (1H, m), 2.26 (3H, m), 2.99 (1H, d, J=12.0 Hz), 3.11 (3H, s), 3.31 (1H, m), 4.02 (1H, d, J=7.6 Hz), 4.17 (1H, s), 2 protons were not observed in CD$_3$OD.

HPLC: 91.8%

MS (ES$^-$) m/z: [M]$^-$=349

Example 57

(2R,5S)-7-oxo-6-(sulfooxy)-N'-(3,3,3-trifluoropropanoyl)-1,6-diazabicyclo[3.2.1]octane-2-carbohydrazide (Compound 28, Table 2)

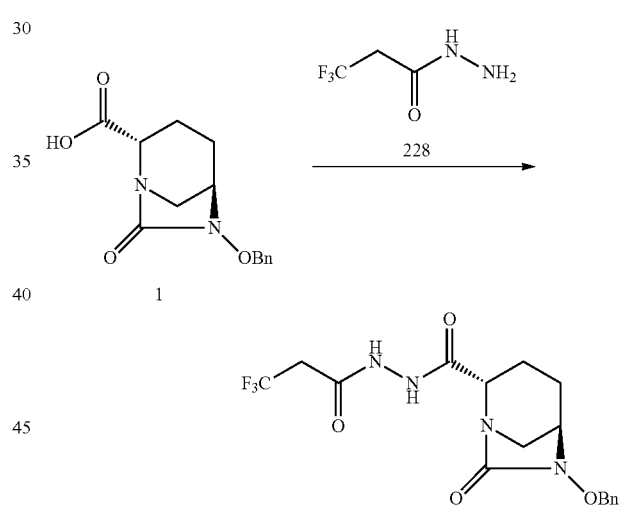

Step 1. (2R,5S)-6-(benzyloxy)-7-oxo-N'-(3,3,3-trifluoropropanoyl)-1,6-diazabicyclo[3.2.1]octane-2-carbohydrazide (229)

To a solution of (2S,5R)-6-(benzyloxy)-7-oxo-1,6-diazabicyclo[3.2.1]octane-2-carboxylic acid 1 (0.25 g, 0.90 mmol) in dry DCM (40 mL) were added 3,3,3-trifluoropropanehydrazide 228 (0.19 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight and concentrated under vacuum. The residue was purified by column chromatography to give (2R,5S)-6-(benzyloxy)-7-oxo-N-(3,3,3-trifluoropropanoyl)-1,6-diazabicyclo[3.2.1]octane-2-carbohydrazide 229 (0.26 g, 72%) as a white solid.

$^1$H NMR (400 MHz, CDCl$_3$): δ 1.60 (1H, m), 1.99 (2H, m), 2.26 (1H, m), 3.08 (2H, m), 3.23 (2H, m), 3.33 (1H, s), 3.97

(1H, d, J=7.2 Hz), 4.89 (1H, d, J=11.2 Hz), 5.02 (1H, d, J=11.2 Hz), 7.39 (5H, m), 8.82 (2H, br s).

Step 2. (2R,5S)-6-hydroxy-7-oxo-N'-(3,3,3-trifluoropropanoyl)-1,6-diazabicyclo[3.2.1]octane-2-carbohydrazide (230)

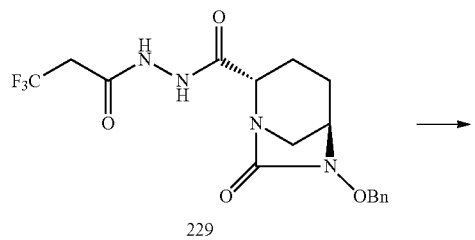
229

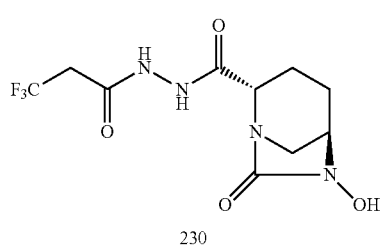
230

To a solution of (2R,5S)-6-(benzyloxy)-7-oxo-N'-(3,3,3-trifluoropropanoyl)-1,6-diazabicyclo[3.2.1]octane-2-carbohydrazide 229 (0.26 g, 0.65 mml) in methanol (20 mL) was added 5% Pd/C (0.30 g). The mixture was hydrogenated under 10 psi hydrogen atmosphere at room temperature for 1 h. The catalyst was filtered out through Celite, and the filtrate was evaporated to give (2R,5S)-6-hydroxy-7-oxo-N'-(3,3,3-trifluoropropanoyl)-1,6-diazabicyclo[3.2.1]octane-2-carbohydrazide 230 (0.19 g, 93.6%) as a colorless foam.

$^1$H NMR (400 MHz, CD$_3$OD): δ 1.76 (1H, m), 1.93 (1H, m), 2.04 (1H, m), 2.28 (1H, m), 3.15-3.34 (4H, m), 3.71 (1H, s), 3.94 (1H, d, J=7.2 Hz), 3 protons were not observed in CD$_3$OD.

Step 3. (2R,5S)-7-oxo-6-(sulfooxy)-N'-(3,3,3-trifluoropropanoyl)-1,6-diazabicyclo[3.2.1]octane-2-carbohydrazide (Compound 28, Table 2):

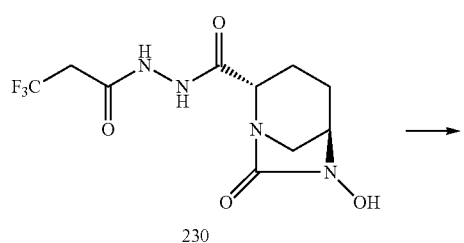
230

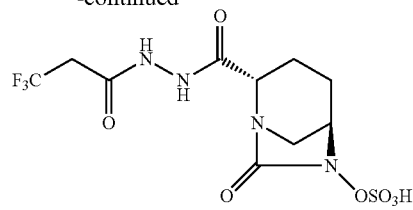
Compound 28, Table 2

To a solution of (2R,5S)-6-hydroxy-7-oxo-N'-(3,3,3-trifluoropropanoyl)-1,6-diazabicyclo[3.2.1]octane-2-carbohydrazide 230 (0.19 g, 0.61 mmol) in dry pyridine (7 mL) under nitrogen atmosphere was added sulfur trioxide pyridine complex (0.70 g, 4.40 mmol). The mixture was stirred at room temperature for 20 h, filtered and evaporated. The residue was purified by column chromatography followed by washing several times with a mixture of methanol and diethyl ether (1:9) to give (2R,5S)-7-oxo-6-(sulfooxy)-N'-(3,3,3-trifluoropropanoyl)-1,6-diazabicyclo[3.2.1]octane-2-carbohydrazide Compound 28 (Table 2) (0.040 g, 16.8%) as a pink solid.

$^1$H NMR (400 MHz, CD$_3$OD): δ 1.80 (1H, m), 1.93 (1H, m), 2.06 (1H, m), 2.27 (1H, m), 3.23-3.34 (4H, m), 4.01 (1H, d, J=7.6 Hz), 4.15 (1H, s), 3 protons were not observed in CD$_3$OD.

HPLC: 94.2%

MS (ES$^-$) m/z: [M]$^-$=389

Example 58

(2R,5S)-N',N'-dimethyl-7-oxo-6-(sulfooxy)-1,6-diazabicyclo[3.2.1]octane-2-carbohydrazide (Compound 4, Table 2)

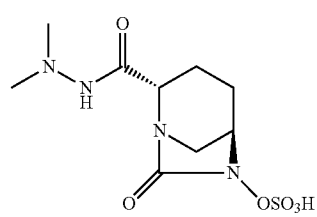

Step 1. (2S,5R)-6-(benzyloxy)-N',N'-dimethyl-7-oxo-1,6-diazabicyclo[3.2.1]octane-2-carbohydrazide (232)

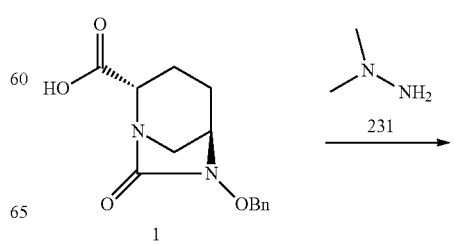
1

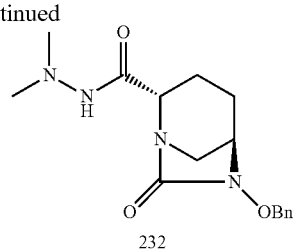

232

To a solution of (2S,5R)-6-(benzyloxy)-7-oxo-1,6-diazabicyclo[3.2.1]octane-2-carboxylic acid 1 (0.276 g, 1.0 mmol) in dry DCM (20 mL) were added 231 (0.09 g, 1.5 mmol), 1-hydroxybenzotriazole (0.203 g, 1.5 mmol), and 1-ethyl-(3-dimethylaminopropyl)carbodiimide hydrochloride (0.288 g, 1.5 mmol) at room temperature. The reaction mixture was stirred at room temperature overnight and concentrated under vacuum. The residue was purified by column chromatography to give 232 (0.25 g, slightly impure) as a colorless oil.

Step 2. (2S,5R)-6-hydroxy-N',N'-dimethyl-7-oxo-1,6-diazabicyclo[3.2.1]octane-2-carbohydrazide (233)

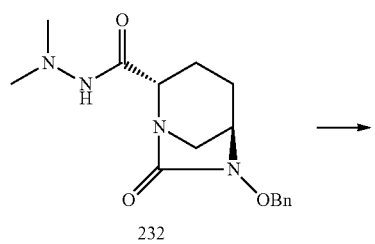

232

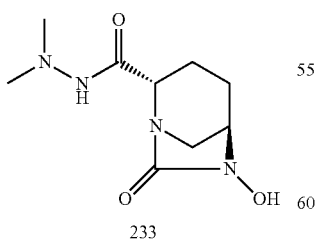

233

A mixture of (2S,5R)-6-(benzyloxy)-N',N'-dimethyl-7-oxo-1,6-diazabicyclo[3.2.1]octane-2-carbohydrazide 232 (0.25 g, 0.78 mmol) and Pd/C (0.30 g) in methanol (80 mL) was hydrogenated at 1 atm at room temperature for 1 h. The mixture was filtered through Celite pad and concentrated to provide 233 (0.17 g) as a white foam which was used in the next step without purification.

Step 3. (2R,5S)-N',N'-dimethyl-7-oxo-6-(sulfooxy)-1,6-diazabicyclo[3.2.1]octane-2-carbohydrazide (Compound 4, Table 2)

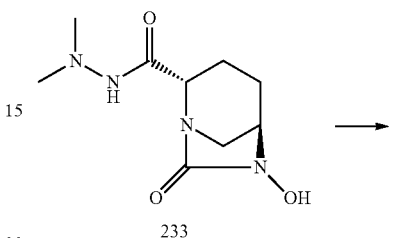

233

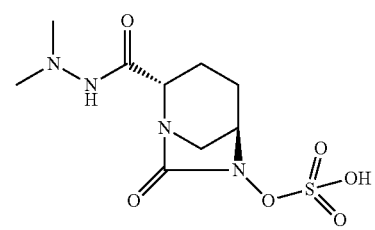

Compound 4, Table 2

To a mixture of (2S,5R)-6-hydroxy-N',N'-dimethyl-7-oxo-1,6-diazabicyclo[3.2.1]octane-2-carbohydrazide 233 (0.17 g, 0.78 mmol) in pyridine (10 mL) was added sulfur trioxide pyridine complex (0.36 g, 2.34 mmol).). The mixture was stirred at room temperature for 24 h and concentrated to provide a residue which was subjected to chromatography followed by HPLC separation to give Compound 4 (Table 2) (0.0036 g, 1.5% for three steps) as a white solid.

$^1$H NMR (400 MHz, D$_2$O): δ 1.68 (2H, m), 1.94 (2H, m), 2.38 (6H, s), 2.90 (1H, d, J=12.0 Hz), 3.13 (1H, d, J=12.4 Hz), 3.81 (1H, d, J=7.2 Hz), 4.02 (1H, s). 2 protons were not observed in D$_2$O.

HPLC: 93.82%

MS (ES$^-$) m/z: [M–H]$^-$ calcd for C$_9$H$_{15}$N$_4$O$_6$S: 307.3. Found: 307.0.

Example 59

(2R,5S)-N'-butanoyl-7-oxo-6-(sulfooxy)-1,6-diazabicyclo[3.2.1]octane-2-carbohydrazide (Compound 25, Table 2)

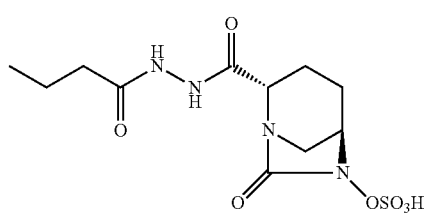

Step 1. (2R,5S)-6-(benzyloxy)-N'-butanoyl-7-oxo-1,6-diazabicyclo[3.2.1]octane-2-carbohydrazide (235)

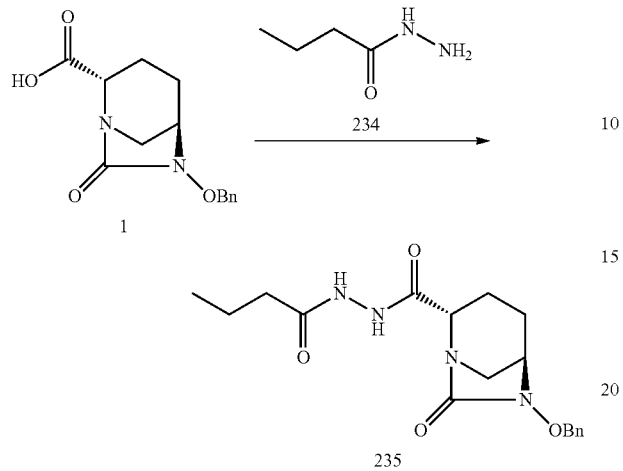

To a solution of (2S,5R)-6-(benzyloxy)-7-oxo-1,6-diazabicyclo[3.2.1]octane-2-carboxylic acid 1 (0.25 g, 0.90 mmol) in dry DCM (40 mL) were added butanehydrazide 234 (0.14 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight, and then concentrated under vacuum. The residue was purified by column chromatography to give (2R,5S)-6-(benzyloxy)-N-butanoyl-7-oxo-1,6-diazabicyclo[3.2.1]octane-2-carbohydrazide 235 (0.31 g, 95%) as a white solid.

$^1$H NMR (400 MHz, CDCl$_3$): δ 0.96 (3H, t, J=7.4 Hz), 1.60-1.72 (3H, m), 1.97 (2H, m), 2.05-2.33 (3H, m), 3.06 (1H, d, J=12.0 Hz), 3.16 (1H, d, J=12.0 Hz), 3.31 (1H, s), 4.00 (1H, d, J=7.2 Hz), 4.90 (1H, d, J=11.2 Hz), 5.04 (1H, d, J=11.6 Hz), 7.38 (5H, m), 7.86 (1H, br s), 8.58 (1H, br s).

Step 2. (2R,5S)-N'-butanoyl-6-hydroxy-7-oxo-1,6-diazabicyclo[3.2.1]octane-2-carbohydrazide (236)

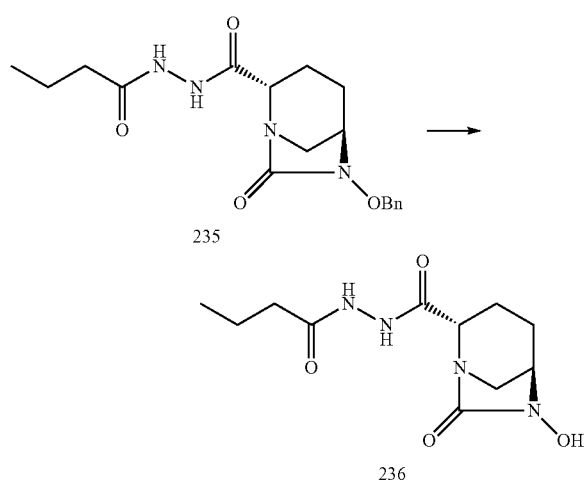

To a solution of (2R,5S)-6-(benzyloxy)-N-butanoyl-7-oxo-1,6-diazabicyclo[3.2.1]octane-2-carbohydrazide 235 (0.31 g, 0.86 mml) in methanol (20 mL) was added 5% Pd/C (0.30 g). The mixture was hydrogenated under 10 psi hydrogen atmosphere at room temperature for 1 h. The catalyst was filtered out through Celite, and the filtrate was evaporated to give (2R,5S)-N'-butanoyl-6-hydroxy-7-oxo-1,6-diazabicyclo[3.2.1]octane-2-carbohydrazide 236 (0.21 g, 90%) as a brown foam.

$^1$H NMR (400 MHz, CD$_3$OD): δ 0.97 (3H, t, J=7.4 Hz), 1.63-1.79 (3H, m), 1.92 (1H, m), 1.98 (1H, m), 2.08-2.30 (3H, m), 3.14 (1H, d, J=11.6 Hz), 3.25 (1H, d, J=12.0 Hz), 3.70 (1H, s), 3.94 (1H, d, J=7.6 Hz), 2 protons were not observed in CD$_3$OD.

Step 3. (2R,5S)-N'-butanoyl-7-oxo-6-(sulfooxy)-1,6-diazabicyclo[3.2.1]octane-2-carbohydrazide (Compound 25, Table 2)

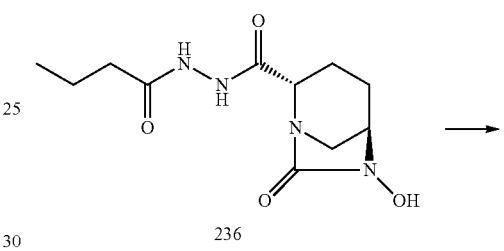

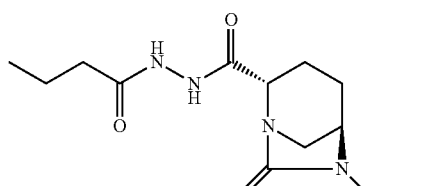

Compound 25, Table 2

To a solution of 236 (0.21 g, 0.77 mmol) in dry pyridine (10 mL) under nitrogen atmosphere was added sulfur trioxide pyridine complex (1.20 g, 7.60 mmol). The mixture was stirred at room temperature for 20 h, filtered and evaporated. The residue was purified first by column chromatography followed by HPLC on a prep-X Bridge-30×100 mm column and freeze-dried to give (2R,5S)-N'-butanoyl-7-oxo-6-(sulfooxy)-1,6-diazabicyclo[3.2.1]octane-2-carbohydrazide Compound 25 (Table 2) (0.020 g, 7.5%) as a pink solid.

$^1$H NMR (400 MHz, CD$_3$OD): δ 97 (3H, t, J=7.4 Hz), 1.67 (2H, m), 1.77 (1H, m), 1.93 (1H, m), 2.07 (1H, m), 2.22-2.30 (3H, m), 3.30 (2H, m), 4.01 (1H, d, J=7.6 Hz), 4.15 (1H, s), 3 protons were not observed in CD$_3$OD.

HPLC: 95.2%

MS (ES$^-$) m/z: [M]$^-$=349

Example 60

(2S,5R)-7-oxo-N'-(pyridin-3-yl)-6-(sulfooxy)-1,6-diazabicyclo[3.2.1]octane-2-carbohydrazide (Compound 95, Table 2)

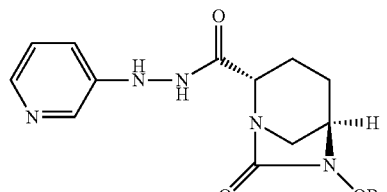

Step 1. (2S,5R)-6-(benzyloxy)-7-oxo-N'-(pyridin-3-yl)-1,6-diazabicyclo[3.2.1]octane-2-carbohydrazide (238)

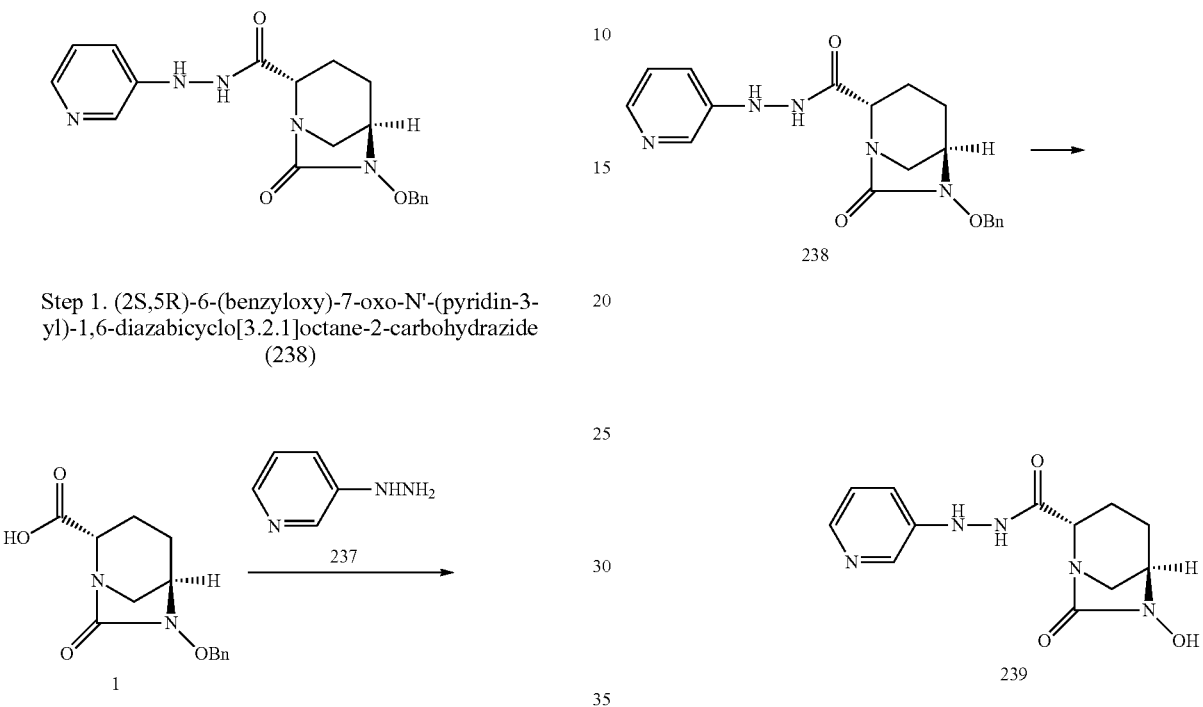

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added 3-hydrazinopyridine dihydrochloride 237 (0.120 g, 1.358 mmol), 1-hydroxybenzotriazole (0.186 g, 1.358 mmol) and 1-ethyl-(3-dimethylamino propyl) carbodiimide hydrochloride (0.260 g, 1.358 mmol) sequentially at room temperature. The mixture was stirred at room temperature overnight, diluted with DCM and concentrated to provide a residue which was subjected to chromatography to give 238 (0.20 g, 60%) as a white foam.

$^1$H NMR (400 MHz, CDCl$_3$): δ 1.62 (1H, m), 1.97 (2H, m), 2.25 (1H, m), 2.84 (1H, d, J=11.6 Hz), 3.14 (1H, d, J=11.2 Hz), 3.34 (1H, m), 4.06 (1H, m), 4.91 (1H, d, J=11.2 Hz), 5.05 (1H, d, J=11.2 Hz), 7.18 (1H, m), 7.42 (5H, m), 8.14 (1H, m), 8.22 (1H, m), 8.67 (1H, s). 2 protons were not observed in moisture-containing CDCl$_3$.

MS (ES$^+$) m/z: [M+H]$^+$ calcd for C$_{11}$H$_{23}$N$_4$O$_4$: 347.2. Found: 347.2.

Step 2. (2S,5R)-6-hydroxy-7-oxo-N'-(pyridin-3-yl)-1,6-diazabicyclo[3.2.1]octane-2-carbohydrazide (239)

A mixture of (2S,5R)-6-(benzyloxy)-7-oxo-N'-(pyridin-3-yl)-1,6-diazabicyclo[3.2.1]octane-2-carbohydrazide 238 (0.20 g, 0.54 mmol) and Pd/C (0.08 g) in methanol (20 mL) was hydrogenated at 1 atm at room temperature for 3 h. The mixture was filtered through Celite pad and concentrated to provide 239 (0.13 g, 87%) as a white foam.

$^1$H NMR (400 MHz, CD$_3$OD): δ 1.80 (1H, m), 2.00 (1H, m), 2.09 (1H, m), 2.22 (1H, m), 3.07 (1H, d, J=11.6 Hz), 3.21 (1H, m), 3.72 (1H, br s), 4.03 (1H, d, J=0.8 Hz), 7.25 (2H, m), 7.96 (1H, m), 8.10 (1H, s). 3 protons were not observed in CD$_3$OD.

MS (ES$^+$) m/z: [M+H]$^+$ calcd for C$_{12}$H$_{16}$N$_5$O$_3$: 278.1. Found: 278.1.

Step 3. (2S,5R)-7-oxo-N'-(pyridin-3-yl)-6-(sulfooxy)-1,6-diazabicyclo[3.2.1]octane-2-carbohydrazide (Compound 95, Table 2)

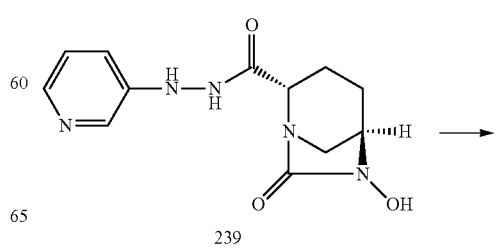

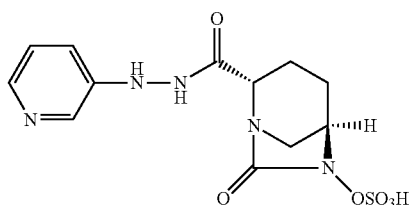

Compound 95, Table 2

To a mixture of (2S,5R)-6-hydroxy-7-oxo-N'-(pyridin-3-yl)-1,6-diazabicyclo[3.2.1]octane-2-carbohydrazide 239 (0.13 g, 0.47 mmol) in pyridine (6.0 mL) was added sulfur trioxide pyridine complex (0.44 g, 2.80 mmol). The mixture was stirred at room temperature for 2 days and concentrated to provide a residue which was subjected to chromatography followed by HPLC separation to give Compound 95 (Table 2) (6.9 mg) as a white solid.

$^1$H NMR (400 MHz, CD$_3$OD): δ 1.81 (1H. m), 2.00 (1H, m), 2.12 (1H, m), 2.26 (1H, m), 3.09 (1H, d, J=11.6 Hz), 3.36 (1H, m), 4.12 (1H, d, J=2.8 Hz), 4.18 (1H, m), 7.74 (2H, m), 8.19 (2H, m). 3 protons were not observed in CD$_3$OD.

HPLC: 94.63%.

MS (ES$^-$) m/z: [M–H]$^-$ calcd for C$_{12}$H$_{14}$N$_5$O$_6$S: 356.1. Found: 356.0

Example 61

(2R,5S)-N'-[(dimethylamino)acetyl]-7-oxo-6-(sulfooxy)-1,6-diazabicyclo[3.2.1]octane-2-carbohydrazide (Compound 27, Table 2)

Step 1. (2R,5S)-6-(benzyloxy)-N'-[(dimethylamino)acetyl]-7-oxo-1,6-diazabicyclo[3.2.1]octane-2-carbohydrazide (241)

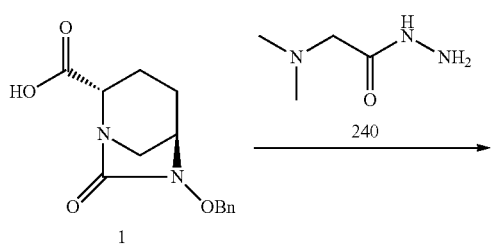

To a solution of (2S,5R)-6-(benzyloxy)-7-oxo-1,6-diazabicyclo[3.2.1]octane-2-carboxylic acid 1 (0.25 g, 0.90 mmol) in dry DCM (40 mL) were added 2-(dimethylamino)acetohydrazide 240 (0.32 g, 1.68 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.40 g, 3.36 mmol) at room temperature. The reaction mixture was stirred at room temperature overnight and concentrated under vacuum. The residue was purified by column chromatography to give (2R,5S)-6-(benzyloxy)-N'-[(dimethylamino)acetyl]-7-oxo-1,6-diazabicyclo[3.2.1]octane-2-carbohydrazide 241 (0.15 g, 44.5%) as a white solid.

$^1$H NMR (400 MHz, CDCl$_3$): δ 1.61 (1H, m), 1.98 (2H, m), 2.33 (7H, m), 3.12 (4H, m), 3.31 (1H, s), 4.03 (1H, d, J=7.2 Hz), 4.90 (1H, d, J=11.2 Hz), 5.05 (1H, d, J=11.6 Hz), 7.38 (5H, m), 8.40 (2H, br s).

Step 2. (2R,5S)-N'-[(dimethylamino)acetyl]-6-hydroxy-7-oxo-1,6-diazabicyclo[3.2.1]octane-2-carbohydrazide (242)

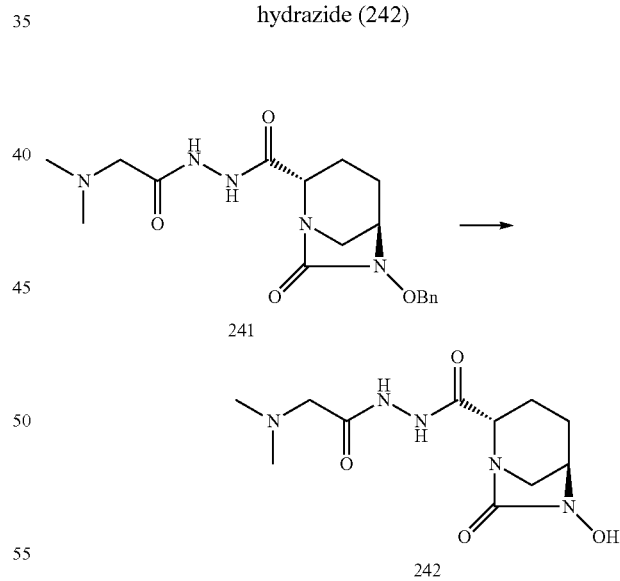

To a solution of (2R,5S)-6-(benzyloxy)-N'-[(dimethylamino)acetyl]-7-oxo-1,6-diazabicyclo[3.2.1]octane-2-carbohydrazide 241 (0.15 g, 0.40 mml) in methanol (20 mL) was added 5% Pd/C (0.20 g). The mixture was hydrogenated under 10 psi hydrogen atmosphere at room temperature for 1 h. The catalyst was filtered out through Celite and the filtrate was evaporated to give (2R,5S)-N'-[(dimethylamino)acetyl]-6-hydroxy-7-oxo-1,6-diazabicyclo[3.2.1]octane-2-carbohydrazide 242 (0.10 g, 88%) as a white foam.

¹H NMR (400 MHz, CD₃OD): δ 1.75 (1H, m), 1.94 (1H, m), 2.05 (1H, m), 2.28 (1H, m), 2.42 (6H, s), 3.27 (4H, m), 3.70 (1H, s), 3.95 (1H, d, J=7.2 Hz), 3 protons were not observed in CD₃OD.

Step 3. (2R,5S)-N'-[(dimethylamino)acetyl]-7-oxo-6-(sulfooxy)-1,6-diazabicyclo[3.2.1]octane-2-carbohydrazide (Compound 27, Table 2)

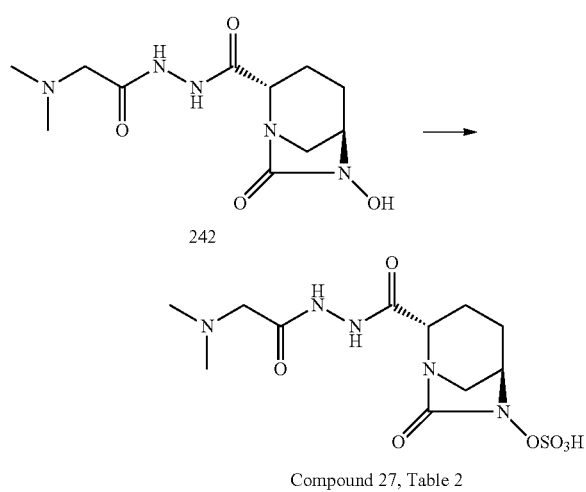

Compound 27, Table 2

To a solution of (2R,5S)-N'-[(dimethylamino)acetyl]-6-hydroxy-7-oxo-1,6-diazabicyclo[3.2.1]octane-2-carbohydrazide 242 (0.10 g, 0.35 mmol) in dry pyridine (6 mL) under nitrogen atmosphere was added sulfur trioxide pyridine complex (0.60 g, 3.80 mmol). The mixture was stirred at room temperature for 20 h, filtered and evaporated. The residue was purified by column chromatography to give (2R,5S)-N'-[(dimethylamino)acetyl]-7-oxo-6-(sulfooxy)-1,6-diazabicyclo[3.2.1]octane-2-carbohydrazide, Compound 27 (Table 2) (0.020 g, 12.7%) as a brown solid.

¹H NMR (400 MHz, CD₃OD): δ 1.72 (1H, m), 1.93 (1H, m), 2.09 (1H, m), 2.30 (1H, m), 2.98 (6H, s), 3.27 (4H, m), 4.06 (1H, d, J=7.6 Hz), 4.17 (1H, s), 3 protons were not observed in CD₃OD.
HPLC: 92.3%
MS (ES⁻) m/z: [M]⁻=364

Example 62

(2R,5S)-N'-[(2,2-dimethylcyclopropyl)carbonyl]-7-oxo-6-(sulfooxy)-1,6-diazabicyclo[3.2.1]octane-2-carbohydrazide (Compound 34, Table 2)

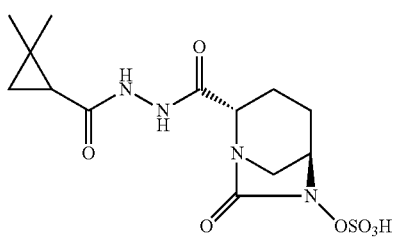

Step 1. (2S,5R)-6-(benzyloxy)-N'-((R)-2,2-dimethylcyclopropanecarbonyl)-7-oxo-1,6-diazabicyclo[3.2.1]octane-2-carbohydrazide (244)

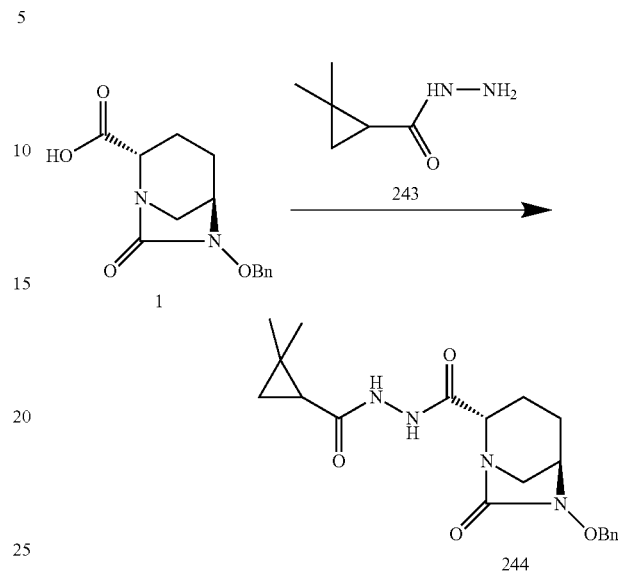

To a solution of (2S,5R)-6-(benzyloxy)-7-oxo-1,6-diazabicyclo[3.2.1]octane-2-carboxylic acid 1 (0.276 g, 1.0 mmol) in dry DCM (20 mL) were added 243 (0.173 g, 1.35 mmol), 1-hydroxybenzotriazole (0.203 g, 1.5 mmol), and 1-ethyl-(3-dimethylaminopropyl)carbodiimide hydrochloride (0.288 g, 1.5 mmol) at room temperature. The reaction mixture was stirred at room temperature overnight and concentrated under vacuum. The residue was purified by column chromatography to give 244 (0.350 g, 91%) as a white foam.

Step 2. (2S,5R)-N'-((S)-2,2-dimethylcyclopropanecarbonyl)-6-hydroxy-7-oxo-1,6-diazabicyclo[3.2.1]octane-2-carbohydrazide (245)

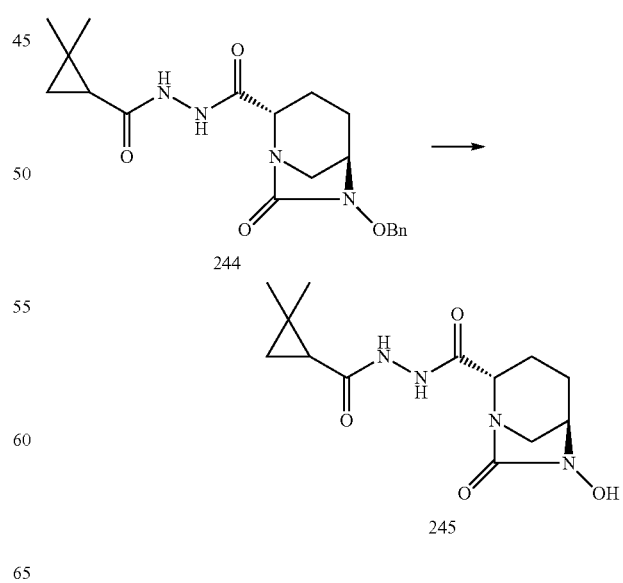

A mixture of (2S,5R)-6-(benzyloxy)-N'-((R)-2,2-dimethylcyclopropanecarbonyl)-7-oxo-1,6-diazabicyclo[3.2.1]octane-2-carbohydrazide 244 (0.35 g, 0.90 mmol) and Pd/C (0.50 g) in methanol (80 mL) was hydrogenated at 1 atm at room temperature for 3 h. The mixture was filtered through Celite pad and concentrated to provide 245 (0.27 g, quant.) as an off-white solid.

Step 3. (2R,5S)-N'-[(2,2-dimethylcyclopropyl)carbonyl]-7-oxo-6-(sulfooxy)-1,6-diazabicyclo[3.2.1]octane-2-carbohydrazide (Compound 34, Table 2)

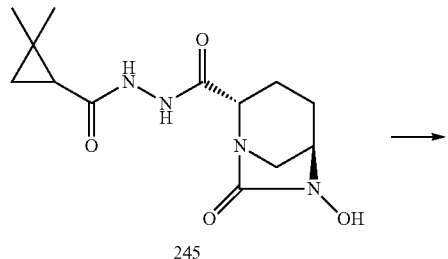

245

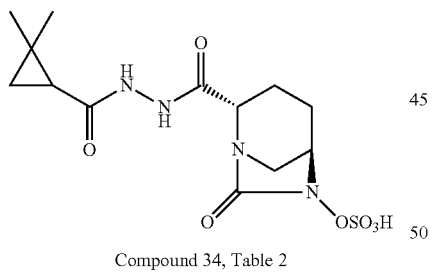

Compound 34, Table 2

To a mixture of (2S,5R)-N'-((S)-2,2-dimethylcyclopropanecarbonyl)-6-hydroxy-7-oxo-1,6-diazabicyclo[3.2.1]octane-2-carbohydrazide 245 (0.27 g, 0.90 mmol) in pyridine (6 mL) was added sulfur trioxide pyridine complex (0.42 g, 2.70 mmol).). The mixture was stirred at room temperature for 24 h and concentrated to provide a residue which was subjected to chromatography to give Compound 34 (Table 2) (0.166 g) as an off-white solid.

$^1$H NMR (400 MHz, D$_2$O): δ 0.80 (1H, m), 0.91 (1H, m), 0.98 (3H, s), 1.04 (3H, s), 1.47 (1H, m), 1.69 (1H, m), 1.84 (1H, m), 1.95 (1H, m), 2.09 (1H, m), 3.10 (1H, t, J=11.0 Hz), 3.22 (1H, d, J=12.0 Hz), 4.03 (1H, d, J=7.2 Hz), 4.09 (1H, s). 3 protons were not observed in D$_2$O.

HPLC: 97.82%

MS (ES$^-$) m/z: [M–H]$^-$ calcd for C$_{13}$H$_{19}$N$_4$O$_7$S: 375.4. Found: 375.0.

Example 63

(2R,5S)-N'-(2-methylbutanoyl)-7-oxo-6-(sulfooxy)-1,6-diazabicyclo[3.2.1]octane-2-carbohydrazide (Compound 26, Table 2)

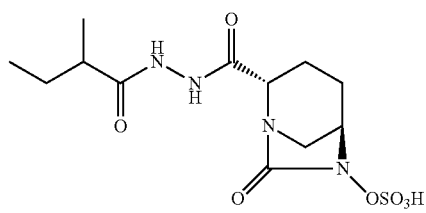

Step 1. (2S,5R)-6-(benzyloxy)-N'-(2-methylbutanoyl)-7-oxo-1,6-diazabicyclo[3.2.1]-octane-2-carbohydrazide (247)

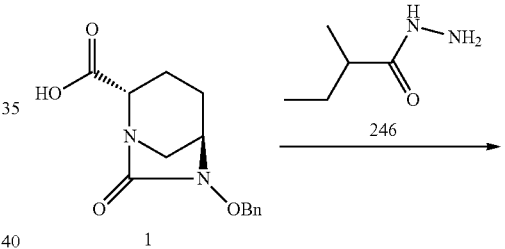

247

To a solution of (2S,5R)-6-(benzyloxy)-7-oxo-1,6-diazabicyclo[3.2.1]octane-2-carboxylic acid 1 (0.276 g, 1.0 mmol) in dry DCM (20 mL) were added 246 (0.174 g, 1.5 mmol), 1-hydroxybenzotriazole (0.203 g, 1.5 mmol), and 1-ethyl-(3-dimethylaminopropyl)carbodiimide hydrochloride (0.288 g, 1.5 mmol) at room temperature. The reaction mixture was stirred at room temperature overnight and concentrated under vacuum. The residue was purified by column chromatography to give 247 (0.260 g, 70%) as a colorless sticky mass.

Step 2. (2S,5R)-6-hydroxy-N'-(2-methylbutanoyl)-7-oxo-1,6-diazabicyclo[3.2.1]octane-2-carbohydrazide (248)

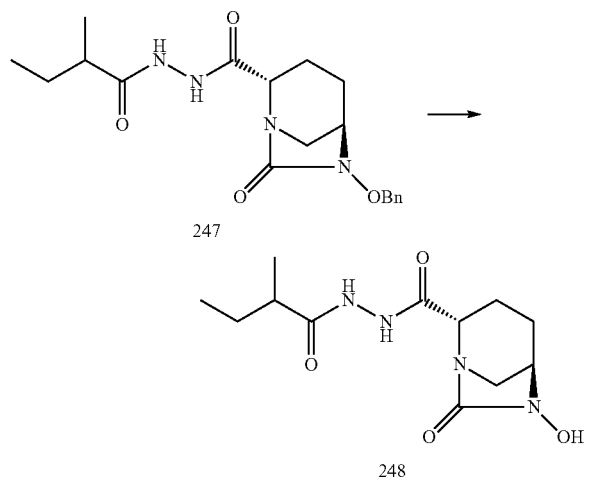

A mixture of (2S,5R)-6-(benzyloxy)-N'-(2-methylbutanoyl)-7-oxo-1,6-diazabicyclo[3.2.1]-octane-2-carbohydrazide 247 (0.26 g, 0.69 mmol) and Pd/C (0.30 g) in methanol (80 mL) was hydrogenated at 1 atm at room temperature for 2.5 h. The mixture was filtered through Celite pad and concentrated to provide 248 (0.18 g) as an off-white solid which was used in the next step without purification.

Step 3. (2R,5S)-N'-(2-methylbutanoyl)-7-oxo-6-(sulfooxy)-1,6-diazabicyclo[3.2.1]octane-2-carbohydrazide (Compound 26, Table 2)

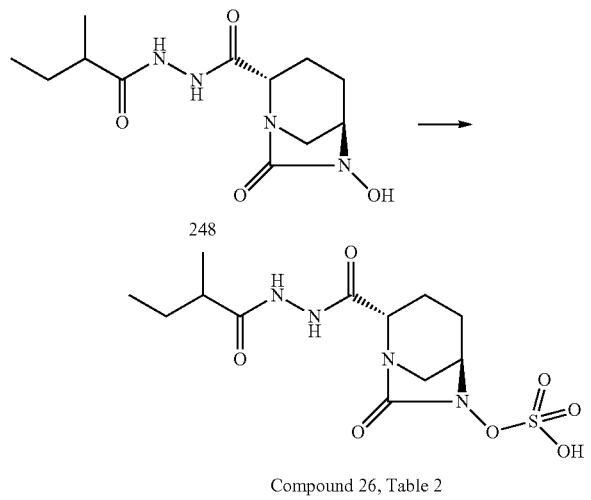

To a mixture of (2S,5R)-6-hydroxy-N'-(2-methylbutanoyl)-7-oxo-1,6-diazabicyclo[3.2.1]octane-2-carbohydrazide 248 (0.18 g, 0.63 mmol) in pyridine (6 mL) was added sulfur trioxide pyridine complex (0.30 g, 1.89 mmol). The mixture was stirred at room temperature for 24 h and concentrated to provide a residue which was subjected to chromatography followed by HPLC separation to give Compound 26 (Table 2) (0.0095 g) as a white solid.

$^1$H NMR (400 MHz, D$_2$O): δ 0.76 (3H, m), 1.00 (3H, d, J=6.8 Hz), 1.40 (2H, m), 1.70 (1H, m), 1.81 (1H, m), 1.96 (1H, m), 2.09 (1H, m), 2.25 (1H, m), 3.10 (1H, d, J=12.0 Hz), 3.21 (1H, d, J=12.0 Hz), 4.03 (1H, d, J=7.6 Hz), 4.08 (1H, s). 3 protons were not observed in D$_2$O.

HPLC: 98.38%

MS (ES$^-$) m/z: [M–H]$^-$ calcd for C$_{12}$H$_{19}$N$_4$O$_7$S: 363.4. Found: 363.0.

Example 64

(2S,5R)-N'-[amino(phenyl)acetyl]-7-oxo-6-(sulfooxy)-1,6-diazabicyclo[3.2.1]octane-2-carbohydrazide trifluoroacetate (Compound 31, Table 2)

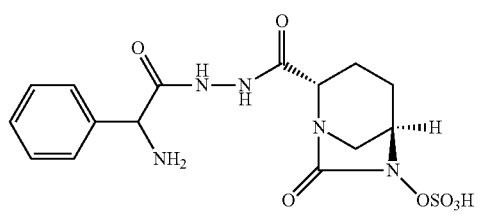

Step 1. tert-butyl[2-(2-{[(2S,5R)-6-(benzyloxy)-7-oxo-1,6-diazabicyclo[3.2.1]oct-2-yl]carbonyl}hydrazinyl)-2-oxo-1-phenylethyl]carbamate (250)

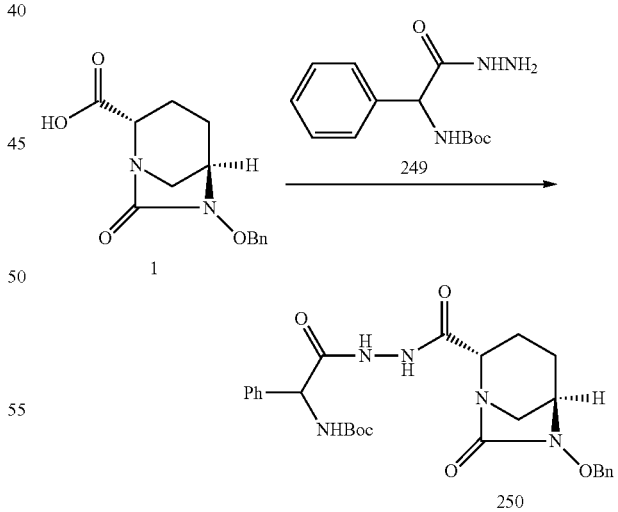

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added tert-butyl (2-hydrazinyl-2-oxo-1-phenylethyl)carbamate 249 (0.360 g, 1.358 mmol), 1-hydroxybenzotriazole (0.186 g, 1.358 mmol) and 1-ethyl-(3-dimethylamino propyl) carbodiimide hydrochloride (0.260 g, 1.358 mmol) sequentially at room temperature.

The mixture was stirred at room temperature overnight, diluted with DCM and concentrated to provide a residue which was subjected to chromatography to give 250 (0.40 g, 84%) as a white foam.

$^1$H NMR (400 MHz, CDCl$_3$): δ 1.42 (9H, s), 1.62 (1H, m), 1.97 (2H, m), 2.25 (1H, m), 3.10 (2H, m), 3.27 (1H, m), 3.94 (1H, m), 4.91 (1H, d, J=11.6 Hz), 5.05 (1H, d, J=11.6 Hz), 5.34 (1H, m), 5.60 (1H, m), 7.42 (10H, m), 8.30-8.50 (2H, m).

MS (ES$^-$) m/z: [M–H]$^-$ calcd for C$_{27}$H$_{32}$N$_5$O$_6$: 522.2. Found: 522.1.

Step 2. tert-butyl[2-(2-{[(2S,5R)-6-hydroxy-7-oxo-1,6-diazabicyclo[3.2.1]oct-2-yl]carbonyl}hydrazinyl)-2-oxo-1-phenylethyl]carbamate (251)

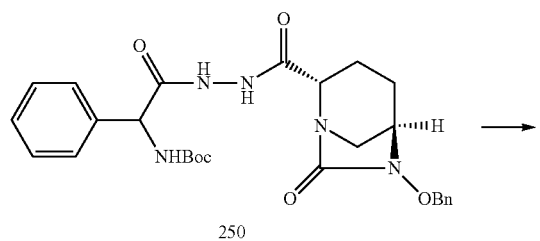

250

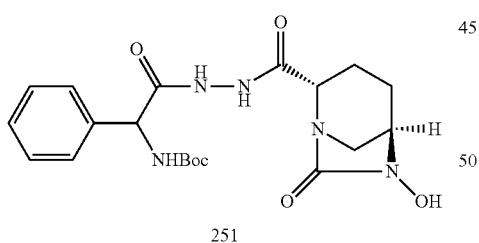

251

A mixture of tert-butyl[2-(2-{[(2S,5R)-6-(benzyloxy)-7-oxo-1,6-diazabicyclo[3.2.1]oct-2-yl]carbonyl}hydrazinyl)-2-oxo-1-phenylethyl]carbamate 250 (0.40 g, 0.76 mmol) and Pd/C (0.20 g) in methanol (15 mL) was hydrogenated at 1 atm at room temperature for 3 h. The mixture was filtered through Celite pad and concentrated to provide 251 (0.34 g, quant. yield) as a white foam.

$^1$H NMR (400 MHz, CD$_3$OD): δ 1.44 (9H, s), 1.45 (1H, m), 1.88 (1H, m), 2.05 (1H, m), 2.25 (1H, m), 3.11-3.28 (2H, m), 3.71 (1H, br s), 3.94 (1H, d, J=7.6 Hz), 5.30 (1H, m), 7.25 (2H, m), 7.30 (3H, m). 4 protons were not observed in CD$_3$OD.

MS (ES$^-$) m/z: [M–H]$^-$ calcd for C$_{20}$H$_{26}$N$_5$O$_6$: 432.2. Found: 432.1.

Step 3. tert-butyl[2-oxo-2-(2-{[(2S,5R)-7-oxo-6-(sulfooxy)-1,6-diazabicyclo[3.2.1]oct-2-yl]carbonyl}hydrazinyl)-1-phenylethyl]carbamate (252)

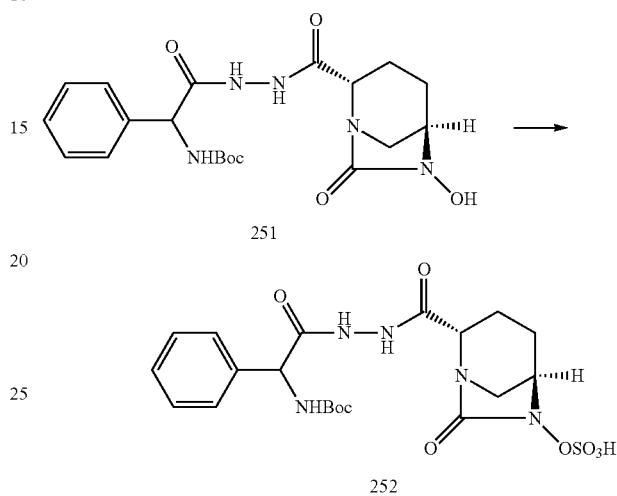

To a mixture of tert-butyl[2-(2-{[(2S,5R)-6-hydroxy-7-oxo-1,6-diazabicyclo[3.2.1]oct-2-yl]carbonyl}hydrazinyl)-2-oxo-1-phenylethyl]carbamate 251 (0.33 g, 0.76 mmol) in pyridine (6.0 mL) was added sulfur trioxide pyridine complex (0.71 g, 4.46 mmol). The mixture was stirred at room temperature for 2 days and concentrated to provide a residue which was subjected to chromatography to give 252 (0.25 g, 64%) as a white solid.

$^1$H NMR (400 MHz, CD$_3$OD): δ 1.44 (9H, s), 1.78 (1H. m), 1.90 (1H, m), 2.12 (1H, m), 2.26 (1H, m), 3.30 (2H, m), 4.12 (2H, m), 5.30 (1H, m), 7.38 (3H, m), 7.45 (2H, m). 4 protons were not observed in CD$_3$OD.

MS (ES$^-$) m/z: [M–H]$^-$ calcd for C$_{20}$H$_{26}$N$_5$O$_9$S: 512.1. Found: 512.1.

Step 4. (2S,5R)-N'-[amino(phenyl)acetyl]-7-oxo-6-(sulfooxy)-1,6-diazabicyclo[3.2.1]octane-2-carbohydrazide trifluoroacetate (Compound 31, Table 2)

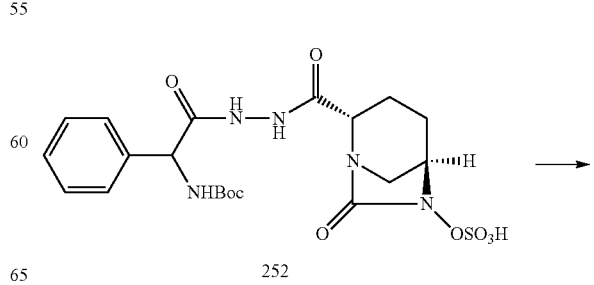

252

309
-continued

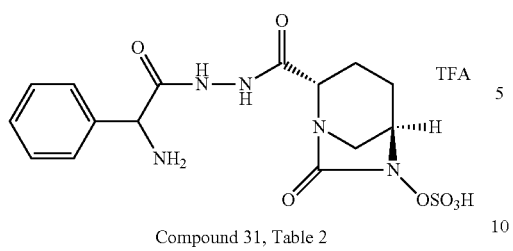

Compound 31, Table 2

To a mixture of tert-butyl[2-oxo-2-(2-{[(2S,5R)-7-oxo-6-(sulfooxy)-1,6-diazabicyclo[3.2.1]oct-2-yl]carbonyl}hydrazinyl)-1-phenylethyl]carbamate 252 (0.25 g, 0.48 mmol) in DCM (8.0 mL) was added trifluoroacetic acid (0.40 mL) at 0° C. The mixture was stirred at 0° C. for 3 h, concentrated and washed with ether to give Compound 31 (Table 2) (0.14 g) as a white solid as a pair of diastereomers in a ratio of 1:2.

$^1$H NMR (400 MHz, D$_2$O): δ 1.65 (1H, m), 1.80 (1H, m), 1.95 (1H, m), 2.08 (1H, m), 3.04 (1H, m), 3.22 (1H, d, J=11.2 Hz), 4.02 (1H, d, J=6.0 Hz), 4.08 (1H, m), 5.15 (1H, s), 7.42 (5H, m). Five protons were not observed in D$_2$O.

HPLC: 92.19%

MS (ES$^-$) m/z: [M–H]$^-$ calcd for C$_{15}$H$_{18}$N$_5$O$_7$S: 412.1. Found: 412.0.

Example 65

(2S,5R)-N'-(2,2-dimethylpropanoyl)-7-oxo-6-(sulfooxy)-1,6-diazabicyclo[3.2.1]octane-2-carbohydrazide (Compound 24, Table 2)

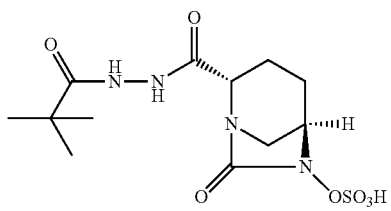

Step 1. (2S,5R)-6-(benzyloxy)-N'-(2,2-dimethylpropanoyl)-7-oxo-1,6-diazabicyclo[3.2.1]octane-2-carbohydrazide (254)

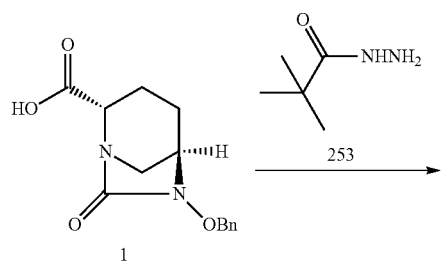

310
-continued

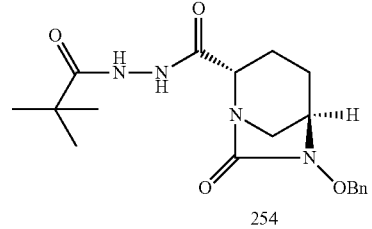

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added 2,2-dimethylpropanehydrazide 253 (0.137 g, 1.358 mmol), 1-hydroxybenzotriazole (0.186 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 254 (0.32 g, 94%) as a white foam.

$^1$H NMR (400 MHz, CDCl$_3$): δ 1.24 (9H, m), 1.62 (1H, m), 1.99 (2H, m), 2.31 (1H, m), 3.10 (2H, m), 3.28 (1H, m), 4.01 (1H, d, J=3.2 Hz), 4.91 (1H, d, J=11.2 Hz), 5.05 (1H, d, J=11.2 Hz), 7.42 (5H, m), 7.64 (1H, s), 8.48 (1H, s).

MS (ES$^-$) m/z: [M–H]$^-$ calcd for C$_{19}$H$_{25}$N$_4$O$_4$: 373.2. Found: 373.1.

Step 2. (2S,5R)-N'-(2,2-dimethylpropanoyl)-6-hydroxy-7-oxo-1,6-diazabicyclo[3.2.1]octane-2-carbohydrazide (255)

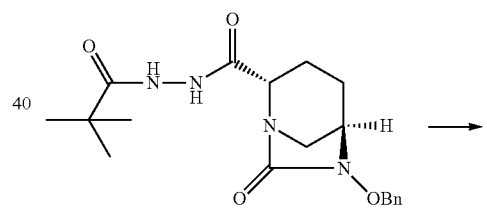

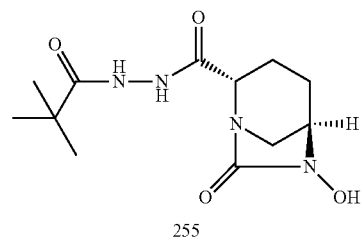

A mixture of (2S,5R)-6-(benzyloxy)-N'-(2,2-dimethylpropanoyl)-7-oxo-1,6-diazabicyclo[3.2.1]octane-2-carbohydrazide 254 (0.32 g, 0.86 mmol) and Pd/C (0.15 g) in methanol (20 mL) was hydrogenated at 1 atm at room temperature overnight. The mixture was filtered through Celite pad and concentrated to provide 255 (0.25 g, quant. yield) as a white foam.

$^1$H NMR (400 MHz, CD$_3$OD): δ 1.25 (9H, s), 1.75 (1H, m), 1.92 (1H, m), 2.05 (1H, m), 2.28 (1H, m), 3.14 (1H, m), 3.30 (1H, m), 3.70 (1H, br s), 3.94 (1H, d, J=7.2 Hz). 3 protons were not observed in CD$_3$OD.

MS (ES⁺) m/z: [M+H]⁺ calcd for $C_{12}H_{21}N_4O_4$: 285.1. Found: 285.1.

Step 3. (2S,5R)-N'-(2,2-dimethylpropanoyl)-7-oxo-6-(sulfooxy)-1,6-diazabicyclo[3.2.1]octane-2-carbohydrazide (Compound 24, Table 2)

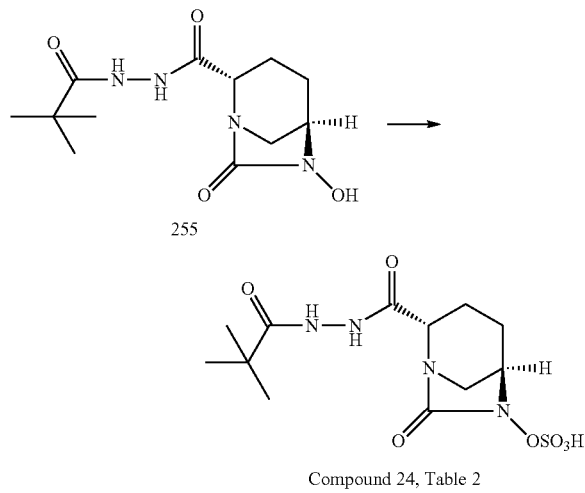

Compound 24, Table 2

To a mixture of (2S,5R)-N'-(2,2-dimethylpropanoyl)-6-hydroxy-7-oxo-1,6-diazabicyclo[3.2.1]octane-2-carbohydrazide 255 (0.25 g, 0.85 mmol) in pyridine (10.0 mL) was added sulfur trioxide pyridine complex (0.42 g, 2.58 mmol). The mixture was stirred at room temperature overnight and concentrated to provide a residue which was subjected to chromatography followed by HPLC separation to give Compound 24 (Table 2) (20 mg) as a white solid.

¹H NMR (400 MHz, D₂O): δ 1.08 (9H, s), 1.65 (1H, m), 1.80 (1H, m), 1.95 (1H, m), 2.10 (1H, m), 3.10 (1H, d, J=12.4 Hz), 3.22 (1H, d, J=12.0 Hz), 4.02 (1H, d, J=7.6 Hz), 4.08 (1H, m). Three protons were not observed in D₂O.

HPLC: 93.08%.

MS (ES⁻) m/z: [M−H]⁻ calcd for $C_{20}H_{19}N_4O_7S$: 363.1. Found: 363.0.

Example 66

(2S,5R)-7-oxo-N-(2-oxopiperidin-1-yl)-6-(sulfooxy)-1,6-diazabicyclo[3.2.1]octane-2-carboxamide (Compound 103, Table 2)

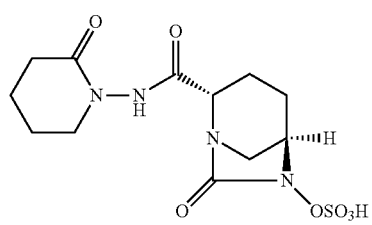

Step 1. (2S,5R)-6-(benzyloxy)-7-oxo-N-(2-oxopiperidin-1-yl)-1,6-diazabicyclo[3.2.1]octane-2-carboxamide (257)

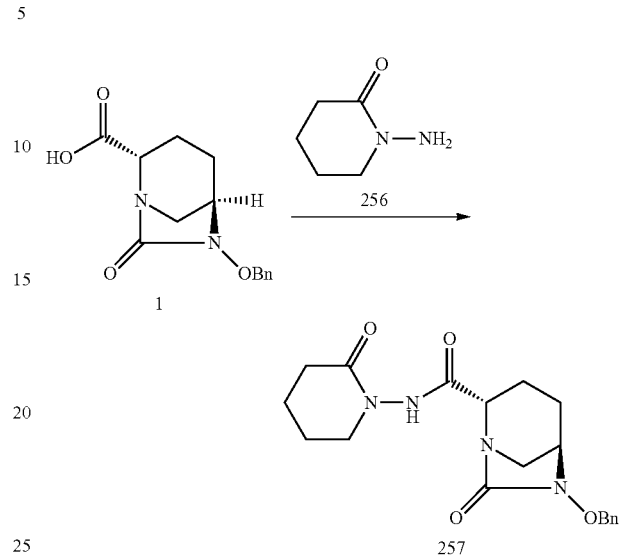

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added 1-aminopiperidin-2-one 256 (31 mg, 0.27 mmol),), HOBt (38 mg, 0.27 mmol), DMAP (32 mg, 0.27 mmol) and EDCI (53 mg, 0.27 mmol). The mixture was stirred at room temperature for 48 h and purified by column to afford 257 as foam (55 mg, 82%).

¹HNMR (CDCl₃): 8.45 (1H, s), 7.40 (5H, m), 4.99 (2H, dd), 4.02 (1H, d), 3.70 (1H, m), 3.43 (1H, m), 3.32 (2H, m), 3.07 (1H, m), 2.40 (3H, m), 1.90 (6H, m), 1.60 (1H, m).

Step 2. (2S,5R)-6-hydroxy-7-oxo-N-(2-oxopiperidin-1-yl)-1,6-diazabicyclo[3.2.1]octane-2-carboxamide (258)

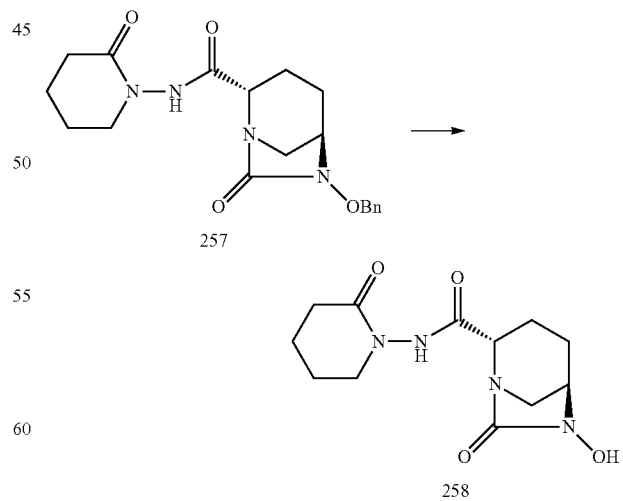

To a solution of compound 257 (55 mg, 0.148 mmol) in 10 mL of MeOH was added 100 mg of Pd/C (10%, wet). The mixture was hydrogenated at room temperature for 2 h. The catalyst was removed by filtration through Celite pad. The filtrate was concentrated to afford compound 258 as a colorless gum (37 mg, 88%).

¹HNMR (CD₃OD): 3.98 (1H, d), 3.72 (1H, m), 3.55 (2H, m), 3.30 (1H, m), 3.18 (1H, m), 2.49 (2H, m), 2.30 (1H, m), 1.90 (7H, m).

Step 3. (2S,5R)-7-oxo-N-(2-oxopiperidin-1-yl)-6-(sulfooxy)-1,6-diazabicyclo[3.2.1]octane-2-carboxamide (Compound 103, Table 2)

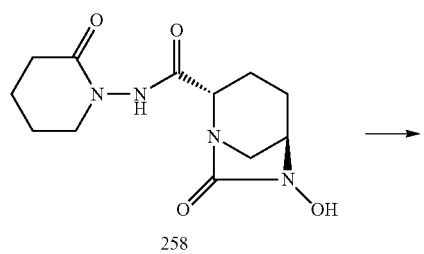

258

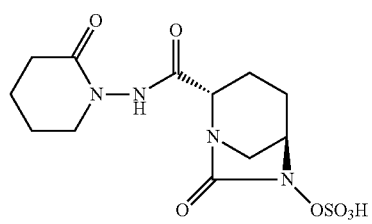

Compound 103, Table 2

To a solution of compound 258 (35 mg, 0.124 mmol) in 5 mL of pyridine was added sulphur trioxide pyridine complex (190 mg, 1.24 mmol). The mixture was stirred at room temperature under nitrogen atmosphere for 72 h. After silica gel column followed by HPLC purification, pure compound 103 (Table 2) was obtained as a white solid (20 mg, 45%) ¹HNMR (CD₃OD): 4.18 (1H, s), 4.03 (1H, d), 3.58 (2H, m), 3.30 (2H, m), 2.50 (2H, m), 2.30 (1H, m), 1.90 (7H, m)

HPLC: 93%.

MS (ES⁻) m/z: [M–H]⁻ Found: 361.0.

Example 67

(2R,5S)-N'-(azetidin-3-ylcarbonyl)-7-oxo-6-(sulfooxy)-1,6-diazabicyclo[3.2.1]octane-2-carbohydrazide (Compound 112, Table 2)

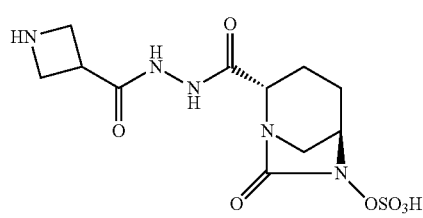

Step 1. tert-butyl 3-[(2-{[(2R,5S)-6-(benzyloxy)-7-oxo-1,6-diazabicyclo[3.2.1]oct-2-yl]carbonyl}hydrazinyl)carbonyl]azetidine-1-carboxylate (260)

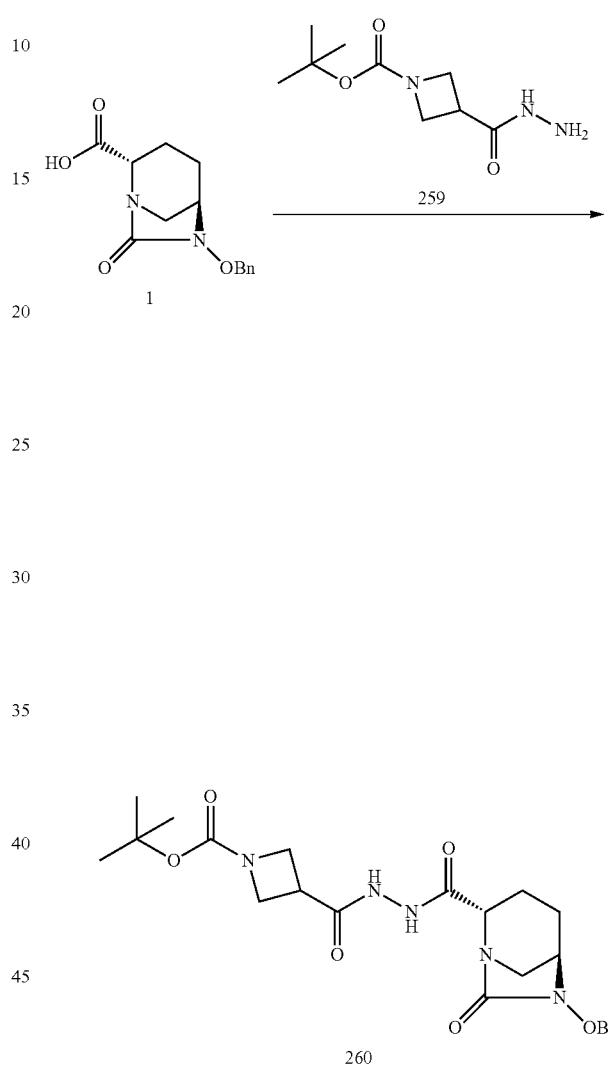

To a solution of (2S,5R)-6-(benzyloxy)-7-oxo-1,6-diazabicyclo[3.2.1]octane-2-carboxylic acid 1 (0.25 g, 0.90 mmol) in dry DCM (30 mL) were added tert-butyl 3-(hydrazinylcarbonyl)azetidine-1-carboxylate 259 (0.29 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight and concentrated under vacuum. The residue was purified by column chromatography to give tert-butyl 3-[(2-{[(2R,5S)-6-(benzyloxy)-7-oxo-1,6-diazabicyclo[3.2.1]oct-2-yl]carbonyl}hydrazinyl)carbonyl]azetidine-1-carboxylate 260 (0.35 g, 81%) as a white solid.

¹H NMR (400 MHz, CDCl₃): δ 1.38 (9H, s), 1.63 (1H, m), 1.99 (2H, m), 2.31 (1H, m), 3.15 (2H, m), 3.28 (2H, s), 4.00

(1H, d, J=7.6 Hz), 4.10 (4H, m), 4.90 (1H, d, J=11.2 Hz), 5.04 (1H, d, J=11.6 Hz), 7.39 (5H, m), 7.86 (1H, br s), 8.54 (1H, br s).

Step 2. tert-butyl 3-[(2-{[(2R,5S)-6-hydroxy-7-oxo-1,6-diazabicyclo[3.2.1]oct-2-yl]carbonyl}hydrazinyl)carbonyl]azetidine-1-carboxylate (261)

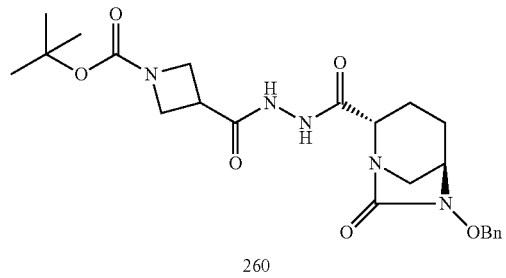

260

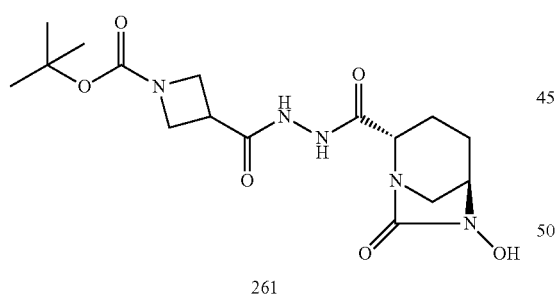

261

To a solution of tert-butyl 3-[(2-{[(2R,5S)-6-(benzyloxy)-7-oxo-1,6-diazabicyclo[3.2.1]oct-2-yl]carbonyl}hydrazinyl)carbonyl]azetidine-1-carboxylate 260 (0.35 g, 0.74 mml) in methanol (25 mL) was added 5% Pd/C (0.40 g). The mixture was hydrogenated under 10 psi hydrogen atmosphere at room temperature for 1 h. The catalyst was filtered out through Celite, and the filtrate was evaporated to give tert-butyl 3-[(2-{[(2R,5S)-6-hydroxy-7-oxo-1,6-diazabicyclo[3.2.1]oct-2-yl]carbonyl}hydrazinyl)carbonyl]azetidine-1-carboxylate 261 (0.25 g, 88%) as a white foam.

$^1$H NMR (400 MHz, CD$_3$OD): δ 1.44 (9H, s), 1.76 (1H, m), 1.91 (1H, m), 2.05 (1H, m), 2.26 (1H, m), 3.15 (1H, m), 3.25 (1H, m), 3.40 (1H, m), 3.71 (1H, s), 3.95 (1H, d, J=7.2 Hz), 4.08 (4H, m), 3 protons were not observed in CD$_3$OD.

Step 3. tert-butyl 3-[(2-{[(2R,5S)-7-oxo-6-(sulfooxy)-1,6-diazabicyclo[3.2.1]oct-2-yl]carbonyl}hydrazinyl)carbonyl]azetidine-1-carboxylate (262)

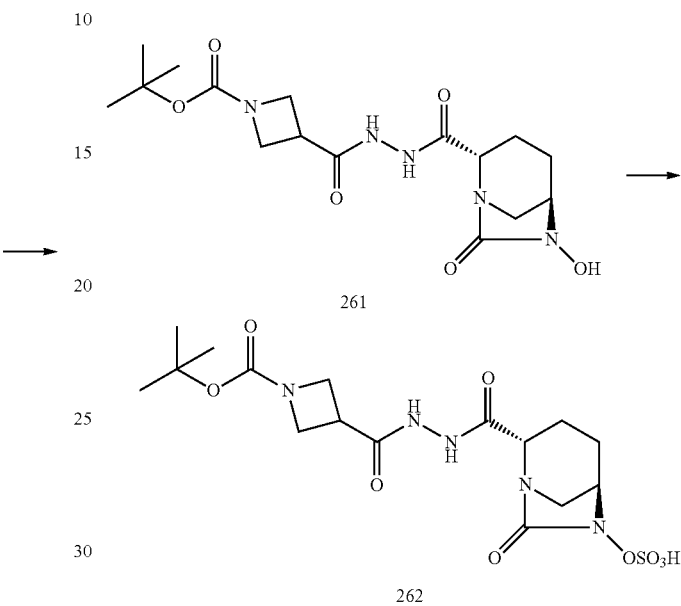

To a solution of tert-butyl 3-[(2-{[(2R,5S)-6-hydroxy-7-oxo-1,6-diazabicyclo[3.2.1]oct-2-yl]carbonyl}hydrazinyl)carbonyl]azetidine-1-carboxylate 261 (0.25 g, 0.65 mmol) in dry pyridine (10 mL) under nitrogen atmosphere was added sulfur trioxide pyridine complex (0.60 g, 3.80 mmol). The mixture was stirred at room temperature for 20 h, filtered and evaporated. The residue was purified first by column chromatography to give tert-butyl 3-[(2-{[(2R,5S)-7-oxo-6-(sulfooxy)-1,6-diazabicyclo[3.2.1]oct-2-yl]carbonyl}hydrazinyhcarbonyl]azetidine-1-carboxylate 262 (0.18 g, 60%) as a white solid.

$^1$H NMR (400 MHz, CD$_3$OD): δ 1.30 (9H, s), 1.81 (1H, m), 1.94 (1H, m), 2.05 (1H, m), 2.26 (1H, m), 3.30 (2H, m), 3.41 (1H, m), 4.04 (5H, m), 4.16 (1H, s), 3 protons were not observed in CD$_3$OD.

Step 4. (2R,5S)-N'-(azetidin-3-ylcarbonyl)-7-oxo-6-(sulfooxy)-1,6-diazabicyclo[3.2.1]octane-2-carbohydrazide (Compound 112, Table 2)

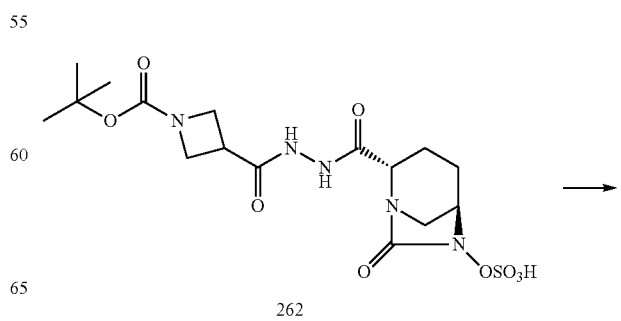

262

-continued

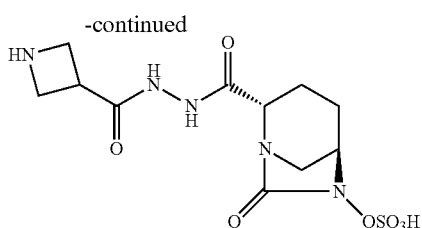

Compound 112, Table 2

To a solution tert-butyl 3-[(2-{[(2R,5S)-7-oxo-6-(sulfooxy)-1,6-diazabicyclo[3.2.1]oct-2-yl]carbonyl}hydrazinyl)carbonyl]azetidine-1-carboxylate 262 (0.18 g, 0.39 mmol) in DCM (18 mL) was added trifluoroacetic acid (1.45 mL, 18.79 mmol) dropwise at 0° C. The reaction mixture was stirred for 1 h then evaporated. Ether was added to the residue and the resulting white precipitate was collected by centrifugation. The solid was triturated with a mixture of MeOH:ether (1:5, 6×) and the white solid was collected by centrifugation to give (2R,5S)—N'-(azetidin-3-ylcarbonyl)-7-oxo-6-(sulfooxy)-1,6-diazabicyclo[3.2.1]octane-2-carbohydrazide Compound 112 (Table 2) (0.04 g, 28%) as a white solid.

$^1$H NMR (400 MHz, D$_2$O): δ 1.66 (1H, m), 1.77 (1H, m), 1.90 (1H, m), 2.04 (1H, m), 3.03 (1H, d, J=12.4 Hz), 3.17 (1H, m), 3.65 (1H, m), 4.02 (2H, m), 4.12 (4H, m), 4 protons were not observed in D$_2$O.

HPLC 92.40%
MS (ES$^-$) m/z: [M]$^-$=362

Example 68

(2S,5R)-7-oxo-N'-(pyrrolidin-2-ylcarbonyl)-6-(sulfooxy)-1,6-diazabicyclo[3.2.1]octane-2-carbohydrazide trifluoroacetate (Compound 41, Table 2)

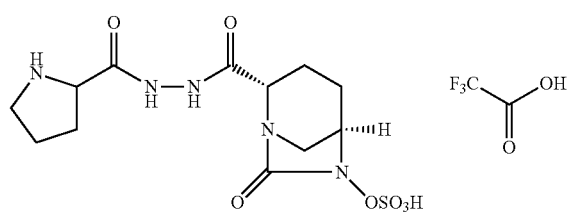

Step 1. tert-butyl 2-(2-((2S,5R)-6-(benzyloxy)-7-oxo-1,6-diazabicyclo[3.2.1]-octane-2-carbonyl)hydrazinecarbonyl)pyrrolidine-1-carboxylate (264)

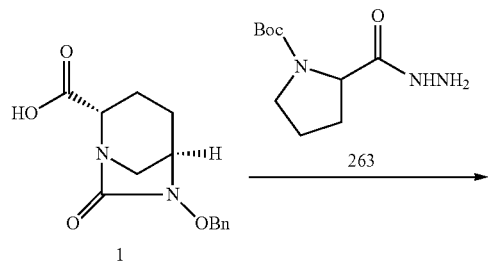

To a mixture of (2S,5R)-6-(benzyloxy)-7-oxo-1,6-diazabicyclo[3.2.1]octane-2-carboxylic acid 1 (0.304 g, 1.10 mmol) in DCM (20.0 mL) were added tert-butyl 3-(hydrazinecarbonyl)pyrrolidine-1-carboxylate 263 (0.380 g, 1.65 mmol), 1-hydroxybenzotriazole (0.223 g, 1.65 mmol) and 1-ethyl-(3-dimethylaminopropyl) carbodiimide hydrochloride (0.315 g, 1.65 mmol) sequentially at room temperature. The mixture was stirred at room temperature overnight, concentrated to provide a residue, which was subjected to chromatography to give 264 (0.34 g) as a white solid.

Step 2. tert-butyl 2-(2-((2S,5R)-6-hydroxy-7-oxo-1,6-diazabicyclo[3.2.1]-octane-2-carbonyl)hydrazinecarbonyl)pyrrolidine-1-carboxylate (265)

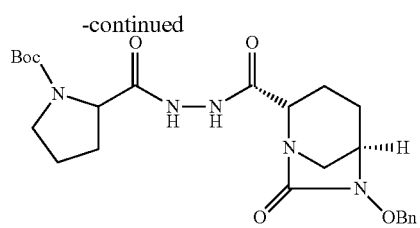

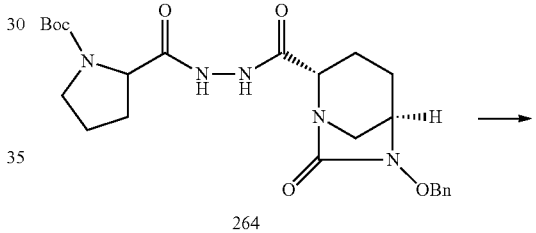

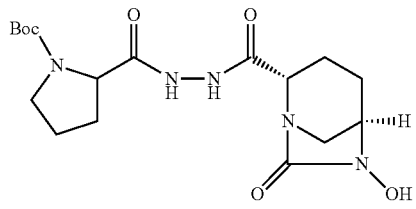

A mixture of tert-butyl 2-(2-((2S,5R)-6-(benzyloxy)-7-oxo-1,6-diazabicyclo[3.2.1]-octane-2-carbonyl)hydrazinecarbonyl)pyrrolidine-1-carboxylate 264 (0.34 g, 0.70 mmol) and Pd/C (0.30 g) in methanol (80 mL) was hydrogenated at 1 atm at room temperature for 3 h. The mixture was filtered through Celite pad and concentrated to give 265 (0.28 g, quant.) as an off-white solid.

Step 3. tert-butyl 2-(2-((2S,5R)-7-oxo-6-(sulfooxy)-1,6-diazabicyclo[3.2.1]-octane-2-carbonyl)hydrazinecarbonyl)pyrrolidine-1-carboxylate (266)

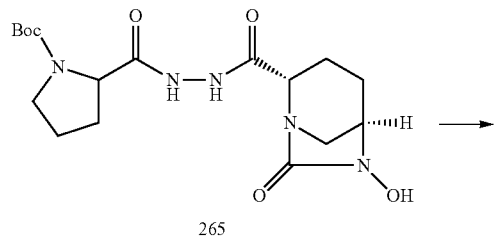
265

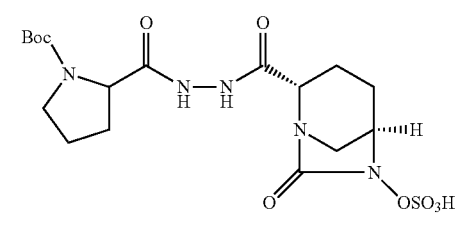
266

To a mixture of tert-butyl 2-(2-((2S,5R)-6-hydroxy-7-oxo-1,6-diazabicyclo[3.2.1]-octane-2-carbonyl)hydrazinecarbonyl)pyrrolidine-1-carboxylate 265 (0.28 g, 0.70 mmol) in pyridine (6 mL) was added sulfur trioxide pyridine complex (0.33 g, 2.10 mmol). The mixture was stirred at room temperature for 24 h and concentrated to provide a residue, which was subjected to chromatography to give 266 (0.290 g, 87%) as an off-white solid.

$^1$H NMR (400 MHz, D$_2$O): δ 1.24 and 1.27 (9H, 2s), 1.60-2.20 (8H, m), 3.02 (1H, m), 3.16 (1H, m), 3.28 (2H, m), 4.01 (2H, m), 4.18 (1H, m). Three protons were not observed in CD$_3$OD.

Step 4. (2S,5R)-7-oxo-N'-(pyrrolidin-2-ylcarbonyl)-6-(sulfooxy)-1,6-diazabicyclo[3.2.1]octane-2-carbohydrazide trifluoroacetate (Compound 41, Table 2)

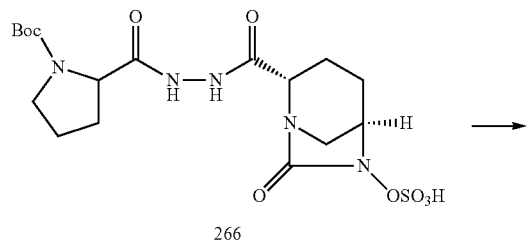
266

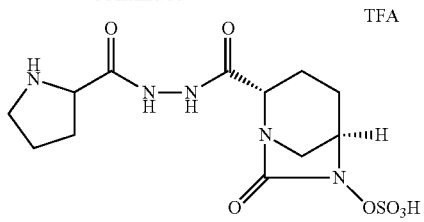
Compound 41, Table 2

To a mixture of tert-butyl 2-(2-((2S,5R)-7-oxo-6-(sulfooxy)-1,6-diazabicyclo[3.2.1]-octane-2-carbonyl)hydrazinecarbonyl)pyrrolidine-1-carboxylate 266 (0.29 g, 0.61 mmol) in DCM (12 mL) was added trifluoroacetic acid (0.60 mL) at 0° C. The mixture was stirred at 0° C. for 2 h, concentrated and washed with ether and MeOH to give Compound 41 (Table 2) (69.8 mg) as a white solid as a pair of diastereomers.

$^1$H NMR (400 MHz, D$_2$O): δ 1.65 (1H, m), 1.81 (1H, m), 1.90-2.10 (5H, m), 2.34 (1H, m), 3.03 (1H, m), 3.16-3.31 (3H, m), 4.03 (2H, m), 4.33 (1H, m). Four protons were not observed in D$_2$O.

$^{19}$F NMR (376.5 MHz, D$_2$O): δ–75.75

HPLC: 94.84%,

MS (ES$^-$) m/z: [M+H]$^+$ calcd for C$_{12}$H$_{20}$N$_5$O$_7$S: 378.4. Found: 378.0.

Example 69

(2S,5R)-N'-[(2,2-difluorocyclopropyl)carbonyl]-7-oxo-6-(sulfooxy)-1,6-diazabicyclo[3.2.1]octane-2-carbohydrazide (Compound 36, Table 2)

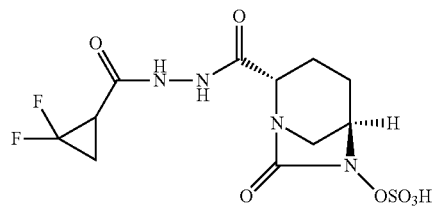

Step 1. (2S,5R)-6-(benzyloxy)-N'-[(2,2-difluorocyclopropyl)carbonyl]-7-oxo-1,6-diazabicyclo[3.2.1]octane-2-carbohydrazide (268)

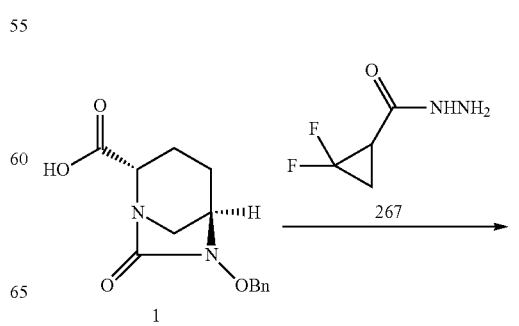
1

321
-continued

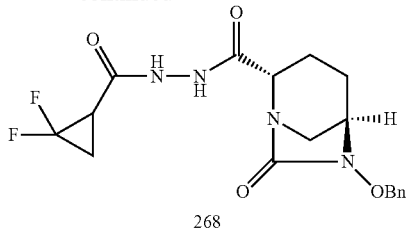
268

To a mixture of (2S,5R)-6-(benzyloxy)-7-oxo-1,6-diazabicyclo[3.2.1]octane-2-carboxylic acid 1 (0.250 g, 0.905 mmol) in DCM (15.0 mL) were added 2,2-difluorocyclopropanecarbohydrazide 267 (0.184 g, 1.358 mmol), 1-hydroxybenzotriazole (0.186 g, 1.358 mmol) and 1-ethyl-(3-dimethylamino propyl) carbodiimide hydrochloride (0.260 g, 1.358 mmol) sequentially at room temperature. The mixture was stirred at room temperature overnight, diluted with DCM and concentrated to provide a residue which was subjected to chromatography to give 268 (0.36 g, quant. yield) as a white foam.

$^1$H NMR (400 MHz, CDCl$_3$): δ 1.62 (1H, m), 1.80 (1H, m), 2.00 (2H, m), 2.18 (1H, m), 2.36 (1H, m), 2.44 (1H, m), 3.10 (1H, m), 3.30 (1H, m), 4.00 (2H, m), 4.91 (1H, d, J=11.2 Hz), 5.05 (1H, d, J=11.2 Hz), 7.42 (5H, m), 8.40 (1H, br s), 8.60 (1H, br s).

MS (ES$^+$) m/z: [M+H]$^+$ calcd for C$_{18}$H$_{21}$F$_2$N$_4$O$_4$: 395.1. Found: 395.1.

Step 2. (2S,5R)-N'-[(2,2-difluorocyclopropyl)carbonyl]-6-hydroxy-7-oxo-1,6-diazabicyclo[3.2.1]octane-2-carbohydrazide (269)

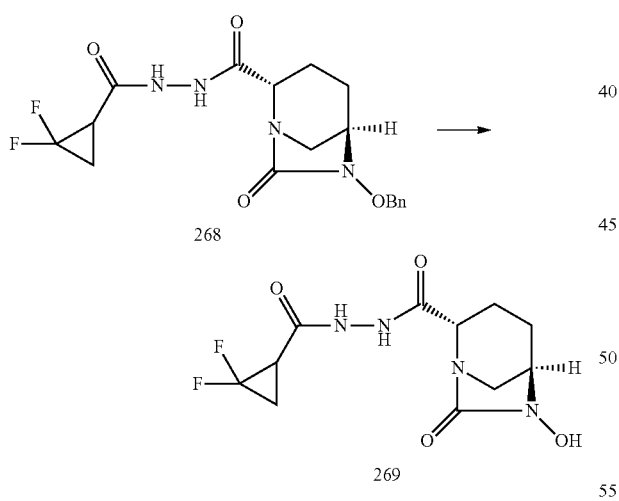

A mixture of (2S,5R)-6-(benzyloxy)-N-[(2,2-difluorocyclopropyl)carbonyl]-7-oxo-1,6-diazabicyclo[3.2.1]octane-2-carbohydrazide 268 (0.36 g, 0.90 mmol) and Pd/C (0.15 g) in methanol (20 mL) was hydrogenated at 1 atm at room temperature overnight. The mixture was filtered through Celite pad and concentrated to provide 269 (0.37 g, quant. yield) as a white foam.

$^1$H NMR (400 MHz, CD$_3$OD): δ 1.75-2.10 (4H, m), 2.25 (1H, m), 2.60 (1H, m), 2.70 (1H, m), 3.20 (2H, m), 3.70 (1H, br s), 3.95 (1H, d, J=7.6 Hz). 3 protons were not observed in CD$_3$OD.

322

MS (ES$^-$) m/z: [M−H]$^-$ calcd for C$_{11}$H$_{13}$F$_2$N$_4$O$_4$: 303.1. Found: 303.0.

Step 3. (2S,5R)-N'-(2,2-dimethylpropanoyl)-7-oxo-6-(sulfooxy)-1,6-diazabicyclo[3.2.1]octane-2-carbohydrazide (Compound 36, Table 2)

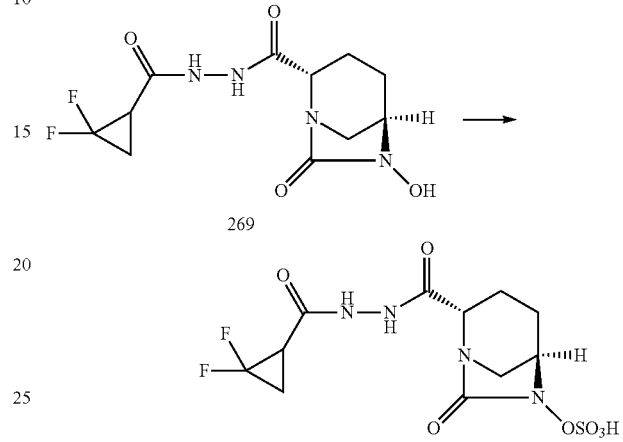

Compound 36, Table 2

To a mixture of (2S,5R)-N'-[(2,2-difluorocyclopropyl)carbonyl]-6-hydroxy-7-oxo-1,6-diazabicyclo[3.2.1]octane-2-carbohydrazide 269 (0.37 g, 1.21 mmol) in pyridine (10.0 mL) was added sulfur trioxide pyridine complex (0.57 g, 3.65 mmol). The mixture was stirred at room temperature overnight and concentrated to provide a residue, which was subjected to chromatography and followed by HPLC separation to give Compound 36, (Table 2) (60 mg) as a white solid as a pair of diastereoisomers.

$^1$H NMR (400 MHz, D$_2$O): δ 1.65 (1H, m), 1.72-2.00 (4H, m), 2.05 (1H, m), 2.52 (1H, m), 3.05 (1H, d, J=12.0 Hz), 3.18 (1H, d, J=12.0 Hz), 4.01-4.05 (2H, m). Three protons were not observed in D$_2$O.

HPLC: 92.75%.

MS (ES$^-$) m/z: [M−H]$^-$ calcd for C$_{11}$H$_{13}$F$_2$N$_4$O$_7$S: 383.1. Found: 382.9.

Example 70

(2S,5R)-7-oxo-N'-[(2S)-piperidin-2-ylcarbonyl]-6-(sulfooxy)-1,6-diazabicyclo[3.2.1]octane-2-carbohydrazide (Compound 43, Table 2)

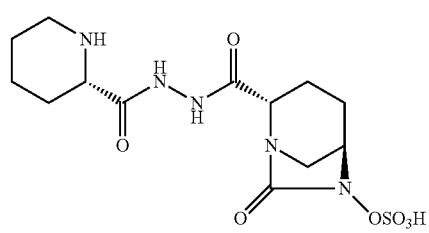

Step 1. tert-butyl (2S)-2-[(2-{[(2S,5R)-6-(benzyloxy)-7-oxo-1,6-diazabicyclo[3.2.1]oct-2-yl]carbonyl}hydrazinyl)carbonyl]piperidine-1-carboxylate (271)

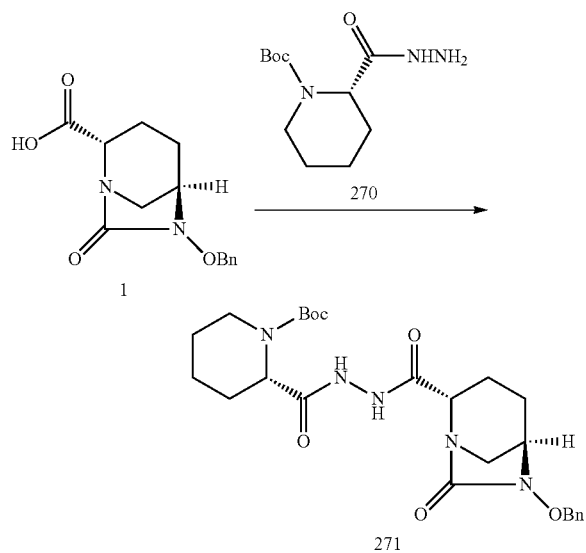

To a solution of (2S,5R)-6-(benzyloxy)-7-oxo-1,6-diazabicyclo[3.2.1]octane-2-carboxylic acid 1 (0.25 g, 0.90 mmol) in dry DCM (30 mL) were added tert-butyl (2S)-2-(hydrazinylcarbonyl)piperidine-1-carboxylate 270 (0.33 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight and concentrated under vacuum. The residue was purified by column chromatography to give tert-butyl (2S)-2-[(2-{[(2S,5R)-6-(benzyloxy)-7-oxo-1,6-diazabicyclo[3.2.1]oct-2-yl]carbonyl}hydrazinyl)carbonyl]piperidine-1-carboxylate 271 (0.37 g, 82%) as a white solid.

$^1$H NMR (400 MHz, CDCl$_3$): δ 1.37-1.72 (15H, m), 1.95 (2H, m), 2.31 (2H, m), 3.05 (2H, m), 3.22 (2H, m), 4.06 (2H, m), 4.86 (1H, m), 4.90 (1H, d, J=11.2 Hz), 5.05 (1H, d, J=11.6 Hz), 7.38 (5H, m), 8.11 (1H, br s), 8.34 (1H, br s).

Step 2. tert-butyl (2S)-2-[(2-{[(2S,5R)-6-hydroxy-7-oxo-1,6-diazabicyclo[3.2.1]oct-2-yl]carbonyl}hydrazinyl)carbonyl]piperidine-1-carboxylate (272)

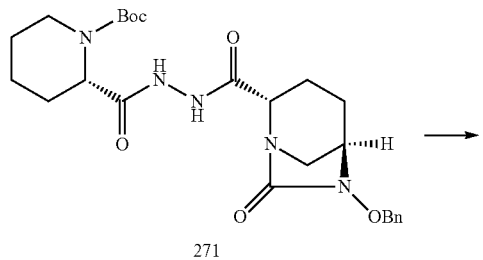

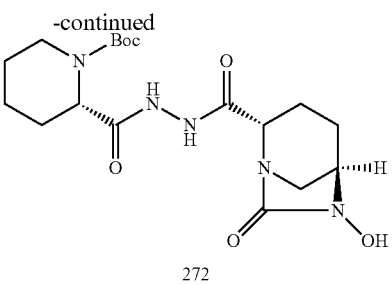

To a solution of tert-butyl (2S)-2-[(2-{[(2S,5R)-6-(benzyloxy)-7-oxo-1,6-diazabicyclo[3.2.1]oct-2-yl]carbonyl}hydrazinyl)carbonyl]piperidine-1-carboxylate 271 (0.37 g, 0.74 mmol) in methanol (25 mL) was added 5% Pd/C (0.40 g). The mixture was hydrogenated under 10 psi hydrogen atmosphere at room temperature for 1 h. The catalyst was filtered out through Celite, and the filtrate was evaporated to give tert-butyl (2 S)-2-[(2-{[(2S,5R)-6-hydroxy-7-oxo-1,6-diazabicyclo[3.2.1]oct-2-yl]carbonyl}hydrazinyl)carbonyl]piperidine-1-carboxylate 272 (0.29 g, 96%) as a white foam.

$^1$H NMR (400 MHz, CD$_3$OD): δ 1.47 (12H, m), 1.65 (2H, m), 1.76 (1H, m), 1.94 (1H, m), 2.04 (1H, m), 2.26 (2H, m), 3.15 (2H, m), 3.26 (1H, m), 3.70 (1H, s), 3.94 (2H, m), 4.79 (1H, m), 3 protons were not observed in CD$_3$OD.

Step 3. tert-butyl (2S)-2-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate (273)

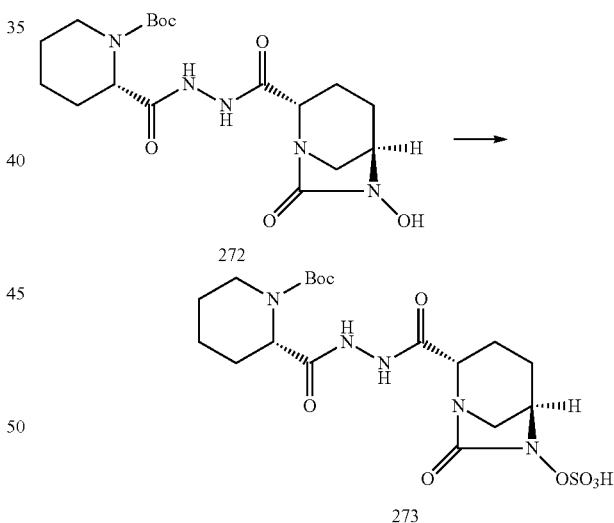

To a solution of tert-butyl (2S)-2-[(2-{[(2S,5R)-6-hydroxy-7-oxo-1,6-diazabicyclo[3.2.1]oct-2-yl]carbonyl}hydrazinyl)carbonyl]piperidine-1-carboxylate 272 (0.29 g, 0.70 mmol) in dry pyridine (10 mL) under nitrogen atmosphere was added sulfur trioxide pyridine complex (0.65 g, 4.12 mmol). The mixture was stirred at room temperature for 20 h, filtered and evaporated. The residue was purified first by column chromatography using DCM:EtAcO:MeOH (20:30:50) as eluent to give tert-butyl (2S)-2-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate 273 (0.30 g, 87%) as a white solid.

¹H NMR (400 MHz, CD₃OD): δ 1.47 (12H, m), 1.64 (2H, m), 1.80 (1H, m), 1.93 (1H, m), 2.01 (1H, m), 2.25 (2H, m), 3.17 (3H, m), 3.99 (2H, m), 4.15 (1H, s), 4.79 (1H, m), 3 protons were not observed in CD₃OD.

Step 4. (2S,5R)-7-oxo-N'-[(2S)-piperidin-2-ylcarbonyl]-6-(sulfooxy)-1,6-diazabicyclo[3.2.1]octane-2-carbohydrazide (Compound 43, Table 2)

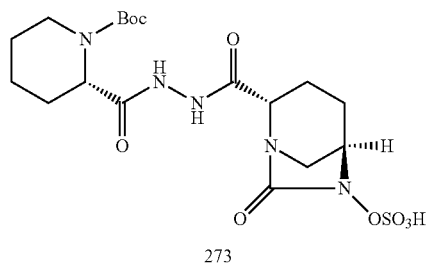

273

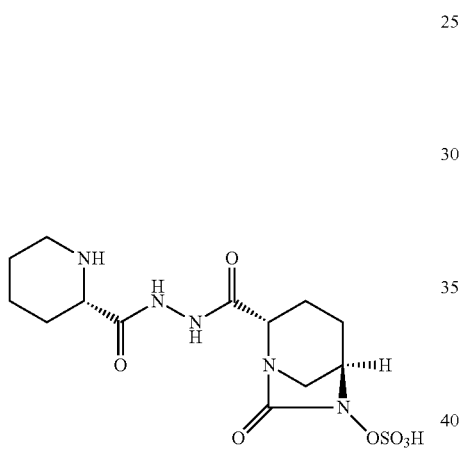

compound 43, Table 2

To a solution tert-butyl (2S)-2-[(2-{[(2S,5R)-7-oxo-6-(sulfooxy)-1,6-diazabicyclo[3.2.1]oct-2-yl]carbonyl}hydrazinyhcarbonyl]piperidine-1-carboxylate 273 (0.30 g, 0.61 mmol) in DCM (30 mL) was added trifluoroacetic acid (2.42 mL, 31.38 mmol) dropwise at 0° C. The reaction mixture was stirred for 1 h then evaporated. Ether was added to the residue and the resulting white precipitate was collected by centrifugation. The solid was triturated with a mixture of MeOH:ether (1:5, 6×) and the white solid was collected by centrifugation to give (2S,5R)-7-oxo-N-[(2S)-piperidin-2-ylcarbonyl]-6-(sulfooxy)-1,6-diazabicyclo[3.2.1]octane-2-carbohydrazide Compound 43 (Table 2) (0.09 g, 38%) as a white solid.

¹H NMR (400 MHz, D₂O): δ 1.51 (2H, m), 1.63 (1H, m), 1.75 (2H, m), 1.93 (1H, m), 2.05 (2H, m), 2.91 (1H, m), 3.03 (1H, d, J=12.4 Hz), 3.18 (2H, m), 3.33 (1H, m), 3.89 (1H, d, J=11.6 Hz), 4.03 (2H, m), 4.54 (1H, m), 4 protons were not observed in D₂O.

HPLC: 93.40%

MS (ES⁻) m/z: [M−H]⁻=390

Example 71

Compound 30, Table 2

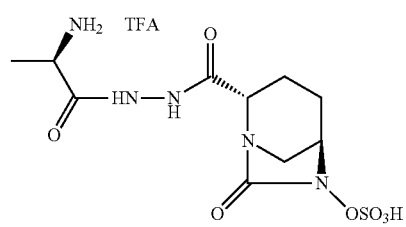

Step 1. tert-butyl [(2R)-1-(2-{[(2S,5R)-6-(benzyloxy)-7-oxo-1,6-diazabicyclo[3.2.1]oct-2-yl]carbonyl}hydrazinyl)-1-oxopropan-2-yl]carbamate (275)

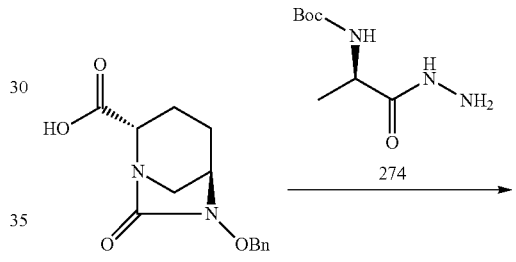

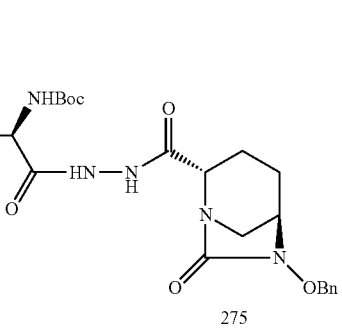

275

To a solution of 1 (250 mg, 0.9 mmol) in 20 mL of DCM were added tert-butyl [(2R)-1-hydrazinyl-1-oxopropan-2-yl]carbamate 274 (275 mg, 1.35 mmol), HOBt (183 mg 1.35 mmol), DMAP (162 mg, 1.35 mmol) and EDCI (260 mg, 1.35 mmol). The mixture was stirred at room temperature for 48 h and purified by column to afford compound 275 as foam (400 mg, 95%).

327

$^1$HNMR (CDCl$_3$): 8.48 (1H, s); 8.35 (1H, s); 7.40 (5H, m); 4.95 (3H, m); 4.25 (1H, m); 4.00 (1H, m); 3.30 (1H, m); 3.08 (2H, m); 2.30 (m, 1H); 2.00 (m, 2H); 1.58 (1H, m); 1.40 (m, 12H).

Step 2. tert-butyl [(2R)-1-(2-{[(2S,5R)-6-hydroxy-7-oxo-1,6-diazabicyclo[3.2.1]oct-2-yl]carbonyl}hydrazinyl)-1-oxopropan-2-yl]carbamate (276)

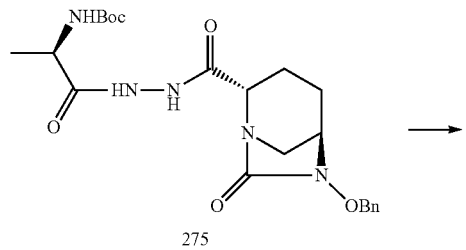

To a solution of compound 275 (400 mg, 0.86 mmol) in 30 mL of MeOH was added 0.8 g of Pd/C (10%, wet). The mixture was hydrogenated at room temperature for 2 h. The catalyst was removed by filtration through a celite pad. The filtrate was concentrated to afford compound 276 as a colorless gum (320 mg, 99%).

$^1$HNMR (CD$_3$OD): 4.15 (1H, m); 3.98 (1H, d); 3.70 (1H, m); 3.20 (2H, m); 2.30 (1H, m); 2.10 (1H, m); 1.90 (1H, m); 1.75 (1H, m); 1.45 (9H, s); 1.35 (3H, d).

Step 3. tert-butyl [(2R)-1-oxo-1-(2-{[(2S,5R)-7-oxo-6-(sulfooxy)-1,6-diazabicyclo[3.2.1]oct-2-yl]carbonyl}hydrazinyl)propan-2-yl]carbamate (277)

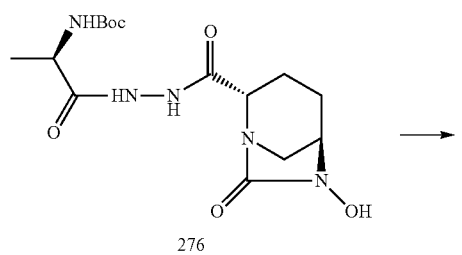

328

-continued

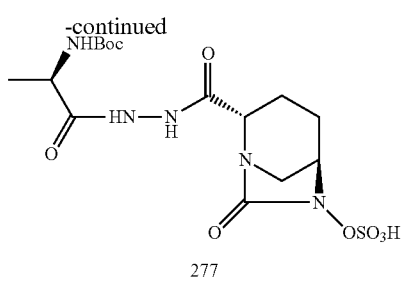

To a solution of compound 276 (320 mg, 0.858 mmol) in 15 mL of pyridine was added sulphur trioxide pyridine complex (1.5 g, 9.6 mmol). The mixture was stirred at room temperature under nitrogen atmosphere for 15 h. After column purification, compound 277 was obtained as foam (300 mg, 77%).

$^1$HNMR (CD$_3$OD): 4.20 (2H, m); 4.00 (1H, d); 3.20 (2H, m); 2.30 (1H, m); 2.10 (1H, m); 1.90 (1H, m); 1.80 (1H, m); 1.45 (9H, s); 1.35 (3H, d).

Step 4. (2S,5R)-N'-[(2R)-2-aminopropanoyl]-7-oxo-6-(sulfooxy)-1,6-diazabicyclo[3.2.1]octane-2-carbohydrazide trifluoroacetate (Compound 30, Table 2)

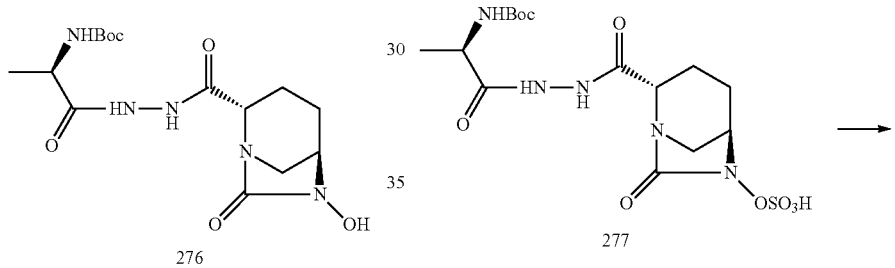

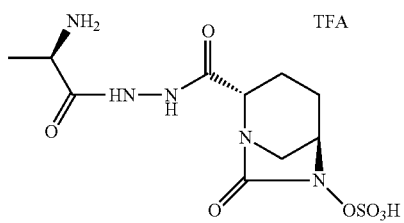

Compound 30, Table 2

To a solution of compound 277 (150 mg, 0.33 mmol) in DCM at 0° C. was added TFA (0.5 mL) slowly. After addition, the mixture was stirred at 0° C. for 2 h then diluted with 50 mL of Et$_2$O. The solid was collected by filtration and washed with additional amount of Et$_2$O and dried to afford the crude product Compound 30 (Table 2) as a white solid (100 mg, HPLC 76%). Re-precipitation of 50 mg of this crude product with MeOH/DCM afforded 20 mg of Compound 30 (Table 2) as a white solid.

$^1$HNMR (D$_2$O): 4.00 (3H, m); 3.20 (1H, m); 3.10 (1H, m); 2.10 (1H, m); 1.90 (1H, m); 1.80 (1H, m); 1.65 (1H, m).

HPLC: 84%.

MS (ES$^-$) m/z: [M−1]$^-$=350

Example 72

(2S,5R)-N-{[(3S)-1-carbamimidoylpyrrolidin-3-yl]oxy}-7-oxo-6-(sulfooxy)-1,6-diazabicyclo[3.2.1]octane-2-carboxamide (Compound 92, Table 1)

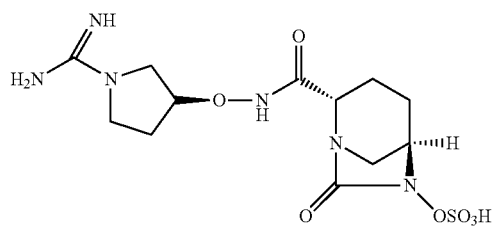

Using the similar procedure as described in Example 14, the intermediate 278 was prepared and used for making compound 92 (Table 1).

Step 1. di-tert-butyl {(3S)-3-[({[(2S,5R)-6-(benzyloxy)-7-oxo-1,6-diazabicyclo[3.2.1]oct-2-yl]carbonyl}amino)oxy]pyrrolidin-1-yl}methylylidene]biscarbamate (279)

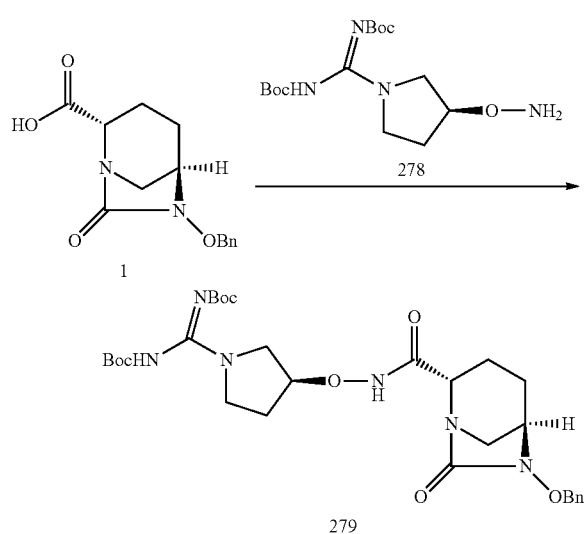

To a mixture of (2S,5R)-6-(benzyloxy)-7-oxo-1,6-diazabicyclo[3.2.1]octane-2-carboxylic acid 1 (0.250 g, 0.905 mmol) in DCM (20.0 mL) were added di-tert-butyl {(E)-[(3S)-3-(aminooxy)pyrrolidin-1-yl]methylylidene}biscarbamate 278 (0.478 g, 1.358 mmol), 1-hydroxybenzotriazole (0.186 g, 1.358 mmol) and 1-ethyl-(3-dimethylaminopropyl) carbodiimide hydrochloride (0.260 g, 1.358 mmol) sequentially at room temperature. The mixture was stirred at room temperature overnight, diluted with DCM and concentrated to provide a residue which was subjected to chromatography to give 279 (0.34 g, 62%) as white foam.

$^1$H NMR (400 MHz, CDCl$_3$): δ 1.45 (18H, s), 1.62 (1H, m), 2.00 (4H, m), 2.30 (2H, m), 2.77 (1H, d, J=12.0 Hz), 2.95 (1H, d, J=10.8 Hz), 3.29 (1H, s), 3.80 (2H, m), 3.92 (2H, m), 4.72 (1H, m), 4.90 (2H, ABq), 7.41 (5H, m). Two protons were not observed in moisture-containing CDCl$_3$.

MS (ES$^+$) m/z: [M+H]$^+$ calcd for C$_{29}$H$_{43}$N$_6$O$_8$: 603.3. Found: 603.2.

Step 2. di-tert-butyl [{(3S)-3-[({[(2S,5R)-6-hydroxy-7-oxo-1,6-diazabicyclo[3.2.1]oct-2-yl]carbonyl}amino)oxy]pyrrolidin-1-yl}methylylidene]biscarbamate (280)

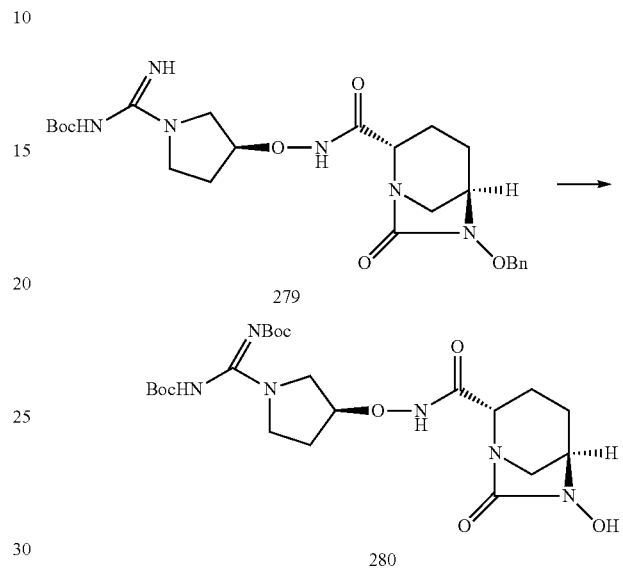

A mixture of di-tert-butyl [{(3S)-3-[({[(2S,5R)-6-(benzyloxy)-7-oxo-1,6-diazabicyclo[3.2.1]oct-2-yl]carbonyl}amino)oxy]pyrrolidin-1-yl}methylylidene]biscarbamate 279 (0.34 g, 0.56 mmol) and Pd/C (0.15 g) in methanol (20 mL) was hydrogenated at 1 atm at room temperature for 3 h. The mixture was filtered through Celite pad and concentrated to provide 280 (0.28 g, 97%) as white solid.

$^1$H NMR (400 MHz, CD$_3$OD): δ 1.48 (19H, m), 1.92 (3H, m), 2.10 (2H, m), 2.25 (1H, m), 3.00 (1H, d, J=11.6 Hz), 3.11 (1H, m), 3.64 (5H, m), 4.62 (1H, m). 3 protons were not observed in CD$_3$OD.

MS (ES$^+$) m/z: [M+H]$^+$ calcd for C$_{22}$H$_{37}$N$_6$O$_8$: 513.2. Found: 513.2.

Step 3. di-tert-butyl [{(3S)-3-[({[(2S,5R)-7-oxo-6-(sulfooxy)-1,6-diazabicyclo[3.2.1]oct-2-yl]carbonyl}amino)oxy]pyrrolidin-1-yl}methylylidene]biscarbamate (281)

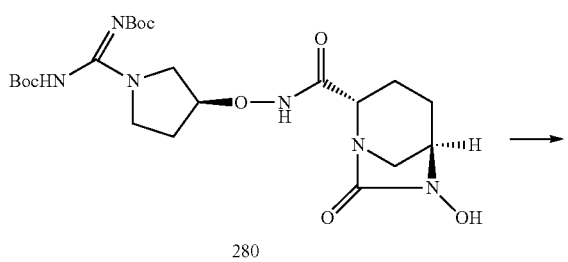

-continued

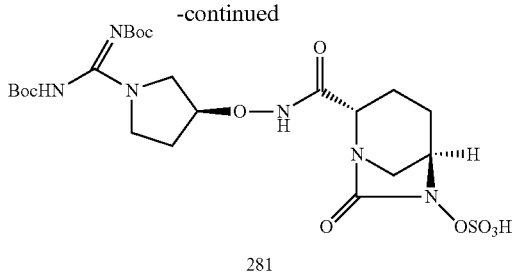

281

To a mixture of di-tert-butyl [{(3S)-3-[({[(2S,5R)-6-hydroxy-7-oxo-1,6-diazabicyclo[3.2.1]oct-2-yl]carbonyl}amino)oxy]pyrrolidin-1-yl}methylylidene]biscarbamate 280 (0.28 g, 0.54 mmol) in pyridine (6.0 mL) was added sulfur trioxide pyridine complex (0.26 g, 1.63 mmol). The mixture was stirred at room temperature overnight and concentrated to provide a residue which was subjected to chromatography to give 281 (0.30 g, 94%) as white solid.

$^1$H NMR (400 MHz, CD$_3$OD): δ 1.47 (18H, s), 1.80 (1H, m), 1.94 (1H, m), 2.10 (1H, m), 2.20 (3H, m), 2.40 (1H, m), 3.05 (1H, d, J=11.6 Hz), 3.33 (1H, m), 3.90 (4H, m), 4.16 (1H, s), 4.70 (1H, s). 3 protons were not observed in CD$_3$OD.

MS (ES$^+$) m/z: [M+H]$^+$ calcd for C$_{22}$H$_{37}$N$_6$O$_{11}$S: 593.2. Found: 593.2.

Step 4. (2S,5R)-N-{[(3S)-1-carbamimidoylpyrrolidin-3-yl]oxy}-7-oxo-6-(sulfooxy)-1,6-diazabicyclo[3.2.1]octane-2-carboxamide (Compound 92, Table 1)

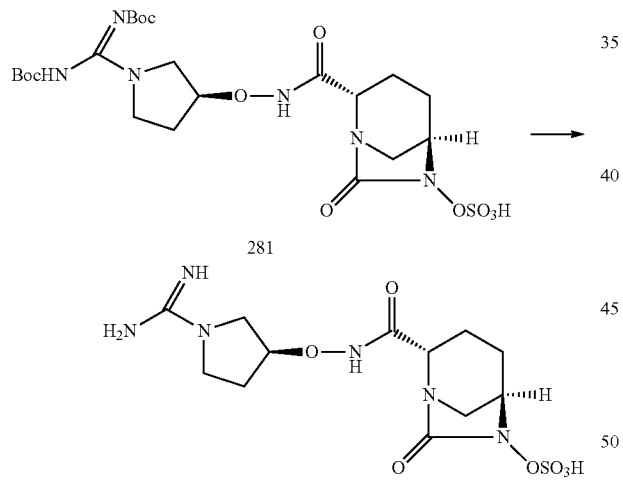

Compound 92, Table 1

To a mixture of di-tert-butyl [{(3S)-3-[({[(2S,5R)-7-oxo-6-(sulfooxy)-1,6-diazabicyclo[3.2.1]oct-2-yl]carbonyl}amino)oxy]pyrrolidin-1-yl}methylylidene]biscarbamate 281 (0.30 g, 0.51 mmol) in DCM (6.0 mL) was added trifluoroacetic acid (0.3 mL) at 0° C. The mixture was stirred at 0° C. for 0.5 h followed by at room temperature for 2 h and concentrated to provide a residue which was purified by HPLC to give Compound 92 (Table 1) (8.8 mg) as white solid.

$^1$H NMR (400 MHz, D$_2$O): δ 1.67-1.82 (2H, m), 1.90-2.11 (3H, m), 2.13-2.22 (1H, m), 2.99 (1H, d, J=11.6 Hz), 3.15 (1H, d, J=11.2 Hz), 3.42-3.58 (4H, m), 3.90 (1H, d, J=6.0 Hz), 4.05 (1H, s), 4.60 (1H, m). 5 protons were not observed in D$_2$O.

HPLC: 96.6

MS (ES$^-$) m/z: [M-H]$^-$ calcd for C$_{12}$H$_{19}$N$_6$O$_7$S: 391.1. Found: 390.9.

Example 73

(2S,5R)-N'-[(3,3-difluorocyclobutyl)carbonyl]-7-oxo-6-(sulfooxy)-1,6-diazabicyclo[3.2.1]octane-2-carbohydrazide (Compound 116, Table 2)

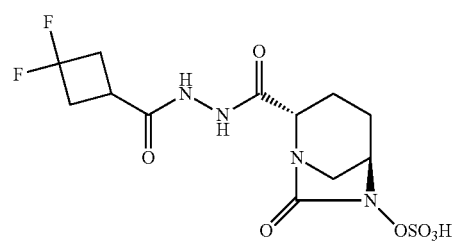

Step 1. (2S,5R)-6-(benzyloxy)-N'-[(3,3-difluorocyclobutyl)carbonyl]-7-oxo-1,6-diazabicyclo[3.2.1]octane-2-carbohydrazide (283)

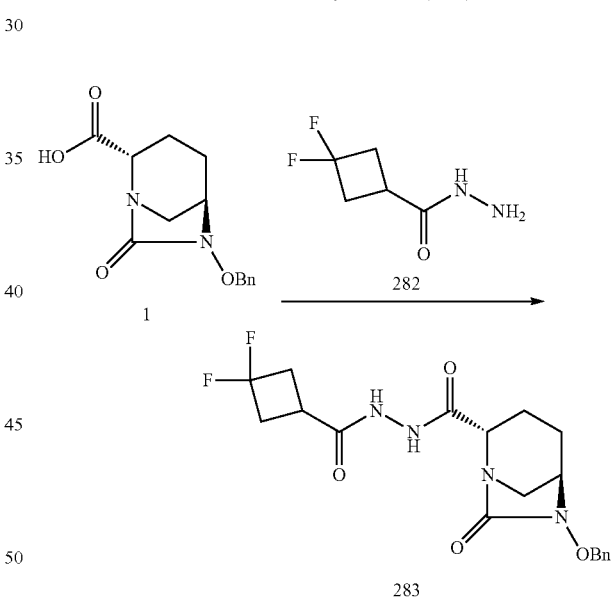

To a solution of (2S,5R)-6-(benzyloxy)-7-oxo-1,6-diazabicyclo[3.2.1]octane-2-carboxylic acid 1 (0.25 g, 0.90 mmol) in dry dichloromethane (30 mL) were added 3,3-difluorocyclobutanecarbohydrazide 282 (0.20 g, 1.35 mmol), 1-hydroxybenzotriazole (0.19 g, 1.35 mmol), 1-ethyl-(3-dimethylaminopropyl)carbodiimide hydrochloride (0.26 g, 1.35 mmol) and 4-(dimethylamino)pyridine (0.16 g, 1.35 mmol) at room temperature. The reaction mixture was stirred at room temperature overnight and concentrated under vacuum. The residue was purified by column chromatography to give 283 (0.32 g, 87%) as a white solid.

$^1$H NMR (400 MHz, CDCl$_3$): δ 1.61 (1H, m), 1.98 (2H, m), 2.28 (1H, m), 2.74 (2H, m), 2.88 (3H, m), 3.10 (2H, m), 3.33

(1H, s), 3.97 (1H, d, J=7.2 Hz), 4.90 (1H, d, J=11.2 Hz), 5.03 (1H, d, J=11.6 Hz), 7.39 (5H, m), 8.31 (1H, br s), 8.66 (1H, br s).

Step 2. (2S,5R)-N'-[(3,3-difluorocyclobutyl)carbonyl]-6-hydroxy-7-oxo-1,6-diazabicyclo[3.2.1]octane-2-carbohydrazide (284):

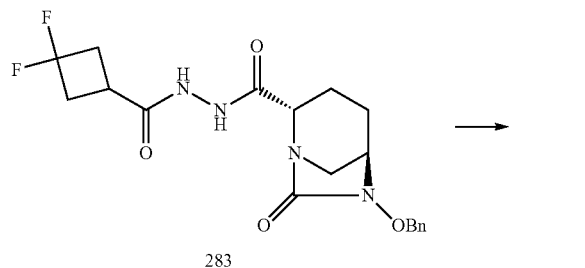

283

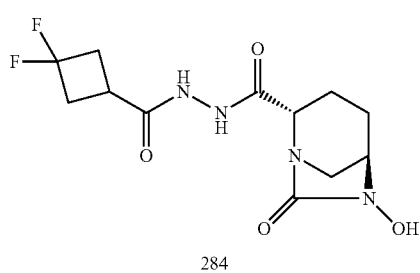

284

To a solution of (2S,5R)-6-(benzyloxy)-N'-[(3,3-difluorocyclobutyl)carbonyl]-7-oxo-1,6-diazabicyclo[3.2.1]octane-2-carbohydrazide 283 (0.32 g, 0.78 mml) in methanol (25 mL) was added 10% Pd/C (0.40 g). The mixture was hydrogenated under 10 psi hydrogen atmosphere at room temperature for 1 h. The catalyst was filtered out through Celite, and the filtrate was evaporated to give 284 (0.24 g, 96%) as a white foam.

$^1$H NMR (400 MHz, CD$_3$OD): δ 1.76 (1H, m), 1.94 (1H, m), 2.05 (1H, m), 2.26 (1H, m), 2.78 (4H, m), 2.98 (1H, m), 3.15 (1H, m), 3.24 (1H, d, J=12.00 Hz), 3.71 (1H, s), 3.94 (1H, d, J=8.0 Hz), 3 protons were not observed in CD$_3$OD.

Step 3. (2S,5R)-N'-[(3,3-difluorocyclobutyl)carbonyl]-7-oxo-6-(sulfooxy)-1,6-diazabicyclo[3.2.1]octane-2-carbohydrazide (Compound 116, Table 2)

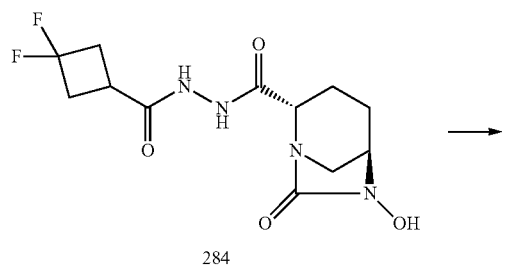

284

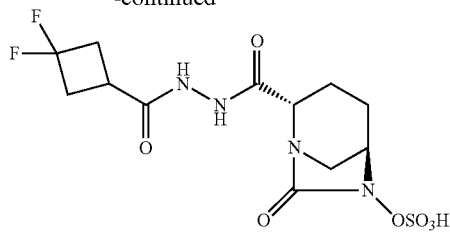

Compound 116, Table 2

To a solution of (2S,5R)-N'-[(3,3-difluorocyclobutyl)carbonyl]-6-hydroxy-7-oxo-1,6-diazabicyclo[3.2.1]octane-2-carbohydrazide 284 (0.24 g, 0.75 mmol) in dry pyridine (10 mL) under nitrogen atmosphere was added sulfur trioxide pyridine complex (0.60 g, 3.80 mmol). The mixture was stirred at room temperature for 20 h, filtered and evaporated. The residue was purified by column chromatography to give (2S,5R)-N-[(3,3-difluorocyclobutyl)carbonyl]-7-oxo-6-(sulfooxy)-1,6-diazabicyclo[3.2.1]octane-2-carbohydrazide Compound 116 (Table 2) (0.12 g, 40%) as a white solid.

$^1$H NMR (400 MHz, CD$_3$OD): δ 1.80 (1H, m), 1.92 (1H, m), 2.06 (1H, m), 2.27 (1H, m), 2.67-2.93 (4H, m), 2.97 (1'H, m), 3.30 (2H, m), 4.03 (1H, d, J=7.2 Hz), 4.15 (1H, s), 3 protons were not observed in CD$_3$OD.

HPLC: 91.0%
MS (ES$^-$) m/z: [M]$^-$=397

Example 74

(2S,5R)-N'-{[(1R,2R)-2-aminocyclopentyl]carbonyl}-7-oxo-6-(sulfooxy)-1,6-diazabicyclo[3.2.1]octane-2-carbohydrazide trifluoroacetate (Compound 40, Table 2)

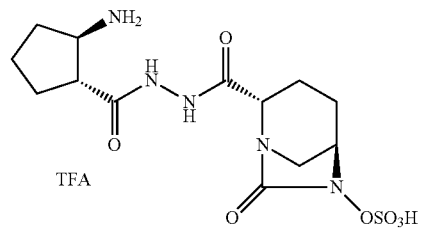

Step 1. tert-butyl {(1R,2R)-2-[(2-{[(2S,5R)-6-(benzyloxy)-7-oxo-1,6-diazabicyclo[3.2.1]oct-2-yl]carbonyl}hydrazinyl)carbonyl]cyclopentyl}carbamate (286)

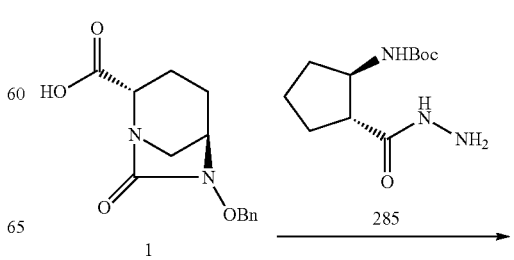

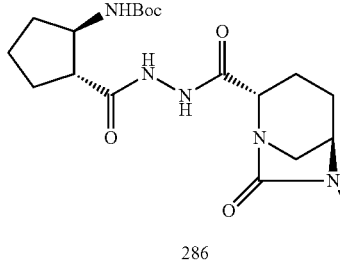

286

To a solution of tert-butyl [(1R,2R)-2-(hydrazinylcarbonyl)cyclopentyl]carbamate 285 (0.15 g, 0.54 mmol) in 20 mL of DCM were added compound 1 (0.2 g, 0.82 mmol), HOBt (0.11 g, 0.82 mmol), DMAP (0.2 g, 1.64 mmol) and EDCI (0.16 g, 0.82 mmol). The mixture was stirred at room temperature for 18 h and purified by column chromatography to afford compound 286 as a solid (0.22 g, 82%).

$^1$HNMR (CDCl$_3$): 1.44 (9H, s), 1.70 (4H, m), 2.00 (4H, m), 2.20 (1H, m), 2.40 (1H, m), 2.80 (1H, s), 3.08 (1H, m), 3.30 (2H, m), 4.10 (2H, m), 4.90 (1H, s), 5.00 (2H, dd), 7.40 (5H, m), 8.33 (1H, s), 9.92 (1H, s).

MS (ES+): 502.

Step 2. tert-butyl {(1R,2R)-2-[(2-{[(2S,5R)-6-hydroxy-7-oxo-1,6-diazabicyclo[3.2.1]oct-2-yl]carbonyl}hydrazinyl)carbonyl]cyclopentyl}carbamate (287)

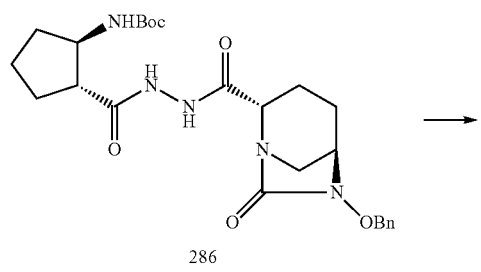

To a solution of compound 286 (0.22 g, 0.44 mmol) in 10 mL of CH$_3$OH was added 0.1 g of Pd—C (10%, wet). The mixture was hydrogenated at room temperature for 16 h. The catalyst was removed by filtration through a pad of celite. The filtrate was concentrated to afford compound 287 as a solid (0.15 g, 83%).

$^1$HNMR (CD$_3$OD): 1.44 (9H, s), 1.80 (3H, m), 2.10 (6H, m), 2.30 (1H, m), 2.60 (1H, m), 3.20 (2H, m), 3.70 (1H, m), 3.98 (1H, d), 4.10 (1H, m).

MS (ES+): 412.

Step 3. tert-butyl {(1R,2R)-2-[(2-{[(2S,5R)-7-oxo-6-(sulfooxy)-1,6-diazabicyclo[3.2.1]oct-2-yl]carbonyl}hydrazinyl)carbonyl]cyclopentyl}carbamate (288)

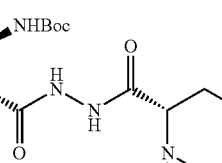

287

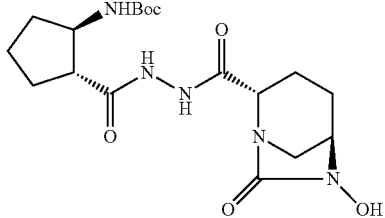

288

To a solution of compound 287 (15 g, 0.36 mmol) in 5 mL of pyridine was added sulphur trioxide pyridine complex (0.58 g, 3.6 mmol). The mixture was stirred at room temperature under nitrogen atmosphere for 16 h. After silica gel column purification, compound 288 was obtained as a solid (0.14 g, 78%).

$^1$HNMR (CD$_3$OD): 1.44 (9H, s), 1.70 (4H, m), 2.10 (6H, m), 2.30 (1H, m), 2.60 (1H, m), 4.20 (4H, m).

MS (ES−): 490

Step 4. (2S,5R)-N'-{[(1R,2R)-2-aminocyclopentyl]carbonyl}-7-oxo-6-(sulfooxy)-1,6-diazabicyclo[3.2.1]octane-2-carbohydrazide trifluoroacetate (Compound 40, Table 2)

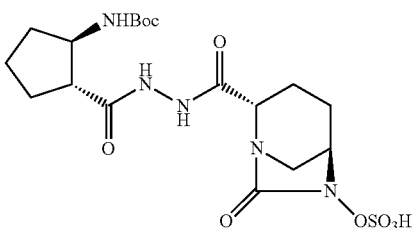

288

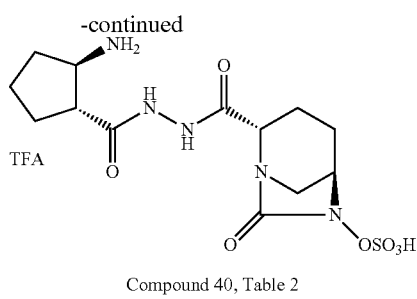

Compound 40, Table 2

To a solution of compound 288 (0.1 g, 0.2 mmol) in DCM (10 mL) at 0° C. was added TFA (0.5 mL) dropwise. After addition, the mixture was stirred at 0° C. for 3 h then diluted with 50 mL of ether. The solid was collected by filtration and washed with additional ether and dried to afford the title compound Compound 40 (Table 2) as a white solid (0.07 g, 72%)

$^1$HNMR (CD$_3$OD): 1.82 (6H, m), 2.23 (4H, m), 2.83 (2H, m), 3.87 (2H, m), 4.04 (1H, d), 4.15 (1H, s).

MS (ES−): 390

Antibacterial Activity and Synergistic Activity:

Compounds of the present invention alone, ceftazidime alone, meropenem alone, aztreonam alone and as a combination with these antibiotics were tested for minimum inhibitory concentration (MIC, μg/mL) against bacteria listed in Tables 3-9. In the Tables 10-12, compounds of the present invention were tested in combination with various antibiotics against metallo β-lactamase producing bacteria.

TABLE 3

Synergy of the inhibitor Ex. 2 (4 μg/mL) in combination with antibiotics

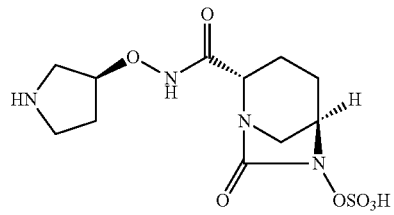

Ex. 2

| Organism | Enzyme | Ex. 2 Alone | Meropenem | Meropenem + Ex. 2 (4 μg/mL) | Ceftazidime | Ceftazidime + Ex. 2 (4 μg/mL) | Aztreonam | Aztreonam + Ex. 2 (4 μg/mL) |
|---|---|---|---|---|---|---|---|---|
| E. coli ATCC 25922 | Wt | 8 | 0.06 | ≤.031 | 0.25 | ≤0.25 | 0.25 | ≤.062 |
| A. baumanii JMI 2659 | Ges-14 (Cpase) | >16 | 64 | 2 | 512 | >16 | 512 | >4 |
| E. coli JMI 4103 | KPC-2, Tem-1, CMY-Type | 16 | 64 | ≤.031 | >512 | 8 | >512 | >4 |
| E. coli JMI 4080 | Tem-10 | 8 | ≤1 | ≤.031 | 64 | 1 | 64 | 1 |
| E. coli JMI 2692 | NDM-1, TEM-1, CTX-M-15 | 4 | 256 | ≤.031 | >512 | ≤0.25 | >512 | 0.25 |
| E. coli JMI 2671 | VIM-19 (Cpase) | 4 | 64 | 2 | 64 | 2 | 64 | ≤.062 |
| E. coli JMI 2665 | CMY-2 (Plasmid Cpase) | 4 | ≤1 | ≤.031 | 8 | ≤0.25 | 8 | ≤.062 |
| K. pneumo JMI 4109 | SHV-1, SHV-12 | 4 | ≤1 | ≤.031 | 8 | ≤0.25 | 8 | ≤.062 |
| K. pneumo JMI 2673 | CTX-M14 (ESBL) | >16 | ≤1 | ≤.031 | 32 | ≤0.25 | 32 | ≤.062 |
| K. pneumo JMI 2674 | CTX-M15 (ESBL) | >16 | ≤1 | 0.062 | 512 | ≤0.25 | 512 | ≤.062 |
| K. pneumo JMI 4088 | KPC-3 (Cpase) | 4 | 512 | 0.062 | >512 | ≤0.25 | >512 | ≤.062 |
| K. pneumo JMI 4106 | KPC-3, TEM-1, SHV-12, SHV-141 | 16 | 128 | ≤.031 | >512 | ≤0.25 | >512 | 0.25 |
| K. pneumo JMI 2693 | NDM-1 (Cpase) | >16 | 8 | 0.062 | >512 | ≤0.25 | >512 | 0.125 |
| K. pneumo JMI 2697 | IMP-4 (Cpase) | 16 | 64 | >2 | >512 | 16 | >512 | 0.25 |
| K. pneumo JMI 2681 | Oxa-48 (Cpase) | >16 | 64 | >2 | 512 | 4 | 512 | 4 |
| K. pneumo JMI 2699 | VIM-1, CTX-M3 | 8 | 32 | 2 | >512 | 16 | >512 | 0.5 |
| P. aerug JMI 2686 | KPC-2 (Cpase) | >16 | 512 | >2 | 512 | 16 | 512 | >4 |
| P. aerug JMI 149 | Bla+++D+ | >16 | 4 | 0.5 | 256 | 4 | 256 | >4 |
| E. cloacae JMI 36 | P99 | >16 | ≤1 | 0.062 | 128 | 1 | 128 | 0.25 |
| E. coli JMI 10767 | Wt | 8 | ≤1 | ≤.031 | ≤1 | ≤0.25 | ≤1 | ≤.062 |
| E. coli JMI 10768 | CTX-M15 (Weak ESBL) | 8 | ≤1 | ≤.031 | 8 | ≤0.25 | 8 | ≤.062 |
| E. coli JMI 10770 | CTX-M15 (Hyper ESBL) | 8 | ≤1 | ≤.031 | 64 | ≤0.25 | 64 | ≤.062 |
| E. coli JMI 11103 | CTX-M15 (Intermediate ESBL) | 8 | ≤1 | ≤.031 | 32 | ≤0.25 | 32 | ≤.062 |

TABLE 4

Synergy of the inhibitor Ex. 4 (4 μg/mL) in combination with antibiotics

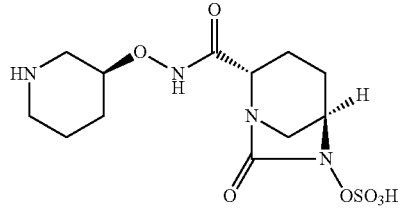

Ex. 4

| Organism | Enzyme | Ex. 4 Alone | Meropenem | Meropenem + Ex. 4 (4 μg/mL) | Ceftazidime | Ceftazidime + Ex. 4 (4 μg/mL) | Aztreonam | Aztreonam + Ex. 4 (4 μg/mL) |
|---|---|---|---|---|---|---|---|---|
| *E. coli* ATCC 25922 | Wt | 1 | 0.06 | ≤.031 | 0.25 | ≤0.25 | 0.25 | ≤.062 |
| *A. baumanii* JMI 2659 | Ges-14 (Cpase) | >16 | 64 | >2 | 512 | >16 | 512 | >4 |
| *E. coli* JMI 4103 | KPC-2, Tem-1, CMY-Type | 8 | 64 | ≤.031 | >512 | 8 | >512 | >4 |
| *E. coli* JMI 4080 | Tem-10 | 4 | ≤1 | ≤.031 | 64 | ≤0.25 | 64 | ≤.062 |
| *E. coli* JMI 2692 | NDM-1, TEM-1, CTX-M-15 | ≤0.5 | 256 | ≤.031 | >512 | ≤0.25 | >512 | ≤.062 |
| *E. coli* JMI 2671 | VIM-19 (Cpase) | >16 | 64 | 0.125 | 64 | 0.5 | 64 | ≤.062 |
| *E. coli* JMI 2665 | CMY-2 (Plasmid Cpase) | ≤0.5 | ≤1 | ≤.031 | 8 | ≤0.25 | 8 | ≤.062 |
| *K. pneumo* JMI 4109 | SHV-1, SHV-12 | 16 | ≤1 | ≤.031 | 8 | ≤0.25 | 8 | ≤.062 |
| *K. pneumo* JMI 2673 | CTX-M14 (ESBL) | >16 | ≤1 | ≤.031 | 32 | ≤0.25 | 32 | ≤.062 |
| *K. pneumo* JMI 2674 | CTX-M15 (ESBL) | >16 | ≤1 | 0.125 | 512 | ≤0.25 | 512 | 0.125 |
| *K. pneumo* JMI 4088 | KPC-3 (Cpase) | 1 | 512 | 0.062 | >512 | ≤0.25 | >512 | 0.5 |
| *K. pneumo* JMI 4106 | KPC-3, TEM-1, SHV-12, SHV-141 | >16 | 128 | ≤.031 | >512 | ≤0.25 | >512 | ≤.062 |
| *K. pneumo* JMI 2693 | NDM-1 (Cpase) | 4 | 8 | ≤.031 | >512 | ≤0.25 | >512 | ≤.062 |
| *K. pneumo* JMI 2697 | IMP-4 (Cpase) | 4 | 64 | ≤.031 | >512 | 0.5 | >512 | ≤.062 |
| *K. pneumo* JMI 2681 | Oxa-48 (Cpase) | >16 | 64 | >2 | 512 | 1 | 512 | 2 |
| *K. pneumo* JMI 2699 | VIM-1, CTX-M3 | 4 | 32 | 0.062 | >512 | ≤0.25 | >512 | ≤.062 |
| *P. aerug* JMI 2686 | KPC-2 (Cpase) | >16 | 512 | >2 | 512 | 16 | 512 | >4 |
| *P. aerug* JMI 149 | Bla+++D+ | >16 | 4 | 0.5 | 256 | 4 | 256 | >4 |
| *E. cloacae* JMI 36 | P99 | >16 | ≤1 | 0.125 | 128 | ≤0.25 | 128 | 0.125 |
| *E. coli* JMI 10767 | Wt | 4 | ≤1 | ≤.031 | ≤1 | ≤0.25 | ≤1 | ≤.062 |
| *E. coli* JMI 10768 | CTX-M15 (Weak ESBL) | 4 | ≤1 | ≤.031 | 8 | ≤0.25 | 8 | ≤.062 |
| *E. coli* JMI 10770 | CTX-M15 (Hyper ESBL) | 4 | ≤1 | ≤.031 | 64 | ≤0.25 | 64 | ≤.062 |
| *E. coli* JMI 11103 | CTX-M15 (Intermediate ESBL) | 4 | ≤1 | ≤.031 | 32 | ≤0.25 | 32 | ≤.062 |

TABLE 5

Synergy of the inhibitor Ex. 9 (4 μg/mL) in combination with antibiotics

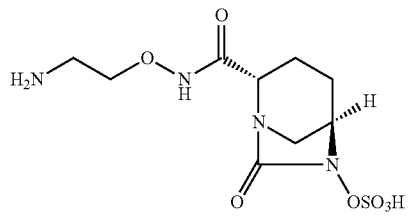

Ex. 9

| Organism | Enzyme | Ex. 9 Alone | Meropenem | Meropenem + Ex. 9 (4 μg/mL) | Ceftazidime | Ceftazidime + Ex. 9 (4 μg/mL) | Aztreonam | Aztreonam + Ex. 9 (4 μg/mL) |
|---|---|---|---|---|---|---|---|---|
| *E. coli* ATCC 25922 | Wt | 2 | 0.06 | ≤0.0312 | 0.25 | ≤0.25 | 0.25 | ≤0.062 |
| *A. baumanii* JMI 2659 | Ges-14 (Cpase) | >16 | 64 | 2 | 512 | >16 | 512 | >4 |
| *E. coli* JMI 4103 | KPC-2, Tem-1, CMY-Type | 4 | 64 | ≤0.0312 | >512 | ≤0.25 | >512 | ≤0.062 |
| *E. coli* JMI 4080 | Tem-10 | 2 | ≤1 | ≤0.0312 | 64 | ≤0.25 | 64 | ≤0.062 |
| *E. coli* JMI 2692 | NDM-1, TEM-1, CTX-M-15 | 2 | 256 | ≤0.0312 | >512 | ≤0.25 | >512 | ≤0.062 |
| *E. coli* JMI 2671 | VIM-19 (Cpase) | 2 | 64 | ≤0.0312 | 64 | ≤0.25 | 64 | ≤0.062 |
| *E. coli* JMI 2665 | CMY-2 (Plasmid Cpase) | 2 | ≤1 | ≤0.0312 | 8 | ≤0.25 | 8 | ≤0.062 |
| *K. pneumo* JMI 4109 | SHV-1, SHV-12 | 2 | ≤1 | ≤0.0312 | 8 | ≤0.25 | 8 | ≤0.062 |
| *K. pneumo* JMI 2673 | CTX-M14 (ESBL) | >16 | ≤1 | ≤0.0312 | 32 | ≤0.25 | 32 | 0.125 |
| *K. pneumo* JMI 2674 | CTX-M15 (ESBL) | >16 | ≤1 | 0.125 | 512 | ≤0.25 | 512 | 0.5 |
| *K. pneumo* JMI 4088 | KPC-3 (Cpase) | 2 | 512 | 0.25 | >512 | ≤0.25 | >512 | 1 |
| *K. pneumo* JMI 4106 | KPC-3, TEM-1, SHV-12, SHV-141 | 2 | 128 | ≤0.0312 | >512 | ≤0.25 | >512 | ≤0.062 |

TABLE 5-continued

Synergy of the inhibitor Ex. 9 (4 µg/mL) in combination with antibiotics

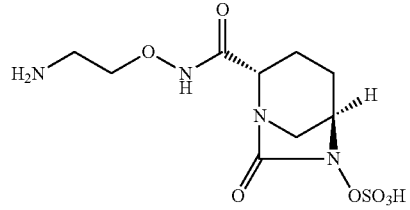

Ex. 9

| Organism | Enzyme | Ex. 9 Alone | Meropenem | Meropenem + Ex. 9 (4 µg/mL) | Ceftazidime | Ceftazidime + Ex. 9 (4 µg/mL) | Aztreonam | Aztreonam + Ex. 9 (4 µg/mL) |
|---|---|---|---|---|---|---|---|---|
| K. pneumo JMI 2693 | NDM-1 (Cpase) | 8 | 8 | ≤0.0312 | >512 | ≤0.25 | >512 | 0.25 |
| K. pneumo JMI 2697 | IMP-4 (Cpase) | 8 | 64 | 0.25 | >512 | 0.5 | >512 | 0.25 |
| K. pneumo JMI 2681 | Oxa-48 (Cpase) | >16 | 64 | 0.5 | 512 | ≤0.25 | 512 | 1 |
| K. pneumo JMI 2699 | VIM-1, CTX-M3 | 4 | 32 | ≤0.0312 | >512 | ≤0.25 | >512 | ≤0.062 |
| P. aerug JMI 2686 | KPC-2 (Cpase) | >16 | 512 | >2 | 512 | 16 | 512 | >4 |
| P. aerug JMI 149 | Bla+++D+ | >16 | 4 | 0.25 | 256 | 4 | 256 | >4 |
| E. cloacae JMI 36 | P99 | >16 | ≤1 | 0.062 | 128 | 0.5 | 128 | >4 |
| E. coli JMI 10767 | Wt | 2 | ≤1 | ≤0.0312 | ≤1 | ≤0.25 | ≤1 | ≤0.062 |
| E. coli JMI 10768 | CTX-M15 (Weak ESBL) | 4 | ≤1 | 0.062 | 8 | ≤0.25 | 8 | ≤0.062 |
| E. coli JMI 10770 | CTX-M15 (Hyper ESBL) | >16 | ≤1 | 0.062 | 64 | 2 | 64 | 8 |
| E. coli JMI 11103 | CTX-M15 (Intermediate ESBL) | 4 | ≤1 | 0.062 | 32 | 0.5 | 32 | 0.5 |

TABLE 6

Synergy of the inhibitor Ex. 40 (4 µg/mL) in combination with antibiotics

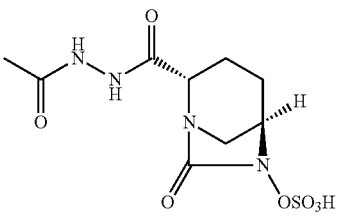

Ex. 40

| Organism | Enzyme | Ex. 40 Alone | Meropenem | Meropenem + Ex. 40 (4 µg/mL) | Ceftazidime | Ceftazidime + Ex. 40 (4 µg/mL) | Aztreonam | Aztreonam + Ex. 40 (4 µg/mL) |
|---|---|---|---|---|---|---|---|---|
| E. coli ATCC 25922 | Wt | 2 | 0.06 | ≤0.031 | 0.25 | ≤0.25 | 0.125 | ≤0.062 |
| A. baumanii JMI 2659 | Ges-14 (Cpase) | >16 | 64 | >2 | 512 | >16 | 256 | >4 |
| E. coli JMI 4103 | KPC-2, Tem-1, CMY-Type | 8 | 64 | ≤0.031 | >512 | ≤0.25 | 256 | ≤0.062 |
| E. coli JMI 4080 | Tem-10 | 2 | ≤1 | ≤0.031 | 64 | ≤0.25 | 125 | ≤0.062 |
| E. coli JMI 2692 | NDM-1, TEM-1, CTX-M-15 | 2 | 256 | ≤0.031 | >512 | ≤0.25 | 256 | ≤0.062 |
| E. coli JMI 2671 | VIM-19 (Cpase) | 16 | 64 | 0.25 | 64 | 2 | 16 | ≤0.062 |
| E. coli JMI 2665 | CMY-2 (Plasmid Cpase) | 2 | ≤1 | ≤0.031 | 8 | ≤0.25 | 64 | ≤0.062 |
| K. pneumo JMI 4109 | SHV-1, SHV-12 | >16 | ≤1 | ≤0.031 | 8 | ≤0.25 | ≤1 | ≤0.062 |
| K. pneumo JMI 2673 | CTX-M14 (ESBL) | >16 | ≤1 | ≤0.031 | 32 | ≤0.25 | 8 | ≤0.062 |
| K. pneumo JMI 2674 | CTX-M15 (ESBL) | >16 | ≤1 | 0.062 | 512 | ≤0.25 | 32 | 0.125 |
| K. pneumo JMI 4088 | KPC-3 (Cpase) | >16 | 512 | 0.125 | >512 | ≤0.25 | 512 | 0.25 |
| K. pneumo JMI 4106 | KPC-3, TEM-1, SHV-12, SHV-141 | >16 | 128 | 2 | >512 | 0.5 | 512 | 1 |
| K. pneumo JMI 2693 | NDM-1 (Cpase) | >16 | 8 | 0.125 | >512 | 0.5 | 256 | 0.5 |
| K. pneumo JMI 2697 | IMP-4 (Cpase) | 16 | 64 | 0.125 | >512 | >2 | 256 | ≤0.062 |
| K. pneumo JMI 2681 | Oxa-48 (Cpase) | 16 | 64 | 2 | 512 | ≤0.25 | 256 | 0.5 |
| K. pneumo JMI 2699 | VIM-1, CTX-M3 | >16 | 32 | ≤0.031 | >512 | 2 | 128 | ≤0.062 |
| P. aerug JMI 2686 | KPC-2 (Cpase) | 16 | 512 | >2 | 512 | >16 | >512 | >4 |
| P. aerug JMI 149 | Bla+++D+ | >16 | 4 | 0.5 | 256 | >16 | 512 | >4 |
| E. cloacae JMI 36 | P99 | >16 | ≤1 | 0.125 | 128 | 16 | 256 | >4 |
| E. coli JMI 10767 | Wt | 8 | ≤1 | ≤0.031 | ≤1 | ≤0.25 | ≤1 | ≤0.062 |
| E. coli JMI 10768 | CTX-M15 (Weak ESBL) | 8 | ≤1 | ≤0.031 | 8 | ≤0.25 | 8 | ≤0.062 |
| E. coli JMI 10770 | CTX-M15 (Hyper ESBL) | 8 | ≤1 | ≤0.031 | 64 | ≤0.25 | 64 | ≤0.062 |
| E. coli JMI 11103 | CTX-M15 (Intermediate ESBL) | 8 | ≤1 | ≤0.031 | 32 | ≤0.25 | 16 | ≤0.062 |

TABLE 7

Synergy of the inhibitor Ex. 47 (4 µg/mL) in combination with antibiotics

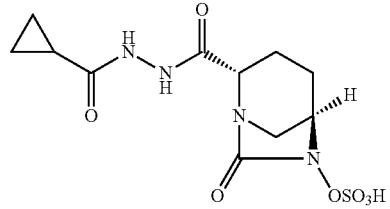

Ex. 47

| Organism | Enzyme | Ex. 47 Alone | Meropenem | Meropenem + Ex. 47 (4 µg/mL) | Ceftazidime | Ceftazidime + Ex. 47 (4 µg/mL) | Aztreonam | Aztreonam + Ex. 47 (4 µg/mL) |
|---|---|---|---|---|---|---|---|---|
| E. coli ATCC 25922 | Wt | >16 | 0.06 | ≤0.0312 | 0.25 | ≤0.25 | 0.25 | ≤0.0625 |
| A. baumanii JMI 2659 | Ges-14 (Cpase) | >16 | 64 | >2 | 512 | >16 | 512 | >4 |
| E. coli JMI 4103 | KPC-2, Tem-1, CMY-Type | 2 | 64 | ≤0.0312 | >512 | ≤0.25 | >512 | ≤0.062 |
| E. coli JMI 4080 | Tem-10 | 4 | ≤1 | ≤0.0312 | 64 | ≤0.25 | 64 | ≤0.062 |
| E. coli JMI 2692 | NDM-1, TEM-1, CTX-M-15 | 8 | 256 | 0.5 | >512 | ≤0.25 | >512 | ≤0.062 |
| E. coli JMI 2671 | VIM-19 (Cpase) | 8 | 64 | 0.5 | 64 | 0.5 | 64 | ≤0.062 |
| E. coli JMI 2665 | CMY-2 (Plasmid Cpase) | 2 | ≤1 | ≤0.0312 | 8 | ≤0.25 | 8 | ≤0.062 |
| K. pneumo JMI 4109 | SHV-1, SHV-12 | 2 | ≤1 | ≤0.0312 | 8 | ≤0.25 | 8 | 0.125 |
| K. pneumo JMI 2673 | CTX-M14 (ESBL) | >16 | ≤1 | ≤0.0312 | 32 | ≤0.25 | 32 | ≤0.062 |
| K. pneumo JMI 2674 | CTX-M15 (ESBL) | >16 | ≤1 | 0.125 | 512 | ≤0.25 | 512 | ≤0.062 |
| K. pneumo JMI 4088 | KPC-3 (Cpase) | >16 | 512 | 1 | >512 | 1 | >512 | 0.125 |
| K. pneumo JMI 4106 | KPC-3, TEM-1, SHV-12, SHV-141 | 16 | 128 | ≤0.0312 | >512 | ≤0.25 | >512 | 0.125 |
| K. pneumo JMI 2693 | NDM-1 (Cpase) | >16 | 8 | 0.25 | >512 | 2 | >512 | 1 |
| K. pneumo JMI 2697 | IMP-4 (Cpase) | >16 | 64 | 2 | >512 | 16 | >512 | ≤0.062 |
| K. pneumo JMI 2681 | Oxa-48 (Cpase) | >16 | 64 | 0.25 | 512 | 0.5 | 512 | 0.25 |
| K. pneumo JMI 2699 | VIM-1, CTX-M3 | 16 | 32 | 0.5 | >512 | 0.5 | >512 | ≤0.062 |
| P. aerug JMI 2686 | KPC-2 (Cpase) | >16 | 512 | >2 | 512 | >16 | 512 | >4 |
| P. aerug JMI 149 | Bla+++D+ | >16 | 4 | >2 | 256 | >16 | 256 | >4 |
| E. cloacae JMI 36 | P99 | >16 | ≤1 | 0.125 | 128 | 0.5 | 128 | 0.125 |
| E. coli JMI 10767 | Wt | 8 | ≤1 | ≤0.0312 | ≤1 | ≤0.25 | ≤1 | ≤0.062 |
| E. coli JMI 10768 | CTX-M15 (Weak ESBL) | 16 | ≤1 | ≤0.0312 | 8 | 2 | 8 | ≤0.062 |
| E. coli JMI 10770 | CTX-M15 (Hyper ESBL) | 8 | ≤1 | ≤0.0312 | 64 | ≤0.25 | 64 | ≤0.062 |
| E. coli JMI 11103 | CTX-M15 (Intermediate ESBL) | 16 | ≤1 | ≤0.0312 | 32 | ≤0.25 | 32 | ≤0.062 |

TABLE 8

Synergy of the inhibitor Ex. 49 (4 µg/mL) in combination with antibiotics

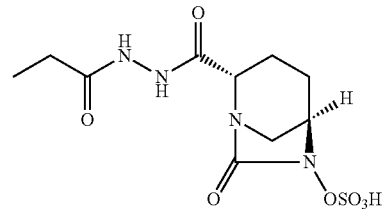

Ex. 49

| Organism | Enzyme | Ex. 49 Alone | Meropenem | Meropenem + Ex. 49 (4 µg/mL) | Ceftazidime | Ceftazidime + Ex. 49 (4 µg/mL) | Aztreonam | Aztreonam + Ex. 49 (4 µg/mL) |
|---|---|---|---|---|---|---|---|---|
| E. coli ATCC 25922 | Wt | 16 | 0.06 | ≤0.0312 | 0.25 | ≤0.25 | 0.125 | ≤0.0625 |
| A. baumanii JMI 2659 | Ges-14 (Cpase) | >16 | 64 | >2 | 512 | >16 | 256 | >4 |
| E. coli JMI 4103 | KPC-2, Tem-1, CMY-Type | 4 | 64 | ≤0.0312 | >512 | ≤0.25 | 256 | ≤0.062 |
| E. coli JMI 4080 | Tem-10 | 4 | ≤1 | ≤0.0312 | 64 | ≤0.25 | 125 | ≤0.062 |
| E. coli JMI 2692 | NDM-1, TEM-1, CTX-M-15 | 4 | 256 | 2 | >512 | ≤0.25 | 256 | ≤0.062 |
| E. coli JMI 2671 | VIM-19 (Cpase) | >16 | 64 | 1 | 64 | 0.5 | 16 | ≤0.062 |
| E. coli JMI 2665 | CMY-2 (Plasmid Cpase) | 4 | ≤1 | ≤0.0312 | 8 | ≤0.25 | 64 | ≤0.062 |
| K. pneumo JMI 4109 | SHV-1, SHV-12 | 4 | ≤1 | ≤0.0312 | 8 | ≤0.25 | ≤1 | ≤0.062 |
| K. pneumo JMI 2673 | CTX-M14 (ESBL) | >16 | ≤1 | ≤0.0312 | 32 | ≤0.25 | 8 | ≤0.062 |
| K. pneumo JMI 2674 | CTX-M15 (ESBL) | >16 | ≤1 | 0.062 | 512 | ≤0.25 | 32 | ≤0.062 |
| K. pneumo JMI 4088 | KPC-3 (Cpase) | >16 | 512 | 0.5 | >512 | 0.5 | 512 | 0.125 |

TABLE 8-continued

Synergy of the inhibitor Ex. 49 (4 µg/mL) in combination with antibiotics

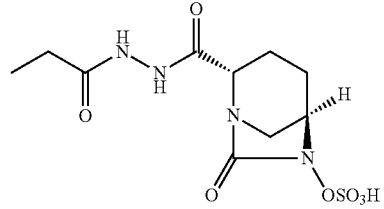

Ex. 49

| Organism | Enzyme | Ex. 49 Alone | Meropenem | Meropenem + Ex. 49 (4 µg/mL) | Ceftazidime | Ceftazidime + Ex. 49 (4 µg/mL) | Aztreonam | Aztreonam + Ex. 49 (4 µg/mL) |
|---|---|---|---|---|---|---|---|---|
| K. pneumo JMI 4106 | KPC-3, TEM-1, SHV-12, SHV-141 | >16 | 128 | ≤0.0312 | >512 | ≤0.25 | 512 | ≤0.062 |
| K. pneumo JMI 2693 | NDM-1 (Cpase) | >16 | 8 | 0.125 | >512 | 8 | 256 | 2 |
| K. pneumo JMI 2697 | IMP-4 (Cpase) | >16 | 64 | 2 | >512 | 16 | 256 | ≤0.062 |
| K. pneumo JMI 2681 | Oxa-48 (Cpase) | >16 | 64 | 0.5 | 512 | ≤0.25 | 256 | 0.125 |
| K. pneumo JMI 2699 | VIM-1, CTX-M3 | >16 | 32 | 0.125 | >512 | ≤0.25 | 128 | ≤0.062 |
| P. aerug JMI 2686 | KPC-2 (Cpase) | >16 | 512 | >2 | 512 | >16 | >512 | >4 |
| P. aerug JMI 149 | Bla+++D+ | >16 | 4 | 0.5 | 256 | >16 | 512 | >4 |
| E. cloacae JMI 36 | P99 | >16 | ≤1 | 0.25 | 128 | 0.5 | 256 | 0.125 |
| E. coli JMI 10767 | Wt | >16 | ≤1 | ≤0.0312 | ≤1 | ≤0.25 | ≤1 | ≤0.062 |
| E. coli JMI 10768 | CTX-M15 (Weak ESBL) | >16 | ≤1 | ≤0.0312 | 8 | ≤0.25 | 8 | ≤0.062 |
| E. coli JMI 10770 | CTX-M15 (Hyper ESBL) | >16 | ≤1 | ≤0.0312 | 64 | ≤0.25 | 64 | ≤0.062 |
| E. coli JMI 11103 | CTX-M15 (Intermediate ESBL) | >16 | ≤1 | ≤0.0312 | 32 | ≤0.25 | 32 | ≤0.062 |

TABLE 9

Synergy of the inhibitor Ex. 67 (4 µg/mL) in combination with antibiotics

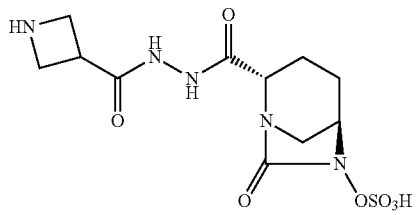

Ex. 67

| Organism | Enzyme | Ex. 67 Alone | Meropenem | Meropenem + Ex. 67 (4 µg/mL) | Ceftazidime | Ceftazidime + Ex. 67 (4 µg/mL) | Aztreonam | Aztreonam + Ex. 67 (4 µg/mL) |
|---|---|---|---|---|---|---|---|---|
| E. coli ATCC 25922 | Wt | >16 | 0.06 | ≤0.03 | 0.25 | ≤0.25 | 0.25 | ≤0.06 |
| A. baumanii JMI 2659 | Ges-14 (Cpase) | >16 | 64 | 2 | 512 | 16 | 512 | >4 |
| E. coli JMI 4103 | KPC-2, Tem-1, CMY-Type | 16 | 64 | 0.06 | >512 | 0.5 | >512 | ≤0.06 |
| E. coli JMI 4080 | Tem-10 | 16 | ≤1 | ≤0.03 | 64 | 0.25 | 64 | ≤0.06 |
| E. coli JMI 2692 | NDM-1, TEM-1, CTX-M-15 | 8 | 256 | 0.125 | >512 | >16 | >512 | 1 |
| E. coli JMI 2671 | VIM-19 (Cpase) | >16 | 64 | 0.125 | 64 | 1 | 64 | ≤0.06 |
| E. coli JMI 2665 | CMY-2 (Plasmid Cpase) | 8 | ≤1 | ≤0.03 | 8 | ≤0.25 | 8 | ≤0.06 |
| K. pneumo JMI 4109 | SHV-1, SHV-12 | 4 | ≤1 | ≤0.03 | 8 | ≤0.25 | 8 | ≤0.06 |
| K. pneumo JMI 2673 | CTX-M14 (ESBL) | >16 | ≤1 | ≤0.03 | 32 | ≤0.25 | 32 | ≤0.06 |
| K. pneumo JMI 2674 | CTX-M15 (ESBL) | >16 | ≤1 | 0.06 | 512 | ≤0.25 | 512 | 0.125 |
| K. pneumo JMI 4088 | KPC-3 (Cpase) | 16 | 512 | 0.06 | >512 | ≤0.25 | >512 | 0.5 |
| K. pneumo JMI 4106 | KPC-3, TEM-1, SHV-12, SHV-141 | 8 | 128 | 0.125 | >512 | ≤0.25 | >512 | 0.5 |
| K. pneumo JMI 2693 | NDM-1 (Cpase) | >16 | 8 | 0.125 | >512 | ≤0.25 | >512 | 0.25 |
| K. pneumo JMI 2697 | IMP-4 (Cpase) | 16 | 64 | 2 | >512 | 8 | >512 | ≤0.06 |
| K. pneumo JMI 2681 | Oxa-48 (Cpase) | >16 | 64 | >2 | 512 | ≤0.25 | 512 | 0.25 |
| K. pneumo JMI 2699 | VIM-1, CTX-M3 | >16 | 32 | 0.5 | >512 | ≤0.25 | >512 | 0.06 |
| P. aerug JMI 2686 | KPC-2 (Cpase) | 16 | 512 | >2 | 512 | >16 | 512 | >4 |
| P. aerug JMI 149 | Bla+++D+ | 16 | 4 | 0.5 | 256 | 16 | 256 | >4 |
| E. cloacae JMI 36 | P99 | >16 | ≤1 | 0.06 | 128 | ≤0.25 | 128 | 0.25 |

TABLE 9-continued

Synergy of the inhibitor Ex. 67 (4 µg/mL) in combination with antibiotics

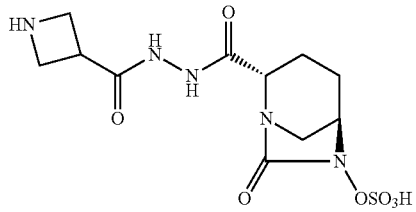

Ex. 67

| Organism | Enzyme | Ex. 67 Alone | Meropenem | Meropenem + Ex. 67 (4 µg/mL) | Ceftazidime | Ceftazidime + Ex. 67 (4 µg/mL) | Aztreonam | Aztreonam + Ex. 67 (4 µg/mL) |
|---|---|---|---|---|---|---|---|---|
| E. coli JMI 10767 | Wt | >16 | ≤1 | ≤0.03 | ≤1 | ≤0.25 | ≤1 | ≤0.06 |
| E. coli JMI 10768 | CTX-M15 (Weak ESBL) | >16 | ≤1 | ≤0.03 | 8 | ≤0.25 | 8 | ≤0.06 |
| E. coli JMI 10770 | CTX-M15 (Hyper ESBL) | >16 | ≤1 | ≤0.03 | 64 | ≤0.25 | 64 | ≤0.06 |
| E. coli JMI 11103 | CTX-M15 (Intermediate ESBL) | >16 | ≤1 | ≤0.03 | 32 | ≤0.25 | 32 | ≤0.06 |

TABLE 10

Synergy of inhibitor Ex. 2 (4 µg/mL) in combination with antibiotics against metallo-β-lactamase producing bacteria

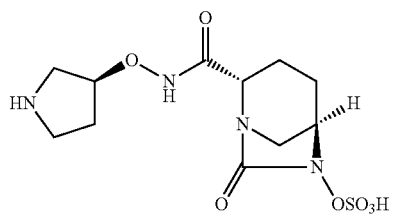

Ex. 2

| Organism | Isolate No | Enzyme | Ex. 2 alone | AZT | AZT + Ex. 2 | CAZ | CAZ + Ex. 2 | MER | MER + Ex. 2 |
|---|---|---|---|---|---|---|---|---|---|
| Citrobacter freundii | 49469 | NDM-1 | >64 | 256 | 0.5 | >256 | >64 | 16 | 8 |
| Enterobacter aerogenes | 47683 | VIM-12 | >64 | 4 | ≤0.03 | 256 | >64 | 8 | 2 |
| Enterobacter aerogenes | 8397 | VIM-1 | >64 | >256 | 0.5 | >256 | >64 | 64 | 64 |
| Enterobacter cloacae | 1874 | IMP-21 | 4 | ≥0.12 | ≤0.03 | 32 | ≤0.03 | 4 | ≤0.03 |
| Enterobacter cloacae | 1280 | VIM-5 | 4 | 8 | ≤0.03 | 64 | ≤0.03 | 4 | ≤0.03 |
| Enterobacter cloacae | 3686 | IMP-1 | 4 | 32 | ≤0.03 | >256 | ≤0.03 | 8 | 0.25 |
| Enterobacter cloacae | 25 | IMP-4 | 8 | 64 | 0.25 | >256 | 64 | 16 | 2 |
| Enterobacter cloacae | 1471 | VIM-1 | 4 | 64 | ≤0.03 | >256 | ≤0.03 | 2 | ≤0.03 |
| Enterobacter cloacae | 10 | IMP-26 | 64 | 128 | 0.12 | >256 | ≤0.03 | 16 | ≤0.03 |
| Enterobacter cloacae | 53477 | NDM-1 | 4 | 128 | ≤0.03 | >256 | ≤0.03 | 32 | ≤0.03 |
| Enterobacter cloacae | 1068 | VIM-2 | 8 | 128 | 0.06 | 128 | 8 | 2 | ≤0.03 |
| Enterobacter cloacae | 4 | VIM-6 | 64 | 128 | 0.12 | 256 | 32 | 2 | 0.25 |
| Escherichia coli | 13 | IMP-1 | 16 | 16 | ≤0.03 | 256 | ≤0.03 | 4 | ≤0.03 |
| Escherichia coli | 49 | NDM-1 | 4 | 128 | ≤0.03 | >256 | ≤0.03 | 8 | ≤0.03 |
| Escherichia coli | 17 | NDM-1 | 4 | >256 | ≤0.03 | >256 | ≤0.03 | 32 | ≤0.03 |
| Escherichia coli | 53749 | NDM-1 | 4 | >256 | ≤0.03 | >256 | 0.06 | 64 | ≤0.03 |
| Klebsiella oxytoca | 31141 | VIM-23 | >64 | 8 | ≤0.03 | 128 | 2 | 2 | 0.5 |
| Klebsiella oxytoca | 24825 | IMP-26 | >64 | 128 | 0.06 | >256 | >64 | 32 | 4 |
| Klebsiella pneumoniae | 38 | NDM-1 | >64 | 64 | ≤0.03 | >256 | ≤0.03 | 32 | ≤0.03 |
| Klebsiella pneumoniae | 16 | VIM-5 | >64 | 256 | ≤0.03 | >256 | ≤0.03 | 8 | ≤0.03 |
| Providencia stuartii | 26582 | VIM-1 | >64 | 32 | 0.06 | >256 | 32 | 1 | 0.5 |
| Serratia marcescens | 35 | IMP-4 | >64 | ≥0.12 | 0.06 | 64 | 64 | 8 | 4 |
| Serratia marcescens | 36098 | IMP-19 | >64 | >256 | 2 | 128 | 64 | 8 | 8 |

TABLE 11

Synergy of inhibitor Ex. 4 (4 µg/mL) in combination with antibiotics against metallo-β-lactamase producing bacteria

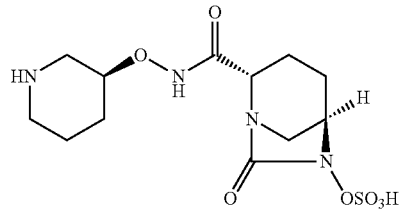

Ex. 4

| Organism | Isolate No | Enzyme | Ex. 4 alone | AZT | AZT + Ex. 4 | CAZ | CAZ + Ex. 4 | MER | MER + Ex. 4 |
|---|---|---|---|---|---|---|---|---|---|
| Citrobacter freundii | 49469 | NDM-1 | >64 | 256 | 0.06 | >256 | >64 | 16 | 4 |
| Enterobacter aerogenes | 47683 | VIM-12 | >64 | 4 | ≤0.03 | 256 | 32 | 8 | 0.5 |
| Enterobacter aerogenes | 8397 | VIM-1 | >64 | >256 | 0.5 | >256 | >64 | 64 | 64 |
| Enterobacter cloacae | 1874 | IMP-21 | 2 | ≥0.12 | ≤0.03 | 32 | 0.06 | 4 | ≤0.03 |
| Enterobacter cloacae | 1280 | VIM-5 | 4 | 8 | ≤0.03 | 64 | ≤0.03 | 4 | ≤0.03 |
| Enterobacter cloacae | 3686 | IMP-1 | 4 | 32 | ≤0.03 | >256 | ≤0.03 | 8 | ≤0.03 |
| Enterobacter cloacae | 25 | IMP-4 | 4 | 64 | ≤0.03 | >256 | 32 | 16 | 2 |
| Enterobacter cloacae | 1471 | VIM-1 | 4 | 64 | 0.06 | >256 | ≤0.03 | 2 | ≤0.03 |
| Enterobacter cloacae | 10 | IMP-26 | 64 | 128 | ≤0.03 | >256 | ≤0.03 | 16 | ≤0.03 |
| Enterobacter cloacae | 53477 | NDM-1 | 8 | 128 | ≤0.03 | >256 | ≤0.03 | 32 | ≤0.03 |
| Enterobacter cloacae | 1068 | VIM-2 | 4 | 128 | ≤0.03 | 128 | ≤0.03 | 2 | ≤0.03 |
| Enterobacter cloacae | 4 | VIM-6 | 64 | 128 | ≤0.03 | 256 | 0.12 | 2 | 0.25 |
| Escherichia coli | 13 | IMP-1 | 2 | 16 | ≤0.03 | 256 | ≤0.03 | 4 | ≤0.03 |
| Escherichia coli | 49 | NDM-1 | 2 | 128 | ≤0.03 | >256 | ≤0.03 | 8 | ≤0.03 |
| Escherichia coli | 17 | NDM-1 | 2 | >256 | ≤0.03 | >256 | ≤0.03 | 32 | ≤0.03 |
| Escherichia coli | 53749 | NDM-1 | 2 | >256 | ≤0.03 | >256 | ≤0.03 | 64 | ≤0.03 |
| Klebsiella oxytoca | 31141 | VIM-23 | >64 | 8 | ≤0.03 | 128 | 0.5 | 2 | 0.25 |
| Klebsiella oxytoca | 24825 | IMP-26 | >64 | 128 | ≤0.03 | >256 | >64 | 32 | 8 |
| Klebsiella pneumoniae | 38 | NDM-1 | >64 | 64 | ≤0.03 | >256 | ≤0.03 | 32 | ≤0.03 |
| Klebsiella pneumoniae | 16 | VIM-5 | >64 | 256 | ≤0.03 | >256 | ≤0.03 | 8 | ≤0.03 |
| Providencia stuartii | 26582 | VIM-1 | >64 | 32 | ≤0.03 | >256 | 16 | 1 | 0.5 |
| Serratia marcescens | 35 | IMP-4 | >64 | ≥0.12 | ≤0.03 | 64 | 32 | 8 | 2 |
| Serratia marcescens | 36098 | IMP-19 | >64 | >256 | 2 | 128 | 64 | 8 | 8 |

TABLE 12

Synergy of inhibitor Ex. 40 (4 µg/mL) in combination with antibiotics against metallo-β-lactamase producing bacteria

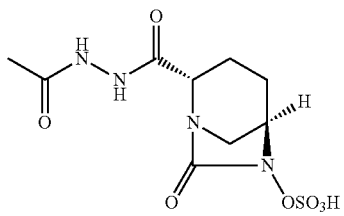

Ex. 40

| Organism | Isolate No | Enzyme | Ex. 40 alone | AZT | AZT + Ex. 40 | CAZ | CAZ + Ex. 40 | MER | MER + Ex. 40 |
|---|---|---|---|---|---|---|---|---|---|
| Citrobacter freundii | 49469 | NDM-1 | >64 | 256 | ≤0.03 | >256 | >64 | 16 | 2 |
| Enterobacter aerogenes | 47683 | VIM-12 | >64 | 4 | ≤0.03 | 256 | 64 | 8 | 1 |
| Enterobacter aerogenes | 8397 | VIM-1 | >64 | >256 | 0.25 | >256 | >64 | 64 | 64 |
| Enterobacter cloacae | 1874 | IMP-21 | 2 | ≥0.12 | ≤0.03 | 32 | ≤0.03 | 4 | ≤0.03 |
| Enterobacter cloacae | 1280 | VIM-5 | 4 | 8 | ≤0.03 | 64 | ≤0.03 | 4 | ≤0.03 |
| Enterobacter cloacae | 3686 | IMP-1 | 2 | 32 | ≤0.03 | >256 | ≤0.03 | 8 | ≤0.03 |
| Enterobacter cloacae | 25 | IMP-4 | 4 | 64 | ≤0.03 | >256 | 32 | 16 | 2 |
| Enterobacter cloacae | 1471 | VIM-1 | 2 | 64 | ≤0.03 | >256 | ≤0.03 | 2 | ≤0.03 |
| Enterobacter cloacae | 10 | IMP-26 | 64 | 128 | ≤0.03 | >256 | ≤0.03 | 16 | ≤0.03 |
| Enterobacter cloacae | 53477 | NDM-1 | 2 | 128 | ≤0.03 | >256 | ≤0.03 | 32 | ≤0.03 |
| Enterobacter cloacae | 1068 | VIM-2 | 4 | 128 | ≤0.03 | 128 | ≤0.03 | 2 | ≤0.03 |
| Enterobacter cloacae | 4 | VIM-6 | 64 | 128 | ≤0.03 | 256 | 0.25 | 2 | 0.25 |
| Escherichia coli | 13 | IMP-1 | 1 | 16 | ≤0.03 | 256 | ≤0.03 | 4 | ≤0.03 |
| Escherichia coli | 49 | NDM-1 | 2 | 128 | ≤0.03 | >256 | ≤0.03 | 8 | ≤0.03 |
| Escherichia coli | 17 | NDM-1 | 2 | >256 | ≤0.03 | >256 | ≤0.03 | 32 | 0.06 |
| Escherichia coli | 53749 | NDM-1 | 2 | >256 | ≤0.03 | >256 | ≤0.03 | 64 | ≤0.03 |

TABLE 12-continued

Synergy of inhibitor Ex. 40 (4 μg/mL) in combination with antibiotics against metallo-β-lactamase producing bacteria Ex. 40

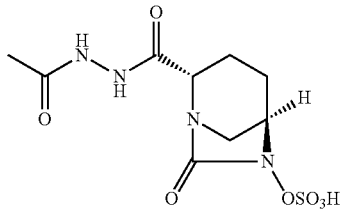

| Organism | Isolate No | Enzyme | Ex. 40 alone | AZT | AZT + Ex. 40 | CAZ | CAZ + Ex. 40 | MER | MER + Ex. 40 |
|---|---|---|---|---|---|---|---|---|---|
| Klebsiella oxytoca | 31141 | VIM-23 | >64 | 8 | ≤0.03 | 128 | 2 | 2 | 0.5 |
| Klebsiella oxytoca | 24825 | IMP-26 | >64 | 128 | ≤0.03 | >256 | >64 | 32 | 8 |
| Klebsiella pneumoniae | 38 | NDM-1 | >64 | 64 | ≤0.03 | >256 | ≤0.03 | 32 | ≤0.03 |
| Klebsiella pneumoniae | 16 | VIM-5 | >64 | 256 | ≤0.03 | >256 | ≤0.03 | 8 | ≤0.03 |
| Providencia stuartii | 26582 | VIM-1 | >64 | 32 | ≤0.03 | >256 | 16 | 1 | 0.5 |
| Serratia marcescens | 35 | IMP-4 | >64 | ≥0.12 | ≤0.03 | 64 | 32 | 8 | 2 |
| Serratia marcescens | 36098 | IMP-19 | >64 | >256 | 0.5 | 128 | 64 | 8 | 8 |

Test for β-Lactamase Inhibitory Activity:

The inhibitory activities of present compounds against various enzymes were measured by spectrophotometric assay using 490 nM and using nitrocefin as a substrate [*J. Antimicrob. Chemother.*, 28, pp 775-776 (1991)]. The concentration of inhibitor ($IC_{50}$) which inhibits by 50% the reaction of hydrolysis of nitrocefin by the enzyme is determined. Table 13 shows the results.

TABLE 13

Test for β-lactamase Inhibitory Activity

| Example No. | $IC_{50}$ (μM) TEM-1 | $IC_{50}$ (μM) CMY-2 | $IC_{50}$ (μM) KPC-2 | $IC_{50}$ (μM) CTX-M-9 |
|---|---|---|---|---|
| Ex. 40 | 0.052 ± 0.004 | 0.008 ± 0.001 | 0.091 ± 0.009 | 0.327 ± 0.020 |

In light of the data described herein, persons of skill in the art would expect that all of the compounds within the scope of formula (I), salts of such compounds, solvates of such compounds and salts thereof, and deuterated compounds of all such compounds, salts and solvates (i.e., compounds of formula (I) modified in that they have been deuterated, salts of compounds of formula (I) modified in that they have been deuterated, and solvates of such compounds and salts, modified in that they have been deuterated) would be effective on their own as antibacterial compounds, and in combination with β-lactam antibiotics.

Efficacy of the β-lactamase inhibitors can be evaluated in combination with ceftazidime (CAZ) aztreonam (AZT), meropenem (MER) and other class of cephalosporins and carbapenems in murine infection models such as septicemia, pneumoniae and thigh infection models (Ref: Andrea Endimiani et. al. *Antimicrob. Agents and Chemother* January 2011, pp-82-85). For murine acute lethal septicemia model, mice were infected by the intraperitoneal injection of the clinical strains resulting in death of the untreated controls within 24-48 hrs. In particular, a fresh predetermined bacterial inoculum of approximately $3.3 \times 10^5$ to $3.6 \times 10^5$ CFU (colony forming units) in 5% hog gastric mucin grown overnight. Thirty minutes post infection, a single subcutaneous dose of CAZ with and without β-lactamase inhibitor was initiated and the survival ratio monitored for 5 days twice daily. For each strain tested, the dosing regimen used are CAZ alone (doses of 512, 1024 & 2048 mg/kg of body weight) and CAZ plus β-lactamase inhibitor at ratio of 2:1, 4:1, 8:1 & 16:1 (CAZ doses were 4, 8, 16, 32 & 64 mg/kg for each ratio). The median effective dose for 50% ($ED_{50}$) of animals was determined by a computerized program of Probit analysis. Survival rates stratified for different dosing regimen were also obtained. For experimental pneumoniae model, immunocompromised mice were used and intratracheally infected with *Klebsiella pneumoniae* strains. Mice in this model develop bacteraemia pneumoniae and fatal disease within 2 to 4 days with lung bacterial burden at 16-18 hrs post infection of $10^{11}$ to $10^{13}$ cfu/gm lung. Treatment with CAZ and inhibitor at a ratio of 2/1 & 4/1 demonstrate efficacy with significant 3 to 6 log reduction in lung counts compared to CAZ alone and is relevant to the clinical situation. Human testing of the β-lactamase inhibitor can be conducted in combination with partner antibiotic at a set ratio utilizing standard clinical development practice.

Below are a series of numbered passages, each of which defines subject matter within the scope of the present inventive subject matter:

Passage 1. A compound of formula (I):

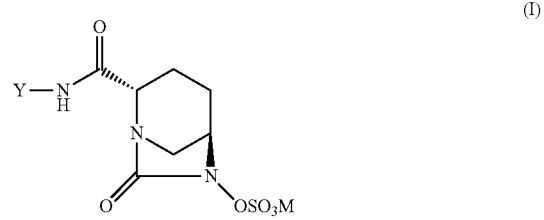

(I)

wherein:
M is hydrogen or a pharmaceutically acceptable salt-forming cation;
Y is $OR^1$;
$R^1$ is a radical selected from the group consisting of:
  (1) $C_{1-6}$ straight or branched chain alkyl which is optionally substituted;

(2) C$_{3-7}$ cycloalkyl which is optionally substituted;
(3) C$_{4-7}$ saturated heterocycles containing at least one heteroatom selected from O, N and S wherein the said heterocycle is optionally substituted, the ring S is optionally oxidized to S(O) or S(O)$_2$ and the free ring N atom may optionally take a substituent;
(4) Heterocyclyl (C$_{1-6}$) alkyl wherein the said heterocycle has the same definition as defined in (3), and the said heterocycle is optionally substituted;
(5) C$_{5-7}$ membered saturated heterocycles optionally fused with a C$_{3-7}$ membered cycloalkyl group to form a bicyclic ring system where the bicyclic ring system so formed is fused either through two adjacent carbon atoms or through a N atom shared by both the rings and the other end of the cycloalkyl chain is attached to the adjacent carbon atom of the molecule, each ring of the said bicyclic ring system independently optionally substituted;
(6) C$_{5-7}$ membered saturated heterocycles optionally fused with another C$_{5-7}$ saturated heterocycle to form a bicyclic ring system where the bicyclic ring system so formed is fused either through two adjacent carbon atoms or through a N atom shared by both the rings, each ring of the said bi-cyclic ring system independently optionally substituted;
(7) C$_{3-7}$ cycloalkyl which is optionally fused with a C$_{5-7}$ membered saturated heterocycle containing at least one heteroatom selected from O, N and S, the said bicyclic ring optionally substituted;
(8) Bridged bicyclic ring system having optionally one or two heteroatoms selected from O, N and S, the bicyclic ring system optionally substituted either at the carbon atom or at the free N atom present in the ring;
(9) C$_{5-7}$ membered saturated heterocycles optionally fused with C$_{5-7}$ membered heteroaryl ring where the bicyclic ring system so formed is fused either through two adjacent carbon atoms or through N atom shared by both the rings;
(10) C$_{5-7}$ membered saturated heterocycles optionally fused to a C$_{3-6}$ membered ring system through a common carbon atom to form a spiro system optionally containing one heteroatom selected from O, N and S that is present in the spiro ring where the ring S is optionally oxidized to S(O) or S(O)$_2$ and the free N atom present in either ring may optionally take a substituent; and
(11) C$_{5-7}$ membered heteroaryl (C$_{1-6}$) alkyl which is optionally substituted,
or a deuterated compound of any such compound.
Passage 2. A compound of formula (I):

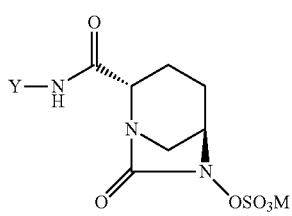

wherein:
M is hydrogen or a pharmaceutically acceptable salt-forming cation;
Y is NR$^2$R$^3$;
R$^2$ is hydrogen or optionally substituted C$_{1-6}$ lower alkyl;

R$^3$ is a radical selected from any of following groups consisting of:
(1) C$_{1-6}$ straight or branched chain alkyl which is optionally substituted;
(2) C$_{3-7}$ cycloalkyl which is optionally substituted;
(3) C$_{4-7}$ saturated heterocycles containing at least one heteroatom selected from O, N and S wherein the said heterocycle is optionally substituted, the ring S is optionally oxidized to S(O) or S(O)$_2$ and the free ring N atom may optionally take a substituent;
(4) C$_{1-6}$ straight or branched chain alkyl carbonyl which is optionally substituted;
(5) C$_{3-7}$ cycloalkyl carbonyl which is optionally substituted;
(6) C$_{4-7}$ membered saturated heterocyclyl carbonyl containing at least one heteroatom selected from O, N and S wherein the said heterocycle is optionally substituted, the ring S is optionally oxidized to S(O) or S(O)$_2$ and the free ring N atom may optionally take a substituent;
(7) C$_{3-7}$ membered saturated heterocyclyl (C$_{1-6}$) alkyl carbonyl wherein the said heterocycle has the same definition as defined in (6), and the free ring N atom may optionally take a substituent;
(8) C$_{6-10}$ aryl carbonyl which is optionally substituted;
(9) C$_{6-10}$ aryl (C$_{1-6}$) alkyl carbonyl which is optionally substituted;
(10) C$_{5-6}$ membered heteroaryl carbonyl containing at least one heteroatom selected from O, S and N wherein the heteroaryl is optionally substituted;
(11) C$_{5-6}$ heteroaryl (C$_{1-6}$) alkyl carbonyl wherein the said heteroaryl has the same definition as defined in (10);
(12) CF$_3$CO—, CH$_3$SO$_2$—, NH$_2$CO—, and NH$_2$SO$_2$—;
(13) C$_{6-10}$ aryl which is optionally substituted;
(14) C$_{5-6}$ membered heteroaryl which is optionally substituted;
(15) or R$^2$ and R$^3$ together may form an optionally substituted ring system and the said ring may contain another heteroatom selected from O, N, and S,
or a deuterated compound of any such compound.
Passage 3. A compound as recited in passage 1 or passage 2, wherein M is hydrogen.
Passage 4. A compound as recited in passage 1 or passage 2, wherein M is a pharmaceutically acceptable salt-forming cation.
Passage 5. A compound as recited in passage 2, wherein R$^2$ is hydrogen or C$_{1-6}$ lower alkyl.
Passage 6. A compound as recited in any one of passages 1-5, wherein R$^1$R$^2$ and R$^3$ are optionally substituted with one or two substituents independently selected from the following:
Lower alkyl, amino, substituted amino, alkoxy, hydroxyalkyl, halogen, hydroxy, carboxy, alkoxycarbonyl, haloalkyl, trifluoromethyl, trifluoromethyloxy, alkylamine, substituted alkylamine, carboxamide, thiocarboxamide, sulfonic acid, sulphate, acylamino, sulfonylamino, substituted or unsubstituted sulfonamide, substituted or unsubstituted urea, substituted or unsubstituted thiourea, oxo, oxyimino, hydroxamic acid, acyl, trifluoromethyl carbonyl, cyano, amidino, guanidino, aryloxy, heterocyclylalkyloxy, and heteroaryloxy.

Passage 7. A compound as recited in passage 1, which is selected from the following group of compounds:
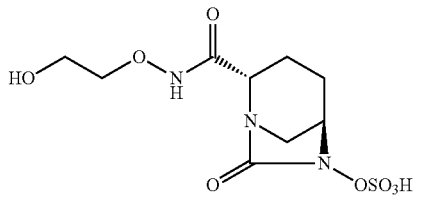
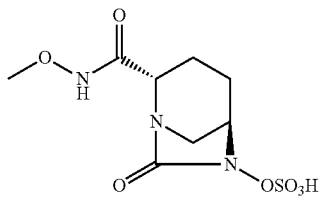
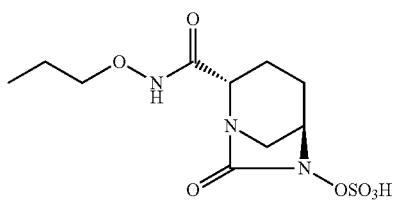
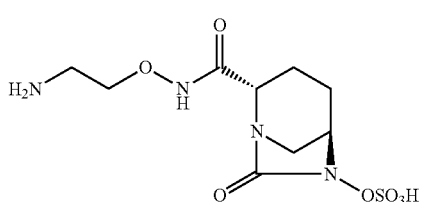
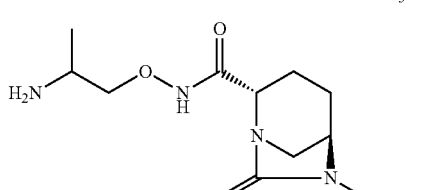
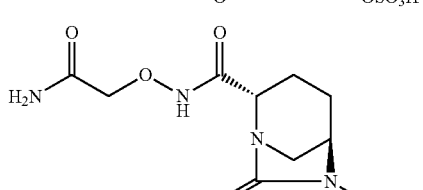
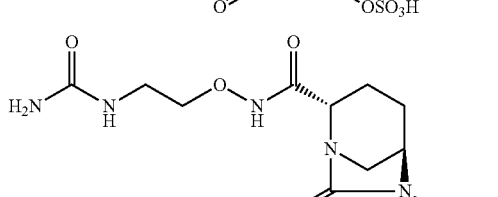
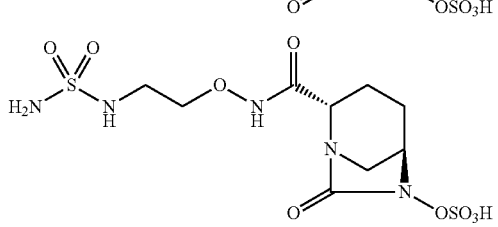
-continued
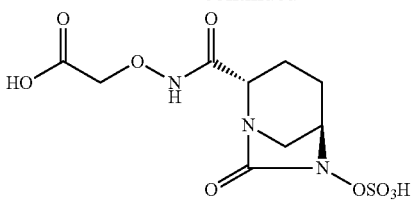
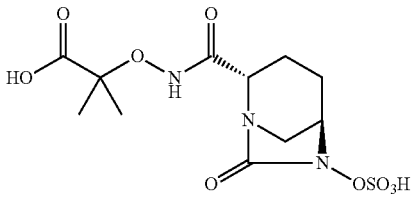
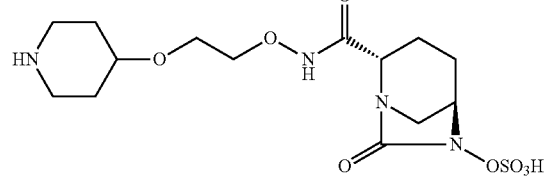
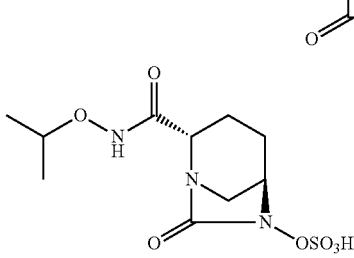
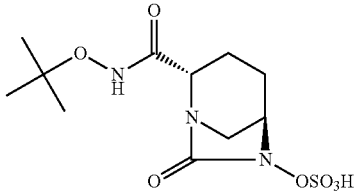
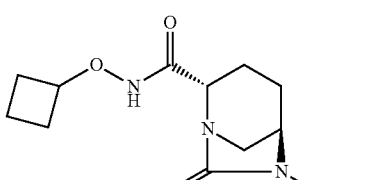
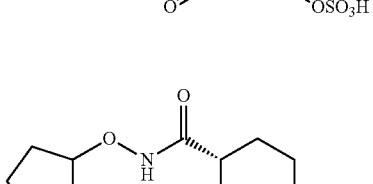
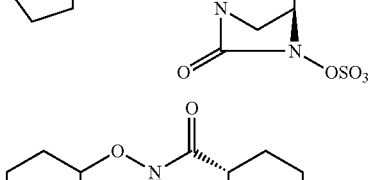
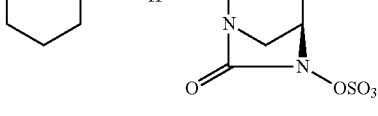

357
-continued
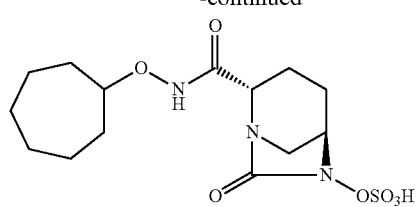
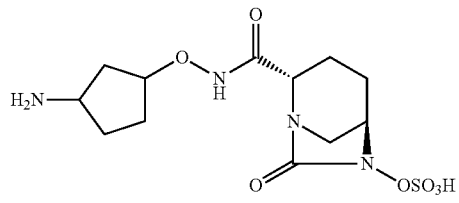
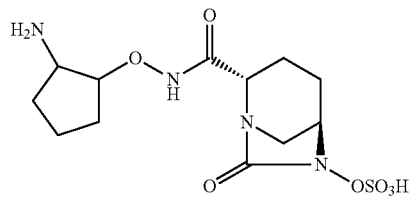
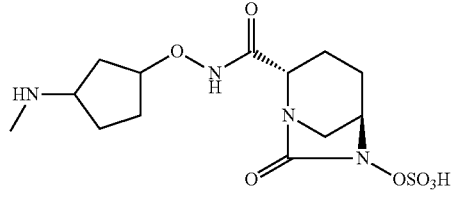
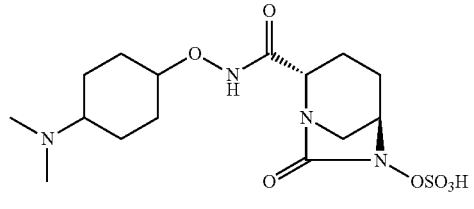
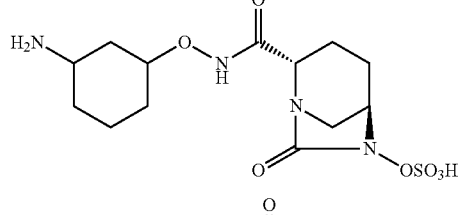
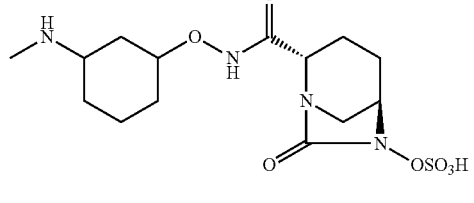
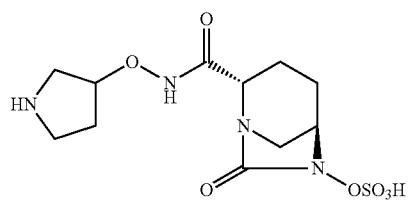
358
-continued
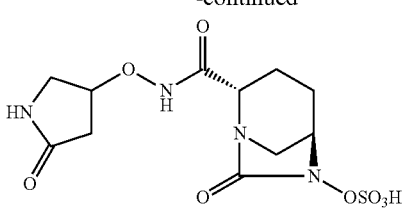
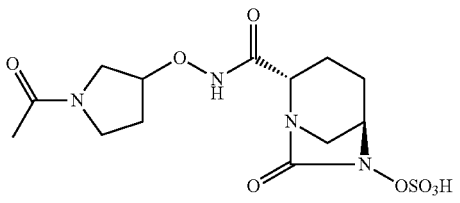
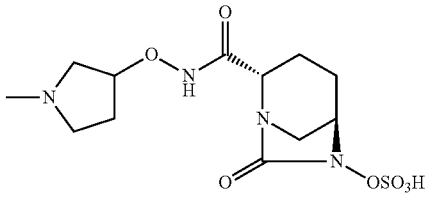
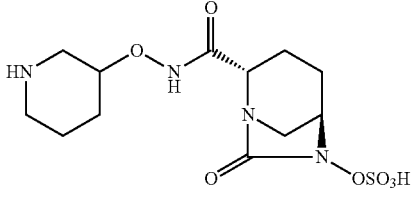
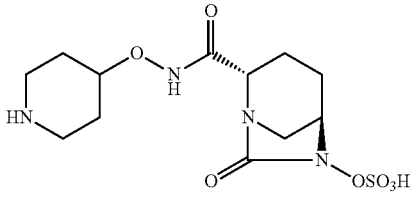
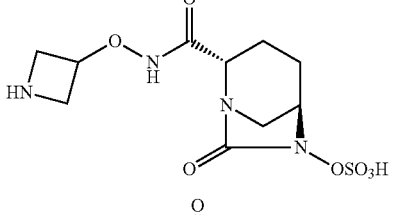
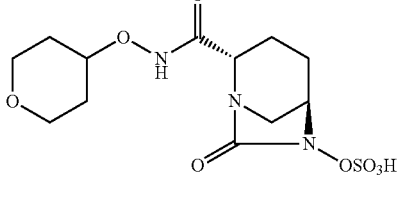
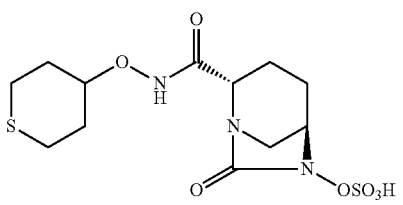

359
-continued
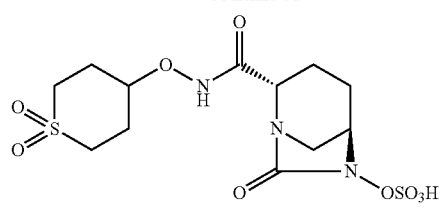
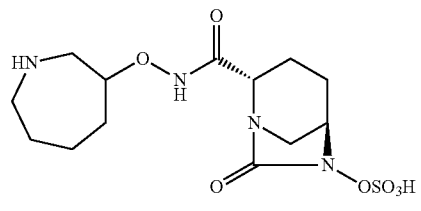
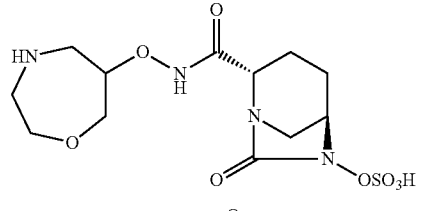
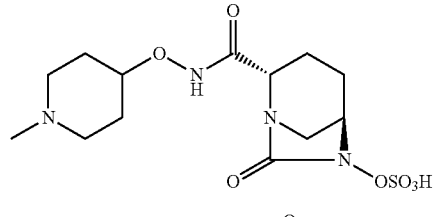
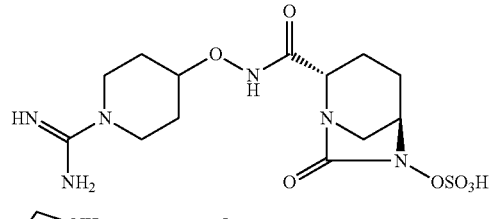
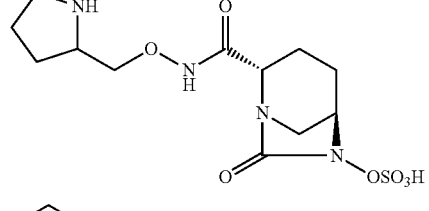
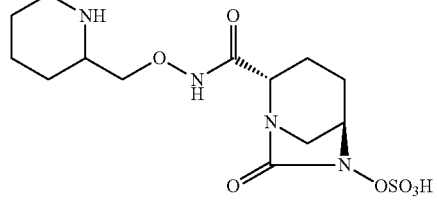
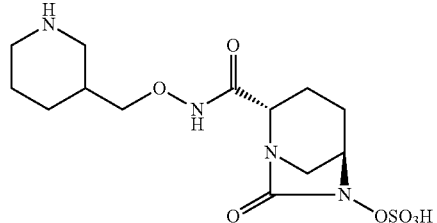
360
-continued
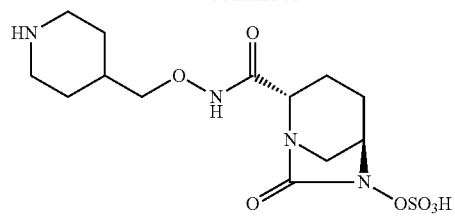
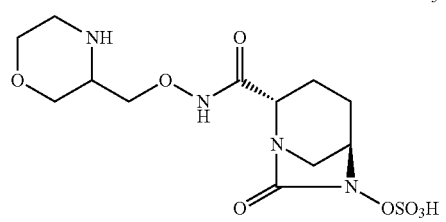
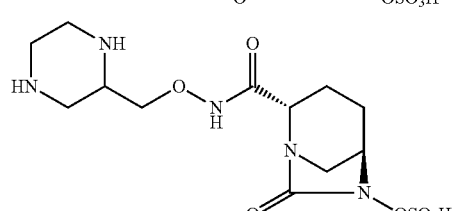
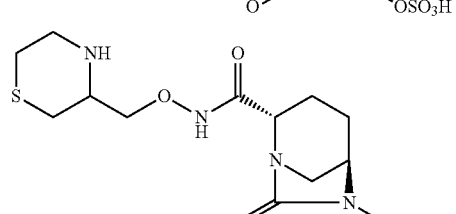
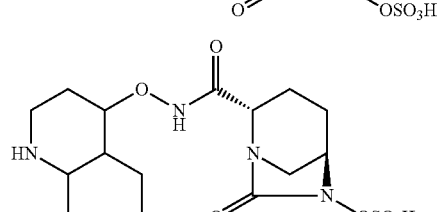
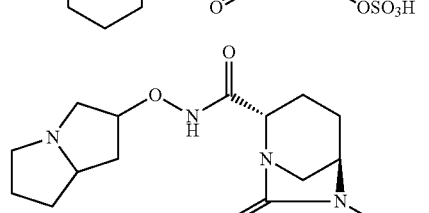
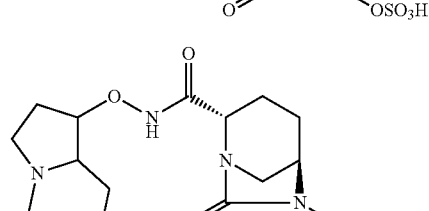
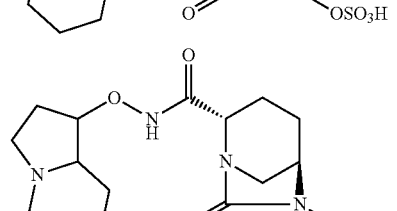

-continued
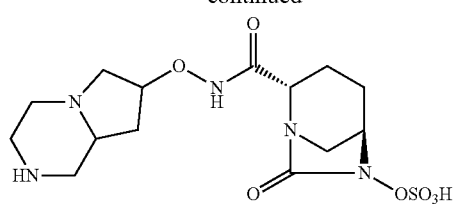
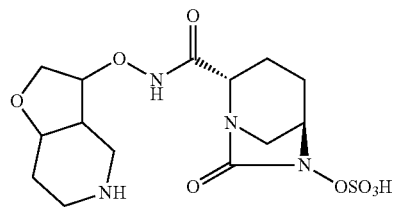
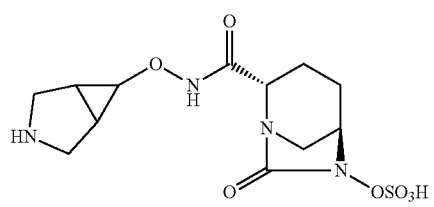
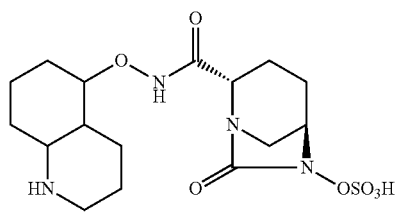
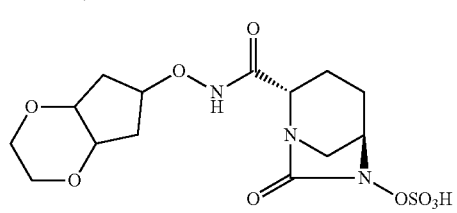
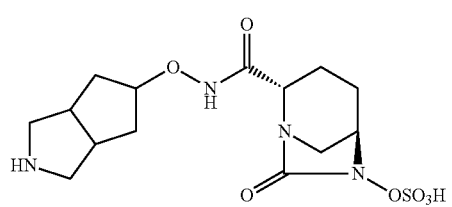
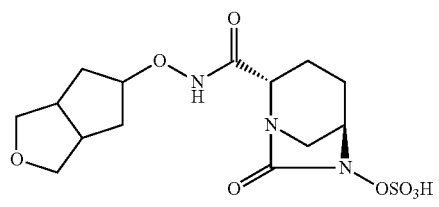
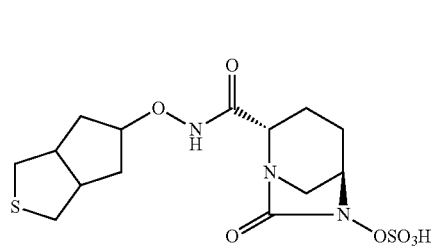
-continued
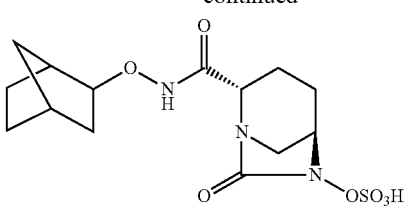
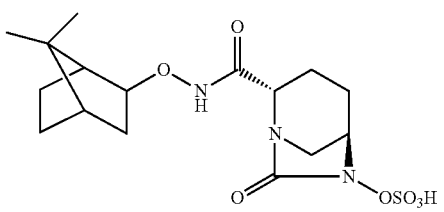
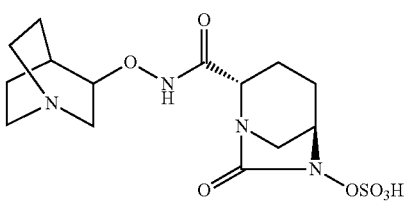
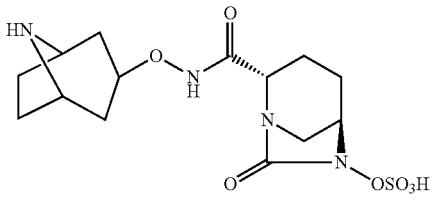
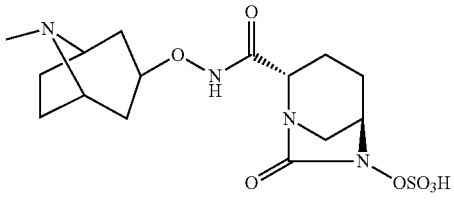
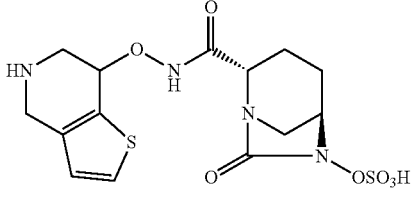
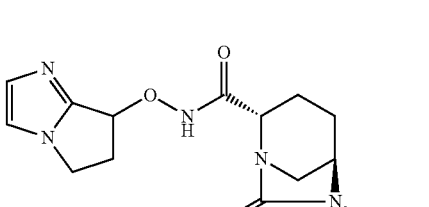
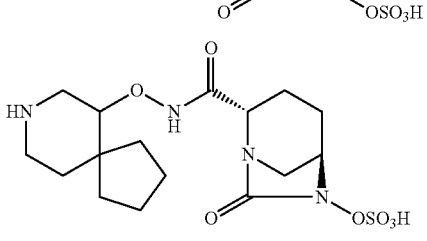

363
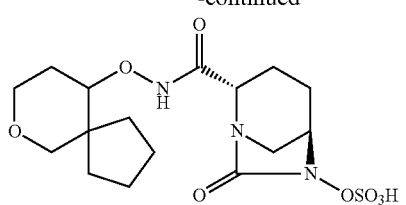
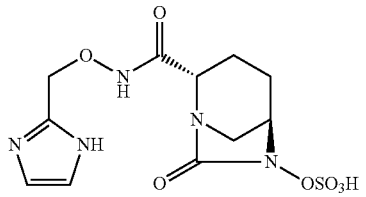
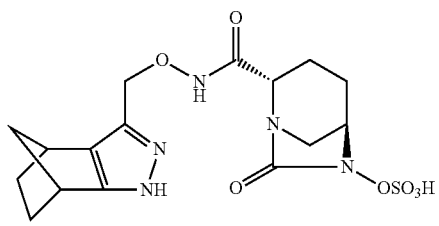
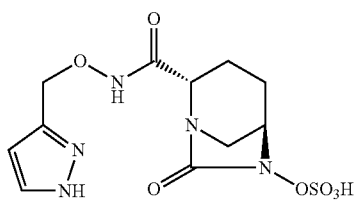
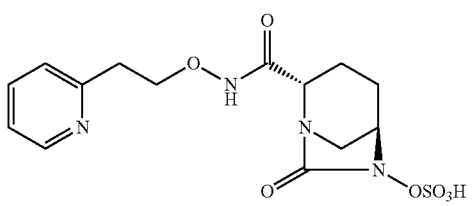
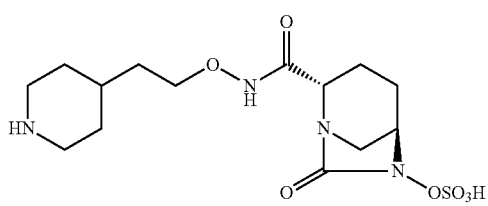
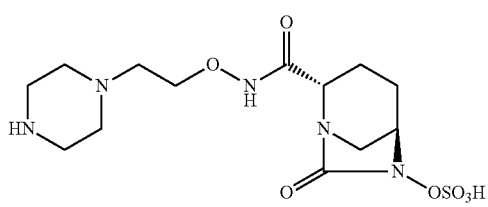
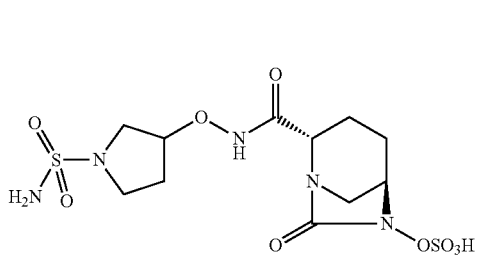
364
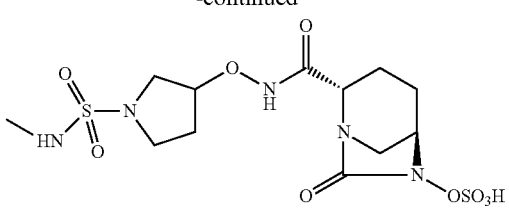
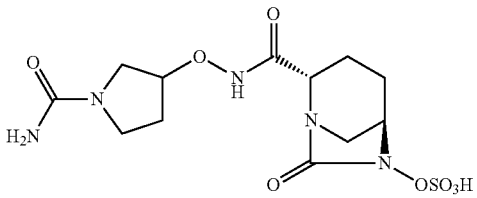
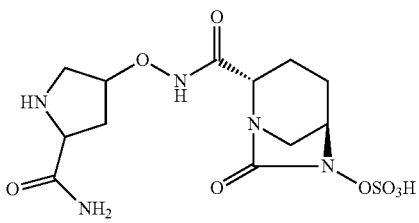
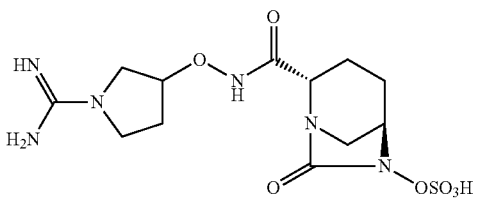
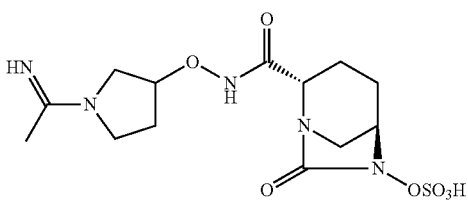
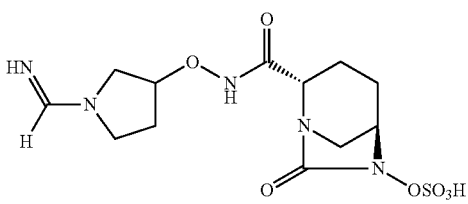
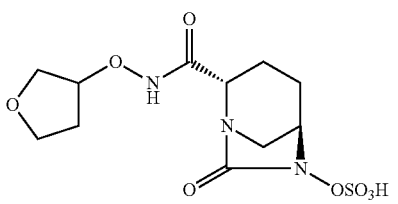
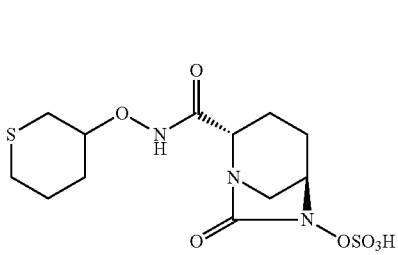

365
-continued
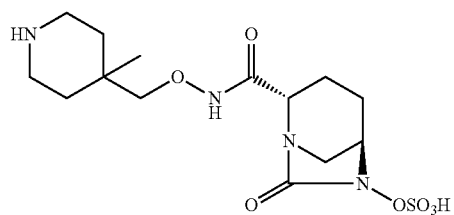
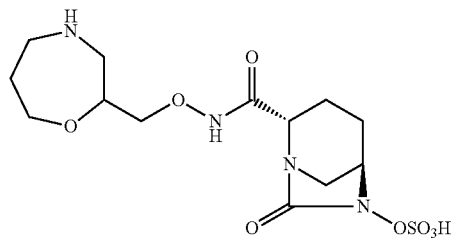
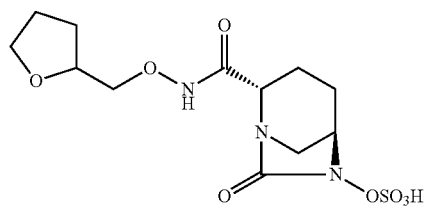
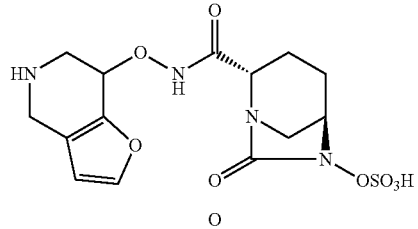
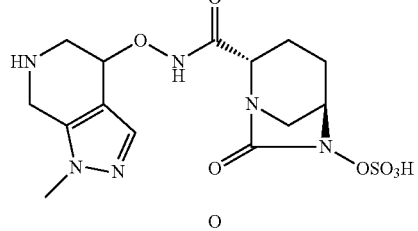
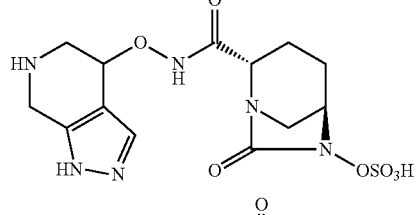
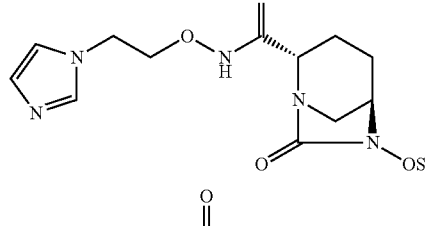
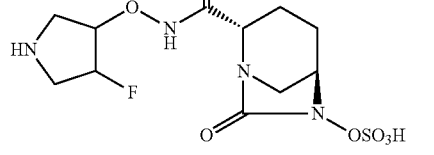
366
-continued
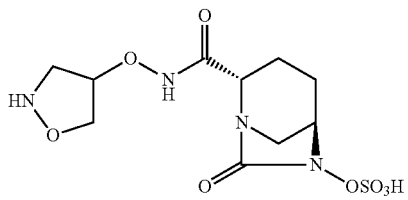
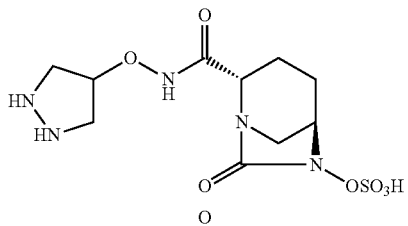
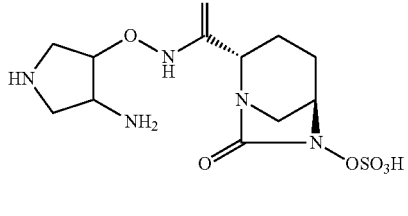
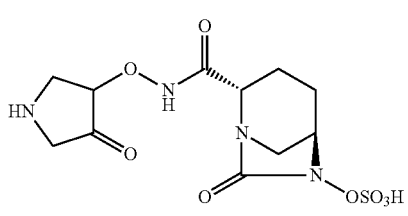
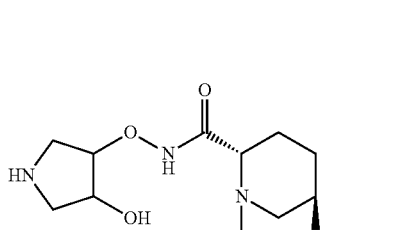
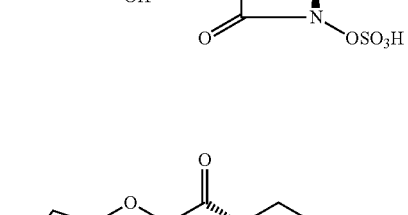
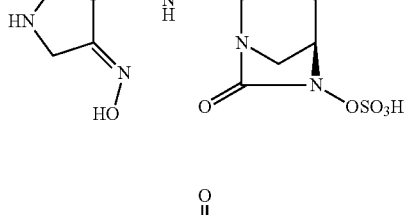
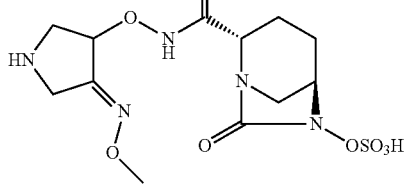

-continued
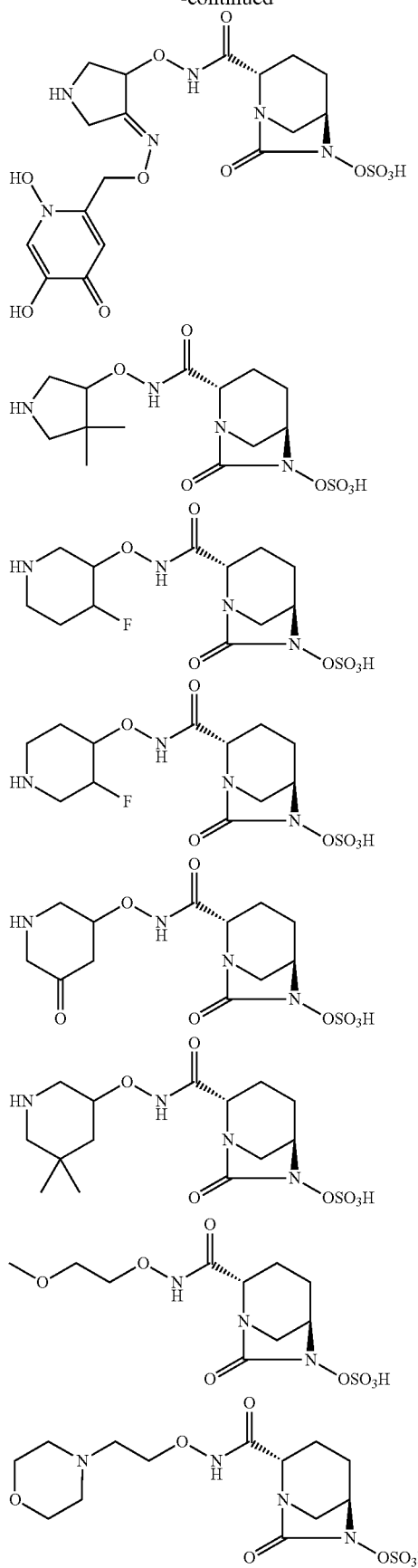
-continued
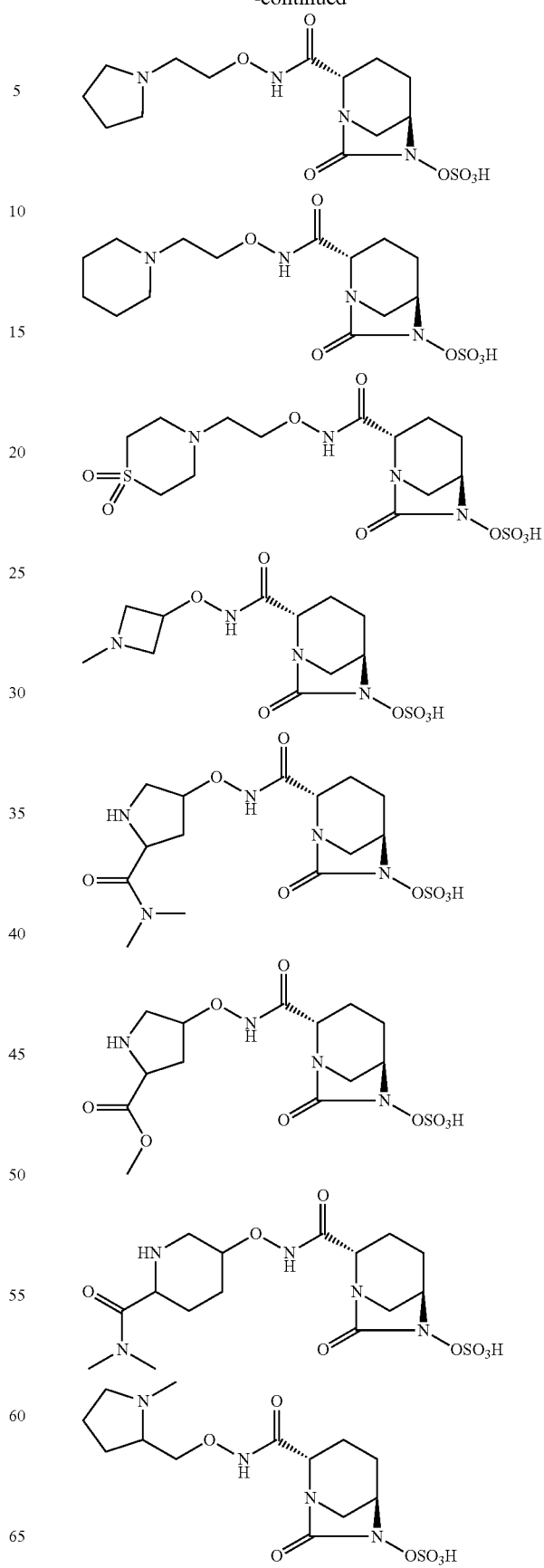

369
-continued
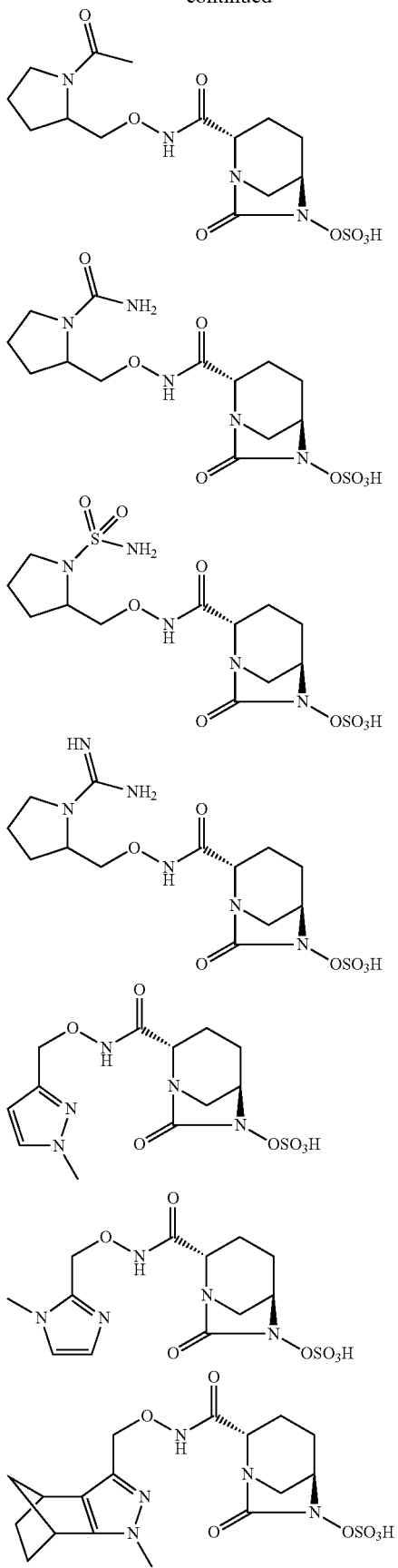
370
-continued
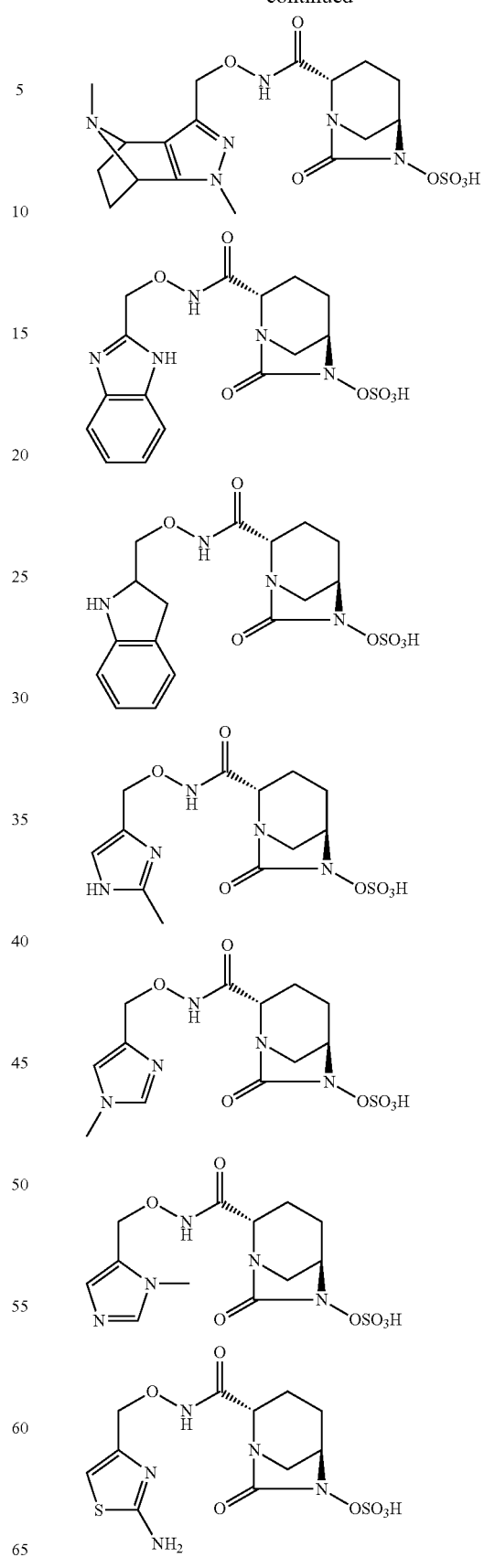

-continued
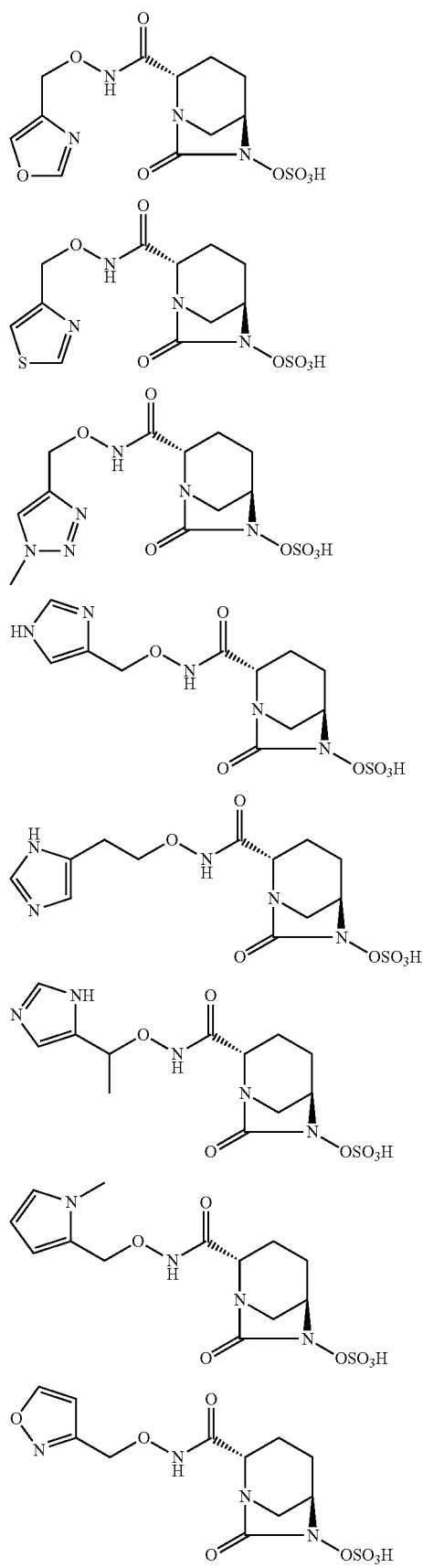
-continued
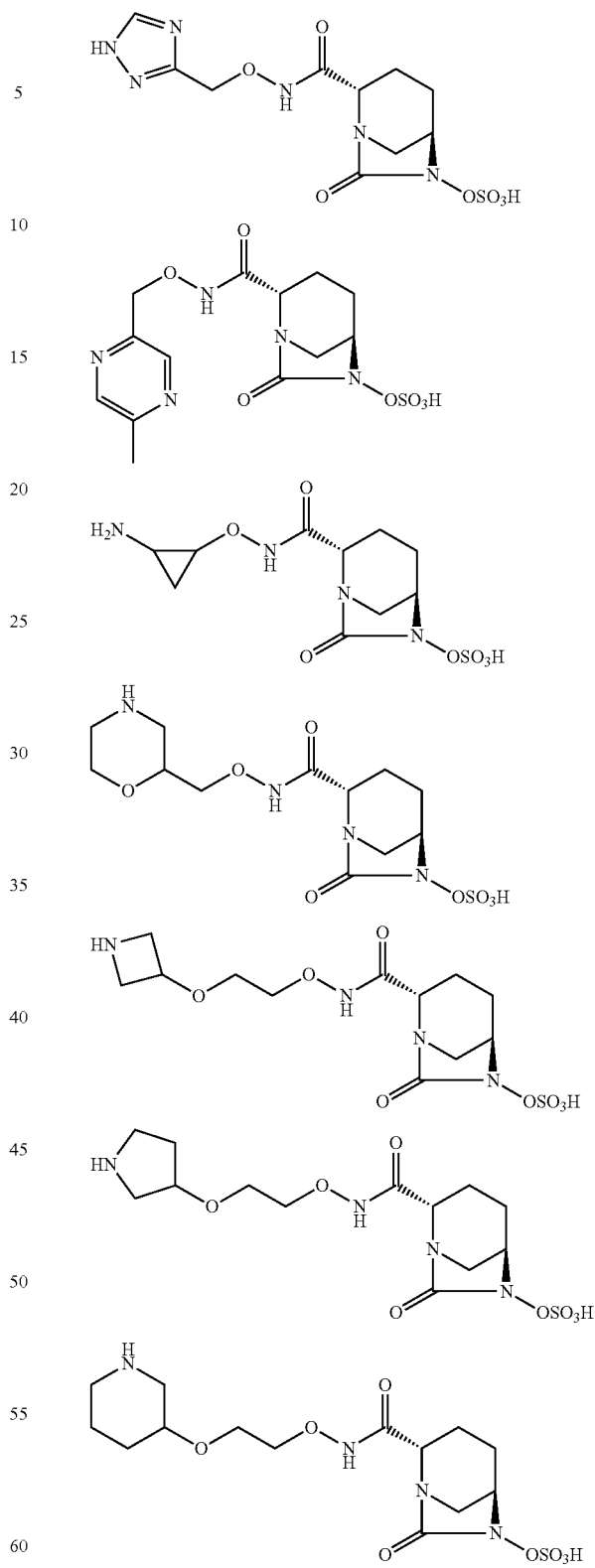
and pharmaceutically acceptable salts of such compounds, and deuterated compounds of such compounds and salts.
Passage 8. A compound as recited in passage 2, which is selected from the following group of compounds:

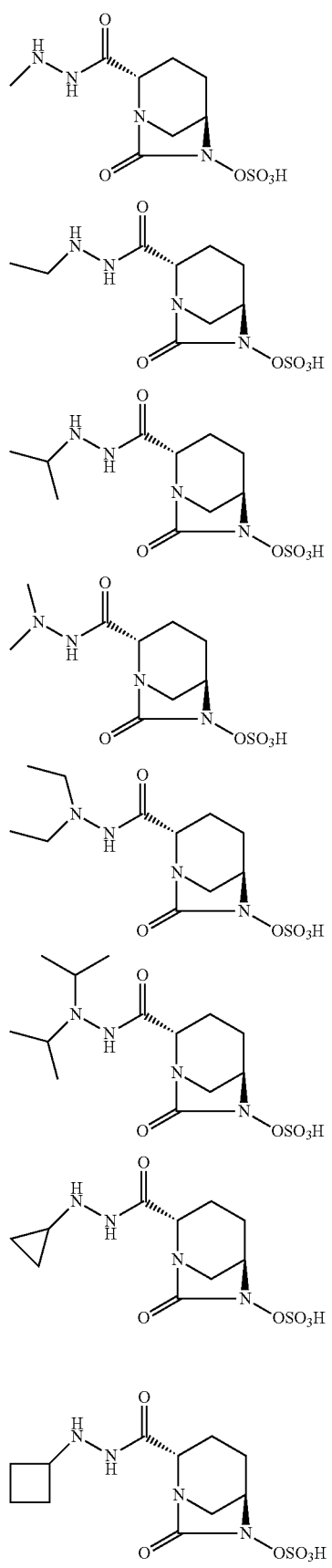
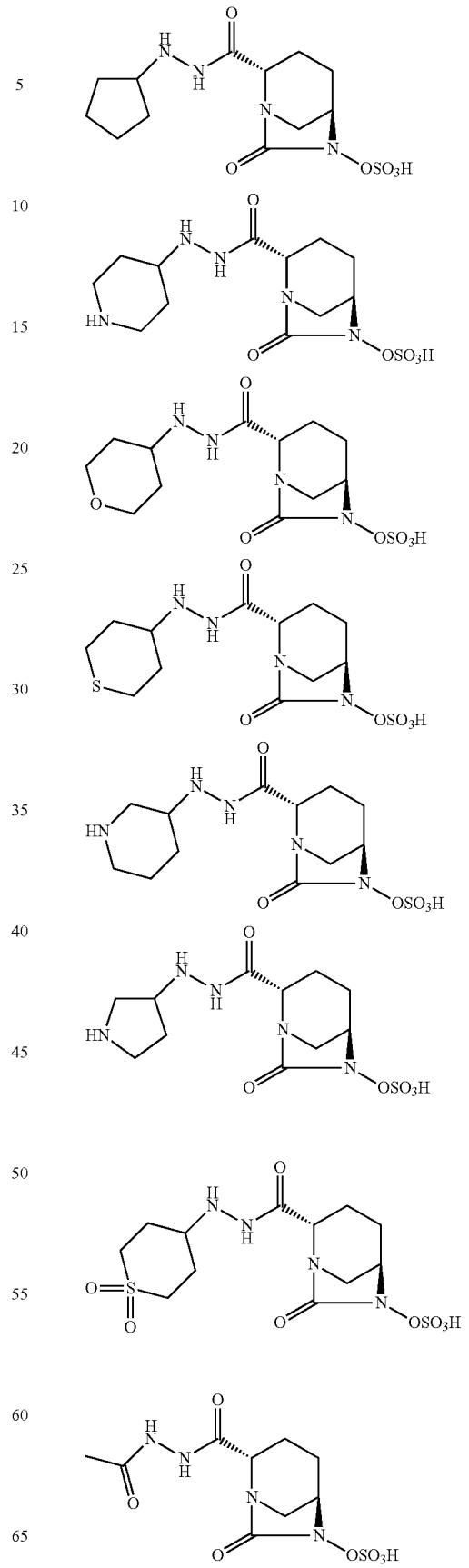

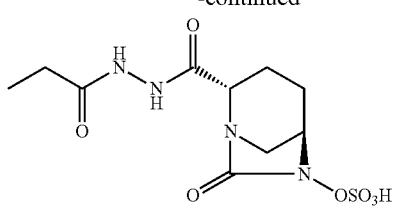
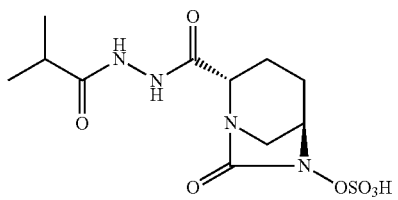
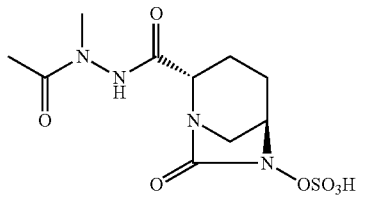
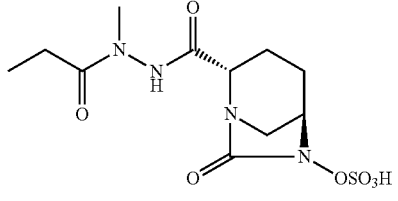
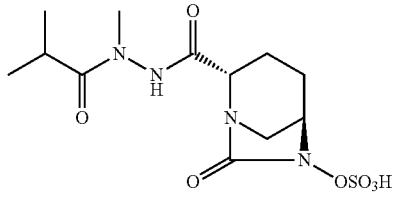
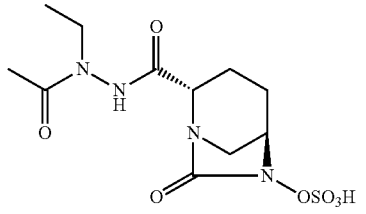
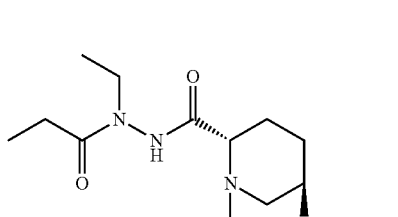
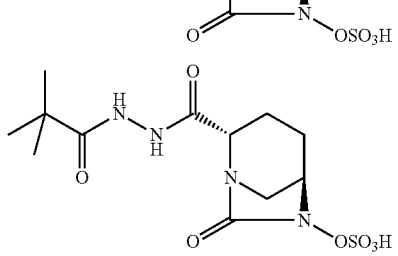
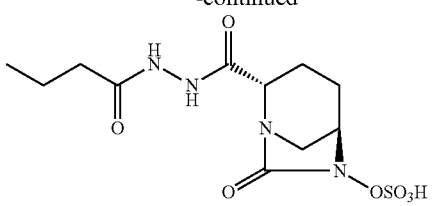
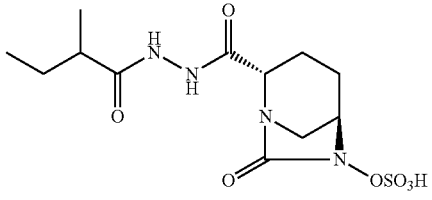
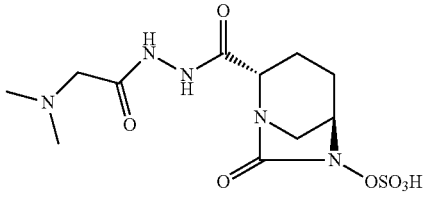
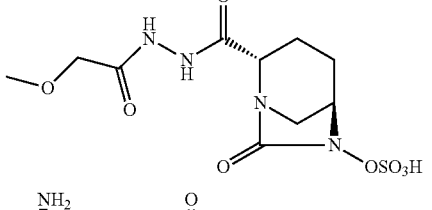
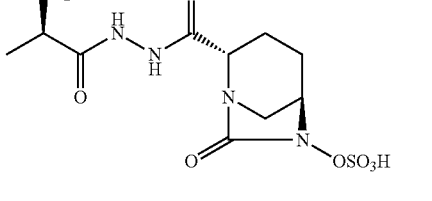
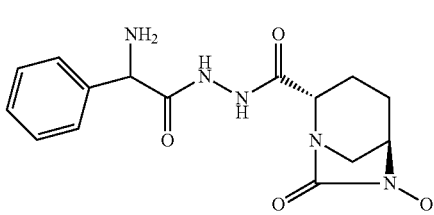
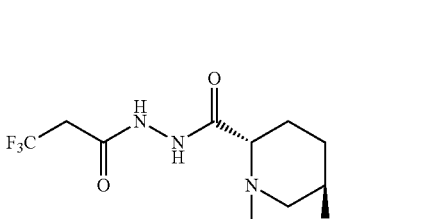
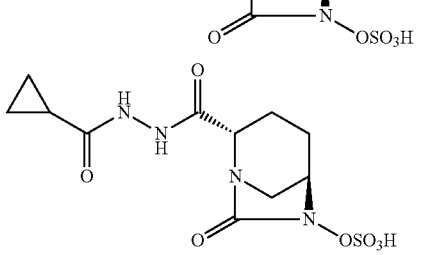

377
-continued
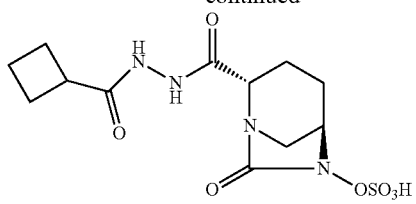
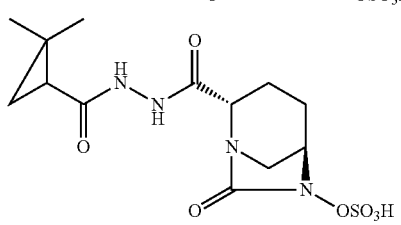
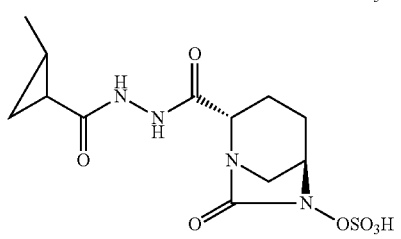
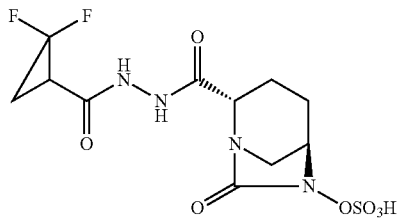
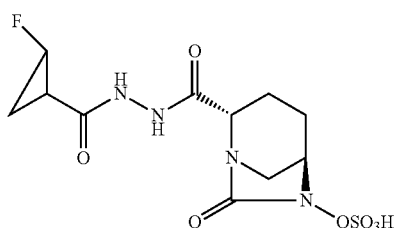
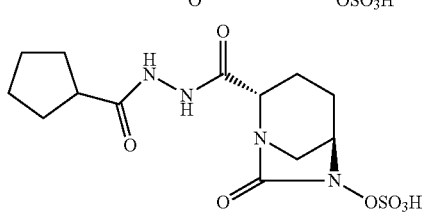
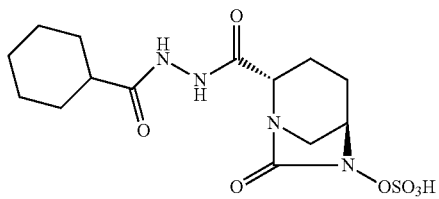
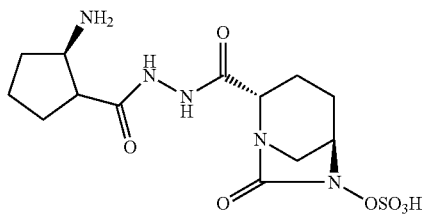
378
-continued
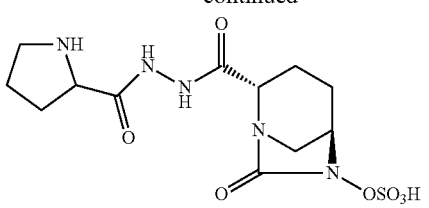
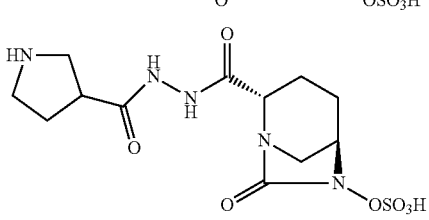
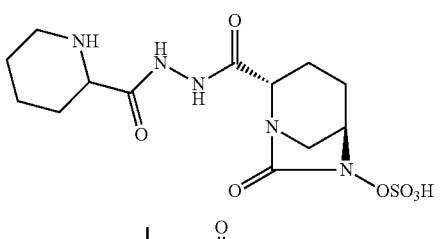
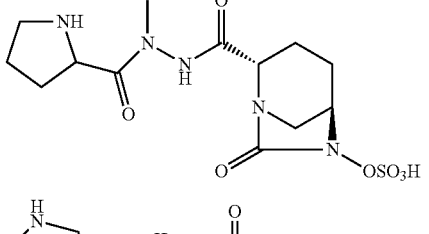
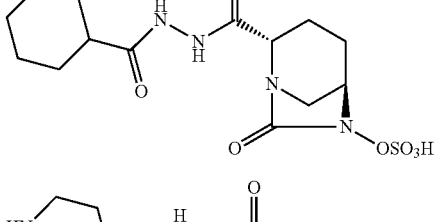
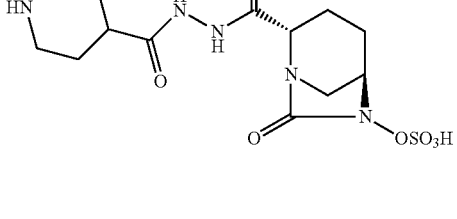
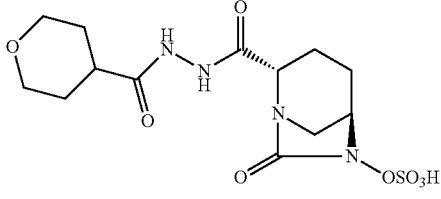
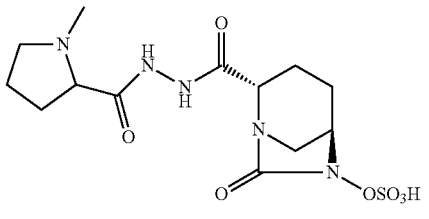

379
-continued
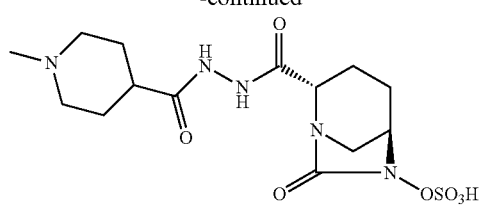
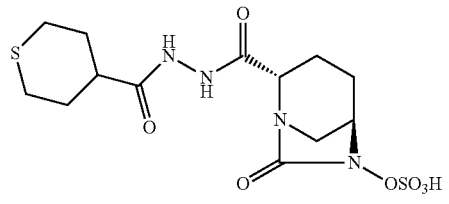
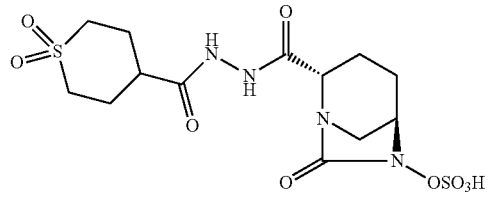
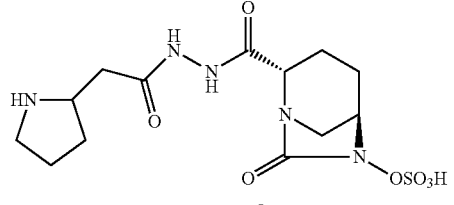
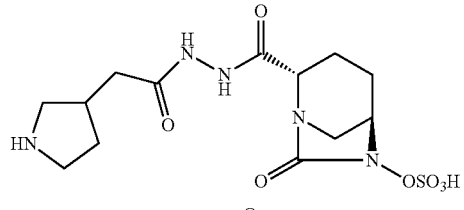
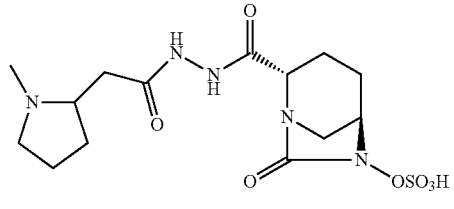
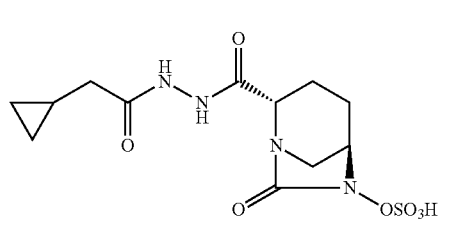
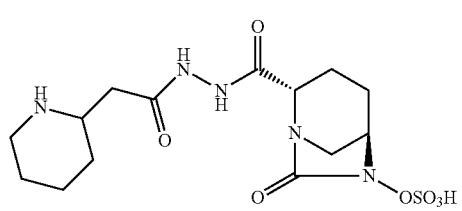
380
-continued
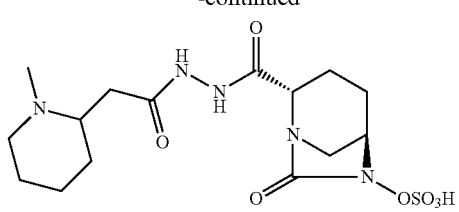
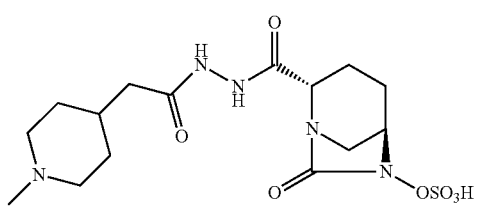
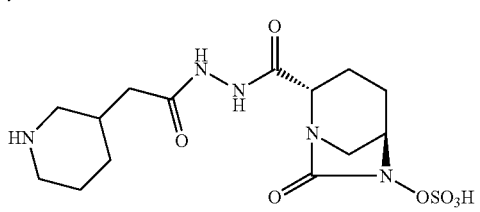
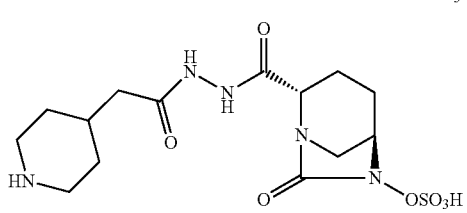
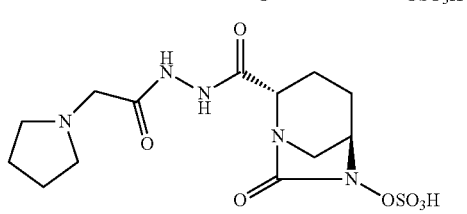
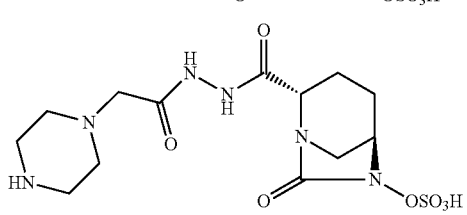
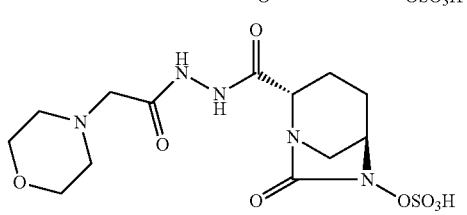
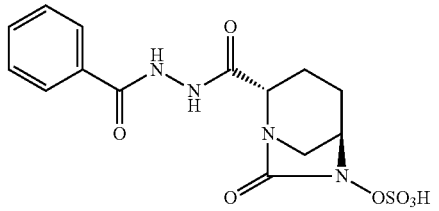

381
-continued
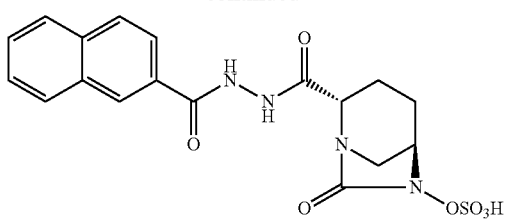
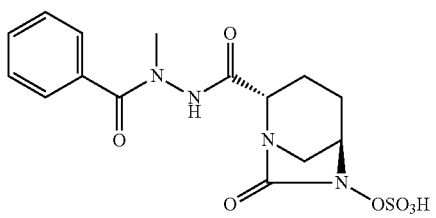
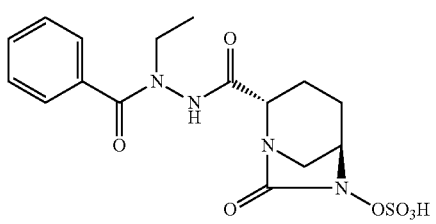
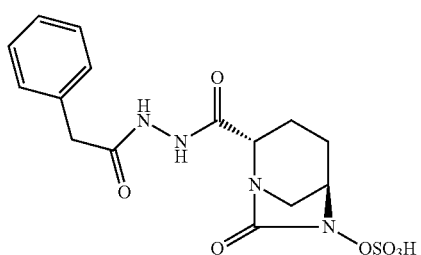
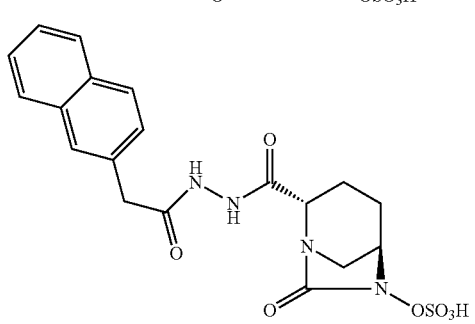
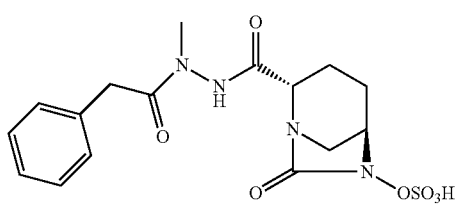
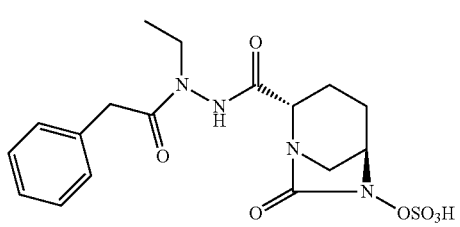
382
-continued
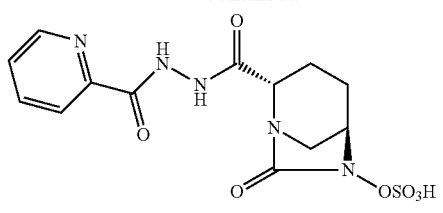
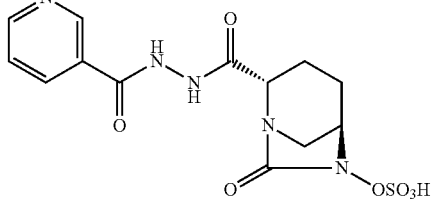
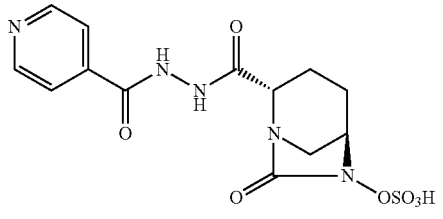
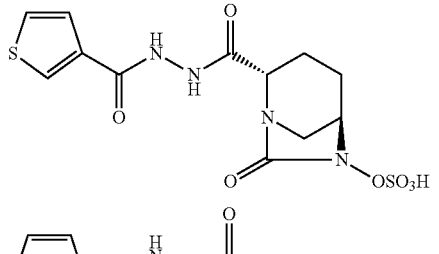
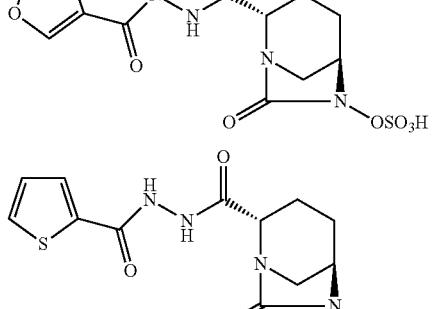
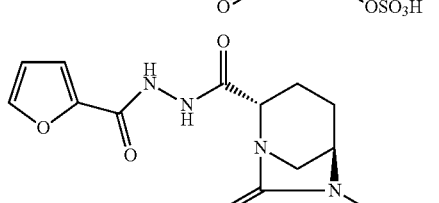
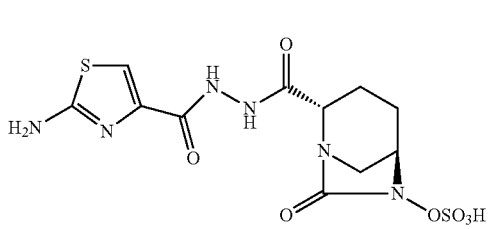

383
-continued
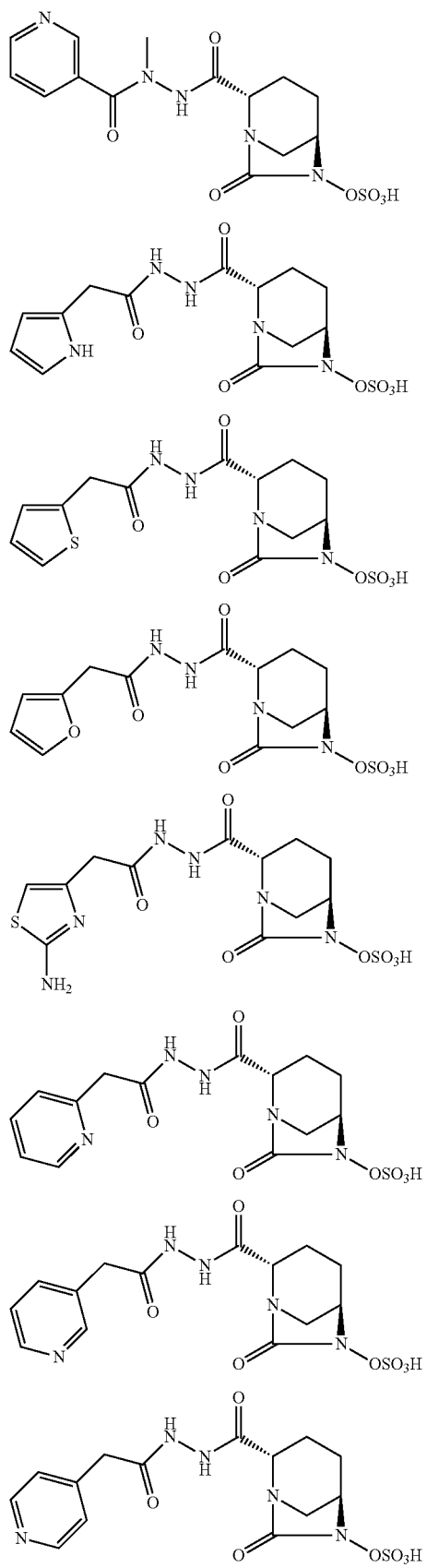
384
-continued
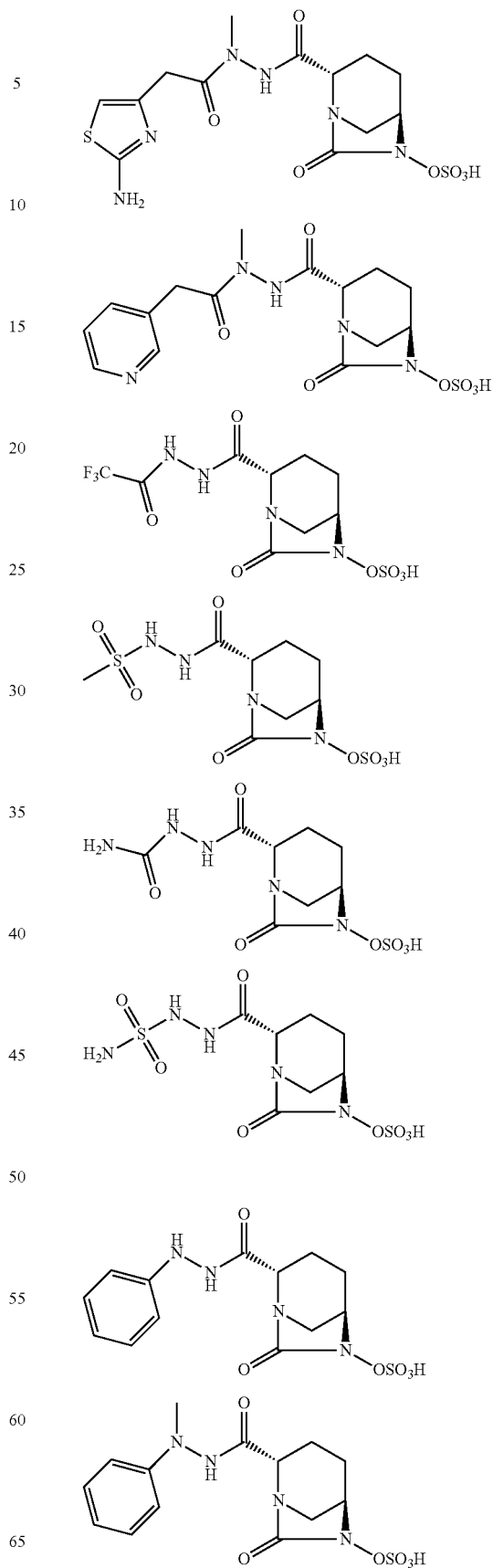

385
-continued
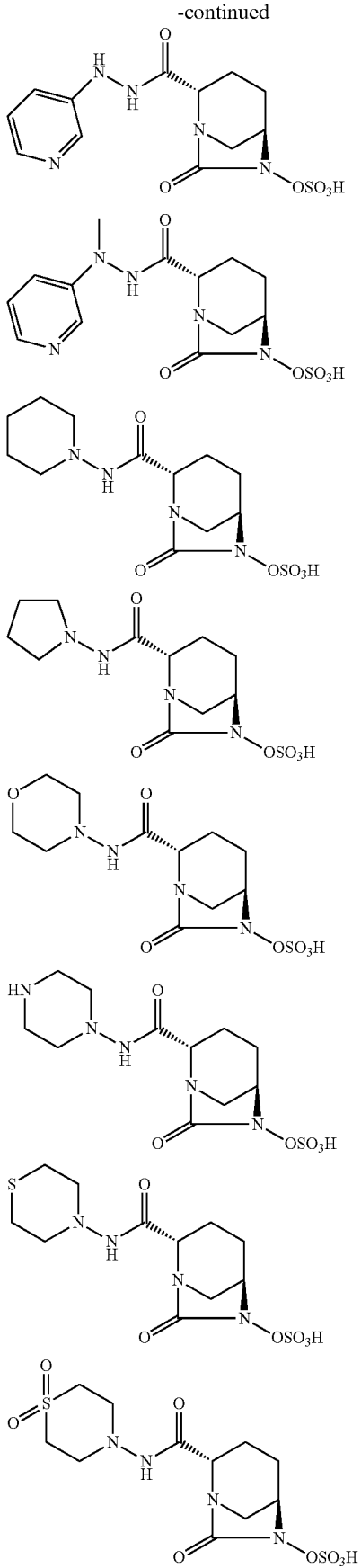
386
-continued
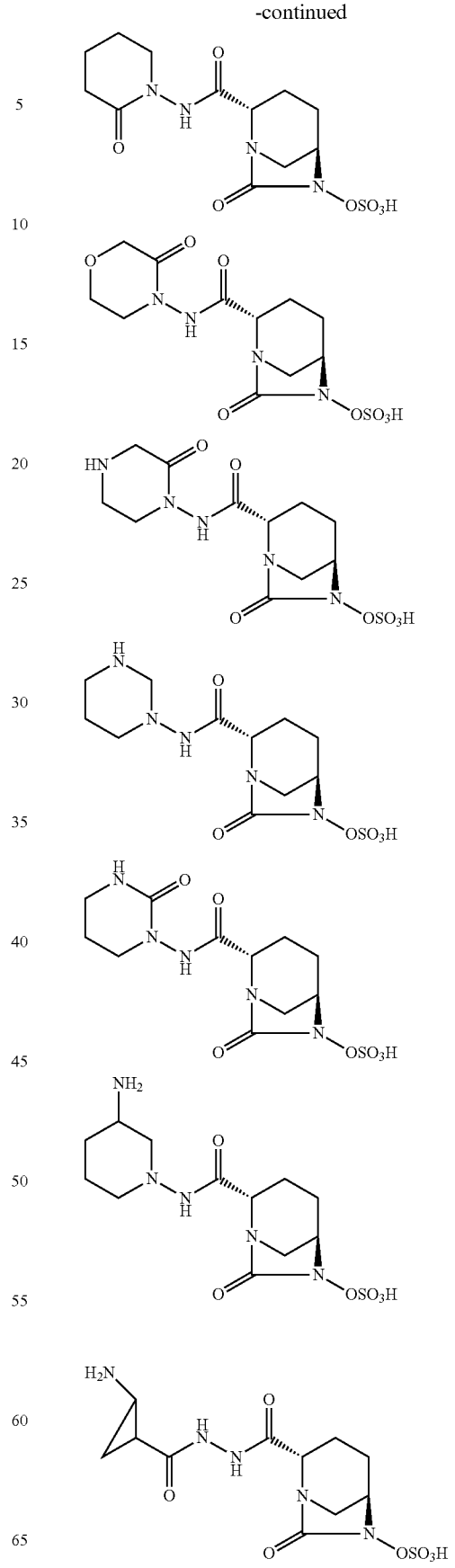

387
-continued

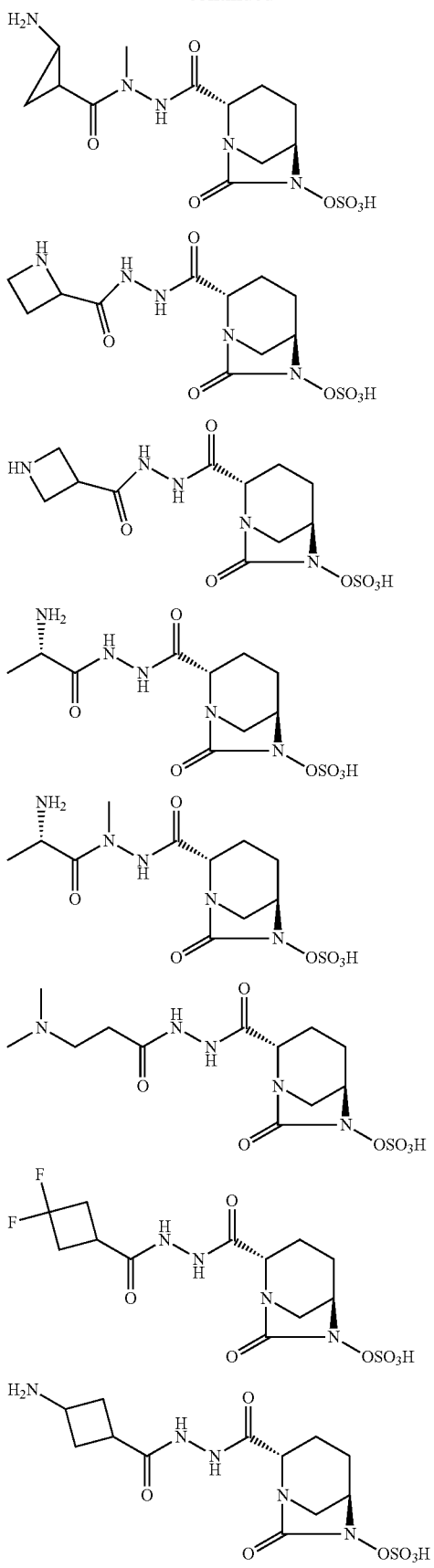

388
-continued

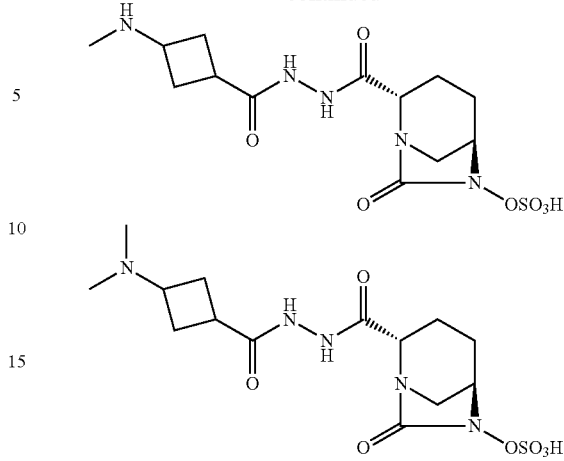

and pharmaceutically acceptable salts of such compounds, and deuterated compounds of such compounds and salts.

Passage 9. A compound of formula (I) as defined in passage 1, wherein the compound is selected from the group consisting of:
(2S,5R)-N-(2-hydroxyethoxy)-7-oxo-6-(sulfooxy)-1,6-diazabicyclo[3.2.1]octane-2-carboxamide
(2S,5R)-N-methoxy-7-oxo-6-(sulfooxy)-1,6-diazabicyclo[3.2.1]octane-2-carboxamide
(2S,5R)-7-oxo-N-propoxy-6-(sulfooxy)-1,6-diazabicyclo[3.2.1]octane-2-carboxamide
(2S,5R)-N-(2-aminoethoxy)-7-oxo-6-(sulfooxy)-1,6-diazabicyclo[3.2.1]octane-2-carboxamide
(2S,5R)-N-(2-aminopropoxy)-7-oxo-6-(sulfooxy)-1,6-diazabicyclo[3.2.1]octane-2-carboxamide
(2S,5R)-N-(2-amino-2-oxoethoxy)-7-oxo-6-(sulfooxy)-1,6-diazabicyclo[3.2.1]octane-2-carboxamide
(2S,5R)-N-[2-(carbamoylamino)ethoxy]-7-oxo-6-(sulfooxy)-1,6-diazabicyclo[3.2.1]octane-2-carboxamide
(2S,5R)-7-oxo-N-[2-(sulfamoylamino)ethoxy]-6-(sulfooxy)-1,6-diazabicyclo[3.2.1]octane-2-carboxamide
[({[(2S,5R)-7-oxo-6-(sulfooxy)-1,6-diazabicyclo[3.2.1]oct-2-yl]carbonyl}amino)oxy]acetic acid
2-methyl-2-[({[(2S,5R)-7-oxo-6-(sulfooxy)-1,6-diazabicyclo[3.2.1]oct-2-yl]carbonyl}amino)oxy]propanoic acid
(2S,5R)-7-oxo-N-[2-(piperidin-4-yloxy)ethoxy]-6-(sulfooxy)-1,6-diazabicyclo[3.2.1]octane-2-carboxamide
(2S,5R)-7-oxo-N-(propan-2-yloxy)-6-(sulfooxy)-1,6-diazabicyclo[3.2.1]octane-2-carboxamide
(2S,5R)-N-tert-butoxy-7-oxo-6-(sulfooxy)-1,6-diazabicyclo[3.2.1]octane-2-carboxamide
(2S,5R)-N-(cyclobutyloxy)-7-oxo-6-(sulfooxy)-1,6-diazabicyclo[3.2.1]octane-2-carboxamide
(2S,5R)-N-(cyclopentyloxy)-7-oxo-6-(sulfooxy)-1,6-diazabicyclo[3.2.1]octane-2-carboxamide
(2S,5R)-N-(cyclohexyloxy)-7-oxo-6-(sulfooxy)-1,6-diazabicyclo[3.2.1]octane-2-carboxamide
(2S,5R)-N-(cycloheptyloxy)-7-oxo-6-(sulfooxy)-1,6-diazabicyclo[3.2.1]octane-2-carboxamide
(2S,5R)-N-[(3-aminocyclopentyl)oxy]-7-oxo-6-(sulfooxy)-1,6-diazabicyclo[3.2.1]octane-2-carboxamide
(2S,5R)-N-[(2-aminocyclopentyl)oxy]-7-oxo-6-(sulfooxy)-1,6-diazabicyclo[3.2.1]octane-2-carboxamide
(2S,5R)-N-{[3-(methylamino)cyclopentyl]oxy}-7-oxo-6-(sulfooxy)-1,6-diazabicyclo[3.2.1]octane-2-carboxamide
(2S,5R)-N-{[4-(dimethylamino)cyclohexyl]oxy}-7-oxo-6-(sulfooxy)-1,6-diazabicyclo[3.2.1]octane-2-carboxamide (2S,5R)-N-[(3-aminocyclohexyl)oxy]-7-oxo-6-(sulfooxy)-1,6-diazabicyclo[3.2.1]octane-2-carboxamide
(2S,5R)-N-{[3-(methylamino)cyclohexyl]oxy}-7-oxo-6-(sulfooxy)-1,6-diazabicyclo[3.2.1]octane-2-carboxamide
(2S,5R)-7-oxo-N-(pyrrolidin-3-yloxy)-6-(sulfooxy)-1,6-diazabicyclo[3.2.1]octane-2-carboxamide
(2S,5R)-7-oxo-N-[(5-oxopyrrolidin-3-yl)oxy]-6-(sulfooxy)-1,6-diazabicyclo[3.2.1]octane-2-carboxamide
(2S,5R)-N-[(1-acetylpyrrolidin-3-yl)oxy]-7-oxo-6-(sulfooxy)-1,6-diazabicyclo[3.2.1]octane-2-carboxamide
(2S,5R)-N-[(1-methylpyrrolidin-3-yl)oxy]-7-oxo-6-(sulfooxy)-1,6-diazabicyclo[3.2.1]octane-2-carboxamide
(2S,5R)-7-oxo-N-(piperidin-3-yloxy)-6-(sulfooxy)-1,6-diazabicyclo[3.2.1]octane-2-carboxamide
(2S,5R)-7-oxo-N-(piperidin-4-yloxy)-6-(sulfooxy)-1,6-diazabicyclo[3.2.1]octane-2-carboxamide
(2S,5R)-N-(azetidin-3-yloxy)-7-oxo-6-(sulfooxy)-1,6-diazabicyclo[3.2.1]octane-2-carboxamide
(2S,5R)-7-oxo-6-(sulfooxy)-N-(tetrahydro-2H-pyran-4-yloxy)-1,6-diazabicyclo[3.2.1]octane-2-carboxamide
(2S,5R)-7-oxo-6-(sulfooxy)-N-(tetrahydro-2H-thiopyran-4-yloxy)-1,6-diazabicyclo[3.2.1]octane-2-carboxamide
(2S,5R)-N-[(1,1-dioxidotetrahydro-2H-thiopyran-4-yl)oxy]-7-oxo-6-(sulfooxy)-1,6-diazabicyclo[3.2.1]octane-2-carboxamide
(2S,5R)-N-(azepan-3-yloxy)-7-oxo-6-(sulfooxy)-1,6-diazabicyclo[3.2.1]octane-2-carboxamide
(2S,5R)-N-(1,4-oxazepan-6-yloxy)-7-oxo-6-(sulfooxy)-1,6-diazabicyclo[3.2.1]octane-2-carboxamide
(2S,5R)-N-[(1-methylpiperidin-4-yl)oxy]-7-oxo-6-(sulfooxy)-1,6-diazabicyclo[3.2.1]octane-2-carboxamide
(2S,5R)-N-[(1-carbamimidoylpiperidin-4-yl)oxy]-7-oxo-6-(sulfooxy)-1,6-diazabicyclo[3.2.1]octane-2-carboxamide
(2S,5R)-7-oxo-N-(pyrrolidin-2-ylmethoxy)-6-(sulfooxy)-1,6-diazabicyclo[3.2.1]octane-2-carboxamide
(2S,5R)-7-oxo-N-(piperidin-2-ylmethoxy)-6-(sulfooxy)-1,6-diazabicyclo[3.2.1]octane-2-carboxamide
(2S,5R)-7-oxo-N-(piperidin-3-ylmethoxy)-6-(sulfooxy)-1,6-diazabicyclo[3.2.1]octane-2-carboxamide
(2S,5R)-7-oxo-N-(piperidin-4-ylmethoxy)-6-(sulfooxy)-1,6-diazabicyclo[3.2.1]octane-2-carboxamide
(2S,5R)-N-(morpholin-3-ylmethoxy)-7-oxo-6-(sulfooxy)-1,6-diazabicyclo[3.2.1]octane-2-carboxamide
(2S,5R)-7-oxo-N-(piperazin-2-ylmethoxy)-6-(sulfooxy)-1,6-diazabicyclo[3.2.1]octane-2-carboxamide
(2S,5R)-7-oxo-6-(sulfooxy)-N-(thiomorpholin-3-ylmethoxy)-1,6-diazabicyclo[3.2.1]octane-2-carboxamide
(2S,5R)-N-(decahydroquinolin-4-yloxy)-7-oxo-6-(sulfooxy)-1,6-diazabicyclo[3.2.1]octane-2-carboxamide
(2S,5R)-N-(hexahydro-1H-pyrrolizin-2-yloxy)-7-oxo-6-(sulfooxy)-1,6-diazabicyclo[3.2.1]octane-2-carboxamide
(2S,5R)-N-(octahydroindolizin-1-yloxy)-7-oxo-6-(sulfooxy)-1,6-diazabicyclo[3.2.1]octane-2-carboxamide
(2S,5R)-N-(octahydropyrrolo[1,2-a]pyrazin-8-yloxy)-7-oxo-6-(sulfooxy)-1,6-diazabicyclo[3.2.1]octane-2-carboxamide
(2S,5R)-N-(octahydropyrrolo[1,2-a]pyrazin-7-yloxy)-7-oxo-6-(sulfooxy)-1,6-diazabicyclo[3.2.1]octane-2-carboxamide
(2S,5R)-N-(octahydrofuro[2,3-c]pyridin-3-yloxy)-7-oxo-6-(sulfooxy)-1,6-diazabicyclo[3.2.1]octane-2-carboxamide
(2S,5R)-N-(3-azabicyclo[3.1.0]hex-6-yloxy)-7-oxo-6-(sulfooxy)-1,6-diazabicyclo[3.2.1]octane-2-carboxamide
(2S,5R)-N-(decahydroquinolin-5-yloxy)-7-oxo-6-(sulfooxy)-1,6-diazabicyclo[3.2.1]octane-2-carboxamide
(2S,5R)-N-(hexahydro-4aH-cyclopenta[b][1,4]dioxin-6-yloxy)-7-oxo-6-(sulfooxy)-1,6-diazabicyclo[3.2.1]octane-2-carboxamide
(2S,5R)-N-(octahydrocyclopenta[c]pyrrol-5-yloxy)-7-oxo-6-(sulfooxy)-1,6-diazabicyclo[3.2.1]octane-2-carboxamide
(2S,5R)-N-(hexahydro-1H-cyclopenta[c]furan-5-yloxy)-7-oxo-6-(sulfooxy)-1,6-diazabicyclo[3.2.1]octane-2-carboxamide
(2S,5R)-N-(hexahydro-1H-cyclopenta[c]thiophen-5-yloxy)-7-oxo-6-(sulfooxy)-1,6-diazabicyclo[3.2.1]octane-2-carboxamide
(2S,5R)-N-(bicyclo[2.2.1]hept-2-yloxy)-7-oxo-6-(sulfooxy)-1,6-diazabicyclo[3.2.1]octane-2-carboxamide
(2S,5R)-N-[(7,7-dimethylbicyclo[2.2.1]hept-2-yl)oxy]-7-oxo-6-(sulfooxy)-1,6-diazabicyclo[3.2.1]octane-2-carboxamide
(2S,5R)-N-(1-azabicyclo[2.2.2]oct-3-yloxy)-7-oxo-6-(sulfooxy)-1,6-diazabicyclo[3.2.1]octane-2-carboxamide
(2S,5R)-N-(8-azabicyclo[3.2.1]oct-3-yloxy)-7-oxo-6-(sulfooxy)-1,6-diazabicyclo[3.2.1]octane-2-carboxamide
(2S,5R)-N-[(8-methyl-8-azabicyclo[3.2.1]oct-3-yl)oxy]-7-oxo-6-(sulfooxy)-1,6-diazabicyclo[3.2.1]octane-2-carboxamide
(2S,5R)-7-oxo-6-(sulfooxy)-N-(4,5,6,7-tetrahydrothieno[3,2-c]pyridin-7-yloxy)-1,6-diazabicyclo[3.2.1]octane-2-carboxamide
(2S,5R)-N-(6,7-dihydro-5H-pyrrolo[1,2-a]imidazol-7-yloxy)-7-oxo-6-(sulfooxy)-1,6-diazabicyclo[3.2.1]octane-2-carboxamide
(2S,5R)-N-(7-azaspiro[4.5]dec-10-yloxy)-7-oxo-6-(sulfooxy)-1,6-diazabicyclo[3.2.1]octane-2-carboxamide
(2S,5R)-N-(7-oxaspiro[4.5]dec-10-yloxy)-7-oxo-6-(sulfooxy)-1,6-diazabicyclo[3.2.1]octane-2-carboxamide
(2S,5R)-N-(1H-imidazol-2-ylmethoxy)-7-oxo-6-(sulfooxy)-1,6-diazabicyclo[3.2.1]octane-2-carboxamide
(2S,5R)-7-oxo-6-(sulfooxy)-N-(4,5,6,7-tetrahydro-1H-4,7-methanoindazol-3-ylmethoxy)-1,6-diazabicyclo[3.2.1]octane-2-carboxamide
(2S,5R)-7-oxo-N-(1H-pyrazol-3-ylmethoxy)-6-(sulfooxy)-1,6-diazabicyclo[3.2.1]octane-2-carboxamide
(2S,5R)-7-oxo-N-[2-(pyridin-2-yl)ethoxy]-6-(sulfooxy)-1,6-diazabicyclo[3.2.1]octane-2-carboxamide
(2S,5R)-7-oxo-N-[2-(piperidin-4-yl)ethoxy]-6-(sulfooxy)-1,6-diazabicyclo[3.2.1]octane-2-carboxamide
(2S,5R)-7-oxo-N-[2-(piperazin-1-yl)ethoxy]-6-(sulfooxy)-1,6-diazabicyclo[3.2.1]octane-2-carboxamide
(2S,5R)-7-oxo-N-[(1-sulfamoylpyrrolidin-3-yl)oxy]-6-(sulfooxy)-1,6-diazabicyclo[3.2.1]octane-2-carboxamide
(2S,5R)-N-{[1-(methylsulfamoyl)pyrrolidin-3-yl]oxy}-7-oxo-6-(sulfooxy)-1,6-diazabicyclo[3.2.1]octane-2-carboxamide
(2S,5R)-N-[(1-carbamoylpyrrolidin-3-yl)oxy]-7-oxo-6-(sulfooxy)-1,6-diazabicyclo[3.2.1]octane-2-carboxamide
(2S,5R)-N-[(5-carbamoylpyrrolidin-3-yl)oxy]-7-oxo-6-(sulfooxy)-1,6-diazabicyclo[3.2.1]octane-2-carboxamide
(2S,5R)-N-[(1-carbamimidoylpyrrolidin-3-yl)oxy]-7-oxo-6-(sulfooxy)-1,6-diazabicyclo[3.2.1]octane-2-carboxamide
(2S,5R)-N-[(1-ethanimidoylpyrrolidin-3-yl)oxy]-7-oxo-6-(sulfooxy)-1,6-diazabicyclo[3.2.1]octane-2-carboxamide
(2S,5R)-N-{[1-(iminomethyl)pyrrolidin-3-yl]oxy}-7-oxo-6-(sulfooxy)-1,6-diazabicyclo[3.2.1]octane-2-carboxamide
(2S,5R)-7-oxo-6-(sulfooxy)-N-(tetrahydrofuran-3-yloxy)-1,6-diazabicyclo[3.2.1]octane-2-carboxamide
(2S,5R)-7-oxo-6-(sulfooxy)-N-(tetrahydro-2H-thiopyran-3-yloxy)-1,6-diazabicyclo[3.2.1]octane-2-carboxamide (2S,5R)-N-[(4-methylpiperidin-4-yl)methoxy]-7-oxo-6-(sulfooxy)-1,6-diazabicyclo[3.2.1]octane-2-carboxamide
(2S,5R)-N-(1,4-oxazepan-2-ylmethoxy)-7-oxo-6-(sulfooxy)-1,6-diazabicyclo[3.2.1]octane-2-carboxamide
(2S,5R)-7-oxo-6-(sulfooxy)-N-(tetrahydrofuran-2-ylmethoxy)-1,6-diazabicyclo[3.2.1]octane-2-carboxamide
(2S,5R)-7-oxo-6-(sulfooxy)-N-(4,5,6,7-tetrahydrofuro[3,2-c]pyridin-7-yloxy)-1,6-diazabicyclo[3.2.1]octane-2-carboxamide
(2S,5R)-N-[(1-methyl-4,5,6,7-tetrahydro-1H-pyrazolo[3,4-c]pyridin-4-yl)oxy]-7-oxo-6-(sulfooxy)-1,6-diazabicyclo[3.2.1]octane-2-carboxamide
(2S,5R)-7-oxo-6-(sulfooxy)-N-(4,5,6,7-tetrahydro-1H-pyrazolo[3,4-c]pyridin-4-yloxy)-1,6-diazabicyclo[3.2.1]octane-2-carboxamide
(2S,5R)-N-[2-(1H-imidazol-1-yl)ethoxy]-7-oxo-6-(sulfooxy)-1,6-diazabicyclo[3.2.1]octane-2-carboxamide
(2S,5R)-N-[(4-fluoropyrrolidin-3-yl)oxy]-7-oxo-6-(sulfooxy)-1,6-diazabicyclo[3.2.1]octane-2-carboxamide
(2S,5R)-N-(1,2-oxazolidin-4-yloxy)-7-oxo-6-(sulfooxy)-1,6-diazabicyclo[3.2.1]octane-2-carboxamide
(2S,5R)-7-oxo-N-(pyrazolidin-4-yloxy)-6-(sulfooxy)-1,6-diazabicyclo[3.2.1]octane-2-carboxamide
(2S,5R)-N-[(4-aminopyrrolidin-3-yl)oxy]-7-oxo-6-(sulfooxy)-1,6-diazabicyclo[3.2.1]octane-2-carboxamide
(2S,5R)-7-oxo-N-[(4-oxopyrrolidin-3-yl)oxy]-6-(sulfooxy)-1,6-diazabicyclo[3.2.1]octane-2-carboxamide
(2S,5R)-N-[(4-hydroxypyrrolidin-3-yl)oxy]-7-oxo-6-(sulfooxy)-1,6-diazabicyclo[3.2.1]octane-2-carboxamide
(2S,5R)-N-{[(4E)-4-(hydroxyimino)pyrrolidin-3-yl]oxy}-7-oxo-6-(sulfooxy)-1,6-diazabicyclo[3.2.1]octane-2-carboxamide
(2S,5R)-N-{[(4E)-4-(methoxyimino)pyrrolidin-3-yl]oxy}-7-oxo-6-(sulfooxy)-1,6-diazabicyclo[3.2.1]octane-2-carboxamide
(2S,5R)-N-{[(4E)-4-{[(1,5-dihydroxy-4-oxo-1,4-dihydropyridin-2-yl)methoxy]imino}pyrrolidin-3-yl]oxy}-7-oxo-6-(sulfooxy)-1,6-diazabicyclo[3.2.1]octane-2-carboxamide
(2S,5R)-N-[(4,4-dimethylpyrrolidin-3-yl)oxy]-7-oxo-6-(sulfooxy)-1,6-diazabicyclo[3.2.1]octane-2-carboxamide
(2S,5R)-N-[(4-fluoropiperidin-3-yl)oxy]-7-oxo-6-(sulfooxy)-1,6-diazabicyclo[3.2.1]octane-2-carboxamide
(2S,5R)-N-[(3-fluoropiperidin-4-yl)oxy]-7-oxo-6-(sulfooxy)-1,6-diazabicyclo[3.2.1]octane-2-carboxamide
(2S,5R)-7-oxo-N-[(5-oxopiperidin-3-yl)oxy]-6-(sulfooxy)-1,6-diazabicyclo[3.2.1]octane-2-carboxamide
(2S,5R)-N-[(5,5-dimethylpiperidin-3-yl)oxy]-7-oxo-6-(sulfooxy)-1,6-diazabicyclo[3.2.1]octane-2-carboxamide
(2S,5R)-N-(2-methoxyethoxy)-7-oxo-6-(sulfooxy)-1,6-diazabicyclo[3.2.1]octane-2-carboxamide
(2S,5R)-N-[2-(morpholin-4-yl)ethoxy]-7-oxo-6-(sulfooxy)-1,6-diazabicyclo[3.2.1]octane-2-carboxamide
(2S,5R)-7-oxo-N-[2-(pyrrolidin-1-yl)ethoxy]-6-(sulfooxy)-1,6-diazabicyclo[3.2.1]octane-2-carboxamide
(2S,5R)-7-oxo-N-[2-(piperidin-1-yl)ethoxy]-6-(sulfooxy)-1,6-diazabicyclo[3.2.1]octane-2-carboxamide
(2S,5R)-N-[2-(1,1-dioxidothiomorpholin-4-yl)ethoxy]-7-oxo-6-(sulfooxy)-1,6-diazabicyclo[3.2.1]octane-2-carboxamide
(2S,5R)-N-[(1-methylazetidin-3-yl)oxy]-7-oxo-6-(sulfooxy)-1,6-diazabicyclo[3.2.1]octane-2-carboxamide
(2S,5R)-N-{[5-(dimethylcarbamoyl)pyrrolidin-3-yl]oxy}-7-oxo-6-(sulfooxy)-1,6-diazabicyclo[3.2.1]octane-2-carboxamide
methyl 4-[({[(2S,5R)-7-oxo-6-(sulfooxy)-1,6-diazabicyclo[3.2.1]oct-2-yl]carbonyl}amino)oxy]prolinate
(2S,5R)-N-{[6-(dimethylcarbamoyl)piperidin-3-yl]oxy}-7-oxo-6-(sulfooxy)-1,6-diazabicyclo[3.2.1]octane-2-carboxamide
(2S,5R)-N-[(1-methylpyrrolidin-2-yl)methoxy]-7-oxo-6-(sulfooxy)-1,6-diazabicyclo[3.2.1]octane-2-carboxamide
(2S,5R)-N-[(1-acetylpyrrolidin-2-yl)methoxy]-7-oxo-6-(sulfooxy)-1,6-diazabicyclo[3.2.1]octane-2-carboxamide
(2S,5R)-N-[(1-carbamoylpyrrolidin-2-yl)methoxy]-7-oxo-6-(sulfooxy)-1,6-diazabicyclo[3.2.1]octane-2-carboxamide
(2S,5R)-7-oxo-N-[(1-sulfamoylpyrrolidin-2-yl)methoxy]-6-(sulfooxy)-1,6-diazabicyclo[3.2.1]octane-2-carboxamide
(2S,5R)-N-[(1-carbamimidoylpyrrolidin-2-yl)methoxy]-7-oxo-6-(sulfooxy)-1,6-diazabicyclo[3.2.1]octane-2-carboxamide
(2S,5R)-N-[(1-methyl-1H-pyrazol-3-yl)methoxy]-7-oxo-6-(sulfooxy)-1,6-diazabicyclo[3.2.1]octane-2-carboxamide
(2S,5R)-N-[(1-methyl-1H-imidazol-2-yl)methoxy]-7-oxo-6-(sulfooxy)-1,6-diazabicyclo[3.2.1]octane-2-carboxamide
(2S,5R)-N-[(1-methyl-4,5,6,7-tetrahydro-1H-4,7-methanoindazol-3-yl)methoxy]-7-oxo-6-(sulfooxy)-1,6-diazabicyclo[3.2.1]octane-2-carboxamide
(2S,5R)-N-[(1,8-dimethyl-4,5,6,7-tetrahydro-1H-4,7-epiminoindazol-3-yl)methoxy]-7-oxo-6-(sulfooxy)-1,6-diazabicyclo[3.2.1]octane-2-carboxamide
(2S,5R)-N-(1H-benzimidazol-2-ylmethoxy)-7-oxo-6-(sulfooxy)-1,6-diazabicyclo[3.2.1]octane-2-carboxamide
(2S,5R)-N-(2,3-dihydro-1H-indol-2-ylmethoxy)-7-oxo-6-(sulfooxy)-1,6-diazabicyclo[3.2.1]octane-2-carboxamide
(2S,5R)-N-[(2-methyl-1H-imidazol-4-yl)methoxy]-7-oxo-6-(sulfooxy)-1,6-diazabicyclo[3.2.1]octane-2-carboxamide
(2S,5R)-N-[(1-methyl-1H-imidazol-4-yl)methoxy]-7-oxo-6-(sulfooxy)-1,6-diazabicyclo[3.2.1]octane-2-carboxamide
(2S,5R)-N-[(1-methyl-1H-imidazol-5-yl)methoxy]-7-oxo-6-(sulfooxy)-1,6-diazabicyclo[3.2.1]octane-2-carboxamide
(2S,5R)-N-[(2-amino-1,3-thiazol-4-yl)methoxy]-7-oxo-6-(sulfooxy)-1,6-diazabicyclo[3.2.1]octane-2-carboxamide
(2S,5R)-N-(1,3-oxazol-4-ylmethoxy)-7-oxo-6-(sulfooxy)-1,6-diazabicyclo[3.2.1]octane-2-carboxamide
(2S,5R)-7-oxo-6-(sulfooxy)-N-(1,3-thiazol-4-ylmethoxy)-1,6-diazabicyclo[3.2.1]octane-2-carboxamide
(2S,5R)-N-[(1-methyl-1H-1,2,3-triazol-4-yl)methoxy]-7-oxo-6-(sulfooxy)-1,6-diazabicyclo[3.2.1]octane-2-carboxamide
(2S,5R)-N-(1H-imidazol-4-ylmethoxy)-7-oxo-6-(sulfooxy)-1,6-diazabicyclo[3.2.1]octane-2-carboxamide
(2S,5R)-N-[2-(1H-imidazol-5-yl)ethoxy]-7-oxo-6-(sulfooxy)-1,6-diazabicyclo[3.2.1]octane-2-carboxamide
(2S,5R)-N-[1-(1H-imidazol-5-yl)ethoxy]-7-oxo-6-(sulfooxy)-1,6-diazabicyclo[3.2.1]octane-2-carboxamide
(2S,5R)-N-[(1-methyl-1H-pyrrol-2-yl)methoxy]-7-oxo-6-(sulfooxy)-1,6-diazabicyclo[3.2.1]octane-2-carboxamide
(2S,5R)-N-(1,2-oxazol-3-ylmethoxy)-7-oxo-6-(sulfooxy)-1,6-diazabicyclo[3.2.1]octane-2-carboxamide
(2S,5R)-7-oxo-6-(sulfooxy)-N-(1H-1,2,4-triazol-3-ylmethoxy)-1,6-diazabicyclo[3.2.1]octane-2-carboxamide
(2S,5R)-N-[(5-methylpyrazin-2-yl)methoxy]-7-oxo-6-(sulfooxy)-1,6-diazabicyclo[3.2.1]octane-2-carboxamide
(2S,5R)-N-[(2-aminocyclopropyl)oxy]-7-oxo-6-(sulfooxy)-1,6-diazabicyclo[3.2.1]octane-2-carboxamide
(2S,5R)-N-(morpholin-2-ylmethoxy)-7-oxo-6-(sulfooxy)-1,6-diazabicyclo[3.2.1]octane-2-carboxamide (2S,5R)-N-[2-(azetidin-3-yloxy)ethoxy]-7-oxo-6-(sulfooxy)-1,6-diazabicyclo[3.2.1]octane-2-carboxamide (2S,5R)-7-oxo-N-[2-(pyrrolidin-3-yloxy)ethoxy]-6-(sulfooxy)-1,6-diazabicyclo[3.2.1]octane-2-carboxamide (2S,5R)-7-oxo-N-[2-(piperidin-3-yloxy)ethoxy]-6-(sulfooxy)-1,6-diazabicyclo[3.2.1]octane-2-carboxamide or a deuterated compound of any such compound.

Passage 10. A compound of formula (I) as defined in passage 2, wherein the compound is selected from the group consisting of:

(2S,5R)-N'-methyl-7-oxo-6-(sulfooxy)-1,6-diazabicyclo[3.2.1]octane-2-carbohydrazide (2S,5R)-N'-ethyl-7-oxo-6-(sulfooxy)-1,6-diazabicyclo[3.2.1]octane-2-carbohydrazide (2S,5R)-7-oxo-N'-(propan-2-yl)-6-(sulfooxy)-1,6-diazabicyclo[3.2.1]octane-2-carbohydrazide (2S,5R)-N',N'-dimethyl-7-oxo-6-(sulfooxy)-1,6-diazabicyclo[3.2.1]octane-2-carbohydrazide (2S,5R)-N',N'-diethyl-7-oxo-6-(sulfooxy)-1,6-diazabicyclo[3.2.1]octane-2-carbohydrazide (2S,5R)-7-oxo-N',N'-di(propan-2-yl)-6-(sulfooxy)-1,6-diazabicyclo[3.2.1]octane-2-carbohydrazide (2S,5R)-N'-cyclopropyl-7-oxo-6-(sulfooxy)-1,6-diazabicyclo[3.2.1]octane-2-carbohydrazide (2S,5R)-N'-cyclobutyl-7-oxo-6-(sulfooxy)-1,6-diazabicyclo[3.2.1]octane-2-carbohydrazide (2S,5R)-N'-cyclopentyl-7-oxo-6-(sulfooxy)-1,6-diazabicyclo[3.2.1]octane-2-carbohydrazide (2S,5R)-7-oxo-N'-(piperidin-4-yl)-6-(sulfooxy)-1,6-diazabicyclo[3.2.1]octane-2-carbohydrazide (2S,5R)-7-oxo-6-(sulfooxy)-N'-(tetrahydro-2H-pyran-4-yl)-1,6-diazabicyclo[3.2.1]octane-2-carbohydrazide (2S,5R)-7-oxo-6-(sulfooxy)-N'-(tetrahydro-2H-thiopyran-4-yl)-1,6-diazabicyclo[3.2.1]octane-2-carbohydrazide (2S,5R)-7-oxo-N'-(piperidin-3-yl)-6-(sulfooxy)-1,6-diazabicyclo[3.2.1]octane-2-carbohydrazide (2S,5R)-7-oxo-N'-(pyrrolidin-3-yl)-6-(sulfooxy)-1,6-diazabicyclo[3.2.1]octane-2-carbohydrazide (2S,5R)-N'-(1,1-dioxidotetrahydro-2H-thiopyran-4-yl)-7-oxo-6-(sulfooxy)-1,6-diazabicyclo[3.2.1]octane-2-carbohydrazide (2S,5R)-N'-acetyl-7-oxo-6-(sulfooxy)-1,6-diazabicyclo[3.2.1]octane-2-carbohydrazide (2S,5R)-7-oxo-N'-propanoyl-6-(sulfooxy)-1,6-diazabicyclo[3.2.1]octane-2-carbohydrazide (2S,5R)-N'-(2-methylpropanoyl)-7-oxo-6-(sulfooxy)-1,6-diazabicyclo[3.2.1]octane-2-carbohydrazide (2S,5R)-N'-acetyl-N'-methyl-7-oxo-6-(sulfooxy)-1,6-diazabicyclo[3.2.1]octane-2-carbohydrazide (2S,5R)-N'-methyl-7-oxo-N'-propanoyl-6-(sulfooxy)-1,6-diazabicyclo[3.2.1]octane-2-carbohydrazide (2S,5R)-N'-methyl-N'-(2-methylpropanoyl)-7-oxo-6-(sulfooxy)-1,6-diazabicyclo[3.2.1]octane-2-carbohydrazide (2S,5R)-N'-acetyl-N'-ethyl-7-oxo-6-(sulfooxy)-1,6-diazabicyclo[3.2.1]octane-2-carbohydrazide (2S,5R)-N'-ethyl-7-oxo-N'-propanoyl-6-(sulfooxy)-1,6-diazabicyclo[3.2.1]octane-2-carbohydrazide (2S,5R)-N'-(2,2-dimethylpropanoyl)-7-oxo-6-(sulfooxy)-1,6-diazabicyclo[3.2.1]octane-2-carbohydrazide (2S,5R)-N'-butanoyl-7-oxo-6-(sulfooxy)-1,6-diazabicyclo[3.2.1]octane-2-carbohydrazide (2S,5R)-N'-(2-methylbutanoyl)-7-oxo-6-(sulfooxy)-1,6-diazabicyclo[3.2.1]octane-2-carbohydrazide (2S,5R)-N'-[(dimethylamino)acetyl]-7-oxo-6-(sulfooxy)-1,6-diazabicyclo[3.2.1]octane-2-carbohydrazide (2S,5R)-7-oxo-6-(sulfooxy)-N'-(4,4,4-trifluoropropanoyl)-1,6-diazabicyclo[3.2.1]octane-2-carbohydrazide (2S,5R)-N'-(methoxyacetyl)-7-oxo-6-(sulfooxy)-1,6-diazabicyclo[3.2.1]octane-2-carbohydrazide (2S,5R)-N'-[(2R)-2-aminopropanoyl]-7-oxo-6-(sulfooxy)-1,6-diazabicyclo[3.2.1]octane-2-carbohydrazide (2S,5R)-N'-[amino(phenyl)acetyl]-7-oxo-6-(sulfooxy)-1,6-diazabicyclo[3.2.1]octane-2-carbohydrazide (2S,5R)-N'-(cyclopropylcarbonyl)-7-oxo-6-(sulfooxy)-1,6-diazabicyclo[3.2.1]octane-2-carbohydrazide (2S,5R)-N'-(cyclobutylcarbonyl)-7-oxo-6-(sulfooxy)-1,6-diazabicyclo[3.2.1]octane-2-carbohydrazide (2S,5R)-N'-[(2,2-dimethylcyclopropyl)carbonyl]-7-oxo-6-(sulfooxy)-1,6-diazabicyclo[3.2.1]octane-2-carbohydrazide (2S,5R)-N'-[(2-methylcyclopropyl)carbonyl]-7-oxo-6-(sulfooxy)-1,6-diazabicyclo[3.2.1]octane-2-carbohydrazide (2S,5R)-N'-[(2,2-difluorocyclopropyl)carbonyl]-7-oxo-6-(sulfooxy)-1,6-diazabicyclo[3.2.1]octane-2-carbohydrazide (2S,5R)-N'-[(2-fluorocyclopropyl)carbonyl]-7-oxo-6-(sulfooxy)-1,6-diazabicyclo[3.2.1]octane-2-carbohydrazide (2S,5R)-N'-(cyclopentylcarbonyl)-7-oxo-6-(sulfooxy)-1,6-diazabicyclo[3.2.1]octane-2-carbohydrazide (2S,5R)-N'-(cyclohexylcarbonyl)-7-oxo-6-(sulfooxy)-1,6-diazabicyclo[3.2.1]octane-2-carbohydrazide (2S,5R)-N'-{[(2R)-2-aminocyclopentyl]carbonyl}-7-oxo-6-(sulfooxy)-1,6-diazabicyclo[3.2.1]octane-2-carbohydrazide (2S,5R)-7-oxo-N'-(pyrrolidin-2-ylcarbonyl)-6-(sulfooxy)-1,6-diazabicyclo[3.2.1]octane-2-carbohydrazide (2S,5R)-7-oxo-N'-(pyrrolidin-3-ylcarbonyl)-6-(sulfooxy)-1,6-diazabicyclo[3.2.1]octane-2-carbohydrazide (2S,5R)-7-oxo-N'-(piperidin-2-ylcarbonyl)-6-(sulfooxy)-1,6-diazabicyclo[3.2.1]octane-2-carbohydrazide (2S,5R)-N'-methyl-7-oxo-N'-(pyrrolidin-2-ylcarbonyl)-6-(sulfooxy)-1,6-diazabicyclo[3.2.1]octane-2-carbohydrazide (2S,5R)-7-oxo-N'-(piperidin-3-ylcarbonyl)-6-(sulfooxy)-1,6-diazabicyclo[3.2.1]octane-2-carbohydrazide (2S,5R)-7-oxo-N'-(piperidin-4-ylcarbonyl)-6-(sulfooxy)-1,6-diazabicyclo[3.2.1]octane-2-carbohydrazide (2S,5R)-7-oxo-6-(sulfooxy)-N'-(tetrahydro-2H-pyran-4-ylcarbonyl)-1,6-diazabicyclo[3.2.1]octane-2-carbohydrazide (2S,5R)-N'-[(1-methylpyrrolidin-2-yl)carbonyl]-7-oxo-6-(sulfooxy)-1,6-diazabicyclo[3.2.1]octane-2-carbohydrazide (2S,5R)-N'-[(1-methylpiperidin-4-yl)carbonyl]-7-oxo-6-(sulfooxy)-1,6-diazabicyclo[3.2.1]octane-2-carbohydrazide (2S,5R)-7-oxo-6-(sulfooxy)-N'-(tetrahydro-2H-thiopyran-4-ylcarbonyl)-1,6-diazabicyclo[3.2.1]octane-2-carbohydrazide (2S,5R)-N'-[(1,1-dioxidotetrahydro-2H-thiopyran-4-yl)carbonyl]-7-oxo-6-(sulfooxy)-1,6-diazabicyclo[3.2.1]octane-2-carbohydrazide (2S,5R)-7-oxo-N'-(pyrrolidin-2-ylacetyl)-6-(sulfooxy)-1,6-diazabicyclo[3.2.1]octane-2-carbohydrazide (2S,5R)-7-oxo-N'-(pyrrolidin-3-ylacetyl)-6-(sulfooxy)-1,6-diazabicyclo[3.2.1]octane-2-carbohydrazide (2S,5R)-N'-[(1-methylpyrrolidin-2-yl)acetyl]-7-oxo-6-(sulfooxy)-1,6-diazabicyclo[3.2.1]octane-2-carbohydrazide (2S,5R)-N'-(cyclopropylacetyl)-7-oxo-6-(sulfooxy)-1,6-diazabicyclo[3.2.1]octane-2-carbohydrazide (2S,5R)-7-oxo-N'-(piperidin-2-ylacetyl)-6-(sulfooxy)-1,6-diazabicyclo[3.2.1]octane-2-carbohydrazide (2S,5R)-N'-[(1-methylpiperidin-2-yl)acetyl]-7-oxo-6-(sulfooxy)-1,6-diazabicyclo[3.2.1]octane-2-carbohydrazide (2S,5R)-7-oxo-N'-(piperidin-3-ylacetyl)-6-(sulfooxy)-1,6-diazabicyclo[3.2.1]octane-2-carbohydrazide
(2S,5R)-7-oxo-N'-(piperidin-4-ylacetyl)-6-(sulfooxy)-1,6-diazabicyclo[3.2.1]octane-2-carbohydrazide
(2S,5R)-N'-[(1-methylpiperidin-4-yl)acetyl]-7-oxo-6-(sulfooxy)-1,6-diazabicyclo[3.2.1]octane-2-carbohydrazide
(2S,5R)-7-oxo-N'-(pyrrolidin-1-ylacetyl)-6-(sulfooxy)-1,6-diazabicyclo[3.2.1]octane-2-carbohydrazide
(2S,5R)-7-oxo-N'-(piperazin-1-ylacetyl)-6-(sulfooxy)-1,6-diazabicyclo[3.2.1]octane-2-carbohydrazide
(2S,5R)-N'-(morpholin-4-ylacetyl)-7-oxo-6-(sulfooxy)-1,6-diazabicyclo[3.2.1]octane-2-carbohydrazide
(2S,5R)-7-oxo-N'-(phenylcarbonyl)-6-(sulfooxy)-1,6-diazabicyclo[3.2.1]octane-2-carbohydrazide
(2S,5R)-N'-(naphthalen-2-ylcarbonyl)-7-oxo-6-(sulfooxy)-1,6-diazabicyclo[3.2.1]octane-2-carbohydrazide
(2S,5R)-N'-methyl-7-oxo-N'-(phenylcarbonyl)-6-(sulfooxy)-1,6-diazabicyclo[3.2.1]octane-2-carbohydrazide
(2S,5R)-N'-ethyl-7-oxo-N'-(phenylcarbonyl)-6-(sulfooxy)-1,6-diazabicyclo[3.2.1]octane-2-carbohydrazide
(2S,5R)-7-oxo-N'-(phenylacetyl)-6-(sulfooxy)-1,6-diazabicyclo[3.2.1]octane-2-carbohydrazide
(2S,5R)-N'-(naphthalen-2-ylacetyl)-7-oxo-6-(sulfooxy)-1,6-diazabicyclo[3.2.1]octane-2-carbohydrazide
(2S,5R)-N'-methyl-7-oxo-N'-(phenylacetyl)-6-(sulfooxy)-1,6-diazabicyclo[3.2.1]octane-2-carbohydrazide
(2S,5R)-N'-ethyl-7-oxo-N'-(phenylacetyl)-6-(sulfooxy)-1,6-diazabicyclo[3.2.1]octane-2-carbohydrazide
(2S,5R)-7-oxo-N'-(pyridin-2-ylcarbonyl)-6-(sulfooxy)-1,6-diazabicyclo[3.2.1]octane-2-carbohydrazide
(2S,5R)-7-oxo-N'-(pyridin-3-ylcarbonyl)-6-(sulfooxy)-1,6-diazabicyclo[3.2.1]octane-2-carbohydrazide
(2S,5R)-7-oxo-N'-(pyridin-4-ylcarbonyl)-6-(sulfooxy)-1,6-diazabicyclo[3.2.1]octane-2-carbohydrazide
(2S,5R)-7-oxo-6-(sulfooxy)-N'-(thiophen-3-ylcarbonyl)-1,6-diazabicyclo[3.2.1]octane-2-carbohydrazide
(2S,5R)-N'-(furan-3-ylcarbonyl)-7-oxo-6-(sulfooxy)-1,6-diazabicyclo[3.2.1]octane-2-carbohydrazide
(2S,5R)-7-oxo-6-(sulfooxy)-N'-(thiophen-2-ylcarbonyl)-1,6-diazabicyclo[3.2.1]octane-2-carbohydrazide
(2S,5R)-N'-(furan-2-ylcarbonyl)-7-oxo-6-(sulfooxy)-1,6-diazabicyclo[3.2.1]octane-2-carbohydrazide
(2S,5R)-N'-methyl-7-oxo-N'-(pyridin-3-ylcarbonyl)-6-(sulfooxy)-1,6-diazabicyclo[3.2.1]octane-2-carbohydrazide
(2S,5R)-7-oxo-N'-(1H-pyrrol-2-ylcarbonyl)-6-(sulfooxy)-1,6-diazabicyclo[3.2.1]octane-2-carbohydrazide
(2S,5R)-7-oxo-6-(sulfooxy)-N'-(thiophen-2-ylacetyl)-1,6-diazabicyclo[3.2.1]octane-2-carbohydrazide
(2S,5R)-N'-[(2-amino-1,3-thiazol-4-yl)carbonyl]-7-oxo-6-(sulfooxy)-1,6-diazabicyclo[3.2.1]octane-2-carbohydrazide
(2S,5R)-N'-(furan-2-ylacetyl)-7-oxo-6-(sulfooxy)-1,6-diazabicyclo[3.2.1]octane-2-carbohydrazide
(2S,5R)-7-oxo-N'-(pyridin-2-ylacetyl)-6-(sulfooxy)-1,6-diazabicyclo[3.2.1]octane-2-carbohydrazide
(2S,5R)-7-oxo-N'-(pyridin-3-ylacetyl)-6-(sulfooxy)-1,6-diazabicyclo[3.2.1]octane-2-carbohydrazide
(2S,5R)-7-oxo-N'-(pyridin-4-ylacetyl)-6-(sulfooxy)-1,6-diazabicyclo[3.2.1]octane-2-carbohydrazide
(2S,5R)-N'-[(2-amino-1,3-thiazol-4-yl)acetyl]-7-oxo-6-(sulfooxy)-1,6-diazabicyclo[3.2.1]octane-2-carbohydrazide
(2S,5R)-N'-[(2-amino-1,3-thiazol-4-yl)acetyl]-N'-methyl-7-oxo-6-(sulfooxy)-1,6-diazabicyclo[3.2.1]octane-2-carbohydrazide
(2S,5R)-N'-methyl-7-oxo-N'-(pyridin-3-ylacetyl)-6-(sulfooxy)-1,6-diazabicyclo[3.2.1]octane-2-carbohydrazide
(2S,5R)-7-oxo-6-(sulfooxy)-N'-(trifluoroacetyl)-1,6-diazabicyclo[3.2.1]octane-2-carbohydrazide
(2S,5R)-N'-(methylsulfonyl)-7-oxo-6-(sulfooxy)-1,6-diazabicyclo[3.2.1]octane-2-carbohydrazide
2-{[(2S,5R)-7-oxo-6-(sulfooxy)-1,6-diazabicyclo[3.2.1]oct-2-yl]carbonyl}hydrazinecarboxamide
2-{[(2S,5R)-7-oxo-6-(sulfooxy)-1,6-diazabicyclo[3.2.1]oct-2-yl]carbonyl}hydrazinesulfonamide
(2S,5R)-7-oxo-N'-phenyl-6-(sulfooxy)-1,6-diazabicyclo[3.2.1]octane-2-carbohydrazide
(2S,5R)-N'-methyl-7-oxo-N-phenyl-6-(sulfooxy)-1,6-diazabicyclo[3.2.1]octane-2-carbohydrazide
(2S,5R)-7-oxo-N'-(pyridin-3-yl)-6-(sulfooxy)-1,6-diazabicyclo[3.2.1]octane-2-carbohydrazide
(2S,5R)-N'-methyl-7-oxo-N-(pyridin-3-yl)-6-(sulfooxy)-1,6-diazabicyclo[3.2.1]octane-2-carbohydrazide
(2S,5R)-7-oxo-N-(piperidin-1-yl)-6-(sulfooxy)-1,6-diazabicyclo[3.2.1]octane-2-carboxamide
(2S,5R)-7-oxo-N-(pyrrolidin-1-yl)-6-(sulfooxy)-1,6-diazabicyclo[3.2.1]octane-2-carboxamide
(2S,5R)-N-(morpholin-4-yl)-7-oxo-6-(sulfooxy)-1,6-diazabicyclo[3.2.1]octane-2-carboxamide
(2S,5R)-7-oxo-N-(piperazin-1-yl)-6-(sulfooxy)-1,6-diazabicyclo[3.2.1]octane-2-carboxamide
(2S,5R)-7-oxo-6-(sulfooxy)-N-(thiomorpholin-4-yl)-1,6-diazabicyclo[3.2.1]octane-2-carboxamide
(2S,5R)-N-(1,1-dioxidothiomorpholin-4-yl)-7-oxo-6-(sulfooxy)-1,6-diazabicyclo[3.2.1]octane-2-carboxamide
(2S,5R)-7-oxo-N-(2-oxopiperidin-1-yl)-6-(sulfooxy)-1,6-diazabicyclo[3.2.1]octane-2-carboxamide
(2S,5R)-7-oxo-N-(3-oxomorpholin-4-yl)-6-(sulfooxy)-1,6-diazabicyclo[3.2.1]octane-2-carboxamide
(2S,5R)-7-oxo-N-(2-oxopiperazin-1-yl)-6-(sulfooxy)-1,6-diazabicyclo[3.2.1]octane-2-carboxamide
(2S,5R)-7-oxo-6-(sulfooxy)-N-(tetrahydropyrimidin-1(2H)-yl)-1,6-diazabicyclo[3.2.1]octane-2-carboxamide
(2S,5R)-7-oxo-N-(2-oxotetrahydropyrimidin-1(2H)-yl)-6-(sulfooxy)-1,6-diazabicyclo[3.2.1]octane-2-carboxamide
(2S,5R)-N-(3-aminopiperidin-1-yl)-7-oxo-6-(sulfooxy)-1,6-diazabicyclo[3.2.1]octane-2-carboxamide
(2S,5R)-N'-[(2-aminocyclopropyl)carbonyl]-7-oxo-6-(sulfooxy)-1,6-diazabicyclo[3.2.1]octane-2-carbohydrazide
(2S,5R)-N'-[(2-aminocyclopropyl)carbonyl]-N'-methyl-7-oxo-6-(sulfooxy)-1,6-diazabicyclo[3.2.1]octane-2-carbohydrazide
(2S,5R)-N'-(azetidin-2-ylcarbonyl)-7-oxo-6-(sulfooxy)-1,6-diazabicyclo[3.2.1]octane-2-carbohydrazide
(2S,5R)-N'-(azetidin-3-ylcarbonyl)-7-oxo-6-(sulfooxy)-1,6-diazabicyclo[3.2.1]octane-2-carbohydrazide
(2S,5R)-N'-[(2S)-2-aminopropanoyl]-7-oxo-6-(sulfooxy)-1,6-diazabicyclo[3.2.1]octane-2-carbohydrazide
(2S,5R)-N'-[(2S)-2-aminopropanoyl]-N'-methyl-7-oxo-6-(sulfooxy)-1,6-diazabicyclo[3.2.1]octane-2-carbohydrazide
(2S,5R)-N'-[3-(dimethylamino)propanoyl]-7-oxo-6-(sulfooxy)-1,6-diazabicyclo[3.2.1]octane-2-carbohydrazide
(2S,5R)-N'-[(3,3-difluorocyclobutyl)carbonyl]-7-oxo-6-(sulfooxy)-1,6-diazabicyclo[3.2.1]octane-2-carbohydrazide
(2S,5R)-N'-[(3-aminocyclobutyl)carbonyl]-7-oxo-6-(sulfooxy)-1,6-diazabicyclo[3.2.1]octane-2-carbohydrazide
(2S,5R)-N'-{[3-(methylamino)cyclobutyl]carbonyl}-7-oxo-6-(sulfooxy)-1,6-diazabicyclo[3.2.1]octane-2-carbohydrazide
(2S,5R)-N'-{[3-(dimethylamino)cyclobutyl]carbonyl}-7-oxo-6-(sulfooxy)-1,6-diazabicyclo[3.2.1]octane-2-carbohydrazide, or a deuterated compound of any such compound.

Passage 11. A method of treating a bacterial infection comprising administering to a mammal in need thereof an antibacterially effective amount of a compound as recited in any one of passages 1-10.

Passage 12. A pharmaceutical composition containing as an active ingredient, at least one compound as recited in any one of passages 1-10.

Passage 13. A pharmaceutical composition containing, as an active ingredient, (i) at least one compound as recited in any one of passages 1-10 and (ii) at least one β-lactam antibiotic, at least one salt of a β-lactam antibiotic, at least one hydrate of a β-lactam antibiotic or at least one prodrug of a β-lactam antibiotic.

Passage 14. A pharmaceutical composition containing, as an active ingredient, (i) at least one compound as recited in any one of passages 1-10 and (ii) at least one antibiotic, at least one salt of an antibiotic, at least one hydrate of an antibiotic or at least one prodrug of an antibiotic.

Passage 15. A pharmaceutical composition suitable for the treatment of bacterial infections in mammals, comprising a pharmaceutical composition as recited in passage 13 or passage 14 and a pharmaceutically acceptable carrier.

Passage 16. A method of treating bacterial infection, comprising administering to a mammal in need thereof a combination of (i) an effective amount of a compound as recited in any one of passages 1-10 and (ii) an effective amount of at least one β-lactam antibiotic, at least one salt of a β-lactam antibiotic, at least one hydrate of a β-lactam antibiotic or at least one prodrug of a β-lactam antibiotic.

Passage 17. A method of treating bacterial infection, comprising administering to a mammal in need thereof a combination of (i) an effective amount of a compound as recited in any one of passages 1-10 and (ii) an effective amount of at least one antibiotic, at least one salt of an antibiotic, at least one hydrate of an antibiotic or at least one prodrug of an antibiotic.

Passage 18. A method for the treatment of bacterial infection, by inhibiting bacterial β-lactamases, comprising administering to a mammal in need thereof a pharmaceutical composition as recited in any one of passages 12-15.

Passage 19. A method as recited in passage 18, wherein the pharmaceutical composition is administered separately, simultaneously or spread over time.

Passage 20. A method or a pharmaceutical composition as recited in passage 13 or passage 16, wherein a ratio of the weight of (i) the compound of formula (I) to the weight of (ii) at least one β-lactam antibiotic, at least one salt of a β-lactam antibiotic, at least one hydrate of a β-lactam antibiotic or at least one prodrug of a β-lactam antibiotic, is in the range of 1:20 to 20:1.

Passage 21. A method or a pharmaceutical composition as recited in passage 14 or passage 17, wherein a ratio of the weight of (i) the compound of formula (I) to the weight of (ii) at least one antibiotic, at least one salt of an antibiotic, at least one hydrate of an antibiotic or at least one prodrug of an antibiotic, is in the range of 1:20 to 20:1.

Passage 22. A molecular complex comprising a compound as recited in any one of passages 1-10 and at least one solvent.

Passage 23. A molecular complex as recited in passage 22, wherein the solvent comprises water.

Passage 24. A process for preparing a compound recited in passage 1, wherein M=H, and wherein the process comprises:

[A] Reacting substituted hydroxylamine (V) with an acid (VI) in presence of a coupling agent selected from the group consisting of EDCI, HOBT-DCC and PyBop to provide an intermediate of formula (VII);

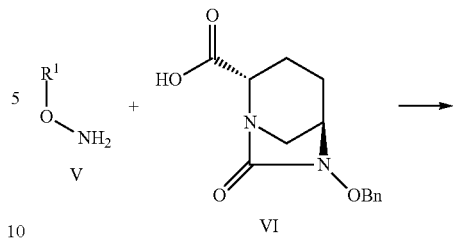

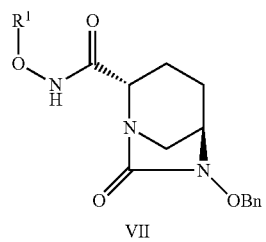

[B] Removing the benzyl protecting group of the intermediate (VII) with a source of hydrogen in presence of Pd catalyst to provide debenzylated product (VIII);

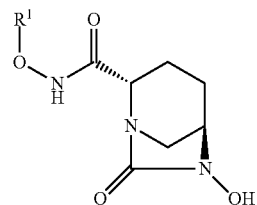

[C] Contacting compound (VIII) with a sulfating agent in the presence of solvent to obtain compound of formula (Ia)

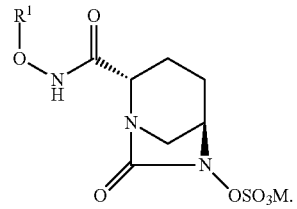

Passage 25. A process for preparing a compound recited in passage 2, wherein M=H, and wherein the process comprises:

[A] Reacting substituted hydrazine (Va) with an acid (VI) in presence of a coupling agent selected from the group consisting of EDCI or HOBT-DCC and PyBop to provide an intermediate of formula (VIIa),

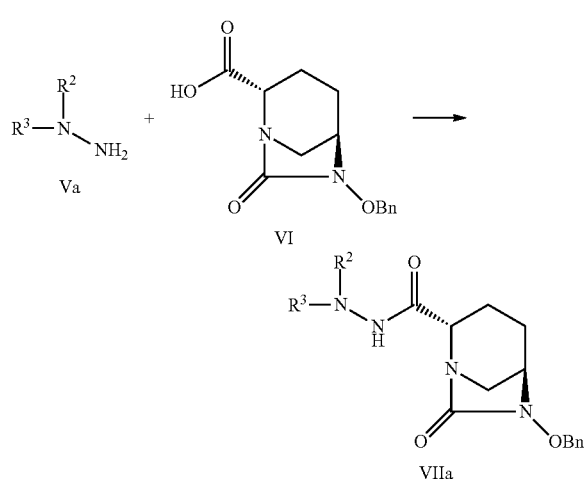

[B] Removing the benzyl protecting group of the intermediate (VIIa) with a source of hydrogen in presence of Pd catalyst to provide the debenzylated product (VIIIa),

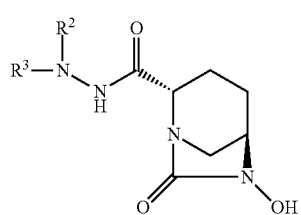

VIIIa

[C] Contacting compound (VIIIa) with a sulfating agent in the presence of solvent to obtain compound of formula (Ib)

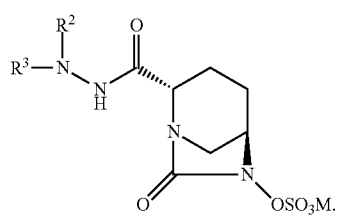

Ib

Passage 26. A method or a pharmaceutical composition as recited in any one of passages 13, 16 and 20, wherein the at least one β-lactam antibiotic, pharmaceutically acceptable salt of a β-lactam antibiotic, hydrate of a β-lactam antibiotic or prodrug of a β-lactam antibiotic is selected from the group consisting of amoxicillin, ampicillin, azlocillin, mezlocillin, hetacillin, bacampicillin, carbenicillin, sulbenicillin, ticarcillin, piperacillin, mecillinam, methicillin, ciclacillin, oxacillin, cloxacillin, dicloxacillin, nafcillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefozopran, cefepime, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, CXA-101, imipenem, meropenem, biapenem, panipenem, ertapenem, doripenem, aztreonam, carumonam, pharmaceutically acceptable salts of said β-lactam antibiotics, hydrates of said β-lactam antibiotics, and prodrugs of said β-lactam antibiotics.

Passage 27. A method or a pharmaceutical composition as recited in any one of passages 14, 17 and 21, wherein the at least one antibiotic, pharmaceutically acceptable salt of an antibiotic, hydrate of an antibiotic or prodrug of an antibiotic is selected from the group consisting of aminoglycosides, quinolones, tetracyclines, glycylcyclines, glycopeptides, lipopeptides, macrolides, ketolides, lincosamides, streptogramin, oxazolidinones, polymyxins.

What we claim is:
1. A method of treating a bacterial infection comprising administering to a mammal in need thereof an antibacterially effective amount of a compound of formula (I):

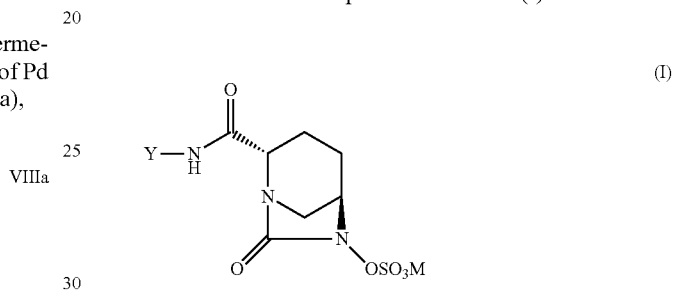

(I)

wherein:
M is hydrogen or a pharmaceutically acceptable salt-forming cation;
Y is $OR^1$;
$R^1$ is a radical selected from the group consisting of:
  (1) $C_{1-6}$ straight or branched chain alkyl which is optionally substituted;
  (2) $C_{3-7}$ cycloalkyl which is optionally substituted;
  (3) $C_{4-7}$ saturated heterocycles containing at least one heteroatom selected from O, N and S wherein the said heterocycle is optionally substituted, the ring S is optionally oxidized to S(O) or $S(O)_2$ and the free ring N atom may optionally take a substituent;
  (4) Heterocyclyl ($C_{1-6}$) alkyl wherein the said heterocycle has the same definition as defined in (3), and the said heterocycle is optionally substituted;
  (5) $C_{5-7}$ membered saturated heterocycles optionally fused with a $C_{3-7}$ membered cycloalkyl group to form a bicyclic ring system where the bicyclic ring system so formed is fused either through two adjacent carbon atoms or through a N atom shared by both the rings and the other end of the cycloalkyl chain is attached to the adjacent carbon atom of the molecule, each ring of the said bicyclic ring system independently optionally substituted;
  (6) $C_{5-7}$ membered saturated heterocycles optionally fused with another $C_{5-7}$ saturated heterocycle to from a bicyclic ring system where the bicyclic ring system so formed is fused either through two adjacent carbon atoms or through a N atom shared by both the rings, each ring of the said bi-cyclic ring system independently optionally substituted;
  (7) $C_{3-7}$ cycloalkyl which is optionally fused with a $C_{5-7}$ membered saturated heterocycle containing at least one heteroatom selected from O, N and S, the said bicyclic ring optionally substituted;

(8) Bridged bicyclic ring system having optionally one or two heteroatoms selected from O, N and S, the bicyclic ring system optionally substituted either at the carbon atom or at the free N atom present in the ring;

(9) $C_{5-7}$ membered saturated heterocycles optionally fused with $C_{5-7}$ membered heteroaryl ring where the bicyclic ring system so formed is fused either through two adjacent carbon atoms or through N atom shared by both the rings;

(10) $C_{5-7}$ membered saturated heterocycles optionally fused to a $C_{3-6}$ membered ring system through a common carbon atom to form a spiro system optionally containing one heteroatom selected from O, N and S that is present in the spiro ring where the ring S is optionally oxidized to S(O) or S(O)$_2$ and the free N atom present in either ring may optionally take a substituent; and

(11) $C_{5-7}$ membered heteroaryl $(C_{1-6})$alkyl which is optionally substituted, or a deuterated compound of any such compound.

2. A method of treating bacterial infection, comprising administering to a mammal in need thereof a combination of (i) an effective amount of a compound of formula (I) and (ii) an effective amount of at least one β-lactam antibiotic, at least one salt of a β-lactam antibiotic, at least one hydrate of a β-lactam antibiotic or at least one prodrug of a β-lactam antibiotic

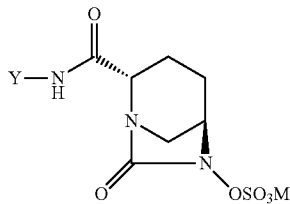

(I)

wherein:
M hydrogen or a pharmaceutically acceptable salt-forming cation;
Y is OR$^1$;
R$^1$ is a radical selected from the group consisting of:
(1) $C_{1-6}$ straight or branched chain alkyl which is optionally substituted;
(2) $C_{3-7}$ cycloalkyl which is optionally substituted;
(3) $C_{4-7}$ saturated heterocycles containing at least one heteroatom selected from O, N and S wherein the said heterocycle is optionally substituted, the ring S is optionally oxidized to S(O) or S(O)$_2$ and the free ring N atom may optionally take a substituent;
(4) Heterocyclyl $(C_{1-6})$ alkyl wherein the said heterocycle has the same definition as defined in (3), and the said heterocycle is optionally substituted;
(5) $C_{5-7}$ membered saturated heterocycles optionally fused with a $C_{3-7}$ membered cycloalkyl group to form a bicyclic ring system where the bicyclic ring system so formed is fused either through two adjacent carbon atoms or through a N atom shared by both the rings and the other end of the cycloalkyl chain is attached to the adjacent carbon atom of the molecule, each ring of the said bicyclic ring system independently optionally substituted;
(6) $C_{5-7}$ membered satyrated heterocycles optionally fused with another $C_{5-7}$ saturated heterocycle to form a bicyclic ring system where the bicyclic ring system so formed is fused either through two adjacent carbon atoms or through a N atom shared by both the rings, each ring of the said bi-cyclic ring system independently optionally substituted;
(7) $C_{3-7}$ cycloalkyl which is optionally fused with a $C_{5-7}$ membered saturated heterocycle containing at least one heteroatom selected from O, N and S, the said bicyclic ring defined in (3), and the said heterocycle is optionally substituted; optionally substituted;
(8) Bridged bicyclic ring system having optionally one or two heteroatoms selected from O, N and S, the bicyclic ring system optionally substituted either at the carbon atom or at the free N atom present in the ring;
(9) $C_{5-7}$ membered saturated heterocycles optionally fused with $C_{5-7}$ membered heteroaryl ring where the bicyclic ring system so formed is fused either through two adjacent carbon atoms or through N atom shared by both the ring;
(10) $C_{5-7}$ membered saturated heterocycles optionally fused to a $C_{3-6}$ membered ring system through a common carbon atom to form a spiro system optionally containing one heteroatom selected from O, N and S that is present in the spiro ring where the ring S is optionally oxidized to S(O)$_2$ and the free N atom present in either ring may optionally take a substituent; and
(11) $C_{5-7}$ membered heteroaryl $(C_{1-6})$alkyl which is optionally substituted, or a deuterated compound of any such compound.

3. A method of treating bacterial infection, comprising administering to a mammal in need thereof a combination of (i) an effective amount of a compound of formula (I) and (ii) an effective amount of at least one antibiotic, at least one salt of an antibiotic, at least one hydrate of an antibiotic or at least one prodrug of an antibiotic

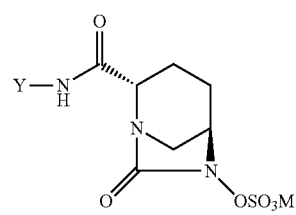

(I)

wherein:
M hydrogen or a pharmaceutically acceptable salt-forming cation;
Y is OR$^1$;
R$^1$ is a radical selected from the group consisting of:
(1) $C_{1-6}$ straight or branched chain alkyl which is optionally substituted;
(2) $C_{3-7}$ cycloalkyl which is optionally substituted;
(3) $C_{4-7}$ saturated heterocycles containing at least one heteroatom selected from O, N and S wherein the said heterocycle is optionally substituted, the ring S is optionally oxidized to S(O) or S(O)$_2$ and the free ring N atom may optionally take a substituent;
(4) Heterocyclyl $(C_{1-6})$ alkyl wherein the said heterocycle has the same definition as defined in (3), and the said heterocycle is optionally substituted;
(5) $C_{5-7}$ membered saturated heterocycles optionally fused with a $C_{3-7}$ membered cycloalkyl group to form a bicyclic ring system where the bicyclic ring system so formed is fused either through two adjacent carbon atoms or through a N atom shared by both the rings and the other end of the cycloalkyl chain is attached to the adjacent carbon atom of the molecule, each ring of the said bicyclic ring system independently optionally substituted;

(6) $C_{5-7}$ membered saturated heterocycles optionally fused with another $C_{5-7}$ saturated heterocycle to form a bicyclic ring system where the bicyclic ring system so formed is fused either through two adjacent carbon atoms or through a N atom shared by both the rings, each ring of the said bi-cyclic ring system independently optionally subststuted;

(7) $C_{3-7}$ cycloalkyl which is optionally fused with a $C_{5-7}$ membered saturated heterocycle containing at least one heteroatom selected from O, N and S, the said bicyclic ring optionally substituted; optionally substituted;

(8) Bridged bicyclic ring system having optionally one or two heteroatoms selected from O, N and S, the bicyclic ring system optionally substituted either at the carbon atom or at the free N atom present in the ring;

(9) $C_{5-7}$ membered saturated heterocycles optionally fused with $C_{5-7}$ membered heteroaryl ring where the bicyclic ring system so formed is fused either through two adjacent carbon atoms or through N atom shared by both the ring;

(10) $C_{5-7}$ membered saturated heterocycles optionally fused to a $C_{3-6}$ membered ring system through a common carbon atom to form a spiro system optionally containing one heteroatom selected from O, N and S that is present in the spiro ring where the ring S is optionally oxidized to $S(O)_2$ and the free N atom present in either ring may optionally take a substituent; and

(11) $C_{5-7}$ membered heteroaryl $(C_{1-6})$alkyl which is optionally substituted, or a deuterated compound of any such compound.

* * * * *